US012263179B1

(12) United States Patent
Robins et al.

(10) Patent No.: US 12,263,179 B1
(45) Date of Patent: Apr. 1, 2025

(54) LYME DISEASE-ASSOCIATED T CELL RECEPTOR-RELATED METHODS

(71) Applicant: Adaptive Biotechnologies Corporation, Seattle, WA (US)

(72) Inventors: Harlan S. Robins, Seattle, WA (US); Thomas M. Snyder, San Bruno, CA (US); Mark Klinger, Seattle, WA (US); Jonathan M. Carlson, Redmond, WA (US); Julia Greissl, Redmond, WA (US)

(73) Assignee: Adaptive Biotechnologies Corporation, Seattle, WA (US)

( * ) Notice: Subject to any disclaimer, the term of this patent is extended or adjusted under 35 U.S.C. 154(b) by 421 days.

(21) Appl. No.: 16/945,701

(22) Filed: Jul. 31, 2020

Related U.S. Application Data

(60) Provisional application No. 62/881,596, filed on Aug. 1, 2019.

(51) Int. Cl.
| | | |
|---|---|---|
| *A61K 31/65* | (2006.01) |
| *A61K 9/00* | (2006.01) |
| *A61K 31/43* | (2006.01) |
| *A61K 31/431* | (2006.01) |
| *A61K 31/53* | (2006.01) |
| *A61P 31/04* | (2006.01) |
| *G01N 33/569* | (2006.01) |
| *G16B 40/00* | (2019.01) |
| *C07K 14/725* | (2006.01) |

(52) U.S. Cl.
CPC ............ *A61K 31/65* (2013.01); *A61K 9/0019* (2013.01); *A61K 31/43* (2013.01); *A61K 31/431* (2013.01); *A61K 31/53* (2013.01); *A61P 31/04* (2018.01); *G01N 33/56972* (2013.01); *G16B 40/00* (2019.02); *G01N 2333/7051* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 5,858,358 A | 1/1999 | June et al. |
| 5,883,223 A | 3/1999 | Gray |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 9,150,905 B2 | 10/2015 | Robins et al. |
| 9,181,590 B2 | 11/2015 | Robins et al. |
| 9,181,591 B2 | 11/2015 | Robins et al. |
| 2010/0330571 A1 | 12/2010 | Robins et al. |
| 2012/0058902 A1 | 3/2012 | Livingston et al. |
| 2013/0253842 A1 | 9/2013 | Sherwood et al. |
| 2013/0288237 A1 | 10/2013 | Robins et al. |
| 2015/0203897 A1 | 6/2015 | Robins et al. |
| 2015/0299785 A1 | 10/2015 | Livingston et al. |

FOREIGN PATENT DOCUMENTS

| | | |
|---|---|---|
| WO | WO2010151416 | 12/2010 |
| WO | WO2011106738 | 9/2011 |
| WO | WO2012027503 | 3/2012 |
| WO | WO2013169957 | 11/2013 |
| WO | WO2013188831 | 12/2013 |
| WO | WO2014055561 | 4/2014 |

OTHER PUBLICATIONS

Curr. Rheum. Rep. 2020, 22: 3, pp. 1-11 (Year: 2020).*
Arstila, et al., (1999) "A direct estimate of the human alpha/beta T cell receptor diversity", Science, vol. 286, pp. 958-961.
Cabaniols, et al., (2001) "Most alpha/beta T cell receptor diversity is due to terminal deoxynucleotideyl transferase", J Exp Med, vol. 194, pp. 1385-1390.
Carlson, et al., (2013) "Using synthetic templates to design an unbiased multiplex PCR assay", Nature Communications, 4:2680, pp. 1-9.
Chu and Sharp, (1981) "SV40 DNA transfection of cells in suspension: analysis of the efficiency of transcription and of T-antigen", Gene, vol. 13, pp. 197-202.

(Continued)

*Primary Examiner* — Michael Szperka
*Assistant Examiner* — Marianne DiBrino
(74) *Attorney, Agent, or Firm* — Brian E. Davy; Bozicevic, Field & Francis LLP

(57) ABSTRACT

Provided are methods for assessing T cell receptor β chain complementary determining region 3 (TCRβ CDR3) sequences. In certain embodiments, the methods comprise assessing TCRβ CDR3 sequences determined from a sample obtained from a subject having or suspected of having a tick bite for the presence or absence of one or more TCRβ CDR3 sequences set forth in the present disclosure. According to some embodiments, at the time of the assessing, the subject is seronegative for Lyme disease and/or has one or more non-specific symptoms consistent with Lyme disease. Also provided are methods comprising administering a Lyme disease therapy to a subject identified as comprising T cells that express a T cell receptor β chain (TCRβ) comprising a TCRβ CDR3 sequence set forth in the present disclosure.

10 Claims, 8 Drawing Sheets
Specification includes a Sequence Listing.

(56) References Cited

OTHER PUBLICATIONS

Emerson, et al., (2017) "Immunosequencing identifies signatures of cytomegalovirus exposure history and HLA-mediated effects on the T cell repertoire", Nature Genetics, doi:10.1038/ng.3822, 10 pages.

Govers, et al., (2010) "T cell receptor gene therapy: strategies for optimizing transgenic TCR pairing", Trends in Molecular Medicine, vol. 16 No. 2, pp. 77-87.

Murray and Sharpiro, (2010) "Lyme Disease", Clin Lab Med., vol. 30, No. 1, pp. 311-328.

Robins, et al., (2009) "Comprehensive assessment of T-cell receptor beta-chain diversity in alpha/beta T cells", Blood, vol. 114, No. 19, pp. 4099-4107.

Robins, et al., (2010) "Overlap and effective size of the human CD8+ T-cell receptor repertoire", Sci. Translat. Med., vol. 2, No. 47, pp. 1-9.

Robins, et al., (2012) "Ultra-sensitive detection of rare T cell clones", J. Immunol. Methods, 375(1-2):14-19.

Sherwood, et al., (2011) "Deep sequencing of the human TCRγ and TCRβ repertoires provides evidence that TCRβ rearranges after αβ, γδ T-cell commitment", Sci. Translat. Med. vol. 3 No. 90, pp. 1-17.

Wormser, et al., (2006) "The clinical assessment, treatment, and prevention of lyme disease, human granulocytic anaplasmosis, and babesiosis: clinical practice guidelines by the Infectious Diseases Society of America" Clin Infect Dis., vol. 43, Issue 9, pp. 1089-1134.

Zhang, et al., (2019) "The Emerging World of TCR-T Cell Trials Against Cancer: A Systematic Review", Technol Cancer Res Treat., vol. 18, pp. 1-13.

Zhao, et al., (2019) "Engineered T Cell Therapy for Cancer in the Clinic", Front. Immunol., vol. 10, Article 2250, pp. 1-20.

\* cited by examiner

| CDR3 | V | Neg_count (8833) | Pos_count (65) | Cluster_size |
|---|---|---|---|---|
| CASSPRGGRNQPQHF | TCRBV18-01 | 7 | 13 | 2 |
| CASS_GGQHYGYTF | TCRBV05-01 | 46 | 13 | 2 |
| CASSLAPLGDEQYF | TCRBV07-06 | 1 | 7 | 2 |
| CASSFE_NYNSPLHF | TCRBV28-01 | 172 | 19 | 4 |
| CASSFE_NYNSPLHF | TCRBV12 | 8 | 12 | 6 |
| CASSYL_LSYEQYF | TCRBV06 | 3 | 25 | 9 |
| CSAR_G_GTGELFF | TCRBV20 | 81 | 26 | 33 |

LYME DISEASE-ASSOCIATED T CELL RECEPTOR-RELATED METHODS

CROSS-REFERENCE TO RELATED APPLICATIONS

This application claims the benefit of U.S. Provisional Patent Application No. 62/881,596, filed Aug. 1, 2019, which application is incorporated herein by reference in its entirety.

INTRODUCTION

Antigen-specific cellular immune responses are mediated by a diverse population of T cells and B cells, each bearing immune cell receptors (TCRs and BCRs, respectively) capable of recognizing a specific antigen (in the case of T cells, an antigen peptide bound to a particular major histocompatibility complex (MHC) molecule on the surface of host cells). Encounter with an antigen leads to the clonal expansion, activation, and maturation of T and B cells, resulting in effector populations of cytotoxic ($CD8^+$ CTL) and helper ($CD4^+$) T cells, or antibodies and memory B cells, respectively. The presence of antigen-specific effector cells is diagnostic of an immune response specific to that antigen.

Activated T cells proliferate by clonal expansion and reside in the memory T cell compartment for many years as a clonal population of cells (clones) with identical-by-descent rearranged TCR genes (Arstila T P, et al. A direct estimate of the human alpha/beta T cell receptor diversity, *Science* 286: 958-961, 1999).

The majority of TCR diversity resides in the beta chain of the TCR alpha/beta heterodimer. Immense diversity is generated by combining noncontiguous TCRβ variable (V), diversity (D), and joining (J) region gene segments, which collectively encode the CDR3 region, the primary region of the TCRβ locus for determining antigen specificity. Deletion and template-independent insertion of nucleotides during rearrangement at the Vβ-Dβ and Dβ-Jβ junctions further add to the potential diversity of receptors that can be encoded (Cabaniols J P, et al. Most alpha/beta T cell receptor diversity is due to terminal deoxynucleotidyl transferase, *J Exp Med* 194: 1385-1390, 2001). Typically, at a given point in time, an adult with a healthy immune system expresses approximately 10 million unique TCRβ chains on their $10^{12}$ circulating T cells (Robins H S, et al. (2009) Comprehensive assessment of T-cell receptor beta-chain diversity in alpha/beta T cells, *Blood* 114: 4099-4107).

The human T-cell repertoire thus dynamically encodes exposure to disease-related antigens through rearrangements of their receptor-encoding genes and so provides an excellent basis for making diagnostic predictions. It has been demonstrated that TCRβ receptors in peripheral blood samples from human subjects can be employed to predict the status of exposure to a disease; i.e., based on the presence and abundance of such receptors in the training cohort (Emerson et al., Immunosequencing identifies signatures of cytomegalovirus exposure history and HLA-mediated effects on the T cell repertoire, *Nature Genetics* April 2017; doi:10.1038/ng.3822).

Lyme disease is caused by the spirochetal bacterium *Borrelia burgdorferi* and transmitted to humans by an infected *Ixodes scapularis* tick. The CDC approximates over 300,000 new cases of Lyme disease in the United States each year. Early initiation of antibiotics decreases the likelihood of developing debilitating chronic symptoms. For individuals presenting days to weeks from the initial tick bite, symptoms may include a characteristic erythema migrans (EM) rash and non-specific flu-like symptoms. Given the specificity of EM rash for Lyme disease and the poor sensitivity and specificity of currently available Lyme diagnostic assays, individuals with EM rash can be treated immediately without further testing. However, approximately 20-30% do not present with an EM rash and for those that do, it may go unnoticed or unreported due to its location, its unrecognized appearance, and/or its transient nature, making a definitive clinical diagnosis challenging.

When Lyme disease is suspected in people without an EM rash, further testing is recommended. Until recently, the only FDA-approved and CDC-recommended testing option for Lyme disease was standard two-tiered testing (STTT), which detects antibodies against *B. burgdorferi* and consists of an enzyme-linked immunosorbent assay (ELISA) and immunoblot. Even in samples from patients with rigorously defined clinical Lyme disease, the STTT has poor sensitivity (20-40%) in the acute phase of disease as antibody responses are developing, but improves to >90% in later stages of the disease (months-years) when untreated patients may have developed serious late stage symptoms. In July 2019, the FDA approved a modified two-tiered ELISA test (MTTT) with improved, but still suboptimal, early stage sensitivity that ranges from ~50-80% in these clinically defined samples.

The specificity of these two-tiered assays, when performed in samples from patients being evaluated for reasons unrelated to Lyme disease symptoms, varies depending on whether testing is done in endemic (~5% false positives) versus non-endemic regions (~1-2% false positives). However, both assays lack specificity in "real world" clinical scenarios. Approximately 10% of individuals in endemic areas who undergo serologic testing for suspicion of Lyme disease have a positive test. These data indicate that approximately 50% of patients in endemic regions who present to their clinician with non-specific symptoms that could be consistent with Lyme disease in fact have an unrelated illness or had a remote diagnosis and/or exposure of Lyme disease that is not related to their current symptomatology. Thus, diagnostic testing with improved sensitivity and specificity for Lyme disease is needed for patients presenting to their health care provider early in the course of illness.

SUMMARY

Provided are methods for assessing T cell receptor β chain complementary determining region 3 (TCRβ CDR3) sequences. In certain embodiments, the methods comprise assessing TCRβ CDR3 sequences determined from a sample obtained from a subject having or suspected of having a tick bite for the presence or absence of one or more TCRβ CDR3 sequences set forth in the present disclosure. According to some embodiments, at the time of the assessing, the subject is seronegative for Lyme disease and/or has one or more non-specific symptoms consistent with Lyme disease. Also provided are methods comprising administering a Lyme disease therapy to a subject identified as comprising T cells that express a T cell receptor β chain (TCRβ) comprising a TCRβ CDR3 sequence set forth in the present disclosure.

BRIEF DESCRIPTION OF THE FIGURES

FIG. 3: Seven TCRβ CDR3 amino acid sequence clusters identified in 205 Lyme disease-associated TCRs. The amino acid sequences from top to bottom are set forth in SEQ ID NO:557, SEQ ID NO:647, SEQ ID NO:1173, SEQ ID NO:183, SEQ ID NO:1234, SEQ ID NO:618 and SEQ ID NO:1404, respectively.

DETAILED DESCRIPTION

Figure 1:
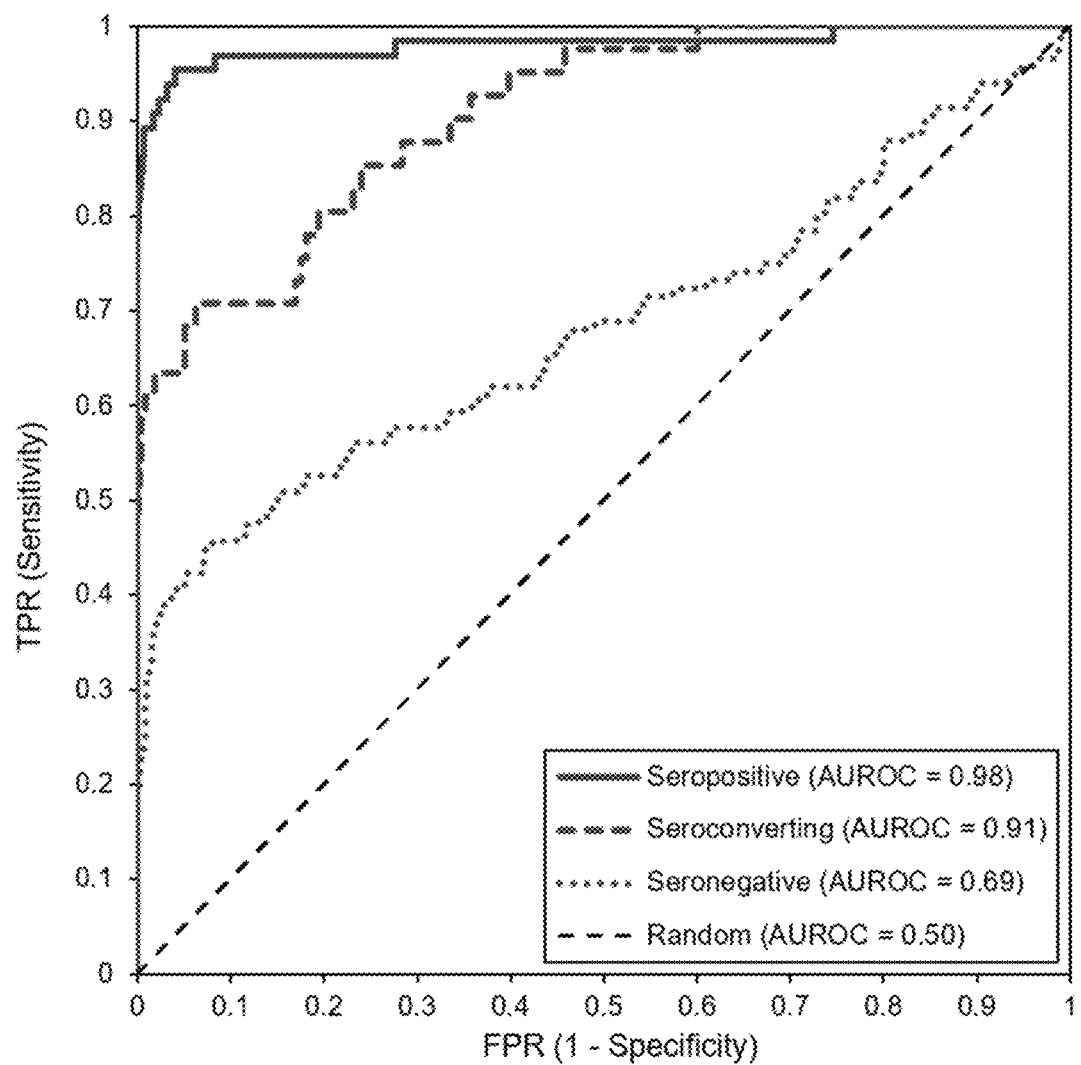
FIG. 1: Analytical performance of Lyme disease diagnostic algorithm. ROC curves for a diagnostic algorithm classifying TCR repertoires according to presence of Lyme disease, stratified by serostatus. The model was trained on 66 samples from Lyme patients seropositive at visit 1 and approximately 1,300 controls, then also assessed on 157 Lyme patients that were seronegative at visit 1 (41 later seroconverted). Results are mean results from 5-fold cross-validation.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods for Assessing TCRβ CDR3 Sequences

The present disclosure provides methods for assessing T cell receptor β chain complementary determining region 3 (TCRβ CDR3) sequences. In certain embodiments, the methods comprise assessing TCRβ CDR3 sequences determined from a sample obtained from a subject having or suspected of having a tick bite for the presence or absence of one or more TCRβ CDR3 sequences set forth in SEQ ID Nos:1-1977 herein. The inventors have determined that TCRs comprising such TCRβ CDR3 sequences are associated with Lyme disease by being statistically more prevalent in individuals having Lyme disease than those who do not have Lyme disease. Accordingly, the methods of the present disclosure find use, for example, in predicting the presence or absence of present or previous *Borrelia burgdorferi* infection in a subject having or suspected of having a tick bite. According to some embodiments, the methods find use in predicting seroconversion of a subject having or suspected of having a tick bite, where "seroconversion" as used herein refers to conversion from being negative for anti-*B. burgdorferi* antibodies to being positive for anti-*B. burgdorferi* antibodies, e.g., as determined by standard two-tiered testing (STTT), modified two-tiered testing (MTTT), or the like. In certain embodiments, the methods find use in diagnosing a subject having or suspected of having a tick bite as having Lyme disease. Such a diagnosis may be a differential diagnosis in which a subject who has one or more non-specific symptoms consistent with Lyme disease is diagnosed as having Lyme disease and not another condition characterized by symptoms which overlap with those of Lyme disease, including but not limited to, multiple sclerosis (MS), chronic fatigue syndrome (CFS), mixed connective tissue disorders (MCTD), rheumatoid arthritis (RA), Lou Gehrig's disease, amyotrophic lateral sclerosis (ALS), lupus, fibromyalgia, depression, mononucleosis, sarcoidosis, endocarditis, colitis, and/or the like. Details regarding the methods of the present disclosure will now be described.

According to some embodiments, the methods of the present disclosure are computer-implemented. By "computer-implemented" is meant at least one step of the method is implemented using one or more processors and one or more non-transitory computer-readable media. For example, in certain embodiments, provided are computer-implemented methods for assessing TCRβ CDR3 sequences, the methods being implemented using one or more processors and one or more non-transitory computer-readable media comprising instructions stored thereon, which when executed by the one or more processors, cause the one or more processors to assess TCRβ CDR3 sequences determined from a sample obtained from a subject having or suspected of having a tick bite for the presence or absence of one or more TCRβ CDR3 sequences set forth in SEQ ID Nos:1-1977 herein. The computer-implemented methods of the present disclosure may further comprise one or more steps that are not computer-implemented, e.g., obtaining a sample (e.g., a blood sample) from the subject, preparing the sample for immune repertoire nucleic acid sequencing, and/or the like.

As noted above, the subject is one having or suspected of having a tick bite. Erythema migrans, the manifestation of early localized disease, appears at the site of the tick bite, 3 to 30 days (typically within 7 to 14 days) after the bite. According to some embodiments, the subject has or is suspected of having a tick bite that occurred within three weeks, within two weeks, within 12 days, within 10 days, within 9 days, within 8 days, within one week, within 6 days, within 5 days, within 4 days, or within three days prior to the assessing. As demonstrated herein, an advantage of the present methods is that they enable detection of *B. burgdorferi* infection in a subject who is seronegative for Lyme disease—that is, a subject who tests negative for anti-*B. burgdorferi* antibodies, e.g., by standard two-tiered testing (STTT), modified two-tiered testing (MTTT), or the like. As such, in certain embodiments of the methods of the present disclosure, the subject is seronegative for Lyme disease at the time of the assessing. According to some embodiments, the subject is seropositive for Lyme disease at the time of the assessing, where such methods find use, e.g., when it is desirable to corroborate a positive serology test result by assessing the sample for the presence or absence of one or more Lyme disease-associated TCRs described herein.

According to some embodiments, the subject has one or more non-specific symptoms consistent with Lyme disease at the time of the assessing. Examples of such non-specific symptoms include, but are not limited to, skin erythema, fatigue, arthralgia, and any combination thereof. As noted above, the methods of the present disclosure find use, e.g., in providing a differential diagnosis based on the assessing in which a subject who has one or more non-specific symptoms consistent with Lyme disease is diagnosed as having Lyme disease and not another condition characterized by symptoms which overlap with those of Lyme disease, including but not limited to, multiple sclerosis (MS), chronic fatigue syndrome (CFS), mixed connective tissue disorders (MCTD), rheumatoid arthritis (RA), Lou Gehrig's disease, amyotrophic lateral sclerosis (ALS), lupus, fibromyalgia, depression, mononucleosis, sarcoidosis, endocarditis, colitis, and/or the like.

As summarized above, the methods of the present disclosure comprise assessing the TCRβ CDR3 sequences determined from the sample obtained from the subject for the presence or absence of one or more TCRβ CDR3 sequences set forth in SEQ ID Nos:1-1977 set forth herein. As noted above, in certain embodiments, the assessing step may be computer-implemented such that it is performed using one or more processors and one or more non-transitory computer-readable media comprising instructions stored thereon, which when executed by the one or more processors, cause the one or more processors to assess the determined TCRβ CDR3 sequences for the presence or absence of one or more TCRβ CDR3 sequences set forth in SEQ ID Nos:1-1977. For example, the instructions may cause the one or more processors to compare each of the determined TCRβ CDR3 sequences (e.g., each determined TCRβ CDR3 sequence or each unique determined TCRβ CDR3 sequence) stored on a computer-readable medium to a database comprising one or more TCRβ CDR3 sequences set forth in SEQ ID Nos:1-1977 stored on the same or a different computer-readable medium. According to some embodiments, the number of TCRβ CDR3 sequences determined from the sample obtained from the subject is from 1,000 to 2,000,000. For example, in certain embodiments, the number of determined TCRβ CDR3 sequences is 2,000,000 or fewer (e.g., 1,500,000 or fewer, 1,250,000 or fewer, 1,000,000 or fewer, 750,000 or fewer, or 500,000 or fewer), but 1,000 or more, 5,000 or more, 10,000 or more, 15,000 or more, 20,000 or more, 25,000 or more, 30,000 or more, 35,000 or more, 40,000 or more, 45,000 or more, 50,000 or more, 55,000 or more, 60,000 or more, 65,000 or more, 70,000 or more, 75,000 or more, 80,000 or more, 85,000 or more, 90,000 or more, 95,000 or more, or 100,000 or more. The number of TCRβ CDR3 sequences set forth in SEQ ID Nos:1-1977 to which the determined TCRβ CDR3 sequences is compared may vary. For example, the determined TCRβ CDR3 sequences may be compared to 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more, 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 950 or more, 1000 or more, 1050 or more, 1100 or more, 1150 or more, 1200 or more, 1250 or more, 1300 or more, 1350 or more, 1400 or more, 1450 or more, 1500 or more, 1550 or more, 1600 or more, 1650 or more, 1700 or more, 1750 or more, 1800 or more, 1850 or more, 1900 or more, 1950 or more, or each of the TCRβ CDR3 sequences set forth in SEQ ID Nos:1-1977. When the determined TCRβ CDR3 sequences are compared to fewer than all of the TCRβ CDR3 sequences set forth in SEQ ID Nos:1-1977, the determined TCRβ CDR3 sequences may be compared to any desired number (e.g., as set forth above) and any desired combination of TCRβ CDR3 sequences set forth in SEQ ID Nos:1-1977.

The methods of the present disclosure may include one or more additional steps based on the results of the assessing step. For example, if it is determined from the assessing step that none of the TCRβ CDR3 sequences set forth in SEQ ID Nos:1-1977 are present in the TCRβ CDR3 sequences determined from the sample obtained from the subject having or suspected of having a tick bite, then the methods may further comprise, e.g., identifying the subject as not having a *B. burgdorferi* infection, identifying the subject as not having Lyme disease, identifying the subject as one who should not be administered a Lyme disease therapy (e.g., an antibiotic-based Lyme disease therapy such as doxycycline administration), and/or the like. Also by way of example, if it is determined from the assessing step that one or more (e.g., 2 or more, 3 or more, 4 or more, 5 or more, or 10 or more) of the TCRβ CDR3 sequences set forth in SEQ ID Nos:1-1977 are present in the TCRβ CDR3 sequences determined from the sample obtained from the subject having or suspected of having a tick bite, then the methods may further comprise, e.g., identifying the subject as having a present or previous *B. burgdorferi* infection, identifying the subject as having Lyme disease, identifying the subject as one who should be administered a Lyme disease therapy, and/or administering a Lyme disease therapy to the subject, e.g., administering to the subject one or more of any of the Lyme disease therapies described elsewhere herein.

In certain embodiments, the methods further comprise subjecting the results of the assessing step to further analysis, such as subjecting the results of the assessing step to a model. For example, the methods may further comprise subjecting the results of the assessing step to a model in order to classify the subject as having a present or previous *B. burgdorferi* infection or not having a present or previous *B. burgdorferi* infection; and/or to classify the subject as having Lyme disease or not having Lyme disease. One of ordinary skill in the art will appreciate that, with the benefit of the TCRβ CDR3 sequences set forth in SEQ ID Nos:1-1977 described herein, a variety of useful models may be applied to the results of the assessment. In one non-limiting example, the methods may further comprise subjecting the results of the assessing step to a two feature logistic regression with features representing the number of Lyme disease-associated TCRβ CDR3 sequences determined from the sample and the total number of unique TCRβ CDR3 sequences determined from the sample. As demonstrated in the Experimental section below, such a model exhibits high specificity for Lyme disease patients and greater sensitivity at diagnosing Lyme disease than STTT.

In certain embodiments, when the methods further comprise subjecting the results of the assessing step to a model for classification purposes (e.g., as described above), the model may take into account the number of unique Lyme disease-associated TCRβ CDR3 sequences that are present in the TCRβ CDR3 sequences determined from the sample, e.g., where the greater the number of unique Lyme disease-associated TCRβ CDR3 sequences, the more likely the model is to classify the subject as having a present or previous *B. burgdorferi* infection and/or having Lyme disease. According to some embodiments, the number of unique Lyme disease-associated TCRβ CDR3 sequences is not a feature utilized by the model to classify the subject. In certain embodiments, the presence and/or frequency of one or more particular unique Lyme disease-associated TCRβ CDR3 sequences is a feature(s) used by the model to classify the subject. For example, the presence and/or frequency of one or more particular unique Lyme disease-associated TCRβ CDR3 sequences may be given relatively greater weight when classifying the subject as compared to the presence and/or frequency of one or more other unique Lyme disease-associated TCRβ CDR3 sequences.

According to some embodiments, when a classification model weighs particular unique Lyme disease-associated TCRβ CDR3 sequences differently than other unique Lyme disease-associated TCRβ CDR3 sequences, the model may use convergent recombination to weigh the sequences differently. Different T cells can show convergent recombination where unique DNA sequences were formed in the recombination for a first T cell, a second T cell, a third T cell, etc., but where each leads to the same protein (CDR3+V-gene+J-gene) which is diagnostic for high likelihood of Lyme disease. This convergent recombination may be more likely for certain Lyme disease-associated TCRβ CDR3 sequences than others, and the model may take into account these aspects of the signal reflective of the interpretable biology of immune response. Accordingly, in some embodiments, sequences may be given differential weight based on convergent recombination.

In certain embodiments, prior to the assessing step, the methods may further include one or more steps for determining the TCRβ CDR3 sequences from the sample obtained from the subject having or suspected of having a tick bite. For example, the determining may include immunosequencing and evaluation of the T cell repertoire in the biological sample obtained from the subject, e.g., by high-throughput sequencing (HTS) as described elsewhere herein. The determining may be partially implemented using a computer. For example, the analysis of the raw sequencing data may be implemented by a computer. Extraction of DNA or RNA from the biological sample, amplification, and sequencing may be performed manually, using a machine, or a combination thereof. In certain embodiments, the methods may further comprise an initial step of obtaining the biological sample from the subject.

The biological sample (e.g., tissue or blood) may be obtained from a variety of subjects. Such subjects may be "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, non-human primates such as chimpanzees, and monkeys). In some embodiments, the subject is a human subject.

Biological samples of interest include those that comprise T cells, including but not limited to, whole blood samples, a fraction of whole blood comprising peripheral blood mononuclear cells (e.g., blood plasma), serum, a peripheral blood mononuclear cell (PBMC) sample, urine, buffy coat, synovial fluid, bone marrow, cerebrospinal fluid, saliva, lymph fluid, seminal fluid, vaginal secretions, urethral secretions, exudate, transdermal exudates, pharyngeal exudates, nasal secretions, sputum, sweat, bronchoalveolar lavage, tracheal aspirations, fluid from joints, or vitreous fluid. T cells can also be obtained from biological samples which may be derived from, for example, solid tissue samples. T-cells may be helper T cells (effector T cells or Th cells), cytotoxic T cells (CTLs), memory T cells, and regulatory T cells. In some embodiments, peripheral blood mononuclear cells (PBMC) are isolated by techniques known to those of skill in the art, e.g., by Ficoll-Hypaque® density gradient separation.

Nucleic acid, such as, genomic DNA or RNA may be extracted from lymphoid cells by methods known to those of skill in the art. Examples include using the QIAamp® DNA blood Mini Kit or a Qiagen DNeasy® Blood extraction kit (both commercially available from Qiagen, Gaithersburg, Md., USA) to extract genomic DNA. In some embodiments, 100,000 to 200,000 cells may be used for analysis of diversity, i.e., about 0.6 to 1.2 µg DNA from diploid T cells. Using PBMCs as a source, the number of T cells can be estimated to be about 30% of total cells. Alternatively, total nucleic acid can be isolated from cells, including both genomic DNA and mRNA. In other embodiments, cDNA is transcribed from mRNA and then used as templates for amplification. The RNA molecules can be transcribed to cDNA using known reverse-transcription kits, such as the SMARTer™ Ultra Low RNA kit for Illumina sequencing (Clontech, Mountain View, Calif.) essentially according to the supplier's instructions.

Immune Repertoire Sequencing (Multiplex PCR and High Throughput Sequencing)

According to some embodiments, TCRβ CDR3 sequences are determined from the sample obtained from the subject having or suspected of having a tick bite by immune cell receptor sequencing, e.g., immune repertoire sequencing.

By "T cell receptor" or "TCR" is meant a disulfide-linked membrane bound heterodimeric protein normally consisting of the highly variable α and β chains expressed as part of a complex with the invariant CD3 chain molecules. T cells expressing these two chains are referred to as α:β (or αβ) T cells, though a minority of T cells express an alternate receptor, formed by variable γ and σ chains, referred as γσ T cells. TCR development occurs through a lymphocyte specific process of gene recombination, which assembles a final sequence from a large number of potential segments. This genetic recombination of TCR gene segments in somatic T cells occurs during the early stages of development in the thymus. The TCRα gene locus contains variable (V) and joining (J) gene segments (Vα and Jα), whereas the TCRβ locus contains a D gene segment in addition to Vβ and Jβ segments. Accordingly, the a chain is generated from VJ recombination and the p chain is involved in VDJ recombination. This is similar for the development of γδ TCRs, in which the TCRγ chain is involved in VJ recombination and the TCRδ gene is generated from VDJ recombination. The TCR α chain gene locus consists of 46 variable segments, 8 joining segments and the constant region. The TCR β chain gene locus consists of 48 variable segments followed by two diversity segments, 12 joining segments and two constant regions. The D and J segments are located within a relatively short 50 kb region while the variable genes are spread over a large region of 1.5 mega bases (TCRα) or 0.67 mega bases (TCRβ).

TCRβ CDR3 sequence determination may involve quantitative detection of sequences of substantially all possible TCR gene rearrangements that can be present in a sample containing lymphoid cell DNA.

Amplified nucleic acid molecules comprising rearranged TCR regions obtained from a biological sample are sequenced using high-throughput sequencing. In one embodiment, a multiplex PCR system is used to amplify rearranged TCR loci from genomic DNA as described in U.S. Pub. No. 2010/0330571, filed on Jun. 4, 2010, U.S. Pub. No. 2012/0058902, filed on Aug. 24, 2011, International App. No. PCT/US2013/062925, filed on Oct. 1, 2013, which is each incorporated by reference in its entirety.

To that end, multiplex PCR is performed using a set of forward primers that specifically hybridize to V segments and a set of reverse primers that specifically hybridize to the J segments of a TCR locus, where a multiplex PCR reaction using the primers allows amplification of all the possible VJ (and VDJ) combinations within a given population of T cells.

Exemplary V segment primers and J segment primers are described in US2012/0058902, US2010/033057, WO2010/151416, WO2011/106738, US2015/0299785, WO2012/027503, US2013/0288237, U.S. Pat. Nos. 9,181,590, 9,181,591, US2013/0253842, WO2013/188831, which are each herein incorporated by reference in their entireties.

A multiplex PCR system can be used to amplify rearranged immune cell receptor loci. In certain embodiments, the CDR3 region is amplified from a TCRB CDR3 region locus. A plurality of V-segment and J-segment primers are used to amplify substantially all (e.g., greater than 90%, 91%, 92%, 93%, 94%, 95%, 96%, 97%, 98% or 99%) rearranged immune cell receptor CDR3-encoding regions to produce a multiplicity of amplified rearranged DNA molecules. In certain embodiments, primers are designed so that each amplified rearranged DNA molecule is less than 600 nucleotides in length, thereby excluding amplification products from non-rearranged immune cell receptor loci.

In some embodiments, two pools of primers are used in a single, highly multiplexed PCR reaction. The "forward" pool of primers can include a plurality of V segment oligonucleotide primers and the reverse pool can include a plurality of J segment oligonucleotide primers. In some embodiments, there is a primer that is specific to (e.g., having a nucleotide sequence complementary to a unique sequence region of) each V region segment and to each J region segment in the respective TCR or Ig gene locus. In other embodiments, a primer can hybridize to one or more V segments or J segments, thereby reducing the number of primers required in the multiplex PCR. In certain embodiments, the J-segment primers anneal to a conserved sequence in the joining ("J") segment.

Each primer can be designed such that a respective amplified DNA segment is obtained that includes a sequence portion of sufficient length to identify each J segment unambiguously based on sequence differences amongst known J-region encoding gene segments in the human genome database, and also to include a sequence portion to which a J-segment-specific primer can anneal for resequencing. This design of V- and J-segment-specific primers enables direct observation of a large fraction of the somatic rearrangements present in the immune cell receptor gene repertoire within the subject.

A multiplex PCR system can use at least 2, 3, 4, 5, 6, 7, 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments at least 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to (i.e., is complementary to) a sequence corresponding to a V region segment. The multiplex PCR system also uses at least 2, 3, 4, 5, 6, or 7, and in certain embodiments, at least 8, 9, 10, 11, 12 or 13 reverse primers, or at least 14, 15, 16, 17, 18, 19, 20, 21, 22, 23, 24, or 25 or more reverse primers, in which each reverse primer specifically hybridizes to or is complementary to a sequence corresponding to a J region segment. Various combinations of V and J segment primers can be used to amplify the full diversity of TCR sequences in the immune cell receptor gene repertoire within the subject.

Further details on multiplex PCR system, including primer oligonucleotide sequences for amplifying TCR sequences are described in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 Sci. Translat. Med. 3:90ra61; US2012/0058902, US2010/033057, WO/2010/151416, WO/2011/106738, US 2015/0299785, WO2012/027503, US2013/0288237, U.S. Pat. Nos. 9,181,590, 9,181,591, US2013/0253842, WO2013/188831, which is each incorporated herein by reference in its entirety.

Oligonucleotides or polynucleotides that are capable of specifically hybridizing or annealing to a target nucleic acid sequence by nucleotide base complementarity can do so under moderate to high stringency conditions. In one embodiment, suitable moderate to high stringency conditions for specific PCR amplification of a target nucleic acid sequence can be between 25 and 80 PCR cycles, with each cycle including a denaturation step (e.g., about 10-30 seconds (s) at greater than about 95° C.), an annealing step (e.g., about 10-30 s at about 60-68° C.), and an extension step (e.g., about 10-60 s at about 60-72° C.), optionally according to certain embodiments with the annealing and extension steps being combined to provide a two-step PCR. As would be recognized by the skilled person, other PCR reagents can be added or changed in the PCR reaction to increase specificity of primer annealing and amplification, such as altering the magnesium concentration, optionally adding DMSO, and/or the use of blocked primers, modified nucleotides, peptide-nucleic acids, and the like.

A primer may be a single-stranded DNA. The appropriate length of a primer depends on the intended use of the primer but typically ranges from 6 to 50 nucleotides, or in certain embodiments, from 15-35 nucleotides in length. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

V- and J-segment primers are used to produce a plurality of amplicons from the multiplex PCR reaction. In certain embodiments, the amplicons range in size from 10, 20, 30, 40, 50, 75, 100, 200, 300, 400, 500, 600, 700, 800 or more nucleotides in length. In certain embodiments, the amplicons have a size between 20-600, 50-600, 20-400, or 50-400 nucleotides in length.

According to non-limiting theory, these embodiments exploit current understanding in the art (also described above) that once a T lymphocyte has rearranged its TCR-encoding genes, its progeny cells possess the same immune cell receptor-encoding gene rearrangement, thus giving rise to a clonal population (clones) that can be uniquely identified by the presence therein of rearranged (e.g., CDR3-encoding) V- and J-gene segments that can be amplified by a specific pairwise combination of V- and J-specific oligonucleotide primers as herein disclosed.

The V segment primers and J segment primers will preferably each include a second sequence at the 5'-end of the primer that is not complementary to the target V or J segment. The second sequence can comprise an oligonucleotide having a sequence that is selected from (i) a universal adaptor oligonucleotide sequence, and (ii) a sequencing platform-specific oligonucleotide sequence that is linked to and positioned 5' to a first universal adaptor oligonucleotide sequence. Examples of universal adaptor oligonucleotide sequences can be pGEX forward and pGEX reverse adaptor sequences.

The resulting amplicons using the V-segment and J-segment primers described above include amplified V and J segments and the universal adaptor oligonucleotide sequences. The universal adaptor sequence can be complementary to an oligonucleotide sequence found in a tailing primer. Tailing primers can be used in a second PCR reaction to generate a second set of amplicons. In some embodiments, tailing primers can have the general formula (I):

$$5'\text{-P-S-B-U-3'} \qquad (I),$$

where P comprises a sequencing platform-specific oligonucleotide, where S comprises a sequencing platform tag-containing oligonucleotide sequence; where B comprises an oligonucleotide barcode sequence and where the oligonucleotide barcode sequence can be used to identify a sample source, and where U comprises a sequence that is complementary to the universal adaptor oligonucleotide sequence or is the same as the universal adaptor oligonucleotide sequence.

Additional description about universal adaptor oligonucleotide sequences, barcodes, and tailing primers are found in WO2013/188831, which is incorporated by reference in its entirety.

Sequencing may be performed using any of a variety of available high throughput single molecule sequencing machines and systems. Illustrative sequence systems include sequence-by-synthesis systems, such as the Illumina Genome Analyzer and associated instruments (Illumina HiSeq) (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), a MinION™, GridIONx5™, PromethION™, or SmidgION™ nanopore-based sequencing system, available from Oxford Nanopore Technologies, or other systems having similar capabilities.

In certain embodiments, sequencing is achieved using a set of sequencing platform-specific oligonucleotides that hybridize to a defined region within the amplified DNA molecules. The sequencing platform-specific oligonucleotides are designed to sequence amplicons, such that the V- and J-encoding gene segments can be uniquely identified by the sequences that are generated. See, e.g., US2012/0058902; US2010/033057; WO2011/106738; US2015/0299785; or WO2012/027503, which is each incorporated by reference in its entirety.

In some embodiments, the raw sequence data is preprocessed to remove errors in the primary sequence of each read and to compress the data. A nearest neighbor algorithm can be used to collapse the data into unique sequences by merging closely related sequences, to remove both PCR and sequencing errors. See, e.g., US2012/0058902; US2010/033057; WO2011/106738; US2015/0299785; or WO2012/027503, which is each incorporated by reference in its entirety.

Sequencing the multiplicity of amplified rearranged TCRβ CDR3-encoding region DNA molecules by high-throughput sequencing (HTS) can be used to produce a TCR clonotype profile comprising at least 10,000 TCR clonotype sequences of 20 to 400 nucleotides in length.

Amplification Bias Control

Multiplex PCR assays can result in a bias in the total numbers of amplicons produced from a sample, given that certain primer sets may be more efficient in amplification than others. To overcome the problem of such biased utilization of subpopulations of amplification primers, methods can be used that provide a template composition for standardizing the amplification efficiencies of the members of an oligonucleotide primer set, where the primer set is capable of amplifying rearranged DNA encoding a plurality of TCRs in a biological sample that comprises DNA from lymphoid cells.

To that end, a template composition is used to standardize the various amplification efficiencies of the primer sets. The template composition can comprise a plurality of diverse template oligonucleotides of general formula (II):

$$5'\text{-U1-B1-V-B2-R-J-B3-U2-3'} \quad \text{(II)}$$

The constituent template oligonucleotides are diverse with respect to the nucleotide sequences of the individual template oligonucleotides. The individual template oligonucleotides can vary in nucleotide sequence considerably from one another as a function of significant sequence variability among the large number of possible TCR variable (V) and joining (J) region polynucleotides. Sequences of individual template oligonucleotide species can also vary from one another as a function of sequence differences in U1, U2, B (B1, B2 and B3) and R oligonucleotides that are included in a particular template within the diverse plurality of templates.

V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of template oligonucleotide sequences V comprises a unique oligonucleotide sequence.

J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of template oligonucleotide sequences J comprises a unique oligonucleotide sequence.

U1 and U2 can be each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence.

B1, B2 and B3 can be each either nothing or each comprise an oligonucleotide B that comprises a first and a second oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 contiguous nucleotides (including all integer values therebetween), wherein in each of the plurality of template oligonucleotide sequences B comprises a unique oligonucleotide sequence in which (i) the first barcode sequence uniquely identifies the unique V oligonucleotide sequence of the template oligonucleotide and (ii) the second barcode sequence uniquely identifies the unique J oligonucleotide sequence of the template oligonucleotide.

R can be either nothing or comprises a restriction enzyme recognition site that comprises an oligonucleotide sequence that is absent from V, J, U1, U2, B1, B2 and B3.

Methods are used with the template composition for determining non-uniform nucleic acid amplification potential among members of a set of oligonucleotide amplification primers that are capable of amplifying productively rearranged DNA encoding one or a plurality of TCRs in a biological sample that comprises DNA from lymphoid cells of a subject. The method can include the steps of: (a) amplifying DNA of a template composition for standardizing amplification efficiency of an oligonucleotide primer set in a multiplex polymerase chain reaction (PCR) that comprises: (i) the template composition (II) described above, wherein each template oligonucleotide in the plurality of template oligonucleotides is present in a substantially equimolar amount, (ii) an oligonucleotide amplification primer set that is capable of amplifying productively rearranged DNA encoding one or a plurality of TCRs in a biological sample that comprises DNA from lymphoid cells of a subject.

The primer set can include: (1) in substantially equimolar amounts, a plurality of V-segment oligonucleotide primers that are each independently capable of specifically hybridizing to at least one polynucleotide encoding a TCR V-region polypeptide or to the complement thereof, wherein each V-segment primer comprises a nucleotide sequence of at least 15 contiguous nucleotides that is complementary to at least one functional TCR V region-encoding gene segment and wherein the plurality of V-segment primers specifically hybridize to substantially all functional TCR V region-encoding gene segments that are present in the template composition, and (2) in substantially equimolar amounts, a plurality of J-segment oligonucleotide primers that are each independently capable of specifically hybridizing to at least one polynucleotide encoding a TCR J-region polypeptide or to the complement thereof, wherein each J-segment primer comprises a nucleotide sequence of at least 15 contiguous nucleotides that is complementary to at least one functional TCR J region-encoding gene segment and wherein the plurality of J-segment primers specifically hybridize to substantially all functional TCR J region-encoding gene segments that are present in the template composition.

The V-segment and J-segment oligonucleotide primers are capable of promoting amplification in said multiplex polymerase chain reaction (PCR) of substantially all template oligonucleotides in the template composition to produce a multiplicity of amplified template DNA molecules, said multiplicity of amplified template DNA molecules being sufficient to quantify diversity of the template oligonucleotides in the template composition, and wherein each amplified template DNA molecule in the multiplicity of amplified template DNA molecules is less than 1000, 900, 800, 700, 600, 500, 400, 300, 200, 100, 90, 80 or 70 nucleotides in length.

Methods for determining non-uniform nucleic acid amplification potential may further include: (b) sequencing all or a sufficient portion of each of said multiplicity of amplified template DNA molecules to determine, for each unique template DNA molecule in said multiplicity of amplified template DNA molecules, (i) a template-specific oligonucleotide DNA sequence and (ii) a relative frequency of occurrence of the template oligonucleotide; and (c) comparing the relative frequency of occurrence for each unique template DNA sequence from said template composition, wherein a non-uniform frequency of occurrence for one or more template DNA sequences indicates non-uniform nucleic acid amplification potential among members of the set of oligonucleotide amplification primers.

Further details concerning the aforementioned bias control methods are provided in US2013/0253842, U.S. Pat. No. 9,150,905, US2015/0203897, and WO2013/169957, which are incorporated by reference in their entireties.

PCR Template Abundance Estimation

To estimate the average read coverage per input template in the multiplex PCR and sequencing approach, a set of synthetic TCR templates (as described above) can be used, comprising each combination of V.beta. and J.beta. gene segments. These synthetic molecules can be those described in general formula (II) above, and in US2013/0253842, U.S. Pat. No. 9,150,905, US2015/0203897, and WO2013/169957, which are incorporated by reference in their entireties.

These synthetic molecules can be included in each PCR reaction at very low concentration so that only some of the synthetic templates are observed. Using the known concentration of the synthetic template pool, the relationship between the number of observed unique synthetic molecules and the total number of synthetic molecules added to reaction can be simulated (this is very nearly one-to-one at the low concentrations that were used). The synthetic molecules allow calculation for each PCR reaction the mean number of sequencing reads obtained per molecule of PCR template, and an estimation of the number of T cells or B cells in the input material bearing each unique TCR rearrangement or Ig rearrangement, respectively.

TABLE 1

Lyme Disease-Associated TCRs

| TCRβ CDR3 Amino Acid Sequence | SEQ ID NO: | V Gene Segment | J Gene Segment |
|---|---|---|---|
| CASSPDRASTDTQYF | 1 | TCRBV05-04 | TCRBJ02-03 |
| CSARLSGSGTGELFF | 2 | TCRBV20-X | TCRBJ02-02 |
| CSARQAGGGTGELFF | 3 | TCRBV20-X | TCRBJ02-02 |
| CASSDTGGVETQYF | 4 | TCRBV07 | TCRBJ02-05 |
| CASRRGNDNSPLHF | 5 | TCRBV27-01 | TCRBJ01-06 |
| CASSYLLLSYEQYF | 6 | TCRBV06 | TCRBJ02-07 |
| CASSLEPAGNQPQHF | 7 | TCRBV28-01 | TCRBJ01-05 |
| CASSALRSGNTIYF | 8 | TCRBV09-01 | TCRBJ01-03 |
| CASSQVRTGGLNEQFF | 9 | TCRBV04-01 | TCRBJ02-01 |
| CASSPSREGKNEQFF | 10 | TCRBV18-01 | TCRBJ02-01 |
| CASSPNRDKNTEAFF | 11 | TCRBV18-01 | TCRBJ01-01 |
| CASSQVLAGVRRNEQFF | 12 | TCRBV04-01 | TCRBJ02-01 |
| CASSQDTASNQPQHF | 13 | TCRBV04-01 | TCRBJ01-05 |
| CSARTPGANIQYF | 14 | TCRBV20-X | TCRBJ02-04 |
| CSARVAGSGTGELFF | 15 | TCRBV20-X | TCRBJ02-02 |
| CSARMSGGGTGELFF | 16 | TCRBV20-X | TCRBJ02-02 |
| CASSPSGRTAYEQYF | 17 | TCRBV18-01 | TCRBJ02-07 |
| CASSVDRGRGEQYF | 18 | TCRBV06 | TCRBJ02-07 |
| CASSLHRNTGELFF | 19 | TCRBV12-X | TCRBJ02-02 |
| CSARFSGSGTGELFF | 20 | TCRBV20-X | TCRBJ02-02 |
| CASSLATDGRNEQFF | 21 | TCRBV05-04 | TCRBJ02-01 |
| CASSFEWNYNSPLHF | 22 | TCRBV12-X | TCRBJ01-06 |
| CASSPAAGNTGELFF | 23 | TCRBV11 | TCRBJ02-02 |
| CSASRDIYYEQYF | 24 | TCRBV20-X | TCRBJ02-07 |
| CASSRSEGGSYEQYF | 25 | TCRBV06 | TCRBJ02-07 |
| CSVGPTGTGEKLFF | 26 | TCRBV29-01 | TCRBJ01-04 |
| CASSLDSNSGANVLTF | 27 | TCRBV05-06 | TCRBJ02-06 |
| CASSPTREANEQFF | 28 | TCRBV07 | TCRBJ02-01 |
| CSARGSGRASDTQYF | 29 | TCRBV20-X | TCRBJ02-03 |
| CASSPRLAADNEQFF | 30 | TCRBV07 | TCRBJ02-01 |
| CASSHPGAGGNNEQFF | 31 | TCRBV03-01/03-02 | TCRBJ02-01 |
| CSARATESSYEQYF | 32 | TCRBV20-X | TCRBJ02-07 |
| CASSTPGHYEQYF | 33 | TCRBV07 | TCRBJ02-07 |
| CSARYGGSGTGELFF | 34 | TCRBV20-X | TCRBJ02-02 |
| CASRGTSGSQETQYF | 35 | TCRBV19-01 | TCRBJ02-05 |
| CASSLAGDIDTQYF | 36 | TCRBV28-01 | TCRBJ02-03 |
| CASSYYNEQFF | 37 | TCRBV07 | TCRBJ02-01 |
| CSARDRGGVPNYGYTF | 38 | TCRBV20-X | TCRBJ01-02 |
| CASSTSVLNEQFF | 39 | TCRBV19-01 | TCRBJ02-01 |
| CASSLDGTIEAFF | 40 | TCRBV05-01 | TCRBJ01-01 |
| CASSLDQGANYGYTF | 41 | TCRBV05-01 | TCRBJ01-02 |
| CASSRSGAYEQYF | 42 | TCRBV28-01 | TCRBJ02-07 |
| CASSFLTSTDTQYF | 43 | TCRBV06 | TCRBJ02-03 |
| CASTDEGSGANVLTF | 44 | TCRBV06 | TCRBJ02-06 |
| CASSQYRAQPQHF | 45 | TCRBV03-01/03-02 | TCRBJ01-05 |
| CASRPDLAGGYNEQFF | 46 | TCRBV02-01 | TCRBJ02-01 |
| CASSTGQGRDNEQFF | 47 | TCRBV06 | TCRBJ02-01 |
| CASNRQGGNTEAFF | 48 | TCRBV10-02 | TCRBJ01-01 |
| CASGQTGVNEKLFF | 49 | TCRBV05-01 | TCRBJ01-04 |
| CASSQRGAGRTNEKLFF | 50 | TCRBV03-01/03-02 | TCRBJ01-04 |
| CASRLQGANEQYF | 51 | TCRBV05-06 | TCRBJ02-07 |
| CSARTSGAGTGELFF | 52 | TCRBV20-X | TCRBJ02-02 |
| CASSYSAPGNNQPQHF | 53 | TCRBV06 | TCRBJ01-05 |
| CASSLTYSNQPQHF | 54 | TCRBV05-08 | TCRBJ01-05 |
| CASSLVSGDRKTQYF | 55 | TCRBV07 | TCRBJ02-05 |
| CSVYTSDTQYF | 56 | TCRBV29-01 | TCRBJ02-03 |
| CASSLGGPPSGQYF | 57 | TCRBV11 | TCRBJ02-03 |
| CASSHAGFNEKLFF | 58 | TCRBV04-01 | TCRBJ01-04 |
| CASSFDSRGNTEAFF | 59 | TCRBV12-X | TCRBJ01-01 |
| CSAPTSGGAWGEQFF | 60 | TCRBV20-X | TCRBJ02-01 |
| CSARVSGAGTGELFF | 61 | TCRBV20-X | TCRBJ02-02 |
| CASSADRVLSYEQYF | 62 | TCRBV02-01 | TCRBJ02-07 |
| CASSGGGTTDTQYF | 63 | TCRBV06 | TCRBJ02-03 |
| CASSFEPNYNSPLHF | 64 | TCRBV12-X | TCRBJ01-06 |
| CSAREITGAEAFF | 65 | TCRBV20-X | TCRBJ01-01 |
| CASSVDGGDEQFF | 66 | TCRBV09-01 | TCRBJ02-01 |
| CSARDRGRGHNQPQHF | 67 | TCRBV20-X | TCRBJ01-05 |
| CASSYGGPYNEQFF | 68 | TCRBV28-01 | TCRBJ02-01 |
| CATAGQISNQPQHF | 69 | TCRBV19-01 | TCRBJ01-05 |
| CASSPKGRGGQPQHF | 70 | TCRBV06 | TCRBJ01-05 |
| CASSELVGGRSYNEQFF | 71 | TCRBV25-01 | TCRBJ02-01 |
| CASSLRRLADTDTQYF | 72 | TCRBV12-X | TCRBJ02-03 |
| CASSLGSGARGEQYF | 73 | TCRBV07 | TCRBJ02-07 |
| CASSPVPEKLFF | 74 | TCRBV18-01 | TCRBJ01-04 |
| CASQSGTGDEKLFF | 75 | TCRBV06 | TCRBJ01-04 |
| CSARATTGGGNQPQHF | 76 | TCRBV20-X | TCRBJ01-05 |
| CASSVAAGVGYNEQFF | 77 | TCRBV09-01 | TCRBJ02-01 |
| CSARASGSGTGELFF | 78 | TCRBV20-X | TCRBJ02-02 |
| CASSPYREGEKLFF | 79 | TCRBV18-01 | TCRBJ01-04 |
| CSARVTLATDTQYF | 80 | TCRBV20-X | TCRBJ02-03 |
| CASSAAGQGYGYTF | 81 | TCRBV11 | TCRBJ01-02 |
| CASSPHDRYYGYTF | 82 | TCRBV28-01 | TCRBJ01-02 |
| CSAVTGGVNEQFF | 83 | TCRBV20-X | TCRBJ02-01 |
| CSAPTPGTTYNEQFF | 84 | TCRBV20-X | TCRBJ02-01 |
| CASSLEAGAWGEQFF | 85 | TCRBV07 | TCRBJ02-01 |
| CASRASGGGLQETQYF | 86 | TCRBV02-01 | TCRBJ02-05 |
| CASSYRRGSSYNEQFF | 87 | TCRBV06 | TCRBJ02-01 |
| CASRRGGRGNEKLFF | 88 | TCRBV06 | TCRBJ01-04 |
| CASSFSAGEAGELFF | 89 | TCRBV12-X | TCRBJ02-02 |
| CASRSHPNEQFF | 90 | TCRBV19-01 | TCRBJ02-01 |
| CASSLAGATRETQYF | 91 | TCRBV07 | TCRBJ02-05 |
| CSAPPSGGNQPQHF | 92 | TCRBV20-X | TCRBJ01-05 |
| CASSQDYGGPNEQFF | 93 | TCRBV03-01/03-02 | TCRBJ02-01 |
| CASSLGGANYGYTF | 94 | TCRBV16-01 | TCRBJ01-02 |
| CASTRKAGELFF | 95 | TCRBV03-01/03-02 | TCRBJ02-02 |
| CASSKGLPTYNEQFF | 96 | TCRBV19-01 | TCRBJ02-01 |
| CASSEGTGRTEAFF | 97 | TCRBV28-01 | TCRBJ01-01 |
| CASRTPGPTDTQYF | 98 | TCRBV19-01 | TCRBJ02-03 |
| CACRTVQETQYF | 99 | TCRBV30-01 | TCRBJ02-05 |
| CASSELGTRGNEQFF | 100 | TCRBV06 | TCRBJ02-01 |
| CASSFAPANTEAFF | 101 | TCRBV05-01 | TCRBJ01-01 |
| CASSAMGAETQYF | 102 | TCRBV09-01 | TCRBJ02-05 |
| CASGLVQVANEKLFF | 103 | TCRBV12-05 | TCRBJ01-04 |
| CASSLOPPYGYTF | 104 | TCRBV05-01 | TCRBJ01-02 |
| CASRSHTDTQYF | 105 | TCRBV05-01 | TCRBJ02-03 |
| CSAPTAPYNEQFF | 106 | TCRBV20-X | TCRBJ02-01 |
| CASSRTQGIEEKLFF | 107 | TCRBV07 | TCRBJ01-04 |
| CASSPPRGVNTEAFF | 108 | TCRBV09-01 | TCRBJ01-01 |
| CSAPLAGGRLETQYF | 109 | TCRBV20-X | TCRBJ02-05 |
| CASSGLVSETQYF | 110 | TCRBV09-01 | TCRBJ02-05 |
| CASSLWGKGETQYF | 111 | TCRBV05-04 | TCRBJ02-05 |
| CASSAWVGEKLFF | 112 | TCRBV27-01 | TCRBJ01-04 |
| CSALLAPYNEQFF | 113 | TCRBV20-X | TCRBJ02-01 |
| CASTPEVGTEAFF | 114 | TCRBV07 | TCRBJ01-01 |
| CASSLAAGTTLNTGELFF | 115 | TCRBV07 | TCRBJ02-02 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASSPPRGVGGSPLHF | 116 | TCRBV18-01 | TCRBJ01-06 |
| CAWSRRGLSNQPQHF | 117 | TCRBV30-01 | TCRBJ01-05 |
| CASSLREDSYNEQFF | 118 | TCRBV11 | TCRBJ02-01 |
| CASSQEVSGGGYEQYF | 119 | TCRBV04-03 | TCRBJ02-07 |
| CASSLAPLADEQYF | 120 | TCRBV07 | TCRBJ02-07 |
| CASSPSGHIYEQYF | 121 | TCRBV05-01 | TCRBJ02-07 |
| CATSRGTRRTDTQYF | 122 | TCRBV24-01 | TCRBJ02-03 |
| CASSEASGRATDTQYF | 123 | TCRBV09-01 | TCRBJ01-05 |
| CASSRGLAGVVEQYF | 124 | TCRBV19-01 | TCRBJ02-07 |
| CASRIRDRGEAFF | 125 | TCRBV05-06 | TCRBJ01-01 |
| CAWIRKSSYNEQFF | 126 | TCRBV30-01 | TCRBJ02-01 |
| CASKTSGVTDTQYF | 127 | TCRBV28-01 | TCRBJ02-03 |
| CASSVEGDPRGEQFF | 128 | TCRBV09-01 | TCRBJ02-01 |
| CSATGTSGGASEQYF | 129 | TCRBV20-X | TCRBJ02-07 |
| CASSLPSGGANTGELFF | 130 | TCRBV27-01 | TCRBJ02-02 |
| CASSLMIGVQETQYF | 131 | TCRBV07 | TCRBJ02-05 |
| CASSFSQGGTGELFF | 132 | TCRBV11 | TCRBJ02-02 |
| CASSLSSRGRGYGYTF | 133 | TCRBV11 | TCRBJ01-02 |
| CASSWQLNQPQHF | 134 | TCRBV07 | TCRBJ01-05 |
| CASSRQGKYEQYF | 135 | TCRBV27-01 | TCRBJ02-07 |
| CAWNSGTQYF | 136 | TCRBV30-01 | TCRBJ02-03 |
| CASSQDPSGQPQETQYF | 137 | TCRBV04-01 | TCRBJ02-05 |
| CASSVDPGEEKLFF | 138 | TCRBV09-01 | TCRBJ01-04 |
| CASSLGTRRTEAFF | 139 | TCRBV11 | TCRBJ01-01 |
| CASQTGTGNEKLFF | 140 | TCRBV06 | TCRBJ01-04 |
| CASSYMHLSYEQYF | 141 | TCRBV06 | TCRBJ02-07 |
| CASSARALDTQYF | 142 | TCRBV12-03/12-04 | TCRBJ02-03 |
| CASSPETLQETQYF | 143 | TCRBV18-01 | TCRBJ02-05 |
| CSARSSGRISDTQYF | 144 | TCRBV20-X | TCRBJ02-03 |
| CASSSQGMRNSPLHF | 145 | TCRBV07 | TCRBJ01-06 |
| CASSSATGNTGELFF | 146 | TCRBV11 | TCRBJ02-02 |
| CASSPAGGWNTEAFF | 147 | TCRBV28-01 | TCRBJ01-01 |
| CASSFTGTGKEKLFF | 148 | TCRBV28-01 | TCRBJ01-04 |
| CASSERGLAGVPDTQYF | 149 | TCRBV10-01 | TCRBJ02-03 |
| CASSGPGTGDYEQYF | 150 | TCRBV25-01 | TCRBJ02-07 |
| CASSSRGTKQETQYF | 151 | TCRBV07 | TCRBJ02-05 |
| CASSHQRNSPLHF | 152 | TCRBV14-01 | TCRBJ01-06 |
| CSASVQTEAFF | 153 | TCRBV20-01 | TCRBJ01-01 |
| CASRTHSSYNEQFF | 154 | TCRBV28-01 | TCRBJ02-01 |
| CSARRAGSGTDTQYF | 155 | TCRBV20-X | TCRBJ02-03 |
| CASRGEPYNSPLHF | 156 | TCRBV28-01 | TCRBJ01-06 |
| CATSRDLRDRNEKLFF | 157 | TCRBV15-01 | TCRBJ01-04 |
| CSARTGGSGTGELFF | 158 | TCRBV20-X | TCRBJ02-02 |
| CASSYSPLAGTQYF | 159 | TCRBV06 | TCRBJ02-03 |
| CASSRGTANEKLFF | 160 | TCRBV19-01 | TCRBJ01-04 |
| CASSFRQGRTEAFF | 161 | TCRBV05-08 | TCRBJ01-01 |
| CASSSRTSGSHETQYF | 162 | TCRBV07 | TCRBJ02-05 |
| CSARAGGGGTGELFF | 163 | TCRBV20-X | TCRBJ02-02 |
| CSAEGSGEAFF | 164 | TCRBV29-01 | TCRBJ01-01 |
| CATSRDKVDGYTF | 165 | TCRBV15-01 | TCRBJ01-02 |
| CSVRTSGETQYF | 166 | TCRBV20-X | TCRBJ02-05 |
| CSAIDGPGPQHF | 167 | TCRBV20-X | TCRBJ01-05 |
| CASSPQGFTGELFF | 168 | TCRBV05-04 | TCRBJ02-02 |
| CASRYRDHGYTF | 169 | TCRBV06 | TCRBJ01-02 |
| CASSAATGNTGELFF | 170 | TCRBV11 | TCRBJ02-02 |
| CSARGVPTNTGELFF | 171 | TCRBV20-X | TCRBJ02-02 |
| CASTDLAGVRNEQFF | 172 | TCRBV06 | TCRBJ02-01 |
| CASSQDVNGYTF | 173 | TCRBV03-01/03-02 | TCRBJ01-02 |
| CASSRGTGPSGANVLTF | 174 | TCRBV05-01 | TCRBJ02-06 |
| CASSYKQGSYNEQFF | 175 | TCRBV07 | TCRBJ02-01 |
| CASSQVLPSGANVLTF | 176 | TCRBV04-03 | TCRBJ02-06 |
| CASRPPGRYYGYTF | 177 | TCRBV28-01 | TCRBJ01-02 |
| CASSLSPRGRGYGYTF | 178 | TCRBV11 | TCRBJ01-02 |
| CSAPPPPYNEQFF | 179 | TCRBV20-X | TCRBJ02-01 |
| CSARGEPANTGELFF | 180 | TCRBV20-X | TCRBJ02-02 |
| CSARKGGAGTGELFF | 181 | TCRBV20-X | TCRBJ02-02 |
| CSARQAGAGTGELFF | 182 | TCRBV20-X | TCRBJ02-02 |
| CASGRQGAYEQYF | 183 | TCRBV28-01 | TCRBJ02-07 |
| CASSLDDPTDTQYF | 184 | TCRBV11 | TCRBJ02-03 |
| CASSTGFNEQFF | 185 | TCRBV06 | TCRBJ02-01 |
| CASSLRLGSETQYF | 186 | TCRBV12-X | TCRBJ02-05 |
| CASSFPRPGTGELFF | 187 | TCRBV12-X | TCRBJ02-02 |
| CASSPSGTPGEKLFF | 188 | TCRBV05-01 | TCRBJ01-04 |
| CASSLLDSSNTGELFF | 189 | TCRBV18-01 | TCRBJ02-02 |
| CASSYGFGTGEETQYF | 190 | TCRBV06 | TCRBJ02-05 |
| CASSVGGNSHNEQFF | 191 | TCRBV09-01 | TCRBJ02-01 |
| CSARSAGGGTGELFF | 192 | TCRBV20-X | TCRBJ02-02 |
| CAWSVGGTYQPQHF | 193 | TCRBV30-01 | TCRBJ01-05 |
| CASTPVGSYNEQFF | 194 | TCRBV06 | TCRBJ02-01 |
| CAWSGTGRKPQHF | 195 | TCRBV30-01 | TCRBJ01-05 |
| CAIRQGQTGELFF | 196 | TCRBV10-03 | TCRBJ02-02 |
| CASSLAPRDRGTQPQHF | 197 | TCRBV07 | TCRBJ01-05 |
| CASSRRGLAGRTDTQYF | 198 | TCRBV07 | TCRBJ02-03 |
| CATSRARGGKTQYF | 199 | TCRBV15-01 | TCRBJ02-05 |
| CASSLAGLNEQFF | 200 | TCRBV07 | TCRBJ02-01 |
| CSAPSPPHNEQFF | 201 | TCRBV20-X | TCRBJ02-01 |
| CSARKSGSGTGELFF | 202 | TCRBV20-X | TCRBJ02-02 |
| CATSRGGRETKNIQYF | 203 | TCRBV15-01 | TCRBJ02-04 |
| CASSPVRDGTGELFF | 204 | TCRBV18-01 | TCRBJ02-02 |
| CASSLRRGGLQETQYF | 205 | TCRBV07 | TCRBJ02-05 |
| CASGTGLYEKLFF | 206 | TCRBV19-01 | TCRBJ01-04 |
| CASSVVPTGGSGNTIYF | 207 | TCRBV09-01 | TCRBJ01-03 |
| CASSYSPSGWTEAFF | 208 | TCRBV06 | TCRBJ01-01 |
| CASSQGTSGDRDEQFF | 209 | TCRBV04-02 | TCRBJ02-01 |
| CASSLWLGSPLHF | 210 | TCRBV28-01 | TCRBJ01-06 |
| CASSRGASRTGELFF | 211 | TCRBV11 | TCRBJ02-02 |
| CASSLSPTSYEQYF | 212 | TCRBV07 | TCRBJ02-07 |
| CSARPSSGRATDTQYF | 213 | TCRBV20-X | TCRBJ02-03 |
| CSAPLAFHNEQFF | 214 | TCRBV20-X | TCRBJ02-01 |
| CASSPWGQGSYEQYF | 215 | TCRBV05-06 | TCRBJ02-07 |
| CSARGSGRVSDTQYF | 216 | TCRBV20-X | TCRBJ02-03 |
| CASSVGRGPNTGELFF | 217 | TCRBV02-01 | TCRBJ02-02 |
| CASRSGSAGNTIYF | 218 | TCRBV12-X | TCRBJ01-03 |
| CATAGPDSYEQYF | 219 | TCRBV10-03 | TCRBJ02-07 |
| CASGFNEQFF | 220 | TCRBV02-01 | TCRBJ02-01 |
| CSASTLEDTQYF | 221 | TCRBV20-01 | TCRBJ02-03 |
| CASSTQENTEAFF | 222 | TCRBV25-01 | TCRBJ01-01 |
| CASSQVAGRGGEQYF | 223 | TCRBV04-03 | TCRBJ02-07 |
| CSATRPPYNEQFF | 224 | TCRBV20-X | TCRBJ02-01 |
| CSAGLAGVLETQYF | 225 | TCRBV20-X | TCRBJ02-05 |
| CSAPGQGDNEQFF | 226 | TCRBV20-X | TCRBJ02-01 |
| CASSLVGGQGFQETQYF | 227 | TCRBV07 | TCRBJ02-05 |
| CSARTSPTNTGELFF | 228 | TCRBV20-X | TCRBJ02-02 |
| CSARGTGGIEQYF | 229 | TCRBV02-01 | TCRBJ02-07 |
| CAWSVGLGVSSPLHF | 230 | TCRBV30-01 | TCRBJ01-06 |
| CSARDSESSYNEQFF | 231 | TCRBV20-X | TCRBJ02-01 |
| CATSKGQGSSGANVLTF | 232 | TCRBV15-01 | TCRBJ02-06 |
| CASSSVPGLAGGEQFF | 233 | TCRBV07 | TCRBJ02-01 |
| CASSLGSSRHSYEQYF | 234 | TCRBV05-01 | TCRBJ02-07 |
| CASSLAPAGDTQYF | 235 | TCRBV07 | TCRBJ02-03 |
| CAIREGQRDEQYF | 236 | TCRBV10-03 | TCRBJ02-07 |
| CASSLAPRDRGDQPQHF | 237 | TCRBV07 | TCRBJ01-05 |
| CASSPSRSYGYTF | 238 | TCRBV11 | TCRBJ01-02 |
| CASSFRGGAYGYTF | 239 | TCRBV07 | TCRBJ01-02 |
| CASSLAHLGGTEAFF | 240 | TCRBV12-X | TCRBJ01-01 |
| CASSSEGGRNQPQHF | 241 | TCRBV18-01 | TCRBJ01-05 |
| CSVQVGTGGYEQYF | 242 | TCRBV29-01 | TCRBJ02-07 |
| CASSPTGKRETQYF | 243 | TCRBV05-01 | TCRBJ02-05 |
| CSATGGRPGANVLTF | 244 | TCRBV20-X | TCRBJ02-06 |
| CASNPSGTTDTQYF | 245 | TCRBV05-01 | TCRBJ02-03 |
| CASSPGGYRAEAFF | 246 | TCRBV18-01 | TCRBJ01-01 |
| CASSQVVGPGTDTQYF | 247 | TCRBV04-03 | TCRBJ02-03 |
| CASSSARGTGELFF | 248 | TCRBV03-01/03-02 | TCRBJ02-02 |
| CATSRGTRLTDTQYF | 249 | TCRBV24-01 | TCRBJ02-03 |
| CSALRVPYNEQFF | 250 | TCRBV20-X | TCRBJ02-01 |
| CATQDGGGNQPQHF | 251 | TCRBV19-01 | TCRBJ01-05 |
| CASSQEGGTGTYNEQFF | 252 | TCRBV04-02 | TCRBJ02-01 |
| CSVKTSGRASDTQYF | 253 | TCRBV20-X | TCRBJ02-03 |
| CASSIDSSGRANTGELFF | 254 | TCRBV19-01 | TCRBJ02-02 |
| CASSLEFNYNSPLHF | 255 | TCRBV12-X | TCRBJ01-06 |
| CASSLETNYNSPLHF | 256 | TCRBV12-X | TCRBJ01-06 |
| CSARNEGPDTQYF | 257 | TCRBV20-X | TCRBJ02-03 |
| CSVEVGLAVNEQFF | 258 | TCRBV29-01 | TCRBJ02-01 |
| CAWNRGGEQYF | 259 | TCRBV30-01 | TCRBJ02-07 |
| CASSFGGTANYGYTF | 260 | TCRBV05-05 | TCRBJ01-02 |
| CSVPGTGRYNEQFF | 261 | TCRBV29-01 | TCRBJ02-01 |
| CSGSGVSGANVLTF | 262 | TCRBV20-X | TCRBJ02-06 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CSAPAGLGYEQYF | 263 | TCRBV20-X | TCRBJ02-07 |
| CASTHRTNTGELFF | 264 | TCRBV19-01 | TCRBJ02-02 |
| CSATDPPYNEQFF | 265 | TCRBV20-X | TCRBJ02-01 |
| CASSSSTGAGANVLTF | 266 | TCRBV09-01 | TCRBJ02-06 |
| CASSERRQKAFF | 267 | TCRBV06 | TCRBJ01-01 |
| CSARSVVEQFF | 268 | TCRBV20-01 | TCRBJ02-01 |
| CASSWDSPSYEQYF | 269 | TCRBV05-04 | TCRBJ02-07 |
| CASSEQRGNEKLFF | 270 | TCRBV06 | TCRBJ01-04 |
| CASSRGTGWQETQYF | 271 | TCRBV03-01/03-02 | TCRBJ02-05 |
| CASSYRKGSSYNEQFF | 272 | TCRBV06 | TCRBJ02-01 |
| CSARPSGSGAGELFF | 273 | TCRBV20-X | TCRBJ02-02 |
| CASRSGQAKNTEAFF | 274 | TCRBV19-01 | TCRBJ01-01 |
| CSAREIGGAGSPLHF | 275 | TCRBV20-X | TCRBJ01-06 |
| CASSLLSGLEQFF | 276 | TCRBV03-01/03-02 | TCRBJ02-01 |
| CASRSSGSPNYGYTF | 277 | TCRBV19-01 | TCRBJ01-02 |
| CASSSGTGGRGYEQYF | 278 | TCRBV06 | TCRBJ02-07 |
| CASRLQGWDTDTQYF | 279 | TCRBV06 | TCRBJ02-03 |
| CASSLAPLTDTQYF | 280 | TCRBV07 | TCRBJ02-03 |
| CSASEPPYNEQFF | 281 | TCRBV20-X | TCRBJ02-01 |
| CASSERGQSEKLFF | 282 | TCRBV06 | TCRBJ01-04 |
| CASSFGGLDGANVLTF | 283 | TCRBV07 | TCRBJ02-06 |
| CSARREGPETQYF | 284 | TCRBV20-X | TCRBJ02-05 |
| CASSLGTSHTDTQYF | 285 | TCRBV28-01 | TCRBJ02-03 |
| CASSKGTGQYF | 286 | TCRBV07 | TCRBJ02-07 |
| CASSFETNYNSPLHF | 287 | TCRBV12-X | TCRBJ01-06 |
| CSARRSGGGTGELFF | 288 | TCRBV20-X | TCRBJ02-02 |
| CSARKGGSGTGELFF | 289 | TCRBV20-X | TCRBJ02-02 |
| CASSITGEDSPLHF | 290 | TCRBV19-01 | TCRBJ01-06 |
| CASSLTMGQPQHF | 291 | TCRBV07 | TCRBJ01-05 |
| CASSYTGADTQYF | 292 | TCRBV07 | TCRBJ02-03 |
| CASSGPRATNEKLFF | 293 | TCRBV02-01 | TCRBJ01-04 |
| CASRDRAPQPQHF | 294 | TCRBV19-01 | TCRBJ01-05 |
| CAARGGYGYTF | 295 | TCRBV30-01 | TCRBJ01-02 |
| CASSLTGEGTQYF | 296 | TCRBV28-01 | TCRBJ02-05 |
| CSARDSSRTDTQYF | 297 | TCRBV20-X | TCRBJ02-03 |
| CSALLPPYNEQFF | 298 | TCRBV20-X | TCRBJ02-01 |
| CASSTDGGRNQPQHF | 299 | TCRBV18-01 | TCRBJ01-05 |
| CASSFRRRSYNEQFF | 300 | TCRBV12-X | TCRBJ02-01 |
| CSALRENQETQYF | 301 | TCRBV20-X | TCRBJ02-05 |
| CASSKEKLYQPQHF | 302 | TCRBV21-01 | TCRBJ01-05 |
| CSARGQPANTGELFF | 303 | TCRBV20-X | TCRBJ02-02 |
| CASSSLWTGSTDTQYF | 304 | TCRBV07 | TCRBJ02-03 |
| CASTPAGRDTGELFF | 305 | TCRBV19-01 | TCRBJ02-02 |
| CSVGPGDTEAFF | 306 | TCRBV20-X | TCRBJ01-01 |
| CASSQPPLAGTYNEQFF | 307 | TCRBV03-01/03-02 | TCRBJ02-01 |
| CSANRQGAGTEAFF | 308 | TCRBV29-01 | TCRBJ01-01 |
| CASSRSGFSYEQYF | 309 | TCRBV06 | TCRBJ02-07 |
| CASSSGLRQPQHF | 310 | TCRBV05-01 | TCRBJ01-05 |
| CASSLAPGAEGYTF | 311 | TCRBV07 | TCRBJ01-02 |
| CASTENSNQPQHF | 312 | TCRBV28-01 | TCRBJ01-05 |
| CSARIGGSGTGELFF | 313 | TCRBV20-X | TCRBJ02-02 |
| CASSAVSGTDTQYF | 314 | TCRBV10-02 | TCRBJ02-03 |
| CSAPVAPYNEQFF | 315 | TCRBV20-X | TCRBJ02-01 |
| CSARGAGGGTGELFF | 316 | TCRBV20-X | TCRBJ02-02 |
| CASSKGFNEQFF | 317 | TCRBV06 | TCRBJ02-01 |
| CASRSPGSKETQYF | 318 | TCRBV28-01 | TCRBJ02-05 |
| CAIRLGQTYEQYF | 319 | TCRBV10-03 | TCRBJ02-07 |
| CSARGSGRAADTQYF | 320 | TCRBV20-X | TCRBJ02-03 |
| CSVARTGGGNEKLFF | 321 | TCRBV29-01 | TCRBJ01-04 |
| CSAIPGGGSDTQYF | 322 | TCRBV20-X | TCRBJ02-03 |
| CASRLGGTLAKNIQYF | 323 | TCRBV28-01 | TCRBJ02-04 |
| CSARTSGSGTGELFF | 324 | TCRBV20-X | TCRBJ02-02 |
| CSALLAASSYNEQFF | 325 | TCRBV20-X | TCRBJ02-01 |
| CASSQPNYEQYF | 326 | TCRBV03-01/03-02 | TCRBJ02-07 |
| CASSVGTSGSVRDTQYF | 327 | TCRBV09-01 | TCRBJ02-03 |
| CSAKWEGPDTQYF | 328 | TCRBV20-X | TCRBJ02-03 |
| CASSLDSVGELFF | 329 | TCRBV05-01 | TCRBJ02-02 |
| CASSRSGGATRETQYF | 330 | TCRBV14-01 | TCRBJ02-05 |
| CASSLGTLPYNEQFF | 331 | TCRBV07 | TCRBJ02-01 |
| CASSTAGLGANVLTF | 332 | TCRBV06 | TCRBJ02-06 |
| CAIKGTSSGNTIYF | 333 | TCRBV10-03 | TCRBJ01-03 |
| CSAPSPPSYEQYF | 334 | TCRBV20-X | TCRBJ02-07 |
| CASSLSGVGTEAFF | 335 | TCRBV05-04 | TCRBJ01-01 |
| CASSFELNYNSPLHF | 336 | TCRBV12-X | TCRBJ01-06 |
| CSAPPPPHNEQFF | 337 | TCRBV20-X | TCRBJ02-01 |
| CASSLSRAYGYTF | 338 | TCRBV11 | TCRBJ01-02 |
| CASSLRTAGGYNEQFF | 339 | TCRBV27-01 | TCRBJ02-01 |
| CASIPGQGNTEAFF | 340 | TCRBV28-01 | TCRBJ01-01 |
| CASSQGYETQYF | 341 | TCRBV05-01 | TCRBJ02-05 |
| CAWSRGGGRNEKLFF | 342 | TCRBV30-01 | TCRBJ01-04 |
| CASSQVWGNQPQHF | 343 | TCRBV03-01/03-02 | TCRBJ01-05 |
| CSADEQGGYGYTF | 344 | TCRBV20-X | TCRBJ01-02 |
| CASSLGGARKNIQYF | 345 | TCRBV28-01 | TCRBJ02-04 |
| CSASPPPRNEQFF | 346 | TCRBV20-X | TCRBJ02-01 |
| CASSLEANYNSPLHF | 347 | TCRBV12-X | TCRBJ01-06 |
| CASSLGSLWGSTDTQYF | 348 | TCRBV05-01 | TCRBJ02-03 |
| CASSRRLAGGPSTDTQYF | 349 | TCRBV06 | TCRBJ02-03 |
| CSARRAGGGTGELFF | 350 | TCRBV20-X | TCRBJ02-02 |
| CASSHEKETQYF | 351 | TCRBV03-01/03-02 | TCRBJ02-05 |
| CSARDNGRSNEQFF | 352 | TCRBV20-X | TCRBJ02-01 |
| CASSGRELGEQYF | 353 | TCRBV02-01 | TCRBJ02-07 |
| CSAPRAPSYEQYF | 354 | TCRBV20-X | TCRBJ02-07 |
| CASSSRETNEKLFF | 355 | TCRBV05-06 | TCRBJ01-04 |
| CASSRGQTNNSPLHF | 356 | TCRBV03-01/03-02 | TCRBJ01-06 |
| CASTRTGNVYGYTF | 357 | TCRBV19-01 | TCRBJ01-02 |
| CASSPLASLSYEQYF | 358 | TCRBV18-01 | TCRBJ02-07 |
| CASEQGRGNEKLFF | 359 | TCRBV06 | TCRBJ01-04 |
| CASSLASGARTYEQYF | 360 | TCRBV05-04 | TCRBJ02-07 |
| CASSLVITGNTIYF | 361 | TCRBV05-08 | TCRBJ01-03 |
| CSASAVEETQYF | 362 | TCRBV20-01 | TCRBJ02-05 |
| CASSSNRGNEKLFF | 363 | TCRBV06 | TCRBJ01-04 |
| CASSYSPSGVLNTGELFF | 364 | TCRBV06 | TCRBJ02-02 |
| CSARDPLPSSYEQYF | 365 | TCRBV20-X | TCRBJ02-07 |
| CAISEAGPNTDTQYF | 366 | TCRBV10-03 | TCRBJ02-03 |
| CASSLGGAGYEQYV | 367 | TCRBV05-04 | TCRBJ02-07 |
| CSARTGGAGTGELFF | 368 | TCRBV20-X | TCRBJ02-02 |
| CAWSHGRNSYNEQFF | 369 | TCRBV30-01 | TCRBJ02-01 |
| CASSYGQGDEQYV | 370 | TCRBV05-01 | TCRBJ02-07 |
| CAWSRRGNYEQYF | 371 | TCRBV30-01 | TCRBJ02-07 |
| CASIQGRGNEKLFF | 372 | TCRBV06 | TCRBJ01-04 |
| CSGGLAGVETQYF | 373 | TCRBV29-01 | TCRBJ02-05 |
| CASSEAGRGPYGYTF | 374 | TCRBV06 | TCRBJ01-02 |
| CSARKAGGGTGELFF | 375 | TCRBV20-X | TCRBJ02-02 |
| CSARPAGSGTGELFF | 376 | TCRBV20-X | TCRBJ02-02 |
| CSARTAGGGTGELFF | 377 | TCRBV20-X | TCRBJ02-02 |
| CASSLGWLDNEQFF | 378 | TCRBV11 | TCRBJ02-01 |
| CARKDRAGANVLTF | 379 | TCRBV02-01 | TCRBJ02-06 |
| CSAERRASGNTIYF | 380 | TCRBV20-X | TCRBJ01-03 |
| CASSRGLAGNNEQFF | 381 | TCRBV07 | TCRBJ02-01 |
| CASSERPTANYGYTF | 382 | TCRBV02-01 | TCRBJ01-02 |
| CAIRQGQENIQYF | 383 | TCRBV10-03 | TCRBJ02-04 |
| CASSLGEGRGRAFF | 384 | TCRBV05-01 | TCRBJ01-01 |
| CSASGGGRESYGYTF | 385 | TCRBV20-X | TCRBJ01-02 |
| CASSLARGSGTGELFF | 386 | TCRBV12-X | TCRBJ02-02 |
| CAGRRGELFF | 387 | TCRBV11 | TCRBJ02-02 |
| CSAARGGDGNQPQHF | 388 | TCRBV20-X | TCRBJ01-05 |
| CASSPTGPGADTQYF | 389 | TCRBV04-03 | TCRBJ02-03 |
| CASSEAVDTIYF | 390 | TCRBV06 | TCRBJ01-03 |
| CASSEGLVNEKLFF | 391 | TCRBV06 | TCRBJ01-04 |
| CASSQQGGAYNEQFF | 392 | TCRBV18-01 | TCRBJ02-01 |
| CATGLAGGLSYNEQFF | 393 | TCRBV10-03 | TCRBJ02-01 |
| CASSVTSGSNTGELFF | 394 | TCRBV19-01 | TCRBJ02-02 |
| CASSTLPGTAEAFF | 395 | TCRBV19-01 | TCRBJ01-01 |
| CASSRGWSTDTQYF | 396 | TCRBV18-01 | TCRBJ02-03 |
| CASSPGRHYEQYF | 397 | TCRBV18-01 | TCRBJ02-07 |
| CASSPGLAGATSTDTQYF | 398 | TCRBV05-04 | TCRBJ02-03 |
| CASSSRAGVGEQYF | 399 | TCRBV07 | TCRBJ02-07 |
| CASSLVTGSGSEKLFF | 400 | TCRBV07 | TCRBJ02-01 |
| CASSQVLAGGHNEQFF | 401 | TCRBV03-01/03-02 | TCRBJ02-01 |
| CASSLGGDAGNYGYTF | 402 | TCRBV05-04 | TCRBJ01-02 |
| CASKTTNEKLFF | 403 | TCRBV28-01 | TCRBJ01-04 |
| CSASADEETQYF | 404 | TCRBV20-01 | TCRBJ02-05 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CSADREGSETQYF | 405 | TCRBV20-X | TCRBJ02-05 |
| CASSPKWAGELFF | 406 | TCRBV18-01 | TCRBJ02-02 |
| CAIKGQSSYNSPLHF | 407 | TCRBV10-03 | TCRBJ01-06 |
| CASSVGGLANEQFF | 408 | TCRBV07 | TCRBJ02-01 |
| CASSLGGREWEKLFF | 409 | TCRBV07 | TCRBJ01-04 |
| CASSRQGTQNTEAFF | 410 | TCRBV12-X | TCRBJ01-01 |
| CASTSDLGEQYF | 411 | TCRBV19-01 | TCRBJ02-07 |
| CASSSGTSGRPGEQFF | 412 | TCRBV28-01 | TCRBJ02-01 |
| CASSPWREAGNEQFF | 413 | TCRBV18-01 | TCRBJ02-01 |
| CASSQDGLAGVTGELFF | 414 | TCRBV04-01 | TCRBJ02-02 |
| CASDGNNSPLHF | 415 | TCRBV28-01 | TCRBJ01-06 |
| CASSVMTSGQETQYF | 416 | TCRBV07 | TCRBJ02-05 |
| CSARGSPTNTGELFF | 417 | TCRBV20-X | TCRBJ02-02 |
| CASTGTTNEKLFF | 418 | TCRBV10-02 | TCRBJ01-04 |
| CASSVGRVDSPLHF | 419 | TCRBV02-01 | TCRBJ01-06 |
| CATSTGAAGYGYTF | 420 | TCRBV15-01 | TCRBJ01-02 |
| CASSQRALYGYTF | 421 | TCRBV12-03/12-04 | TCRBJ01-02 |
| CSAAGVSTDTQYF | 422 | TCRBV29-01 | TCRBJ02-03 |
| CASSQGSRGRGYGYTF | 423 | TCRBV14-01 | TCRBJ01-02 |
| CASSLYEGQETQYF | 424 | TCRBV05-01 | TCRBJ02-05 |
| CASSLARTSNTEAFF | 425 | TCRBV27-01 | TCRBJ01-01 |
| CSARIAGAGTGELFF | 426 | TCRBV20-X | TCRBJ02-02 |
| CASSFIQGPNEQFF | 427 | TCRBV05-01 | TCRBJ02-01 |
| CASSTRRNEQFF | 428 | TCRBV03-01/03-02 | TCRBJ02-01 |
| CASRGPGQPQHF | 429 | TCRBV28-01 | TCRBJ01-05 |
| CASSLGPKGPNSPLHF | 430 | TCRBV07 | TCRBJ01-06 |
| CASSRGRPGTDTQYF | 431 | TCRBV05-01 | TCRBJ02-03 |
| CASSFDSGRQETQYF | 432 | TCRBV07 | TCRBJ02-05 |
| CASRPSQGAGELFF | 433 | TCRBV12-X | TCRBJ02-02 |
| CASSPPGSQETQYF | 434 | TCRBV05-05 | TCRBJ02-05 |
| CAISPRLAYNEQFF | 435 | TCRBV10-03 | TCRBJ02-01 |
| CASSLARTSGINEQFF | 436 | TCRBV13-01 | TCRBJ02-01 |
| CSARDGAPEQFF | 437 | TCRBV20-X | TCRBJ02-01 |
| CASSDQTDTQYF | 438 | TCRBV07 | TCRBJ02-03 |
| CASRPYRGDQPQHF | 439 | TCRBV27-01 | TCRBJ01-05 |
| CSAREGRQSSYNSPLHF | 440 | TCRBV20-X | TCRBJ01-06 |
| CASESGGNTIYF | 441 | TCRBV19-01 | TCRBJ01-03 |
| CASRRDRGDEQYF | 442 | TCRBV27-01 | TCRBJ02-07 |
| CASSQDLGGQGYQPQHF | 443 | TCRBV04-03 | TCRBJ01-05 |
| CASSLAGRTSTDTQYF | 444 | TCRBV07 | TCRBJ02-03 |
| CASSVDRDYEQYF | 445 | TCRBV05-06 | TCRBJ02-07 |
| CASSWTSSSYNEQFF | 446 | TCRBV18-01 | TCRBJ02-01 |
| CASSRTRQGYEQYF | 447 | TCRBV28-01 | TCRBJ02-07 |
| CSARGTLASYEQYF | 448 | TCRBV20-X | TCRBJ02-07 |
| CASSFKGTTGELFF | 449 | TCRBV05-04 | TCRBJ02-02 |
| CASSLTVRGRETQYF | 450 | TCRBV05-01 | TCRBJ02-05 |
| CSARGSLASYEQYF | 451 | TCRBV20-X | TCRBJ02-07 |
| CSARESGQNGYTF | 452 | TCRBV20-X | TCRBJ01-02 |
| CASRGRGLAKNIQYF | 453 | TCRBV02-01 | TCRBJ02-04 |
| CASSLVTTGNTIYF | 454 | TCRBV05-08 | TCRBJ01-03 |
| CATSRDSGSGETQYF | 455 | TCRBV15-01 | TCRBJ02-05 |
| CATKGWTSGTDTQYF | 456 | TCRBV06 | TCRBJ02-03 |
| CSATGTPTNQPQHF | 457 | TCRBV20-X | TCRBJ01-05 |
| CASSSGGTSGRDTQYF | 458 | TCRBV06 | TCRBJ02-03 |
| CASSRQGGYEQYF | 459 | TCRBV28-01 | TCRBJ02-07 |
| CSARPGGGTGELFF | 460 | TCRBV20-X | TCRBJ02-02 |
| CASSTGRVYNEQFF | 461 | TCRBV19-01 | TCRBJ02-01 |
| CASTPTGNTGELFF | 462 | TCRBV10-02 | TCRBJ02-02 |
| CASSALTGGTDTQYF | 463 | TCRBV09-01 | TCRBJ02-03 |
| CASSGLLAYEQYF | 464 | TCRBV02-01 | TCRBJ02-07 |
| CSARLRDYPYEQYF | 465 | TCRBV20-X | TCRBJ02-07 |
| CASSTTGPYSGNTIYF | 466 | TCRBV11 | TCRBJ01-03 |
| CASRPSGVGDEQYF | 467 | TCRBV19-01 | TCRBJ02-07 |
| CASSQFDEQFF | 468 | TCRBV28-01 | TCRBJ02-01 |
| CSASPPGQTQETQYF | 469 | TCRBV20-X | TCRBJ02-05 |
| CASSSGRGDEKLFF | 470 | TCRBV06 | TCRBJ01-04 |
| CASSSPGSYTF | 471 | TCRBV19-01 | TCRBJ01-02 |
| CSARVVPYNEQFF | 472 | TCRBV05-01 | TCRBJ02-01 |
| CASSLQAASGNTIYF | 473 | TCRBV07 | TCRBJ01-03 |
| CSAPDRGWQETQYF | 474 | TCRBV20-X | TCRBJ02-05 |
| CASSLDLAGKTQYF | 475 | TCRBV07 | TCRBJ02-05 |
| CASSGRQGAPEAFF | 476 | TCRBV06 | TCRBJ01-01 |
| CASGRLGSTDTQYF | 477 | TCRBV12-X | TCRBJ02-03 |
| CASSTLAGGGQETQYF | 478 | TCRBV05-04 | TCRBJ02-05 |
| CAWSVQGAVKNIQYF | 479 | TCRBV30-01 | TCRBJ02-04 |
| CATSRDKGSGNSPLHF | 480 | TCRBV15-01 | TCRBJ01-06 |
| CASSSPGWGETQYF | 481 | TCRBV27-01 | TCRBJ02-05 |
| CASSQVNEYEQYF | 482 | TCRBV14-01 | TCRBJ02-07 |
| CSGCTGVNTEAFF | 483 | TCRBV29-01 | TCRBJ01-01 |
| CASSDGQVFYGYTF | 484 | TCRBV19-01 | TCRBJ01-02 |
| CASSLDPTRSTDTQYF | 485 | TCRBV07 | TCRBJ02-03 |
| CASSAWTGELQETQYF | 486 | TCRBV09-01 | TCRBJ02-05 |
| CASSPGRGFEKLFF | 487 | TCRBV06 | TCRBJ01-04 |
| CASSPVEGGYTF | 488 | TCRBV05-01 | TCRBJ01-02 |
| CSARAAGAGTGELFF | 489 | TCRBV20-X | TCRBJ02-02 |
| CSARAGGHGTGELFF | 490 | TCRBV20-X | TCRBJ02-02 |
| CSAREGGGGTGELFF | 491 | TCRBV20-X | TCRBJ02-02 |
| CASRGAGSADTQYF | 492 | TCRBV02-01 | TCRBJ02-03 |
| CASSYGGAGSDTQYF | 493 | TCRBV06 | TCRBJ02-03 |
| CASSLVAGGETQYF | 494 | TCRBV05-08 | TCRBJ02-05 |
| CAALAGGYNEQFF | 495 | TCRBV28-01 | TCRBJ02-01 |
| CASSLVRGLNNEKLFF | 496 | TCRBV05-06 | TCRBJ01-04 |
| CASFPGQGNTEAFF | 497 | TCRBV28-01 | TCRBJ01-01 |
| CASRPGTGYQPQHF | 498 | TCRBV19-01 | TCRBJ01-05 |
| CASTMTGIDTEAFF | 499 | TCRBV06 | TCRBJ01-01 |
| CASSFAGGAFNEQFF | 500 | TCRBV07 | TCRBJ02-01 |
| CASRVGLRQPQHF | 501 | TCRBV06 | TCRBJ01-05 |
| CASSFGSGKYNEQFF | 502 | TCRBV07 | TCRBJ02-01 |
| CASSPSLAGGPTDTQYF | 503 | TCRBV06 | TCRBJ02-03 |
| CASSPQRDRSSGNTIYF | 504 | TCRBV18-01 | TCRBJ01-03 |
| CASSFLTGLSGANVLTF | 505 | TCRBV27-01 | TCRBJ02-06 |
| CASCRGTTYEQYF | 506 | TCRBV06 | TCRBJ02-07 |
| CSARDPYLSSYEQYF | 507 | TCRBV20-X | TCRBJ02-07 |
| CASSSPSGRADEQFF | 508 | TCRBV09-01 | TCRBJ02-01 |
| CAIKGTSSYNSPLHF | 509 | TCRBV10-03 | TCRBJ01-06 |
| CAIRMGQTYEQYF | 510 | TCRBV10-03 | TCRBJ02-07 |
| CASSQGGAREQFF | 511 | TCRBV14-01 | TCRBJ02-01 |
| CASSRTSSPDTQYF | 512 | TCRBV06 | TCRBJ02-03 |
| CATSPQGGDQPQHF | 513 | TCRBV24-01 | TCRBJ01-05 |
| CSAQDPGTTEAFF | 514 | TCRBV20-X | TCRBJ01-01 |
| CASSLNRGVSQPQHF | 515 | TCRBV12-X | TCRBJ01-05 |
| CASTLTSSEQYF | 516 | TCRBV02-01 | TCRBJ02-07 |
| CASSIAGLRPDTQYF | 517 | TCRBV19-01 | TCRBJ02-03 |
| CASSHGQGALDTQYF | 518 | TCRBV03-01/03-02 | TCRBJ02-03 |
| CASTRGDRGQETQYF | 519 | TCRBV12-X | TCRBJ02-05 |
| CSAPARGETQYF | 520 | TCRBV29-01 | TCRBJ02-05 |
| CASSQEVTADSPLHF | 521 | TCRBV04-01 | TCRBJ01-06 |
| CASSLVLGGMNTEAFF | 522 | TCRBV07 | TCRBJ01-01 |
| CASKRQGLYEQYF | 523 | TCRBV27-01 | TCRBJ02-07 |
| CASSTQTSPLHF | 524 | TCRBV19-01 | TCRBJ01-06 |
| CASGGTGQPNQPQHF | 525 | TCRBV12-05 | TCRBJ01-05 |
| CASSYPGLPSTDTQYF | 526 | TCRBV05-06 | TCRBJ02-03 |
| CASMSGTGNEKLFF | 527 | TCRBV06 | TCRBJ01-04 |
| CSARDGQATQYF | 528 | TCRBV20-X | TCRBJ02-03 |
| CASSLSNRGRGYGYTF | 529 | TCRBV11 | TCRBJ01-02 |
| CASSLSRRGRGYGYTF | 530 | TCRBV11 | TCRBJ01-02 |
| CASTRAVQETQYF | 531 | TCRBV07 | TCRBJ02-05 |
| CASSLGDTGAEAFF | 532 | TCRBV07 | TCRBJ01-01 |
| CSAPGSWTEAFF | 533 | TCRBV20-X | TCRBJ01-01 |
| CASSLAGLASGEQFF | 534 | TCRBV05-01 | TCRBJ02-01 |
| CSVGGDPNEKLFF | 535 | TCRBV29-01 | TCRBJ01-04 |
| CSARQSSYEQYF | 536 | TCRBV29-01 | TCRBJ02-07 |
| CASSQDFPAGVRTDTQYF | 537 | TCRBV03-01/03-02 | TCRBJ02-03 |
| CASSPNGGRNQPQHF | 538 | TCRBV18-01 | TCRBJ01-05 |
| CSARGSGSGTGELFF | 539 | TCRBV20-X | TCRBJ02-02 |
| CSARRSGAGTGELFF | 540 | TCRBV20-X | TCRBJ02-02 |
| CASSQSSGGAETQYF | 541 | TCRBV07 | TCRBJ02-05 |
| CASSLSHSQETQYF | 542 | TCRBV11 | TCRBJ02-05 |
| CASSELDRTGELFF | 543 | TCRBV06 | TCRBJ02-02 |
| CSARFPSGRVNEQFF | 544 | TCRBV20-X | TCRBJ02-01 |
| CASSSRSRNTEAFF | 545 | TCRBV05-01 | TCRBJ01-01 |
| CAWSVVGGVRGYTF | 546 | TCRBV30-01 | TCRBJ01-02 |
| CASSPLLASSYNEQFF | 547 | TCRBV03-01/03-02 | TCRBJ02-01 |
| CASSLLAGDRKTQYF | 548 | TCRBV07 | TCRBJ02-05 |
| CASRLQGGNEQFF | 549 | TCRBV05-06 | TCRBJ02-01 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASSFLAGDTGELFF | 550 | TCRBV12-X | TCRBJ02-02 |
| CSARDEGPETQYF | 551 | TCRBV20-X | TCRBJ02-05 |
| CAISGDRGSSGANVLTF | 552 | TCRBV10-03 | TCRBJ02-06 |
| CSAIGQPSNQPQHF | 553 | TCRBV20-X | TCRBJ01-05 |
| CASSLGQRALNTEAFF | 554 | TCRBV05-05 | TCRBJ01-01 |
| CAWSVRRGESGYTF | 555 | TCRBV30-01 | TCRBJ01-02 |
| CASSLGGFQSTDTQYF | 556 | TCRBV07 | TCRBJ02-03 |
| CASSPDGGRNQPQHF | 557 | TCRBV18-01 | TCRBJ01-05 |
| CASSLAAGYTGELFF | 558 | TCRBV28-01 | TCRBJ02-02 |
| CASSPTDPSGNTIYF | 559 | TCRBV05-01 | TCRBJ01-03 |
| CASSFHPGEGYEQYF | 560 | TCRBV12-X | TCRBJ02-07 |
| CASSLKGHNQPQHF | 561 | TCRBV12-X | TCRBJ01-05 |
| CASSLQGANEQFF | 562 | TCRBV28-01 | TCRBJ02-01 |
| CASPGESGANVLTF | 563 | TCRBV07 | TCRBJ02-06 |
| CASSFLGTGKNTEAFF | 564 | TCRBV05-01 | TCRBJ01-01 |
| CSARASGAGTGELFF | 565 | TCRBV20-X | TCRBJ02-02 |
| CSASSPPDNEQFF | 566 | TCRBV20-01 | TCRBJ02-01 |
| CASSYTGDVDQPQHF | 567 | TCRBV04-02 | TCRBJ01-05 |
| CASSPSWQRNTEAFF | 568 | TCRBV18-01 | TCRBJ01-01 |
| CASSYGLQGHYGYTF | 569 | TCRBV06 | TCRBJ01-02 |
| CASSKNSSNQPQHF | 570 | TCRBV21-01 | TCRBJ01-05 |
| CASEAAYGYTF | 571 | TCRBV06 | TCRBJ01-02 |
| CSATSGRIYNEQFF | 572 | TCRBV20-X | TCRBJ02-01 |
| CASSPSSGGSYEQYF | 573 | TCRBV28-01 | TCRBJ02-07 |
| CSVTRTGGGADTQYF | 574 | TCRBV29-01 | TCRBJ02-03 |
| CASSLRPGGRDEQYF | 575 | TCRBV05-01 | TCRBJ02-07 |
| CASSLVVSGNTIYF | 576 | TCRBV05-08 | TCRBJ01-03 |
| CSARLGGGGTGELFF | 577 | TCRBV20-X | TCRBJ02-02 |
| CASSSGSGADTQYF | 578 | TCRBV07 | TCRBJ02-03 |
| CASGLAGNQETQYF | 579 | TCRBV28-01 | TCRBJ02-05 |
| CASSGTLAGGRTDTQYF | 580 | TCRBV05-06 | TCRBJ02-03 |
| CSAPLPPYNEQFF | 581 | TCRBV20-X | TCRBJ02-01 |
| CASSVGGRGAETQYF | 582 | TCRBV09-01 | TCRBJ02-05 |
| CASSLDGRSSYNEQFF | 583 | TCRBV07 | TCRBJ02-01 |
| CASSQSRDSAYEQYF | 584 | TCRBV18-01 | TCRBJ02-07 |
| CASSQEGRDTQYF | 585 | TCRBV14-01 | TCRBJ02-03 |
| CASILTGGNEQFF | 586 | TCRBV02-01 | TCRBJ02-01 |
| CASSLLLGTGYEQYF | 587 | TCRBV12-X | TCRBJ02-07 |
| CSAGTGTLNEQFF | 588 | TCRBV20-X | TCRBJ02-01 |
| CASSFSGGSIYGYTF | 589 | TCRBV12-X | TCRBJ01-02 |
| CAWSPGRGAYNEQFF | 590 | TCRBV30-01 | TCRBJ02-01 |
| CAIREGQTDTQYF | 591 | TCRBV10-03 | TCRBJ02-03 |
| CASRWQGSSYEQYF | 592 | TCRBV05-01 | TCRBJ02-07 |
| CSAPQPPYNEQFF | 593 | TCRBV20-X | TCRBJ02-01 |
| CASSPSKGRGTEAFF | 594 | TCRBV18-01 | TCRBJ01-01 |
| CASSPSGSRRETQYF | 595 | TCRBV19-01 | TCRBJ02-05 |
| CASSLTQGGTDTQYF | 596 | TCRBV05-06 | TCRBJ02-03 |
| CAWSVGDNSGNTIYF | 597 | TCRBV30-01 | TCRBJ01-03 |
| CASRTSGIGETQYF | 598 | TCRBV02-01 | TCRBJ02-05 |
| CSAKGQPTNTGELFF | 599 | TCRBV20-X | TCRBJ02-02 |
| CASSPGEASTDTQYF | 600 | TCRBV11 | TCRBJ02-03 |
| CATSSLGQGAREQYF | 601 | TCRBV15-01 | TCRBJ02-07 |
| CSATRGEDYGYTF | 602 | TCRBV20-X | TCRBJ01-02 |
| CSASWPNSPLHF | 603 | TCRBV20-01 | TCRBJ01-06 |
| CSATRGRGASTDTQYF | 604 | TCRBV20-X | TCRBJ02-03 |
| CASSFEGNYNSPLHF | 605 | TCRBV12-X | TCRBJ01-06 |
| CATSDLRTGDNEQFF | 606 | TCRBV24-01 | TCRBJ02-01 |
| CSVSWGSTNEKLFF | 607 | TCRBV29-01 | TCRBJ01-04 |
| CASSKHQNTGELFF | 608 | TCRBV19-01 | TCRBJ02-05 |
| CASSETWTQYF | 609 | TCRBV06 | TCRBJ02-05 |
| CASSLRQGYLETQYF | 610 | TCRBV05-06 | TCRBJ02-05 |
| CASSKNRGSNQPQHF | 611 | TCRBV12-X | TCRBJ01-05 |
| CASSYGEYSNQPQHF | 612 | TCRBV06 | TCRBJ01-05 |
| CASSRPSASYEQYF | 613 | TCRBV18-01 | TCRBJ02-07 |
| CASSLIAYDEQFF | 614 | TCRBV11 | TCRBJ02-01 |
| CASSEARSNTEAFF | 615 | TCRBV05-01 | TCRBJ01-01 |
| CASSSLGGWGYTF | 616 | TCRBV05-06 | TCRBJ01-02 |
| CASSVQGVAFF | 617 | TCRBV07 | TCRBJ01-01 |
| CASSYLHLSYEQYF | 618 | TCRBV06 | TCRBJ02-07 |
| CASSPEGRGLGYGYTF | 619 | TCRBV07 | TCRBJ01-02 |
| CASSPSGGSADTQYF | 620 | TCRBV18-01 | TCRBJ02-03 |
| CASIPTASYEQYF | 621 | TCRBV06 | TCRBJ02-07 |
| CASSLGLRTGGANVLTF | 622 | TCRBV07 | TCRBJ02-06 |
| CASSLAPLGDEQYF | 623 | TCRBV07 | TCRBJ02-07 |
| CASSSPVAGGRTDTQYF | 624 | TCRBV05-06 | TCRBJ02-03 |
| CSAAPGGSGNTIYF | 625 | TCRBV29-01 | TCRBJ01-03 |
| CASEASGVYEQYF | 626 | TCRBV02-01 | TCRBJ02-07 |
| CASSLDGVDSNQPQHF | 627 | TCRBV05-01 | TCRBJ01-05 |
| CASSLRDRAHTQYF | 628 | TCRBV05-01 | TCRBJ02-03 |
| CSASRVAGVEQFF | 629 | TCRBV20-01 | TCRBJ02-01 |
| CASRRGGPSYNEQFF | 630 | TCRBV06 | TCRBJ02-01 |
| CASSAPRETQYF | 631 | TCRBV18-01 | TCRBJ02-05 |
| CASSPGRGHEKLFF | 632 | TCRBV06 | TCRBJ01-04 |
| CASSNRQETQYF | 633 | TCRBV19-01 | TCRBJ02-05 |
| CASSSHGTGADTQYF | 634 | TCRBV05-01 | TCRBJ02-03 |
| CASSRGQGEGQPQHF | 635 | TCRBV11 | TCRBJ01-05 |
| CASRRTSGDYEQYV | 636 | TCRBV06 | TCRBJ02-07 |
| CASSWRDRGTYEQYF | 637 | TCRBV07 | TCRBJ02-07 |
| CASSLGEASTDTQYF | 638 | TCRBV11 | TCRBJ02-03 |
| CASSLAPLSETQYF | 639 | TCRBV07 | TCRBJ02-05 |
| CASAIQGSYEQYF | 640 | TCRBV18-01 | TCRBJ02-07 |
| CASSLTGTVNEKLFF | 641 | TCRBV03-01/ 03-02 | TCRBJ01-04 |
| CASRPTPTGELFF | 642 | TCRBV27-01 | TCRBJ02-02 |
| CATSRGARLTDTQYF | 643 | TCRBV24-01 | TCRBJ02-03 |
| CASSLGTSGRTLQETQYF | 644 | TCRBV07 | TCRBJ02-05 |
| CSARTTSGGVLSTDTQYF | 645 | TCRBV20-X | TCRBJ02-03 |
| CAISERSGSTDTQYF | 646 | TCRBV10-03 | TCRBJ02-03 |
| CASSAGGQGHYGYTF | 647 | TCRBV05-01 | TCRBJ01-02 |
| CASSERGETQYF | 648 | TCRBV09-01 | TCRBJ02-05 |
| CASSPGRPGSNQPQHF | 649 | TCRBV18-01 | TCRBJ01-05 |
| CSASPPPQETQYF | 650 | TCRBV20-X | TCRBJ02-05 |
| CASSLEGLAVYNEQFF | 651 | TCRBV05-06 | TCRBJ02-01 |
| CASSLQASSSNEQFF | 652 | TCRBV07 | TCRBJ02-01 |
| CASSVEPGGLTEAFF | 653 | TCRBV09-01 | TCRBJ01-01 |
| CSARGAGAGTGELFF | 654 | TCRBV20-X | TCRBJ02-02 |
| CAWNGINEKLFF | 655 | TCRBV30-01 | TCRBJ01-04 |
| CASSPEIPSGNTIYF | 656 | TCRBV28-01 | TCRBJ01-03 |
| CASSSVGGNEQYF | 657 | TCRBV07 | TCRBJ02-07 |
| CASSLVGPETQYF | 658 | TCRBV13-01 | TCRBJ02-05 |
| CASSFPGSVEQYF | 659 | TCRBV05-01 | TCRBJ02-07 |
| CASSLGGRPSPLHF | 660 | TCRBV28-01 | TCRBJ01-06 |
| CASSYTGDEDQPQHF | 661 | TCRBV04-02 | TCRBJ01-05 |
| CASSRRLAGGPRTDTQYF | 662 | TCRBV06 | TCRBJ02-03 |
| CSAARAPYNEQFF | 663 | TCRBV20-X | TCRBJ02-01 |
| CATSGTDKETQYF | 664 | TCRBV24-01 | TCRBJ02-05 |
| CSAGGQPVAKNIQYF | 665 | TCRBV20-X | TCRBJ02-04 |
| CASSYSVNTGANVLTF | 666 | TCRBV06 | TCRBJ02-06 |
| CASSADRVWNQPQHF | 667 | TCRBV06 | TCRBJ01-05 |
| CASRTRDNSPLHF | 668 | TCRBV02-01 | TCRBJ01-06 |
| CASSLTRPPGELFF | 669 | TCRBV12-X | TCRBJ02-02 |
| CASSLPWVEQYF | 670 | TCRBV28-01 | TCRBJ02-07 |
| CASSPLGGATYGYTF | 671 | TCRBV07 | TCRBJ01-02 |
| CASTWTSGSSYEQYF | 672 | TCRBV19-01 | TCRBJ02-07 |
| CASSLDGFYEQYF | 673 | TCRBV07 | TCRBJ02-07 |
| CASRRRTGVQPQHF | 674 | TCRBV06 | TCRBJ01-05 |
| CATSVTGGVDTQYF | 675 | TCRBV24-01 | TCRBJ02-03 |
| CSARPGGSGTGELFF | 676 | TCRBV20-X | TCRBJ02-02 |
| CSVPQQGGQETQYF | 677 | TCRBV29-01 | TCRBJ02-05 |
| CASSMFPGPYGYTF | 678 | TCRBV19-01 | TCRBJ01-02 |
| CASSPQARGLGYGYTF | 679 | TCRBV07 | TCRBJ01-02 |
| CATRRRLYEQYF | 680 | TCRBV28-01 | TCRBJ02-07 |
| CASSPASGNTGELFF | 681 | TCRBV11 | TCRBJ02-02 |
| CASSQALAGGYNEQFF | 682 | TCRBV14-01 | TCRBJ02-01 |
| CSARPRQGLQETQYF | 683 | TCRBV20-X | TCRBJ02-05 |
| CASSLGRGDSPLHF | 684 | TCRBV27-01 | TCRBJ01-06 |
| CSARGLAFTYEQFF | 685 | TCRBV20-X | TCRBJ02-01 |
| CASSLAAKPNTEAFF | 686 | TCRBV07 | TCRBJ01-01 |
| CASSSTNSNQPQHF | 687 | TCRBV05-05 | TCRBJ01-05 |
| CASSLVSSTHEQYF | 688 | TCRBV05-01 | TCRBJ02-07 |
| CASSFGQGEVQPQHF | 689 | TCRBV12-X | TCRBJ01-05 |
| CASSFEVNYNSPLHF | 690 | TCRBV12-X | TCRBJ01-06 |
| CASSLDTRSREQYF | 691 | TCRBV05-01 | TCRBJ02-07 |
| CSARDRDRGHGNTIYF | 692 | TCRBV20-X | TCRBJ01-03 |
| CASSLARLRSAGELFF | 693 | TCRBV05-04 | TCRBJ02-02 |
| CASSYSSGYTF | 694 | TCRBV19-01 | TCRBJ01-02 |
| CAISESTYQETQYF | 695 | TCRBV10-03 | TCRBJ02-05 |
| CASSVRRFQETQYF | 696 | TCRBV05-05 | TCRBJ02-05 |
| CAWGRRGRYEQYF | 697 | TCRBV30-01 | TCRBJ02-07 |
| CSADRVTHEQYF | 698 | TCRBV20-X | TCRBJ02-07 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CAWTRGTPDTQYF | 699 | TCRBV30-01 | TCRBJ02-03 |
| CASSYLALSYEQYF | 700 | TCRBV06 | TCRBJ02-07 |
| CASSLRQGRGNQPQHF | 701 | TCRBV12-X | TCRBJ01-05 |
| CSARGSGRSSDTQYF | 702 | TCRBV20-X | TCRBJ02-03 |
| CAISGGPEEQYF | 703 | TCRBV10-03 | TCRBJ02-07 |
| CASSQPSPSTDTQYF | 704 | TCRBV04-01 | TCRBJ02-03 |
| CASSLEGDTEAFF | 705 | TCRBV19-01 | TCRBJ01-01 |
| CASSQDLTREAFF | 706 | TCRBV03-01/03-02 | TCRBJ01-01 |
| CASSRTRTSYEQYF | 707 | TCRBV28-01 | TCRBJ02-07 |
| CASSRGWTSGSYEQYF | 708 | TCRBV07 | TCRBJ02-07 |
| CASSPPDENTQYF | 709 | TCRBV18-01 | TCRBJ02-03 |
| CASSLAPRDRGNQPQHF | 710 | TCRBV07 | TCRBJ01-05 |
| CASSTQGGGTDTQYF | 711 | TCRBV28-01 | TCRBJ02-03 |
| CSARLAGAGTGELFF | 712 | TCRBV20-X | TCRBJ02-02 |
| CASSSDRDGEAFF | 713 | TCRBV11 | TCRBJ01-01 |
| CSARSVPTNTGELFF | 714 | TCRBV20-X | TCRBJ02-02 |
| CASSPPRGPTYNEQFF | 715 | TCRBV18-01 | TCRBJ02-01 |
| CASSPRDNQNTEAFF | 716 | TCRBV18-01 | TCRBJ01-01 |
| CASSTGTQYYEQYF | 717 | TCRBV19-01 | TCRBJ02-07 |
| CASSQGLDEQYF | 718 | TCRBV05-01 | TCRBJ02-07 |
| CATSRASRVSNQPQHF | 719 | TCRBV15-01 | TCRBJ01-05 |
| CASSQEGSGGSYEQFF | 720 | TCRBV04-02 | TCRBJ02-01 |
| CSATGLAGDRSSYEQYF | 721 | TCRBV20-X | TCRBJ02-07 |
| CSASPEGDTQYF | 722 | TCRBV20-X | TCRBJ02-03 |
| CASIPGLSYNEQFF | 723 | TCRBV12-X | TCRBJ02-01 |
| CSASNQNQPQHF | 724 | TCRBV20-X | TCRBJ01-05 |
| CASSPGASGGAKETQYF | 725 | TCRBV07 | TCRBJ02-05 |
| CSARGQPTNTGELFF | 726 | TCRBV20-X | TCRBJ02-02 |
| CASIRPNTGELFF | 727 | TCRBV27-01 | TCRBJ02-02 |
| CASSSYREYTEAFF | 728 | TCRBV18-01 | TCRBJ01-01 |
| CSARNEGPETQYF | 729 | TCRBV20-X | TCRBJ02-05 |
| CASSFLTVPYEQYF | 730 | TCRBV27-01 | TCRBJ02-07 |
| CSVRVANEQFF | 731 | TCRBV29-01 | TCRBJ02-01 |
| CASSQESGTYNSPLHF | 732 | TCRBV04-01 | TCRBJ01-06 |
| CASSPIARNTEAFF | 733 | TCRBV18-01 | TCRBJ01-01 |
| CASKRQGAYEQYF | 734 | TCRBV27-01 | TCRBJ02-07 |
| CATSREAGGHEKLFF | 735 | TCRBV15-01 | TCRBJ01-04 |
| CASSPVGPYGYTF | 736 | TCRBV05-04 | TCRBJ01-02 |
| CASSELGLNTEAFF | 737 | TCRBV03-01/03-02 | TCRBJ01-01 |
| CAISELRQETQYF | 738 | TCRBV10-03 | TCRBJ02-05 |
| CASSLVGWDTEAFF | 739 | TCRBV13-01 | TCRBJ01-01 |
| CASSLQGQNEKLFF | 740 | TCRBV09-01 | TCRBJ01-04 |
| CSALRAPYNEQFF | 741 | TCRBV20-X | TCRBJ02-01 |
| CSASSVEDEQFF | 742 | TCRBV20-X | TCRBJ02-01 |
| CASTSLGRNYGYTF | 743 | TCRBV05-05 | TCRBJ01-02 |
| CSAKTGGDGTGELFF | 744 | TCRBV20-X | TCRBJ02-02 |
| CSARDKTGFRYGYTF | 745 | TCRBV20-X | TCRBJ01-02 |
| CASSFGLAGDPDTQYF | 746 | TCRBV12-X | TCRBJ02-03 |
| CASSRGGGSPQETQYF | 747 | TCRBV05-04 | TCRBJ02-05 |
| CASSGSGGRSYEQYF | 748 | TCRBV27-01 | TCRBJ02-07 |
| CASSKGLAEISYEQYF | 749 | TCRBV21-01 | TCRBJ02-07 |
| CASSPRDSQNTEAFF | 750 | TCRBV18-01 | TCRBJ01-01 |
| CASSYLTLSYEQYF | 751 | TCRBV06 | TCRBJ02-07 |
| CSAGLAPYNEQFF | 752 | TCRBV20-X | TCRBJ02-01 |
| CSARAAGGGTGELFF | 753 | TCRBV20-X | TCRBJ02-02 |
| CSARFSGGGTGELFF | 754 | TCRBV20-X | TCRBJ02-02 |
| CASNGWENTEAFF | 755 | TCRBV02-01 | TCRBJ01-01 |
| CASSPGLAGRTDTQYF | 756 | TCRBV10-01 | TCRBJ02-03 |
| CASSQEGAGSYEQYF | 757 | TCRBV14-01 | TCRBJ02-07 |
| CASSENRVEETQYF | 758 | TCRBV25-01 | TCRBJ02-05 |
| CASSLLAMGETQYF | 759 | TCRBV07 | TCRBJ02-05 |
| CASSIAPGDSYNEQFF | 760 | TCRBV19-01 | TCRBJ02-01 |
| CSAPGVPYNEQFF | 761 | TCRBV20-01 | TCRBJ02-01 |
| CAIRQGQTYEQYF | 762 | TCRBV10-03 | TCRBJ02-07 |
| CAIREGQEETQYF | 763 | TCRBV10-03 | TCRBJ02-05 |
| CASSFRDLIYGYTF | 764 | TCRBV28-01 | TCRBJ01-02 |
| CSVEEVQGAGGYTF | 765 | TCRBV29-01 | TCRBJ01-02 |
| CSARLGTPQETQYF | 766 | TCRBV20-X | TCRBJ02-05 |
| CSARVGGSGTGELFF | 767 | TCRBV20-X | TCRBJ02-02 |
| CASRQGKAGELFF | 768 | TCRBV19-01 | TCRBJ02-02 |
| CASSFGQGEAGELFF | 769 | TCRBV12-X | TCRBJ02-02 |
| CATRRGTTDTQYF | 770 | TCRBV06 | TCRBJ02-03 |
| CAGSLSSNQPQHF | 771 | TCRBV06 | TCRBJ01-05 |
| CASSQWRGDEQYF | 772 | TCRBV03-01/03-02 | TCRBJ02-07 |
| CASSLGQGGRYGYTF | 773 | TCRBV27-01 | TCRBJ01-02 |
| CSARSGGAGTGELFF | 774 | TCRBV20-X | TCRBJ02-02 |
| CASSPVPSGYTF | 775 | TCRBV18-01 | TCRBJ01-02 |
| CSASTGSTNEKLFF | 776 | TCRBV29-01 | TCRBJ01-04 |
| CAAGLETQYF | 777 | TCRBV03-01/03-02 | TCRBJ02-05 |
| CASSPDQGANYGYTF | 778 | TCRBV05-01 | TCRBJ01-02 |
| CSARRGGAGTGELFF | 779 | TCRBV20-X | TCRBJ02-02 |
| CSAPRPPHNEQFF | 780 | TCRBV20-X | TCRBJ02-01 |
| CSARAVVEQYF | 781 | TCRBV20-X | TCRBJ02-07 |
| CASRRDRGDIQYF | 782 | TCRBV27-01 | TCRBJ02-04 |
| CSAPFPGQGYNEQFF | 783 | TCRBV20-X | TCRBJ02-01 |
| CASSLELANTGELFF | 784 | TCRBV05-01 | TCRBJ02-02 |
| CASSPLGSLTYEQYF | 785 | TCRBV18-01 | TCRBJ02-07 |
| CASSLDSRSETQYF | 786 | TCRBV05-04 | TCRBJ02-05 |
| CSAAQDEETQYF | 787 | TCRBV20-X | TCRBJ02-05 |
| CASSLNQGALSEQYF | 788 | TCRBV07 | TCRBJ02-07 |
| CASSIYSGAYEQYF | 789 | TCRBV19-01 | TCRBJ02-07 |
| CASSQDLAGRNYNEQFF | 790 | TCRBV04-03 | TCRBJ02-01 |
| CASSSGRGNEKLFF | 791 | TCRBV06 | TCRBJ01-04 |
| CASAPGQNTEAFF | 792 | TCRBV07 | TCRBJ01-01 |
| CASRYRDQYF | 793 | TCRBV06 | TCRBJ01-02 |
| CASSDSGSSDTQYF | 794 | TCRBV06 | TCRBJ02-03 |
| CSARDEGRQFF | 795 | TCRBV20-01 | TCRBJ02-01 |
| CASSIGRGDSPLHF | 796 | TCRBV27-01 | TCRBJ01-06 |
| CASSYQTGGGYNEQFF | 797 | TCRBV06 | TCRBJ02-01 |
| CASSPTEPSGNTIYF | 798 | TCRBV05-01 | TCRBJ01-03 |
| CASSINAGNYGYTF | 799 | TCRBV19-01 | TCRBJ01-02 |
| CASSGTGAKNIQYF | 800 | TCRBV10-02 | TCRBJ02-04 |
| CATSGTGIPGELFF | 801 | TCRBV24-01 | TCRBJ02-02 |
| CASMTGTGNEKLFF | 802 | TCRBV06 | TCRBJ01-04 |
| CASSPWREVNTEAFF | 803 | TCRBV18-01 | TCRBJ01-01 |
| CSARRVTEQYF | 804 | TCRBV20-01 | TCRBJ02-07 |
| CASSTDGTGDTEAFF | 805 | TCRBV19-01 | TCRBJ01-01 |
| CASSSIRSGANVLTF | 806 | TCRBV05-05 | TCRBJ02-06 |
| CASSQGLAGPRDNEQFF | 807 | TCRBV04-01 | TCRBJ02-01 |
| CSAKGGGPDTQYF | 808 | TCRBV20-X | TCRBJ02-03 |
| CSAPLSLNTEAFF | 809 | TCRBV20-X | TCRBJ01-01 |
| CSAPTPPYNEQFF | 810 | TCRBV20-X | TCRBJ02-01 |
| CSARAGGAGTGELFF | 811 | TCRBV20-X | TCRBJ02-02 |
| CSARGSARPTDTQYF | 812 | TCRBV20-X | TCRBJ02-03 |
| CSAGTGTPNTGELFF | 813 | TCRBV20-X | TCRBJ02-02 |
| CASRGGQGLTDTQYF | 814 | TCRBV28-01 | TCRBJ02-03 |
| CASSSSQTASYEQYF | 815 | TCRBV11 | TCRBJ02-07 |
| CASSFNSRRNQPQHF | 816 | TCRBV27-01 | TCRBJ01-05 |
| CASSVGSTGGNTEAFF | 817 | TCRBV09-01 | TCRBJ01-01 |
| CASSPRLGSETQYF | 818 | TCRBV12-X | TCRBJ02-05 |
| CASSLPPELNEQFF | 819 | TCRBV11 | TCRBJ02-01 |
| CASNPAENTGELFF | 820 | TCRBV05-01 | TCRBJ02-02 |
| CASSKDRSETQYF | 821 | TCRBV12-03/12-04 | TCRBJ02-05 |
| CASSDRGPFSGANVLTF | 822 | TCRBV19-01 | TCRBJ02-06 |
| CAWRPAGRNQPQHF | 823 | TCRBV30-01 | TCRBJ01-05 |
| CASSEDIAGNTIYF | 824 | TCRBV10-01 | TCRBJ01-03 |
| CASSLDGTYQPQHF | 825 | TCRBV06 | TCRBJ01-05 |
| CSARDKYEAFF | 826 | TCRBV20-01 | TCRBJ01-01 |
| CATSDLPTNTGELFF | 827 | TCRBV24-01 | TCRBJ02-02 |
| CASRSRLYGYTF | 828 | TCRBV28-01 | TCRBJ01-02 |
| CSARDSLAGRSYNEQFF | 829 | TCRBV20-X | TCRBJ02-01 |
| CASSVQWTDTQYF | 830 | TCRBV09-01 | TCRBJ02-03 |
| CASRRGLAGGTGELFF | 831 | TCRBV27-01 | TCRBJ02-02 |
| CASSLGPASHEQYF | 832 | TCRBV07 | TCRBJ02-07 |
| CASSGSGGKDTQYF | 833 | TCRBV02-01 | TCRBJ02-03 |
| CASIVDRVNTEAFF | 834 | TCRBV28-01 | TCRBJ01-01 |
| CAIRMGQQETQYF | 835 | TCRBV10-03 | TCRBJ02-05 |
| CASSTGHYGYTF | 836 | TCRBV11 | TCRBJ01-02 |
| CSAREAGAGTGELFF | 837 | TCRBV20-X | TCRBJ02-02 |
| CSARKAGAGTGELFF | 838 | TCRBV20-X | TCRBJ02-02 |
| CSARDGTPEQYF | 839 | TCRBV20-X | TCRBJ02-07 |
| CASTSWGGSGYTF | 840 | TCRBV06 | TCRBJ01-02 |
| CASKRGHLYEQYF | 841 | TCRBV06 | TCRBJ02-07 |
| CASSLVWSYEQYF | 842 | TCRBV07 | TCRBJ02-07 |
| CRARRGGAGTGELFF | 843 | TCRBV20-X | TCRBJ02-02 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CATSRGGTSGRNEQFF | 844 | TCRBV15-01 | TCRBJ02-01 |
| CSARASPTNTGELFF | 845 | TCRBV20-X | TCRBJ02-02 |
| CASSLAGGPGTDTQYF | 846 | TCRBV07 | TCRBJ02-03 |
| CASSRDREVDQPQHF | 847 | TCRBV19-01 | TCRBJ01-05 |
| CASGLGGRGTEAFF | 848 | TCRBV12-X | TCRBJ01-01 |
| CAWSRRGLYEQYF | 849 | TCRBV30-01 | TCRBJ02-07 |
| CASSRAGGYEQYF | 850 | TCRBV06 | TCRBJ02-07 |
| CASSQMTGTDTQYF | 851 | TCRBV11 | TCRBJ02-03 |
| CASSKPGRVNTEAFF | 852 | TCRBV19-01 | TCRBJ01-01 |
| CASSQGAAREQYF | 853 | TCRBV14-01 | TCRBJ02-07 |
| CASSLAAGTYLLNTEAFF | 854 | TCRBV07 | TCRBJ01-01 |
| CSARGTPANTGELFF | 855 | TCRBV20-X | TCRBJ02-02 |
| CASSLGTSNYNEQFF | 856 | TCRBV11 | TCRBJ02-01 |
| CASSVDHNYGYTF | 857 | TCRBV28-01 | TCRBJ01-02 |
| CASSFEANYGNTIYF | 858 | TCRBV12-X | TCRBJ01-03 |
| CASSRDRVLSYEQYF | 859 | TCRBV20-01 | TCRBJ02-07 |
| CASSFLAGGITSTDTQYF | 860 | TCRBV07 | TCRBJ02-03 |
| CASSPGHPSGANVLTF | 861 | TCRBV12-X | TCRBJ02-06 |
| CASNAAGGTDTQYF | 862 | TCRBV19-01 | TCRBJ02-03 |
| CASSPLGGRRPYEQYF | 863 | TCRBV05-05 | TCRBJ02-07 |
| CSAPLAPHNEQFF | 864 | TCRBV20-X | TCRBJ02-01 |
| CATSGIGGDQPQHF | 865 | TCRBV24-01 | TCRBJ01-05 |
| CSAKGRGTNTGELFF | 866 | TCRBV20-X | TCRBJ02-02 |
| CASSPQEGLGANVLTF | 867 | TCRBV18-01 | TCRBJ02-06 |
| CSASRPPDNEQFF | 868 | TCRBV20-01 | TCRBJ02-01 |
| CASSLEPRTNTGELFF | 869 | TCRBV11 | TCRBJ02-02 |
| CASSDRGPGNQPQHF | 870 | TCRBV19-01 | TCRBJ01-05 |
| CASSIGEKTQYF | 871 | TCRBV19-01 | TCRBJ02-05 |
| CASSLGAHSNTGELFF | 872 | TCRBV07 | TCRBJ02-02 |
| CASSFAGLYNSPLHF | 873 | TCRBV27-01 | TCRBJ01-06 |
| CSARLSGGGTGELFF | 874 | TCRBV20-X | TCRBJ02-02 |
| CSARIAGGGTGELFF | 875 | TCRBV20-X | TCRBJ02-02 |
| CSARVEGWETQYF | 876 | TCRBV20-X | TCRBJ02-05 |
| CAWSRRGRYEQYF | 877 | TCRBV30-01 | TCRBJ02-07 |
| CASMTGKGDEKLFF | 878 | TCRBV06 | TCRBJ01-04 |
| CASSEQRGHEKLFF | 879 | TCRBV06 | TCRBJ01-04 |
| CSARGWASGRTYEQYF | 880 | TCRBV20-X | TCRBJ02-07 |
| CASSLLGQGLNTEAFF | 881 | TCRBV14-01 | TCRBJ01-01 |
| CSAPRPPYNEQFF | 882 | TCRBV20-X | TCRBJ02-01 |
| CSAREWGGLYEQYF | 883 | TCRBV20-X | TCRBJ02-07 |
| CSARDREGLQETQYF | 884 | TCRBV20-X | TCRBJ02-05 |
| CSARMGGAGTGELFF | 885 | TCRBV20-X | TCRBJ02-02 |
| CSARARTAGTGELFF | 886 | TCRBV20-X | TCRBJ02-02 |
| CATSDSWLADNEQFF | 887 | TCRBV24-01 | TCRBJ02-01 |
| CASSLVGTSGGARDTQYF | 888 | TCRBV07 | TCRBJ02-03 |
| CATSDLPGASQETQYF | 889 | TCRBV24-01 | TCRBJ02-05 |
| CSAPEPPYNEQFF | 890 | TCRBV20-X | TCRBJ02-01 |
| CASSFQGGRNTIYF | 891 | TCRBV28-01 | TCRBJ01-03 |
| CASSLRDFQETQYF | 892 | TCRBV05-08 | TCRBJ02-05 |
| CASKRQGFYEQYF | 893 | TCRBV28-01 | TCRBJ02-07 |
| CASSSPTSGSNEQFF | 894 | TCRBV07 | TCRBJ02-01 |
| CASSYGSGGPHEQFF | 895 | TCRBV06 | TCRBJ02-01 |
| CASSDGQVDYGYTF | 896 | TCRBV05-01 | TCRBJ01-02 |
| CSARISGGGTGELFF | 897 | TCRBV20-X | TCRBJ02-02 |
| CASSLRTGGTYGYTF | 898 | TCRBV05-06 | TCRBJ01-02 |
| CSASTSTSTDTQYF | 899 | TCRBV29-01 | TCRBJ02-03 |
| CASSAGTSGKNEQFF | 900 | TCRBV10-01 | TCRBJ02-01 |
| CSARAGAQGETQYF | 901 | TCRBV20-X | TCRBJ02-05 |
| CASRLGRGTGELFF | 902 | TCRBV28-01 | TCRBJ02-02 |
| CASSRQGLYGYTF | 903 | TCRBV18-01 | TCRBJ01-02 |
| CASSIDRDRETQYF | 904 | TCRBV07 | TCRBJ02-05 |
| CASSLPAGGEKLFF | 905 | TCRBV05-01 | TCRBJ01-04 |
| CASSLSGTASNTGELFF | 906 | TCRBV07 | TCRBJ02-02 |
| CATSRQGGDQPQHF | 907 | TCRBV24-01 | TCRBJ01-05 |
| CASSLEINYNSPLHF | 908 | TCRBV12-X | TCRBJ01-06 |
| CASTGPGTGTEAFF | 909 | TCRBV05-01 | TCRBJ01-01 |
| CSARGQPSNTGELFF | 910 | TCRBV20-X | TCRBJ02-02 |
| CASIGESSYNSPLHF | 911 | TCRBV06 | TCRBJ01-06 |
| CSARGSGRTSDTQYF | 912 | TCRBV20-X | TCRBJ02-03 |
| CATSDNREGQETQYF | 913 | TCRBV24-01 | TCRBJ02-05 |
| CSVEPTEAFF | 914 | TCRBV29-01 | TCRBJ01-01 |
| CASSSPGINEQFF | 915 | TCRBV05-01 | TCRBJ02-01 |
| CASSQDWGGDTQYF | 916 | TCRBV14-01 | TCRBJ02-03 |
| CAIREGQNNEQFF | 917 | TCRBV10-03 | TCRBJ02-01 |
| CSARGQPSTNEKLFF | 918 | TCRBV20-X | TCRBJ01-04 |
| CAIRPTGGNTGELFF | 919 | TCRBV10-03 | TCRBJ02-02 |
| CSARLGGAGTGELFF | 920 | TCRBV20-X | TCRBJ02-02 |
| CSARMAGGGTGELFF | 921 | TCRBV20-X | TCRBJ02-02 |
| CASSLPTSGSPNEQFF | 922 | TCRBV13-01 | TCRBJ02-01 |
| CASSSRPTVSNQPQHF | 923 | TCRBV12-X | TCRBJ01-05 |
| CASTPDGRVYNEQFF | 924 | TCRBV19-01 | TCRBJ02-01 |
| CASRGRLYGYTF | 925 | TCRBV28-01 | TCRBJ01-02 |
| CASTLNSNQPQHF | 926 | TCRBV28-01 | TCRBJ01-05 |
| CSAPNPPYNEQFF | 927 | TCRBV20-X | TCRBJ02-01 |
| CASSSDRFDEQFF | 928 | TCRBV07 | TCRBJ02-01 |
| CASSRTDGNEKLFF | 929 | TCRBV06 | TCRBJ01-04 |
| CASSPGGGRIDTQYF | 930 | TCRBV12-X | TCRBJ02-03 |
| CASNPAGGRAGELFF | 931 | TCRBV06 | TCRBJ02-02 |
| CSVRMSGETQYF | 932 | TCRBV20-X | TCRBJ02-05 |
| CATSDVGRNQPQHF | 933 | TCRBV24-01 | TCRBJ01-05 |
| CSARQGVYYGYTF | 934 | TCRBV20-X | TCRBJ01-02 |
| CSARYSGSGTGELFF | 935 | TCRBV20-X | TCRBJ02-02 |
| CASSLKPAGNYGYTF | 936 | TCRBV07 | TCRBJ01-02 |
| CSARGQGAYNQPQHF | 937 | TCRBV20-X | TCRBJ01-05 |
| CASRVYSNQPQHF | 938 | TCRBV07 | TCRBJ01-05 |
| CASSLRPDSGANVLTF | 939 | TCRBV07 | TCRBJ02-06 |
| CSARDWYTF | 940 | TCRBV20-01 | TCRBJ01-02 |
| CASRLGQGSYEQYF | 941 | TCRBV05-06 | TCRBJ02-07 |
| CASRPQGSNYGYTF | 942 | TCRBV05-01 | TCRBJ01-02 |
| CASSIPWASGNTGELFF | 943 | TCRBV19-01 | TCRBJ02-02 |
| CASRSGTRGFF | 944 | TCRBV06 | TCRBJ02-01 |
| CASSIRTANEKLFF | 945 | TCRBV19-01 | TCRBJ01-04 |
| CASSPSGSRGTGELFF | 946 | TCRBV07 | TCRBJ02-02 |
| CASSSPGRDTGELFF | 947 | TCRBV05-04 | TCRBJ02-02 |
| CASSQEQGISYEQYF | 948 | TCRBV14-01 | TCRBJ02-07 |
| CASSSGSGGYTDTQYF | 949 | TCRBV28-01 | TCRBJ02-03 |
| CASSPTSGTGANVLTF | 950 | TCRBV05-01 | TCRBJ02-06 |
| CSARDGSRSNYGYTF | 951 | TCRBV20-X | TCRBJ01-02 |
| CASSYLHISYEQYF | 952 | TCRBV06 | TCRBJ02-07 |
| CATTGGVNTGELFF | 953 | TCRBV28-01 | TCRBJ02-02 |
| CASSLAPLSDTQYF | 954 | TCRBV07 | TCRBJ02-03 |
| CASSPPSGLENTGELFF | 955 | TCRBV18-01 | TCRBJ02-02 |
| CSASLSLNTEAFF | 956 | TCRBV20-X | TCRBJ01-01 |
| CASSSGQGRTYEQYF | 957 | TCRBV06 | TCRBJ02-07 |
| CASSFEADYNSPLHF | 958 | TCRBV12-X | TCRBJ01-06 |
| CASSLDSGNKNIQYF | 959 | TCRBV05-04 | TCRBJ02-04 |
| CASSQARDSFNYGYTF | 960 | TCRBV04-01 | TCRBJ01-02 |
| CASSELSGKTGELFF | 961 | TCRBV06 | TCRBJ02-02 |
| CASSVGTGAGGADTQYF | 962 | TCRBV09-01 | TCRBJ02-03 |
| CSVEARGWTGELFF | 963 | TCRBV29-01 | TCRBJ02-02 |
| CSARTSGSGNGELFF | 964 | TCRBV20-X | TCRBJ02-02 |
| CASSLALIAGGSTDTQYF | 965 | TCRBV07 | TCRBJ02-03 |
| CSASLAPYNEQFF | 966 | TCRBV20-01 | TCRBJ02-01 |
| CASSLERRENIQYF | 967 | TCRBV07 | TCRBJ02-04 |
| CSARVSGGGTGELFF | 968 | TCRBV20-X | TCRBJ02-02 |
| CASSLETNYGNTIYF | 969 | TCRBV12-X | TCRBJ01-03 |
| CASSRGQGLAQPQHF | 970 | TCRBV03-01/03-02 | TCRBJ01-05 |
| CSARDLAGNGETQYF | 971 | TCRBV20-X | TCRBJ02-05 |
| CASSLLGGGGSEAFF | 972 | TCRBV07 | TCRBJ01-01 |
| CASKGVYNSPLHF | 973 | TCRBV28-01 | TCRBJ01-06 |
| CASSVGTRTADTQYF | 974 | TCRBV09-01 | TCRBJ02-03 |
| CSARFRGATGELFF | 975 | TCRBV20-X | TCRBJ02-02 |
| CASRPGTGGRGNEKLFF | 976 | TCRBV06 | TCRBJ01-04 |
| CASSINRWDGYTF | 977 | TCRBV19-01 | TCRBJ01-02 |
| CASGVGTDTQYF | 978 | TCRBV03-01/03-02 | TCRBJ02-03 |
| CASSIETDYEQYF | 979 | TCRBV19-01 | TCRBJ02-07 |
| CAISGGRVLNTEAFF | 980 | TCRBV10-03 | TCRBJ01-01 |
| CASSQAMASGYNEQFF | 981 | TCRBV14-01 | TCRBJ02-01 |
| CASRREDTDTQYF | 982 | TCRBV04-02 | TCRBJ02-03 |
| CASSPETPTGELFF | 983 | TCRBV18-01 | TCRBJ02-02 |
| CASSQDRVLSYEQYF | 984 | TCRBV02-01 | TCRBJ02-07 |
| CASSYLSLSYEQYF | 985 | TCRBV06 | TCRBJ02-07 |
| CASSLEAADTQYF | 986 | TCRBV11 | TCRBJ02-03 |
| CASRPQLATNEKLFF | 987 | TCRBV19-01 | TCRBJ01-04 |
| CASSVGVARVGEKLFF | 988 | TCRBV09-01 | TCRBJ01-04 |
| CSAPPGMNEQFF | 989 | TCRBV20-X | TCRBJ02-01 |
| CASSLTGVSTEAFF | 990 | TCRBV05-04 | TCRBJ01-01 |
| CASSQGQSANTGELFF | 991 | TCRBV03-01/ | TCRBJ02-02 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASTGGIADTQYF | 992 | TCRBV07 | TCRBJ02-03 |
| CASSLVGSGTYNEQFF | 993 | TCRBV07 | TCRBJ02-01 |
| CASSSGRGSEKLFF | 994 | TCRBV06 | TCRBJ01-04 |
| CAISVGPISGANVLTF | 995 | TCRBV10-03 | TCRBJ02-06 |
| CASSLAPRDLGNQPQHF | 996 | TCRBV07 | TCRBJ01-05 |
| CSARSSGRVSDTQYF | 997 | TCRBV20-X | TCRBJ02-03 |
| CASRDSPGNQPQHF | 998 | TCRBV19-01 | TCRBJ01-05 |
| CSAPIPGQNEKLFF | 999 | TCRBV20-X | TCRBJ01-04 |
| CASSYLLLTYEQYF | 1000 | TCRBV06 | TCRBJ02-07 |
| CASSPTGRETQYF | 1001 | TCRBV05-04 | TCRBJ02-05 |
| CASRSPGGPQHF | 1002 | TCRBV28-01 | TCRBJ01-05 |
| CASSPYGTENTEAFF | 1003 | TCRBV18-01 | TCRBJ01-01 |
| CSARVSGSGTGELFF | 1004 | TCRBV20-X | TCRBJ02-02 |
| CSATSGVNSPLHF | 1005 | TCRBV20-X | TCRBJ01-06 |
| CATSSGGRRYNEQFF | 1006 | TCRBV15-01 | TCRBJ02-01 |
| CASSLAPGAPETQYF | 1007 | TCRBV07 | TCRBJ02-05 |
| CASSYPESGSSYNEQFF | 1008 | TCRBV06 | TCRBJ02-01 |
| CASSESALNTGELFF | 1009 | TCRBV10-01 | TCRBJ02-02 |
| CASRRTGPNTGELFF | 1010 | TCRBV07 | TCRBJ02-02 |
| CSARRAGAGTGELFF | 1011 | TCRBV20-X | TCRBJ02-02 |
| CASSLGAASYEQYF | 1012 | TCRBV07 | TCRBJ02-07 |
| CSARGSGGGTGELFF | 1013 | TCRBV20-X | TCRBJ02-02 |
| CASRPAGGGTDTQYF | 1014 | TCRBV06 | TCRBJ02-03 |
| CASSPDRGYSTNEKLFF | 1015 | TCRBV16-01 | TCRBJ01-04 |
| CATSGTTYQPQHF | 1016 | TCRBV15-01 | TCRBJ01-05 |
| CASSPSSGHLNEQFF | 1017 | TCRBV07 | TCRBJ02-01 |
| CASSPLAGGPRELFF | 1018 | TCRBV12-X | TCRBJ02-02 |
| CSASADEETQYF | 404 | TCRBV20-X | TCRBJ02-05 |
| CASSAGTGGYEQFF | 1019 | TCRBV25-01 | TCRBJ02-01 |
| CAWRQGQPNSPLHF | 1020 | TCRBV30-01 | TCRBJ01-06 |
| CAWRGTGKNQPQHF | 1021 | TCRBV30-01 | TCRBJ01-05 |
| CASSLDRVRNTQYF | 1022 | TCRBV05-01 | TCRBJ02-03 |
| CASSLPTGPNYEQYF | 1023 | TCRBV28-01 | TCRBJ02-07 |
| CASSQFRDTSYEQYF | 1024 | TCRBV16-01 | TCRBJ02-07 |
| CSAIAPPYNEQFF | 1025 | TCRBV20-X | TCRBJ02-01 |
| CSARLAGGGTGELFF | 1026 | TCRBV20-X | TCRBJ02-02 |
| CASSGGQGPGYTF | 1027 | TCRBV28-01 | TCRBJ01-02 |
| CASSPDRPSTDTQYF | 1028 | TCRBV05-04 | TCRBJ02-03 |
| CSVRTSAETQYF | 1029 | TCRBV20-X | TCRBJ02-05 |
| CASRRGTDQPQHF | 1030 | TCRBV05-01 | TCRBJ01-05 |
| CASSFERNYNSPLHF | 1031 | TCRBV12-X | TCRBJ01-06 |
| CASSPPGGLENTGELFF | 1032 | TCRBV18-01 | TCRBJ02-02 |
| CASSPPEGLENTGELFF | 1033 | TCRBV18-01 | TCRBJ02-02 |
| CASSLIGGMETQYF | 1034 | TCRBV12-X | TCRBJ02-05 |
| CSATTTGAEAFF | 1035 | TCRBV20-X | TCRBJ01-01 |
| CASSDKGRTGELFF | 1036 | TCRBV02-01 | TCRBJ02-02 |
| CASSLALVGSTDTQYF | 1037 | TCRBV05-04 | TCRBJ02-03 |
| CASSVEGEGLQETQYF | 1038 | TCRBV09-01 | TCRBJ02-05 |
| CASSNRVSGANVLTF | 1039 | TCRBV19-01 | TCRBJ02-06 |
| CSAAGQGSTDTQYF | 1040 | TCRBV20-X | TCRBJ02-03 |
| CASSTDRDREQFF | 1041 | TCRBV19-01 | TCRBJ02-01 |
| CAWSRRGAYEQYF | 1042 | TCRBV30-01 | TCRBJ02-07 |
| CSARRAGAGTDTQYF | 1043 | TCRBV20-X | TCRBJ02-03 |
| CASSSGSIAEAFF | 1044 | TCRBV06 | TCRBJ01-01 |
| CASSTHDRGEQYF | 1045 | TCRBV07 | TCRBJ02-07 |
| CASSLAGLNEQYF | 1046 | TCRBV07 | TCRBJ02-07 |
| CASSLAPRDRGNSPLHF | 1047 | TCRBV07 | TCRBJ01-06 |
| CASNRRQGYNEQFF | 1048 | TCRBV06 | TCRBJ02-01 |
| CASSRGGRGNEQFF | 1049 | TCRBV05-04 | TCRBJ02-01 |
| CASRETGEGPQHF | 1050 | TCRBV02-01 | TCRBJ01-05 |
| CASSVLQGLSTDTQYF | 1051 | TCRBV09-01 | TCRBJ02-03 |
| CASSVSGGNTIYF | 1052 | TCRBV19-01 | TCRBJ01-03 |
| CASSLSPRGRGYGYTF | 178 | TCRBV07 | TCRBJ01-02 |
| CASSLMSGSGNEQFF | 1053 | TCRBV07 | TCRBJ02-01 |
| CASSFRRTDYEQYF | 1054 | TCRBV27-01 | TCRBJ02-07 |
| CASSRGLVVYEQYF | 1055 | TCRBV07 | TCRBJ02-07 |
| CASLAPGELFF | 1056 | TCRBV12-03/12-04 | TCRBJ02-02 |
| CSARQVVEQYF | 1057 | TCRBV20-X | TCRBJ02-07 |
| CASSLDLGPGNEQFF | 1058 | TCRBV05-04 | TCRBJ02-01 |
| CASSRQGSLNEQFF | 1059 | TCRBV02-01 | TCRBJ02-01 |
| CASSRETANYGYTF | 1060 | TCRBV14-01 | TCRBJ01-02 |
| CASSRGQKGEKLFF | 1061 | TCRBV04-01 | TCRBJ01-04 |
| CASRGGVRSYEQYF | 1062 | TCRBV07 | TCRBJ02-07 |
| CASSLSPLSETQYF | 1063 | TCRBV07 | TCRBJ02-05 |
| CASSPMGGRGNEQFF | 1064 | TCRBV28-01 | TCRBJ02-01 |
| CASQLGYEQYF | 1065 | TCRBV27-01 | TCRBJ02-07 |
| CATSREDRGLSYEQYF | 1066 | TCRBV15-01 | TCRBJ02-07 |
| CSARQQPSNTGELFF | 1067 | TCRBV20-X | TCRBJ02-02 |
| CASSQDGGSWYEQYF | 1068 | TCRBV03-01/03-02 | TCRBJ02-07 |
| CSAPQGVAYEQYF | 1069 | TCRBV20-X | TCRBJ02-07 |
| CASSQEQGVNQPQHF | 1070 | TCRBV03-01/03-02 | TCRBJ01-05 |
| CASSPRETGGGGYTF | 1071 | TCRBV05-01 | TCRBJ01-02 |
| CARGTGFSEQYF | 1072 | TCRBV02-01 | TCRBJ02-07 |
| CASNGGVRETQYF | 1073 | TCRBV28-01 | TCRBJ02-05 |
| CSARHDGDTEAFF | 1074 | TCRBV20-X | TCRBJ01-01 |
| CASSLVLGNTQYF | 1075 | TCRBV05-01 | TCRBJ02-03 |
| CASSTRRGDEQYF | 1076 | TCRBV19-01 | TCRBJ02-07 |
| CASSLGQGRRTYEQYF | 1077 | TCRBV07 | TCRBJ02-07 |
| CSAGPLAGGYEQYF | 1078 | TCRBV20-X | TCRBJ02-07 |
| CASTGGGANVLTF | 1079 | TCRBV10-02 | TCRBJ02-06 |
| CASNPSGGSPLHF | 1080 | TCRBV02-01 | TCRBJ01-06 |
| CASSLGNSGDPPDTQYF | 1081 | TCRBV05-01 | TCRBJ02-03 |
| CASSTSSGSPYNEQFF | 1082 | TCRBV19-01 | TCRBJ02-01 |
| CSARISGSGTGELFF | 1083 | TCRBV20-X | TCRBJ02-02 |
| CSARVGGAGTGELFF | 1084 | TCRBV20-X | TCRBJ02-02 |
| CASSLGLAGGRADTQYF | 1085 | TCRBV13-01 | TCRBJ02-03 |
| CASKRGTHTDTQYF | 1086 | TCRBV10-02 | TCRBJ02-03 |
| CSARSSGRASDTQYF | 1087 | TCRBV20-X | TCRBJ02-03 |
| CSAFRGGYEQYF | 1088 | TCRBV20-X | TCRBJ02-07 |
| CATSDSNLAGGYNEQFF | 1089 | TCRBV24-01 | TCRBJ02-01 |
| CASSLSSGVSGYTF | 1090 | TCRBV12-X | TCRBJ01-02 |
| CASSNRRRATNEKLFF | 1091 | TCRBV28-01 | TCRBJ01-04 |
| CASGLETQYF | 1092 | TCRBV03-01/03-02 | TCRBJ02-05 |
| CASSVDRVLSYEQYF | 1093 | TCRBV02-01 | TCRBJ02-07 |
| CASSLAERPETQYF | 1094 | TCRBV07 | TCRBJ02-05 |
| CAWNRRGLYEQYF | 1095 | TCRBV30-01 | TCRBJ02-07 |
| CSVDLGGEQYF | 1096 | TCRBV29-01 | TCRBJ02-07 |
| CASISGQGGQPQHF | 1097 | TCRBV19-01 | TCRBJ01-05 |
| CASKTGAYNSPLHF | 1098 | TCRBV07 | TCRBJ01-06 |
| CSARDRPTTSGANVLTF | 1099 | TCRBV20-X | TCRBJ02-06 |
| CASSFEGNYGNTIYF | 1100 | TCRBV12-X | TCRBJ01-03 |
| CASSFSSANNEQFF | 1101 | TCRBV06 | TCRBJ02-01 |
| CATSRELAGGSDTQYF | 1102 | TCRBV15-01 | TCRBJ02-03 |
| CASSEDRVPSYEQYF | 1103 | TCRBV06 | TCRBJ02-07 |
| CASSPSRGSYNEQFF | 1104 | TCRBV04-01 | TCRBJ02-01 |
| CASSSGGQGHYGYTF | 1105 | TCRBV05-01 | TCRBJ01-02 |
| CASSIRPSGANVLTF | 1106 | TCRBV06 | TCRBJ02-06 |
| CASSDPLAGGRTDTQYF | 1107 | TCRBV02-01 | TCRBJ02-03 |
| CSARDPGQPSGANVLTF | 1108 | TCRBV20-X | TCRBJ02-06 |
| CASSRPRDYEQYF | 1109 | TCRBV12-03/12-04 | TCRBJ02-07 |
| CASSSDRKGYEQYF | 1110 | TCRBV27-01 | TCRBJ02-07 |
| CASSLLRGYSSYEQYF | 1111 | TCRBV28-01 | TCRBJ02-07 |
| CAIKEWSSGNTIYF | 1112 | TCRBV10-03 | TCRBJ01-03 |
| CASSQARGQGVTEAFF | 1113 | TCRBV03-01/03-02 | TCRBJ01-01 |
| CASTQRGGANEQFF | 1114 | TCRBV05-01 | TCRBJ02-01 |
| CASSLGSRWGSTDTQYF | 1115 | TCRBV05-01 | TCRBJ02-03 |
| CASSLFSGEGETQYF | 1116 | TCRBV05-05 | TCRBJ02-05 |
| CSARRGGQGTGELFF | 1117 | TCRBV20-X | TCRBJ02-02 |
| CASSYLDLSYEQYF | 1118 | TCRBV06 | TCRBJ02-07 |
| CASSPVSSISYEQYF | 1119 | TCRBV18-01 | TCRBJ02-07 |
| CASSSVDSSYEQYF | 1120 | TCRBV05-01 | TCRBJ02-07 |
| CSVVPGGVDTQYF | 1121 | TCRBV29-01 | TCRBJ02-03 |
| CSAKSPGFTDTQYF | 1122 | TCRBV20-X | TCRBJ02-03 |
| CASSLAGGTFYEQYF | 1123 | TCRBV05-05 | TCRBJ02-07 |
| CASSLGASFSGNTIYF | 1124 | TCRBV07 | TCRBJ01-03 |
| CASSRRLAGGPGTDTQYF | 1125 | TCRBV06 | TCRBJ02-03 |
| CASSEASKGYEQYF | 1126 | TCRBV06 | TCRBJ02-07 |
| CSAGQISNQPQHF | 1127 | TCRBV19-01 | TCRBJ01-05 |
| CASSAPGTSFYEQYF | 1128 | TCRBV09-01 | TCRBJ02-07 |
| CASSQDIGGTYGYTF | 1129 | TCRBV04-02 | TCRBJ01-02 |
| CSARLTSGGGTGELFF | 1130 | TCRBV20-X | TCRBJ02-02 |
| CAWESGRSTDTQYF | 1131 | TCRBV30-01 | TCRBJ02-03 |
| CASSVGLELTDTQYF | 1132 | TCRBV09-01 | TCRBJ02-03 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASSPGGRGDQPQHF | 1133 | TCRBV27-01 | TCRBJ01-05 |
| CASSSAGQDNQPQHF | 1134 | TCRBV05-05 | TCRBJ01-05 |
| CASSPGSLPDTQYF | 1135 | TCRBV19-01 | TCRBJ02-03 |
| CASSLELVDTQYF | 1136 | TCRBV07 | TCRBJ02-03 |
| CASSQWGGSGYTF | 1137 | TCRBV03-01/03-02 | TCRBJ01-02 |
| CASSVWAGRGETQYF | 1138 | TCRBV09-01 | TCRBJ02-05 |
| CSARDGSATQYF | 1139 | TCRBV20-X | TCRBJ02-05 |
| CASSYSGDAADTQYF | 1140 | TCRBV06 | TCRBJ02-03 |
| CASSSVGTTYNEQFF | 1141 | TCRBV05-01 | TCRBJ02-01 |
| CSAYPRLVSYEQYF | 1142 | TCRBV20-X | TCRBJ02-07 |
| CASSSDRFTYNEQFF | 1143 | TCRBV19-01 | TCRBJ02-01 |
| CASSQTGGRSGELFF | 1144 | TCRBV10-02 | TCRBJ02-02 |
| CASSQAPLTDTQYF | 1145 | TCRBV07 | TCRBJ02-03 |
| CSARVLAGGQYNEQFF | 1146 | TCRBV20-X | TCRBJ02-01 |
| CASSFRPRGANVLTF | 1147 | TCRBV07 | TCRBJ02-06 |
| CSARRQPSNTGELFF | 1148 | TCRBV20-X | TCRBJ02-02 |
| CASSPGAAHQPQHF | 1149 | TCRBV07 | TCRBJ01-05 |
| CASSLQAGAYNEQFF | 1150 | TCRBV06 | TCRBJ02-01 |
| CASSLGRNNEQFF | 1151 | TCRBV07 | TCRBJ02-01 |
| CSAPYSGQGYNEQFF | 1152 | TCRBV20-X | TCRBJ02-01 |
| CASTLPGLAGVNEQFF | 1153 | TCRBV28-01 | TCRBJ02-01 |
| CASSTGRGANEKLFF | 1154 | TCRBV11 | TCRBJ01-04 |
| CSAGRLAGSEQFF | 1155 | TCRBV20-X | TCRBJ02-01 |
| CSARWTSLDTQYF | 1156 | TCRBV20-X | TCRBJ02-03 |
| CASSPPATDTQYF | 1157 | TCRBV28-01 | TCRBJ02-03 |
| CASSQTTSGRGNEQFF | 1158 | TCRBV04-02 | TCRBJ02-01 |
| CASSLAGVGKLFF | 1159 | TCRBV05-05 | TCRBJ01-04 |
| CASSYGQGDTEAFF | 1160 | TCRBV12-X | TCRBJ01-01 |
| CSARRTSGGGTGELFF | 1161 | TCRBV20-X | TCRBJ02-02 |
| CASSLVGTSGGARDEQFF | 1162 | TCRBV07 | TCRBJ02-01 |
| CASSPGTVIMNTEAFF | 1163 | TCRBV05-01 | TCRBJ01-01 |
| CASSPGTGGSDGYTF | 1164 | TCRBV19-01 | TCRBJ01-02 |
| CASRQGPNTEAFF | 1165 | TCRBV04-02 | TCRBJ01-01 |
| CAIRGREQETQYF | 1166 | TCRBV10-03 | TCRBJ02-05 |
| CASRYRDKGYTF | 1167 | TCRBV06 | TCRBJ01-02 |
| CASSPGTSSSTDTQYF | 1168 | TCRBV11 | TCRBJ02-03 |
| CASSARDTHYEQYF | 1169 | TCRBV02-01 | TCRBJ02-07 |
| CASSLARGRDTGELFF | 1170 | TCRBV05-06 | TCRBJ02-02 |
| CASSSGQVFGEKLFF | 1171 | TCRBV07 | TCRBJ01-04 |
| CSAPVPADTQYF | 1172 | TCRBV29-01 | TCRBJ02-03 |
| CASSLAPLGDEQFF | 1173 | TCRBV07 | TCRBJ02-01 |
| CSARSSGAGTGELFF | 1174 | TCRBV20-X | TCRBJ02-02 |
| CASSGGTKNTEAFF | 1175 | TCRBV12-X | TCRBJ01-01 |
| CASLGVSSYNEQFF | 1176 | TCRBV06 | TCRBJ02-01 |
| CASSLLVDEQFF | 1177 | TCRBV13-01 | TCRBJ02-01 |
| CASSVATGGKGTDTQYF | 1178 | TCRBV09-01 | TCRBJ02-03 |
| CASRIAGGPTDTQYF | 1179 | TCRBV02-01 | TCRBJ02-03 |
| CASSFRGPGYTF | 1180 | TCRBV13-01 | TCRBJ01-02 |
| CASSSVTGRGNTIYF | 1181 | TCRBV11 | TCRBJ01-03 |
| CASSPTTWGEKLFF | 1182 | TCRBV07 | TCRBJ01-04 |
| CASSWQTNEKLFF | 1183 | TCRBV28-01 | TCRBJ01-04 |
| CASSQLGFLNTEAFF | 1184 | TCRBV03-01/03-02 | TCRBJ01-01 |
| CSARGAGSGTGELFF | 1185 | TCRBV20-X | TCRBJ02-02 |
| CSARGSGRAGDTQYF | 1186 | TCRBV20-X | TCRBJ02-03 |
| CASSRRGQADSPLHF | 1187 | TCRBV06 | TCRBJ01-06 |
| CASSPTFDGEAFF | 1188 | TCRBV05-01 | TCRBJ01-01 |
| CASSQDTSGGWGETQYF | 1189 | TCRBV04-03 | TCRBJ02-05 |
| CASSASHGSNQPQHF | 1190 | TCRBV09-01 | TCRBJ01-05 |
| CASSEQGAIEQYF | 1191 | TCRBV10-02 | TCRBJ02-07 |
| CASTSDTQYF | 1192 | TCRBV05-04 | TCRBJ02-03 |
| CASSLGLADPSTDTQYF | 1193 | TCRBV28-01 | TCRBJ02-03 |
| CASSPRQGTAYEQYF | 1194 | TCRBV19-01 | TCRBJ02-07 |
| CASSPRLVGDEQFF | 1195 | TCRBV18-01 | TCRBJ02-01 |
| CVGGRDYNEQFF | 1196 | TCRBV07 | TCRBJ02-01 |
| CASSLAPGGTYNEQFF | 1197 | TCRBV05-01 | TCRBJ02-01 |
| CSARDGTPEQFF | 1198 | TCRBV20-X | TCRBJ02-01 |
| CASSPSDLSSYNEQFF | 1199 | TCRBV28-01 | TCRBJ02-01 |
| CSALRPPYNEQFF | 1200 | TCRBV20-X | TCRBJ02-01 |
| CASSSNPGQGSYNEQFF | 1201 | TCRBV05-01 | TCRBJ02-01 |
| CASSSPGREKYF | 1202 | TCRBV06 | TCRBJ02-07 |
| CASSPRTENTDTQYF | 1203 | TCRBV07 | TCRBJ02-03 |
| CASRSGAGGANVLTF | 1204 | TCRBV07 | TCRBJ02-06 |
| CSASDPPYNEQFF | 1205 | TCRBV20-X | TCRBJ02-01 |
| CASKNSGTYEQYF | 1206 | TCRBV12-03/12-04 | TCRBJ02-07 |
| CASSWYRGNGYTF | 1207 | TCRBV12-03/12-04 | TCRBJ01-02 |
| CSARGQGQSYNSPLHF | 1208 | TCRBV20-X | TCRBJ01-06 |
| CASSPSTGSRQPQHF | 1209 | TCRBV06 | TCRBJ01-05 |
| CASSIWAEPNSPLHF | 1210 | TCRBV19-01 | TCRBJ01-06 |
| CASSLGDTGYTF | 1211 | TCRBV12-03/12-04 | TCRBJ01-02 |
| CSARRAGSGTGELFF | 1212 | TCRBV20-X | TCRBJ02-02 |
| CASSQGGLAGVYNEQFF | 1213 | TCRBV04-01 | TCRBJ02-01 |
| CSASSTEETQYF | 1214 | TCRBV20-01 | TCRBJ02-05 |
| CASSPEGVENTEAFF | 1215 | TCRBV18-01 | TCRBJ01-01 |
| CASRNDRATNTEAFF | 1216 | TCRBV06 | TCRBJ01-01 |
| CASRLQGANEQFF | 1217 | TCRBV05-06 | TCRBJ02-01 |
| CASSQGIVQETQYF | 1218 | TCRBV04-01 | TCRBJ02-05 |
| CASSYLQLSYEQYF | 1219 | TCRBV06 | TCRBJ02-07 |
| CSARDPLAGKADTQYF | 1220 | TCRBV20-X | TCRBJ02-03 |
| CSARRGGSGTGELFF | 1221 | TCRBV20-X | TCRBJ02-02 |
| CSATLAPYNEQFF | 1222 | TCRBV20-X | TCRBJ02-01 |
| CSAPGRKGNQPQHF | 1223 | TCRBV20-X | TCRBJ01-05 |
| CASSPSLANIQYF | 1224 | TCRBV07 | TCRBJ02-04 |
| CASSYLDNSYEQYF | 1225 | TCRBV06 | TCRBJ02-07 |
| CSARFTRSYEQYF | 1226 | TCRBV20-X | TCRBJ02-07 |
| CASSVRDTGELFF | 1227 | TCRBV05-06 | TCRBJ02-02 |
| CSVVGGPSYNEQFF | 1228 | TCRBV29-01 | TCRBJ02-01 |
| CASSSPGGTGVDEQYF | 1229 | TCRBV28-01 | TCRBJ02-07 |
| CASSLWSGEQFF | 1230 | TCRBV05-04 | TCRBJ02-01 |
| CASSGDRYNEKLFF | 1231 | TCRBV02-01 | TCRBJ01-04 |
| CASSLGAQTNEKLFF | 1232 | TCRBV11 | TCRBJ01-04 |
| CASSIRGFEEKLFF | 1233 | TCRBV19-01 | TCRBJ01-04 |
| CASSFEANYNSPLHF | 1234 | TCRBV12-X | TCRBJ01-06 |
| CSVRRGMHEQFF | 1235 | TCRBV29-01 | TCRBJ02-01 |
| CASSRTGSFSPLHF | 1236 | TCRBV14-01 | TCRBJ01-06 |
| CASREGGGTGNTIYF | 1237 | TCRBV06 | TCRBJ01-03 |
| CASSLMTNYEQYF | 1238 | TCRBV05-01 | TCRBJ02-07 |
| CSAGGSVGEKLFF | 1239 | TCRBV20-X | TCRBJ01-04 |
| CASGFGQGTNTGELFF | 1240 | TCRBV12-05 | TCRBJ02-02 |
| CASSFEQNYNSPLHF | 1241 | TCRBV12-X | TCRBJ01-06 |
| CSVETGVDTQYF | 1242 | TCRBV29-01 | TCRBJ02-03 |
| CASSTGQGVDNEQFF | 1243 | TCRBV05-05 | TCRBJ02-01 |
| CSARDGTPEAFF | 1244 | TCRBV20-X | TCRBJ01-01 |
| CASSPAGTGYQETQYF | 1245 | TCRBV19-01 | TCRBJ02-05 |
| CASSTGLRDTEAFF | 1246 | TCRBV19-01 | TCRBJ01-01 |
| CSARGSARSTDTQYF | 1247 | TCRBV20-X | TCRBJ02-03 |
| CAWSVHLTGGNTIYF | 1248 | TCRBV30-01 | TCRBJ01-03 |
| CASSLEGTGGGEQFF | 1249 | TCRBV05-04 | TCRBJ02-01 |
| CASSPRASGTNTGELFF | 1250 | TCRBV12-X | TCRBJ02-02 |
| CASSLPPGETQYF | 1251 | TCRBV05-05 | TCRBJ02-05 |
| CASSLTSGGIAKNIQYF | 1252 | TCRBV28-01 | TCRBJ02-04 |
| CASSNQENTEAFF | 1253 | TCRBV07 | TCRBJ01-01 |
| CAWNPGGTGELFF | 1254 | TCRBV30-01 | TCRBJ02-02 |
| CASSQGRNNEQFF | 1255 | TCRBV11 | TCRBJ02-01 |
| CSATLRQGGSNQPQHF | 1256 | TCRBV20-X | TCRBJ01-05 |
| CSAPARSGNTIYF | 1257 | TCRBV29-01 | TCRBJ01-03 |
| CSARPSGSGTGELFF | 1258 | TCRBV20-X | TCRBJ02-02 |
| CASSPAGQGADGYTF | 1259 | TCRBV07 | TCRBJ01-02 |
| CASSSPRQPNTEAFF | 1260 | TCRBV27-01 | TCRBJ01-01 |
| CASSVSSGSVYEQFF | 1261 | TCRBV09-01 | TCRBJ02-01 |
| CASSLEASGGWNEQFF | 1262 | TCRBV05-01 | TCRBJ02-01 |
| CASSHSGAKNIQYF | 1263 | TCRBV28-01 | TCRBJ02-04 |
| CASSVLSTSTGELFF | 1264 | TCRBV09-01 | TCRBJ02-02 |
| CSARKSPTNTGELFF | 1265 | TCRBV20-X | TCRBJ02-02 |
| CASSSVQSSYNEQFF | 1266 | TCRBV11 | TCRBJ02-01 |
| CASSPRTGSGELFF | 1267 | TCRBV18-01 | TCRBJ02-02 |
| CASSPHRVPMNTEAFF | 1268 | TCRBV28-01 | TCRBJ01-01 |
| CASSSPLAGGRSDTQYF | 1269 | TCRBV28-01 | TCRBJ02-03 |
| CASSSTEPSGNTIYF | 1270 | TCRBV05-01 | TCRBJ01-03 |
| CASSQDRELGETQYF | 1271 | TCRBV03-01/03-02 | TCRBJ02-05 |
| CSARPAGGGTGELFF | 1272 | TCRBV20-X | TCRBJ02-02 |
| CASSLSRRGHTGELFF | 1273 | TCRBV07 | TCRBJ02-02 |
| CASSPQGGIDTQYF | 1274 | TCRBV07 | TCRBJ02-03 |
| CASSTQGLGPQHF | 1275 | TCRBV07 | TCRBJ01-05 |
| CASSRGQLSTDTQYF | 1276 | TCRBV07 | TCRBJ02-03 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASGAGGDYGYTF | 1277 | TCRBV07 | TCRBJ01-02 |
| CASSSPTGLNTEAFF | 1278 | TCRBV05-05 | TCRBJ01-01 |
| CATSPGGGPQETQYF | 1279 | TCRBV15-01 | TCRBJ02-05 |
| CASSYGQGATNTGELFF | 1280 | TCRBV06 | TCRBJ02-02 |
| CSATQQGNTEAFF | 1281 | TCRBV20-X | TCRBJ01-01 |
| CASSQASLAGLYEQYF | 1282 | TCRBV04-01 | TCRBJ02-07 |
| CASSGSSTDTQYF | 1283 | TCRBV05-04 | TCRBJ02-03 |
| CASSGRDRGPTNEKLFF | 1284 | TCRBV19-01 | TCRBJ01-04 |
| CASSRDGGRNQPQHF | 1285 | TCRBV18-01 | TCRBJ01-05 |
| CASSSNRGHEKLFF | 1286 | TCRBV06 | TCRBJ01-04 |
| CASSPGTGKDEQFF | 1287 | TCRBV18-01 | TCRBJ02-01 |
| CASSPSRGRNYGYTF | 1288 | TCRBV09-01 | TCRBJ01-02 |
| CASSEYGVGDTEAFF | 1289 | TCRBV02-01 | TCRBJ01-01 |
| CASSLTGGLSGTGELFF | 1290 | TCRBV18-01 | TCRBJ02-02 |
| CASRPTVATNEKLFF | 1291 | TCRBV25-01 | TCRBJ01-04 |
| CASRPTGFLNTEAFF | 1292 | TCRBV12-X | TCRBJ01-01 |
| CASSLGGDSSNEQFF | 1293 | TCRBV05-04 | TCRBJ02-01 |
| CATSETGAVTDTQYF | 1294 | TCRBV24-01 | TCRBJ02-03 |
| CSAVRGGPTGELFF | 1295 | TCRBV20-X | TCRBJ02-02 |
| CASSWDQETQYF | 1296 | TCRBV05-05 | TCRBJ02-05 |
| CASSPRRRGFNEKLFF | 1297 | TCRBV28-01 | TCRBJ01-04 |
| CASSPHGTENTEAFF | 1298 | TCRBV18-01 | TCRBJ01-01 |
| CASSLEVNYNSPLHF | 1299 | TCRBV12-X | TCRBJ01-06 |
| CSARAAGSGTGELFF | 1300 | TCRBV20-X | TCRBJ02-02 |
| CASSPPGRTTDTQYF | 1301 | TCRBV12-X | TCRBJ02-03 |
| CASSAPASGGAGEQFF | 1302 | TCRBV02-01 | TCRBJ02-01 |
| CASSFLAGRDEQFF | 1303 | TCRBV13-01 | TCRBJ02-01 |
| CASSTGLATETQYF | 1304 | TCRBV06 | TCRBJ02-05 |
| CASKRDTHYEQYF | 1305 | TCRBV06 | TCRBJ02-07 |
| CSARRQGNDQPQHF | 1306 | TCRBV20-X | TCRBJ01-05 |
| CASSSWDRVTYEQYF | 1307 | TCRBV05-06 | TCRBJ02-07 |
| CASSPNVGGNTEAFF | 1308 | TCRBV03-01/03-02 | TCRBJ01-01 |
| CASSPATGVYNEQFF | 1309 | TCRBV12-X | TCRBJ02-01 |
| CASSTSYEQYV | 1310 | TCRBV21-01 | TCRBJ02-07 |
| CSVGRLYEQYF | 1311 | TCRBV20-01 | TCRBJ02-07 |
| CASSLGQRNYGYTF | 1312 | TCRBV05-06 | TCRBJ01-02 |
| CSARASGGGTGELFF | 1313 | TCRBV20-X | TCRBJ02-02 |
| CSARGSGAGTGELFF | 1314 | TCRBV20-X | TCRBJ02-02 |
| CSASALEDEQFF | 1315 | TCRBV20-X | TCRBJ02-01 |
| CASSQESGRFADTQYF | 1316 | TCRBV03-01/03-02 | TCRBJ02-03 |
| CASSQGQGQYQETQYF | 1317 | TCRBV04-01 | TCRBJ02-05 |
| CASRKISTGNTEAFF | 1318 | TCRBV06 | TCRBJ01-01 |
| CASSPRGQGIGGYTF | 1319 | TCRBV05-06 | TCRBJ01-02 |
| CASKRQGGYEQYF | 1320 | TCRBV27-01 | TCRBJ02-07 |
| CSARKAGSGTGELFF | 1321 | TCRBV20-X | TCRBJ02-02 |
| CASSLGGGLNEQYF | 1322 | TCRBV07 | TCRBJ02-07 |
| CASMGWGQPQHF | 1323 | TCRBV06 | TCRBJ01-05 |
| CASSLMTSLSYEQYF | 1324 | TCRBV11 | TCRBJ02-07 |
| CASSPLAGDRKTQYF | 1325 | TCRBV07 | TCRBJ02-05 |
| CASSRPTGGRETQYF | 1326 | TCRBV28-01 | TCRBJ02-05 |
| CASSLAPASYEQYF | 1327 | TCRBV07 | TCRBJ02-07 |
| CSAPQSLNTEAFF | 1328 | TCRBV20-X | TCRBJ01-01 |
| CSARAVVEQFF | 1329 | TCRBV20-01 | TCRBJ02-01 |
| CASSLLPVGTEAFF | 1330 | TCRBV07 | TCRBJ01-01 |
| CANRRGLNTEAFF | 1331 | TCRBV12-03/12-04 | TCRBJ01-01 |
| CASSGGTSASTDTQYF | 1332 | TCRBV11 | TCRBJ02-03 |
| CATSAGWYNEQFF | 1333 | TCRBV24-01 | TCRBJ02-01 |
| CASSPQGNNEQFF | 1334 | TCRBV14-01 | TCRBJ02-01 |
| CASSPLGRTNYEQYF | 1335 | TCRBV18-01 | TCRBJ02-07 |
| CASRADRKNTEAFF | 1336 | TCRBV05-01 | TCRBJ01-01 |
| CATSRGARRTDTQYF | 1337 | TCRBV24-01 | TCRBJ02-03 |
| CSARRSGSGTGELFF | 1338 | TCRBV20-X | TCRBJ02-02 |
| CASSRTGGLDTQYF | 1339 | TCRBV18-01 | TCRBJ02-03 |
| CSAREWGEHTEAFF | 1340 | TCRBV20-X | TCRBJ01-01 |
| CASSITGFGANVLTF | 1341 | TCRBV06 | TCRBJ02-06 |
| CASSMGALNNEQFF | 1342 | TCRBV19-01 | TCRBJ02-01 |
| CASSVGWDYGYTF | 1343 | TCRBV28-01 | TCRBJ01-02 |
| CSARASQGVNQPQHF | 1344 | TCRBV20-X | TCRBJ01-05 |
| CSAPPSVNSPLHF | 1345 | TCRBV20-X | TCRBJ01-06 |
| CASSPSGRRNTQYF | 1346 | TCRBV07 | TCRBJ02-03 |
| CASSSTGTAGNTIYF | 1347 | TCRBV18-01 | TCRBJ01-03 |
| CSATPGTTEAFF | 1348 | TCRBV20-X | TCRBJ01-01 |
| CSAPPGLGRADTQYF | 1349 | TCRBV20-X | TCRBJ02-03 |
| CSAGRGRKTQYF | 1350 | TCRBV20-X | TCRBJ02-05 |
| CASSLDLGGVTDTQYF | 1351 | TCRBV07 | TCRBJ02-03 |
| CASSRTGGGSDTQYF | 1352 | TCRBV19-01 | TCRBJ02-03 |
| CASSSGTGSEKLFF | 1353 | TCRBV06 | TCRBJ01-04 |
| CSAREPPYNEQFF | 1354 | TCRBV20-X | TCRBJ02-01 |
| CASSPTRDDYGYTF | 1355 | TCRBV04-02 | TCRBJ01-02 |
| CAIKGTSGGNEQFF | 1356 | TCRBV10-03 | TCRBJ02-01 |
| CASRTGGGETQYF | 1357 | TCRBV07 | TCRBJ02-05 |
| CASSAPQGTGNTIYF | 1358 | TCRBV06 | TCRBJ01-03 |
| CASSGRGRANTEAFF | 1359 | TCRBV19-01 | TCRBJ01-01 |
| CSARGSARTTDTQYF | 1360 | TCRBV20-X | TCRBJ02-03 |
| CSARQGVGNIQYF | 1361 | TCRBV20-X | TCRBJ02-04 |
| CAWGRRGLYEQYF | 1362 | TCRBV30-01 | TCRBJ02-07 |
| CASSERASGIYNEQFF | 1363 | TCRBV06 | TCRBJ02-01 |
| CSARIGGAGTGELFF | 1364 | TCRBV20-X | TCRBJ02-02 |
| CASKQGSGELFF | 1365 | TCRBV07 | TCRBJ02-02 |
| CASSSRTGGTYGYTF | 1366 | TCRBV05-06 | TCRBJ01-02 |
| CSARGGLGGTYNEQFF | 1367 | TCRBV20-X | TCRBJ02-01 |
| CASSFEINYNSPLHF | 1368 | TCRBV12-X | TCRBJ01-06 |
| CASSQEDRRNYGYTF | 1369 | TCRBV03-01/03-02 | TCRBJ01-02 |
| CASRGGVHTGELFF | 1370 | TCRBV12-X | TCRBJ02-02 |
| CASSLEQNYNSPLHF | 1371 | TCRBV12-X | TCRBJ01-06 |
| CSVGAKNTEAFF | 1372 | TCRBV29-01 | TCRBJ01-01 |
| CASSLAVGTTYNEQFF | 1373 | TCRBV07 | TCRBJ02-01 |
| CASSPFRTSGGPSTDTQYF | 1374 | TCRBV18-01 | TCRBJ02-03 |
| CASSTGTGLEKLFF | 1375 | TCRBV06 | TCRBJ01-04 |
| CASSYLGGGVYNEQFF | 1376 | TCRBV06 | TCRBJ02-01 |
| CASSILGGTSVYEQYF | 1377 | TCRBV19-01 | TCRBJ02-07 |
| CASSYSGRLSYNEQFF | 1378 | TCRBV06 | TCRBJ02-01 |
| CASSRTSGQSTDTQYF | 1379 | TCRBV09-01 | TCRBJ02-03 |
| CASSFESNYNSPLHF | 1380 | TCRBV12-X | TCRBJ01-06 |
| CASSLGDRGYTF | 1381 | TCRBV12-03/12-04 | TCRBJ01-02 |
| CSAKGQPSNTGELFF | 1382 | TCRBV20-X | TCRBJ02-02 |
| CSARLSGAGTGELFF | 1383 | TCRBV20-X | TCRBJ02-02 |
| CSARSQPSNTGELFF | 1384 | TCRBV20-X | TCRBJ02-02 |
| CASSQDLIQETQYF | 1385 | TCRBV04-03 | TCRBJ02-05 |
| CASSPALIQETQYF | 1386 | TCRBV04-03 | TCRBJ02-05 |
| CSAGPQVQETQYF | 1387 | TCRBV20-X | TCRBJ02-05 |
| CAAVGSGNTIYF | 1388 | TCRBV07 | TCRBJ01-03 |
| CASSILGTANNQPQHF | 1389 | TCRBV19-01 | TCRBJ01-05 |
| CATSSGREIETQYF | 1390 | TCRBV15-01 | TCRBJ02-05 |
| CSAMREGPETQYF | 1391 | TCRBV20-X | TCRBJ02-05 |
| CSAGLAGRQETQYF | 1392 | TCRBV20-X | TCRBJ02-05 |
| CASSFEYNYNSPLHF | 1393 | TCRBV12-X | TCRBJ01-06 |
| CSAPRAPYNEQFF | 1394 | TCRBV20-X | TCRBJ02-01 |
| CASSLVGVSGTGELFF | 1395 | TCRBV05-01 | TCRBJ02-02 |
| CASTLAGKSYNEQFF | 1396 | TCRBV02-01 | TCRBJ02-01 |
| CASRSGTDYEQYF | 1397 | TCRBV28-01 | TCRBJ02-07 |
| CASSIRRDKNIQYF | 1398 | TCRBV19-01 | TCRBJ02-04 |
| CASSLSKEYEQYF | 1399 | TCRBV05-01 | TCRBJ02-07 |
| CASSKAGLYTEAFF | 1400 | TCRBV12-X | TCRBJ01-01 |
| CASSDQGVRETQYF | 1401 | TCRBV19-01 | TCRBJ02-05 |
| CASSPLASTSYEQYF | 1402 | TCRBV18-01 | TCRBJ02-07 |
| CSARRQPTNTGELFF | 1403 | TCRBV20-X | TCRBJ02-02 |
| CSARGGGAGTGELFF | 1404 | TCRBV20-X | TCRBJ02-02 |
| CASSMGPTNTQYF | 1405 | TCRBV19-01 | TCRBJ02-03 |
| CASSIGGSGGIYEQYF | 1406 | TCRBV19-01 | TCRBJ02-07 |
| CASRTPGDTQYF | 1407 | TCRBV28-01 | TCRBJ02-03 |
| CATSSNSGNQPQHF | 1408 | TCRBV15-01 | TCRBJ01-05 |
| CASTASDRAYEQYF | 1409 | TCRBV28-01 | TCRBJ02-07 |
| CATSDQTSGNRNEQFF | 1410 | TCRBV24-01 | TCRBJ02-01 |
| CASRYKDTEAFF | 1411 | TCRBV06 | TCRBJ01-01 |
| CASSLGQGDTEAFF | 1412 | TCRBV12-X | TCRBJ01-01 |
| CASSFNRGNTGELFF | 1413 | TCRBV12-X | TCRBJ02-02 |
| CASSPRGRGVSGYTF | 1414 | TCRBV07 | TCRBJ01-02 |
| CASSRTRSSYEQYF | 1415 | TCRBV28-01 | TCRBJ02-07 |
| CASSLLLGQGYEQYF | 1416 | TCRBV12-X | TCRBJ02-07 |
| CASRPGLAYDTQYF | 1417 | TCRBV06 | TCRBJ02-03 |
| CASRYRDSGYTF | 1418 | TCRBV06 | TCRBJ01-02 |
| CSARLDRGGYEQYF | 1419 | TCRBV20-X | TCRBJ02-07 |
| CASSGPGTSGNNEQFF | 1420 | TCRBV09-01 | TCRBJ02-01 |
| CSARVAGAGTGELFF | 1421 | TCRBV20-X | TCRBJ02-02 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASSLAPLGDTQYF | 1422 | TCRBV07 | TCRBJ02-03 |
| CASSSGRGHEKLFF | 1423 | TCRBV06 | TCRBJ01-04 |
| CASSLSGTPYNEQFF | 1424 | TCRBV03-01/03-02 | TCRBJ02-01 |
| CASTPGQEAYEQYF | 1425 | TCRBV28-01 | TCRBJ02-07 |
| CASSSVQYNEQFF | 1426 | TCRBV05-01 | TCRBJ02-01 |
| CASSQWQDTQYF | 1427 | TCRBV03-01/03-02 | TCRBJ02-03 |
| CSAEEGAETQYF | 1428 | TCRBV20-X | TCRBJ02-05 |
| CASSLDRGQNIQYF | 1429 | TCRBV06 | TCRBJ02-04 |
| CASSITGGPRDTQYF | 1430 | TCRBV19-01 | TCRBJ02-03 |
| CASSSGRASGANVLTF | 1431 | TCRBV05-01 | TCRBJ02-06 |
| CASSRGQPFSGNTIYF | 1432 | TCRBV12-X | TCRBJ01-03 |
| CASRYRDTEAFF | 1433 | TCRBV06 | TCRBJ01-01 |
| CASSLEFGPNEQFF | 1434 | TCRBV07 | TCRBJ02-01 |
| CASREGGKTGELFF | 1435 | TCRBV19-01 | TCRBJ02-02 |
| CASSIDFGQGDSPLHF | 1436 | TCRBV19-01 | TCRBJ01-06 |
| CASRYKDEKLFF | 1437 | TCRBV06 | TCRBJ01-04 |
| CASSLAGAGPSTDTQYF | 1438 | TCRBV05-05 | TCRBJ02-03 |
| CASRTGHRYGYTF | 1439 | TCRBV28-01 | TCRBJ01-02 |
| CATSRASRVSGNTIYF | 1440 | TCRBV15-01 | TCRBJ01-03 |
| CSAPVPPNTEAFF | 1441 | TCRBV20-X | TCRBJ01-01 |
| CASSSPGHDEQYF | 1442 | TCRBV19-01 | TCRBJ02-07 |
| CAIREGQTYEQYF | 1443 | TCRBV10-03 | TCRBJ02-07 |
| CASSFGGEGSPLHF | 1444 | TCRBV05-01 | TCRBJ01-06 |
| CASSRAPANTEAFF | 1445 | TCRBV05-01 | TCRBJ01-01 |
| CAWSVNRGRTEAFF | 1446 | TCRBV30-01 | TCRBJ01-01 |
| CASSPSRLMNTEAFF | 1447 | TCRBV05-01 | TCRBJ01-01 |
| CASSPPGLAGGSTGELFF | 1448 | TCRBV18-01 | TCRBJ02-02 |
| CASSQGLASSYNEQFF | 1449 | TCRBV05-06 | TCRBJ02-01 |
| CASSQSRGKLFF | 1450 | TCRBV04-03 | TCRBJ01-04 |
| CSARFSGRASDTQYF | 1451 | TCRBV20-X | TCRBJ02-03 |
| CASSLFQRGGSYNEQFF | 1452 | TCRBV27-01 | TCRBJ02-01 |
| CASSPGTWGDTQYF | 1453 | TCRBV07 | TCRBJ02-03 |
| CASAGPWTQYF | 1454 | TCRBV06 | TCRBJ02-05 |
| CAWKVRANTGELFF | 1455 | TCRBV30-01 | TCRBJ02-02 |
| CASSLLAGQGVETQYF | 1456 | TCRBV11 | TCRBJ02-05 |
| CATSFSGNTIYF | 1457 | TCRBV12-03/12-04 | TCRBJ01-03 |
| CASSSRTGPTSTDTQYF | 1458 | TCRBV12-X | TCRBJ02-03 |
| CASIQGFNQPQHF | 1459 | TCRBV12-03/12-04 | TCRBJ01-05 |
| CASSLGSIWGSTDTQYF | 1460 | TCRBV05-01 | TCRBJ02-03 |
| CASSQGSDFGYGYTF | 1461 | TCRBV04-03 | TCRBJ01-02 |
| CSARDASVSDTQYF | 1462 | TCRBV20-X | TCRBJ02-03 |
| CSARVGGGGTGELFF | 1463 | TCRBV20-X | TCRBJ02-02 |
| CASSEGRGIQYF | 1464 | TCRBV06 | TCRBJ02-04 |
| CASSTQGGRNQPQHF | 1465 | TCRBV18-01 | TCRBJ01-05 |
| CASSPDRGDEKLFF | 1466 | TCRBV05-01 | TCRBJ01-04 |
| CSAPAISGNTIYF | 1467 | TCRBV29-01 | TCRBJ01-03 |
| CASRIGLVYNEQFF | 1468 | TCRBV02-01 | TCRBJ02-01 |
| CSARDQGQRNSPLHF | 1469 | TCRBV20-X | TCRBJ01-06 |
| CASRYRDYGYTF | 1470 | TCRBV06 | TCRBJ01-02 |
| CASSEGGGGGQPQHF | 1471 | TCRBV06 | TCRBJ01-05 |
| CASSQDPTGEGYGYTF | 1472 | TCRBV04-03 | TCRBJ01-02 |
| CSVVGQFETQYF | 1473 | TCRBV29-01 | TCRBJ02-05 |
| CSARFGTGAEKLFF | 1474 | TCRBV20-X | TCRBJ01-04 |
| CATSENRNTEAFF | 1475 | TCRBV24-01 | TCRBJ01-01 |
| CASSNNGNTIYF | 1476 | TCRBV21-01 | TCRBJ01-03 |
| CASSSSPLTDTQYF | 1477 | TCRBV07 | TCRBJ02-03 |
| CASSLPRARYEQYF | 1478 | TCRBV05-06 | TCRBJ02-07 |
| CASRLGLGGYTF | 1479 | TCRBV09-01 | TCRBJ01-02 |
| CASSPQWYQETQYF | 1480 | TCRBV18-01 | TCRBJ02-05 |
| CASSSPTSGGRTDTQYF | 1481 | TCRBV05-06 | TCRBJ02-03 |
| CASSMGRGAGANVLTF | 1482 | TCRBV19-01 | TCRBJ02-06 |
| CASSLGIGDTQYF | 1483 | TCRBV05-08 | TCRBJ02-03 |
| CAWNRRDEAFF | 1484 | TCRBV30-01 | TCRBJ01-01 |
| CSAPLPGLDTQYF | 1485 | TCRBV20-X | TCRBJ02-03 |
| CSAQGQPTNTGELFF | 1486 | TCRBV20-X | TCRBJ02-02 |
| CASSSPLGGGADTQYF | 1487 | TCRBV28-01 | TCRBJ02-03 |
| CASSGALAVTGELFF | 1488 | TCRBV07 | TCRBJ02-02 |
| CASRAGREDTEAFF | 1489 | TCRBV28-01 | TCRBJ01-01 |
| CAIREGQKETQYF | 1490 | TCRBV10-03 | TCRBJ02-05 |
| CASSLGPHPYEQYF | 1491 | TCRBV07 | TCRBJ02-07 |
| CASGROGGYEQYF | 1492 | TCRBV28-01 | TCRBJ02-07 |
| CASSLADSVSGNTIYF | 1493 | TCRBV07 | TCRBJ01-03 |
| CASSEKAGGSSYEQYF | 1494 | TCRBV06 | TCRBJ02-07 |
| CSASIAPYNEQFF | 1495 | TCRBV20-01 | TCRBJ02-01 |
| CASSQDRDLYGYTF | 1496 | TCRBV05-04 | TCRBJ01-02 |
| CASGLQDNEQFF | 1497 | TCRBV12-05 | TCRBJ02-01 |
| CASSLAGSGGGQETQYF | 1498 | TCRBV05-01 | TCRBJ02-05 |
| CSARVASGSSDTQYF | 1499 | TCRBV20-X | TCRBJ02-03 |
| CASSQDVGRQFF | 1500 | TCRBV03-01/03-02 | TCRBJ02-01 |
| CASSWPGTGANVLTF | 1501 | TCRBV28-01 | TCRBJ02-06 |
| CASTQGTIGNTIYF | 1502 | TCRBV06 | TCRBJ01-03 |
| CSARDGQAEQYF | 1503 | TCRBV20-X | TCRBJ02-07 |
| CASSTRRAPYNEQFF | 1504 | TCRBV19-01 | TCRBJ02-01 |
| CASSLAPASGEQYF | 1505 | TCRBV07 | TCRBJ02-07 |
| CSARDRQGLQETQYF | 1506 | TCRBV20-X | TCRBJ02-05 |
| CASIWTAYNSPLHF | 1507 | TCRBV06 | TCRBJ01-06 |
| CAIRLREQETQYF | 1508 | TCRBV10-03 | TCRBJ02-05 |
| CASSLTRTSGSGEQYF | 1509 | TCRBV07 | TCRBJ02-07 |
| CASSPLAGEKDTQYF | 1510 | TCRBV07 | TCRBJ02-03 |
| CASSLVESGSGNTIYF | 1511 | TCRBV07 | TCRBJ01-03 |
| CATSVGSGGRDTQYF | 1512 | TCRBV24-01 | TCRBJ02-03 |
| CASSPWPGTDTQYF | 1513 | TCRBV18-01 | TCRBJ02-03 |
| CASSQGTEFYGYTF | 1514 | TCRBV14-01 | TCRBJ01-02 |
| CASSLVGLVRDTQYF | 1515 | TCRBV07 | TCRBJ02-03 |
| CASSPTGGKSDTQYF | 1516 | TCRBV07 | TCRBJ02-03 |
| CASSDRSQETQYF | 1517 | TCRBV19-01 | TCRBJ02-05 |
| CAISPRDSLQETQYF | 1518 | TCRBV10-03 | TCRBJ02-05 |
| CASGDRGQTGANVLTF | 1519 | TCRBV06 | TCRBJ02-06 |
| CASSVGLTGSEQYF | 1520 | TCRBV09-01 | TCRBJ02-07 |
| CASQRQGAYEQYF | 1521 | TCRBV27-01 | TCRBJ02-07 |
| CASTLRSGANYGYTF | 1522 | TCRBV12-X | TCRBJ01-02 |
| CSAREGGAGTGELFF | 1523 | TCRBV20-X | TCRBJ02-02 |
| CASSIEVGFGANVLTF | 1524 | TCRBV19-01 | TCRBJ02-06 |
| CASSGLTGYTDTQYF | 1525 | TCRBV02-01 | TCRBJ02-03 |
| CASTKGGAAGNTIYF | 1526 | TCRBV06 | TCRBJ01-03 |
| CASTRGPEGSPLHF | 1527 | TCRBV06 | TCRBJ01-06 |
| CASSPGSHTIYF | 1528 | TCRBV07 | TCRBJ01-03 |
| CASSPRPGTGTNTEAFF | 1529 | TCRBV04-01 | TCRBJ01-01 |
| CASSPQGVGNEQFF | 1530 | TCRBV05-04 | TCRBJ02-01 |
| CASSQRAVNYGYTF | 1531 | TCRBV04-01 | TCRBJ01-02 |
| CSARTVAGASTDTQYF | 1532 | TCRBV20-X | TCRBJ02-03 |
| CASSLDGRTHSPLHF | 1533 | TCRBV05-01 | TCRBJ01-06 |
| CASTKDGSYGYTF | 1534 | TCRBV05-01 | TCRBJ01-02 |
| CASSPTGLGAYEQYF | 1535 | TCRBV18-01 | TCRBJ02-07 |
| CSASSVPYNEQFF | 1536 | TCRBV20-01 | TCRBJ02-01 |
| CASSRGQIYEQYF | 1537 | TCRBV10-02 | TCRBJ02-07 |
| CASSARLVPGELFF | 1538 | TCRBV09-01 | TCRBJ02-02 |
| CASSQDLVRTEAFF | 1539 | TCRBV03-01/03-02 | TCRBJ01-01 |
| CASSQGVLAGHYNEQFF | 1540 | TCRBV03-01/03-02 | TCRBJ02-01 |
| CASSSTGAPEEKLFF | 1541 | TCRBV05-01 | TCRBJ01-04 |
| CSASNLAGHNEQFF | 1542 | TCRBV20-X | TCRBJ02-01 |
| CSARYGGAGTGELFF | 1543 | TCRBV20-X | TCRBJ02-02 |
| CATSRVGQGNEQFF | 1544 | TCRBV15-01 | TCRBJ02-01 |
| CSARVRNRNSPLHF | 1545 | TCRBV20-X | TCRBJ01-06 |
| CASSERQGAGTGELFF | 1546 | TCRBV06 | TCRBJ02-02 |
| CASSPRTSSTGELFF | 1547 | TCRBV03-01/03-02 | TCRBJ02-02 |
| CASSLGGSGEETQYF | 1548 | TCRBV13-01 | TCRBJ02-05 |
| CSARVGRSVETQYF | 1549 | TCRBV20-X | TCRBJ02-05 |
| CASSRSGYSYEQYF | 1550 | TCRBV06 | TCRBJ02-07 |
| CAISRGGYTEAFF | 1551 | TCRBV10-03 | TCRBJ01-01 |
| CSATQGVNTEAFF | 1552 | TCRBV29-01 | TCRBJ01-01 |
| CASSGPQGYNSPLHF | 1553 | TCRBV05-04 | TCRBJ01-06 |
| CASSQDLTGTEAFF | 1554 | TCRBV06 | TCRBJ01-01 |
| CASSFEHNYNSPLHF | 1555 | TCRBV12-X | TCRBJ01-06 |
| CSARDPWRDTDTQYF | 1556 | TCRBV20-X | TCRBJ02-03 |
| CASSYSFASGETQYF | 1557 | TCRBV06 | TCRBJ02-05 |
| CSARTSGGGTGELFF | 1558 | TCRBV20-X | TCRBJ02-02 |
| CASSQLVGSYNEQFF | 1559 | TCRBV12-X | TCRBJ02-01 |
| CASSPFTSGGSYNEQFF | 1560 | TCRBV18-01 | TCRBJ02-01 |
| CASSFPSSETQYF | 1561 | TCRBV06 | TCRBJ02-05 |
| CASSLGRTGRDYGYTF | 1562 | TCRBV11 | TCRBJ01-02 |
| CASGGVQETQYF | 1563 | TCRBV09-01 | TCRBJ02-05 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASSQRDSYTEAFF | 1564 | TCRBV11 | TCRBJ01-01 |
| CASSQLPGRTNSPLHF | 1565 | TCRBV03-01/03-02 | TCRBJ01-06 |
| CASSSPLAGGRTDTQYF | 1566 | TCRBV28-01 | TCRBJ02-03 |
| CASSSPGDYTF | 1567 | TCRBV19-01 | TCRBJ01-02 |
| CSARHGGAGTGELFF | 1568 | TCRBV20-X | TCRBJ02-02 |
| CATSDVGTNEKLFF | 1569 | TCRBV24-01 | TCRBJ01-04 |
| CASSLGPSGNNEQFF | 1570 | TCRBV11 | TCRBJ02-01 |
| CSARRGGGGTGELFF | 1571 | TCRBV20-X | TCRBJ02-02 |
| CSARRDRGPGNYGYTF | 1572 | TCRBV20-X | TCRBJ01-02 |
| CASSRVPQSSYEQYF | 1573 | TCRBV11 | TCRBJ02-07 |
| CASSFTGWQETQYF | 1574 | TCRBV05-01 | TCRBJ02-05 |
| CASSFQASDTQYF | 1575 | TCRBV07 | TCRBJ02-03 |
| CSALSPPYNEQFF | 1576 | TCRBV20-X | TCRBJ02-01 |
| CASGASGNTIYF | 1577 | TCRBV05-05 | TCRBJ01-03 |
| CASSLDPRAYNEQFF | 1578 | TCRBV07 | TCRBJ02-01 |
| CASSSNGQHYEQYF | 1579 | TCRBV19-01 | TCRBJ02-07 |
| CSVERSGAYEQYF | 1580 | TCRBV29-01 | TCRBJ02-07 |
| CAILSSNQPQHF | 1581 | TCRBV28-01 | TCRBJ01-05 |
| CASSLAPAGYEQYF | 1582 | TCRBV07 | TCRBJ02-07 |
| CASSLESNYNSPLHF | 1583 | TCRBV12-X | TCRBJ01-06 |
| CASSPRDINEQFF | 1584 | TCRBV11 | TCRBJ02-01 |
| CASSSAGGRGETQYF | 1585 | TCRBV05-01 | TCRBJ02-05 |
| CSAPLAPYNEQFF | 1586 | TCRBV20-X | TCRBJ02-01 |
| CSARLTGDYSNQPQHF | 1587 | TCRBV20-X | TCRBJ01-05 |
| CASRGTGTPSNQPQHF | 1588 | TCRBV06 | TCRBJ01-05 |
| CSARDEGPDTQYF | 1589 | TCRBV20-X | TCRBJ02-03 |
| CASSLEPNYNSPLHF | 1590 | TCRBV12-X | TCRBJ01-06 |
| CASSKGFNEQYF | 1591 | TCRBV06 | TCRBJ02-07 |
| CASSLGHWNEKLFF | 1592 | TCRBV07 | TCRBJ01-04 |
| CASSQGRGGKETQYF | 1593 | TCRBV04-03 | TCRBJ02-05 |
| CSVRTSSETQYF | 1594 | TCRBV20-X | TCRBJ02-05 |
| CASSFGLAGVGNEQFF | 1595 | TCRBV27-01 | TCRBJ02-01 |
| CASSGRGQGSTDTQYF | 1596 | TCRBV19-01 | TCRBJ02-03 |
| CATSRGDRTQETQYF | 1597 | TCRBV15-01 | TCRBJ02-05 |
| CASSPSPGGHTEAFF | 1598 | TCRBV09-01 | TCRBJ01-01 |
| CASSQTRSGANVLTF | 1599 | TCRBV14-01 | TCRBJ02-06 |
| CASRPGTGTYGYTF | 1600 | TCRBV04-01 | TCRBJ01-02 |
| CASSLGGQGHYGYTF | 1601 | TCRBV05-01 | TCRBJ01-02 |
| CASSSPGGYTF | 1602 | TCRBV19-01 | TCRBJ01-02 |
| CSAPRSLNTEAFF | 1603 | TCRBV20-X | TCRBJ01-01 |
| CAISGRDKNSPLHF | 1604 | TCRBV10-03 | TCRBJ01-06 |
| CASRRGTDTEAFF | 1605 | TCRBV05-01 | TCRBJ01-01 |
| CASSPGGARYEQYF | 1606 | TCRBV05-05 | TCRBJ02-07 |
| CASSGGGRTSSYNEQFF | 1607 | TCRBV02-01 | TCRBJ02-01 |
| CASSSPLAGGRTDTQYF | 1566 | TCRBV12-X | TCRBJ02-03 |
| CASSLTLSLSYEQYF | 1608 | TCRBV07 | TCRBJ02-07 |
| CASSYPGLETQYF | 1609 | TCRBV28-01 | TCRBJ02-05 |
| CASSGFRDYTEAFF | 1610 | TCRBV02-01 | TCRBJ01-01 |
| CSASGAVSSYEQYF | 1611 | TCRBV20-01 | TCRBJ02-07 |
| CSARTSGSGAGELFF | 1612 | TCRBV20-X | TCRBJ02-02 |
| CASSLLDSANTGELFF | 1613 | TCRBV18-01 | TCRBJ02-02 |
| CASSYSSRAHYEQYF | 1614 | TCRBV06 | TCRBJ02-07 |
| CASSRGQGTSNQPQHF | 1615 | TCRBV04-02 | TCRBJ01-05 |
| CASSLVGQGPANYGYTF | 1616 | TCRBV05-01 | TCRBJ01-02 |
| CASTFSGRTDTQYF | 1617 | TCRBV02-01 | TCRBJ02-03 |
| CASSSVGADTEAFF | 1618 | TCRBV05-01 | TCRBJ01-01 |
| CAWNPSTDTQYF | 1619 | TCRBV30-01 | TCRBJ02-03 |
| CASSFRRSSSYNEQFF | 1620 | TCRBV12-X | TCRBJ02-01 |
| CASSPRGGLNIQYF | 1621 | TCRBV07 | TCRBJ02-04 |
| CASRDLTSSYNEQFF | 1622 | TCRBV06 | TCRBJ02-01 |
| CASSFFGGRRNTEAFF | 1623 | TCRBV05-06 | TCRBJ01-01 |
| CAWGLGTDTQYF | 1624 | TCRBV12-03/12-04 | TCRBJ02-03 |
| CASRPPESGNTIYF | 1625 | TCRBV05-01 | TCRBJ01-03 |
| CASSPGQGRFETQYF | 1626 | TCRBV06 | TCRBJ02-05 |
| CSASPPPHNEQFF | 1627 | TCRBV20-X | TCRBJ02-01 |
| CASSRASGTSSYEQYF | 1628 | TCRBV04-02 | TCRBJ02-07 |
| CAWSHGRASYNEQFF | 1629 | TCRBV30-01 | TCRBJ02-01 |
| CASSLAPRDRGNEQFF | 1630 | TCRBV07 | TCRBJ02-01 |
| CASSLGQGGTYNEQFF | 1631 | TCRBV05-01 | TCRBJ02-01 |
| CSARDPLGQETQYF | 1632 | TCRBV20-X | TCRBJ02-05 |
| CASRRDRGDEQFF | 1633 | TCRBV27-01 | TCRBJ02-01 |
| CASSRDRGRGETQYF | 1634 | TCRBV06 | TCRBJ02-05 |
| CASSGRGIYNEQFF | 1635 | TCRBV03-01/03-02 | TCRBJ02-01 |
| CASSLAGTGTHGYTF | 1636 | TCRBV07 | TCRBJ01-02 |
| CASSRTYSNQPQHF | 1637 | TCRBV05-08 | TCRBJ01-05 |
| CASSEGSAETQYF | 1638 | TCRBV10-02 | TCRBJ02-05 |
| CASSIHPNEQFF | 1639 | TCRBV19-01 | TCRBJ02-01 |
| CASSSGGSGGYTF | 1640 | TCRBV11 | TCRBJ01-02 |
| CASSVEGGGTDTQYF | 1641 | TCRBV02-01 | TCRBJ02-03 |
| CASSQDTGREQYF | 1642 | TCRBV04-02 | TCRBJ02-07 |
| CASTPRVSSYNEQFF | 1643 | TCRBV09-01 | TCRBJ02-01 |
| CASSATGGDQPQHF | 1644 | TCRBV25-01 | TCRBJ01-05 |
| CASSEALRRGGQPQHF | 1645 | TCRBV02-01 | TCRBJ01-05 |
| CASSPDRPTKNIQYF | 1646 | TCRBV06 | TCRBJ02-04 |
| CASSYLGLSYEQYV | 1647 | TCRBV06 | TCRBJ02-07 |
| CASSQGGYEQFF | 1648 | TCRBV28-01 | TCRBJ02-07 |
| CSARGSGRPSDTQYF | 1649 | TCRBV20-X | TCRBJ02-03 |
| CASSVLQGNAGELFF | 1650 | TCRBV09-01 | TCRBJ02-02 |
| CASSFRAGTETQYF | 1651 | TCRBV07 | TCRBJ02-05 |
| CASRRRLYEQYF | 1652 | TCRBV28-01 | TCRBJ02-07 |
| CSADGTSGYNEQFF | 1653 | TCRBV20-X | TCRBJ02-01 |
| CASSVVSGASYEQYF | 1654 | TCRBV07 | TCRBJ02-07 |
| CASSESGDWETQYF | 1655 | TCRBV10-02 | TCRBJ02-05 |
| CSARGRTYNEQFF | 1656 | TCRBV20-X | TCRBJ02-01 |
| CASTSPGAPYGYTF | 1657 | TCRBV07 | TCRBJ01-02 |
| CASSQGVLAGGTYEQYF | 1658 | TCRBV14-01 | TCRBJ02-07 |
| CASSHQLAGADTQYF | 1659 | TCRBV04-03 | TCRBJ02-03 |
| CASSEGAVSYGYTF | 1660 | TCRBV02-01 | TCRBJ01-02 |
| CASSLAGRTRETQYF | 1661 | TCRBV07 | TCRBJ02-05 |
| CSARDEGPDGYTF | 1662 | TCRBV20-X | TCRBJ01-02 |
| CASSRTSGNPEQYF | 1663 | TCRBV06 | TCRBJ02-07 |
| CASSTGLAGEEQFF | 1664 | TCRBV05-04 | TCRBJ02-01 |
| CSIPGSGNTIYF | 1665 | TCRBV20-X | TCRBJ01-03 |
| CASSITPVNEKLFF | 1666 | TCRBV05-01 | TCRBJ01-04 |
| CASSPMGGYEQYF | 1667 | TCRBV14-01 | TCRBJ02-07 |
| CASSLTGGRGAKNIQYF | 1668 | TCRBV05-06 | TCRBJ02-04 |
| CASSLALAGRTQYF | 1669 | TCRBV07 | TCRBJ02-05 |
| CASSRQGAYEQYF | 1670 | TCRBV28-01 | TCRBJ02-07 |
| CASSLLTVSTDTQYF | 1671 | TCRBV18-01 | TCRBJ02-03 |
| CASSIGLRDIQYF | 1672 | TCRBV19-01 | TCRBJ02-04 |
| CASSERPVTDTQYF | 1673 | TCRBV02-01 | TCRBJ02-03 |
| CASSDIGGVGYTF | 1674 | TCRBV06 | TCRBJ01-02 |
| CASSLQRGAGEQYF | 1675 | TCRBV03-01/03-02 | TCRBJ02-07 |
| CASSLTGSGTQYF | 1676 | TCRBV12-03/12-04 | TCRBJ02-05 |
| CASSFTNQETQYF | 1677 | TCRBV06 | TCRBJ02-05 |
| CSVPPGLAGGYNEQFF | 1678 | TCRBV29-01 | TCRBJ02-01 |
| CSARELQGAGEQYF | 1679 | TCRBV20-X | TCRBJ02-07 |
| CASSLAGVSTEAFF | 1680 | TCRBV05-04 | TCRBJ01-01 |
| CSARSSGRSSDTQYF | 1681 | TCRBV20-X | TCRBJ02-03 |
| CATSRGAGGSYEQYF | 1682 | TCRBV24-01 | TCRBJ02-07 |
| CSARSTLASYEQYF | 1683 | TCRBV20-X | TCRBJ02-07 |
| CASSLAGGTYISYNEQFF | 1684 | TCRBV07 | TCRBJ02-01 |
| CASSQDRQDEQYF | 1685 | TCRBV14-01 | TCRBJ02-07 |
| CASSEPGTGVYNEQFF | 1686 | TCRBV06 | TCRBJ02-01 |
| CSARSSGSGTGELFF | 1687 | TCRBV20-X | TCRBJ02-02 |
| CSARVAGGGTGELFF | 1688 | TCRBV20-X | TCRBJ02-02 |
| CASSYSTFRNEQFF | 1689 | TCRBV06 | TCRBJ02-01 |
| CSDAGTGGETQYF | 1690 | TCRBV29-01 | TCRBJ02-05 |
| CASRIGRHSGNTIYF | 1691 | TCRBV28-01 | TCRBJ01-03 |
| CASSPQDGNEKLFF | 1692 | TCRBV06 | TCRBJ01-04 |
| CASSPGTGTYNEQFF | 1693 | TCRBV06 | TCRBJ02-01 |
| CSASGQHSGYTF | 1694 | TCRBV20-X | TCRBJ01-02 |
| CSAQHITGELFF | 1695 | TCRBV20-X | TCRBJ02-02 |
| CASSENRNTEAFF | 1696 | TCRBV25-01 | TCRBJ01-01 |
| CSANGQGFTDTQYF | 1697 | TCRBV20-X | TCRBJ02-03 |
| CSAGLAGGFYEQYF | 1698 | TCRBV20-X | TCRBJ02-07 |
| CASSPTSGRAYEQYF | 1699 | TCRBV05-01 | TCRBJ02-07 |
| CAWAGLSGANVLTF | 1700 | TCRBV30-01 | TCRBJ02-06 |
| CATSRGVRRTDTQYF | 1701 | TCRBV24-01 | TCRBJ02-03 |
| CASSLLAGAGLSTDTQYF | 1702 | TCRBV07 | TCRBJ02-03 |
| CASSKDDRGSGNTIYF | 1703 | TCRBV21-01 | TCRBJ01-03 |
| CSAPRVPYNEQFF | 1704 | TCRBV20-X | TCRBJ02-01 |
| CSARPGGAGTGELFF | 1705 | TCRBV20-X | TCRBJ02-02 |

TABLE 1-continued

Lyme Disease-Associated TCRs

| TCRβ CDR3 Amino Acid Sequence | SEQ ID NO: | V Gene Segment | J Gene Segment |
|---|---|---|---|
| CASSQAGRADTQYF | 1706 | TCRBV07 | TCRBJ02-03 |
| CASSSSRQGRNNSPLHF | 1707 | TCRBV27-01 | TCRBJ01-06 |
| CASSSGLAGGTSSYEQYF | 1708 | TCRBV06 | TCRBJ02-07 |
| CASSQGTSGSYNEQFF | 1709 | TCRBV03-01/03-02 | TCRBJ02-01 |
| CASSLPGLGVAFF | 1710 | TCRBV07 | TCRBJ01-01 |
| CASSVGFAGGSDTQYF | 1711 | TCRBV09-01 | TCRBJ02-03 |
| CASSSRGQGVHEQYF | 1712 | TCRBV19-01 | TCRBJ02-07 |
| CASSYRGETDTQYF | 1713 | TCRBV05-04 | TCRBJ02-03 |
| CASSLLTTYEQYF | 1714 | TCRBV18-01 | TCRBJ02-07 |
| CSARMDRGRNEQFF | 1715 | TCRBV20-X | TCRBJ02-01 |
| CATRGGGATNEKLFF | 1716 | TCRBV28-01 | TCRBJ01-04 |
| CASSFRTGGPGANVLTF | 1717 | TCRBV07 | TCRBJ02-06 |
| CSARSSGGGTGELFF | 1718 | TCRBV20-X | TCRBJ02-02 |
| CASSLEQGTYNEQFF | 1719 | TCRBV07 | TCRBJ02-01 |
| CSARDRRGLQETQYF | 1720 | TCRBV20-X | TCRBJ02-05 |
| CASSQAGRQGGYNEQFF | 1721 | TCRBV04-01 | TCRBJ02-01 |
| CAISGDGGGYTEAFF | 1722 | TCRBV10-03 | TCRBJ01-01 |
| CASSPIGGQGNQPQHF | 1723 | TCRBV07 | TCRBJ01-05 |
| CASSPGRGWEKLFF | 1724 | TCRBV06 | TCRBJ01-04 |
| CATSSPGTGGRNEQFF | 1725 | TCRBV15-01 | TCRBJ02-01 |
| CASSRGNEQYF | 1726 | TCRBV09-01 | TCRBJ02-07 |
| CASTPLGDYNEQFF | 1727 | TCRBV06 | TCRBJ02-01 |
| CASSRDRVGNTGELFF | 1728 | TCRBV18-01 | TCRBJ02-02 |
| CASSADGTGGEKLFF | 1729 | TCRBV05-01 | TCRBJ01-04 |
| CSASEPPYNEQFF | 1733 | TCRBV20-01 | TCRBJ02-01 |
| CASSLKRVQETQYF | 1730 | TCRBV13-01 | TCRBJ02-05 |
| CASTRQDTQYF | 1731 | TCRBV06 | TCRBJ02-03 |
| CASSAGQWDEQYF | 1732 | TCRBV07 | TCRBJ02-07 |
| CASSHPLREETQYF | 1733 | TCRBV03-01/03-02 | TCRBJ02-05 |
| CASSQEARSDTQYF | 1734 | TCRBV04-01 | TCRBJ02-03 |
| CSARFGGAGTGELFF | 1735 | TCRBV20-X | TCRBJ02-02 |
| CSARGQPVNTGELFF | 1736 | TCRBV20-X | TCRBJ02-02 |
| CASSLDATFTDTQYF | 1737 | TCRBV05-01 | TCRBJ02-03 |
| CASSEGTGSSPLHF | 1738 | TCRBV27-01 | TCRBJ01-06 |
| CASSRGQPLSGNTIYF | 1739 | TCRBV05-06 | TCRBJ01-03 |
| CASSIGGTSTDTQYF | 1740 | TCRBV19-01 | TCRBJ02-03 |
| CASSNRRGRSYGYTF | 1741 | TCRBV06 | TCRBJ01-02 |
| CASTLAGVTYEQYF | 1742 | TCRBV07 | TCRBJ02-07 |
| CASSLGTGAGANVLTF | 1743 | TCRBV12-X | TCRBJ02-06 |
| CASRLRDSYEQYF | 1744 | TCRBV05-05 | TCRBJ02-07 |
| CAWTPGGTYQPQHF | 1745 | TCRBV30-01 | TCRBJ01-05 |
| CSASLGAQGYGYTF | 1746 | TCRBV20-01 | TCRBJ01-02 |
| CASKEDGANTGELFF | 1747 | TCRBV02-01 | TCRBJ02-02 |
| CSAREGVGALAKNIQYF | 1748 | TCRBV20-X | TCRBJ02-04 |
| CASKEAGDNEQFF | 1749 | TCRBV19-01 | TCRBJ02-01 |
| CSARGTDYQETQYF | 1750 | TCRBV20-X | TCRBJ02-05 |
| CASSPLAGLENTGELFF | 1751 | TCRBV18-01 | TCRBJ02-02 |
| CASSEREGVNTEAFF | 1752 | TCRBV25-01 | TCRBJ01-01 |
| CASSPSFSGEQYF | 1753 | TCRBV18-01 | TCRBJ02-07 |
| CASSSEGRGLGNTIYF | 1754 | TCRBV07 | TCRBJ01-03 |
| CSAPLVPYNEQFF | 1755 | TCRBV20-X | TCRBJ02-01 |
| CASTSPGANVLTF | 1756 | TCRBV05-06 | TCRBJ02-06 |
| CASSARSDTQYF | 1757 | TCRBV19-01 | TCRBJ02-03 |
| CASSSGGGAPGELFF | 1758 | TCRBV05-01 | TCRBJ02-02 |
| CASSSPGAGSSYNEQFF | 1759 | TCRBV07 | TCRBJ02-01 |
| CASTPGQDNSPLHF | 1760 | TCRBV05-05 | TCRBJ01-06 |
| CSAGPGTGNTGELFF | 1761 | TCRBV20-X | TCRBJ02-02 |
| CSARRVPYNEQFF | 1762 | TCRBV20-X | TCRBJ02-01 |
| CASSSARGVWETQYF | 1763 | TCRBV07 | TCRBJ02-05 |
| CASTPKSYGYTF | 1764 | TCRBV28-01 | TCRBJ01-02 |
| CAISGDGGSYNEQFF | 1765 | TCRBV10-03 | TCRBJ02-01 |
| CASSLKGDEDGYTF | 1766 | TCRBV05-01 | TCRBJ01-02 |
| CASGGLAGGPKETQYF | 1767 | TCRBV02-01 | TCRBJ02-05 |
| CASSPRTGGSQPQHF | 1768 | TCRBV20-01 | TCRBJ01-05 |
| CASSFSGTGFNSPLHF | 1769 | TCRBV05-06 | TCRBJ01-06 |
| CASRYGTGDQPQHF | 1770 | TCRBV07 | TCRBJ01-05 |
| CASSSTLSLSYEQYF | 1771 | TCRBV07 | TCRBJ02-07 |
| CASSVVMGRTDTQYF | 1772 | TCRBV09-01 | TCRBJ02-03 |
| CSARPAGAGTGELFF | 1773 | TCRBV20-X | TCRBJ02-02 |
| CSVGGLREQYF | 1774 | TCRBV29-01 | TCRBJ02-07 |
| CASSLPESSYEQYF | 1775 | TCRBV05-01 | TCRBJ02-07 |
| CSAKWEGTDTQYF | 1776 | TCRBV20-X | TCRBJ02-03 |
| CASSGAFNSPLHF | 1777 | TCRBV02-01 | TCRBJ01-06 |
| CASIEAGFTDTQYF | 1778 | TCRBV06 | TCRBJ02-03 |
| CASSKGQAYSGNTIYF | 1779 | TCRBV06 | TCRBJ01-03 |
| CASSVEGSSYEQYF | 1780 | TCRBV05-05 | TCRBJ02-07 |
| CSAPSPPYNEQFF | 1781 | TCRBV20-X | TCRBJ02-01 |
| CSARLAGSGTGELFF | 1782 | TCRBV20-X | TCRBJ02-02 |
| CSARSEGPDTQYF | 1783 | TCRBV20-X | TCRBJ02-03 |
| CSGVRGGNEQFF | 1784 | TCRBV29-01 | TCRBJ02-01 |
| CSASQVEDTQYF | 1785 | TCRBV20-X | TCRBJ02-03 |
| CASSSESADTQYF | 1786 | TCRBV11 | TCRBJ02-03 |
| CASSFGLAGDPGELFF | 1787 | TCRBV12-X | TCRBJ02-02 |
| CASSLGDVGYTF | 1788 | TCRBV12-03/12-04 | TCRBJ01-02 |
| CASSPTGTENTEAFF | 1789 | TCRBV18-01 | TCRBJ01-01 |
| CASTLPSYEQYF | 1790 | TCRBV06 | TCRBJ02-07 |
| CASSPRGRSSYNEQFF | 1791 | TCRBV04-02 | TCRBJ02-01 |
| CATSRSTGDNQPQHF | 1792 | TCRBV15-01 | TCRBJ01-05 |
| CASSLLWTGSTDTQYF | 1793 | TCRBV07 | TCRBJ02-03 |
| CASSLVPTGFNSPLHF | 1794 | TCRBV07 | TCRBJ01-06 |
| CATVGQGNSPLHF | 1795 | TCRBV19-01 | TCRBJ01-06 |
| CSASPGTGSTDTQYF | 1796 | TCRBV20-01 | TCRBJ02-03 |
| CASSLAPSITDTQYF | 1797 | TCRBV05-05 | TCRBJ02-03 |
| CSAKPGPREQYF | 1798 | TCRBV20-X | TCRBJ02-07 |
| CSARVPPYNEQFF | 1799 | TCRBV20-X | TCRBJ02-01 |
| CASSHLLGAGDTQYF | 1800 | TCRBV04-02 | TCRBJ02-03 |
| CASSLEANYNQPQHF | 1801 | TCRBV12-X | TCRBJ01-05 |
| CASSYLHMSYEQYF | 1802 | TCRBV06 | TCRBJ02-07 |
| CASSQVHFHNEQFF | 1803 | TCRBV03-01/03-02 | TCRBJ02-01 |
| CASSSPGQGSEQFF | 1804 | TCRBV28-01 | TCRBJ02-01 |
| CASSPQQSLSGNTIYF | 1805 | TCRBV07 | TCRBJ01-03 |
| CASRSSGGAVNEQFF | 1806 | TCRBV28-01 | TCRBJ02-01 |
| CASSGQGGRNQPQHF | 1807 | TCRBV18-01 | TCRBJ01-05 |
| CASSLDGLYEQYF | 1808 | TCRBV07 | TCRBJ02-07 |
| CASSYLGLSYEQYF | 1809 | TCRBV06 | TCRBJ02-07 |
| CASSLGRAGRDEQYF | 1810 | TCRBV05-01 | TCRBJ02-07 |
| CSAPLALNTEAFF | 1811 | TCRBV20-X | TCRBJ01-01 |
| CAWTLQGANGYTF | 1812 | TCRBV30-01 | TCRBJ01-02 |
| CSARAGGLSNEKLFF | 1813 | TCRBV20-X | TCRBJ01-04 |
| CASKGGTFTDTQYF | 1814 | TCRBV06 | TCRBJ02-03 |
| CSMGLQETQYF | 1815 | TCRBV20-01 | TCRBJ02-05 |
| CASSSRTGNPEQYF | 1816 | TCRBV07 | TCRBJ02-07 |
| CSAREGGSGTGELFF | 1817 | TCRBV20-X | TCRBJ02-02 |
| CASSLVGDRVRETQYF | 1818 | TCRBV11 | TCRBJ02-05 |
| CASSYRVQSPLHF | 1819 | TCRBV06 | TCRBJ01-06 |
| CATSDVGSNEKLFF | 1820 | TCRBV24-01 | TCRBJ01-04 |
| CSARSAGAGTGELFF | 1821 | TCRBV20-X | TCRBJ02-02 |
| CASSQGVSVTGELFF | 1822 | TCRBV04-02 | TCRBJ02-02 |
| CSVEEPPGVGTEAFF | 1823 | TCRBV29-01 | TCRBJ01-01 |
| CASSPSRAYGYTF | 1824 | TCRBV11 | TCRBJ01-02 |
| CASSVRLAEYNEQFF | 1825 | TCRBV09-01 | TCRBJ02-01 |
| CSARKGGGGTGELFF | 1826 | TCRBV20-X | TCRBJ02-02 |
| CASSPREGREDTQYF | 1827 | TCRBV09-01 | TCRBJ02-03 |
| CASSTPRRGQETQYF | 1828 | TCRBV06 | TCRBJ02-05 |
| CASSLAPANTEAFF | 1829 | TCRBV05-01 | TCRBJ01-01 |
| CSARVARGRDTQYF | 1830 | TCRBV20-X | TCRBJ02-03 |
| CASSLTSAGELFF | 1831 | TCRBV18-01 | TCRBJ02-02 |
| CASSLWQGAGANVLTF | 1832 | TCRBV05-01 | TCRBJ02-06 |
| CASSYQHSSTDTQYF | 1833 | TCRBV06 | TCRBJ02-03 |
| CASSWEANYNSPLHF | 1834 | TCRBV12-X | TCRBJ01-06 |
| CASSYTPGGRNEQFF | 1835 | TCRBV06 | TCRBJ02-01 |
| CASSPPNRQGGYEQYF | 1836 | TCRBV18-01 | TCRBJ02-07 |

In Tables 1-3 herein, the amino acid sequence represents the TCRβ CDR3 segment of the TCR, while V##-## or J##-## refers to a standard two level coding system [family]-[gene] for a particular part of the human genome that can be used as part of a TCR rearrangement formed in response to antigen exposure. The first two digits reflect a member of a family and the second two digits reflect a particular gene from within that family if present. So, by way of example, TCRBV06 would indicate a match of sequence to a specific family of variable (V) chain sequences where TCRBV06-05 indicates a more precise identification to a specific gene from within a family of variable chain sequences.

Identifies of these V- and J-gene sequences can be found at the international ImMunoGeneTics information system (available at "www" followed by ".imgt.org"), including at "www" followed by ".imgt.org/download/V-QUEST/IM-GT_V-QUEST_reference_directory/Homo_sapiens/TR/TRBV.fasta".

Therapeutic Methods

Also provided by the present disclosure are therapeutic methods. According to some embodiments, provided are methods comprising administering a Lyme disease therapy to a subject identified as comprising T cells that express a T cell receptor β chain (TCRβ) comprising a TCRβ CDR3 sequence set forth in SEQ ID Nos:1-1977. In certain embodiments, the methods comprise administering a Lyme disease therapy to a subject identified as comprising T cells that express two or more (e.g., two or more unique) TCRβ comprising a TCRβ CDR3 sequence set forth in SEQ ID Nos:1-1977. According to some embodiments, the methods comprise administering a Lyme disease therapy to a subject identified using a model/classifier as described elsewhere herein as having a present or previous B. burgdorferi infection and/or having Lyme disease. Such models include, but are not limited to, those that employ a two feature logistic regression with features representing the number of Lyme disease-associated TCRβ CDR3 sequences determined from the sample and the total number of unique TCRβ CDR3 sequences determined from the sample. As demonstrated in the Experimental section below, such a model exhibits high specificity for Lyme disease patients and greater sensitivity at diagnosing Lyme disease than STTT. In certain embodiments, the model may take into account the number of unique Lyme disease-associated TCRβ CDR3 sequences that are present in the TCRβ CDR3 sequences determined from the sample, e.g., where the greater the number of unique Lyme disease-associated TCRβ CDR3 sequences, the more likely the model is to classify the subject as having a present or previous B. burgdorferi infection and/or having Lyme disease. According to some embodiments, the number of unique Lyme disease-associated TCRβ CDR3 sequences is not a feature utilized by the model to classify the subject. In certain embodiments, the presence and/or frequency of one or more particular unique Lyme disease-associated TCRβ CDR3 sequences is a feature(s) used by the model to classify the subject. For example, the presence and/or frequency of one or more particular unique Lyme disease-associated TCRβ CDR3 sequences may be given relatively greater weight when classifying the subject as compared to the presence and/or frequency of one or more other unique Lyme disease-associated TCRβ CDR3 sequences. According to some embodiments, when a classification model weighs particular unique Lyme disease-associated TCRβ CDR3 sequences differently than other unique Lyme disease-associated TCRβ CDR3 sequences, the model may use convergent recombination to weigh the sequences differently, as described elsewhere herein.

Any suitable Lyme disease therapy may be administered to a subject identified as described above. Lyme disease therapies are known and may vary depending upon the age of the patient and stage of the disease: stage 1 (early localized—characterized by erythema migrans); stage 2 (early disseminated—characterized by multiple erythema migrans, isolated cranial nerve palsy, meningoradiculoneuritis, meningitis, carditis, and/or borrelial lymphocytoma); and stage 3 (late—characterized by arthritis, recurrent arthritis after oral therapy, encephalitis, and/or acrodematitis chronica atrophicans). Guidelines for antimicrobial therapy for specific stages of Lyme disease have been published by the Infectious Disease Society of America. See, e.g., Wormser et al. (2006) The clinical assessment, treatment, and prevention of lyme disease, human granulocytic anaplasmosis, and babesiosis: clinical practice guidelines by the Infectious Diseases Society of America. *Clin Infect Dis.* 43(9): 1089-1134; and Murray & Shapiro (2010) *Clin Lab Med.* 30(1): 311-328; the disclosures of which are incorporated herein by reference in their entireties for all purposes.

In certain embodiments, the Lyme disease therapy comprises an oral antibiotic therapy. According to some embodiments, the oral antibiotic therapy comprises oral administration of a therapeutically effective amount of an antibiotic selected from the group consisting of: doxycycline, amoxicillin, cefuroxime axetil, and any combination thereof. In certain embodiments, the antibiotic is doxycycline. Doxycycline is typically used in most patients except in children and pregnant women. In children, amoxicillin is typically the preferred antibiotic. Ceftriaxone has been shown to be effective in pregnant women. According to some embodiments, the Lyme disease therapy comprises an intravenous antibiotic therapy. Such intravenous antibiotic therapy is typically used in subjects with stage 2 or stage 3 Lyme disease and may include intravenous administration of a therapeutically effective amount of an antibiotic selected from ceftriaxone, cefotaxime, penicillin G, and any combination thereof.

As used herein, the terms "treatment," "treating," and the like, refer to obtaining a desired pharmacologic and/or physiologic effect. The effect may be therapeutic in terms of a partial or complete cure for a disease and/or adverse effect attributable to the disease. "Treatment," as used herein, covers any treatment of a disease in a mammal, including in a human, and includes: (a) inhibiting the disease, i.e., arresting its development; and (b) relieving the disease, i.e., causing regression of the disease.

A "therapeutically effective amount" or "efficacious amount" refers to the amount of a therapeutic agent that, when administered to a mammal or other subject for treating a disease, is sufficient to affect such treatment for the disease. The "therapeutically effective amount" will vary depending on the therapeutic agent, the disease and its severity and the age, weight, etc., of the subject to be treated.

The Lyme disease therapy comprises administering a therapeutic agent to the identified subject. As used herein, a "therapeutic agent" is a physiologically or pharmacologically active substance that can produce a desired biological effect in a targeted site in an animal, such as a mammal or in a human. The therapeutic agent may be any inorganic or organic compound. A therapeutic agent may decrease, suppress, attenuate, diminish, arrest, or stabilize the development or progression of the disease in an animal such as a mammal or human. Examples include, without limitation, peptides, proteins, nucleic acids (including siRNA, miRNA and DNA), polymers, and small molecules. In various embodiments, the therapeutic agents may be characterized or uncharacterized.

In some embodiments, the Lyme disease therapy is an adoptive cell therapy. Non-limiting examples of adoptive cell therapies include those involving administering to the subject an effective amount of recombinant cells (e.g., recombinant immune cells such as T cells) that express a T cell receptor comprising the Lyme disease-associated TCRβ CDR3 sequence identified as being present in TCRs expressed by T cells in the subject. Similar to CAR therapies, TCR therapies modify the patient's T lymphocytes ex vivo before being administered back into the patient's body. The target antigens identified by CAR-T cell therapy are all cell surface proteins, while TCR-T cell therapy can recognize intracellular antigen fragments presented by MHC molecules, so TCR-T cell therapy has a wider range of targets. Approaches for TCR therapy are known and described in, e.g., Zhang et al. (2019) *Technol Cancer Res Treat.* 18:1533033819831068; Govers et al. (2010) Trends in Molecular Medicine 16(2):77-87; Zhao et al. (2019) Front. Immunol. 10:2250.

Nucleic acids that encode a T cell receptor β chain comprising a TCRβ CDR3 sequence set forth in SEQ ID Nos:1-1977 are also provided. For example, in certain embodiments, provided is an expression vector comprising a nucleic acid sequence that encodes a T cell receptor β chain comprising a TCRβ CDR3 sequence set forth in SEQ ID Nos:1-1977 operably linked to a nucleic acid expression control sequence. A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

In order to express a desired T cell receptor β chain comprising a TCRβ CDR3 sequence setforth in SEQ ID Nos:1-1977, a nucleotide sequence encoding the T cell receptor β chain can be inserted into an appropriate vector, e.g., using recombinant DNA techniques known in the art. Exemplary viral vectors include, without limitation, retrovirus (including lentivirus), adenovirus, adeno-associated virus, herpesvirus (e.g., herpes simplex virus), poxvirus, papillomavirus, and papovavirus (e.g., SV40). Illustrative examples of expression vectors include, but are not limited to pClneo vectors (Promega) for expression in mammalian cells; pLenti4/V 5-DEST™, pLenti6/V 5-DEST™, murine stem cell virus (MSCV), MSGV, moloney murine leukemia virus (MMLV), and pLenti6.2/V5-GW/lacZ (Invitrogen) for lentivirus-mediated gene transfer and expression in mammalian cells. In certain embodiments, a nucleic acid sequence encoding the T cell receptor β chain may be ligated into any such expression vectors for the expression of the T cell receptor β chain in mammalian cells.

Expression control sequences, control elements, or regulatory sequences present in an expression vector are those non-translated regions of the vector—origin of replication, selection cassettes, promoters, enhancers, translation initiation signals (Shine Dalgarno sequence or Kozak sequence), introns, a polyadenylation sequence, 5' and 3' untranslated regions, and/or the like—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Components of the expression vector are operably linked such that they are in a relationship permitting them to function in their intended manner. In some embodiments, the term refers to a functional linkage between a nucleic acid expression control sequence (such as a promoter, and/or enhancer) and a second polynucleotide sequence, e.g., a nucleic acid encoding the T cell receptor β chain, where the expression control sequence directs transcription of the nucleic acid encoding the T cell receptor β chain.

In some embodiments, the expression vector is an episomal vector or a vector that is maintained extrachromosomally. As used herein, the term "episomal" refers to a vector that is able to replicate without integration into the host cell's chromosomal DNA and without gradual loss from a dividing host cell also meaning that said vector replicates extrachromosomally or episomally. Such a vector may be engineered to harbor the sequence coding for the origin of DNA replication or "ori" from an alpha, beta, or gamma herpesvirus, an adenovirus, SV40, a bovine papilloma virus, a yeast, or the like. The host cell may include a viral replication transactivator protein that activates the replication. Alpha herpes viruses have a relatively short reproductive cycle, variable host range, efficiently destroy infected cells and establish latent infections primarily in sensory ganglia. Illustrative examples of alpha herpes viruses include HSV 1, HSV 2, and VZV. Beta herpesviruses have long reproductive cycles and a restricted host range. Infected cells often enlarge. Non-limiting examples of beta herpes viruses include CMV, HHV-6 and HHV-7. Gamma-herpesviruses are specific for either T or B lymphocytes, and latency is often demonstrated in lymphoid tissue. Illustrative examples of gamma herpes viruses include EBV and HHV-8.

Also provided are recombinant cells that comprise any of the expression vectors of the present disclosure comprising a nucleic acid that encodes a T cell receptor β chain comprising a TCRβ CDR3 sequence set forth in SEQ ID Nos:1-1977. In certain aspects, provided are cells that express a TCR comprising a T cell receptor β chain comprising a TCRβ CDR3 sequence set forth in SEQ ID Nos:1-1977 on the surface of the cell.

In some embodiments, the cells of the present disclosure are eukaryotic cells. Eukaryotic cells of interest include, but are not limited to, yeast cells, insect cells, mammalian cells, and the like. Mammalian cells of interest include, e.g., murine cells, non-human primate cells, human cells, and the like.

"Recombinant host cells," "host cells," "cells," "cell lines," "cell cultures," and other such terms denoting microorganisms or higher eukaryotic cell lines, refer to cells which can be, or have been, used as recipients for a recombinant vector or other transferred DNA, and include the progeny of the cell which has been transfected. Host cells may be cultured as unicellular or multicellular entities (e.g., tissue, organs, or organoids) including an expression vector of the present disclosure.

In one aspect, the cells provided herein include immune cells. Non-limiting examples of recombinant immune cells which may include any of the expression vectors of the present disclosure include T cells, B cells, natural killer (NK) cells, macrophages, monocytes, neutrophils, dendritic cells, mast cells, basophils, and eosinophils. In some embodiments, the immune cell is a T cell. Examples of T cells include naive T cells ($T_N$), cytotoxic T cells ($T_{CTL}$), memory T cells ($T_{MEM}$), T memory stem cells ($T_{SCM}$), central memory T cells ($T_{CM}$), effector memory T cells ($T_{EM}$), tissue resident memory T cells ($T_{RM}$), effector T cells ($T_{EFF}$), regulatory T cells ($T_{REGs}$), helper T cells ($T_H$, $T_H1$, $T_H2$, $T_H17$) CD4+ T cells, CD8+ T cells, virus-specific T cells, alpha beta T cells ($T_{\alpha\beta}$), and gamma delta T cells ($T_{\gamma\delta}$). In another aspect, the cells provided herein comprise stem cells, e.g., an embryonic stem cell or an adult stem cell.

Also provided are methods of making the cells of the present disclosure. In some embodiments, such methods include transfecting or transducing cells with a nucleic acid or expression vector of the present disclosure, e.g., an expression vector comprising a nucleic acid that encodes a T cell receptor β chain comprising a TCRβ CDR3 sequence set forth in SEQ ID Nos:1-1977. The term "transfection" or "transduction" is used to refer to the introduction of foreign DNA into a cell. A cell has been "transfected" when exogenous DNA has been introduced inside the cell membrane. A number of transfection techniques are generally known in the art. See, e.g., Sambrook et al. (2001) Molecular Cloning, a laboratory manual, 3$^{rd}$ edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material.

In some embodiments, a cell of the present disclosure is produced by transfecting the cell with a viral vector encoding the T cell receptor β chain comprising a TCRβ CDR3 sequence set forth in SEQ ID Nos:1-1977. In some embodiments, such methods include activating a population of T cells (e.g., T cells obtained from an individual to whom a TCR T cell therapy will be administered), stimulating the population of T cells to proliferate, and transducing the T cell with a viral vector encoding the T cell receptor β chain comprising a TCRβ CDR3 sequence set forth in SEQ ID Nos:1-1977. In some embodiments, the T cells are transduced with a retroviral vector, e.g., a gamma retroviral vector or a lentiviral vector, encoding the T cell receptor β chain comprising a TCRβ CDR3 sequence set forth in SEQ ID Nos:1-1977. In some embodiments, the T cells are transduced with a lentiviral vector encoding the T cell receptor β chain comprising a TCRβ CDR3 sequence set forth in SEQ ID Nos:1-1977.

Cells of the present disclosure may be autologous/autogeneic ("self") or non-autologous ("non-self," e.g., allogeneic, syngeneic or xenogeneic). "Autologous" as used herein, refers to cells from the same individual. "Allogeneic" as used herein refers to cells of the same species that differ genetically from the cell in comparison. "Syngeneic," as used herein, refers to cells of a different individual that are genetically identical to the cell in comparison. In some embodiments, the cells are T cells obtained from a mammal. In some embodiments, the mammal is a primate. In some embodiments, the primate is a human.

T cells may be obtained from a number of sources including, but not limited to, peripheral blood, peripheral blood mononuclear cells, bone marrow, lymph node tissue, cord blood, thymus tissue, tissue from a site of infection, ascites, pleural effusion, spleen tissue, and tumors. In certain embodiments, T cells can be obtained from a unit of blood collected from an individual using any number of known techniques such as sedimentation, e.g., FICOLL™ separation.

In some embodiments, an isolated or purified population of T cells is used. In some embodiments, $T_{CTL}$ and $T_H$ lymphocytes are purified from PBMCs. In some embodiments, the $T_{CTL}$ and $T_H$ lymphocytes are sorted into naïve ($T_N$), memory ($T_{MEM}$), and effector ($T_{EFF}$) T cell subpopulations either before or after activation, expansion, and/or genetic modification. Suitable approaches for such sorting are known and include, e.g., magnetic-activated cell sorting (MACS), where TN are CD45RA$^+$ CD62L$^+$ CD95$^-$; TSCM are CD45RA$^+$ CD62L$^+$ CD95$^+$; TCM are CD45RO$^+$ CD62L$^+$ CD95$^+$; and TEM are CD45RO$^+$ CD62L$^-$ CD95$^+$. An example approach for such sorting is described in Wang et al. (2016) *Blood* 127(24):2980-90.

A specific subpopulation of T cells expressing one or more of the following markers: CD3, CD4, CD8, CD28, CD45RA, CD45RO, CD62, CD127, and HLA-DR can be further isolated by positive or negative selection techniques. In some embodiments, a specific subpopulation of T cells, expressing one or more of the markers selected from the group consisting of CD62L, CCR7, CD28, CD27, CD122, CD127, CD197; or CD38 or CD62L, CD127, CD197, and CD38, is further isolated by positive or negative selection techniques. In some embodiments, the manufactured T cell compositions do not express one or more of the following markers: CD57, CD244, CD 160, PD-1, CTLA4, TIM3, and LAG3. In some embodiments, the manufactured T cell compositions do not substantially express one or more of the following markers: CD57, CD244, CD 160, PD-1, CTLA4, TIM3, and LAG3.

In order to achieve therapeutically effective doses of T cell compositions, the T cells may be subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety for all purposes. In some embodiments, T cells are activated and expanded for about 1 to 21 days, e.g., about 5 to 21 days. In some embodiments, T cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of a nucleic acid (e.g., expression vector) encoding the polypeptide into the T cells.

In some embodiments, T cells are activated and expanded for about 6 hours, about 12 hours, about 18 hours or about 24 hours prior to introduction of a nucleic acid (e.g., expression vector) encoding the T cell receptor β chain comprising a TCRβ CDR3 sequence set forth in SEQ ID Nos:1-1977 into the T cells. In some embodiments, T cells are activated at the same time that a nucleic acid (e.g., an expression vector) encoding the T cell receptor β chain is introduced into the T cells.

In some embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan. Further illustrative examples of cell culture media include, but are not limited to RPMI 1640, Clicks, AEVI-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

In some embodiments, the nucleic acid (e.g., an expression vector) encoding the T cell receptor β chain is introduced into the cell (e.g., a T cell) by microinjection, transfection, lipofection, heat-shock, electroporation, transduction, gene gun, microinjection, DEAE-dextran-mediated transfer, and the like. In some embodiments, the nucleic acid (e.g., expression vector) encoding the T cell receptor β chain is introduced into the cell (e.g., a T cell) by AAV transduction. The AAV vector may comprise ITRs from AAV2, and a serotype from any one of AAV1, AAV2, AAV3, AAV4, AAV5, AAV6, AAV7, AAV8, AAV9, or AAV 10. In some embodiments, the AAV vector comprises ITRs from AAV2 and a serotype from AAV6. In some embodiments, the nucleic acid (e.g., expression vector) encoding the T cell receptor β chain is introduced into the cell (e.g., a T cell) by lentiviral transduction. The lentiviral vector backbone may be derived from HIV-1, HIV-2, visna-maedi virus (VMV) virus, caprine arthritis-encephalitis virus (CAEV), equine infectious anemia virus (EIAV), feline immunodeficiency virus (FIV), bovine immune deficiency virus (BIV), or simian immunodeficiency virus (SIV). The lentiviral vector may be integration competent or an integrase deficient lentiviral vector (TDLV). In one embodiment, IDLV vectors including an HIV-based vector backbone (i.e., HIV cis-acting sequence elements) are employed.

Computer-Readable Media and Systems

Also provided by the present disclosure are computer-readable media and systems.

In certain aspects, provided are one or more computer-readable media having stored thereon one or more TCRβ CDR3 sequences set forth in SEQ ID Nos:1-1977. The number of TCRβ CDR3 sequences set forth in SEQ ID Nos:1-1977 stored on the one or more computer-readable media may vary. For example, the one or more computer-readable media may have stored thereon 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more, 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 950 or more, 1000 or more, 1050 or more, 1100 or more, 1150 or more, 1200 or more, 1250 or more, 1300 or more, 1350 or more, 1400 or more, 1450 or more, 1500 or more, 1550 or more, 1600 or more, 1650 or more, 1700 or more, 1750 or more, 1800 or more, 1850 or more, 1900 or more, 1950 or more, or each of the TCRβ CDR3 sequences set forth in SEQ ID Nos:1-1977. When fewer than all of the TCRβ CDR3 sequences set forth in SEQ ID Nos:1-1977 are stored on the one or more computer-readable media, the one or more computer-readable media may have stored thereon any desired number (e.g., as set forth above) and combination of TCRβ CDR3 sequences set forth in SEQ ID Nos:1-1977. In some embodiments, the one or more computer-readable media may have stored thereon 1800 or fewer, 1750 or fewer, 1700 or fewer, 1650 or fewer, 1600 or fewer, 1550 or fewer, 1500 or fewer, 1450 or fewer, 1400 or fewer, 1350 or fewer, 1300 or fewer, 1250 or fewer, 1200 or fewer, 1150 or fewer, 1100 or fewer, 1050 or fewer, 1000 or fewer, 950 or fewer, 900 or fewer, 850 or fewer, 800 or fewer, 750 or fewer, 700 or fewer, 650 or fewer, 600 or fewer, 550 or fewer, 500 or fewer, 450 or fewer, 400 or fewer, 350 or fewer, 300 or fewer, 250 or fewer, 200 or fewer, 190 or fewer, 180 or fewer, 170 or fewer, 160 or fewer, 150 or fewer, 140 or fewer, 130 or fewer, 120 or fewer, 110 or fewer, 100 or fewer, 90 or fewer, 80 or fewer, 70 or fewer, 60 or fewer, 50 or fewer, 40 or fewer, 30 or fewer, 20 or fewer, or 10 or fewer of the TCRβ CDR3 sequences set forth in SEQ ID Nos:1-1977, in any desired combination.

Also provided are systems for assessing TCRβ CDR3 sequences. According to some embodiments, provided are systems for assessing TCRβ CDR3 sequences, such systems comprising one or more processors and one or more computer-readable media. The one or more computer-readable media comprise instructions stored thereon, which when executed by the one or more processors, cause the one or more processors to assess TCRβ CDR3 sequences determined from a sample obtained from a subject having or suspected of having a tick bite for the presence or absence of one or more TCRβ CDR3 sequences set forth in SEQ ID Nos:1-1977. According to some embodiments, the number of TCRβ CDR3 sequences determined from the sample obtained from the subject is from 1,000 to 2,000,000. For example, in certain embodiments, the number of determined TCRβ CDR3 sequences is 2,000,000 or fewer (e.g., 1,500,000 or fewer, 1,250,000 or fewer, 1,000,000 or fewer, 750,000 or fewer, or 500,000 or fewer), but 1,000 or more, 5,000 or more, 10,000 or more, 15,000 or more, 20,000 or more, 25,000 or more, 30,000 or more, 35,000 or more, 40,000 or more, 45,000 or more, 50,000 or more, 55,000 or more, 60,000 or more, 65,000 or more, 70,000 or more, 75,000 or more, 80,000 or more, 85,000 or more, 90,000 or more, 95,000 or more, or 100,000 or more. The number of TCRβ CDR3 sequences set forth in SEQ ID Nos:1-1977 to which the determined TCRβ CDR3 sequences is compared may vary. For example, the determined TCRβ CDR3 sequences may be compared to 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more, 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 950 or more, 1000 or more, 1050 or more, 1100 or more, 1150 or more, 1200 or more, 1250 or more, 1300 or more, 1350 or more, 1400 or more, 1450 or more, 1500 or more, 1550 or more, 1600 or more, 1650 or more, 1700 or more, 1750 or more, 1800 or more, 1850 or more, 1900 or more, 1950 or more, or each of the TCRβ CDR3 sequences set forth in SEQ ID Nos:1-1977. When the determined TCRβ CDR3 sequences are compared to fewer than all of the TCRβ CDR3 sequences set forth in SEQ ID Nos:1-1977, the determined TCRβ CDR3 sequences may be compared to any desired number (e.g., as set forth above) and combination of TCRβ CDR3 sequences set forth in SEQ ID Nos:1-1977.

The one or more computer-readable media may further comprise instructions stored thereon, which when executed by the one or more processors, cause the one or more processors to perform one or more additional steps based on the results of the assessing step. For example, if it is determined from the assessing step that none of the TCRβ CDR3 sequences set forth in SEQ ID Nos:1-1977 are present in the TCRβ CDR3 sequences determined from the sample obtained from the subject having or suspected of having a tick bite, then the instructions may further cause the one or more processors to, e.g., identify the subject as not having a *B. burgdorferi* infection, identify the subject as not having Lyme disease, identify the subject as one who should not be administered a Lyme disease therapy (e.g., an antibiotic-based Lyme disease therapy such as doxycycline administration), and/or the like. Also, by way of example, if it is determined from the assessing step that one or more (e.g., 2 or more, 3 or more, 4 or more, 5 or more, or 10 or more) of the TCRβ CDR3 sequences set forth in SEQ ID Nos:1-1977 are present in the TCRβ CDR3 sequences determined from the sample obtained from the subject having or suspected of having a tick bite, then the instructions may further cause the one or more processors to, e.g., identify the subject as having a present or previous *B. burgdorferi* infection, identify the subject as having Lyme disease, and/or identify the subject as one who should be administered a Lyme disease therapy, e.g., any of the Lyme disease therapies described elsewhere herein.

In certain embodiments, the one or more computer-readable media may further comprise instructions stored thereon, which when executed by the one or more processors, cause the one or more processors to subject the results of the assessing step to further analysis, such as subjecting the results of the assessing step to a model. For example, the instructions may cause the one or more processors to subject the results of the assessing step to a model in order to classify the subject as having a present or previous *B. burgdorferi* infection or not having a present or previous *B. burgdorferi* infection; and/or to classify the subject as having Lyme disease or not having Lyme disease. One of ordinary skill in the art will appreciate that, with the benefit of the TCRβ CDR3 sequences set forth in SEQ ID Nos:1-1977 described herein, a variety of useful models may be applied to the results of the assessment. In one non-limiting example, the instructions may cause the one or more processors to subject the results of the assessing step to a two feature logistic regression with features representing the number of Lyme disease-associated TCRβ CDR3 sequences determined from the sample and the total number of unique TCRβ CDR3 sequences determined from the sample. As demonstrated in the Experimental section below, such a model exhibits high specificity for Lyme disease patients and greater sensitivity at diagnosing Lyme disease than STTT.

In certain embodiments, when the one or more computer-readable media further comprise instructions stored thereon, which when executed by the one or more processors, cause the one or more processors to subject the results of the assessing step to a model for classification purposes (e.g., as described above), the model may take into account the number of unique Lyme disease-associated TCRβ CDR3 sequences that are present in the TCRβ CDR3 sequences determined from the sample, e.g., where the greater the number of unique Lyme disease-associated TCRβ CDR3 sequences, the more likely the model is to classify the subject as having a present or previous *B. burgdorferi* infection and/or having Lyme disease. According to some embodiments, the number of unique Lyme disease-associated TCRβ CDR3 sequences is not a feature utilized by the model to classify the subject. In certain embodiments, the presence and/or frequency of one or more particular unique Lyme disease-associated TCRβ CDR3 sequences is a feature (s) used by the model to classify the subject. For example, the presence and/or frequency of one or more particular unique Lyme disease-associated TCRβ CDR3 sequences may be given relatively greater weight when classifying the subject as compared to the presence and/or frequency of one or more other unique Lyme disease-associated TCRβ CDR3 sequences.

A variety of processor-based systems may be employed to implement the embodiments of the present disclosure. Such systems may include system architecture wherein the components of the system are in electrical communication with each other using a bus. System architecture can include a processing unit (CPU or processor), as well as a cache, that are variously coupled to the system bus. The bus couples various system components including system memory, (e.g., read only memory (ROM) and random access memory (RAM), to the processor.

System architecture can include a cache of high-speed memory connected directly with, in close proximity to, or integrated as part of the processor. System architecture can copy data from the memory and/or the storage device to the cache for quick access by the processor. In this way, the cache can provide a performance boost that avoids processor delays while waiting for data. These and other modules can control or be configured to control the processor to perform various actions. Other system memory may be available for use as well. Memory can include multiple different types of memory with different performance characteristics. Processor can include any general purpose processor and a hardware module or software module, such as first, second and third modules stored in the storage device, configured to control the processor as well as a special-purpose processor where software instructions are incorporated into the actual processor design. The processor may essentially be a completely self-contained computing system, containing multiple cores or processors, a bus, memory controller, cache, etc. A multi-core processor may be symmetric or asymmetric.

To enable user interaction with the computing system architecture, an input device can represent any number of input mechanisms, such as a microphone for speech, a touch-sensitive screen for gesture or graphical input, keyboard, mouse, motion input, speech and so forth. An output device can also be one or more of a number of output mechanisms. In some instances, multimodal systems can enable a user to provide multiple types of input to communicate with the computing system architecture. A communications interface can generally govern and manage the user input and system output. There is no restriction on operating on any particular hardware arrangement and therefore the basic features here may easily be substituted for improved hardware or firmware arrangements as they are developed.

The storage device is typically a non-volatile memory and can be a hard disk or other types of computer-readable media which can store data that are accessible by a computer, such as magnetic cassettes, flash memory cards, solid state memory devices, digital versatile disks, cartridges, random access memories (RAMs), read only memory (ROM), and hybrids thereof.

The storage device can include software modules for controlling the processor. Other hardware or software modules are contemplated. The storage device can be connected to the system bus. In one aspect, a hardware module that performs a particular function can include the software component stored in a computer-readable medium in connection with the necessary hardware components, such as the processor, bus, output device, and so forth, to carry out various functions of the disclosed technology.

Embodiments within the scope of the present disclosure may also include tangible and/or non-transitory computer-readable storage media or devices for carrying or having computer-executable instructions or data structures stored thereon. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform tasks or implement abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The following examples are offered by way of illustration and not by way of limitation.

EXPERIMENTAL

Example 1—Prediction of Lyme Disease from TCR Repertoire Data

A pseudolabeling procedure as described in U.S. patent application Ser. No. 16/887,758 (the disclosure of which is incorporated herein by reference in its entirety for all purposes) was applied to a set of PBMC samples from 223 Lyme disease patients (with serology results for comparison) yielded a classifier test for Lyme disease with an overall sensitivity of approximately 50% compared to the 17-40% reported for two-tier serology.

Briefly, TCR repertoires from 66 Lyme patients who were seropositive by standard two-tier serology at their first physician visit were compared to TCR repertoires from approximately 1,300 controls (putatively Lyme-negative). TCRs associated with Lyme disease were identified as those statistically more prevalent in cases than controls. A classifier was constructed from these Lyme-associated TCRs to distinguish Lyme from non-Lyme repertoires, as shown in Table 2 below.

TABLE 2

Lyme Disease-Associated TCRs

| V Gene Segment | TCRβ CDR3 Amino Acid Sequence | SEQ ID NO | J Gene Segment | # Lyme Samples (out of 66) | # Control Samples (out of ~1300) | P value for Lyme Association |
|---|---|---|---|---|---|---|
| TCRBV05-01 | CASRRGTDQPQHF | 1030 | TCRBJ01-05 | 5 | 0 | 2.07E−07 |
| TCRBV05-01 | CASSAGGQGHYGYTF | 647 | TCRBJ01-02 | 4 | 0 | 4.68E−06 |
| TCRBV05-01 | CASSLGGQGHYGYTF | 1601 | TCRBJ01-02 | 12 | 10 | 1.76E−11 |
| TCRBV05-01 | CASSLGVGTYNEQFF | 1837 | TCRBJ02-01 | 6 | 6 | 6.66E−06 |
| TCRBV06 | CASSYLDLSYEQYF | 1118 | TCRBJ02-07 | 7 | 2 | 1.28E−08 |
| TCRBV06 | CASSYLGLSYEQYF | 1809 | TCRBJ02-07 | 7 | 6 | 5.26E−07 |
| TCRBV06 | CASSYLHLSYEQYF | 618 | TCRBJ02-07 | 21 | 2 | 4.94E−28 |
| TCRBV06-05 | CASRYKDTEAFF | 1411 | TCRBJ01-01 | 7 | 0 | 3.83E−10 |
| TCRBV06-05 | CASRYRDTEAFF | 1433 | TCRBJ01-01 | 6 | 6 | 6.66E−06 |
| TCRBV06-05 | CASSYLGLSYEQYF | 1809 | TCRBJ02-07 | 8 | 5 | 1.71E−08 |
| TCRBV06-05 | CASSYRRGSSYNEQFF | 87 | TCRBJ02-01 | 6 | 5 | 3.46E−06 |
| TCRBV06-06 | CASSSGTGSEKLFF | 1353 | TCRBJ01-04 | 7 | 3 | 4.12E−08 |
| TCRBV06-06 | CASSYLALSYEQYF | 700 | TCRBJ02-07 | 4 | 0 | 4.68E−06 |
| TCRBV06-06 | CASSYLDLSYEQYF | 1118 | TCRBJ02-07 | 5 | 0 | 2.07E−07 |
| TCRBV06-06 | CASSYLGLSYEQYF | 1809 | TCRBJ02-07 | 17 | 4 | 1.13E−20 |
| TCRBV06-06 | CASSYLHLSYEQYF | 618 | TCRBJ02-07 | 5 | 1 | 1.20E−06 |
| TCRBV07 | CASSLAGLNEQFF | 200 | TCRBJ02-01 | 8 | 6 | 3.84E−08 |
| TCRBV07-02 | CASSLAPRDRGNQPQHF | 710 | TCRBJ01-05 | 5 | 0 | 2.07E−07 |

TABLE 2-continued

Lyme Disease-Associated TCRs

| V Gene Segment | TCRβ CDR3 Amino Acid Sequence | SEQ ID NO | J Gene Segment | # Lyme Samples (out of 66) | # Control Samples (out of ~1300) | P value for Lyme Association |
|---|---|---|---|---|---|---|
| TCRBV07-02 | CASSLVGSGTYNEQFF | 993 | TCRBJ02-01 | 7 | 10 | 5.14E−06 |
| TCRBV07-06 | CASSLAGLNEQFF | 200 | TCRBJ02-01 | 15 | 11 | 9.93E−15 |
| TCRBV07-06 | CASSLAGLNEQYF | 1046 | TCRBJ02-07 | 10 | 2 | 1.60E−12 |
| TCRBV07-06 | CASSLAPGANVLTF | 1838 | TCRBJ02-06 | 6 | 6 | 6.66E−06 |
| TCRBV07-06 | CASSLAPLGDEQFF | 1173 | TCRBJ02-01 | 6 | 0 | 9.01E−09 |
| TCRBV07-06 | CASSLAPLGDEQYF | 623 | TCRBJ02-07 | 6 | 0 | 9.01E−09 |
| TCRBV07-06 | CASSLAPLTDTQYF | 280 | TCRBJ02-03 | 9 | 1 | 6.28E−12 |
| TCRBV07-06 | CASSLGAASYEQYF | 1012 | TCRBJ02-07 | 10 | 7 | 3.92E−10 |
| TCRBV07-06 | CASSLGATNEKLFF | 1839 | TCRBJ01-04 | 14 | 64 | 5.91E−06 |
| TCRBV07-06 | CASSLGAVNTEAFF | 1840 | TCRBJ01-01 | 9 | 7 | 5.77E−09 |
| TCRBV09-01 | CASSVVTGRTDTQYF | 1841 | TCRBJ02-03 | 5 | 2 | 4.05E−06 |
| TCRBV11 | CASSLSPRGRGYGYTF | 178 | TCRBJ01-02 | 6 | 0 | 9.01E−09 |
| TCRBV11-03 | CASSPGTSSSTDTQYF | 1168 | TCRBJ02-03 | 5 | 0 | 2.07E−07 |
| TCRBV12 | CASSFEANYNSPLHF | 1234 | TCRBJ01-06 | 6 | 0 | 9.01E−09 |
| TCRBV12 | CASSFEPNYNSPLHF | 64 | TCRBJ01-06 | 4 | 0 | 4.68E−06 |
| TCRBV12 | CASSFETNYNSPLHF | 287 | TCRBJ01-06 | 6 | 0 | 9.01E−09 |
| TCRBV12 | CASSFEVNYNSPLHF | 690 | TCRBJ01-06 | 6 | 2 | 2.34E−07 |
| TCRBV12 | CASSFLAGDTGELFF | 550 | TCRBJ02-02 | 8 | 10 | 4.83E−07 |
| TCRBV12 | CASSLEANYNSPLHF | 347 | TCRBJ01-06 | 11 | 1 | 1.17E−14 |
| TCRBV12 | CASSLETNYNSPLHF | 256 | TCRBJ01-06 | 4 | 0 | 4.68E−06 |
| TCRBV12 | CASSLEVNYNSPLHF | 1299 | TCRBJ01-06 | 5 | 1 | 1.20E−06 |
| TCRBV18-01 | CASSPDGGRNQPQHF | 557 | TCRBJ01-05 | 6 | 6 | 6.66E−06 |
| TCRBV18-01 | CASSPETLQETQYF | 143 | TCRBJ02-05 | 4 | 0 | 4.68E−06 |
| TCRBV18-01 | CASSPTGTENTEAFF | 1789 | TCRBJ01-01 | 8 | 15 | 4.50E−06 |
| TCRBV19-01 | CASRMDRGTDTQYF | 1842 | TCRBJ02-03 | 4 | 0 | 4.68E−06 |
| TCRBV19-01 | CASSIHPNEQFF | 1639 | TCRBJ02-01 | 4 | 0 | 4.68E−06 |
| TCRBV19-01 | CASSIRTANEKLFF | 945 | TCRBJ01-04 | 10 | 24 | 1.43E−06 |
| TCRBV20 | CSADGTSGYNEQFF | 1653 | TCRBJ02-01 | 7 | 8 | 1.83E−06 |
| TCRBV20 | CSAKGARETQYF | 1843 | TCRBJ02-05 | 4 | 0 | 4.68E−06 |
| TCRBV20 | CSAPRSLNTEAFF | 1603 | TCRBJ01-01 | 8 | 6 | 3.84E−08 |
| TCRBV20 | CSARAAGAGTGELFF | 489 | TCRBJ02-02 | 4 | 0 | 4.68E−06 |
| TCRBV20 | CSARAAGGGTGELFF | 753 | TCRBJ02-02 | 6 | 5 | 3.46E−06 |
| TCRBV20 | CSARAGGAGTGELFF | 811 | TCRBJ02-02 | 9 | 9 | 2.28E−08 |
| TCRBV20 | CSARASGSGTGELFF | 78 | TCRBJ02-02 | 9 | 7 | 5.77E−09 |
| TCRBV20 | CSARDEGPETQYF | 551 | TCRBJ02-05 | 7 | 7 | 1.01E−06 |
| TCRBV20 | CSAREGGSGTGELFF | 1817 | TCRBJ02-02 | 7 | 7 | 1.01E−06 |
| TCRBV20 | CSARKGGAGTGELFF | 181 | TCRBJ02-02 | 9 | 2 | 3.33E−11 |
| TCRBV20 | CSARKGGGGTGELFF | 1826 | TCRBJ02-02 | 6 | 2 | 2.34E−07 |
| TCRBV20 | CSARKGGSGTGELFF | 289 | TCRBJ02-02 | 6 | 1 | 6.08E−08 |
| TCRBV20 | CSARKSGSGTGELFF | 202 | TCRBJ02-02 | 4 | 0 | 4.68E−06 |
| TCRBV20 | CSARLAGAGTGELFF | 712 | TCRBJ02-02 | 11 | 13 | 1.59E−09 |
| TCRBV20 | CSARLAGGGTGELFF | 1026 | TCRBJ02-02 | 17 | 21 | 3.17E−14 |
| TCRBV20 | CSARPGGAGTGELFF | 1705 | TCRBJ02-02 | 8 | 8 | 1.53E−07 |
| TCRBV20 | CSARPGGSGTGELFF | 676 | TCRBJ02-02 | 9 | 6 | 2.62E−09 |
| TCRBV20 | CSARRAGGGTGELFF | 350 | TCRBJ02-02 | 12 | 13 | 1.27E−10 |
| TCRBV20 | CSARRGGAGTGELFF | 779 | TCRBJ02-02 | 11 | 7 | 2.51E−11 |
| TCRBV20 | CSARRGGGGTGELFF | 1571 | TCRBJ02-02 | 10 | 7 | 3.92E−10 |
| TCRBV20 | CSARRGGSGTGELFF | 1221 | TCRBJ02-02 | 10 | 7 | 3.92E−10 |
| TCRBV20 | CSARTGGAGTGELFF | 368 | TCRBJ02-02 | 12 | 12 | 6.85E−11 |
| TCRBV20 | CSARTSGGGTGELFF | 1558 | TCRBJ02-02 | 12 | 44 | 4.53E−06 |
| TCRBV20 | CSARTSGSGTGELFF | 324 | TCRBJ02-02 | 12 | 12 | 6.85E−11 |
| TCRBV20 | CSARVAGAGTGELFF | 1421 | TCRBJ02-02 | 8 | 6 | 3.84E−08 |
| TCRBV20 | CSARVAGGGTGELFF | 1688 | TCRBJ02-02 | 21 | 30 | 1.01E−16 |
| TCRBV20 | CSARVGGAGTGELFF | 1084 | TCRBJ02-02 | 13 | 14 | 1.78E−11 |
| TCRBV20 | CSARVSGSGTGELFF | 1004 | TCRBJ02-02 | 6 | 5 | 3.46E−06 |

TABLE 2-continued

Lyme Disease-Associated TCRs

| V Gene Segment | TCRβ CDR3 Amino Acid Sequence | SEQ ID NO | J Gene Segment | # Lyme Samples (out of 66) | # Control Samples (out of ~1300) | P value for Lyme Association |
|---|---|---|---|---|---|---|
| TCRBV24-01 | CATSDVGSNEKLFF | 1820 | TCRBJ01-04 | 5 | 1 | 1.20E−06 |
| TCRBV24-01 | CATSENRNTEAFF | 1475 | TCRBJ01-01 | 8 | 5 | 1.71E−08 |
| TCRBV25-01 | CASSEREGVNTEAFF | 1752 | TCRBJ01-01 | 4 | 0 | 4.68E−06 |
| TCRBV27-01 | CASSFRRGTDTQYF | 1844 | TCRBJ02-03 | 6 | 6 | 6.66E−06 |
| TCRBV28-01 | CASRGPGQPQHF | 429 | TCRBJ01-05 | 6 | 6 | 6.66E−06 |
| TCRBV28-01 | CASRTPGDTQYF | 1407 | TCRBJ02-03 | 10 | 7 | 3.92E−10 |
| TCRBV28-01 | CASSFGGFGNTIYF | 1845 | TCRBJ01-03 | 4 | 0 | 4.68E−06 |
| TCRBV28-01 | CASSRQGAYEQYF | 1670 | TCRBJ02-05, TCRBJ02-07 | 15 | 43 | 1.31E−08 |
| TCRBV28-01 | CASSRQGGYEQYF | 459 | TCRBJ02-07 | 10 | 17 | 1.18E−07 |
| TCRBV28-01 | CASSSPLAGGRTDTQYF | 1566 | TCRBJ02-03 | 4 | 0 | 4.68E−06 |
| TCRBV28-01 | CASSTQGGGTDTQYF | 711 | TCRBJ02-03 | 6 | 3 | 6.77E−07 |
| TCRBV30-01 | CAWSRRGLYEQYF | 849 | TCRBJ02-07 | 7 | 7 | 1.01E−06 |
| TCRBV30-01 | CAWSVGDNSGNTIYF | 597 | TCRBJ01-03 | 6 | 3 | 6.77E−07 |

Shown in FIG. 1 are results on all Lyme patients, stratified by serostatus. Results are the mean performance across 5-fold cross-validation, i.e., holding out 20% of the data, training on the remaining 80% and then assessing the held-out portion and repeating the entire process 5 times. Classification of Lyme disease by TCR analysis was more accurate in this cohort than standard 2-tier serology, with approximately 50% sensitivity compared to 30% by serology.

Example 2—a Diagnostic for Lyme Disease Based on the Cellular Immune Response to *Borrelia burgdorferi*

Described in this example is a diagnostic based on the cellular immune response to *Borrelia burgdorferi* which addresses the diagnostic deficiencies of STTT which is based on a humoral response. The cellular immune response is far more dynamic to changes, including onset and clearing of an infection, increasing rapidly in early stages and then decreasing once the infection is cleared. It therefore has the potential to have a lower false positive rate in patients who have been infected previously and has the potential to detect infection prior to seroconversion.

The human cellular adaptive immune system identifies infections or aberrant cells through binding of T-cell receptors (TCRs) on the surface of T cells to short, disease-specific peptides (peptide antigens) presented by HLA molecules on the surface of the diseased cell or an antigen-presenting cell (APC). Each T-cell clone has a set of genes encoding its TCR that is independently somatically rearranged, creating a large pool of circulating naïve T-cells that bind with high specificity to peptides presented by diseased cells or APCs. Upon antigen recognition, activated T cells proliferate by clonal expansion and some become part of the memory compartment, where they can reside for many years as clonal populations of cells with identical TCR rearrangements.

Although the pool of potential peptides in a pathogen's proteome is large, the specific set of peptides that are presented is restricted by an individual's expressed HLA allotypes. Moreover, individuals who express the same HLA allotypes frequently mount T-cell responses to the same subset of HLA-presented peptides through a process called immunodominance. Moreover, although healthy adults express only about $10^7$ unique TCRB chains out of a possible $10^{18}$, the generation of these TCRs is not uniformly random but is heavily biased toward certain rearrangements, such that antigen-specific T-cells isolated from different donors frequently utilize the same TCR rearrangement. Because the shared "public" clones are antigen and HLA specific, they serve as a signature of infection in a given HLA context. Using high-throughput TCR sequencing techniques, it has previously been shown that such disease-associated public TCR clones can be used to diagnose a viral infection (Emerson et al., Immunosequencing identifies signatures of cytomegalovirus exposure history and HLA-mediated effects on the T cell repertoire, *Nature Genetics* April 2017; doi:10.1038/ng.3822).

In order to identify a set of public TCRs specific for *B. burgdorferi*, two independent cohorts were analyzed: 1) a collection of 288 suspected and diagnostically confirmed Lyme disease cases from 16 primary care practices in endemic regions enrolled in a study through the Bay Area Lyme Foundation (BALF); and 2) 235 confirmed Lyme disease cases from patients at the Johns Hopkins Lyme Disease Research Center who enrolled in the SLICE study. Due to the more restrictive enrollment and exclusion criteria of the SLICE cohort, as well as the availability of longitudinal follow up samples, BALF was treated as the primary training dataset to identify Lyme-associated TCR signatures, and the diagnostic performance of these signatures on the samples from the SLICE study was evaluated.

Lyme-Associated TCRs are Consistent Across Cohorts and Observed in Both Seropositive and Seronegative Lyme Patients To identify Lyme-associated TCRs, a one sided Fisher's exact test was used to identify TCRs that were enriched in the N=55 BALF patients who were seropositive and had at least a 5 cm rash (the Lyme Positive, LP, cohort) compared to N=3770 presumed Lyme Negative (LN) individuals who were drawn from a database of healthy individuals. Out of millions of public TCRs that were observed in multiple individuals, 205 Lyme-associated TCRs were identified as significant at a bootstrap-estimate FDR<YY (p<1e-4; Table 3).

TABLE 3

Lyme Disease-Associated TCRs

| TCRβ CDR3 Amino Acid Sequence | SEQ ID NO: | V Gene Segment | J Gene Segment |
|---|---|---|---|
| CASSYLHLSYEQYF | 618 | TCRBV06-02/06-03 | TCRBJ02-07 |
| CASSYLGLSYEQYF | 1809 | TCRBV06-06 | TCRBJ02-07 |
| CSARVGGAGTGELFF | 1084 | TCRBV20-X | TCRBJ02-02 |
| CSARLAGGGTGELFF | 1026 | TCRBV20-X | TCRBJ02-02 |
| CSARRAGGGTGELFF | 350 | TCRBV20-X | TCRBJ02-02 |
| CASSLAGLNEQFF | 200 | TCRBV07-06 | TCRBJ02-01 |
| CSARTSGSGTGELFF | 324 | TCRBV20-X | TCRBJ02-02 |
| CASSPAAGNTGELFF | 23 | TCRBV11-03 | TCRBJ02-02 |
| CASSLAPRDRGNQPQHF | 710 | TCRBV07-02 | TCRBJ01-05 |
| CSARVAGGGTGELFF | 1688 | TCRBV20-X | TCRBJ02-02 |
| CSARLAGAGTGELFF | 712 | TCRBV20-X | TCRBJ02-02 |
| CSARLAGSGTGELFF | 1782 | TCRBV20-X | TCRBJ02-02 |
| CASSYLDLSYEQYF | 1118 | TCRBV06-06 | TCRBJ02-07 |
| CASSLAPLGDEQFF | 1173 | TCRBV07-06 | TCRBJ02-01 |
| CASSLAGLNEQYF | 1046 | TCRBV07-06 | TCRBJ02-07 |
| CASSTDTQYF | 1846 | TCRBV03-01/03-02 | TCRBJ02-03 |
| CSARRGGAGTGELFF | 779 | TCRBV20-X | TCRBJ02-02 |
| CASSLAPLTDTQYF | 280 | TCRBV07-06 | TCRBJ02-03 |
| CASSYLALSYEQYF | 700 | TCRBV06-06 | TCRBJ02-07 |
| CASSLAPLGDEQYF | 623 | TCRBV07-06 | TCRBJ02-07 |
| CASSLGAVNTEAFF | 1840 | TCRBV07-06 | TCRBJ01-01 |
| CSARRGGSGTGELFF | 1221 | TCRBV20-X | TCRBJ02-02 |
| CSARPGGAGTGELFF | 1705 | TCRBV20-X | TCRBJ02-02 |
| CSARTGGAGTGELFF | 368 | TCRBV20-X | TCRBJ02-02 |
| CASSPASGNTGELFF | 681 | TCRBV11-03 | TCRBJ02-02 |
| CASSLEVNYNSPLHF | 1299 | TCRBV12-X | TCRBJ01-06 |
| CSARGTLASYEQYF | 448 | TCRBV20-X | TCRBJ02-07 |
| CSARLGGAGTGELFF | 920 | TCRBV20-X | TCRBJ02-02 |
| CASSLEGNIQYF | 1847 | TCRBV05-05 | TCRBJ02-04 |
| CASSLAPLTDTQYF | 280 | TCRBV07-X | TCRBJ02-03 |
| CASSFSQGGTGELFF | 132 | TCRBV11-X | TCRBJ02-02 |
| CASSYLDNSYEQYF | 1225 | TCRBV06-06 | TCRBJ02-07 |

TABLE 3-continued

Lyme Disease-Associated TCRs

| TCRβ CDR3 Amino Acid Sequence | SEQ ID NO: | V Gene Segment | J Gene Segment |
|---|---|---|---|
| CASSLAPGANVLTF | 1838 | TCRBV07-06 | TCRBJ02-06 |
| CASSFLAGDTGELFF | 550 | TCRBV12-X | TCRBJ02-02 |
| CASSYLDLSYEQYF | 1118 | TCRBV06-02/06-03 | TCRBJ02-07 |
| CATSRGARLTDTQYF | 643 | TCRBV24-01 | TCRBJ02-03 |
| CSATVDPNQPQHF | 1848 | TCRBV20-X | TCRBJ01-05 |
| CATGRGLGETQYF | 1849 | TCRBV02-01 | TCRBJ02-05 |
| CASSSPTSGGRTDTQYF | 1481 | TCRBV05-06 | TCRBJ02-03 |
| CASSLGASYTEAFF | 1850 | TCRBV07-06 | TCRBJ01-01 |
| CASSRPPGATNEKLFF | 1851 | TCRBV06-02/06-03 | TCRBJ01-04 |
| CASSLVTTGNTIYF | 454 | TCRBV05-08 | TCRBJ01-03 |
| CASSFELNYNSPLHF | 336 | TCRBV12-X | TCRBJ01-06 |
| CSVDSGGAREQFF | 1852 | TCRBV29-01 | TCRBJ02-01 |
| CASSPNELDTQYF | 1853 | TCRBV18-01 | TCRBJ02-03 |
| CASSESAGAEQFF | 1854 | TCRBV10-01 | TCRBJ02-01 |
| CAWIRKSSYNEQFF | 126 | TCRBV30-01 | TCRBJ02-01 |
| CASSLSPGSGTGELFF | 1855 | TCRBV07-06 | TCRBJ02-02 |
| CSARSGGAGTGELFF | 774 | TCRBV20-X | TCRBJ02-02 |
| CASSLAPASYEQYF | 1327 | TCRBV07-06 | TCRBJ02-07 |
| CASSLAGLNEQFF | 200 | TCRBV07-X | TCRBJ02-01 |
| CAWSRRGLYEQYF | 849 | TCRBV30-01 | TCRBJ02-07 |
| CSARRAGAGTGELFF | 1011 | TCRBV20-X | TCRBJ02-02 |
| CSARVGGSGTGELFF | 767 | TCRBV20-X | TCRBJ02-02 |
| CASSPDRGDEKLFF | 1466 | TCRBV05-06 | TCRBJ01-04 |
| CASSYSSQGAGYTF | 1856 | TCRBV06-05 | TCRBJ01-02 |
| CASSLAGQLNEKLFF | 1857 | TCRBV05-01 | TCRBJ01-04 |
| CASSLRGIYGYTF | 1858 | TCRBV13-01 | TCRBJ01-02 |
| CSARPLETTDTQYF | 1859 | TCRBV20-X | TCRBJ02-03 |
| CASSEVWGGYGYTF | 1860 | TCRBV06-01 | TCRBJ01-02 |
| CASTTGVGANVLTF | 1861 | TCRBV05-01 | TCRBJ02-06 |
| CASSDPLAGGRTDTQYF | 1107 | TCRBV02-01 | TCRBJ02-03 |
| CSVGGTRAYEQYF | 1862 | TCRBV29-01 | TCRBJ02-07 |
| CSARQTGITEAFF | 1863 | TCRBV20-X | TCRBJ01-01 |
| CASSPLASTSYEQYF | 1402 | TCRBV18-01 | TCRBJ02-07 |
| CASSLADPTDTQYF | 1864 | TCRBV19-01 | TCRBJ02-03 |
| CASSLVGRPGETQYF | 1865 | TCRBV07-09 | TCRBJ02-05 |
| CASSFLAGGYQETQYF | 1866 | TCRBV13-01 | TCRBJ02-05 |
| CASSRIRDEKLFF | 1867 | TCRBV03-01/03-02 | TCRBJ01-04 |
| CAISEPGLAGGRDTQYF | 1868 | TCRBV10-03 | TCRBJ02-03 |

TABLE 3-continued

Lyme Disease-Associated TCRs

| TCRβ CDR3 Amino Acid Sequence | SEQ ID NO: | V Gene Segment | J Gene Segment |
|---|---|---|---|
| CASSVTGAETEAFF | 1869 | TCRBV05-01 | TCRBJ01-01 |
| CASSLGHPTEAFF | 1870 | TCRBV11-X | TCRBJ01-01 |
| CASSLVPGSNEQYF | 1871 | TCRBV11-03 | TCRBJ02-07 |
| CASSLSGSRGEAFF | 1872 | TCRBV27-01 | TCRBJ01-01 |
| CASSPSGSRNEQYF | 1873 | TCRBV12-X | TCRBJ02-07 |
| CASRRGTDQPQHF | 1030 | TCRBV05-01 | TCRBJ01-05 |
| CASSPETPTGELFF | 983 | TCRBV18-01 | TCRBJ02-02 |
| CASRQGLRPQHF | 1874 | TCRBV06-X | TCRBJ01-05 |
| CASSYLHLSYEQYF | 618 | TCRBV06-06 | TCRBJ02-07 |
| CASSPRQGLTYNEQFF | 1875 | TCRBV28-01 | TCRBJ02-01 |
| CASSRDRVLSYEQYF | 859 | TCRBV02-01 | TCRBJ02-07 |
| CASSYLQLSYEQYF | 1219 | TCRBV06-06 | TCRBJ02-07 |
| CASSLGQALNEKLFF | 1876 | TCRBV07-02 | TCRBJ01-04 |
| CASSLRTWDTGELFF | 1877 | TCRBV05-01 | TCRBJ02-02 |
| CASSFVEDQPQHF | 1878 | TCRBV07-02 | TCRBJ01-05 |
| CASRIAGGPTDTQYF | 1179 | TCRBV02-01 | TCRBJ02-03 |
| CSVETGQGADTQYF | 1879 | TCRBV29-01 | TCRBJ02-03 |
| CATSRGTRDTGELFF | 1880 | TCRBV15-01 | TCRBJ02-02 |
| CASGLETQYF | 1092 | TCRBV03-01/03-02 | TCRBJ02-05 |
| CASSLDVSPLHF | 1881 | TCRBV05-05 | TCRBJ01-06 |
| CASSLAGQGVSEAFF | 1882 | TCRBV05-01 | TCRBJ01-01 |
| CSARTAGGGTGELFF | 377 | TCRBV20-X | TCRBJ02-02 |
| CASRGPESPLHF | 1883 | TCRBV28-01 | TCRBJ01-06 |
| CASSIRRDKNIQYF | 1398 | TCRBV19-01 | TCRBJ02-04 |
| CASRYKDTEAFF | 1411 | TCRBV06-05 | TCRBJ01-01 |
| CAWAFYNSPLHF | 1884 | TCRBV30-01 | TCRBJ01-06 |
| CASRDTGGDYGYTF | 1885 | TCRBV03-01/03-02 | TCRBJ01-02 |
| CASSLVGGTGEQFF | 1886 | TCRBV05-04 | TCRBJ02-01 |
| CATKREGSYEQYF | 1887 | TCRBV06-05 | TCRBJ02-07 |
| CASWDGFYEQYF | 1888 | TCRBV19-01 | TCRBJ02-07 |
| CASGFPGPTDTQYF | 1889 | TCRBV12-05 | TCRBJ02-03 |
| CRVGGSNQPQHF | 1890 | TCRBV20-X | TCRBJ01-05 |
| CASSLVPDEKLFF | 1891 | TCRBV05-05 | TCRBJ01-04 |
| CASSVGRAGGRTDTQYF | 1892 | TCRBV09-01 | TCRBJ02-03 |
| CASSQDRVYGYTF | 1893 | TCRBV25-01 | TCRBJ01-02 |
| CASGEYQPQHF | 1894 | TCRBV02-01 | TCRBJ01-05 |
| CASSRGGRGNEQFF | 1049 | TCRBV05-04 | TCRBJ02-01 |

TABLE 3-continued

Lyme Disease-Associated TCRs

| TCRβ CDR3 Amino Acid Sequence | SEQ ID NO: | V Gene Segment | J Gene Segment |
|---|---|---|---|
| CASSLGGGFSPLHF | 1895 | TCRBV05-04 | TCRBJ01-06 |
| CSARVARGRDTQYF | 1830 | TCRBV20-X | TCRBJ02-03 |
| CASSLGLAGTSGANVLTF | 1896 | TCRBV05-04 | TCRBJ02-06 |
| CASSPQGSLNTEAFF | 1897 | TCRBV19-01 | TCRBJ01-01 |
| CASSLNRETGELFF | 1898 | TCRBV12-X | TCRBJ02-02 |
| CASSYGTENQPQHF | 1899 | TCRBV18-01 | TCRBJ01-05 |
| CSAPPGLGRADTQYF | 1349 | TCRBV20-X | TCRBJ02-03 |
| CASSYPTNNEQFF | 1900 | TCRBV06-06 | TCRBJ02-01 |
| CASSIFQGYEQYF | 1901 | TCRBV19-01 | TCRBJ02-07 |
| CASSPGLAGAGNEQFF | 1902 | TCRBV05-04 | TCRBJ02-01 |
| CASGLQDNEQFF | 1497 | TCRBV12-05 | TCRBJ02-01 |
| CASSPGTSGANTGELFF | 1903 | TCRBV11-X | TCRBJ02-02 |
| CASSLSTAGETQYF | 1904 | TCRBV27-01 | TCRBJ02-05 |
| CASSVDQGAGYEQYF | 1905 | TCRBV09-01 | TCRBJ02-07 |
| CASSSTNQETQYF | 1906 | TCRBV07-03 | TCRBJ02-05 |
| CASSYSYTQYF | 1907 | TCRBV06-02/06-03 | TCRBJ02-03 |
| CSARTSGAGTGELFF | 52 | TCRBV20-X | TCRBJ02-02 |
| CASSLGAASYEQYF | 1012 | TCRBV07-06 | TCRBJ02-07 |
| CATSRVDAYEQYF | 1908 | TCRBV15-01 | TCRBJ02-07 |
| CASSQDGANTGELFF | 1909 | TCRBV03-01/03-02 | TCRBJ02-02 |
| CASSLNARGELFF | 1910 | TCRBV07-03 | TCRBJ02-02 |
| CASSTRTGGNNEQFF | 1911 | TCRBV19-01 | TCRBJ02-01 |
| CASSPGLAGVRQFF | 1912 | TCRBV06-05 | TCRBJ02-01 |
| CAWGRRGRYEQYF | 697 | TCRBV30-01 | TCRBJ02-07 |
| CATSGSTDTQYF | 1913 | TCRBV10-01 | TCRBJ02-03 |
| CASSTSGGGRQPQHF | 1914 | TCRBV19-01 | TCRBJ01-05 |
| CASSTGGLGTEAFF | 1915 | TCRBV05-04 | TCRBJ01-01 |
| CASSLVDSGYEQYF | 1916 | TCRBV11-X | TCRBJ02-07 |
| CASRGGQSYEQYF | 1917 | TCRBV03-01/03-02 | TCRBJ02-07 |
| CSARGQPTNTGELFF | 726 | TCRBV20-X | TCRBJ02-02 |
| CSARSSGRASDTQYF | 1087 | TCRBV20-X | TCRBJ02-03 |
| CASSARLAGGGNEQFF | 1918 | TCRBV07-08 | TCRBJ02-01 |
| CAWAGNEQYF | 1919 | TCRBV30-01 | TCRBJ02-07 |
| CASSSLGHQPQHF | 1920 | TCRBV12-03/12-04 | TCRBJ01-05 |
| CASSPGTRREQYF | 1921 | TCRBV07-09 | TCRBJ02-07 |
| CAWSGQVSTEAFF | 1922 | TCRBV30-01 | TCRBJ01-01 |
| CASSQDNSPYEQYF | 1923 | TCRBV04-03 | TCRBJ02-07 |
| CASRRTVGYTF | 1924 | TCRBV06-05 | TCRBJ01-02 |

TABLE 3-continued

Lyme Disease-Associated TCRs

| TCRβ CDR3 Amino Acid Sequence | SEQ ID NO: | V Gene Segment | J Gene Segment |
|---|---|---|---|
| CASMRGDTGELFF | 1925 | TCRBV28-01 | TCRBJ02-02 |
| CASSTGQGEDEQYF | 1926 | TCRBV05-01 | TCRBJ02-07 |
| CSARDQGQVAYGYTF | 1927 | TCRBV20-X | TCRBJ01-02 |
| CASSILTGFNQPQHF | 1928 | TCRBV19-01 | TCRBJ01-05 |
| CSVQGNDYGYTF | 1929 | TCRBV29-01 | TCRBJ01-02 |
| CASSPDRGQSEAFF | 1930 | TCRBV18-01 | TCRBJ01-01 |
| CASSQDRGTADTQYF | 1931 | TCRBV14-01 | TCRBJ02-03 |
| CASSRDSSSGNTIYF | 1932 | TCRBV05-01 | TCRBJ01-03 |
| CASSRTPDGYTF | 1933 | TCRBV18-01 | TCRBJ01-02 |
| CASSQGTGGRGETQYF | 1934 | TCRBV03-01/03-02 | TCRBJ02-05 |
| CASSLLEGRGYTF | 1935 | TCRBV27-01 | TCRBJ01-02 |
| CSAPGRDNQPQHF | 1936 | TCRBV20-X | TCRBJ01-05 |
| CASSLGQGGGQETQYF | 1937 | TCRBV28-01 | TCRBJ02-05 |
| CASSTRRGDEQYF | 1076 | TCRBV19-01 | TCRBJ02-07 |
| CSARKGGAGTGELFF | 181 | TCRBV20-X | TCRBJ02-02 |
| CASSEVRGPNYGYTF | 1938 | TCRBV06-01 | TCRBJ01-02 |
| CSAPSGDGYTF | 1939 | TCRBV20-01 | TCRBJ01-02 |
| CSARKGGGGTGELFF | 1826 | TCRBV20-X | TCRBJ02-02 |
| CAISPGQGVQETQYF | 1940 | TCRBV10-03 | TCRBJ02-05 |
| CASSGRGELFF | 1941 | TCRBV12-03/12-04 | TCRBJ02-02 |
| CSARGQPANTGELFF | 303 | TCRBV20-X | TCRBJ02-02 |
| CASSLGAQGYNEQFF | 1942 | TCRBV07-02 | TCRBJ02-01 |
| CAWSRSRGQTEAFF | 1943 | TCRBV30-01 | TCRBJ01-01 |
| CASLSGGSGANVLTF | 1944 | TCRBV28-01 | TCRBJ02-06 |
| CASWTGGRYEQYF | 1945 | TCRBV27-01 | TCRBJ02-07 |
| CASSGQSPEAFF | 1946 | TCRBV02-01 | TCRBJ01-01 |
| CASSLVGISSYNSPLHF | 1947 | TCRBV07-02 | TCRBJ01-06 |
| CASSRPRGGGETQYF | 1948 | TCRBV28-01 | TCRBJ02-05 |
| CASSQANRNTGELFF | 1949 | TCRBV03-01/03-02 | TCRBJ02-02 |
| CAISESQGQGSTDTQYF | 1950 | TCRBV10-03 | TCRBJ02-03 |
| CATSDASGPQHF | 1951 | TCRBV24-01 | TCRBJ01-05 |
| CASSQESGRRYEQYF | 1952 | TCRBV04-03 | TCRBJ02-07 |
| CASSLQAASGNTIYF | 473 | TCRBV07-02 | TCRBJ01-03 |
| CASSPGSGVYNEQFF | 1953 | TCRBV27-01 | TCRBJ02-01 |
| CASSPSSGLEAFF | 1954 | TCRBV14-01 | TCRBJ01-01 |
| CASSRRGDYNSPLHF | 1955 | TCRBV06-05 | TCRBJ01-06 |
| CASSYVGQGSPLHF | 1956 | TCRBV06-02/06-03 | TCRBJ01-06 |

TABLE 3-continued

Lyme Disease-Associated TCRs

| TCRβ CDR3 Amino Acid Sequence | SEQ ID NO: | V Gene Segment | J Gene Segment |
|---|---|---|---|
| CASSSSGRVQETQYF | 1957 | TCRBV05-01 | TCRBJ02-05 |
| CASSSNRGPGEKLFF | 1958 | TCRBV07-02 | TCRBJ01-04 |
| CSASGATGNQPQHF | 1959 | TCRBV20-X | TCRBJ01-05 |
| CASSFEPNYNSPLHF | 64 | TCRBV12-X | TCRBJ01-06 |
| CAWSAQGATGYTF | 1960 | TCRBV30-01 | TCRBJ01-02 |
| CASSDGQGYSPLHF | 1961 | TCRBV28-01 | TCRBJ01-06 |
| CASSPTSGSEQFF | 1962 | TCRBV03-01/03-02 | TCRBJ02-01 |
| CASSVGHRNTEAFF | 1963 | TCRBV06-X | TCRBJ01-01 |
| CASSQDRVYQETQYF | 1964 | TCRBV14-01 | TCRBJ02-05 |
| CAISPDTTNEKLFF | 1965 | TCRBV10-03 | TCRBJ01-04 |
| CASSSGGNQETQYF | 1966 | TCRBV07-08 | TCRBJ02-05 |
| CASRLAGVAYNEQFF | 1967 | TCRBV12-X | TCRBJ02-01 |
| CASREDRGNYGYTF | 1968 | TCRBV28-01 | TCRBJ01-02 |
| CASSRTRAYEQYF | 1969 | TCRBV07-08 | TCRBJ02-07 |
| CASGLDRPGELFF | 1970 | TCRBV12-05 | TCRBJ02-02 |
| CASSTWGNYGYTF | 1971 | TCRBV27-01 | TCRBJ01-02 |
| CASSELAADNEQFF | 1972 | TCRBV09-01 | TCRBJ02-01 |
| CASSLVGGGTDTQYF | 1973 | TCRBV02-01 | TCRBJ02-03 |
| CASSPGLAGATSTDTQYF | 398 | TCRBV05-04 | TCRBJ02-03 |
| CASSPRTSGREYQETQYF | 1974 | TCRBV07-08 | TCRBJ02-05 |
| CASSQQGAGYNEQFF | 1975 | TCRBV05-04 | TCRBJ02-01 |
| CASSSRRGDEQFF | 1976 | TCRBV06-05 | TCRBJ02-01 |
| CASSSRAGSYEQYF | 1977 | TCRBV09-01 | TCRBJ02-07 |

Figure 2:
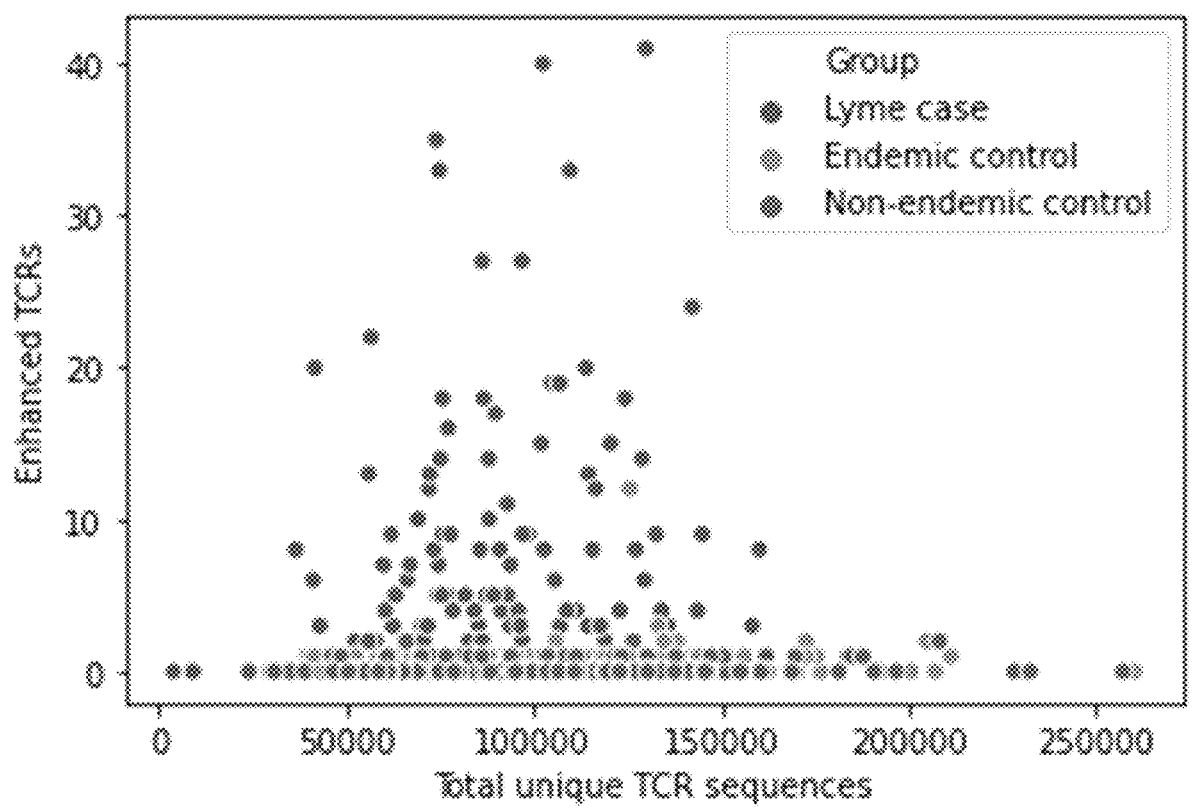
FIG. 2: Data demonstrating that Lyme-associated TCRs identified in BALF are enriched in the independent SLICE cohort.

To confirm that these TCRs are associated with Lyme disease and not other potential immunological characteristics of the BALF cohort, these sequences were validated in the SLICE dataset (both seropositive and seronegative subjects). Collectively, LP patients in the SLICE study had significantly more Lyme-associated TCRs (median=approx. 8) than individuals in either held-out non-endemic controls (Median=1) or endemic controls that were collected as part of the SLICE study (Median=1) (FIG. 2). Moreover, when a Lyme-associated TCR was observed, it was encoded by more TCR clones in the LP cohort than in the two control cohorts, and the overall frequency of the clones was higher.

Notably, although Lyme-associated TCRs were identified specifically among individuals with a detectible antibody response, the TCRs were enriched both among both seropositive and seronegative individuals in the SLICE cohort. While the frequency and magnitude of these responses was reduced in seronegative individuals compared to seropositive individuals, their presence in a substantial fraction of the latter group indicates that an active T-cell response is common in both seropositive and seronegative Lyme patients during early infection.

Lyme-Associated TCRs Form Putatively Antigen-Specific Clusters

A striking feature of the 205 Lyme-associated TCRs is that they can be easily clustered based on sequence similarity. Using a simple 1-edit distance clustering rule, these sequences cluster into 7 groups, the largest of which contains 19 TCRs (FIG. 3). Given that the TCR sequence determines antigen specificity, with hundreds to thousands of similar TCR sequences encoding specificity to any given antigen, it was hypothesized that these clusters represent distinct antigens, which are apparently immunodominant in the context of Lyme disease.

As a first step to test this hypothesis, the specific Human Leukocyte Antigen class I (HLA-1) and class II (HLA-II) alleles expressed by each individual were determined, followed by identification of HLA alleles that were statistically associated with each cluster. Using this approach, 1 out of 7 clusters were statistically associated with one or more HLA alleles. There are also several clusters that are very public in the Lyme positives and yet do not appear to have a strong association with a single HLA allele. The most public sequence for Cluster 1, for example, occurs in 19 out of the 55 LP (35%) and yet none of the 8 sequences in this cluster could be strongly associated with one HLA type. 25 out of the 55 LP samples contain at least one member of this cluster compared to 33 of the 3770 LN (P=9.6e-33). Similarly, the most public member for cluster 7 with 19 TCR members occurs in 16 out of 55 LP (29%) and yet none of the 19 TCRs could be assigned to an HLA type. 37 out of the 55 LP contain at least one TCR in this cluster compared to 646 out of the 3770 SN (5e-16).

To further explore potential antigen specificity of these Lyme-associated TCRs, these sequence profiles were compared to those of TCRs that were mapped to putative Lyme antigens using the MIRA (Multiplexed Identification of T cell Receptor Antigen Specificity) assay. TCRs from naïve repertoires of healthy people are screened against HLA-presented peptide antigens derived from the bacterial genome to determine potential interactions to create a direct map between TCRs and specific antigens. This map is used as a reference for the 205 TCRs enriched in the Lyme positive cases. 79,478 TCRs have been mapped, including representative TCRs from 5 clusters. The 5 clusters were associated with *B. burgdorferi* proteins VlsE (Clusters Z1 and Z2), OspC (Cluster Z3), DbpA (Cluster Z4), and BBK32 (Cluster Z5) were associated based on these mappings.

Lyme-Associated TCRs Wane Post Treatment

Figure 4:
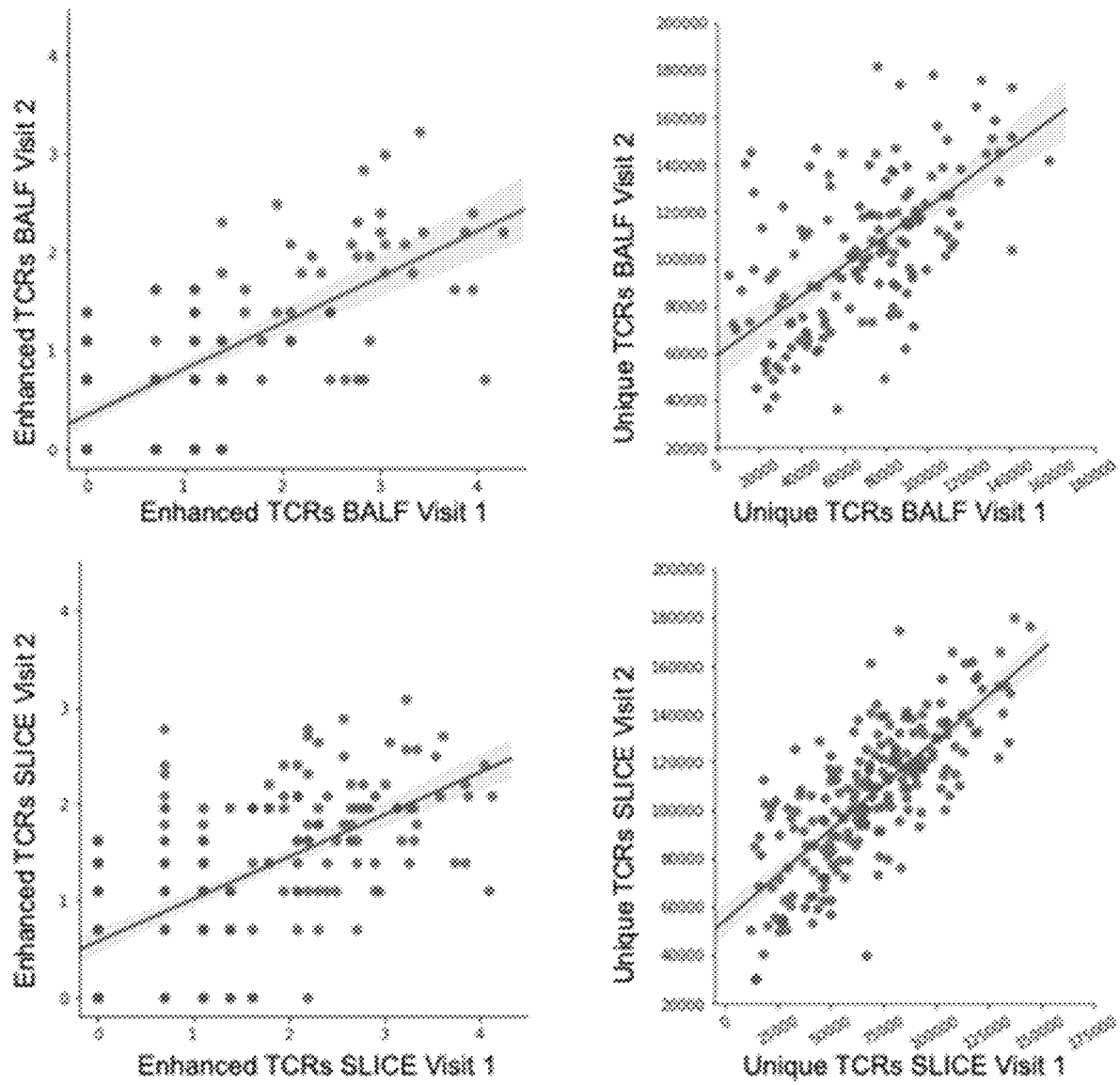
FIG. 4: Data showing the median number of unique Lyme disease-associated TCRs, as well as the total abundance of Lyme disease-associated TCRs, over time.

Patients who enrolled in the SLICE study underwent treatment with doxycycline. Successful treatment with this antibiotic eliminates the *B. burgdorferi* bacteria and associated antigens and will likely lead to a reduction in the magnitude of the T-cell response as effector T-cells are replaced by smaller numbers of memory T-cells. Available samples from the second and fifth visits were therefore immunosequenced. As expected, the median number of unique Lyme-associated TCRs, as well as the total abundance of Lyme-associated TCRs, waned overtime (FIG. 4).

Lyme-Associated TCRs are More Sensitive at Diagnosing Lyme Disease than STTT

That Lyme-associated TCRs identified in BALF are strongly associated with Lyme disease in the independent SLICE cohort suggested that they can be harnessed as a useful diagnostic of Lyme disease. To this end, a machine learning model was trained based on the principle of identifying Lyme-associated TCRs. To maximize the training data, while acknowledging that qualitative difference in the immune response of seronegative compared to seropositive Lyme patients, the model was trained using a semi-supervised approach in which positive labels were assigned to seropositive individuals, negative labels were assigned to non-endemic controls, and seronegative individuals were treated as unlabeled data. Endemic controls were not used in training. The final model is a simple two feature logistic regression with features representing the number of Lyme-associated TCRs and the total number of unique TCRs. Five-fold cross-validation was used to obtain out-of-sample predictions to assess model performance. To confirm the generalizability of the model, further trained were separate models for SLICE and BALF, validating that each model performed well on both cohorts.

Figure 5:
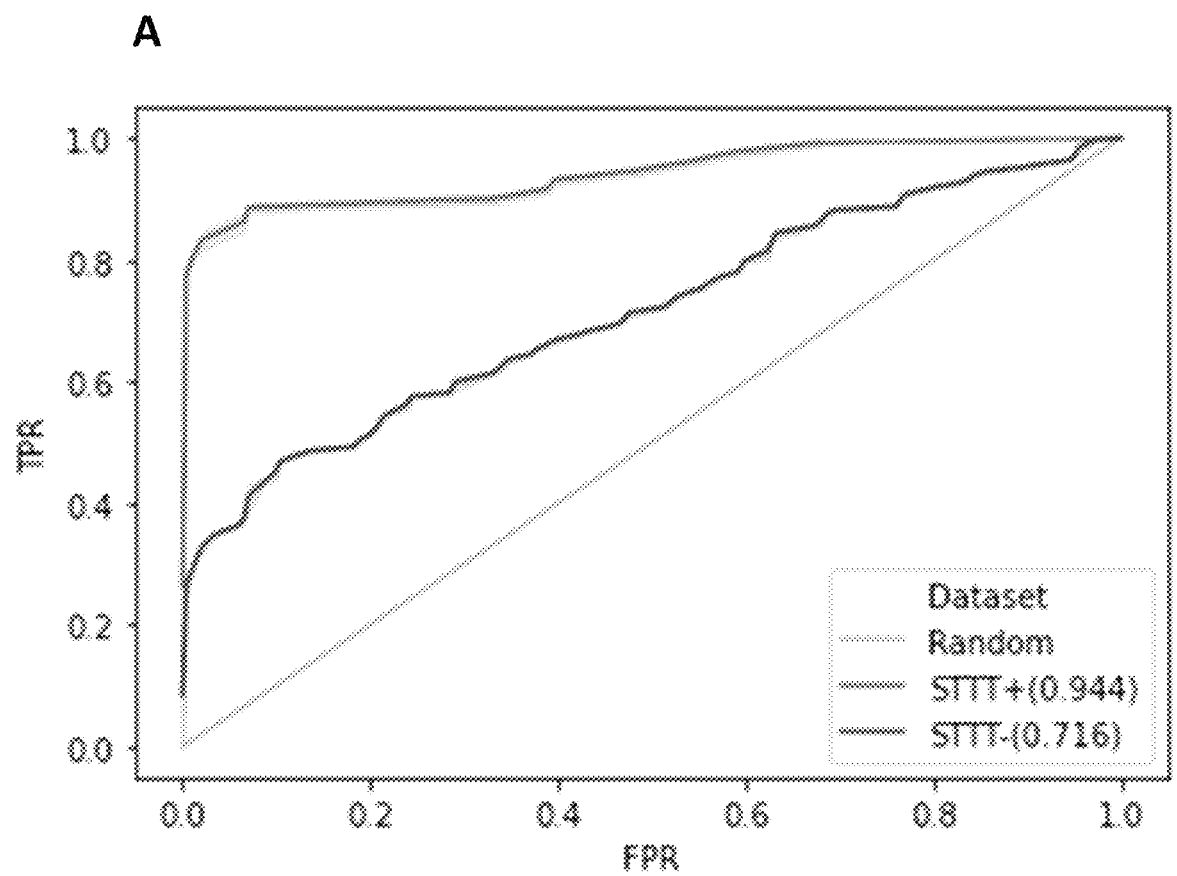
FIG. 5: Data demonstrating that Lyme disease-associated TCRs are more sensitive at diagnosing Lyme disease than STTT. Panel A: ROC for SLICE seropositive; SLICE seronegative; BALF seropositive, vs non-endemic controls. Panel B: Model scores for Lyme, Endemic control, Non-endemic control. Panel C: Model scores by serology status.
Figure 5:
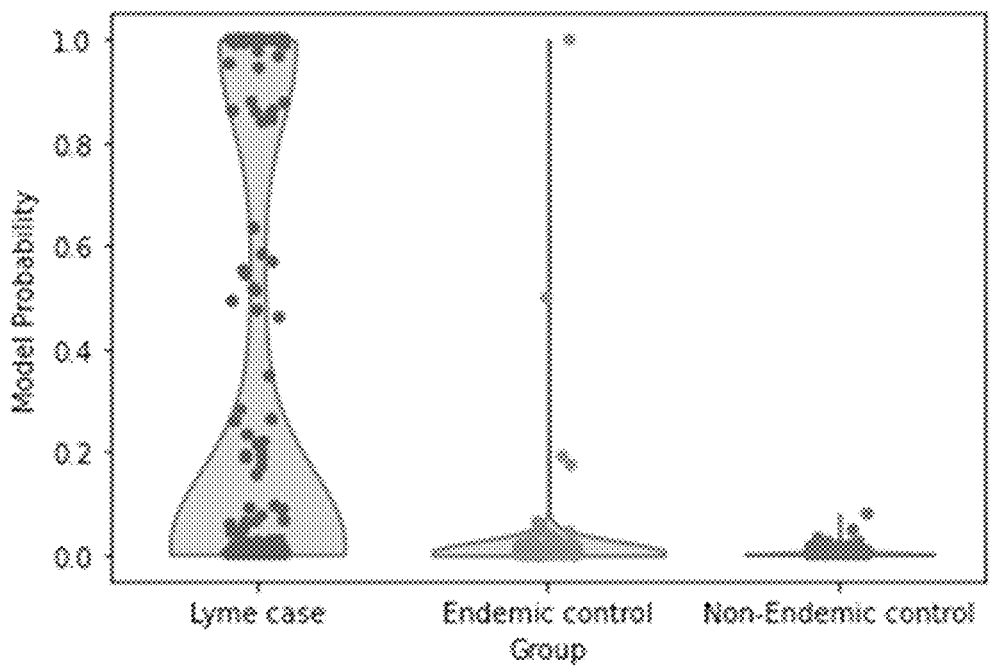
Figure 5:
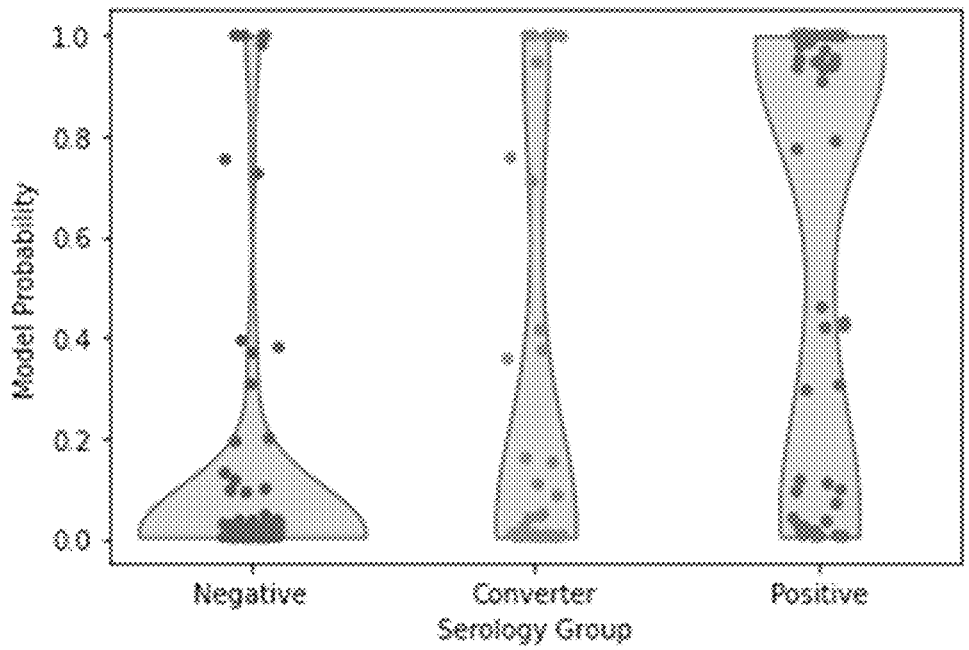

As expected, the resulting model showed high specificity for Lyme disease patients (FIG. 5, panel A). Notably, 52% of SLICE Lyme+ individuals had model scores higher than 99.5% of non-endemic controls (FIG. 5, panel B). By sampling with replacement, it is estimated that a diagnostic based on this TCR model has a sensitivity of 52%+/−4% at a specificity of 99%+/−1% in a population similar to that of the SLICE study, compared to STTT, which has a sensitivity of 30%+/−X % in this population (FIG. 5, panel C).

Notably, 82% seropositive individuals are positive by the TCR-based classifier, as are about 33% of the seronegative individuals. Moreover, the presence of a TCR signal among seronegative individuals is predictive of seroconversion by the time of the second visit. These data are consistent with a T-cell response being required for and preceding the B cell response and highlight the utility of a T cell-based diagnostic to provide improved sensitivity during early infection.

Clinical Correlates of the Measured TCR Response

The magnitude of the T-cell response may be correlated with disease severity, due to (for example) complex interactions between pathogen load and the immune response. Furthermore, immunological differences associated with biological sex or increasing age may alter the T-cell response in subtle ways. Accordingly, potential clinical correlates of the T-cell response were investigated, as quantified in the present TCR-based classifier. The following factors were investigated:

1) Model score by patient age;
2) Model score by patient sex;
3) the number of days between symptom onset and when the blood sample was taken,
4) measured EM rash area;
5) binary assessment of whether the patient presented a single or disseminated rash;
6) binary assessment of whether the patient appeared lymphopenic;
7) binary assessment of whether the patient had elevated levels of liver damage biomarkers
8) number of symptoms.

Figure 6:
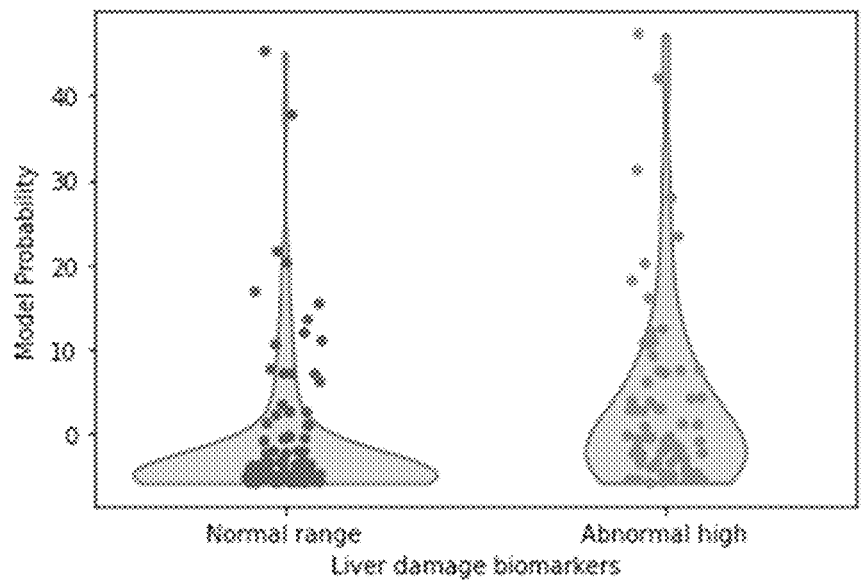
FIG. 6: Data showing clinical correlates of TCR score. Panel A: Classifier performance in those with and without signs of liver damage. Panel B: Classifier performance in those with and without lymphopenia. Panel C: Classifier performance in those with single or disseminated rashes.
Figure 6:
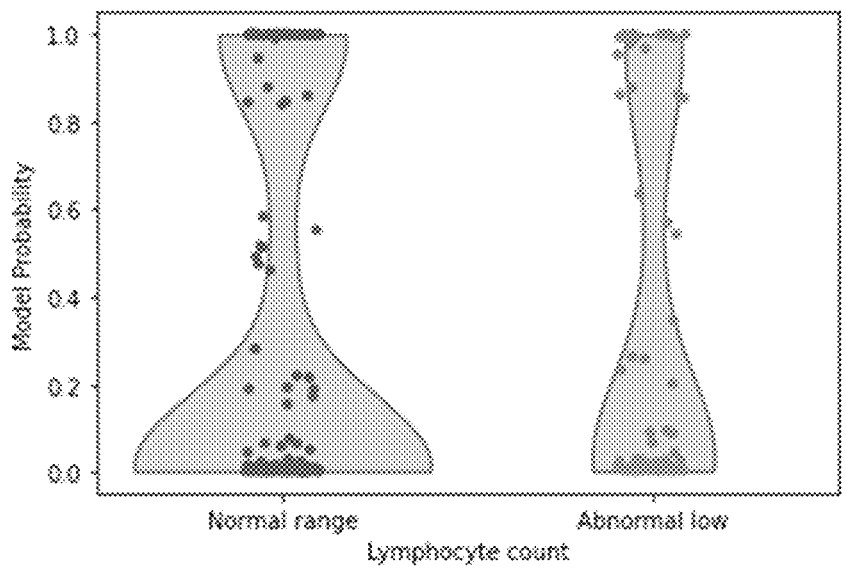
Figure 6:
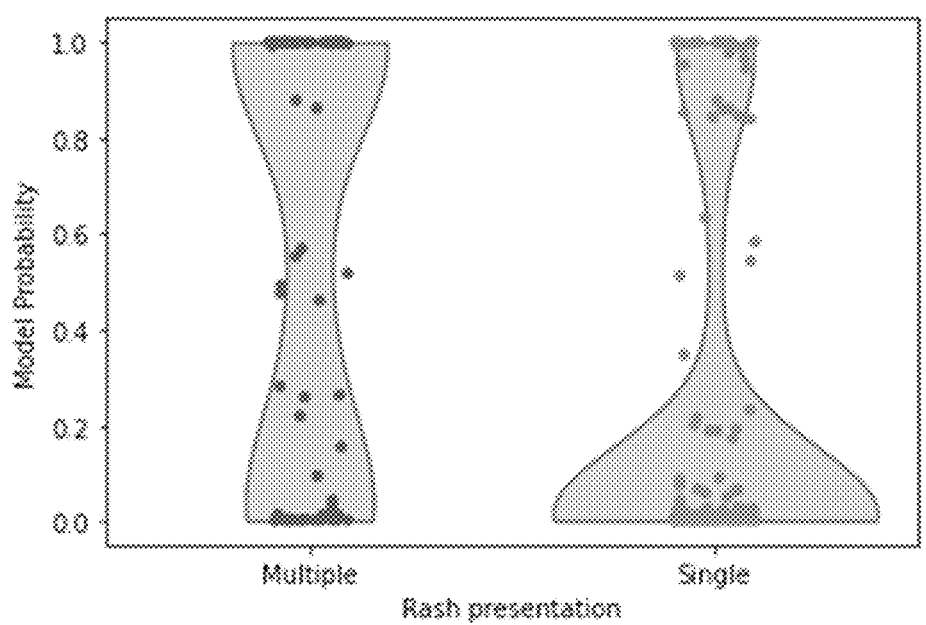

Factors 5-8 were found to be independently significant with p<0.01 in each case ($R^2$=0.3 for combined model). In contrast, a multiple logit regression of STTT result for the same subjects against the same factors identified factors 4, 5, and 8 as independently significant with p<0.01 in each case (pseudo $R^2$=0.31 for combined model). Data is shown in FIG. 6, panels A-C.

Methods

Cohorts

Cohort 1: Enrollment sites were selected based on their location in areas of endemicity and their ability to identify and enroll patients with early Lyme disease (LD). Individuals with signs or symptoms consistent with early LD were enrolled, including patients presenting with EM or an erythematous, annular, expanding skin lesion (annular lesion) and individuals presenting with signs or symptoms but without an EM/annular lesion and with a suspected tick exposure or tick bite. While individuals with annular lesions of 55 cm suspicious of LD were included, those with tick-bite reactions (e.g., a non-annular erythematous macule at the site of the tick bite) were excluded. Uninfected individuals from the same regions (controls from areas of endemicity [EC]) were also eligible to participate. Controls were defined as healthy individuals living in an area of endemicity with no history of LD or TBI.

Cohort 2: Human subjects protocols were approved by the institutional review boards of Johns Hopkins University and Stanford University, and all subjects provided written informed consent in accordance with the Declaration of Helsinki. Bb-infected patients with an erythema migrans (EM) rash of at least 5 cm and either multiple skin lesions or at least one new-onset concurrent symptom were included in the study. Patients were recruited and enrolled at a suburban clinical practice in Maryland, and those with a previous history of Lyme disease, or preexisting confounding medical conditions associated with fatigue, pain, or neurocognitive symptoms were excluded. Following Infectious Diseases Society of America (IDSA) treatment guidelines, all patients were treated with 3 weeks of oral doxycycline (DOI: 10.1086/508667). Lyme patients were seen regularly over the course of 2 years for a total of four study visits (at the acute-phase pretreatment visit, at 1-month posttreatment, 6-month posttreatment, and 2-year posttreatment). Samples from healthy controls were collected at an initial visit, 6 months, and 1 year. To differentiate between subjects who returned to health following treatment and those with persistent symptoms, applied was a previously published definition of post-treatment Lyme disease syndrome (PTLDS), which is based on the IDSA's proposed case definition and incorporates the presence of fatigue, pain, and/or cognitive complaints with functional impact determined by scores on the SF-36, with a composite T score of less than 45 (DOI: 10.1086/508667, Ware 2002, DOI: 10.1016/j.ijid.2013.01.008). This definition was applied at all study visits after 6 months from initial diagnosis and treatment. This case definition was chosen on the basis of its previously demonstrated sensitivity for determining the impact of symptoms on the daily function of Lyme disease patients. Subjects with disseminated EM rash were defined as those having more than one visible rash site, while local rash applied to those with a single EM rash site.

T-Cell Receptor Variable Beta Chain Sequencing

Immunosequencing of the CDR3 regions of human TCRβ chains was performed using the ImmunoSEQ® assay (Adaptive Biotechnologies, Seattle, WA). Extracted genomic DNA was amplified in a bias-controlled multiplex PCR, followed by high-throughput sequencing. Sequences were collapsed and filtered in order to identify and quantitate the absolute abundance of each unique TCRβ CDR3 region for further analysis as previously described. See Robins et al. (2009) Blood 114(19):4099-4107; Carlson et al. (2013) Nature Communications 4:2680; and Robins et al. (2012) J. Immunol. Methods 375(1-2):14-9.

Statistical Analyses of TCR-p Sequencing Results

Clonality was defined as 1−Peilou's eveness[4] and was calculated on productive rearrangements by:

$$1 + \frac{\sum_{i}^{N} p_i \log_2(p_i)}{\log_2(N)}$$

where $p_i$ is the proportional abundance of rearrangement i and N is the total number of rearrangements. Clonality values range from 0 to 1 and describe the shape of the frequency distribution: clonality values approaching 0 indicate a very even distribution of frequencies, whereas values approaching 1 indicate an increasingly asymmetric distribution in which a few clones are present at high frequencies. Statistical analysis was performed in R version 3.2.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A computer-implemented method for assessing T cell receptor β chain complementary determining region 3 (TCRβ CDR3) sequences, the method comprising:
    assessing TCRβ CDR3 sequences determined from a sample comprising T cells obtained from a subject for the presence or absence of one or more TCRβ CDR3 sequences set forth in SEQ ID NOs: 200, 280, 347, 618, 779, 1026, 1046, 1084, 1688, and 1809;
    identifying the subject as having Lyme disease based on the assessment when the one or more TCRβ CDR3 sequences are present; and
    administering a therapeutically effective amount of a Lyme disease therapy to the subject, wherein the Lyme disease therapy comprises an oral antibiotic therapy, an intravenous antibiotic therapy, or a combination thereof.

2. The computer-implemented method of claim 1, wherein the subject has or is suspected of having a tick bite that occurred within two weeks prior to the assessing.

3. The computer-implemented method of claim 1, wherein the subject is seronegative for Lyme disease at the time of the assessing.

4. The computer-implemented method of claim 1, wherein the subject has one or more non-specific symptoms consistent with Lyme disease at the time of the assessing, wherein the one or more non-specific symptoms are selected from the group consisting of: skin erythema, fatigue, arthralgia, and any combination thereof.

5. The computer-implemented method of claim 1, comprising assessing the TCRβ CDR3 sequences for the presence or absence of three or more TCRβ CDR3 sequences set forth in SEQ ID NOs: 200, 280, 347, 618, 779, 1026, 1046, 1084, 1688, and 1809.

6. The computer-implemented method of claim 1, comprising assessing the TCR(CDR3 sequences for the presence or absence of each of the TCRβ CDR3 sequences set forth in SEQ ID NOs: 200, 280, 347, 618, 779, 1026, 1046, 1084, 1688, and 1809.

7. The computer-implemented method of claim 1, wherein the Lyme disease therapy comprises an oral antibiotic therapy.

8. The computer-implemented method of claim 7, wherein the oral antibiotic therapy comprises oral administration of a therapeutically effective amount of an antibiotic selected from the group consisting of: doxycycline, amoxicillin, cefuroxime axetil, and any combination thereof.

9. The computer-implemented method of claim 1, wherein the Lyme disease therapy comprises an intravenous antibiotic therapy antibiotic therapy.

10. The computer-implemented method of claim 9, wherein the intravenous antibiotic therapy comprises intravenous administration of a therapeutically effective amount of an antibiotic selected from the group consisting of: ceftriaxone, cefotaxime, penicillin G, and any combination thereof.

\* \* \* \* \*

UNITED STATES PATENT AND TRADEMARK OFFICE
CERTIFICATE OF CORRECTION

PATENT NO. : 12,263,179 B1  
APPLICATION NO. : 16/945701  
DATED : April 1, 2025  
INVENTOR(S) : Harlan S. Robins et al.

Page 1 of 1

It is certified that error appears in the above-identified patent and that said Letters Patent is hereby corrected as shown below:

In the Specification

In Column 9, Line 42, delete "a" and insert -- α --.

In Column 9, Line 43, delete "p" and insert -- β --.

In Column 10, Line 17, delete "TCRB" and insert -- TCRβ --.

In Column 14, Line 10, delete "amount," and insert -- amount; --.

In Column 41, Line 67, delete "acrodematitis" and insert -- acrodermatitis --.

In Column 43, Line 29, delete "setforth" and insert -- set forth --.

In Column 56, Line 42, delete "TCRB" and insert -- TCRβ --.

In Column 68, Line 59, delete "(HLA-1)" and insert -- (HLA-I) --.

In Column 69, Line 35, delete "overtime" and insert -- over time --.

In Column 70, Line 22, delete "taken," and insert -- taken; --.

In Column 70, Line 29, after "biomarkers" insert -- ; --.

In Column 70, Line 49, delete "55" and insert -- ≤5 --.

In the Claims

In Column 628, Line 64, in Claim 6, delete "TCR(CDR3" and insert -- TCRβ CDR3 --.

Signed and Sealed this  
Fifteenth Day of July, 2025

Coke Morgan Stewart  
*Acting Director of the United States Patent and Trademark Office*

SEQUENCE LISTING

<160> NUMBER OF SEQ ID NOS: 1977

<210> SEQ ID NO 1
<211> LENGTH: 15
<212> TYPE: PRT
<213> ORGANISM: Homo sapiens

<400> SEQUENCE: 1

Cys Ala Ser Ser Pro Asp Arg Ala Ser Thr Asp Thr Gln Tyr Phe
1               5                   10                  15

<210> SEQ ID NO 2
<211> LENGTH: 15
<212> TYPE: PRT
<213> ORGANISM: Homo sapiens

<400> SEQUENCE: 2

Cys Ser Ala Arg Leu Ser Gly Ser Gly Thr Gly Glu Leu Phe Phe
1               5                   10                  15

<210> SEQ ID NO 3
<211> LENGTH: 15
<212> TYPE: PRT
<213> ORGANISM: Homo sapiens

<400> SEQUENCE: 3

Cys Ser Ala Arg Gln Ala Gly Gly Thr Gly Glu Leu Phe Phe
1               5                   10                  15

<210> SEQ ID NO 4
<211> LENGTH: 14
<212> TYPE: PRT
<213> ORGANISM: Homo sapiens

<400> SEQUENCE: 4

Cys Ala Ser Ser Asp Thr Gly Gly Val Glu Thr Gln Tyr Phe
1               5                   10

<210> SEQ ID NO 5
<211> LENGTH: 14
<212> TYPE: PRT
<213> ORGANISM: Homo sapiens

<400> SEQUENCE: 5

Cys Ala Ser Arg Arg Gly Asn Asp Asn Ser Pro Leu His Phe
1               5                   10

<210> SEQ ID NO 6
<211> LENGTH: 14
<212> TYPE: PRT
<213> ORGANISM: Homo sapiens

<400> SEQUENCE: 6

Cys Ala Ser Ser Tyr Leu Leu Leu Ser Tyr Glu Gln Tyr Phe
1               5                   10

<210> SEQ ID NO 7
<211> LENGTH: 15
<212> TYPE: PRT
<213> ORGANISM: Homo sapiens

<400> SEQUENCE: 7

Cys Ala Ser Ser Leu Glu Pro Ala Gly Asn Gln Pro Gln His Phe
1               5                   10                  15

<210> SEQ ID NO 8
<211> LENGTH: 14
<212> TYPE: PRT
<213> ORGANISM: Homo sapiens

<400> SEQUENCE: 8

Cys Ala Ser Ser Ala Leu Arg Ser Gly Asn Thr Ile Tyr Phe
1               5                   10

<210> SEQ ID NO 9
<211> LENGTH: 16
<212> TYPE: PRT
<213> ORGANISM: Homo sapiens

<400> SEQUENCE: 9

Cys Ala Ser Ser Gln Val Arg Thr Gly Gly Leu Asn Glu Gln Phe Phe
1               5                   10                  15

<210> SEQ ID NO 10
<211> LENGTH: 15
<212> TYPE: PRT
<213> ORGANISM: Homo sapiens

<400> SEQUENCE: 10

Cys Ala Ser Ser Pro Ser Arg Glu Gly Lys Asn Glu Gln Phe Phe

```
                1               5               10              15

<210> SEQ ID NO 11
<211> LENGTH: 15
<212> TYPE: PRT
<213> ORGANISM: Homo sapiens

<400> SEQUENCE: 11

Cys Ala Ser Ser Pro Asn Arg Asp Lys Asn Thr Glu Ala Phe Phe
1               5                   10                  15

<210> SEQ ID NO 12
<211> LENGTH: 17
<212> TYPE: PRT
<213> ORGANISM: Homo sapiens

<400> SEQUENCE: 12

Cys Ala Ser Ser Gln Val Leu Ala Gly Val Arg Arg Asn Glu Gln Phe
1               5                   10                  15

Phe

<210> SEQ ID NO 13
<211> LENGTH: 15
<212> TYPE: PRT
<213> ORGANISM: Homo sapiens

<400> SEQUENCE: 13

Cys Ala Ser Ser Gln Asp Thr Ala Ser Asn Gln Pro Gln His Phe
1               5                   10                  15

<210> SEQ ID NO 14
<211> LENGTH: 13
<212> TYPE: PRT
<213> ORGANISM: Homo sapiens

<400> SEQUENCE: 14

Cys Ser Ala Arg Thr Pro Gly Ala Asn Ile Gln Tyr Phe
1               5                   10

<210> SEQ ID NO 15
<211> LENGTH: 15
<212> TYPE: PRT
<213> ORGANISM: Homo sapiens

<400> SEQUENCE: 15

Cys Ser Ala Arg Val Ala Gly Ser Gly Thr Gly Glu Leu Phe Phe
1               5                   10                  15

<210> SEQ ID NO 16
<211> LENGTH: 15
<212> TYPE: PRT
<213> ORGANISM: Homo sapiens

<400> SEQUENCE: 16

Cys Ser Ala Arg Met Ser Gly Gly Gly Thr Gly Glu Leu Phe Phe
1               5                   10                  15

<210> SEQ ID NO 17
<211> LENGTH: 15
<212> TYPE: PRT
<213> ORGANISM: Homo sapiens

<400> SEQUENCE: 17

Cys Ala Ser Ser Pro Ser Gly Arg Thr Ala Tyr Glu Gln Tyr Phe
```

-continued

```
1               5                   10                  15
```

<210> SEQ ID NO 18
<211> LENGTH: 14
<212> TYPE: PRT
<213> ORGANISM: Homo sapiens

<400> SEQUENCE: 18

```
Cys Ala Ser Ser Val Asp Arg Gly Arg Gly Glu Gln Tyr Phe
1               5                   10
```

<210> SEQ ID NO 19
<211> LENGTH: 14
<212> TYPE: PRT
<213> ORGANISM: Homo sapiens

<400> SEQUENCE: 19

```
Cys Ala Ser Ser Leu His Arg Asn Thr Gly Glu Leu Phe Phe
1               5                   10
```

<210> SEQ ID NO 20
<211> LENGTH: 15
<212> TYPE: PRT
<213> ORGANISM: Homo sapiens

<400> SEQUENCE: 20

```
Cys Ser Ala Arg Phe Ser Gly Ser Gly Thr Gly Glu Leu Phe Phe
1               5                   10                  15
```

<210> SEQ ID NO 21
<211> LENGTH: 15
<212> TYPE: PRT
<213> ORGANISM: Homo sapiens

<400> SEQUENCE: 21

```
Cys Ala Ser Ser Leu Ala Thr Asp Gly Arg Asn Glu Gln Phe Phe
1               5                   10                  15
```

<210> SEQ ID NO 22
<211> LENGTH: 15
<212> TYPE: PRT
<213> ORGANISM: Homo sapiens

<400> SEQUENCE: 22

```
Cys Ala Ser Ser Phe Glu Trp Asn Tyr Asn Ser Pro Leu His Phe
1               5                   10                  15
```

<210> SEQ ID NO 23
<211> LENGTH: 15
<212> TYPE: PRT
<213> ORGANISM: Homo sapiens

<400> SEQUENCE: 23

```
Cys Ala Ser Ser Pro Ala Ala Gly Asn Thr Gly Glu Leu Phe Phe
1               5                   10                  15
```

<210> SEQ ID NO 24
<211> LENGTH: 13
<212> TYPE: PRT
<213> ORGANISM: Homo sapiens

<400> SEQUENCE: 24

```
Cys Ser Ala Ser Arg Asp Ile Tyr Tyr Glu Gln Tyr Phe
1               5                   10
```

```
<210> SEQ ID NO 25
<211> LENGTH: 15
<212> TYPE: PRT
<213> ORGANISM: Homo sapiens

<400> SEQUENCE: 25

Cys Ala Ser Ser Arg Ser Glu Gly Gly Ser Tyr Glu Gln Tyr Phe
1               5                   10                  15

<210> SEQ ID NO 26
<211> LENGTH: 14
<212> TYPE: PRT
<213> ORGANISM: Homo sapiens

<400> SEQUENCE: 26

Cys Ser Val Gly Pro Thr Gly Thr Gly Glu Lys Leu Phe Phe
1               5                   10

<210> SEQ ID NO 27
<211> LENGTH: 16
<212> TYPE: PRT
<213> ORGANISM: Homo sapiens

<400> SEQUENCE: 27

Cys Ala Ser Ser Leu Asp Ser Asn Ser Gly Ala Asn Val Leu Thr Phe
1               5                   10                  15

<210> SEQ ID NO 28
<211> LENGTH: 14
<212> TYPE: PRT
<213> ORGANISM: Homo sapiens

<400> SEQUENCE: 28

Cys Ala Ser Ser Pro Thr Arg Glu Ala Asn Glu Gln Phe Phe
1               5                   10

<210> SEQ ID NO 29
<211> LENGTH: 15
<212> TYPE: PRT
<213> ORGANISM: Homo sapiens

<400> SEQUENCE: 29

Cys Ser Ala Arg Gly Ser Gly Arg Ala Ser Asp Thr Gln Tyr Phe
1               5                   10                  15

<210> SEQ ID NO 30
<211> LENGTH: 15
<212> TYPE: PRT
<213> ORGANISM: Homo sapiens

<400> SEQUENCE: 30

Cys Ala Ser Ser Pro Arg Leu Ala Ala Asp Asn Glu Gln Phe Phe
1               5                   10                  15

<210> SEQ ID NO 31
<211> LENGTH: 16
<212> TYPE: PRT
<213> ORGANISM: Homo sapiens

<400> SEQUENCE: 31

Cys Ala Ser Ser His Pro Gly Ala Gly Gly Asn Asn Glu Gln Phe Phe
1               5                   10                  15

<210> SEQ ID NO 32
```

```
<211> LENGTH: 14
<212> TYPE: PRT
<213> ORGANISM: Homo sapiens

<400> SEQUENCE: 32

Cys Ser Ala Arg Ala Thr Glu Ser Ser Tyr Glu Gln Tyr Phe
1               5                   10

<210> SEQ ID NO 33
<211> LENGTH: 13
<212> TYPE: PRT
<213> ORGANISM: Homo sapiens

<400> SEQUENCE: 33

Cys Ala Ser Ser Thr Pro Gly His Tyr Glu Gln Tyr Phe
1               5                   10

<210> SEQ ID NO 34
<211> LENGTH: 15
<212> TYPE: PRT
<213> ORGANISM: Homo sapiens

<400> SEQUENCE: 34

Cys Ser Ala Arg Tyr Gly Gly Ser Gly Thr Gly Glu Leu Phe Phe
1               5                   10                  15

<210> SEQ ID NO 35
<211> LENGTH: 15
<212> TYPE: PRT
<213> ORGANISM: Homo sapiens

<400> SEQUENCE: 35

Cys Ala Ser Arg Gly Thr Ser Gly Ser Gln Glu Thr Gln Tyr Phe
1               5                   10                  15

<210> SEQ ID NO 36
<211> LENGTH: 14
<212> TYPE: PRT
<213> ORGANISM: Homo sapiens

<400> SEQUENCE: 36

Cys Ala Ser Ser Leu Ala Gly Asp Ile Asp Thr Gln Tyr Phe
1               5                   10

<210> SEQ ID NO 37
<211> LENGTH: 11
<212> TYPE: PRT
<213> ORGANISM: Homo sapiens

<400> SEQUENCE: 37

Cys Ala Ser Ser Tyr Tyr Asn Glu Gln Phe Phe
1               5                   10

<210> SEQ ID NO 38
<211> LENGTH: 16
<212> TYPE: PRT
<213> ORGANISM: Homo sapiens

<400> SEQUENCE: 38

Cys Ser Ala Arg Asp Arg Gly Gly Val Pro Asn Tyr Gly Tyr Thr Phe
1               5                   10                  15

<210> SEQ ID NO 39
<211> LENGTH: 13
<212> TYPE: PRT
```

```
<213> ORGANISM: Homo sapiens

<400> SEQUENCE: 39

Cys Ala Ser Ser Thr Ser Val Leu Asn Glu Gln Phe Phe
1               5                   10

<210> SEQ ID NO 40
<211> LENGTH: 13
<212> TYPE: PRT
<213> ORGANISM: Homo sapiens

<400> SEQUENCE: 40

Cys Ala Ser Ser Leu Asp Gly Thr Ile Glu Ala Phe Phe
1               5                   10

<210> SEQ ID NO 41
<211> LENGTH: 15
<212> TYPE: PRT
<213> ORGANISM: Homo sapiens

<400> SEQUENCE: 41

Cys Ala Ser Ser Leu Asp Gln Gly Ala Asn Tyr Gly Tyr Thr Phe
1               5                   10                  15

<210> SEQ ID NO 42
<211> LENGTH: 13
<212> TYPE: PRT
<213> ORGANISM: Homo sapiens

<400> SEQUENCE: 42

Cys Ala Ser Ser Arg Ser Gly Ala Tyr Glu Gln Tyr Phe
1               5                   10

<210> SEQ ID NO 43
<211> LENGTH: 14
<212> TYPE: PRT
<213> ORGANISM: Homo sapiens

<400> SEQUENCE: 43

Cys Ala Ser Ser Phe Leu Thr Ser Thr Asp Thr Gln Tyr Phe
1               5                   10

<210> SEQ ID NO 44
<211> LENGTH: 15
<212> TYPE: PRT
<213> ORGANISM: Homo sapiens

<400> SEQUENCE: 44

Cys Ala Ser Thr Asp Glu Gly Ser Gly Ala Asn Val Leu Thr Phe
1               5                   10                  15

<210> SEQ ID NO 45
<211> LENGTH: 13
<212> TYPE: PRT
<213> ORGANISM: Homo sapiens

<400> SEQUENCE: 45

Cys Ala Ser Ser Gln Tyr Arg Ala Gln Pro Gln His Phe
1               5                   10

<210> SEQ ID NO 46
<211> LENGTH: 16
<212> TYPE: PRT
<213> ORGANISM: Homo sapiens
```

```
<400> SEQUENCE: 46

Cys Ala Ser Arg Pro Asp Leu Ala Gly Gly Tyr Asn Glu Gln Phe Phe
1               5                   10                  15

<210> SEQ ID NO 47
<211> LENGTH: 15
<212> TYPE: PRT
<213> ORGANISM: Homo sapiens

<400> SEQUENCE: 47

Cys Ala Ser Ser Thr Gly Gln Gly Arg Asp Asn Glu Gln Phe Phe
1               5                   10                  15

<210> SEQ ID NO 48
<211> LENGTH: 14
<212> TYPE: PRT
<213> ORGANISM: Homo sapiens

<400> SEQUENCE: 48

Cys Ala Ser Asn Arg Gln Gly Gly Asn Thr Glu Ala Phe Phe
1               5                   10

<210> SEQ ID NO 49
<211> LENGTH: 14
<212> TYPE: PRT
<213> ORGANISM: Homo sapiens

<400> SEQUENCE: 49

Cys Ala Ser Gly Gln Thr Gly Val Asn Glu Lys Leu Phe Phe
1               5                   10

<210> SEQ ID NO 50
<211> LENGTH: 17
<212> TYPE: PRT
<213> ORGANISM: Homo sapiens

<400> SEQUENCE: 50

Cys Ala Ser Ser Gln Arg Gly Ala Gly Arg Thr Asn Glu Lys Leu Phe
1               5                   10                  15

Phe

<210> SEQ ID NO 51
<211> LENGTH: 13
<212> TYPE: PRT
<213> ORGANISM: Homo sapiens

<400> SEQUENCE: 51

Cys Ala Ser Arg Leu Gln Gly Ala Asn Glu Gln Tyr Phe
1               5                   10

<210> SEQ ID NO 52
<211> LENGTH: 15
<212> TYPE: PRT
<213> ORGANISM: Homo sapiens

<400> SEQUENCE: 52

Cys Ser Ala Arg Thr Ser Gly Ala Gly Thr Gly Glu Leu Phe Phe
1               5                   10                  15

<210> SEQ ID NO 53
<211> LENGTH: 16
<212> TYPE: PRT
<213> ORGANISM: Homo sapiens
```

```
<400> SEQUENCE: 53

Cys Ala Ser Ser Tyr Ser Ala Pro Gly Asn Asn Gln Pro Gln His Phe
1               5                   10                  15

<210> SEQ ID NO 54
<211> LENGTH: 14
<212> TYPE: PRT
<213> ORGANISM: Homo sapiens

<400> SEQUENCE: 54

Cys Ala Ser Ser Leu Thr Tyr Ser Asn Gln Pro Gln His Phe
1               5                   10

<210> SEQ ID NO 55
<211> LENGTH: 15
<212> TYPE: PRT
<213> ORGANISM: Homo sapiens

<400> SEQUENCE: 55

Cys Ala Ser Ser Leu Val Ser Gly Asp Arg Lys Thr Gln Tyr Phe
1               5                   10                  15

<210> SEQ ID NO 56
<211> LENGTH: 11
<212> TYPE: PRT
<213> ORGANISM: Homo sapiens

<400> SEQUENCE: 56

Cys Ser Val Tyr Thr Ser Asp Thr Gln Tyr Phe
1               5                   10

<210> SEQ ID NO 57
<211> LENGTH: 14
<212> TYPE: PRT
<213> ORGANISM: Homo sapiens

<400> SEQUENCE: 57

Cys Ala Ser Ser Leu Gly Gly Pro Pro Ser Gly Gln Tyr Phe
1               5                   10

<210> SEQ ID NO 58
<211> LENGTH: 14
<212> TYPE: PRT
<213> ORGANISM: Homo sapiens

<400> SEQUENCE: 58

Cys Ala Ser Ser His Ala Gly Phe Asn Glu Lys Leu Phe Phe
1               5                   10

<210> SEQ ID NO 59
<211> LENGTH: 15
<212> TYPE: PRT
<213> ORGANISM: Homo sapiens

<400> SEQUENCE: 59

Cys Ala Ser Ser Phe Asp Ser Arg Gly Asn Thr Glu Ala Phe Phe
1               5                   10                  15

<210> SEQ ID NO 60
<211> LENGTH: 15
<212> TYPE: PRT
<213> ORGANISM: Homo sapiens

<400> SEQUENCE: 60
```

Cys Ser Ala Pro Thr Ser Gly Gly Ala Trp Gly Glu Gln Phe Phe
1               5                   10                  15

<210> SEQ ID NO 61
<211> LENGTH: 15
<212> TYPE: PRT
<213> ORGANISM: Homo sapiens

<400> SEQUENCE: 61

Cys Ser Ala Arg Val Ser Gly Ala Gly Thr Gly Glu Leu Phe Phe
1               5                   10                  15

<210> SEQ ID NO 62
<211> LENGTH: 15
<212> TYPE: PRT
<213> ORGANISM: Homo sapiens

<400> SEQUENCE: 62

Cys Ala Ser Ser Ala Asp Arg Val Leu Ser Tyr Glu Gln Tyr Phe
1               5                   10                  15

<210> SEQ ID NO 63
<211> LENGTH: 14
<212> TYPE: PRT
<213> ORGANISM: Homo sapiens

<400> SEQUENCE: 63

Cys Ala Ser Ser Gly Gly Gly Thr Thr Asp Thr Gln Tyr Phe
1               5                   10

<210> SEQ ID NO 64
<211> LENGTH: 15
<212> TYPE: PRT
<213> ORGANISM: Homo sapiens

<400> SEQUENCE: 64

Cys Ala Ser Ser Phe Glu Pro Asn Tyr Asn Ser Pro Leu His Phe
1               5                   10                  15

<210> SEQ ID NO 65
<211> LENGTH: 13
<212> TYPE: PRT
<213> ORGANISM: Homo sapiens

<400> SEQUENCE: 65

Cys Ser Ala Arg Glu Ile Thr Gly Ala Glu Ala Phe Phe
1               5                   10

<210> SEQ ID NO 66
<211> LENGTH: 13
<212> TYPE: PRT
<213> ORGANISM: Homo sapiens

<400> SEQUENCE: 66

Cys Ala Ser Ser Val Asp Gly Gly Asp Glu Gln Phe Phe
1               5                   10

<210> SEQ ID NO 67
<211> LENGTH: 16
<212> TYPE: PRT
<213> ORGANISM: Homo sapiens

<400> SEQUENCE: 67

Cys Ser Ala Arg Asp Arg Gly Arg Gly His Asn Gln Pro Gln His Phe
1               5                   10                  15

```
<210> SEQ ID NO 68
<211> LENGTH: 14
<212> TYPE: PRT
<213> ORGANISM: Homo sapiens

<400> SEQUENCE: 68

Cys Ala Ser Ser Tyr Gly Gly Pro Tyr Asn Glu Gln Phe Phe
1               5                   10

<210> SEQ ID NO 69
<211> LENGTH: 14
<212> TYPE: PRT
<213> ORGANISM: Homo sapiens

<400> SEQUENCE: 69

Cys Ala Thr Ala Gly Gln Ile Ser Asn Gln Pro Gln His Phe
1               5                   10

<210> SEQ ID NO 70
<211> LENGTH: 15
<212> TYPE: PRT
<213> ORGANISM: Homo sapiens

<400> SEQUENCE: 70

Cys Ala Ser Ser Pro Lys Gly Arg Gly Gly Gln Pro Gln His Phe
1               5                   10                  15

<210> SEQ ID NO 71
<211> LENGTH: 17
<212> TYPE: PRT
<213> ORGANISM: Homo sapiens

<400> SEQUENCE: 71

Cys Ala Ser Ser Glu Leu Val Gly Gly Arg Ser Tyr Asn Glu Gln Phe
1               5                   10                  15

Phe

<210> SEQ ID NO 72
<211> LENGTH: 16
<212> TYPE: PRT
<213> ORGANISM: Homo sapiens

<400> SEQUENCE: 72

Cys Ala Ser Ser Leu Arg Arg Leu Ala Asp Thr Asp Thr Gln Tyr Phe
1               5                   10                  15

<210> SEQ ID NO 73
<211> LENGTH: 15
<212> TYPE: PRT
<213> ORGANISM: Homo sapiens

<400> SEQUENCE: 73

Cys Ala Ser Ser Leu Gly Ser Gly Ala Arg Gly Glu Gln Tyr Phe
1               5                   10                  15

<210> SEQ ID NO 74
<211> LENGTH: 12
<212> TYPE: PRT
<213> ORGANISM: Homo sapiens

<400> SEQUENCE: 74

Cys Ala Ser Ser Pro Val Pro Glu Lys Leu Phe Phe
1               5                   10
```

<210> SEQ ID NO 75
<211> LENGTH: 14
<212> TYPE: PRT
<213> ORGANISM: Homo sapiens

<400> SEQUENCE: 75

Cys Ala Ser Gln Ser Gly Thr Gly Asp Glu Lys Leu Phe Phe
1               5                   10

<210> SEQ ID NO 76
<211> LENGTH: 16
<212> TYPE: PRT
<213> ORGANISM: Homo sapiens

<400> SEQUENCE: 76

Cys Ser Ala Arg Ala Thr Thr Gly Gly Gly Asn Gln Pro Gln His Phe
1               5                   10                  15

<210> SEQ ID NO 77
<211> LENGTH: 16
<212> TYPE: PRT
<213> ORGANISM: Homo sapiens

<400> SEQUENCE: 77

Cys Ala Ser Ser Val Ala Ala Gly Val Gly Tyr Asn Glu Gln Phe Phe
1               5                   10                  15

<210> SEQ ID NO 78
<211> LENGTH: 15
<212> TYPE: PRT
<213> ORGANISM: Homo sapiens

<400> SEQUENCE: 78

Cys Ser Ala Arg Ala Ser Gly Ser Gly Thr Gly Glu Leu Phe Phe
1               5                   10                  15

<210> SEQ ID NO 79
<211> LENGTH: 14
<212> TYPE: PRT
<213> ORGANISM: Homo sapiens

<400> SEQUENCE: 79

Cys Ala Ser Ser Pro Tyr Arg Glu Gly Glu Lys Leu Phe Phe
1               5                   10

<210> SEQ ID NO 80
<211> LENGTH: 14
<212> TYPE: PRT
<213> ORGANISM: Homo sapiens

<400> SEQUENCE: 80

Cys Ser Ala Arg Val Thr Leu Ala Thr Asp Thr Gln Tyr Phe
1               5                   10

<210> SEQ ID NO 81
<211> LENGTH: 14
<212> TYPE: PRT
<213> ORGANISM: Homo sapiens

<400> SEQUENCE: 81

Cys Ala Ser Ser Ala Ala Gly Gln Gly Tyr Gly Tyr Thr Phe
1               5                   10

```
<210> SEQ ID NO 82
<211> LENGTH: 14
<212> TYPE: PRT
<213> ORGANISM: Homo sapiens

<400> SEQUENCE: 82

Cys Ala Ser Ser Pro His Asp Arg Tyr Tyr Gly Tyr Thr Phe
1               5                   10

<210> SEQ ID NO 83
<211> LENGTH: 13
<212> TYPE: PRT
<213> ORGANISM: Homo sapiens

<400> SEQUENCE: 83

Cys Ser Ala Val Thr Gly Gly Val Asn Glu Gln Phe Phe
1               5                   10

<210> SEQ ID NO 84
<211> LENGTH: 15
<212> TYPE: PRT
<213> ORGANISM: Homo sapiens

<400> SEQUENCE: 84

Cys Ser Ala Pro Thr Pro Gly Thr Thr Tyr Asn Glu Gln Phe Phe
1               5                   10                  15

<210> SEQ ID NO 85
<211> LENGTH: 15
<212> TYPE: PRT
<213> ORGANISM: Homo sapiens

<400> SEQUENCE: 85

Cys Ala Ser Ser Leu Glu Ala Gly Ala Trp Gly Glu Gln Phe Phe
1               5                   10                  15

<210> SEQ ID NO 86
<211> LENGTH: 16
<212> TYPE: PRT
<213> ORGANISM: Homo sapiens

<400> SEQUENCE: 86

Cys Ala Ser Arg Ala Ser Gly Gly Gly Leu Gln Glu Thr Gln Tyr Phe
1               5                   10                  15

<210> SEQ ID NO 87
<211> LENGTH: 16
<212> TYPE: PRT
<213> ORGANISM: Homo sapiens

<400> SEQUENCE: 87

Cys Ala Ser Ser Tyr Arg Arg Gly Ser Ser Tyr Asn Glu Gln Phe Phe
1               5                   10                  15

<210> SEQ ID NO 88
<211> LENGTH: 15
<212> TYPE: PRT
<213> ORGANISM: Homo sapiens

<400> SEQUENCE: 88

Cys Ala Ser Arg Arg Gly Gly Arg Gly Asn Glu Lys Leu Phe Phe
1               5                   10                  15

<210> SEQ ID NO 89
<211> LENGTH: 15
```

```
<212> TYPE: PRT
<213> ORGANISM: Homo sapiens

<400> SEQUENCE: 89

Cys Ala Ser Ser Phe Ser Ala Gly Glu Ala Gly Glu Leu Phe Phe
1               5                   10                  15

<210> SEQ ID NO 90
<211> LENGTH: 12
<212> TYPE: PRT
<213> ORGANISM: Homo sapiens

<400> SEQUENCE: 90

Cys Ala Ser Arg Ser His Pro Asn Glu Gln Phe Phe
1               5                   10

<210> SEQ ID NO 91
<211> LENGTH: 15
<212> TYPE: PRT
<213> ORGANISM: Homo sapiens

<400> SEQUENCE: 91

Cys Ala Ser Ser Leu Ala Gly Ala Thr Arg Glu Thr Gln Tyr Phe
1               5                   10                  15

<210> SEQ ID NO 92
<211> LENGTH: 14
<212> TYPE: PRT
<213> ORGANISM: Homo sapiens

<400> SEQUENCE: 92

Cys Ser Ala Pro Pro Ser Gly Gly Asn Gln Pro Gln His Phe
1               5                   10

<210> SEQ ID NO 93
<211> LENGTH: 15
<212> TYPE: PRT
<213> ORGANISM: Homo sapiens

<400> SEQUENCE: 93

Cys Ala Ser Ser Gln Asp Tyr Gly Gly Pro Asn Glu Gln Phe Phe
1               5                   10                  15

<210> SEQ ID NO 94
<211> LENGTH: 14
<212> TYPE: PRT
<213> ORGANISM: Homo sapiens

<400> SEQUENCE: 94

Cys Ala Ser Ser Leu Gly Gly Ala Asn Tyr Gly Tyr Thr Phe
1               5                   10

<210> SEQ ID NO 95
<211> LENGTH: 12
<212> TYPE: PRT
<213> ORGANISM: Homo sapiens

<400> SEQUENCE: 95

Cys Ala Ser Thr Arg Lys Ala Gly Glu Leu Phe Phe
1               5                   10

<210> SEQ ID NO 96
<211> LENGTH: 15
<212> TYPE: PRT
<213> ORGANISM: Homo sapiens
```

<400> SEQUENCE: 96

Cys Ala Ser Ser Lys Gly Leu Pro Thr Tyr Asn Glu Gln Phe Phe
1               5                   10                  15

<210> SEQ ID NO 97
<211> LENGTH: 14
<212> TYPE: PRT
<213> ORGANISM: Homo sapiens

<400> SEQUENCE: 97

Cys Ala Ser Ser Glu Gly Thr Gly Arg Thr Glu Ala Phe Phe
1               5                   10

<210> SEQ ID NO 98
<211> LENGTH: 14
<212> TYPE: PRT
<213> ORGANISM: Homo sapiens

<400> SEQUENCE: 98

Cys Ala Ser Arg Thr Pro Gly Pro Thr Asp Thr Gln Tyr Phe
1               5                   10

<210> SEQ ID NO 99
<211> LENGTH: 12
<212> TYPE: PRT
<213> ORGANISM: Homo sapiens

<400> SEQUENCE: 99

Cys Ala Cys Arg Thr Val Gln Glu Thr Gln Tyr Phe
1               5                   10

<210> SEQ ID NO 100
<211> LENGTH: 15
<212> TYPE: PRT
<213> ORGANISM: Homo sapiens

<400> SEQUENCE: 100

Cys Ala Ser Ser Glu Leu Gly Thr Arg Gly Asn Glu Gln Phe Phe
1               5                   10                  15

<210> SEQ ID NO 101
<211> LENGTH: 14
<212> TYPE: PRT
<213> ORGANISM: Homo sapiens

<400> SEQUENCE: 101

Cys Ala Ser Ser Phe Ala Pro Ala Asn Thr Glu Ala Phe Phe
1               5                   10

<210> SEQ ID NO 102
<211> LENGTH: 13
<212> TYPE: PRT
<213> ORGANISM: Homo sapiens

<400> SEQUENCE: 102

Cys Ala Ser Ser Ala Met Gly Ala Glu Thr Gln Tyr Phe
1               5                   10

<210> SEQ ID NO 103
<211> LENGTH: 15
<212> TYPE: PRT
<213> ORGANISM: Homo sapiens

<400> SEQUENCE: 103

```
Cys Ala Ser Gly Leu Val Gln Val Ala Asn Glu Lys Leu Phe Phe
1               5                   10                  15
```

<210> SEQ ID NO 104
<211> LENGTH: 13
<212> TYPE: PRT
<213> ORGANISM: Homo sapiens

<400> SEQUENCE: 104

```
Cys Ala Ser Ser Leu Gln Pro Pro Tyr Gly Tyr Thr Phe
1               5                   10
```

<210> SEQ ID NO 105
<211> LENGTH: 12
<212> TYPE: PRT
<213> ORGANISM: Homo sapiens

<400> SEQUENCE: 105

```
Cys Ala Ser Arg Ser His Thr Asp Thr Gln Tyr Phe
1               5                   10
```

<210> SEQ ID NO 106
<211> LENGTH: 13
<212> TYPE: PRT
<213> ORGANISM: Homo sapiens

<400> SEQUENCE: 106

```
Cys Ser Ala Pro Thr Ala Pro Tyr Asn Glu Gln Phe Phe
1               5                   10
```

<210> SEQ ID NO 107
<211> LENGTH: 15
<212> TYPE: PRT
<213> ORGANISM: Homo sapiens

<400> SEQUENCE: 107

```
Cys Ala Ser Ser Arg Thr Gln Gly Ile Glu Glu Lys Leu Phe Phe
1               5                   10                  15
```

<210> SEQ ID NO 108
<211> LENGTH: 15
<212> TYPE: PRT
<213> ORGANISM: Homo sapiens

<400> SEQUENCE: 108

```
Cys Ala Ser Ser Pro Pro Arg Gly Val Asn Thr Glu Ala Phe Phe
1               5                   10                  15
```

<210> SEQ ID NO 109
<211> LENGTH: 15
<212> TYPE: PRT
<213> ORGANISM: Homo sapiens

<400> SEQUENCE: 109

```
Cys Ser Ala Pro Leu Ala Gly Gly Arg Leu Glu Thr Gln Tyr Phe
1               5                   10                  15
```

<210> SEQ ID NO 110
<211> LENGTH: 13
<212> TYPE: PRT
<213> ORGANISM: Homo sapiens

<400> SEQUENCE: 110

```
Cys Ala Ser Ser Gly Leu Val Ser Glu Thr Gln Tyr Phe
```

```
1               5                    10
```

<210> SEQ ID NO 111
<211> LENGTH: 14
<212> TYPE: PRT
<213> ORGANISM: Homo sapiens

<400> SEQUENCE: 111

```
Cys Ala Ser Ser Leu Trp Gly Lys Gly Glu Thr Gln Tyr Phe
1               5                   10
```

<210> SEQ ID NO 112
<211> LENGTH: 13
<212> TYPE: PRT
<213> ORGANISM: Homo sapiens

<400> SEQUENCE: 112

```
Cys Ala Ser Ser Ala Trp Val Gly Glu Lys Leu Phe Phe
1               5                   10
```

<210> SEQ ID NO 113
<211> LENGTH: 13
<212> TYPE: PRT
<213> ORGANISM: Homo sapiens

<400> SEQUENCE: 113

```
Cys Ser Ala Leu Leu Ala Pro Tyr Asn Glu Gln Phe Phe
1               5                   10
```

<210> SEQ ID NO 114
<211> LENGTH: 13
<212> TYPE: PRT
<213> ORGANISM: Homo sapiens

<400> SEQUENCE: 114

```
Cys Ala Ser Thr Pro Glu Val Gly Thr Glu Ala Phe Phe
1               5                   10
```

<210> SEQ ID NO 115
<211> LENGTH: 18
<212> TYPE: PRT
<213> ORGANISM: Homo sapiens

<400> SEQUENCE: 115

```
Cys Ala Ser Ser Leu Ala Ala Gly Thr Thr Leu Asn Thr Gly Glu Leu
1               5                   10                  15

Phe Phe
```

<210> SEQ ID NO 116
<211> LENGTH: 16
<212> TYPE: PRT
<213> ORGANISM: Homo sapiens

<400> SEQUENCE: 116

```
Cys Ala Ser Ser Pro Pro Arg Gly Val Gly Gly Ser Pro Leu His Phe
1               5                   10                  15
```

<210> SEQ ID NO 117
<211> LENGTH: 15
<212> TYPE: PRT
<213> ORGANISM: Homo sapiens

<400> SEQUENCE: 117

```
Cys Ala Trp Ser Arg Arg Gly Leu Ser Asn Gln Pro Gln His Phe
```

```
<210> SEQ ID NO 118
<211> LENGTH: 15
<212> TYPE: PRT
<213> ORGANISM: Homo sapiens

<400> SEQUENCE: 118

Cys Ala Ser Ser Leu Arg Glu Asp Ser Tyr Asn Glu Gln Phe Phe
1               5                   10                  15

<210> SEQ ID NO 119
<211> LENGTH: 16
<212> TYPE: PRT
<213> ORGANISM: Homo sapiens

<400> SEQUENCE: 119

Cys Ala Ser Ser Gln Glu Val Ser Gly Gly Gly Tyr Glu Gln Tyr Phe
1               5                   10                  15

<210> SEQ ID NO 120
<211> LENGTH: 14
<212> TYPE: PRT
<213> ORGANISM: Homo sapiens

<400> SEQUENCE: 120

Cys Ala Ser Ser Leu Ala Pro Leu Ala Asp Glu Gln Tyr Phe
1               5                   10

<210> SEQ ID NO 121
<211> LENGTH: 14
<212> TYPE: PRT
<213> ORGANISM: Homo sapiens

<400> SEQUENCE: 121

Cys Ala Ser Ser Pro Ser Gly His Ile Tyr Glu Gln Tyr Phe
1               5                   10

<210> SEQ ID NO 122
<211> LENGTH: 15
<212> TYPE: PRT
<213> ORGANISM: Homo sapiens

<400> SEQUENCE: 122

Cys Ala Thr Ser Arg Gly Thr Arg Arg Thr Asp Thr Gln Tyr Phe
1               5                   10                  15

<210> SEQ ID NO 123
<211> LENGTH: 16
<212> TYPE: PRT
<213> ORGANISM: Homo sapiens

<400> SEQUENCE: 123

Cys Ala Ser Ser Glu Ala Ser Gly Arg Ala Thr Asp Thr Gln Tyr Phe
1               5                   10                  15

<210> SEQ ID NO 124
<211> LENGTH: 15
<212> TYPE: PRT
<213> ORGANISM: Homo sapiens

<400> SEQUENCE: 124

Cys Ala Ser Ser Arg Gly Leu Ala Gly Val Val Glu Gln Tyr Phe
1               5                   10                  15
```

```
<210> SEQ ID NO 125
<211> LENGTH: 13
<212> TYPE: PRT
<213> ORGANISM: Homo sapiens

<400> SEQUENCE: 125

Cys Ala Ser Arg Ile Arg Asp Arg Gly Glu Ala Phe Phe
1               5                   10

<210> SEQ ID NO 126
<211> LENGTH: 14
<212> TYPE: PRT
<213> ORGANISM: Homo sapiens

<400> SEQUENCE: 126

Cys Ala Trp Ile Arg Lys Ser Ser Tyr Asn Glu Gln Phe Phe
1               5                   10

<210> SEQ ID NO 127
<211> LENGTH: 14
<212> TYPE: PRT
<213> ORGANISM: Homo sapiens

<400> SEQUENCE: 127

Cys Ala Ser Lys Thr Ser Gly Val Thr Asp Thr Gln Tyr Phe
1               5                   10

<210> SEQ ID NO 128
<211> LENGTH: 15
<212> TYPE: PRT
<213> ORGANISM: Homo sapiens

<400> SEQUENCE: 128

Cys Ala Ser Ser Val Glu Gly Asp Pro Arg Gly Glu Gln Phe Phe
1               5                   10                  15

<210> SEQ ID NO 129
<211> LENGTH: 15
<212> TYPE: PRT
<213> ORGANISM: Homo sapiens

<400> SEQUENCE: 129

Cys Ser Ala Thr Gly Thr Ser Gly Gly Ala Ser Glu Gln Tyr Phe
1               5                   10                  15

<210> SEQ ID NO 130
<211> LENGTH: 17
<212> TYPE: PRT
<213> ORGANISM: Homo sapiens

<400> SEQUENCE: 130

Cys Ala Ser Ser Leu Pro Ser Gly Gly Ala Asn Thr Gly Glu Leu Phe
1               5                   10                  15

Phe

<210> SEQ ID NO 131
<211> LENGTH: 15
<212> TYPE: PRT
<213> ORGANISM: Homo sapiens

<400> SEQUENCE: 131

Cys Ala Ser Ser Leu Met Ile Gly Val Gln Glu Thr Gln Tyr Phe
1               5                   10                  15
```

<210> SEQ ID NO 132
<211> LENGTH: 15
<212> TYPE: PRT
<213> ORGANISM: Homo sapiens

<400> SEQUENCE: 132

Cys Ala Ser Ser Phe Ser Gln Gly Gly Thr Gly Glu Leu Phe Phe
1               5                   10                  15

<210> SEQ ID NO 133
<211> LENGTH: 16
<212> TYPE: PRT
<213> ORGANISM: Homo sapiens

<400> SEQUENCE: 133

Cys Ala Ser Ser Leu Ser Ser Arg Gly Arg Gly Tyr Gly Tyr Thr Phe
1               5                   10                  15

<210> SEQ ID NO 134
<211> LENGTH: 13
<212> TYPE: PRT
<213> ORGANISM: Homo sapiens

<400> SEQUENCE: 134

Cys Ala Ser Ser Trp Gln Leu Asn Gln Pro Gln His Phe
1               5                   10

<210> SEQ ID NO 135
<211> LENGTH: 13
<212> TYPE: PRT
<213> ORGANISM: Homo sapiens

<400> SEQUENCE: 135

Cys Ala Ser Ser Arg Gln Gly Lys Tyr Glu Gln Tyr Phe
1               5                   10

<210> SEQ ID NO 136
<211> LENGTH: 10
<212> TYPE: PRT
<213> ORGANISM: Homo sapiens

<400> SEQUENCE: 136

Cys Ala Trp Asn Ser Gly Thr Gln Tyr Phe
1               5                   10

<210> SEQ ID NO 137
<211> LENGTH: 17
<212> TYPE: PRT
<213> ORGANISM: Homo sapiens

<400> SEQUENCE: 137

Cys Ala Ser Ser Gln Asp Pro Ser Gly Gln Pro Gln Glu Thr Gln Tyr
1               5                   10                  15

Phe

<210> SEQ ID NO 138
<211> LENGTH: 14
<212> TYPE: PRT
<213> ORGANISM: Homo sapiens

<400> SEQUENCE: 138

Cys Ala Ser Ser Val Asp Pro Gly Glu Glu Lys Leu Phe Phe
1               5                   10

<210> SEQ ID NO 139
<211> LENGTH: 14
<212> TYPE: PRT
<213> ORGANISM: Homo sapiens

<400> SEQUENCE: 139

Cys Ala Ser Ser Leu Gly Thr Arg Arg Thr Glu Ala Phe Phe
1               5                   10

<210> SEQ ID NO 140
<211> LENGTH: 14
<212> TYPE: PRT
<213> ORGANISM: Homo sapiens

<400> SEQUENCE: 140

Cys Ala Ser Gln Thr Gly Thr Gly Asn Glu Lys Leu Phe Phe
1               5                   10

<210> SEQ ID NO 141
<211> LENGTH: 14
<212> TYPE: PRT
<213> ORGANISM: Homo sapiens

<400> SEQUENCE: 141

Cys Ala Ser Ser Tyr Met His Leu Ser Tyr Glu Gln Tyr Phe
1               5                   10

<210> SEQ ID NO 142
<211> LENGTH: 13
<212> TYPE: PRT
<213> ORGANISM: Homo sapiens

<400> SEQUENCE: 142

Cys Ala Ser Ser Ala Arg Ala Leu Asp Thr Gln Tyr Phe
1               5                   10

<210> SEQ ID NO 143
<211> LENGTH: 14
<212> TYPE: PRT
<213> ORGANISM: Homo sapiens

<400> SEQUENCE: 143

Cys Ala Ser Ser Pro Glu Thr Leu Gln Glu Thr Gln Tyr Phe
1               5                   10

<210> SEQ ID NO 144
<211> LENGTH: 15
<212> TYPE: PRT
<213> ORGANISM: Homo sapiens

<400> SEQUENCE: 144

Cys Ser Ala Arg Ser Ser Gly Arg Ile Ser Asp Thr Gln Tyr Phe
1               5                   10                  15

<210> SEQ ID NO 145
<211> LENGTH: 15
<212> TYPE: PRT
<213> ORGANISM: Homo sapiens

<400> SEQUENCE: 145

Cys Ala Ser Ser Ser Gln Gly Met Arg Asn Ser Pro Leu His Phe
1               5                   10                  15

<210> SEQ ID NO 146

```
<211> LENGTH: 15
<212> TYPE: PRT
<213> ORGANISM: Homo sapiens

<400> SEQUENCE: 146

Cys Ala Ser Ser Ala Thr Gly Asn Thr Gly Glu Leu Phe Phe
1               5                   10                  15

<210> SEQ ID NO 147
<211> LENGTH: 15
<212> TYPE: PRT
<213> ORGANISM: Homo sapiens

<400> SEQUENCE: 147

Cys Ala Ser Ser Pro Ala Gly Gly Trp Asn Thr Glu Ala Phe Phe
1               5                   10                  15

<210> SEQ ID NO 148
<211> LENGTH: 15
<212> TYPE: PRT
<213> ORGANISM: Homo sapiens

<400> SEQUENCE: 148

Cys Ala Ser Ser Phe Thr Gly Thr Gly Lys Glu Lys Leu Phe Phe
1               5                   10                  15

<210> SEQ ID NO 149
<211> LENGTH: 17
<212> TYPE: PRT
<213> ORGANISM: Homo sapiens

<400> SEQUENCE: 149

Cys Ala Ser Ser Glu Arg Gly Leu Ala Gly Val Pro Asp Thr Gln Tyr
1               5                   10                  15

Phe

<210> SEQ ID NO 150
<211> LENGTH: 15
<212> TYPE: PRT
<213> ORGANISM: Homo sapiens

<400> SEQUENCE: 150

Cys Ala Ser Ser Gly Pro Gly Thr Gly Asp Tyr Glu Gln Tyr Phe
1               5                   10                  15

<210> SEQ ID NO 151
<211> LENGTH: 15
<212> TYPE: PRT
<213> ORGANISM: Homo sapiens

<400> SEQUENCE: 151

Cys Ala Ser Ser Ser Arg Gly Thr Lys Gln Glu Thr Gln Tyr Phe
1               5                   10                  15

<210> SEQ ID NO 152
<211> LENGTH: 13
<212> TYPE: PRT
<213> ORGANISM: Homo sapiens

<400> SEQUENCE: 152

Cys Ala Ser Ser His Gln Arg Asn Ser Pro Leu His Phe
1               5                   10

<210> SEQ ID NO 153
```

```
<211> LENGTH: 11
<212> TYPE: PRT
<213> ORGANISM: Homo sapiens

<400> SEQUENCE: 153

Cys Ser Ala Ser Val Gln Thr Glu Ala Phe Phe
1               5                   10

<210> SEQ ID NO 154
<211> LENGTH: 14
<212> TYPE: PRT
<213> ORGANISM: Homo sapiens

<400> SEQUENCE: 154

Cys Ala Ser Arg Thr His Ser Ser Tyr Asn Glu Gln Phe Phe
1               5                   10

<210> SEQ ID NO 155
<211> LENGTH: 15
<212> TYPE: PRT
<213> ORGANISM: Homo sapiens

<400> SEQUENCE: 155

Cys Ser Ala Arg Arg Ala Gly Ser Gly Thr Asp Thr Gln Tyr Phe
1               5                   10                  15

<210> SEQ ID NO 156
<211> LENGTH: 14
<212> TYPE: PRT
<213> ORGANISM: Homo sapiens

<400> SEQUENCE: 156

Cys Ala Ser Arg Gly Glu Pro Tyr Asn Ser Pro Leu His Phe
1               5                   10

<210> SEQ ID NO 157
<211> LENGTH: 16
<212> TYPE: PRT
<213> ORGANISM: Homo sapiens

<400> SEQUENCE: 157

Cys Ala Thr Ser Arg Asp Leu Arg Asp Arg Asn Glu Lys Leu Phe Phe
1               5                   10                  15

<210> SEQ ID NO 158
<211> LENGTH: 15
<212> TYPE: PRT
<213> ORGANISM: Homo sapiens

<400> SEQUENCE: 158

Cys Ser Ala Arg Thr Gly Gly Ser Gly Thr Gly Glu Leu Phe Phe
1               5                   10                  15

<210> SEQ ID NO 159
<211> LENGTH: 14
<212> TYPE: PRT
<213> ORGANISM: Homo sapiens

<400> SEQUENCE: 159

Cys Ala Ser Ser Tyr Ser Pro Leu Ala Gly Thr Gln Tyr Phe
1               5                   10

<210> SEQ ID NO 160
<211> LENGTH: 14
<212> TYPE: PRT
```

<213> ORGANISM: Homo sapiens

<400> SEQUENCE: 160

Cys Ala Ser Ser Arg Gly Thr Ala Asn Glu Lys Leu Phe Phe
1               5                   10

<210> SEQ ID NO 161
<211> LENGTH: 14
<212> TYPE: PRT
<213> ORGANISM: Homo sapiens

<400> SEQUENCE: 161

Cys Ala Ser Ser Phe Arg Gln Gly Arg Thr Glu Ala Phe Phe
1               5                   10

<210> SEQ ID NO 162
<211> LENGTH: 16
<212> TYPE: PRT
<213> ORGANISM: Homo sapiens

<400> SEQUENCE: 162

Cys Ala Ser Ser Ser Arg Thr Ser Gly Ser His Glu Thr Gln Tyr Phe
1               5                   10                  15

<210> SEQ ID NO 163
<211> LENGTH: 15
<212> TYPE: PRT
<213> ORGANISM: Homo sapiens

<400> SEQUENCE: 163

Cys Ser Ala Arg Ala Gly Gly Gly Gly Thr Gly Glu Leu Phe Phe
1               5                   10                  15

<210> SEQ ID NO 164
<211> LENGTH: 11
<212> TYPE: PRT
<213> ORGANISM: Homo sapiens

<400> SEQUENCE: 164

Cys Ser Ala Glu Gly Ser Gly Glu Ala Phe Phe
1               5                   10

<210> SEQ ID NO 165
<211> LENGTH: 13
<212> TYPE: PRT
<213> ORGANISM: Homo sapiens

<400> SEQUENCE: 165

Cys Ala Thr Ser Arg Asp Lys Val Asp Gly Tyr Thr Phe
1               5                   10

<210> SEQ ID NO 166
<211> LENGTH: 12
<212> TYPE: PRT
<213> ORGANISM: Homo sapiens

<400> SEQUENCE: 166

Cys Ser Val Arg Thr Ser Gly Glu Thr Gln Tyr Phe
1               5                   10

<210> SEQ ID NO 167
<211> LENGTH: 12
<212> TYPE: PRT
<213> ORGANISM: Homo sapiens

<400> SEQUENCE: 167

Cys Ser Ala Ile Asp Gly Pro Gly Pro Gln His Phe
1               5                   10

<210> SEQ ID NO 168
<211> LENGTH: 14
<212> TYPE: PRT
<213> ORGANISM: Homo sapiens

<400> SEQUENCE: 168

Cys Ala Ser Ser Pro Gln Gly Phe Thr Gly Glu Leu Phe Phe
1               5                   10

<210> SEQ ID NO 169
<211> LENGTH: 12
<212> TYPE: PRT
<213> ORGANISM: Homo sapiens

<400> SEQUENCE: 169

Cys Ala Ser Arg Tyr Arg Asp His Gly Tyr Thr Phe
1               5                   10

<210> SEQ ID NO 170
<211> LENGTH: 15
<212> TYPE: PRT
<213> ORGANISM: Homo sapiens

<400> SEQUENCE: 170

Cys Ala Ser Ser Ala Ala Thr Gly Asn Thr Gly Glu Leu Phe Phe
1               5                   10                  15

<210> SEQ ID NO 171
<211> LENGTH: 15
<212> TYPE: PRT
<213> ORGANISM: Homo sapiens

<400> SEQUENCE: 171

Cys Ser Ala Arg Gly Val Pro Thr Asn Thr Gly Glu Leu Phe Phe
1               5                   10                  15

<210> SEQ ID NO 172
<211> LENGTH: 15
<212> TYPE: PRT
<213> ORGANISM: Homo sapiens

<400> SEQUENCE: 172

Cys Ala Ser Thr Asp Leu Ala Gly Val Arg Asn Glu Gln Phe Phe
1               5                   10                  15

<210> SEQ ID NO 173
<211> LENGTH: 12
<212> TYPE: PRT
<213> ORGANISM: Homo sapiens

<400> SEQUENCE: 173

Cys Ala Ser Ser Gln Asp Val Asn Gly Tyr Thr Phe
1               5                   10

<210> SEQ ID NO 174
<211> LENGTH: 17
<212> TYPE: PRT
<213> ORGANISM: Homo sapiens

<400> SEQUENCE: 174

-continued

Cys Ala Ser Ser Arg Gly Thr Gly Pro Ser Gly Ala Asn Val Leu Thr
1               5                   10                  15

Phe

<210> SEQ ID NO 175
<211> LENGTH: 15
<212> TYPE: PRT
<213> ORGANISM: Homo sapiens

<400> SEQUENCE: 175

Cys Ala Ser Ser Tyr Lys Gln Gly Ser Tyr Asn Glu Gln Phe Phe
1               5                   10                  15

<210> SEQ ID NO 176
<211> LENGTH: 16
<212> TYPE: PRT
<213> ORGANISM: Homo sapiens

<400> SEQUENCE: 176

Cys Ala Ser Ser Gln Val Leu Pro Ser Gly Ala Asn Val Leu Thr Phe
1               5                   10                  15

<210> SEQ ID NO 177
<211> LENGTH: 14
<212> TYPE: PRT
<213> ORGANISM: Homo sapiens

<400> SEQUENCE: 177

Cys Ala Ser Arg Pro Pro Gly Arg Tyr Tyr Gly Tyr Thr Phe
1               5                   10

<210> SEQ ID NO 178
<211> LENGTH: 16
<212> TYPE: PRT
<213> ORGANISM: Homo sapiens

<400> SEQUENCE: 178

Cys Ala Ser Ser Leu Ser Pro Arg Gly Arg Gly Tyr Gly Tyr Thr Phe
1               5                   10                  15

<210> SEQ ID NO 179
<211> LENGTH: 13
<212> TYPE: PRT
<213> ORGANISM: Homo sapiens

<400> SEQUENCE: 179

Cys Ser Ala Pro Pro Pro Tyr Asn Glu Gln Phe Phe
1               5                   10

<210> SEQ ID NO 180
<211> LENGTH: 15
<212> TYPE: PRT
<213> ORGANISM: Homo sapiens

<400> SEQUENCE: 180

Cys Ser Ala Arg Gly Glu Pro Ala Asn Thr Gly Glu Leu Phe Phe
1               5                   10                  15

<210> SEQ ID NO 181
<211> LENGTH: 15
<212> TYPE: PRT
<213> ORGANISM: Homo sapiens

<400> SEQUENCE: 181

Cys Ser Ala Arg Lys Gly Gly Ala Gly Thr Gly Glu Leu Phe Phe
1               5                   10                  15

<210> SEQ ID NO 182
<211> LENGTH: 15
<212> TYPE: PRT
<213> ORGANISM: Homo sapiens

<400> SEQUENCE: 182

Cys Ser Ala Arg Gln Ala Gly Ala Gly Thr Gly Glu Leu Phe Phe
1               5                   10                  15

<210> SEQ ID NO 183
<211> LENGTH: 13
<212> TYPE: PRT
<213> ORGANISM: Homo sapiens

<400> SEQUENCE: 183

Cys Ala Ser Gly Arg Gln Gly Ala Tyr Glu Gln Tyr Phe
1               5                   10

<210> SEQ ID NO 184
<211> LENGTH: 14
<212> TYPE: PRT
<213> ORGANISM: Homo sapiens

<400> SEQUENCE: 184

Cys Ala Ser Ser Leu Asp Asp Pro Thr Asp Thr Gln Tyr Phe
1               5                   10

<210> SEQ ID NO 185
<211> LENGTH: 12
<212> TYPE: PRT
<213> ORGANISM: Homo sapiens

<400> SEQUENCE: 185

Cys Ala Ser Ser Thr Gly Phe Asn Glu Gln Phe Phe
1               5                   10

<210> SEQ ID NO 186
<211> LENGTH: 14
<212> TYPE: PRT
<213> ORGANISM: Homo sapiens

<400> SEQUENCE: 186

Cys Ala Ser Ser Leu Arg Leu Gly Ser Glu Thr Gln Tyr Phe
1               5                   10

<210> SEQ ID NO 187
<211> LENGTH: 15
<212> TYPE: PRT
<213> ORGANISM: Homo sapiens

<400> SEQUENCE: 187

Cys Ala Ser Ser Phe Pro Arg Pro Gly Thr Gly Glu Leu Phe Phe
1               5                   10                  15

<210> SEQ ID NO 188
<211> LENGTH: 15
<212> TYPE: PRT
<213> ORGANISM: Homo sapiens

<400> SEQUENCE: 188

Cys Ala Ser Ser Pro Ser Gly Thr Pro Gly Glu Lys Leu Phe Phe
1               5                   10                  15

```
<210> SEQ ID NO 189
<211> LENGTH: 16
<212> TYPE: PRT
<213> ORGANISM: Homo sapiens

<400> SEQUENCE: 189

Cys Ala Ser Ser Leu Leu Asp Ser Ser Asn Thr Gly Glu Leu Phe Phe
1               5                   10                  15

<210> SEQ ID NO 190
<211> LENGTH: 16
<212> TYPE: PRT
<213> ORGANISM: Homo sapiens

<400> SEQUENCE: 190

Cys Ala Ser Ser Tyr Gly Phe Gly Thr Gly Glu Glu Thr Gln Tyr Phe
1               5                   10                  15

<210> SEQ ID NO 191
<211> LENGTH: 15
<212> TYPE: PRT
<213> ORGANISM: Homo sapiens

<400> SEQUENCE: 191

Cys Ala Ser Ser Val Gly Gly Asn Ser His Asn Glu Gln Phe Phe
1               5                   10                  15

<210> SEQ ID NO 192
<211> LENGTH: 15
<212> TYPE: PRT
<213> ORGANISM: Homo sapiens

<400> SEQUENCE: 192

Cys Ser Ala Arg Ser Ala Gly Gly Gly Thr Gly Glu Leu Phe Phe
1               5                   10                  15

<210> SEQ ID NO 193
<211> LENGTH: 14
<212> TYPE: PRT
<213> ORGANISM: Homo sapiens

<400> SEQUENCE: 193

Cys Ala Trp Ser Val Gly Gly Thr Tyr Gln Pro Gln His Phe
1               5                   10

<210> SEQ ID NO 194
<211> LENGTH: 14
<212> TYPE: PRT
<213> ORGANISM: Homo sapiens

<400> SEQUENCE: 194

Cys Ala Ser Thr Pro Val Gly Ser Tyr Asn Glu Gln Phe Phe
1               5                   10

<210> SEQ ID NO 195
<211> LENGTH: 13
<212> TYPE: PRT
<213> ORGANISM: Homo sapiens

<400> SEQUENCE: 195

Cys Ala Trp Ser Gly Thr Gly Arg Lys Pro Gln His Phe
1               5                   10
```

```
<210> SEQ ID NO 196
<211> LENGTH: 13
<212> TYPE: PRT
<213> ORGANISM: Homo sapiens

<400> SEQUENCE: 196

Cys Ala Ile Arg Gln Gly Gln Thr Gly Glu Leu Phe Phe
1               5                   10

<210> SEQ ID NO 197
<211> LENGTH: 17
<212> TYPE: PRT
<213> ORGANISM: Homo sapiens

<400> SEQUENCE: 197

Cys Ala Ser Ser Leu Ala Pro Arg Asp Arg Gly Thr Gln Pro Gln His
1               5                   10                  15

Phe

<210> SEQ ID NO 198
<211> LENGTH: 17
<212> TYPE: PRT
<213> ORGANISM: Homo sapiens

<400> SEQUENCE: 198

Cys Ala Ser Ser Arg Arg Gly Leu Ala Gly Arg Thr Asp Thr Gln Tyr
1               5                   10                  15

Phe

<210> SEQ ID NO 199
<211> LENGTH: 14
<212> TYPE: PRT
<213> ORGANISM: Homo sapiens

<400> SEQUENCE: 199

Cys Ala Thr Ser Arg Ala Arg Gly Gly Lys Thr Gln Tyr Phe
1               5                   10

<210> SEQ ID NO 200
<211> LENGTH: 13
<212> TYPE: PRT
<213> ORGANISM: Homo sapiens

<400> SEQUENCE: 200

Cys Ala Ser Ser Leu Ala Gly Leu Asn Glu Gln Phe Phe
1               5                   10

<210> SEQ ID NO 201
<211> LENGTH: 13
<212> TYPE: PRT
<213> ORGANISM: Homo sapiens

<400> SEQUENCE: 201

Cys Ser Ala Pro Ser Pro Pro His Asn Glu Gln Phe Phe
1               5                   10

<210> SEQ ID NO 202
<211> LENGTH: 15
<212> TYPE: PRT
<213> ORGANISM: Homo sapiens

<400> SEQUENCE: 202

Cys Ser Ala Arg Lys Ser Gly Ser Gly Thr Gly Glu Leu Phe Phe
1               5                   10                  15
```

<210> SEQ ID NO 203
<211> LENGTH: 16
<212> TYPE: PRT
<213> ORGANISM: Homo sapiens

<400> SEQUENCE: 203

Cys Ala Thr Ser Arg Gly Gly Arg Glu Thr Lys Asn Ile Gln Tyr Phe
1               5                   10                  15

<210> SEQ ID NO 204
<211> LENGTH: 15
<212> TYPE: PRT
<213> ORGANISM: Homo sapiens

<400> SEQUENCE: 204

Cys Ala Ser Ser Pro Val Arg Asp Gly Thr Gly Glu Leu Phe Phe
1               5                   10                  15

<210> SEQ ID NO 205
<211> LENGTH: 16
<212> TYPE: PRT
<213> ORGANISM: Homo sapiens

<400> SEQUENCE: 205

Cys Ala Ser Ser Leu Arg Arg Gly Gly Leu Gln Glu Thr Gln Tyr Phe
1               5                   10                  15

<210> SEQ ID NO 206
<211> LENGTH: 13
<212> TYPE: PRT
<213> ORGANISM: Homo sapiens

<400> SEQUENCE: 206

Cys Ala Ser Gly Thr Gly Leu Tyr Glu Lys Leu Phe Phe
1               5                   10

<210> SEQ ID NO 207
<211> LENGTH: 17
<212> TYPE: PRT
<213> ORGANISM: Homo sapiens

<400> SEQUENCE: 207

Cys Ala Ser Ser Val Val Pro Thr Gly Gly Ser Gly Asn Thr Ile Tyr
1               5                   10                  15

Phe

<210> SEQ ID NO 208
<211> LENGTH: 15
<212> TYPE: PRT
<213> ORGANISM: Homo sapiens

<400> SEQUENCE: 208

Cys Ala Ser Ser Tyr Ser Pro Ser Gly Trp Thr Glu Ala Phe Phe
1               5                   10                  15

<210> SEQ ID NO 209
<211> LENGTH: 16
<212> TYPE: PRT
<213> ORGANISM: Homo sapiens

<400> SEQUENCE: 209

Cys Ala Ser Ser Gln Gly Thr Ser Gly Asp Arg Asp Glu Gln Phe Phe
1               5                   10                  15

<210> SEQ ID NO 210
<211> LENGTH: 13
<212> TYPE: PRT
<213> ORGANISM: Homo sapiens

<400> SEQUENCE: 210

Cys Ala Ser Ser Leu Trp Leu Gly Ser Pro Leu His Phe
1               5                   10

<210> SEQ ID NO 211
<211> LENGTH: 15
<212> TYPE: PRT
<213> ORGANISM: Homo sapiens

<400> SEQUENCE: 211

Cys Ala Ser Ser Arg Gly Ala Ser Arg Thr Gly Glu Leu Phe Phe
1               5                   10                  15

<210> SEQ ID NO 212
<211> LENGTH: 14
<212> TYPE: PRT
<213> ORGANISM: Homo sapiens

<400> SEQUENCE: 212

Cys Ala Ser Ser Leu Ser Pro Thr Ser Tyr Glu Gln Tyr Phe
1               5                   10

<210> SEQ ID NO 213
<211> LENGTH: 16
<212> TYPE: PRT
<213> ORGANISM: Homo sapiens

<400> SEQUENCE: 213

Cys Ser Ala Arg Pro Ser Ser Gly Arg Ala Thr Asp Thr Gln Tyr Phe
1               5                   10                  15

<210> SEQ ID NO 214
<211> LENGTH: 13
<212> TYPE: PRT
<213> ORGANISM: Homo sapiens

<400> SEQUENCE: 214

Cys Ser Ala Pro Leu Ala Phe His Asn Glu Gln Phe Phe
1               5                   10

<210> SEQ ID NO 215
<211> LENGTH: 15
<212> TYPE: PRT
<213> ORGANISM: Homo sapiens

<400> SEQUENCE: 215

Cys Ala Ser Ser Pro Trp Gly Gln Gly Ser Tyr Glu Gln Tyr Phe
1               5                   10                  15

<210> SEQ ID NO 216
<211> LENGTH: 15
<212> TYPE: PRT
<213> ORGANISM: Homo sapiens

<400> SEQUENCE: 216

Cys Ser Ala Arg Gly Ser Gly Arg Val Ser Asp Thr Gln Tyr Phe
1               5                   10                  15

```
<210> SEQ ID NO 217
<211> LENGTH: 16
<212> TYPE: PRT
<213> ORGANISM: Homo sapiens

<400> SEQUENCE: 217

Cys Ala Ser Ser Val Gly Arg Gly Pro Asn Thr Gly Glu Leu Phe Phe
1               5                   10                  15

<210> SEQ ID NO 218
<211> LENGTH: 14
<212> TYPE: PRT
<213> ORGANISM: Homo sapiens

<400> SEQUENCE: 218

Cys Ala Ser Arg Ser Gly Ser Ala Gly Asn Thr Ile Tyr Phe
1               5                   10

<210> SEQ ID NO 219
<211> LENGTH: 13
<212> TYPE: PRT
<213> ORGANISM: Homo sapiens

<400> SEQUENCE: 219

Cys Ala Thr Ala Gly Pro Asp Ser Tyr Glu Gln Tyr Phe
1               5                   10

<210> SEQ ID NO 220
<211> LENGTH: 10
<212> TYPE: PRT
<213> ORGANISM: Homo sapiens

<400> SEQUENCE: 220

Cys Ala Ser Gly Phe Asn Glu Gln Phe Phe
1               5                   10

<210> SEQ ID NO 221
<211> LENGTH: 12
<212> TYPE: PRT
<213> ORGANISM: Homo sapiens

<400> SEQUENCE: 221

Cys Ser Ala Ser Thr Leu Glu Asp Thr Gln Tyr Phe
1               5                   10

<210> SEQ ID NO 222
<211> LENGTH: 13
<212> TYPE: PRT
<213> ORGANISM: Homo sapiens

<400> SEQUENCE: 222

Cys Ala Ser Ser Thr Gln Glu Asn Thr Glu Ala Phe Phe
1               5                   10

<210> SEQ ID NO 223
<211> LENGTH: 15
<212> TYPE: PRT
<213> ORGANISM: Homo sapiens

<400> SEQUENCE: 223

Cys Ala Ser Ser Gln Val Ala Gly Arg Gly Gly Glu Gln Tyr Phe
1               5                   10                  15

<210> SEQ ID NO 224
<211> LENGTH: 13
```

```
<212> TYPE: PRT
<213> ORGANISM: Homo sapiens

<400> SEQUENCE: 224

Cys Ser Ala Thr Arg Pro Pro Tyr Asn Glu Gln Phe Phe
1               5                   10

<210> SEQ ID NO 225
<211> LENGTH: 14
<212> TYPE: PRT
<213> ORGANISM: Homo sapiens

<400> SEQUENCE: 225

Cys Ser Ala Gly Leu Ala Gly Val Leu Glu Thr Gln Tyr Phe
1               5                   10

<210> SEQ ID NO 226
<211> LENGTH: 13
<212> TYPE: PRT
<213> ORGANISM: Homo sapiens

<400> SEQUENCE: 226

Cys Ser Ala Pro Gly Gln Gly Asp Asn Glu Gln Phe Phe
1               5                   10

<210> SEQ ID NO 227
<211> LENGTH: 17
<212> TYPE: PRT
<213> ORGANISM: Homo sapiens

<400> SEQUENCE: 227

Cys Ala Ser Ser Leu Val Gly Gly Gln Gly Phe Gln Glu Thr Gln Tyr
1               5                   10                  15

Phe

<210> SEQ ID NO 228
<211> LENGTH: 15
<212> TYPE: PRT
<213> ORGANISM: Homo sapiens

<400> SEQUENCE: 228

Cys Ser Ala Arg Thr Ser Pro Thr Asn Thr Gly Glu Leu Phe Phe
1               5                   10                  15

<210> SEQ ID NO 229
<211> LENGTH: 13
<212> TYPE: PRT
<213> ORGANISM: Homo sapiens

<400> SEQUENCE: 229

Cys Ala Ser Arg Gly Thr Gly Gly Ile Glu Gln Tyr Phe
1               5                   10

<210> SEQ ID NO 230
<211> LENGTH: 15
<212> TYPE: PRT
<213> ORGANISM: Homo sapiens

<400> SEQUENCE: 230

Cys Ala Trp Ser Val Gly Leu Gly Val Ser Ser Pro Leu His Phe
1               5                   10                  15

<210> SEQ ID NO 231
<211> LENGTH: 15
```

```
<212> TYPE: PRT
<213> ORGANISM: Homo sapiens

<400> SEQUENCE: 231

Cys Ser Ala Arg Asp Ser Glu Ser Ser Tyr Asn Glu Gln Phe Phe
1               5                   10                  15

<210> SEQ ID NO 232
<211> LENGTH: 17
<212> TYPE: PRT
<213> ORGANISM: Homo sapiens

<400> SEQUENCE: 232

Cys Ala Thr Ser Lys Gly Gln Gly Ser Ser Gly Ala Asn Val Leu Thr
1               5                   10                  15

Phe

<210> SEQ ID NO 233
<211> LENGTH: 16
<212> TYPE: PRT
<213> ORGANISM: Homo sapiens

<400> SEQUENCE: 233

Cys Ala Ser Ser Ser Val Pro Gly Leu Ala Gly Gly Glu Gln Phe Phe
1               5                   10                  15

<210> SEQ ID NO 234
<211> LENGTH: 16
<212> TYPE: PRT
<213> ORGANISM: Homo sapiens

<400> SEQUENCE: 234

Cys Ala Ser Ser Leu Gly Ser Ser Arg His Ser Tyr Glu Gln Tyr Phe
1               5                   10                  15

<210> SEQ ID NO 235
<211> LENGTH: 14
<212> TYPE: PRT
<213> ORGANISM: Homo sapiens

<400> SEQUENCE: 235

Cys Ala Ser Ser Leu Ala Pro Ala Gly Asp Thr Gln Tyr Phe
1               5                   10

<210> SEQ ID NO 236
<211> LENGTH: 13
<212> TYPE: PRT
<213> ORGANISM: Homo sapiens

<400> SEQUENCE: 236

Cys Ala Ile Arg Glu Gly Gln Arg Asp Glu Gln Tyr Phe
1               5                   10

<210> SEQ ID NO 237
<211> LENGTH: 17
<212> TYPE: PRT
<213> ORGANISM: Homo sapiens

<400> SEQUENCE: 237

Cys Ala Ser Ser Leu Ala Pro Arg Asp Arg Gly Asp Gln Pro Gln His
1               5                   10                  15

Phe
```

```
<210> SEQ ID NO 238
<211> LENGTH: 13
<212> TYPE: PRT
<213> ORGANISM: Homo sapiens

<400> SEQUENCE: 238

Cys Ala Ser Ser Pro Ser Arg Ser Tyr Gly Tyr Thr Phe
1               5                   10

<210> SEQ ID NO 239
<211> LENGTH: 14
<212> TYPE: PRT
<213> ORGANISM: Homo sapiens

<400> SEQUENCE: 239

Cys Ala Ser Ser Phe Arg Gly Gly Ala Tyr Gly Tyr Thr Phe
1               5                   10

<210> SEQ ID NO 240
<211> LENGTH: 15
<212> TYPE: PRT
<213> ORGANISM: Homo sapiens

<400> SEQUENCE: 240

Cys Ala Ser Ser Leu Ala His Leu Gly Gly Thr Glu Ala Phe Phe
1               5                   10                  15

<210> SEQ ID NO 241
<211> LENGTH: 15
<212> TYPE: PRT
<213> ORGANISM: Homo sapiens

<400> SEQUENCE: 241

Cys Ala Ser Ser Ser Glu Gly Gly Arg Asn Gln Pro Gln His Phe
1               5                   10                  15

<210> SEQ ID NO 242
<211> LENGTH: 14
<212> TYPE: PRT
<213> ORGANISM: Homo sapiens

<400> SEQUENCE: 242

Cys Ser Val Gln Val Gly Thr Gly Gly Tyr Glu Gln Tyr Phe
1               5                   10

<210> SEQ ID NO 243
<211> LENGTH: 14
<212> TYPE: PRT
<213> ORGANISM: Homo sapiens

<400> SEQUENCE: 243

Cys Ala Ser Ser Pro Thr Gly Lys Arg Glu Thr Gln Tyr Phe
1               5                   10

<210> SEQ ID NO 244
<211> LENGTH: 15
<212> TYPE: PRT
<213> ORGANISM: Homo sapiens

<400> SEQUENCE: 244

Cys Ser Ala Thr Gly Gly Arg Pro Gly Ala Asn Val Leu Thr Phe
1               5                   10                  15

<210> SEQ ID NO 245
<211> LENGTH: 14
```

<212> TYPE: PRT
<213> ORGANISM: Homo sapiens

<400> SEQUENCE: 245

Cys Ala Ser Asn Pro Ser Gly Thr Thr Asp Thr Gln Tyr Phe
1               5                   10

<210> SEQ ID NO 246
<211> LENGTH: 14
<212> TYPE: PRT
<213> ORGANISM: Homo sapiens

<400> SEQUENCE: 246

Cys Ala Ser Ser Pro Gly Gly Tyr Arg Ala Glu Ala Phe Phe
1               5                   10

<210> SEQ ID NO 247
<211> LENGTH: 16
<212> TYPE: PRT
<213> ORGANISM: Homo sapiens

<400> SEQUENCE: 247

Cys Ala Ser Ser Gln Val Val Gly Pro Gly Thr Asp Thr Gln Tyr Phe
1               5                   10                  15

<210> SEQ ID NO 248
<211> LENGTH: 14
<212> TYPE: PRT
<213> ORGANISM: Homo sapiens

<400> SEQUENCE: 248

Cys Ala Ser Ser Ser Ala Arg Gly Thr Gly Glu Leu Phe Phe
1               5                   10

<210> SEQ ID NO 249
<211> LENGTH: 15
<212> TYPE: PRT
<213> ORGANISM: Homo sapiens

<400> SEQUENCE: 249

Cys Ala Thr Ser Arg Gly Thr Arg Leu Thr Asp Thr Gln Tyr Phe
1               5                   10                  15

<210> SEQ ID NO 250
<211> LENGTH: 13
<212> TYPE: PRT
<213> ORGANISM: Homo sapiens

<400> SEQUENCE: 250

Cys Ser Ala Leu Arg Val Pro Tyr Asn Glu Gln Phe Phe
1               5                   10

<210> SEQ ID NO 251
<211> LENGTH: 14
<212> TYPE: PRT
<213> ORGANISM: Homo sapiens

<400> SEQUENCE: 251

Cys Ala Thr Gln Asp Gly Gly Gly Asn Gln Pro Gln His Phe
1               5                   10

<210> SEQ ID NO 252
<211> LENGTH: 17
<212> TYPE: PRT
<213> ORGANISM: Homo sapiens

```
<400> SEQUENCE: 252

Cys Ala Ser Ser Gln Glu Gly Gly Thr Gly Thr Tyr Asn Glu Gln Phe
1               5                   10                  15

Phe

<210> SEQ ID NO 253
<211> LENGTH: 15
<212> TYPE: PRT
<213> ORGANISM: Homo sapiens

<400> SEQUENCE: 253

Cys Ser Val Lys Thr Ser Gly Arg Ala Ser Asp Thr Gln Tyr Phe
1               5                   10                  15

<210> SEQ ID NO 254
<211> LENGTH: 18
<212> TYPE: PRT
<213> ORGANISM: Homo sapiens

<400> SEQUENCE: 254

Cys Ala Ser Ser Ile Asp Ser Ser Gly Arg Ala Asn Thr Gly Glu Leu
1               5                   10                  15

Phe Phe

<210> SEQ ID NO 255
<211> LENGTH: 15
<212> TYPE: PRT
<213> ORGANISM: Homo sapiens

<400> SEQUENCE: 255

Cys Ala Ser Ser Leu Glu Phe Asn Tyr Asn Ser Pro Leu His Phe
1               5                   10                  15

<210> SEQ ID NO 256
<211> LENGTH: 15
<212> TYPE: PRT
<213> ORGANISM: Homo sapiens

<400> SEQUENCE: 256

Cys Ala Ser Ser Leu Glu Thr Asn Tyr Asn Ser Pro Leu His Phe
1               5                   10                  15

<210> SEQ ID NO 257
<211> LENGTH: 13
<212> TYPE: PRT
<213> ORGANISM: Homo sapiens

<400> SEQUENCE: 257

Cys Ser Ala Arg Asn Glu Gly Pro Asp Thr Gln Tyr Phe
1               5                   10

<210> SEQ ID NO 258
<211> LENGTH: 14
<212> TYPE: PRT
<213> ORGANISM: Homo sapiens

<400> SEQUENCE: 258

Cys Ser Val Glu Val Gly Leu Ala Val Asn Glu Gln Phe Phe
1               5                   10

<210> SEQ ID NO 259
<211> LENGTH: 11
```

-continued

```
<212> TYPE: PRT
<213> ORGANISM: Homo sapiens

<400> SEQUENCE: 259

Cys Ala Trp Asn Arg Gly Gly Glu Gln Tyr Phe
1               5                   10

<210> SEQ ID NO 260
<211> LENGTH: 15
<212> TYPE: PRT
<213> ORGANISM: Homo sapiens

<400> SEQUENCE: 260

Cys Ala Ser Ser Phe Gly Gly Thr Ala Asn Tyr Gly Tyr Thr Phe
1               5                   10                  15

<210> SEQ ID NO 261
<211> LENGTH: 14
<212> TYPE: PRT
<213> ORGANISM: Homo sapiens

<400> SEQUENCE: 261

Cys Ser Val Pro Gly Thr Gly Arg Tyr Asn Glu Gln Phe Phe
1               5                   10

<210> SEQ ID NO 262
<211> LENGTH: 14
<212> TYPE: PRT
<213> ORGANISM: Homo sapiens

<400> SEQUENCE: 262

Cys Ser Gly Ser Gly Val Ser Gly Ala Asn Val Leu Thr Phe
1               5                   10

<210> SEQ ID NO 263
<211> LENGTH: 13
<212> TYPE: PRT
<213> ORGANISM: Homo sapiens

<400> SEQUENCE: 263

Cys Ser Ala Pro Ala Gly Leu Gly Tyr Glu Gln Tyr Phe
1               5                   10

<210> SEQ ID NO 264
<211> LENGTH: 14
<212> TYPE: PRT
<213> ORGANISM: Homo sapiens

<400> SEQUENCE: 264

Cys Ala Ser Thr His Arg Thr Asn Thr Gly Glu Leu Phe Phe
1               5                   10

<210> SEQ ID NO 265
<211> LENGTH: 13
<212> TYPE: PRT
<213> ORGANISM: Homo sapiens

<400> SEQUENCE: 265

Cys Ser Ala Thr Asp Pro Pro Tyr Asn Glu Gln Phe Phe
1               5                   10

<210> SEQ ID NO 266
<211> LENGTH: 16
<212> TYPE: PRT
<213> ORGANISM: Homo sapiens
```

<400> SEQUENCE: 266

Cys Ala Ser Ser Ser Thr Gly Ala Gly Ala Asn Val Leu Thr Phe
1               5                   10                  15

<210> SEQ ID NO 267
<211> LENGTH: 12
<212> TYPE: PRT
<213> ORGANISM: Homo sapiens

<400> SEQUENCE: 267

Cys Ala Ser Ser Glu Arg Arg Gln Lys Ala Phe Phe
1               5                   10

<210> SEQ ID NO 268
<211> LENGTH: 11
<212> TYPE: PRT
<213> ORGANISM: Homo sapiens

<400> SEQUENCE: 268

Cys Ser Ala Arg Ser Val Val Glu Gln Phe Phe
1               5                   10

<210> SEQ ID NO 269
<211> LENGTH: 14
<212> TYPE: PRT
<213> ORGANISM: Homo sapiens

<400> SEQUENCE: 269

Cys Ala Ser Ser Trp Asp Ser Pro Ser Tyr Glu Gln Tyr Phe
1               5                   10

<210> SEQ ID NO 270
<211> LENGTH: 14
<212> TYPE: PRT
<213> ORGANISM: Homo sapiens

<400> SEQUENCE: 270

Cys Ala Ser Ser Glu Gln Arg Gly Asn Glu Lys Leu Phe Phe
1               5                   10

<210> SEQ ID NO 271
<211> LENGTH: 15
<212> TYPE: PRT
<213> ORGANISM: Homo sapiens

<400> SEQUENCE: 271

Cys Ala Ser Ser Arg Gly Thr Gly Trp Gln Glu Thr Gln Tyr Phe
1               5                   10                  15

<210> SEQ ID NO 272
<211> LENGTH: 16
<212> TYPE: PRT
<213> ORGANISM: Homo sapiens

<400> SEQUENCE: 272

Cys Ala Ser Ser Tyr Arg Lys Gly Ser Ser Tyr Asn Glu Gln Phe Phe
1               5                   10                  15

<210> SEQ ID NO 273
<211> LENGTH: 15
<212> TYPE: PRT
<213> ORGANISM: Homo sapiens

<400> SEQUENCE: 273

Cys Ser Ala Arg Pro Ser Gly Ser Gly Ala Gly Glu Leu Phe Phe
1               5                   10                  15

<210> SEQ ID NO 274
<211> LENGTH: 15
<212> TYPE: PRT
<213> ORGANISM: Homo sapiens

<400> SEQUENCE: 274

Cys Ala Ser Arg Ser Gly Gln Ala Lys Asn Thr Glu Ala Phe Phe
1               5                   10                  15

<210> SEQ ID NO 275
<211> LENGTH: 15
<212> TYPE: PRT
<213> ORGANISM: Homo sapiens

<400> SEQUENCE: 275

Cys Ser Ala Arg Glu Ile Gly Gly Ala Gly Ser Pro Leu His Phe
1               5                   10                  15

<210> SEQ ID NO 276
<211> LENGTH: 13
<212> TYPE: PRT
<213> ORGANISM: Homo sapiens

<400> SEQUENCE: 276

Cys Ala Ser Ser Leu Leu Ser Gly Leu Glu Gln Phe Phe
1               5                   10

<210> SEQ ID NO 277
<211> LENGTH: 15
<212> TYPE: PRT
<213> ORGANISM: Homo sapiens

<400> SEQUENCE: 277

Cys Ala Ser Arg Ser Ser Gly Ser Pro Asn Tyr Gly Tyr Thr Phe
1               5                   10                  15

<210> SEQ ID NO 278
<211> LENGTH: 16
<212> TYPE: PRT
<213> ORGANISM: Homo sapiens

<400> SEQUENCE: 278

Cys Ala Ser Ser Ser Gly Thr Gly Gly Arg Gly Tyr Glu Gln Tyr Phe
1               5                   10                  15

<210> SEQ ID NO 279
<211> LENGTH: 15
<212> TYPE: PRT
<213> ORGANISM: Homo sapiens

<400> SEQUENCE: 279

Cys Ala Ser Arg Leu Gln Gly Trp Asp Thr Asp Thr Gln Tyr Phe
1               5                   10                  15

<210> SEQ ID NO 280
<211> LENGTH: 14
<212> TYPE: PRT
<213> ORGANISM: Homo sapiens

<400> SEQUENCE: 280

Cys Ala Ser Ser Leu Ala Pro Leu Thr Asp Thr Gln Tyr Phe

```
1               5                   10
```

<210> SEQ ID NO 281
<211> LENGTH: 13
<212> TYPE: PRT
<213> ORGANISM: Homo sapiens

<400> SEQUENCE: 281

```
Cys Ser Ala Ser Glu Pro Pro Tyr Asn Glu Gln Phe Phe
1               5                   10
```

<210> SEQ ID NO 282
<211> LENGTH: 14
<212> TYPE: PRT
<213> ORGANISM: Homo sapiens

<400> SEQUENCE: 282

```
Cys Ala Ser Ser Glu Arg Gly Gln Ser Glu Lys Leu Phe Phe
1               5                   10
```

<210> SEQ ID NO 283
<211> LENGTH: 16
<212> TYPE: PRT
<213> ORGANISM: Homo sapiens

<400> SEQUENCE: 283

```
Cys Ala Ser Ser Phe Gly Gly Leu Asp Gly Ala Asn Val Leu Thr Phe
1               5                   10                  15
```

<210> SEQ ID NO 284
<211> LENGTH: 13
<212> TYPE: PRT
<213> ORGANISM: Homo sapiens

<400> SEQUENCE: 284

```
Cys Ser Ala Arg Arg Glu Gly Pro Glu Thr Gln Tyr Phe
1               5                   10
```

<210> SEQ ID NO 285
<211> LENGTH: 15
<212> TYPE: PRT
<213> ORGANISM: Homo sapiens

<400> SEQUENCE: 285

```
Cys Ala Ser Ser Leu Gly Thr Ser His Thr Asp Thr Gln Tyr Phe
1               5                   10              15
```

<210> SEQ ID NO 286
<211> LENGTH: 11
<212> TYPE: PRT
<213> ORGANISM: Homo sapiens

<400> SEQUENCE: 286

```
Cys Ala Ser Ser Lys Gly Thr Gly Gln Tyr Phe
1               5                   10
```

<210> SEQ ID NO 287
<211> LENGTH: 15
<212> TYPE: PRT
<213> ORGANISM: Homo sapiens

<400> SEQUENCE: 287

```
Cys Ala Ser Ser Phe Glu Thr Asn Tyr Asn Ser Pro Leu His Phe
1               5                   10              15
```

<210> SEQ ID NO 288
<211> LENGTH: 15
<212> TYPE: PRT
<213> ORGANISM: Homo sapiens

<400> SEQUENCE: 288

Cys Ser Ala Arg Arg Ser Gly Gly Gly Thr Gly Glu Leu Phe Phe
1               5                   10                  15

<210> SEQ ID NO 289
<211> LENGTH: 15
<212> TYPE: PRT
<213> ORGANISM: Homo sapiens

<400> SEQUENCE: 289

Cys Ser Ala Arg Lys Gly Gly Ser Gly Thr Gly Glu Leu Phe Phe
1               5                   10                  15

<210> SEQ ID NO 290
<211> LENGTH: 14
<212> TYPE: PRT
<213> ORGANISM: Homo sapiens

<400> SEQUENCE: 290

Cys Ala Ser Ser Ile Thr Gly Glu Asp Ser Pro Leu His Phe
1               5                   10

<210> SEQ ID NO 291
<211> LENGTH: 13
<212> TYPE: PRT
<213> ORGANISM: Homo sapiens

<400> SEQUENCE: 291

Cys Ala Ser Ser Leu Thr Met Gly Gln Pro Gln His Phe
1               5                   10

<210> SEQ ID NO 292
<211> LENGTH: 13
<212> TYPE: PRT
<213> ORGANISM: Homo sapiens

<400> SEQUENCE: 292

Cys Ala Ser Ser Tyr Thr Gly Ala Asp Thr Gln Tyr Phe
1               5                   10

<210> SEQ ID NO 293
<211> LENGTH: 15
<212> TYPE: PRT
<213> ORGANISM: Homo sapiens

<400> SEQUENCE: 293

Cys Ala Ser Ser Gly Pro Arg Ala Thr Asn Glu Lys Leu Phe Phe
1               5                   10                  15

<210> SEQ ID NO 294
<211> LENGTH: 13
<212> TYPE: PRT
<213> ORGANISM: Homo sapiens

<400> SEQUENCE: 294

Cys Ala Ser Arg Asp Arg Ala Pro Gln Pro Gln His Phe
1               5                   10

<210> SEQ ID NO 295

```
<211> LENGTH: 11
<212> TYPE: PRT
<213> ORGANISM: Homo sapiens

<400> SEQUENCE: 295

Cys Ala Ala Arg Gly Gly Tyr Gly Tyr Thr Phe
1               5                   10

<210> SEQ ID NO 296
<211> LENGTH: 13
<212> TYPE: PRT
<213> ORGANISM: Homo sapiens

<400> SEQUENCE: 296

Cys Ala Ser Ser Leu Thr Gly Glu Gly Thr Gln Tyr Phe
1               5                   10

<210> SEQ ID NO 297
<211> LENGTH: 14
<212> TYPE: PRT
<213> ORGANISM: Homo sapiens

<400> SEQUENCE: 297

Cys Ser Ala Arg Asp Ser Ser Arg Thr Asp Thr Gln Tyr Phe
1               5                   10

<210> SEQ ID NO 298
<211> LENGTH: 13
<212> TYPE: PRT
<213> ORGANISM: Homo sapiens

<400> SEQUENCE: 298

Cys Ser Ala Leu Leu Pro Pro Tyr Asn Glu Gln Phe Phe
1               5                   10

<210> SEQ ID NO 299
<211> LENGTH: 15
<212> TYPE: PRT
<213> ORGANISM: Homo sapiens

<400> SEQUENCE: 299

Cys Ala Ser Ser Thr Asp Gly Gly Arg Asn Gln Pro Gln His Phe
1               5                   10                  15

<210> SEQ ID NO 300
<211> LENGTH: 15
<212> TYPE: PRT
<213> ORGANISM: Homo sapiens

<400> SEQUENCE: 300

Cys Ala Ser Ser Phe Arg Arg Arg Ser Tyr Asn Glu Gln Phe Phe
1               5                   10                  15

<210> SEQ ID NO 301
<211> LENGTH: 13
<212> TYPE: PRT
<213> ORGANISM: Homo sapiens

<400> SEQUENCE: 301

Cys Ser Ala Leu Arg Glu Asn Gln Glu Thr Gln Tyr Phe
1               5                   10

<210> SEQ ID NO 302
<211> LENGTH: 14
<212> TYPE: PRT
```

```
<213> ORGANISM: Homo sapiens

<400> SEQUENCE: 302

Cys Ala Ser Ser Lys Glu Lys Leu Tyr Gln Pro Gln His Phe
1               5                   10

<210> SEQ ID NO 303
<211> LENGTH: 15
<212> TYPE: PRT
<213> ORGANISM: Homo sapiens

<400> SEQUENCE: 303

Cys Ser Ala Arg Gly Gln Pro Ala Asn Thr Gly Glu Leu Phe Phe
1               5                   10                  15

<210> SEQ ID NO 304
<211> LENGTH: 16
<212> TYPE: PRT
<213> ORGANISM: Homo sapiens

<400> SEQUENCE: 304

Cys Ala Ser Ser Ser Leu Trp Thr Gly Ser Thr Asp Thr Gln Tyr Phe
1               5                   10                  15

<210> SEQ ID NO 305
<211> LENGTH: 15
<212> TYPE: PRT
<213> ORGANISM: Homo sapiens

<400> SEQUENCE: 305

Cys Ala Ser Thr Pro Ala Gly Arg Asp Thr Gly Glu Leu Phe Phe
1               5                   10                  15

<210> SEQ ID NO 306
<211> LENGTH: 12
<212> TYPE: PRT
<213> ORGANISM: Homo sapiens

<400> SEQUENCE: 306

Cys Ser Val Gly Pro Gly Asp Thr Glu Ala Phe Phe
1               5                   10

<210> SEQ ID NO 307
<211> LENGTH: 17
<212> TYPE: PRT
<213> ORGANISM: Homo sapiens

<400> SEQUENCE: 307

Cys Ala Ser Ser Gln Pro Pro Leu Ala Gly Thr Tyr Asn Glu Gln Phe
1               5                   10                  15

Phe

<210> SEQ ID NO 308
<211> LENGTH: 14
<212> TYPE: PRT
<213> ORGANISM: Homo sapiens

<400> SEQUENCE: 308

Cys Ser Ala Asn Arg Gln Gly Ala Gly Thr Glu Ala Phe Phe
1               5                   10

<210> SEQ ID NO 309
<211> LENGTH: 14
<212> TYPE: PRT
```

<213> ORGANISM: Homo sapiens

<400> SEQUENCE: 309

Cys Ala Ser Ser Arg Ser Gly Phe Ser Tyr Glu Gln Tyr Phe
1               5                   10

<210> SEQ ID NO 310
<211> LENGTH: 13
<212> TYPE: PRT
<213> ORGANISM: Homo sapiens

<400> SEQUENCE: 310

Cys Ala Ser Ser Ser Gly Leu Arg Gln Pro Gln His Phe
1               5                   10

<210> SEQ ID NO 311
<211> LENGTH: 14
<212> TYPE: PRT
<213> ORGANISM: Homo sapiens

<400> SEQUENCE: 311

Cys Ala Ser Ser Leu Ala Pro Gly Ala Glu Gly Tyr Thr Phe
1               5                   10

<210> SEQ ID NO 312
<211> LENGTH: 13
<212> TYPE: PRT
<213> ORGANISM: Homo sapiens

<400> SEQUENCE: 312

Cys Ala Ser Thr Glu Asn Ser Asn Gln Pro Gln His Phe
1               5                   10

<210> SEQ ID NO 313
<211> LENGTH: 15
<212> TYPE: PRT
<213> ORGANISM: Homo sapiens

<400> SEQUENCE: 313

Cys Ser Ala Arg Ile Gly Gly Ser Gly Thr Gly Glu Leu Phe Phe
1               5                   10                  15

<210> SEQ ID NO 314
<211> LENGTH: 14
<212> TYPE: PRT
<213> ORGANISM: Homo sapiens

<400> SEQUENCE: 314

Cys Ala Ser Ser Ala Val Ser Gly Thr Asp Thr Gln Tyr Phe
1               5                   10

<210> SEQ ID NO 315
<211> LENGTH: 13
<212> TYPE: PRT
<213> ORGANISM: Homo sapiens

<400> SEQUENCE: 315

Cys Ser Ala Pro Val Ala Pro Tyr Asn Glu Gln Phe Phe
1               5                   10

<210> SEQ ID NO 316
<211> LENGTH: 15
<212> TYPE: PRT
<213> ORGANISM: Homo sapiens

<400> SEQUENCE: 316

Cys Ser Ala Arg Gly Ala Gly Gly Thr Gly Glu Leu Phe Phe
1               5                   10                  15

<210> SEQ ID NO 317
<211> LENGTH: 12
<212> TYPE: PRT
<213> ORGANISM: Homo sapiens

<400> SEQUENCE: 317

Cys Ala Ser Ser Lys Gly Phe Asn Glu Gln Phe Phe
1               5                   10

<210> SEQ ID NO 318
<211> LENGTH: 14
<212> TYPE: PRT
<213> ORGANISM: Homo sapiens

<400> SEQUENCE: 318

Cys Ala Ser Arg Ser Pro Gly Ser Lys Glu Thr Gln Tyr Phe
1               5                   10

<210> SEQ ID NO 319
<211> LENGTH: 13
<212> TYPE: PRT
<213> ORGANISM: Homo sapiens

<400> SEQUENCE: 319

Cys Ala Ile Arg Leu Gly Gln Thr Tyr Glu Gln Tyr Phe
1               5                   10

<210> SEQ ID NO 320
<211> LENGTH: 15
<212> TYPE: PRT
<213> ORGANISM: Homo sapiens

<400> SEQUENCE: 320

Cys Ser Ala Arg Gly Ser Gly Arg Ala Ala Asp Thr Gln Tyr Phe
1               5                   10                  15

<210> SEQ ID NO 321
<211> LENGTH: 15
<212> TYPE: PRT
<213> ORGANISM: Homo sapiens

<400> SEQUENCE: 321

Cys Ser Val Ala Arg Thr Gly Gly Gly Asn Glu Lys Leu Phe Phe
1               5                   10                  15

<210> SEQ ID NO 322
<211> LENGTH: 14
<212> TYPE: PRT
<213> ORGANISM: Homo sapiens

<400> SEQUENCE: 322

Cys Ser Ala Ile Pro Gly Gly Gly Ser Asp Thr Gln Tyr Phe
1               5                   10

<210> SEQ ID NO 323
<211> LENGTH: 16
<212> TYPE: PRT
<213> ORGANISM: Homo sapiens

<400> SEQUENCE: 323

```
Cys Ala Ser Arg Leu Gly Gly Thr Leu Ala Lys Asn Ile Gln Tyr Phe
1               5                   10                  15
```

<210> SEQ ID NO 324
<211> LENGTH: 15
<212> TYPE: PRT
<213> ORGANISM: Homo sapiens

<400> SEQUENCE: 324

```
Cys Ser Ala Arg Thr Ser Gly Ser Gly Thr Gly Glu Leu Phe Phe
1               5                   10                  15
```

<210> SEQ ID NO 325
<211> LENGTH: 15
<212> TYPE: PRT
<213> ORGANISM: Homo sapiens

<400> SEQUENCE: 325

```
Cys Ser Ala Leu Leu Ala Ala Ser Ser Tyr Asn Glu Gln Phe Phe
1               5                   10                  15
```

<210> SEQ ID NO 326
<211> LENGTH: 12
<212> TYPE: PRT
<213> ORGANISM: Homo sapiens

<400> SEQUENCE: 326

```
Cys Ala Ser Ser Gln Pro Asn Tyr Glu Gln Tyr Phe
1               5                   10
```

<210> SEQ ID NO 327
<211> LENGTH: 17
<212> TYPE: PRT
<213> ORGANISM: Homo sapiens

<400> SEQUENCE: 327

```
Cys Ala Ser Ser Val Gly Thr Ser Gly Ser Val Arg Asp Thr Gln Tyr
1               5                   10                  15

Phe
```

<210> SEQ ID NO 328
<211> LENGTH: 13
<212> TYPE: PRT
<213> ORGANISM: Homo sapiens

<400> SEQUENCE: 328

```
Cys Ser Ala Lys Trp Glu Gly Pro Asp Thr Gln Tyr Phe
1               5                   10
```

<210> SEQ ID NO 329
<211> LENGTH: 13
<212> TYPE: PRT
<213> ORGANISM: Homo sapiens

<400> SEQUENCE: 329

```
Cys Ala Ser Ser Leu Asp Ser Val Gly Glu Leu Phe Phe
1               5                   10
```

<210> SEQ ID NO 330
<211> LENGTH: 16
<212> TYPE: PRT
<213> ORGANISM: Homo sapiens

<400> SEQUENCE: 330

Cys Ala Ser Ser Arg Ser Gly Gly Ala Thr Arg Glu Thr Gln Tyr Phe
1               5                   10                  15

<210> SEQ ID NO 331
<211> LENGTH: 15
<212> TYPE: PRT
<213> ORGANISM: Homo sapiens

<400> SEQUENCE: 331

Cys Ala Ser Ser Leu Gly Thr Leu Pro Tyr Asn Glu Gln Phe Phe
1               5                   10                  15

<210> SEQ ID NO 332
<211> LENGTH: 15
<212> TYPE: PRT
<213> ORGANISM: Homo sapiens

<400> SEQUENCE: 332

Cys Ala Ser Ser Thr Ala Gly Leu Gly Ala Asn Val Leu Thr Phe
1               5                   10                  15

<210> SEQ ID NO 333
<211> LENGTH: 14
<212> TYPE: PRT
<213> ORGANISM: Homo sapiens

<400> SEQUENCE: 333

Cys Ala Ile Lys Gly Thr Ser Ser Gly Asn Thr Ile Tyr Phe
1               5                   10

<210> SEQ ID NO 334
<211> LENGTH: 13
<212> TYPE: PRT
<213> ORGANISM: Homo sapiens

<400> SEQUENCE: 334

Cys Ser Ala Pro Ser Pro Pro Ser Tyr Glu Gln Tyr Phe
1               5                   10

<210> SEQ ID NO 335
<211> LENGTH: 14
<212> TYPE: PRT
<213> ORGANISM: Homo sapiens

<400> SEQUENCE: 335

Cys Ala Ser Ser Leu Ser Gly Val Gly Thr Glu Ala Phe Phe
1               5                   10

<210> SEQ ID NO 336
<211> LENGTH: 15
<212> TYPE: PRT
<213> ORGANISM: Homo sapiens

<400> SEQUENCE: 336

Cys Ala Ser Ser Phe Glu Leu Asn Tyr Asn Ser Pro Leu His Phe
1               5                   10                  15

<210> SEQ ID NO 337
<211> LENGTH: 13
<212> TYPE: PRT
<213> ORGANISM: Homo sapiens

<400> SEQUENCE: 337

Cys Ser Ala Pro Pro Pro His Asn Glu Gln Phe Phe
1               5                   10

```
<210> SEQ ID NO 338
<211> LENGTH: 13
<212> TYPE: PRT
<213> ORGANISM: Homo sapiens

<400> SEQUENCE: 338

Cys Ala Ser Ser Leu Ser Arg Ala Tyr Gly Tyr Thr Phe
1               5                   10

<210> SEQ ID NO 339
<211> LENGTH: 16
<212> TYPE: PRT
<213> ORGANISM: Homo sapiens

<400> SEQUENCE: 339

Cys Ala Ser Ser Leu Arg Thr Ala Gly Gly Tyr Asn Glu Gln Phe Phe
1               5                   10                  15

<210> SEQ ID NO 340
<211> LENGTH: 14
<212> TYPE: PRT
<213> ORGANISM: Homo sapiens

<400> SEQUENCE: 340

Cys Ala Ser Ile Pro Gly Gln Gly Asn Thr Glu Ala Phe Phe
1               5                   10

<210> SEQ ID NO 341
<211> LENGTH: 12
<212> TYPE: PRT
<213> ORGANISM: Homo sapiens

<400> SEQUENCE: 341

Cys Ala Ser Ser Gln Gly Tyr Glu Thr Gln Tyr Phe
1               5                   10

<210> SEQ ID NO 342
<211> LENGTH: 15
<212> TYPE: PRT
<213> ORGANISM: Homo sapiens

<400> SEQUENCE: 342

Cys Ala Trp Ser Arg Gly Gly Gly Arg Asn Glu Lys Leu Phe Phe
1               5                   10                  15

<210> SEQ ID NO 343
<211> LENGTH: 14
<212> TYPE: PRT
<213> ORGANISM: Homo sapiens

<400> SEQUENCE: 343

Cys Ala Ser Ser Gln Val Trp Gly Asn Gln Pro Gln His Phe
1               5                   10

<210> SEQ ID NO 344
<211> LENGTH: 13
<212> TYPE: PRT
<213> ORGANISM: Homo sapiens

<400> SEQUENCE: 344

Cys Ser Ala Asp Glu Gln Gly Gly Tyr Gly Tyr Thr Phe
1               5                   10
```

```
<210> SEQ ID NO 345
<211> LENGTH: 15
<212> TYPE: PRT
<213> ORGANISM: Homo sapiens

<400> SEQUENCE: 345

Cys Ala Ser Ser Leu Gly Gly Ala Arg Lys Asn Ile Gln Tyr Phe
1               5                   10                  15

<210> SEQ ID NO 346
<211> LENGTH: 13
<212> TYPE: PRT
<213> ORGANISM: Homo sapiens

<400> SEQUENCE: 346

Cys Ser Ala Ser Pro Pro Pro Arg Asn Glu Gln Phe Phe
1               5                   10

<210> SEQ ID NO 347
<211> LENGTH: 15
<212> TYPE: PRT
<213> ORGANISM: Homo sapiens

<400> SEQUENCE: 347

Cys Ala Ser Ser Leu Glu Ala Asn Tyr Asn Ser Pro Leu His Phe
1               5                   10                  15

<210> SEQ ID NO 348
<211> LENGTH: 17
<212> TYPE: PRT
<213> ORGANISM: Homo sapiens

<400> SEQUENCE: 348

Cys Ala Ser Ser Leu Gly Ser Leu Trp Gly Ser Thr Asp Thr Gln Tyr
1               5                   10                  15

Phe

<210> SEQ ID NO 349
<211> LENGTH: 18
<212> TYPE: PRT
<213> ORGANISM: Homo sapiens

<400> SEQUENCE: 349

Cys Ala Ser Ser Arg Arg Leu Ala Gly Gly Pro Ser Thr Asp Thr Gln
1               5                   10                  15

Tyr Phe

<210> SEQ ID NO 350
<211> LENGTH: 15
<212> TYPE: PRT
<213> ORGANISM: Homo sapiens

<400> SEQUENCE: 350

Cys Ser Ala Arg Arg Ala Gly Gly Gly Thr Gly Glu Leu Phe Phe
1               5                   10                  15

<210> SEQ ID NO 351
<211> LENGTH: 12
<212> TYPE: PRT
<213> ORGANISM: Homo sapiens

<400> SEQUENCE: 351

Cys Ala Ser Ser His Glu Lys Glu Thr Gln Tyr Phe
1               5                   10
```

```
<210> SEQ ID NO 352
<211> LENGTH: 14
<212> TYPE: PRT
<213> ORGANISM: Homo sapiens

<400> SEQUENCE: 352

Cys Ser Ala Arg Asp Asn Gly Arg Ser Asn Glu Gln Phe Phe
1               5                   10

<210> SEQ ID NO 353
<211> LENGTH: 13
<212> TYPE: PRT
<213> ORGANISM: Homo sapiens

<400> SEQUENCE: 353

Cys Ala Ser Ser Gly Arg Glu Leu Gly Glu Gln Tyr Phe
1               5                   10

<210> SEQ ID NO 354
<211> LENGTH: 13
<212> TYPE: PRT
<213> ORGANISM: Homo sapiens

<400> SEQUENCE: 354

Cys Ser Ala Pro Arg Ala Pro Ser Tyr Glu Gln Tyr Phe
1               5                   10

<210> SEQ ID NO 355
<211> LENGTH: 14
<212> TYPE: PRT
<213> ORGANISM: Homo sapiens

<400> SEQUENCE: 355

Cys Ala Ser Ser Ser Arg Glu Thr Asn Glu Lys Leu Phe Phe
1               5                   10

<210> SEQ ID NO 356
<211> LENGTH: 15
<212> TYPE: PRT
<213> ORGANISM: Homo sapiens

<400> SEQUENCE: 356

Cys Ala Ser Ser Arg Gly Gln Thr Asn Asn Ser Pro Leu His Phe
1               5                   10                  15

<210> SEQ ID NO 357
<211> LENGTH: 14
<212> TYPE: PRT
<213> ORGANISM: Homo sapiens

<400> SEQUENCE: 357

Cys Ala Ser Thr Arg Thr Gly Asn Val Tyr Gly Tyr Thr Phe
1               5                   10

<210> SEQ ID NO 358
<211> LENGTH: 15
<212> TYPE: PRT
<213> ORGANISM: Homo sapiens

<400> SEQUENCE: 358

Cys Ala Ser Ser Pro Leu Ala Ser Leu Ser Tyr Glu Gln Tyr Phe
1               5                   10                  15
```

```
<210> SEQ ID NO 359
<211> LENGTH: 14
<212> TYPE: PRT
<213> ORGANISM: Homo sapiens

<400> SEQUENCE: 359

Cys Ala Ser Glu Gln Gly Arg Gly Asn Glu Lys Leu Phe Phe
1               5                   10

<210> SEQ ID NO 360
<211> LENGTH: 16
<212> TYPE: PRT
<213> ORGANISM: Homo sapiens

<400> SEQUENCE: 360

Cys Ala Ser Ser Leu Ala Ser Gly Ala Arg Thr Tyr Glu Gln Tyr Phe
1               5                   10                  15

<210> SEQ ID NO 361
<211> LENGTH: 14
<212> TYPE: PRT
<213> ORGANISM: Homo sapiens

<400> SEQUENCE: 361

Cys Ala Ser Ser Leu Val Ile Thr Gly Asn Thr Ile Tyr Phe
1               5                   10

<210> SEQ ID NO 362
<211> LENGTH: 12
<212> TYPE: PRT
<213> ORGANISM: Homo sapiens

<400> SEQUENCE: 362

Cys Ser Ala Ser Ala Val Glu Glu Thr Gln Tyr Phe
1               5                   10

<210> SEQ ID NO 363
<211> LENGTH: 14
<212> TYPE: PRT
<213> ORGANISM: Homo sapiens

<400> SEQUENCE: 363

Cys Ala Ser Ser Ser Asn Arg Gly Asn Glu Lys Leu Phe Phe
1               5                   10

<210> SEQ ID NO 364
<211> LENGTH: 18
<212> TYPE: PRT
<213> ORGANISM: Homo sapiens

<400> SEQUENCE: 364

Cys Ala Ser Ser Tyr Ser Pro Ser Gly Val Leu Asn Thr Gly Glu Leu
1               5                   10                  15

Phe Phe

<210> SEQ ID NO 365
<211> LENGTH: 15
<212> TYPE: PRT
<213> ORGANISM: Homo sapiens

<400> SEQUENCE: 365

Cys Ser Ala Arg Asp Pro Leu Pro Ser Ser Tyr Glu Gln Tyr Phe
1               5                   10                  15
```

```
<210> SEQ ID NO 366
<211> LENGTH: 15
<212> TYPE: PRT
<213> ORGANISM: Homo sapiens

<400> SEQUENCE: 366

Cys Ala Ile Ser Glu Ala Gly Pro Asn Thr Asp Thr Gln Tyr Phe
1               5                   10                  15

<210> SEQ ID NO 367
<211> LENGTH: 14
<212> TYPE: PRT
<213> ORGANISM: Homo sapiens

<400> SEQUENCE: 367

Cys Ala Ser Ser Leu Gly Gly Ala Gly Tyr Glu Gln Tyr Val
1               5                   10

<210> SEQ ID NO 368
<211> LENGTH: 15
<212> TYPE: PRT
<213> ORGANISM: Homo sapiens

<400> SEQUENCE: 368

Cys Ser Ala Arg Thr Gly Gly Ala Gly Thr Gly Glu Leu Phe Phe
1               5                   10                  15

<210> SEQ ID NO 369
<211> LENGTH: 15
<212> TYPE: PRT
<213> ORGANISM: Homo sapiens

<400> SEQUENCE: 369

Cys Ala Trp Ser His Gly Arg Asn Ser Tyr Asn Glu Gln Phe Phe
1               5                   10                  15

<210> SEQ ID NO 370
<211> LENGTH: 13
<212> TYPE: PRT
<213> ORGANISM: Homo sapiens

<400> SEQUENCE: 370

Cys Ala Ser Ser Tyr Gly Gln Gly Asp Glu Gln Tyr Val
1               5                   10

<210> SEQ ID NO 371
<211> LENGTH: 13
<212> TYPE: PRT
<213> ORGANISM: Homo sapiens

<400> SEQUENCE: 371

Cys Ala Trp Ser Arg Arg Gly Asn Tyr Glu Gln Tyr Phe
1               5                   10

<210> SEQ ID NO 372
<211> LENGTH: 14
<212> TYPE: PRT
<213> ORGANISM: Homo sapiens

<400> SEQUENCE: 372

Cys Ala Ser Ile Gln Gly Arg Gly Asn Glu Lys Leu Phe Phe
1               5                   10

<210> SEQ ID NO 373
<211> LENGTH: 13
```

```
<212> TYPE: PRT
<213> ORGANISM: Homo sapiens

<400> SEQUENCE: 373

Cys Ser Gly Gly Leu Ala Gly Val Glu Thr Gln Tyr Phe
1               5                   10

<210> SEQ ID NO 374
<211> LENGTH: 15
<212> TYPE: PRT
<213> ORGANISM: Homo sapiens

<400> SEQUENCE: 374

Cys Ala Ser Ser Glu Ala Gly Arg Gly Pro Tyr Gly Tyr Thr Phe
1               5                   10                  15

<210> SEQ ID NO 375
<211> LENGTH: 15
<212> TYPE: PRT
<213> ORGANISM: Homo sapiens

<400> SEQUENCE: 375

Cys Ser Ala Arg Lys Ala Gly Gly Gly Thr Gly Glu Leu Phe Phe
1               5                   10                  15

<210> SEQ ID NO 376
<211> LENGTH: 15
<212> TYPE: PRT
<213> ORGANISM: Homo sapiens

<400> SEQUENCE: 376

Cys Ser Ala Arg Pro Ala Gly Ser Gly Thr Gly Glu Leu Phe Phe
1               5                   10                  15

<210> SEQ ID NO 377
<211> LENGTH: 15
<212> TYPE: PRT
<213> ORGANISM: Homo sapiens

<400> SEQUENCE: 377

Cys Ser Ala Arg Thr Ala Gly Gly Gly Thr Gly Glu Leu Phe Phe
1               5                   10                  15

<210> SEQ ID NO 378
<211> LENGTH: 14
<212> TYPE: PRT
<213> ORGANISM: Homo sapiens

<400> SEQUENCE: 378

Cys Ala Ser Ser Leu Gly Trp Leu Asp Asn Glu Gln Phe Phe
1               5                   10

<210> SEQ ID NO 379
<211> LENGTH: 14
<212> TYPE: PRT
<213> ORGANISM: Homo sapiens

<400> SEQUENCE: 379

Cys Ala Arg Lys Asp Arg Ala Gly Ala Asn Val Leu Thr Phe
1               5                   10

<210> SEQ ID NO 380
<211> LENGTH: 14
<212> TYPE: PRT
<213> ORGANISM: Homo sapiens
```

<400> SEQUENCE: 380

Cys Ser Ala Glu Arg Arg Ala Ser Gly Asn Thr Ile Tyr Phe
1               5                   10

<210> SEQ ID NO 381
<211> LENGTH: 15
<212> TYPE: PRT
<213> ORGANISM: Homo sapiens

<400> SEQUENCE: 381

Cys Ala Ser Ser Arg Gly Leu Ala Gly Asn Asn Glu Gln Phe Phe
1               5                   10                  15

<210> SEQ ID NO 382
<211> LENGTH: 15
<212> TYPE: PRT
<213> ORGANISM: Homo sapiens

<400> SEQUENCE: 382

Cys Ala Ser Ser Glu Arg Pro Thr Ala Asn Tyr Gly Tyr Thr Phe
1               5                   10                  15

<210> SEQ ID NO 383
<211> LENGTH: 13
<212> TYPE: PRT
<213> ORGANISM: Homo sapiens

<400> SEQUENCE: 383

Cys Ala Ile Arg Gln Gly Gln Glu Asn Ile Gln Tyr Phe
1               5                   10

<210> SEQ ID NO 384
<211> LENGTH: 14
<212> TYPE: PRT
<213> ORGANISM: Homo sapiens

<400> SEQUENCE: 384

Cys Ala Ser Ser Leu Gly Glu Gly Arg Gly Arg Ala Phe Phe
1               5                   10

<210> SEQ ID NO 385
<211> LENGTH: 15
<212> TYPE: PRT
<213> ORGANISM: Homo sapiens

<400> SEQUENCE: 385

Cys Ser Ala Ser Gly Gly Gly Arg Glu Ser Tyr Gly Tyr Thr Phe
1               5                   10                  15

<210> SEQ ID NO 386
<211> LENGTH: 16
<212> TYPE: PRT
<213> ORGANISM: Homo sapiens

<400> SEQUENCE: 386

Cys Ala Ser Ser Leu Ala Arg Gly Ser Gly Thr Gly Glu Leu Phe Phe
1               5                   10                  15

<210> SEQ ID NO 387
<211> LENGTH: 11
<212> TYPE: PRT
<213> ORGANISM: Homo sapiens

<400> SEQUENCE: 387

Cys Ala Gly Arg Arg Gly Gly Glu Leu Phe Phe
1               5                   10

<210> SEQ ID NO 388
<211> LENGTH: 15
<212> TYPE: PRT
<213> ORGANISM: Homo sapiens

<400> SEQUENCE: 388

Cys Ser Ala Ala Arg Gly Gly Asp Gly Asn Gln Pro Gln His Phe
1               5                   10                  15

<210> SEQ ID NO 389
<211> LENGTH: 15
<212> TYPE: PRT
<213> ORGANISM: Homo sapiens

<400> SEQUENCE: 389

Cys Ala Ser Ser Pro Thr Gly Pro Gly Ala Asp Thr Gln Tyr Phe
1               5                   10                  15

<210> SEQ ID NO 390
<211> LENGTH: 12
<212> TYPE: PRT
<213> ORGANISM: Homo sapiens

<400> SEQUENCE: 390

Cys Ala Ser Ser Glu Ala Val Asp Thr Ile Tyr Phe
1               5                   10

<210> SEQ ID NO 391
<211> LENGTH: 14
<212> TYPE: PRT
<213> ORGANISM: Homo sapiens

<400> SEQUENCE: 391

Cys Ala Ser Ser Glu Gly Leu Val Asn Glu Lys Leu Phe Phe
1               5                   10

<210> SEQ ID NO 392
<211> LENGTH: 15
<212> TYPE: PRT
<213> ORGANISM: Homo sapiens

<400> SEQUENCE: 392

Cys Ala Ser Ser Gln Gln Gly Gly Ala Tyr Asn Glu Gln Phe Phe
1               5                   10                  15

<210> SEQ ID NO 393
<211> LENGTH: 16
<212> TYPE: PRT
<213> ORGANISM: Homo sapiens

<400> SEQUENCE: 393

Cys Ala Thr Gly Leu Ala Gly Gly Leu Ser Tyr Asn Glu Gln Phe Phe
1               5                   10                  15

<210> SEQ ID NO 394
<211> LENGTH: 16
<212> TYPE: PRT
<213> ORGANISM: Homo sapiens

<400> SEQUENCE: 394

Cys Ala Ser Ser Val Thr Ser Gly Ser Asn Thr Gly Glu Leu Phe Phe

```
                1               5                  10                 15
```

<210> SEQ ID NO 395
<211> LENGTH: 14
<212> TYPE: PRT
<213> ORGANISM: Homo sapiens

<400> SEQUENCE: 395

Cys Ala Ser Ser Thr Leu Pro Gly Thr Ala Glu Ala Phe Phe
1               5                   10

<210> SEQ ID NO 396
<211> LENGTH: 14
<212> TYPE: PRT
<213> ORGANISM: Homo sapiens

<400> SEQUENCE: 396

Cys Ala Ser Ser Arg Gly Trp Ser Thr Asp Thr Gln Tyr Phe
1               5                   10

<210> SEQ ID NO 397
<211> LENGTH: 13
<212> TYPE: PRT
<213> ORGANISM: Homo sapiens

<400> SEQUENCE: 397

Cys Ala Ser Ser Pro Gly Arg His Tyr Glu Gln Tyr Phe
1               5                   10

<210> SEQ ID NO 398
<211> LENGTH: 18
<212> TYPE: PRT
<213> ORGANISM: Homo sapiens

<400> SEQUENCE: 398

Cys Ala Ser Ser Pro Gly Leu Ala Gly Ala Thr Ser Thr Asp Thr Gln
1               5                   10                  15

Tyr Phe

<210> SEQ ID NO 399
<211> LENGTH: 14
<212> TYPE: PRT
<213> ORGANISM: Homo sapiens

<400> SEQUENCE: 399

Cys Ala Ser Ser Ser Arg Ala Gly Val Gly Glu Gln Tyr Phe
1               5                   10

<210> SEQ ID NO 400
<211> LENGTH: 16
<212> TYPE: PRT
<213> ORGANISM: Homo sapiens

<400> SEQUENCE: 400

Cys Ala Ser Ser Leu Val Thr Gly Ser Gly Ser Glu Lys Leu Phe Phe
1               5                   10                  15

<210> SEQ ID NO 401
<211> LENGTH: 16
<212> TYPE: PRT
<213> ORGANISM: Homo sapiens

<400> SEQUENCE: 401

Cys Ala Ser Ser Gln Val Leu Ala Gly Gly His Asn Glu Gln Phe Phe

```
1               5                   10                  15

<210> SEQ ID NO 402
<211> LENGTH: 16
<212> TYPE: PRT
<213> ORGANISM: Homo sapiens

<400> SEQUENCE: 402

Cys Ala Ser Ser Leu Gly Gly Asp Ala Gly Asn Tyr Gly Tyr Thr Phe
1               5                   10                  15

<210> SEQ ID NO 403
<211> LENGTH: 12
<212> TYPE: PRT
<213> ORGANISM: Homo sapiens

<400> SEQUENCE: 403

Cys Ala Ser Lys Thr Thr Asn Glu Lys Leu Phe Phe
1               5                   10

<210> SEQ ID NO 404
<211> LENGTH: 12
<212> TYPE: PRT
<213> ORGANISM: Homo sapiens

<400> SEQUENCE: 404

Cys Ser Ala Ser Ala Asp Glu Glu Thr Gln Tyr Phe
1               5                   10

<210> SEQ ID NO 405
<211> LENGTH: 13
<212> TYPE: PRT
<213> ORGANISM: Homo sapiens

<400> SEQUENCE: 405

Cys Ser Ala Asp Arg Glu Gly Ser Glu Thr Gln Tyr Phe
1               5                   10

<210> SEQ ID NO 406
<211> LENGTH: 13
<212> TYPE: PRT
<213> ORGANISM: Homo sapiens

<400> SEQUENCE: 406

Cys Ala Ser Ser Pro Lys Trp Ala Gly Glu Leu Phe Phe
1               5                   10

<210> SEQ ID NO 407
<211> LENGTH: 15
<212> TYPE: PRT
<213> ORGANISM: Homo sapiens

<400> SEQUENCE: 407

Cys Ala Ile Lys Gly Gln Ser Ser Tyr Asn Ser Pro Leu His Phe
1               5                   10                  15

<210> SEQ ID NO 408
<211> LENGTH: 14
<212> TYPE: PRT
<213> ORGANISM: Homo sapiens

<400> SEQUENCE: 408

Cys Ala Ser Ser Val Gly Gly Leu Ala Asn Glu Gln Phe Phe
1               5                   10
```

<210> SEQ ID NO 409
<211> LENGTH: 15
<212> TYPE: PRT
<213> ORGANISM: Homo sapiens

<400> SEQUENCE: 409

Cys Ala Ser Ser Leu Gly Gly Arg Glu Trp Glu Lys Leu Phe Phe
1               5                   10                  15

<210> SEQ ID NO 410
<211> LENGTH: 15
<212> TYPE: PRT
<213> ORGANISM: Homo sapiens

<400> SEQUENCE: 410

Cys Ala Ser Ser Arg Gln Gly Thr Gln Asn Thr Glu Ala Phe Phe
1               5                   10                  15

<210> SEQ ID NO 411
<211> LENGTH: 12
<212> TYPE: PRT
<213> ORGANISM: Homo sapiens

<400> SEQUENCE: 411

Cys Ala Ser Thr Ser Asp Leu Gly Glu Gln Tyr Phe
1               5                   10

<210> SEQ ID NO 412
<211> LENGTH: 16
<212> TYPE: PRT
<213> ORGANISM: Homo sapiens

<400> SEQUENCE: 412

Cys Ala Ser Ser Ser Gly Thr Ser Gly Arg Pro Gly Glu Gln Phe Phe
1               5                   10                  15

<210> SEQ ID NO 413
<211> LENGTH: 15
<212> TYPE: PRT
<213> ORGANISM: Homo sapiens

<400> SEQUENCE: 413

Cys Ala Ser Ser Pro Trp Arg Glu Ala Gly Asn Glu Gln Phe Phe
1               5                   10                  15

<210> SEQ ID NO 414
<211> LENGTH: 17
<212> TYPE: PRT
<213> ORGANISM: Homo sapiens

<400> SEQUENCE: 414

Cys Ala Ser Ser Gln Asp Gly Leu Ala Gly Val Thr Gly Glu Leu Phe
1               5                   10                  15

Phe

<210> SEQ ID NO 415
<211> LENGTH: 12
<212> TYPE: PRT
<213> ORGANISM: Homo sapiens

<400> SEQUENCE: 415

Cys Ala Ser Asp Gly Asn Asn Ser Pro Leu His Phe
1               5                   10

<210> SEQ ID NO 416
<211> LENGTH: 15
<212> TYPE: PRT
<213> ORGANISM: Homo sapiens

<400> SEQUENCE: 416

Cys Ala Ser Ser Val Met Thr Ser Gly Gln Glu Thr Gln Tyr Phe
1               5                   10                  15

<210> SEQ ID NO 417
<211> LENGTH: 15
<212> TYPE: PRT
<213> ORGANISM: Homo sapiens

<400> SEQUENCE: 417

Cys Ser Ala Arg Gly Ser Pro Thr Asn Thr Gly Glu Leu Phe Phe
1               5                   10                  15

<210> SEQ ID NO 418
<211> LENGTH: 13
<212> TYPE: PRT
<213> ORGANISM: Homo sapiens

<400> SEQUENCE: 418

Cys Ala Ser Thr Gly Thr Thr Asn Glu Lys Leu Phe Phe
1               5                   10

<210> SEQ ID NO 419
<211> LENGTH: 14
<212> TYPE: PRT
<213> ORGANISM: Homo sapiens

<400> SEQUENCE: 419

Cys Ala Ser Ser Val Gly Arg Val Asp Ser Pro Leu His Phe
1               5                   10

<210> SEQ ID NO 420
<211> LENGTH: 14
<212> TYPE: PRT
<213> ORGANISM: Homo sapiens

<400> SEQUENCE: 420

Cys Ala Thr Ser Thr Gly Ala Ala Gly Tyr Gly Tyr Thr Phe
1               5                   10

<210> SEQ ID NO 421
<211> LENGTH: 13
<212> TYPE: PRT
<213> ORGANISM: Homo sapiens

<400> SEQUENCE: 421

Cys Ala Ser Ser Gln Arg Ala Leu Tyr Gly Tyr Thr Phe
1               5                   10

<210> SEQ ID NO 422
<211> LENGTH: 13
<212> TYPE: PRT
<213> ORGANISM: Homo sapiens

<400> SEQUENCE: 422

Cys Ser Ala Ala Gly Val Ser Thr Asp Thr Gln Tyr Phe
1               5                   10

<210> SEQ ID NO 423

```
<211> LENGTH: 16
<212> TYPE: PRT
<213> ORGANISM: Homo sapiens

<400> SEQUENCE: 423

Cys Ala Ser Ser Gln Gly Ser Arg Gly Arg Gly Tyr Gly Tyr Thr Phe
1               5                   10                  15

<210> SEQ ID NO 424
<211> LENGTH: 14
<212> TYPE: PRT
<213> ORGANISM: Homo sapiens

<400> SEQUENCE: 424

Cys Ala Ser Ser Leu Tyr Glu Gly Gln Glu Thr Gln Tyr Phe
1               5                   10

<210> SEQ ID NO 425
<211> LENGTH: 15
<212> TYPE: PRT
<213> ORGANISM: Homo sapiens

<400> SEQUENCE: 425

Cys Ala Ser Ser Leu Ala Arg Thr Ser Asn Thr Glu Ala Phe Phe
1               5                   10                  15

<210> SEQ ID NO 426
<211> LENGTH: 15
<212> TYPE: PRT
<213> ORGANISM: Homo sapiens

<400> SEQUENCE: 426

Cys Ser Ala Arg Ile Ala Gly Ala Gly Thr Gly Glu Leu Phe Phe
1               5                   10                  15

<210> SEQ ID NO 427
<211> LENGTH: 14
<212> TYPE: PRT
<213> ORGANISM: Homo sapiens

<400> SEQUENCE: 427

Cys Ala Ser Ser Phe Ile Gln Gly Pro Asn Glu Gln Phe Phe
1               5                   10

<210> SEQ ID NO 428
<211> LENGTH: 12
<212> TYPE: PRT
<213> ORGANISM: Homo sapiens

<400> SEQUENCE: 428

Cys Ala Ser Ser Thr Arg Arg Asn Glu Gln Phe Phe
1               5                   10

<210> SEQ ID NO 429
<211> LENGTH: 12
<212> TYPE: PRT
<213> ORGANISM: Homo sapiens

<400> SEQUENCE: 429

Cys Ala Ser Arg Gly Pro Gly Gln Pro Gln His Phe
1               5                   10

<210> SEQ ID NO 430
<211> LENGTH: 16
<212> TYPE: PRT
```

```
<213> ORGANISM: Homo sapiens

<400> SEQUENCE: 430

Cys Ala Ser Ser Leu Gly Pro Lys Gly Pro Asn Ser Pro Leu His Phe
1               5                   10                  15

<210> SEQ ID NO 431
<211> LENGTH: 15
<212> TYPE: PRT
<213> ORGANISM: Homo sapiens

<400> SEQUENCE: 431

Cys Ala Ser Ser Arg Gly Arg Pro Gly Thr Asp Thr Gln Tyr Phe
1               5                   10                  15

<210> SEQ ID NO 432
<211> LENGTH: 15
<212> TYPE: PRT
<213> ORGANISM: Homo sapiens

<400> SEQUENCE: 432

Cys Ala Ser Ser Phe Asp Ser Gly Arg Gln Glu Thr Gln Tyr Phe
1               5                   10                  15

<210> SEQ ID NO 433
<211> LENGTH: 14
<212> TYPE: PRT
<213> ORGANISM: Homo sapiens

<400> SEQUENCE: 433

Cys Ala Ser Arg Pro Ser Gln Gly Ala Gly Glu Leu Phe Phe
1               5                   10

<210> SEQ ID NO 434
<211> LENGTH: 14
<212> TYPE: PRT
<213> ORGANISM: Homo sapiens

<400> SEQUENCE: 434

Cys Ala Ser Ser Pro Pro Gly Ser Gln Glu Thr Gln Tyr Phe
1               5                   10

<210> SEQ ID NO 435
<211> LENGTH: 14
<212> TYPE: PRT
<213> ORGANISM: Homo sapiens

<400> SEQUENCE: 435

Cys Ala Ile Ser Pro Arg Leu Ala Tyr Asn Glu Gln Phe Phe
1               5                   10

<210> SEQ ID NO 436
<211> LENGTH: 16
<212> TYPE: PRT
<213> ORGANISM: Homo sapiens

<400> SEQUENCE: 436

Cys Ala Ser Ser Leu Ala Arg Thr Ser Gly Ile Asn Glu Gln Phe Phe
1               5                   10                  15

<210> SEQ ID NO 437
<211> LENGTH: 12
<212> TYPE: PRT
<213> ORGANISM: Homo sapiens
```

<400> SEQUENCE: 437

Cys Ser Ala Arg Asp Gly Ala Pro Glu Gln Phe Phe
1               5                   10

<210> SEQ ID NO 438
<211> LENGTH: 12
<212> TYPE: PRT
<213> ORGANISM: Homo sapiens

<400> SEQUENCE: 438

Cys Ala Ser Ser Asp Gln Thr Asp Thr Gln Tyr Phe
1               5                   10

<210> SEQ ID NO 439
<211> LENGTH: 14
<212> TYPE: PRT
<213> ORGANISM: Homo sapiens

<400> SEQUENCE: 439

Cys Ala Ser Arg Pro Tyr Arg Gly Asp Gln Pro Gln His Phe
1               5                   10

<210> SEQ ID NO 440
<211> LENGTH: 17
<212> TYPE: PRT
<213> ORGANISM: Homo sapiens

<400> SEQUENCE: 440

Cys Ser Ala Arg Glu Gly Arg Gln Ser Ser Tyr Asn Ser Pro Leu His
1               5                   10                  15

Phe

<210> SEQ ID NO 441
<211> LENGTH: 12
<212> TYPE: PRT
<213> ORGANISM: Homo sapiens

<400> SEQUENCE: 441

Cys Ala Ser Glu Ser Gly Gly Asn Thr Ile Tyr Phe
1               5                   10

<210> SEQ ID NO 442
<211> LENGTH: 13
<212> TYPE: PRT
<213> ORGANISM: Homo sapiens

<400> SEQUENCE: 442

Cys Ala Ser Arg Arg Asp Arg Gly Asp Glu Gln Tyr Phe
1               5                   10

<210> SEQ ID NO 443
<211> LENGTH: 17
<212> TYPE: PRT
<213> ORGANISM: Homo sapiens

<400> SEQUENCE: 443

Cys Ala Ser Ser Gln Asp Leu Gly Gly Gln Gly Tyr Gln Pro Gln His
1               5                   10                  15

Phe

<210> SEQ ID NO 444
<211> LENGTH: 16
<212> TYPE: PRT

<213> ORGANISM: Homo sapiens

<400> SEQUENCE: 444

Cys Ala Ser Ser Leu Ala Gly Arg Thr Ser Thr Asp Thr Gln Tyr Phe
1               5                   10                  15

<210> SEQ ID NO 445
<211> LENGTH: 13
<212> TYPE: PRT
<213> ORGANISM: Homo sapiens

<400> SEQUENCE: 445

Cys Ala Ser Ser Val Asp Arg Asp Tyr Glu Gln Tyr Phe
1               5                   10

<210> SEQ ID NO 446
<211> LENGTH: 15
<212> TYPE: PRT
<213> ORGANISM: Homo sapiens

<400> SEQUENCE: 446

Cys Ala Ser Ser Trp Thr Ser Ser Tyr Asn Glu Gln Phe Phe
1               5                   10                  15

<210> SEQ ID NO 447
<211> LENGTH: 14
<212> TYPE: PRT
<213> ORGANISM: Homo sapiens

<400> SEQUENCE: 447

Cys Ala Ser Ser Arg Thr Arg Gln Gly Tyr Glu Gln Tyr Phe
1               5                   10

<210> SEQ ID NO 448
<211> LENGTH: 14
<212> TYPE: PRT
<213> ORGANISM: Homo sapiens

<400> SEQUENCE: 448

Cys Ser Ala Arg Gly Thr Leu Ala Ser Tyr Glu Gln Tyr Phe
1               5                   10

<210> SEQ ID NO 449
<211> LENGTH: 14
<212> TYPE: PRT
<213> ORGANISM: Homo sapiens

<400> SEQUENCE: 449

Cys Ala Ser Ser Phe Lys Gly Thr Thr Gly Glu Leu Phe Phe
1               5                   10

<210> SEQ ID NO 450
<211> LENGTH: 15
<212> TYPE: PRT
<213> ORGANISM: Homo sapiens

<400> SEQUENCE: 450

Cys Ala Ser Ser Leu Thr Val Arg Gly Arg Glu Thr Gln Tyr Phe
1               5                   10                  15

<210> SEQ ID NO 451
<211> LENGTH: 14
<212> TYPE: PRT
<213> ORGANISM: Homo sapiens

```
<400> SEQUENCE: 451

Cys Ser Ala Arg Gly Ser Leu Ala Ser Tyr Glu Gln Tyr Phe
1               5                   10

<210> SEQ ID NO 452
<211> LENGTH: 13
<212> TYPE: PRT
<213> ORGANISM: Homo sapiens

<400> SEQUENCE: 452

Cys Ser Ala Arg Glu Ser Gly Gln Asn Gly Tyr Thr Phe
1               5                   10

<210> SEQ ID NO 453
<211> LENGTH: 15
<212> TYPE: PRT
<213> ORGANISM: Homo sapiens

<400> SEQUENCE: 453

Cys Ala Ser Arg Gly Arg Gly Leu Ala Lys Asn Ile Gln Tyr Phe
1               5                   10                  15

<210> SEQ ID NO 454
<211> LENGTH: 14
<212> TYPE: PRT
<213> ORGANISM: Homo sapiens

<400> SEQUENCE: 454

Cys Ala Ser Ser Leu Val Thr Thr Gly Asn Thr Ile Tyr Phe
1               5                   10

<210> SEQ ID NO 455
<211> LENGTH: 15
<212> TYPE: PRT
<213> ORGANISM: Homo sapiens

<400> SEQUENCE: 455

Cys Ala Thr Ser Arg Asp Ser Gly Ser Gly Glu Thr Gln Tyr Phe
1               5                   10                  15

<210> SEQ ID NO 456
<211> LENGTH: 15
<212> TYPE: PRT
<213> ORGANISM: Homo sapiens

<400> SEQUENCE: 456

Cys Ala Thr Lys Gly Trp Thr Ser Gly Thr Asp Thr Gln Tyr Phe
1               5                   10                  15

<210> SEQ ID NO 457
<211> LENGTH: 14
<212> TYPE: PRT
<213> ORGANISM: Homo sapiens

<400> SEQUENCE: 457

Cys Ser Ala Thr Gly Thr Pro Thr Asn Gln Pro Gln His Phe
1               5                   10

<210> SEQ ID NO 458
<211> LENGTH: 16
<212> TYPE: PRT
<213> ORGANISM: Homo sapiens

<400> SEQUENCE: 458
```

-continued

Cys Ala Ser Ser Ser Gly Gly Thr Ser Gly Arg Asp Thr Gln Tyr Phe
1               5                   10                  15

<210> SEQ ID NO 459
<211> LENGTH: 13
<212> TYPE: PRT
<213> ORGANISM: Homo sapiens

<400> SEQUENCE: 459

Cys Ala Ser Ser Arg Gln Gly Gly Tyr Glu Gln Tyr Phe
1               5                   10

<210> SEQ ID NO 460
<211> LENGTH: 15
<212> TYPE: PRT
<213> ORGANISM: Homo sapiens

<400> SEQUENCE: 460

Cys Ser Ala Arg Pro Gly Gly Gly Thr Gly Glu Leu Phe Phe
1               5                   10                  15

<210> SEQ ID NO 461
<211> LENGTH: 14
<212> TYPE: PRT
<213> ORGANISM: Homo sapiens

<400> SEQUENCE: 461

Cys Ala Ser Ser Thr Gly Arg Val Tyr Asn Glu Gln Phe Phe
1               5                   10

<210> SEQ ID NO 462
<211> LENGTH: 14
<212> TYPE: PRT
<213> ORGANISM: Homo sapiens

<400> SEQUENCE: 462

Cys Ala Ser Thr Pro Thr Gly Asn Thr Gly Glu Leu Phe Phe
1               5                   10

<210> SEQ ID NO 463
<211> LENGTH: 15
<212> TYPE: PRT
<213> ORGANISM: Homo sapiens

<400> SEQUENCE: 463

Cys Ala Ser Ser Ala Leu Thr Gly Gly Thr Asp Thr Gln Tyr Phe
1               5                   10                  15

<210> SEQ ID NO 464
<211> LENGTH: 13
<212> TYPE: PRT
<213> ORGANISM: Homo sapiens

<400> SEQUENCE: 464

Cys Ala Ser Ser Gly Leu Leu Ala Tyr Glu Gln Tyr Phe
1               5                   10

<210> SEQ ID NO 465
<211> LENGTH: 14
<212> TYPE: PRT
<213> ORGANISM: Homo sapiens

<400> SEQUENCE: 465

Cys Ser Ala Arg Leu Arg Asp Tyr Pro Tyr Glu Gln Tyr Phe
1               5                   10

<210> SEQ ID NO 466
<211> LENGTH: 16
<212> TYPE: PRT
<213> ORGANISM: Homo sapiens

<400> SEQUENCE: 466

Cys Ala Ser Ser Thr Thr Gly Pro Tyr Ser Gly Asn Thr Ile Tyr Phe
1               5                   10                  15

<210> SEQ ID NO 467
<211> LENGTH: 14
<212> TYPE: PRT
<213> ORGANISM: Homo sapiens

<400> SEQUENCE: 467

Cys Ala Ser Arg Pro Ser Gly Val Gly Asp Glu Gln Tyr Phe
1               5                   10

<210> SEQ ID NO 468
<211> LENGTH: 11
<212> TYPE: PRT
<213> ORGANISM: Homo sapiens

<400> SEQUENCE: 468

Cys Ala Ser Ser Gln Phe Asp Glu Gln Phe Phe
1               5                   10

<210> SEQ ID NO 469
<211> LENGTH: 15
<212> TYPE: PRT
<213> ORGANISM: Homo sapiens

<400> SEQUENCE: 469

Cys Ser Ala Ser Pro Pro Gly Gln Thr Gln Glu Thr Gln Tyr Phe
1               5                   10                  15

<210> SEQ ID NO 470
<211> LENGTH: 14
<212> TYPE: PRT
<213> ORGANISM: Homo sapiens

<400> SEQUENCE: 470

Cys Ala Ser Ser Ser Gly Arg Gly Asp Glu Lys Leu Phe Phe
1               5                   10

<210> SEQ ID NO 471
<211> LENGTH: 11
<212> TYPE: PRT
<213> ORGANISM: Homo sapiens

<400> SEQUENCE: 471

Cys Ala Ser Ser Ser Pro Gly Ser Tyr Thr Phe
1               5                   10

<210> SEQ ID NO 472
<211> LENGTH: 13
<212> TYPE: PRT
<213> ORGANISM: Homo sapiens

<400> SEQUENCE: 472

Cys Ser Ala Arg Val Val Pro Tyr Asn Glu Gln Phe Phe
1               5                   10

<210> SEQ ID NO 473
<211> LENGTH: 15
<212> TYPE: PRT
<213> ORGANISM: Homo sapiens

<400> SEQUENCE: 473

Cys Ala Ser Ser Leu Gln Ala Ala Ser Gly Asn Thr Ile Tyr Phe
1               5                   10                  15

<210> SEQ ID NO 474
<211> LENGTH: 14
<212> TYPE: PRT
<213> ORGANISM: Homo sapiens

<400> SEQUENCE: 474

Cys Ser Ala Pro Asp Arg Gly Trp Gln Glu Thr Gln Tyr Phe
1               5                   10

<210> SEQ ID NO 475
<211> LENGTH: 14
<212> TYPE: PRT
<213> ORGANISM: Homo sapiens

<400> SEQUENCE: 475

Cys Ala Ser Ser Leu Asp Leu Ala Gly Lys Thr Gln Tyr Phe
1               5                   10

<210> SEQ ID NO 476
<211> LENGTH: 14
<212> TYPE: PRT
<213> ORGANISM: Homo sapiens

<400> SEQUENCE: 476

Cys Ala Ser Ser Gly Arg Gln Gly Ala Pro Glu Ala Phe Phe
1               5                   10

<210> SEQ ID NO 477
<211> LENGTH: 14
<212> TYPE: PRT
<213> ORGANISM: Homo sapiens

<400> SEQUENCE: 477

Cys Ala Ser Gly Arg Leu Gly Ser Thr Asp Thr Gln Tyr Phe
1               5                   10

<210> SEQ ID NO 478
<211> LENGTH: 16
<212> TYPE: PRT
<213> ORGANISM: Homo sapiens

<400> SEQUENCE: 478

Cys Ala Ser Ser Thr Leu Ala Gly Gly Gly Gln Glu Thr Gln Tyr Phe
1               5                   10                  15

<210> SEQ ID NO 479
<211> LENGTH: 15
<212> TYPE: PRT
<213> ORGANISM: Homo sapiens

<400> SEQUENCE: 479

Cys Ala Trp Ser Val Gln Gly Ala Val Lys Asn Ile Gln Tyr Phe
1               5                   10                  15

<210> SEQ ID NO 480
<211> LENGTH: 16

```
<212> TYPE: PRT
<213> ORGANISM: Homo sapiens

<400> SEQUENCE: 480

Cys Ala Thr Ser Arg Asp Lys Gly Ser Gly Asn Ser Pro Leu His Phe
1               5                   10                  15

<210> SEQ ID NO 481
<211> LENGTH: 14
<212> TYPE: PRT
<213> ORGANISM: Homo sapiens

<400> SEQUENCE: 481

Cys Ala Ser Ser Ser Pro Gly Trp Gly Glu Thr Gln Tyr Phe
1               5                   10

<210> SEQ ID NO 482
<211> LENGTH: 13
<212> TYPE: PRT
<213> ORGANISM: Homo sapiens

<400> SEQUENCE: 482

Cys Ala Ser Ser Gln Val Asn Glu Tyr Glu Gln Tyr Phe
1               5                   10

<210> SEQ ID NO 483
<211> LENGTH: 13
<212> TYPE: PRT
<213> ORGANISM: Homo sapiens

<400> SEQUENCE: 483

Cys Ser Gly Cys Thr Gly Val Asn Thr Glu Ala Phe Phe
1               5                   10

<210> SEQ ID NO 484
<211> LENGTH: 14
<212> TYPE: PRT
<213> ORGANISM: Homo sapiens

<400> SEQUENCE: 484

Cys Ala Ser Ser Asp Gly Gln Val Phe Tyr Gly Tyr Thr Phe
1               5                   10

<210> SEQ ID NO 485
<211> LENGTH: 16
<212> TYPE: PRT
<213> ORGANISM: Homo sapiens

<400> SEQUENCE: 485

Cys Ala Ser Ser Leu Asp Pro Thr Arg Ser Thr Asp Thr Gln Tyr Phe
1               5                   10                  15

<210> SEQ ID NO 486
<211> LENGTH: 16
<212> TYPE: PRT
<213> ORGANISM: Homo sapiens

<400> SEQUENCE: 486

Cys Ala Ser Ser Ala Trp Thr Gly Glu Leu Gln Glu Thr Gln Tyr Phe
1               5                   10                  15

<210> SEQ ID NO 487
<211> LENGTH: 14
<212> TYPE: PRT
<213> ORGANISM: Homo sapiens
```

<400> SEQUENCE: 487

Cys Ala Ser Ser Pro Gly Arg Gly Phe Glu Lys Leu Phe Phe
1               5                   10

<210> SEQ ID NO 488
<211> LENGTH: 12
<212> TYPE: PRT
<213> ORGANISM: Homo sapiens

<400> SEQUENCE: 488

Cys Ala Ser Ser Pro Val Glu Gly Gly Tyr Thr Phe
1               5                   10

<210> SEQ ID NO 489
<211> LENGTH: 15
<212> TYPE: PRT
<213> ORGANISM: Homo sapiens

<400> SEQUENCE: 489

Cys Ser Ala Arg Ala Ala Gly Ala Gly Thr Gly Glu Leu Phe Phe
1               5                   10                  15

<210> SEQ ID NO 490
<211> LENGTH: 15
<212> TYPE: PRT
<213> ORGANISM: Homo sapiens

<400> SEQUENCE: 490

Cys Ser Ala Arg Ala Gly Gly His Gly Thr Gly Glu Leu Phe Phe
1               5                   10                  15

<210> SEQ ID NO 491
<211> LENGTH: 15
<212> TYPE: PRT
<213> ORGANISM: Homo sapiens

<400> SEQUENCE: 491

Cys Ser Ala Arg Glu Gly Gly Gly Gly Thr Gly Glu Leu Phe Phe
1               5                   10                  15

<210> SEQ ID NO 492
<211> LENGTH: 14
<212> TYPE: PRT
<213> ORGANISM: Homo sapiens

<400> SEQUENCE: 492

Cys Ala Ser Arg Gly Ala Gly Ser Ala Asp Thr Gln Tyr Phe
1               5                   10

<210> SEQ ID NO 493
<211> LENGTH: 15
<212> TYPE: PRT
<213> ORGANISM: Homo sapiens

<400> SEQUENCE: 493

Cys Ala Ser Ser Tyr Gly Gly Ala Gly Ser Asp Thr Gln Tyr Phe
1               5                   10                  15

<210> SEQ ID NO 494
<211> LENGTH: 14
<212> TYPE: PRT
<213> ORGANISM: Homo sapiens

<400> SEQUENCE: 494

Cys Ala Ser Ser Leu Val Ala Gly Gly Glu Thr Gln Tyr Phe
1               5                   10

<210> SEQ ID NO 495
<211> LENGTH: 13
<212> TYPE: PRT
<213> ORGANISM: Homo sapiens

<400> SEQUENCE: 495

Cys Ala Ala Leu Ala Gly Gly Tyr Asn Glu Gln Phe Phe
1               5                   10

<210> SEQ ID NO 496
<211> LENGTH: 16
<212> TYPE: PRT
<213> ORGANISM: Homo sapiens

<400> SEQUENCE: 496

Cys Ala Ser Ser Leu Val Arg Gly Leu Asn Asn Glu Lys Leu Phe Phe
1               5                   10                  15

<210> SEQ ID NO 497
<211> LENGTH: 14
<212> TYPE: PRT
<213> ORGANISM: Homo sapiens

<400> SEQUENCE: 497

Cys Ala Ser Phe Pro Gly Gln Gly Asn Thr Glu Ala Phe Phe
1               5                   10

<210> SEQ ID NO 498
<211> LENGTH: 14
<212> TYPE: PRT
<213> ORGANISM: Homo sapiens

<400> SEQUENCE: 498

Cys Ala Ser Arg Pro Gly Thr Gly Tyr Gln Pro Gln His Phe
1               5                   10

<210> SEQ ID NO 499
<211> LENGTH: 14
<212> TYPE: PRT
<213> ORGANISM: Homo sapiens

<400> SEQUENCE: 499

Cys Ala Ser Thr Met Thr Gly Ile Asp Thr Glu Ala Phe Phe
1               5                   10

<210> SEQ ID NO 500
<211> LENGTH: 15
<212> TYPE: PRT
<213> ORGANISM: Homo sapiens

<400> SEQUENCE: 500

Cys Ala Ser Ser Phe Ala Gly Gly Ala Phe Asn Glu Gln Phe Phe
1               5                   10                  15

<210> SEQ ID NO 501
<211> LENGTH: 13
<212> TYPE: PRT
<213> ORGANISM: Homo sapiens

<400> SEQUENCE: 501

Cys Ala Ser Arg Val Gly Leu Arg Gln Pro Gln His Phe

```
                1               5                    10
```

<210> SEQ ID NO 502
<211> LENGTH: 15
<212> TYPE: PRT
<213> ORGANISM: Homo sapiens

<400> SEQUENCE: 502

```
Cys Ala Ser Ser Phe Gly Ser Gly Lys Tyr Asn Glu Gln Phe Phe
1               5                   10                  15
```

<210> SEQ ID NO 503
<211> LENGTH: 17
<212> TYPE: PRT
<213> ORGANISM: Homo sapiens

<400> SEQUENCE: 503

```
Cys Ala Ser Ser Pro Ser Leu Ala Gly Gly Pro Thr Asp Thr Gln Tyr
1               5                   10                  15
Phe
```

<210> SEQ ID NO 504
<211> LENGTH: 17
<212> TYPE: PRT
<213> ORGANISM: Homo sapiens

<400> SEQUENCE: 504

```
Cys Ala Ser Ser Pro Gln Arg Asp Arg Ser Ser Gly Asn Thr Ile Tyr
1               5                   10                  15
Phe
```

<210> SEQ ID NO 505
<211> LENGTH: 17
<212> TYPE: PRT
<213> ORGANISM: Homo sapiens

<400> SEQUENCE: 505

```
Cys Ala Ser Ser Phe Leu Thr Gly Leu Ser Gly Ala Asn Val Leu Thr
1               5                   10                  15
Phe
```

<210> SEQ ID NO 506
<211> LENGTH: 13
<212> TYPE: PRT
<213> ORGANISM: Homo sapiens

<400> SEQUENCE: 506

```
Cys Ala Ser Cys Arg Gly Thr Thr Tyr Glu Gln Tyr Phe
1               5                   10
```

<210> SEQ ID NO 507
<211> LENGTH: 15
<212> TYPE: PRT
<213> ORGANISM: Homo sapiens

<400> SEQUENCE: 507

```
Cys Ser Ala Arg Asp Pro Tyr Leu Ser Ser Tyr Glu Gln Tyr Phe
1               5                   10                  15
```

<210> SEQ ID NO 508
<211> LENGTH: 15
<212> TYPE: PRT
<213> ORGANISM: Homo sapiens

```
<400> SEQUENCE: 508

Cys Ala Ser Ser Ser Pro Ser Gly Arg Ala Asp Glu Gln Phe Phe
1               5                   10                  15

<210> SEQ ID NO 509
<211> LENGTH: 15
<212> TYPE: PRT
<213> ORGANISM: Homo sapiens

<400> SEQUENCE: 509

Cys Ala Ile Lys Gly Thr Ser Ser Tyr Asn Ser Pro Leu His Phe
1               5                   10                  15

<210> SEQ ID NO 510
<211> LENGTH: 13
<212> TYPE: PRT
<213> ORGANISM: Homo sapiens

<400> SEQUENCE: 510

Cys Ala Ile Arg Met Gly Gln Thr Tyr Glu Gln Tyr Phe
1               5                   10

<210> SEQ ID NO 511
<211> LENGTH: 13
<212> TYPE: PRT
<213> ORGANISM: Homo sapiens

<400> SEQUENCE: 511

Cys Ala Ser Ser Gln Gly Gly Ala Arg Glu Gln Phe Phe
1               5                   10

<210> SEQ ID NO 512
<211> LENGTH: 14
<212> TYPE: PRT
<213> ORGANISM: Homo sapiens

<400> SEQUENCE: 512

Cys Ala Ser Ser Arg Thr Ser Ser Pro Asp Thr Gln Tyr Phe
1               5                   10

<210> SEQ ID NO 513
<211> LENGTH: 14
<212> TYPE: PRT
<213> ORGANISM: Homo sapiens

<400> SEQUENCE: 513

Cys Ala Thr Ser Pro Gln Gly Gly Asp Gln Pro Gln His Phe
1               5                   10

<210> SEQ ID NO 514
<211> LENGTH: 13
<212> TYPE: PRT
<213> ORGANISM: Homo sapiens

<400> SEQUENCE: 514

Cys Ser Ala Gln Asp Pro Gly Thr Thr Glu Ala Phe Phe
1               5                   10

<210> SEQ ID NO 515
<211> LENGTH: 15
<212> TYPE: PRT
<213> ORGANISM: Homo sapiens

<400> SEQUENCE: 515
```

Cys Ala Ser Ser Leu Asn Arg Gly Val Ser Gln Pro Gln His Phe
1               5                   10                  15

<210> SEQ ID NO 516
<211> LENGTH: 12
<212> TYPE: PRT
<213> ORGANISM: Homo sapiens

<400> SEQUENCE: 516

Cys Ala Ser Thr Leu Thr Ser Ser Glu Gln Tyr Phe
1               5                   10

<210> SEQ ID NO 517
<211> LENGTH: 15
<212> TYPE: PRT
<213> ORGANISM: Homo sapiens

<400> SEQUENCE: 517

Cys Ala Ser Ser Ile Ala Gly Leu Arg Pro Asp Thr Gln Tyr Phe
1               5                   10                  15

<210> SEQ ID NO 518
<211> LENGTH: 15
<212> TYPE: PRT
<213> ORGANISM: Homo sapiens

<400> SEQUENCE: 518

Cys Ala Ser Ser His Gly Gln Gly Ala Leu Asp Thr Gln Tyr Phe
1               5                   10                  15

<210> SEQ ID NO 519
<211> LENGTH: 15
<212> TYPE: PRT
<213> ORGANISM: Homo sapiens

<400> SEQUENCE: 519

Cys Ala Ser Thr Arg Gly Asp Arg Gly Gln Glu Thr Gln Tyr Phe
1               5                   10                  15

<210> SEQ ID NO 520
<211> LENGTH: 12
<212> TYPE: PRT
<213> ORGANISM: Homo sapiens

<400> SEQUENCE: 520

Cys Ser Ala Pro Ala Arg Gly Glu Thr Gln Tyr Phe
1               5                   10

<210> SEQ ID NO 521
<211> LENGTH: 15
<212> TYPE: PRT
<213> ORGANISM: Homo sapiens

<400> SEQUENCE: 521

Cys Ala Ser Ser Gln Glu Val Thr Ala Asp Ser Pro Leu His Phe
1               5                   10                  15

<210> SEQ ID NO 522
<211> LENGTH: 16
<212> TYPE: PRT
<213> ORGANISM: Homo sapiens

<400> SEQUENCE: 522

Cys Ala Ser Ser Leu Val Leu Gly Gly Met Asn Thr Glu Ala Phe Phe

<210> SEQ ID NO 523
<211> LENGTH: 13
<212> TYPE: PRT
<213> ORGANISM: Homo sapiens

<400> SEQUENCE: 523

Cys Ala Ser Lys Arg Gln Gly Leu Tyr Glu Gln Tyr Phe
1               5                   10

<210> SEQ ID NO 524
<211> LENGTH: 12
<212> TYPE: PRT
<213> ORGANISM: Homo sapiens

<400> SEQUENCE: 524

Cys Ala Ser Ser Thr Gln Thr Ser Pro Leu His Phe
1               5                   10

<210> SEQ ID NO 525
<211> LENGTH: 15
<212> TYPE: PRT
<213> ORGANISM: Homo sapiens

<400> SEQUENCE: 525

Cys Ala Ser Gly Gly Thr Gly Gln Pro Asn Gln Pro Gln His Phe
1               5                   10                  15

<210> SEQ ID NO 526
<211> LENGTH: 16
<212> TYPE: PRT
<213> ORGANISM: Homo sapiens

<400> SEQUENCE: 526

Cys Ala Ser Ser Tyr Pro Gly Leu Pro Ser Thr Asp Thr Gln Tyr Phe
1               5                   10                  15

<210> SEQ ID NO 527
<211> LENGTH: 14
<212> TYPE: PRT
<213> ORGANISM: Homo sapiens

<400> SEQUENCE: 527

Cys Ala Ser Met Ser Gly Thr Gly Asn Glu Lys Leu Phe Phe
1               5                   10

<210> SEQ ID NO 528
<211> LENGTH: 12
<212> TYPE: PRT
<213> ORGANISM: Homo sapiens

<400> SEQUENCE: 528

Cys Ser Ala Arg Asp Gly Gln Ala Thr Gln Tyr Phe
1               5                   10

<210> SEQ ID NO 529
<211> LENGTH: 16
<212> TYPE: PRT
<213> ORGANISM: Homo sapiens

<400> SEQUENCE: 529

Cys Ala Ser Ser Leu Ser Asn Arg Gly Arg Gly Tyr Gly Tyr Thr Phe
1               5                   10                  15

<210> SEQ ID NO 530
<211> LENGTH: 16
<212> TYPE: PRT
<213> ORGANISM: Homo sapiens

<400> SEQUENCE: 530

Cys Ala Ser Ser Leu Ser Arg Arg Gly Arg Gly Tyr Gly Tyr Thr Phe
1               5                   10                  15

<210> SEQ ID NO 531
<211> LENGTH: 13
<212> TYPE: PRT
<213> ORGANISM: Homo sapiens

<400> SEQUENCE: 531

Cys Ala Ser Thr Arg Ala Val Gln Glu Thr Gln Tyr Phe
1               5                   10

<210> SEQ ID NO 532
<211> LENGTH: 14
<212> TYPE: PRT
<213> ORGANISM: Homo sapiens

<400> SEQUENCE: 532

Cys Ala Ser Ser Leu Gly Asp Thr Gly Ala Glu Ala Phe Phe
1               5                   10

<210> SEQ ID NO 533
<211> LENGTH: 12
<212> TYPE: PRT
<213> ORGANISM: Homo sapiens

<400> SEQUENCE: 533

Cys Ser Ala Pro Gly Ser Trp Thr Glu Ala Phe Phe
1               5                   10

<210> SEQ ID NO 534
<211> LENGTH: 15
<212> TYPE: PRT
<213> ORGANISM: Homo sapiens

<400> SEQUENCE: 534

Cys Ala Ser Ser Leu Ala Gly Leu Ala Ser Gly Glu Gln Phe Phe
1               5                   10                  15

<210> SEQ ID NO 535
<211> LENGTH: 13
<212> TYPE: PRT
<213> ORGANISM: Homo sapiens

<400> SEQUENCE: 535

Cys Ser Val Gly Gly Asp Pro Asn Glu Lys Leu Phe Phe
1               5                   10

<210> SEQ ID NO 536
<211> LENGTH: 12
<212> TYPE: PRT
<213> ORGANISM: Homo sapiens

<400> SEQUENCE: 536

Cys Ser Ala Arg Gln Ser Ser Tyr Glu Gln Tyr Phe
1               5                   10

<210> SEQ ID NO 537

<211> LENGTH: 18
<212> TYPE: PRT
<213> ORGANISM: Homo sapiens

<400> SEQUENCE: 537

Cys Ala Ser Ser Gln Asp Phe Pro Ala Gly Val Arg Thr Asp Thr Gln
1               5                   10                  15

Tyr Phe

<210> SEQ ID NO 538
<211> LENGTH: 15
<212> TYPE: PRT
<213> ORGANISM: Homo sapiens

<400> SEQUENCE: 538

Cys Ala Ser Ser Pro Asn Gly Gly Arg Asn Gln Pro Gln His Phe
1               5                   10                  15

<210> SEQ ID NO 539
<211> LENGTH: 15
<212> TYPE: PRT
<213> ORGANISM: Homo sapiens

<400> SEQUENCE: 539

Cys Ser Ala Arg Gly Ser Gly Ser Gly Thr Gly Glu Leu Phe Phe
1               5                   10                  15

<210> SEQ ID NO 540
<211> LENGTH: 15
<212> TYPE: PRT
<213> ORGANISM: Homo sapiens

<400> SEQUENCE: 540

Cys Ser Ala Arg Arg Ser Gly Ala Gly Thr Gly Glu Leu Phe Phe
1               5                   10                  15

<210> SEQ ID NO 541
<211> LENGTH: 15
<212> TYPE: PRT
<213> ORGANISM: Homo sapiens

<400> SEQUENCE: 541

Cys Ala Ser Ser Gln Ser Ser Gly Gly Ala Glu Thr Gln Tyr Phe
1               5                   10                  15

<210> SEQ ID NO 542
<211> LENGTH: 14
<212> TYPE: PRT
<213> ORGANISM: Homo sapiens

<400> SEQUENCE: 542

Cys Ala Ser Ser Leu Ser His Ser Gln Glu Thr Gln Tyr Phe
1               5                   10

<210> SEQ ID NO 543
<211> LENGTH: 14
<212> TYPE: PRT
<213> ORGANISM: Homo sapiens

<400> SEQUENCE: 543

Cys Ala Ser Ser Glu Leu Asp Arg Thr Gly Glu Leu Phe Phe
1               5                   10

<210> SEQ ID NO 544

<211> LENGTH: 15
<212> TYPE: PRT
<213> ORGANISM: Homo sapiens

<400> SEQUENCE: 544

Cys Ser Ala Arg Phe Pro Ser Gly Arg Val Asn Glu Gln Phe Phe
1               5                   10                  15

<210> SEQ ID NO 545
<211> LENGTH: 14
<212> TYPE: PRT
<213> ORGANISM: Homo sapiens

<400> SEQUENCE: 545

Cys Ala Ser Ser Ser Arg Ser Arg Asn Thr Glu Ala Phe Phe
1               5                   10

<210> SEQ ID NO 546
<211> LENGTH: 14
<212> TYPE: PRT
<213> ORGANISM: Homo sapiens

<400> SEQUENCE: 546

Cys Ala Trp Ser Val Val Gly Gly Val Arg Gly Tyr Thr Phe
1               5                   10

<210> SEQ ID NO 547
<211> LENGTH: 16
<212> TYPE: PRT
<213> ORGANISM: Homo sapiens

<400> SEQUENCE: 547

Cys Ala Ser Ser Pro Leu Leu Ala Ser Ser Tyr Asn Glu Gln Phe Phe
1               5                   10                  15

<210> SEQ ID NO 548
<211> LENGTH: 15
<212> TYPE: PRT
<213> ORGANISM: Homo sapiens

<400> SEQUENCE: 548

Cys Ala Ser Ser Leu Leu Ala Gly Asp Arg Lys Thr Gln Tyr Phe
1               5                   10                  15

<210> SEQ ID NO 549
<211> LENGTH: 13
<212> TYPE: PRT
<213> ORGANISM: Homo sapiens

<400> SEQUENCE: 549

Cys Ala Ser Arg Leu Gln Gly Gly Asn Glu Gln Phe Phe
1               5                   10

<210> SEQ ID NO 550
<211> LENGTH: 15
<212> TYPE: PRT
<213> ORGANISM: Homo sapiens

<400> SEQUENCE: 550

Cys Ala Ser Ser Phe Leu Ala Gly Asp Thr Gly Glu Leu Phe Phe
1               5                   10                  15

<210> SEQ ID NO 551
<211> LENGTH: 13
<212> TYPE: PRT

<213> ORGANISM: Homo sapiens

<400> SEQUENCE: 551

Cys Ser Ala Arg Asp Glu Gly Pro Glu Thr Gln Tyr Phe
1               5                   10

<210> SEQ ID NO 552
<211> LENGTH: 17
<212> TYPE: PRT
<213> ORGANISM: Homo sapiens

<400> SEQUENCE: 552

Cys Ala Ile Ser Gly Asp Arg Gly Ser Gly Ala Asn Val Leu Thr
1               5                   10                  15

Phe

<210> SEQ ID NO 553
<211> LENGTH: 14
<212> TYPE: PRT
<213> ORGANISM: Homo sapiens

<400> SEQUENCE: 553

Cys Ser Ala Ile Gly Gln Pro Ser Asn Gln Pro Gln His Phe
1               5                   10

<210> SEQ ID NO 554
<211> LENGTH: 16
<212> TYPE: PRT
<213> ORGANISM: Homo sapiens

<400> SEQUENCE: 554

Cys Ala Ser Ser Leu Gly Gln Arg Ala Leu Asn Thr Glu Ala Phe Phe
1               5                   10                  15

<210> SEQ ID NO 555
<211> LENGTH: 14
<212> TYPE: PRT
<213> ORGANISM: Homo sapiens

<400> SEQUENCE: 555

Cys Ala Trp Ser Val Arg Arg Gly Glu Ser Gly Tyr Thr Phe
1               5                   10

<210> SEQ ID NO 556
<211> LENGTH: 16
<212> TYPE: PRT
<213> ORGANISM: Homo sapiens

<400> SEQUENCE: 556

Cys Ala Ser Ser Leu Gly Gly Phe Gln Ser Thr Asp Thr Gln Tyr Phe
1               5                   10                  15

<210> SEQ ID NO 557
<211> LENGTH: 15
<212> TYPE: PRT
<213> ORGANISM: Homo sapiens

<400> SEQUENCE: 557

Cys Ala Ser Ser Pro Asp Gly Gly Arg Asn Gln Pro Gln His Phe
1               5                   10                  15

<210> SEQ ID NO 558
<211> LENGTH: 15
<212> TYPE: PRT

<213> ORGANISM: Homo sapiens

<400> SEQUENCE: 558

Cys Ala Ser Ser Leu Ala Ala Gly Tyr Thr Gly Glu Leu Phe Phe
1               5                   10                  15

<210> SEQ ID NO 559
<211> LENGTH: 15
<212> TYPE: PRT
<213> ORGANISM: Homo sapiens

<400> SEQUENCE: 559

Cys Ala Ser Ser Pro Thr Asp Pro Ser Gly Asn Thr Ile Tyr Phe
1               5                   10                  15

<210> SEQ ID NO 560
<211> LENGTH: 15
<212> TYPE: PRT
<213> ORGANISM: Homo sapiens

<400> SEQUENCE: 560

Cys Ala Ser Ser Phe His Pro Gly Glu Gly Tyr Glu Gln Tyr Phe
1               5                   10                  15

<210> SEQ ID NO 561
<211> LENGTH: 14
<212> TYPE: PRT
<213> ORGANISM: Homo sapiens

<400> SEQUENCE: 561

Cys Ala Ser Ser Leu Lys Gly His Asn Gln Pro Gln His Phe
1               5                   10

<210> SEQ ID NO 562
<211> LENGTH: 13
<212> TYPE: PRT
<213> ORGANISM: Homo sapiens

<400> SEQUENCE: 562

Cys Ala Ser Ser Leu Gln Gly Ala Asn Glu Gln Phe Phe
1               5                   10

<210> SEQ ID NO 563
<211> LENGTH: 14
<212> TYPE: PRT
<213> ORGANISM: Homo sapiens

<400> SEQUENCE: 563

Cys Ala Ser Pro Gly Glu Ser Gly Ala Asn Val Leu Thr Phe
1               5                   10

<210> SEQ ID NO 564
<211> LENGTH: 16
<212> TYPE: PRT
<213> ORGANISM: Homo sapiens

<400> SEQUENCE: 564

Cys Ala Ser Ser Phe Leu Gly Thr Gly Lys Asn Thr Glu Ala Phe Phe
1               5                   10                  15

<210> SEQ ID NO 565
<211> LENGTH: 15
<212> TYPE: PRT
<213> ORGANISM: Homo sapiens

<400> SEQUENCE: 565

Cys Ser Ala Arg Ala Ser Gly Ala Gly Thr Gly Glu Leu Phe Phe
1               5                   10                  15

<210> SEQ ID NO 566
<211> LENGTH: 13
<212> TYPE: PRT
<213> ORGANISM: Homo sapiens

<400> SEQUENCE: 566

Cys Ser Ala Ser Ser Pro Pro Asp Asn Glu Gln Phe Phe
1               5                   10

<210> SEQ ID NO 567
<211> LENGTH: 15
<212> TYPE: PRT
<213> ORGANISM: Homo sapiens

<400> SEQUENCE: 567

Cys Ala Ser Ser Tyr Thr Gly Asp Val Asp Gln Pro Gln His Phe
1               5                   10                  15

<210> SEQ ID NO 568
<211> LENGTH: 15
<212> TYPE: PRT
<213> ORGANISM: Homo sapiens

<400> SEQUENCE: 568

Cys Ala Ser Ser Pro Ser Trp Gln Arg Asn Thr Glu Ala Phe Phe
1               5                   10                  15

<210> SEQ ID NO 569
<211> LENGTH: 15
<212> TYPE: PRT
<213> ORGANISM: Homo sapiens

<400> SEQUENCE: 569

Cys Ala Ser Ser Tyr Gly Leu Gln Gly His Tyr Gly Tyr Thr Phe
1               5                   10                  15

<210> SEQ ID NO 570
<211> LENGTH: 14
<212> TYPE: PRT
<213> ORGANISM: Homo sapiens

<400> SEQUENCE: 570

Cys Ala Ser Ser Lys Asn Ser Ser Asn Gln Pro Gln His Phe
1               5                   10

<210> SEQ ID NO 571
<211> LENGTH: 11
<212> TYPE: PRT
<213> ORGANISM: Homo sapiens

<400> SEQUENCE: 571

Cys Ala Ser Glu Ala Ala Tyr Gly Tyr Thr Phe
1               5                   10

<210> SEQ ID NO 572
<211> LENGTH: 14
<212> TYPE: PRT
<213> ORGANISM: Homo sapiens

<400> SEQUENCE: 572

Cys Ser Ala Thr Ser Gly Arg Ile Tyr Asn Glu Gln Phe Phe
1               5                   10

<210> SEQ ID NO 573
<211> LENGTH: 15
<212> TYPE: PRT
<213> ORGANISM: Homo sapiens

<400> SEQUENCE: 573

Cys Ala Ser Ser Pro Ser Ser Gly Gly Ser Tyr Glu Gln Tyr Phe
1               5                   10                  15

<210> SEQ ID NO 574
<211> LENGTH: 15
<212> TYPE: PRT
<213> ORGANISM: Homo sapiens

<400> SEQUENCE: 574

Cys Ser Val Thr Arg Thr Gly Gly Gly Ala Asp Thr Gln Tyr Phe
1               5                   10                  15

<210> SEQ ID NO 575
<211> LENGTH: 15
<212> TYPE: PRT
<213> ORGANISM: Homo sapiens

<400> SEQUENCE: 575

Cys Ala Ser Ser Leu Arg Pro Gly Gly Arg Asp Glu Gln Tyr Phe
1               5                   10                  15

<210> SEQ ID NO 576
<211> LENGTH: 14
<212> TYPE: PRT
<213> ORGANISM: Homo sapiens

<400> SEQUENCE: 576

Cys Ala Ser Ser Leu Val Val Ser Gly Asn Thr Ile Tyr Phe
1               5                   10

<210> SEQ ID NO 577
<211> LENGTH: 15
<212> TYPE: PRT
<213> ORGANISM: Homo sapiens

<400> SEQUENCE: 577

Cys Ser Ala Arg Leu Gly Gly Gly Thr Gly Glu Leu Phe Phe
1               5                   10                  15

<210> SEQ ID NO 578
<211> LENGTH: 14
<212> TYPE: PRT
<213> ORGANISM: Homo sapiens

<400> SEQUENCE: 578

Cys Ala Ser Ser Ser Gly Ser Gly Ala Asp Thr Gln Tyr Phe
1               5                   10

<210> SEQ ID NO 579
<211> LENGTH: 14
<212> TYPE: PRT
<213> ORGANISM: Homo sapiens

<400> SEQUENCE: 579

Cys Ala Ser Gly Leu Ala Gly Asn Gln Glu Thr Gln Tyr Phe
1               5                   10

<210> SEQ ID NO 580
<211> LENGTH: 17
<212> TYPE: PRT
<213> ORGANISM: Homo sapiens

<400> SEQUENCE: 580

Cys Ala Ser Ser Gly Thr Leu Ala Gly Gly Arg Thr Asp Thr Gln Tyr
1               5                   10                  15
Phe

<210> SEQ ID NO 581
<211> LENGTH: 13
<212> TYPE: PRT
<213> ORGANISM: Homo sapiens

<400> SEQUENCE: 581

Cys Ser Ala Pro Leu Pro Pro Tyr Asn Glu Gln Phe Phe
1               5                   10

<210> SEQ ID NO 582
<211> LENGTH: 15
<212> TYPE: PRT
<213> ORGANISM: Homo sapiens

<400> SEQUENCE: 582

Cys Ala Ser Ser Val Gly Gly Arg Gly Ala Glu Thr Gln Tyr Phe
1               5                   10                  15

<210> SEQ ID NO 583
<211> LENGTH: 16
<212> TYPE: PRT
<213> ORGANISM: Homo sapiens

<400> SEQUENCE: 583

Cys Ala Ser Ser Leu Asp Gly Arg Ser Ser Tyr Asn Glu Gln Phe Phe
1               5                   10                  15

<210> SEQ ID NO 584
<211> LENGTH: 15
<212> TYPE: PRT
<213> ORGANISM: Homo sapiens

<400> SEQUENCE: 584

Cys Ala Ser Ser Gln Ser Arg Asp Ser Ala Tyr Glu Gln Tyr Phe
1               5                   10                  15

<210> SEQ ID NO 585
<211> LENGTH: 13
<212> TYPE: PRT
<213> ORGANISM: Homo sapiens

<400> SEQUENCE: 585

Cys Ala Ser Ser Gln Glu Gly Arg Asp Thr Gln Tyr Phe
1               5                   10

<210> SEQ ID NO 586
<211> LENGTH: 13
<212> TYPE: PRT
<213> ORGANISM: Homo sapiens

<400> SEQUENCE: 586

Cys Ala Ser Ile Leu Thr Gly Gly Asn Glu Gln Phe Phe
1               5                   10

<210> SEQ ID NO 587
<211> LENGTH: 15
<212> TYPE: PRT
<213> ORGANISM: Homo sapiens

<400> SEQUENCE: 587

Cys Ala Ser Ser Leu Leu Gly Thr Gly Tyr Glu Gln Tyr Phe
1               5                   10                  15

<210> SEQ ID NO 588
<211> LENGTH: 13
<212> TYPE: PRT
<213> ORGANISM: Homo sapiens

<400> SEQUENCE: 588

Cys Ser Ala Gly Thr Gly Thr Leu Asn Glu Gln Phe Phe
1               5                   10

<210> SEQ ID NO 589
<211> LENGTH: 15
<212> TYPE: PRT
<213> ORGANISM: Homo sapiens

<400> SEQUENCE: 589

Cys Ala Ser Ser Phe Ser Gly Gly Ser Ile Tyr Gly Tyr Thr Phe
1               5                   10                  15

<210> SEQ ID NO 590
<211> LENGTH: 15
<212> TYPE: PRT
<213> ORGANISM: Homo sapiens

<400> SEQUENCE: 590

Cys Ala Trp Ser Pro Gly Arg Gly Ala Tyr Asn Glu Gln Phe Phe
1               5                   10                  15

<210> SEQ ID NO 591
<211> LENGTH: 13
<212> TYPE: PRT
<213> ORGANISM: Homo sapiens

<400> SEQUENCE: 591

Cys Ala Ile Arg Glu Gly Gln Thr Asp Thr Gln Tyr Phe
1               5                   10

<210> SEQ ID NO 592
<211> LENGTH: 14
<212> TYPE: PRT
<213> ORGANISM: Homo sapiens

<400> SEQUENCE: 592

Cys Ala Ser Arg Trp Gln Gly Ser Ser Tyr Glu Gln Tyr Phe
1               5                   10

<210> SEQ ID NO 593
<211> LENGTH: 13
<212> TYPE: PRT
<213> ORGANISM: Homo sapiens

<400> SEQUENCE: 593

Cys Ser Ala Pro Gln Pro Pro Tyr Asn Glu Gln Phe Phe
1               5                   10

```
<210> SEQ ID NO 594
<211> LENGTH: 15
<212> TYPE: PRT
<213> ORGANISM: Homo sapiens

<400> SEQUENCE: 594

Cys Ala Ser Ser Pro Ser Lys Gly Arg Gly Thr Glu Ala Phe Phe
1               5                   10                  15

<210> SEQ ID NO 595
<211> LENGTH: 15
<212> TYPE: PRT
<213> ORGANISM: Homo sapiens

<400> SEQUENCE: 595

Cys Ala Ser Ser Pro Ser Gly Ser Arg Arg Glu Thr Gln Tyr Phe
1               5                   10                  15

<210> SEQ ID NO 596
<211> LENGTH: 15
<212> TYPE: PRT
<213> ORGANISM: Homo sapiens

<400> SEQUENCE: 596

Cys Ala Ser Ser Leu Thr Gln Gly Gly Thr Asp Thr Gln Tyr Phe
1               5                   10                  15

<210> SEQ ID NO 597
<211> LENGTH: 15
<212> TYPE: PRT
<213> ORGANISM: Homo sapiens

<400> SEQUENCE: 597

Cys Ala Trp Ser Val Gly Asp Asn Ser Gly Asn Thr Ile Tyr Phe
1               5                   10                  15

<210> SEQ ID NO 598
<211> LENGTH: 14
<212> TYPE: PRT
<213> ORGANISM: Homo sapiens

<400> SEQUENCE: 598

Cys Ala Ser Arg Thr Ser Gly Ile Gly Glu Thr Gln Tyr Phe
1               5                   10

<210> SEQ ID NO 599
<211> LENGTH: 15
<212> TYPE: PRT
<213> ORGANISM: Homo sapiens

<400> SEQUENCE: 599

Cys Ser Ala Lys Gly Gln Pro Thr Asn Thr Gly Glu Leu Phe Phe
1               5                   10                  15

<210> SEQ ID NO 600
<211> LENGTH: 15
<212> TYPE: PRT
<213> ORGANISM: Homo sapiens

<400> SEQUENCE: 600

Cys Ala Ser Ser Pro Gly Glu Ala Ser Thr Asp Thr Gln Tyr Phe
1               5                   10                  15

<210> SEQ ID NO 601
<211> LENGTH: 15
```

-continued

<212> TYPE: PRT
<213> ORGANISM: Homo sapiens

<400> SEQUENCE: 601

Cys Ala Thr Ser Ser Leu Gly Gln Gly Ala Arg Glu Gln Tyr Phe
1               5                   10                  15

<210> SEQ ID NO 602
<211> LENGTH: 13
<212> TYPE: PRT
<213> ORGANISM: Homo sapiens

<400> SEQUENCE: 602

Cys Ser Ala Thr Arg Gly Glu Asp Tyr Gly Tyr Thr Phe
1               5                   10

<210> SEQ ID NO 603
<211> LENGTH: 12
<212> TYPE: PRT
<213> ORGANISM: Homo sapiens

<400> SEQUENCE: 603

Cys Ser Ala Ser Trp Pro Asn Ser Pro Leu His Phe
1               5                   10

<210> SEQ ID NO 604
<211> LENGTH: 16
<212> TYPE: PRT
<213> ORGANISM: Homo sapiens

<400> SEQUENCE: 604

Cys Ser Ala Thr Arg Gly Arg Gly Ala Ser Thr Asp Thr Gln Tyr Phe
1               5                   10                  15

<210> SEQ ID NO 605
<211> LENGTH: 15
<212> TYPE: PRT
<213> ORGANISM: Homo sapiens

<400> SEQUENCE: 605

Cys Ala Ser Ser Phe Glu Gly Asn Tyr Asn Ser Pro Leu His Phe
1               5                   10                  15

<210> SEQ ID NO 606
<211> LENGTH: 15
<212> TYPE: PRT
<213> ORGANISM: Homo sapiens

<400> SEQUENCE: 606

Cys Ala Thr Ser Asp Leu Arg Thr Gly Asp Asn Glu Gln Phe Phe
1               5                   10                  15

<210> SEQ ID NO 607
<211> LENGTH: 14
<212> TYPE: PRT
<213> ORGANISM: Homo sapiens

<400> SEQUENCE: 607

Cys Ser Val Ser Trp Gly Ser Thr Asn Glu Lys Leu Phe Phe
1               5                   10

<210> SEQ ID NO 608
<211> LENGTH: 14
<212> TYPE: PRT
<213> ORGANISM: Homo sapiens

<400> SEQUENCE: 608

Cys Ala Ser Ser Lys His Gln Asn Thr Gly Glu Leu Phe Phe
1               5                   10

<210> SEQ ID NO 609
<211> LENGTH: 11
<212> TYPE: PRT
<213> ORGANISM: Homo sapiens

<400> SEQUENCE: 609

Cys Ala Ser Ser Glu Thr Trp Thr Gln Tyr Phe
1               5                   10

<210> SEQ ID NO 610
<211> LENGTH: 15
<212> TYPE: PRT
<213> ORGANISM: Homo sapiens

<400> SEQUENCE: 610

Cys Ala Ser Ser Leu Arg Gln Gly Tyr Leu Glu Thr Gln Tyr Phe
1               5                   10                  15

<210> SEQ ID NO 611
<211> LENGTH: 15
<212> TYPE: PRT
<213> ORGANISM: Homo sapiens

<400> SEQUENCE: 611

Cys Ala Ser Ser Lys Asn Arg Gly Ser Asn Gln Pro Gln His Phe
1               5                   10                  15

<210> SEQ ID NO 612
<211> LENGTH: 15
<212> TYPE: PRT
<213> ORGANISM: Homo sapiens

<400> SEQUENCE: 612

Cys Ala Ser Ser Tyr Gly Glu Tyr Ser Asn Gln Pro Gln His Phe
1               5                   10                  15

<210> SEQ ID NO 613
<211> LENGTH: 14
<212> TYPE: PRT
<213> ORGANISM: Homo sapiens

<400> SEQUENCE: 613

Cys Ala Ser Ser Arg Pro Ser Ala Ser Tyr Glu Gln Tyr Phe
1               5                   10

<210> SEQ ID NO 614
<211> LENGTH: 13
<212> TYPE: PRT
<213> ORGANISM: Homo sapiens

<400> SEQUENCE: 614

Cys Ala Ser Ser Leu Ile Ala Tyr Asp Glu Gln Phe Phe
1               5                   10

<210> SEQ ID NO 615
<211> LENGTH: 14
<212> TYPE: PRT
<213> ORGANISM: Homo sapiens

<400> SEQUENCE: 615

-continued

Cys Ala Ser Ser Glu Ala Arg Ser Asn Thr Glu Ala Phe Phe
1               5                   10

<210> SEQ ID NO 616
<211> LENGTH: 13
<212> TYPE: PRT
<213> ORGANISM: Homo sapiens

<400> SEQUENCE: 616

Cys Ala Ser Ser Ser Leu Gly Gly Trp Gly Tyr Thr Phe
1               5                   10

<210> SEQ ID NO 617
<211> LENGTH: 11
<212> TYPE: PRT
<213> ORGANISM: Homo sapiens

<400> SEQUENCE: 617

Cys Ala Ser Ser Val Gln Gly Val Ala Phe Phe
1               5                   10

<210> SEQ ID NO 618
<211> LENGTH: 14
<212> TYPE: PRT
<213> ORGANISM: Homo sapiens

<400> SEQUENCE: 618

Cys Ala Ser Ser Tyr Leu His Leu Ser Tyr Glu Gln Tyr Phe
1               5                   10

<210> SEQ ID NO 619
<211> LENGTH: 16
<212> TYPE: PRT
<213> ORGANISM: Homo sapiens

<400> SEQUENCE: 619

Cys Ala Ser Ser Pro Glu Gly Arg Gly Leu Gly Tyr Gly Tyr Thr Phe
1               5                   10                  15

<210> SEQ ID NO 620
<211> LENGTH: 15
<212> TYPE: PRT
<213> ORGANISM: Homo sapiens

<400> SEQUENCE: 620

Cys Ala Ser Ser Pro Ser Gly Gly Ser Ala Asp Thr Gln Tyr Phe
1               5                   10                  15

<210> SEQ ID NO 621
<211> LENGTH: 13
<212> TYPE: PRT
<213> ORGANISM: Homo sapiens

<400> SEQUENCE: 621

Cys Ala Ser Ile Pro Thr Ala Ser Tyr Glu Gln Tyr Phe
1               5                   10

<210> SEQ ID NO 622
<211> LENGTH: 17
<212> TYPE: PRT
<213> ORGANISM: Homo sapiens

<400> SEQUENCE: 622

Cys Ala Ser Ser Leu Gly Leu Arg Thr Gly Gly Ala Asn Val Leu Thr

Phe

<210> SEQ ID NO 623
<211> LENGTH: 14
<212> TYPE: PRT
<213> ORGANISM: Homo sapiens

<400> SEQUENCE: 623

Cys Ala Ser Ser Leu Ala Pro Leu Gly Asp Glu Gln Tyr Phe
1               5                   10

<210> SEQ ID NO 624
<211> LENGTH: 17
<212> TYPE: PRT
<213> ORGANISM: Homo sapiens

<400> SEQUENCE: 624

Cys Ala Ser Ser Ser Pro Val Ala Gly Gly Arg Thr Asp Thr Gln Tyr
1               5                   10                  15

Phe

<210> SEQ ID NO 625
<211> LENGTH: 14
<212> TYPE: PRT
<213> ORGANISM: Homo sapiens

<400> SEQUENCE: 625

Cys Ser Ala Ala Pro Gly Gly Ser Gly Asn Thr Ile Tyr Phe
1               5                   10

<210> SEQ ID NO 626
<211> LENGTH: 13
<212> TYPE: PRT
<213> ORGANISM: Homo sapiens

<400> SEQUENCE: 626

Cys Ala Ser Glu Ala Ser Gly Val Tyr Glu Gln Tyr Phe
1               5                   10

<210> SEQ ID NO 627
<211> LENGTH: 16
<212> TYPE: PRT
<213> ORGANISM: Homo sapiens

<400> SEQUENCE: 627

Cys Ala Ser Ser Leu Asp Gly Val Asp Ser Asn Gln Pro Gln His Phe
1               5                   10                  15

<210> SEQ ID NO 628
<211> LENGTH: 14
<212> TYPE: PRT
<213> ORGANISM: Homo sapiens

<400> SEQUENCE: 628

Cys Ala Ser Ser Leu Arg Asp Arg Ala His Thr Gln Tyr Phe
1               5                   10

<210> SEQ ID NO 629
<211> LENGTH: 13
<212> TYPE: PRT
<213> ORGANISM: Homo sapiens

<400> SEQUENCE: 629

Cys Ser Ala Ser Arg Val Ala Gly Val Glu Gln Phe Phe
1               5                   10

<210> SEQ ID NO 630
<211> LENGTH: 15
<212> TYPE: PRT
<213> ORGANISM: Homo sapiens

<400> SEQUENCE: 630

Cys Ala Ser Arg Arg Gly Gly Pro Ser Tyr Asn Glu Gln Phe Phe
1               5                   10                  15

<210> SEQ ID NO 631
<211> LENGTH: 12
<212> TYPE: PRT
<213> ORGANISM: Homo sapiens

<400> SEQUENCE: 631

Cys Ala Ser Ser Ala Pro Arg Glu Thr Gln Tyr Phe
1               5                   10

<210> SEQ ID NO 632
<211> LENGTH: 14
<212> TYPE: PRT
<213> ORGANISM: Homo sapiens

<400> SEQUENCE: 632

Cys Ala Ser Ser Pro Gly Arg Gly His Glu Lys Leu Phe Phe
1               5                   10

<210> SEQ ID NO 633
<211> LENGTH: 12
<212> TYPE: PRT
<213> ORGANISM: Homo sapiens

<400> SEQUENCE: 633

Cys Ala Ser Ser Asn Arg Gln Glu Thr Gln Tyr Phe
1               5                   10

<210> SEQ ID NO 634
<211> LENGTH: 15
<212> TYPE: PRT
<213> ORGANISM: Homo sapiens

<400> SEQUENCE: 634

Cys Ala Ser Ser Ser His Gly Thr Gly Ala Asp Thr Gln Tyr Phe
1               5                   10                  15

<210> SEQ ID NO 635
<211> LENGTH: 15
<212> TYPE: PRT
<213> ORGANISM: Homo sapiens

<400> SEQUENCE: 635

Cys Ala Ser Ser Arg Gly Gln Gly Glu Gly Gln Pro Gln His Phe
1               5                   10                  15

<210> SEQ ID NO 636
<211> LENGTH: 14
<212> TYPE: PRT
<213> ORGANISM: Homo sapiens

<400> SEQUENCE: 636

Cys Ala Ser Arg Arg Thr Ser Gly Asp Tyr Glu Gln Tyr Val
1               5                   10

```
1               5                   10
```

<210> SEQ ID NO 637
<211> LENGTH: 15
<212> TYPE: PRT
<213> ORGANISM: Homo sapiens

<400> SEQUENCE: 637

```
Cys Ala Ser Ser Trp Arg Asp Arg Gly Thr Tyr Glu Gln Tyr Phe
1               5                   10                  15
```

<210> SEQ ID NO 638
<211> LENGTH: 15
<212> TYPE: PRT
<213> ORGANISM: Homo sapiens

<400> SEQUENCE: 638

```
Cys Ala Ser Ser Leu Gly Glu Ala Ser Thr Asp Thr Gln Tyr Phe
1               5                   10                  15
```

<210> SEQ ID NO 639
<211> LENGTH: 14
<212> TYPE: PRT
<213> ORGANISM: Homo sapiens

<400> SEQUENCE: 639

```
Cys Ala Ser Ser Leu Ala Pro Leu Ser Glu Thr Gln Tyr Phe
1               5                   10
```

<210> SEQ ID NO 640
<211> LENGTH: 13
<212> TYPE: PRT
<213> ORGANISM: Homo sapiens

<400> SEQUENCE: 640

```
Cys Ala Ser Ala Ile Gln Gly Ser Tyr Glu Gln Tyr Phe
1               5                   10
```

<210> SEQ ID NO 641
<211> LENGTH: 15
<212> TYPE: PRT
<213> ORGANISM: Homo sapiens

<400> SEQUENCE: 641

```
Cys Ala Ser Ser Leu Thr Gly Thr Val Asn Glu Lys Leu Phe Phe
1               5                   10                  15
```

<210> SEQ ID NO 642
<211> LENGTH: 13
<212> TYPE: PRT
<213> ORGANISM: Homo sapiens

<400> SEQUENCE: 642

```
Cys Ala Ser Arg Pro Thr Pro Thr Gly Glu Leu Phe Phe
1               5                   10
```

<210> SEQ ID NO 643
<211> LENGTH: 15
<212> TYPE: PRT
<213> ORGANISM: Homo sapiens

<400> SEQUENCE: 643

```
Cys Ala Thr Ser Arg Gly Ala Arg Leu Thr Asp Thr Gln Tyr Phe
1               5                   10                  15
```

<210> SEQ ID NO 644
<211> LENGTH: 18
<212> TYPE: PRT
<213> ORGANISM: Homo sapiens

<400> SEQUENCE: 644

Cys Ala Ser Ser Leu Gly Thr Ser Gly Arg Thr Leu Gln Glu Thr Gln
1               5                   10                  15
Tyr Phe

<210> SEQ ID NO 645
<211> LENGTH: 18
<212> TYPE: PRT
<213> ORGANISM: Homo sapiens

<400> SEQUENCE: 645

Cys Ser Ala Arg Thr Thr Ser Gly Gly Val Leu Ser Thr Asp Thr Gln
1               5                   10                  15
Tyr Phe

<210> SEQ ID NO 646
<211> LENGTH: 15
<212> TYPE: PRT
<213> ORGANISM: Homo sapiens

<400> SEQUENCE: 646

Cys Ala Ile Ser Glu Arg Ser Gly Ser Thr Asp Thr Gln Tyr Phe
1               5                   10                  15

<210> SEQ ID NO 647
<211> LENGTH: 15
<212> TYPE: PRT
<213> ORGANISM: Homo sapiens

<400> SEQUENCE: 647

Cys Ala Ser Ser Ala Gly Gly Gln Gly His Tyr Gly Tyr Thr Phe
1               5                   10                  15

<210> SEQ ID NO 648
<211> LENGTH: 12
<212> TYPE: PRT
<213> ORGANISM: Homo sapiens

<400> SEQUENCE: 648

Cys Ala Ser Ser Glu Arg Gly Glu Thr Gln Tyr Phe
1               5                   10

<210> SEQ ID NO 649
<211> LENGTH: 16
<212> TYPE: PRT
<213> ORGANISM: Homo sapiens

<400> SEQUENCE: 649

Cys Ala Ser Ser Pro Gly Arg Pro Gly Ser Asn Gln Pro Gln His Phe
1               5                   10                  15

<210> SEQ ID NO 650
<211> LENGTH: 13
<212> TYPE: PRT
<213> ORGANISM: Homo sapiens

<400> SEQUENCE: 650

Cys Ser Ala Ser Pro Pro Pro Gln Glu Thr Gln Tyr Phe

```
1               5                    10
```

<210> SEQ ID NO 651
<211> LENGTH: 16
<212> TYPE: PRT
<213> ORGANISM: Homo sapiens

<400> SEQUENCE: 651

```
Cys Ala Ser Ser Leu Glu Gly Leu Ala Val Tyr Asn Glu Gln Phe Phe
1               5                   10                  15
```

<210> SEQ ID NO 652
<211> LENGTH: 15
<212> TYPE: PRT
<213> ORGANISM: Homo sapiens

<400> SEQUENCE: 652

```
Cys Ala Ser Ser Leu Gln Ala Ser Ser Asn Glu Gln Phe Phe
1               5                   10                  15
```

<210> SEQ ID NO 653
<211> LENGTH: 15
<212> TYPE: PRT
<213> ORGANISM: Homo sapiens

<400> SEQUENCE: 653

```
Cys Ala Ser Ser Val Glu Pro Gly Gly Leu Thr Glu Ala Phe Phe
1               5                   10                  15
```

<210> SEQ ID NO 654
<211> LENGTH: 15
<212> TYPE: PRT
<213> ORGANISM: Homo sapiens

<400> SEQUENCE: 654

```
Cys Ser Ala Arg Gly Ala Gly Ala Gly Thr Gly Glu Leu Phe Phe
1               5                   10                  15
```

<210> SEQ ID NO 655
<211> LENGTH: 12
<212> TYPE: PRT
<213> ORGANISM: Homo sapiens

<400> SEQUENCE: 655

```
Cys Ala Trp Asn Gly Ile Asn Glu Lys Leu Phe Phe
1               5                   10
```

<210> SEQ ID NO 656
<211> LENGTH: 15
<212> TYPE: PRT
<213> ORGANISM: Homo sapiens

<400> SEQUENCE: 656

```
Cys Ala Ser Ser Pro Glu Ile Pro Ser Gly Asn Thr Ile Tyr Phe
1               5                   10                  15
```

<210> SEQ ID NO 657
<211> LENGTH: 13
<212> TYPE: PRT
<213> ORGANISM: Homo sapiens

<400> SEQUENCE: 657

```
Cys Ala Ser Ser Ser Val Gly Gly Asn Glu Gln Tyr Phe
1               5                   10
```

<210> SEQ ID NO 658
<211> LENGTH: 13
<212> TYPE: PRT
<213> ORGANISM: Homo sapiens

<400> SEQUENCE: 658

Cys Ala Ser Ser Leu Val Gly Pro Glu Thr Gln Tyr Phe
1               5                   10

<210> SEQ ID NO 659
<211> LENGTH: 13
<212> TYPE: PRT
<213> ORGANISM: Homo sapiens

<400> SEQUENCE: 659

Cys Ala Ser Ser Phe Pro Gly Ser Val Glu Gln Tyr Phe
1               5                   10

<210> SEQ ID NO 660
<211> LENGTH: 14
<212> TYPE: PRT
<213> ORGANISM: Homo sapiens

<400> SEQUENCE: 660

Cys Ala Ser Ser Leu Gly Gly Arg Pro Ser Pro Leu His Phe
1               5                   10

<210> SEQ ID NO 661
<211> LENGTH: 15
<212> TYPE: PRT
<213> ORGANISM: Homo sapiens

<400> SEQUENCE: 661

Cys Ala Ser Ser Tyr Thr Gly Asp Glu Asp Gln Pro Gln His Phe
1               5                   10                  15

<210> SEQ ID NO 662
<211> LENGTH: 18
<212> TYPE: PRT
<213> ORGANISM: Homo sapiens

<400> SEQUENCE: 662

Cys Ala Ser Ser Arg Arg Leu Ala Gly Gly Pro Arg Thr Asp Thr Gln
1               5                   10                  15

Tyr Phe

<210> SEQ ID NO 663
<211> LENGTH: 13
<212> TYPE: PRT
<213> ORGANISM: Homo sapiens

<400> SEQUENCE: 663

Cys Ser Ala Ala Arg Ala Pro Tyr Asn Glu Gln Phe Phe
1               5                   10

<210> SEQ ID NO 664
<211> LENGTH: 13
<212> TYPE: PRT
<213> ORGANISM: Homo sapiens

<400> SEQUENCE: 664

Cys Ala Thr Ser Gly Thr Asp Lys Glu Thr Gln Tyr Phe
1               5                   10

```
<210> SEQ ID NO 665
<211> LENGTH: 15
<212> TYPE: PRT
<213> ORGANISM: Homo sapiens

<400> SEQUENCE: 665

Cys Ser Ala Gly Gly Gln Pro Val Ala Lys Asn Ile Gln Tyr Phe
1               5                   10                  15

<210> SEQ ID NO 666
<211> LENGTH: 16
<212> TYPE: PRT
<213> ORGANISM: Homo sapiens

<400> SEQUENCE: 666

Cys Ala Ser Ser Tyr Ser Val Asn Thr Gly Ala Asn Val Leu Thr Phe
1               5                   10                  15

<210> SEQ ID NO 667
<211> LENGTH: 15
<212> TYPE: PRT
<213> ORGANISM: Homo sapiens

<400> SEQUENCE: 667

Cys Ala Ser Ser Ala Asp Arg Val Trp Asn Gln Pro Gln His Phe
1               5                   10                  15

<210> SEQ ID NO 668
<211> LENGTH: 13
<212> TYPE: PRT
<213> ORGANISM: Homo sapiens

<400> SEQUENCE: 668

Cys Ala Ser Arg Thr Arg Asp Asn Ser Pro Leu His Phe
1               5                   10

<210> SEQ ID NO 669
<211> LENGTH: 14
<212> TYPE: PRT
<213> ORGANISM: Homo sapiens

<400> SEQUENCE: 669

Cys Ala Ser Ser Leu Thr Arg Pro Pro Gly Glu Leu Phe Phe
1               5                   10

<210> SEQ ID NO 670
<211> LENGTH: 12
<212> TYPE: PRT
<213> ORGANISM: Homo sapiens

<400> SEQUENCE: 670

Cys Ala Ser Ser Leu Pro Trp Val Glu Gln Tyr Phe
1               5                   10

<210> SEQ ID NO 671
<211> LENGTH: 15
<212> TYPE: PRT
<213> ORGANISM: Homo sapiens

<400> SEQUENCE: 671

Cys Ala Ser Ser Pro Leu Gly Gly Ala Thr Tyr Gly Tyr Thr Phe
1               5                   10                  15

<210> SEQ ID NO 672
```

```
<211> LENGTH: 15
<212> TYPE: PRT
<213> ORGANISM: Homo sapiens

<400> SEQUENCE: 672

Cys Ala Ser Thr Trp Thr Ser Gly Ser Ser Tyr Glu Gln Tyr Phe
1               5                   10                  15

<210> SEQ ID NO 673
<211> LENGTH: 13
<212> TYPE: PRT
<213> ORGANISM: Homo sapiens

<400> SEQUENCE: 673

Cys Ala Ser Ser Leu Asp Gly Phe Tyr Glu Gln Tyr Phe
1               5                   10

<210> SEQ ID NO 674
<211> LENGTH: 14
<212> TYPE: PRT
<213> ORGANISM: Homo sapiens

<400> SEQUENCE: 674

Cys Ala Ser Arg Arg Arg Thr Gly Val Gln Pro Gln His Phe
1               5                   10

<210> SEQ ID NO 675
<211> LENGTH: 14
<212> TYPE: PRT
<213> ORGANISM: Homo sapiens

<400> SEQUENCE: 675

Cys Ala Thr Ser Val Thr Gly Gly Val Asp Thr Gln Tyr Phe
1               5                   10

<210> SEQ ID NO 676
<211> LENGTH: 15
<212> TYPE: PRT
<213> ORGANISM: Homo sapiens

<400> SEQUENCE: 676

Cys Ser Ala Arg Pro Gly Gly Ser Gly Thr Gly Glu Leu Phe Phe
1               5                   10                  15

<210> SEQ ID NO 677
<211> LENGTH: 13
<212> TYPE: PRT
<213> ORGANISM: Homo sapiens

<400> SEQUENCE: 677

Cys Ser Val Pro Gln Gln Gly Gln Glu Thr Gln Tyr Phe
1               5                   10

<210> SEQ ID NO 678
<211> LENGTH: 14
<212> TYPE: PRT
<213> ORGANISM: Homo sapiens

<400> SEQUENCE: 678

Cys Ala Ser Ser Met Phe Pro Gly Pro Tyr Gly Tyr Thr Phe
1               5                   10

<210> SEQ ID NO 679
<211> LENGTH: 16
<212> TYPE: PRT
```

<213> ORGANISM: Homo sapiens

<400> SEQUENCE: 679

Cys Ala Ser Ser Pro Gln Ala Arg Gly Leu Gly Tyr Gly Tyr Thr Phe
1               5                   10                  15

<210> SEQ ID NO 680
<211> LENGTH: 12
<212> TYPE: PRT
<213> ORGANISM: Homo sapiens

<400> SEQUENCE: 680

Cys Ala Thr Arg Arg Arg Leu Tyr Glu Gln Tyr Phe
1               5                   10

<210> SEQ ID NO 681
<211> LENGTH: 15
<212> TYPE: PRT
<213> ORGANISM: Homo sapiens

<400> SEQUENCE: 681

Cys Ala Ser Ser Pro Ala Ser Gly Asn Thr Gly Glu Leu Phe Phe
1               5                   10                  15

<210> SEQ ID NO 682
<211> LENGTH: 16
<212> TYPE: PRT
<213> ORGANISM: Homo sapiens

<400> SEQUENCE: 682

Cys Ala Ser Ser Gln Ala Leu Ala Gly Gly Tyr Asn Glu Gln Phe Phe
1               5                   10                  15

<210> SEQ ID NO 683
<211> LENGTH: 15
<212> TYPE: PRT
<213> ORGANISM: Homo sapiens

<400> SEQUENCE: 683

Cys Ser Ala Arg Pro Arg Gln Gly Leu Gln Glu Thr Gln Tyr Phe
1               5                   10                  15

<210> SEQ ID NO 684
<211> LENGTH: 14
<212> TYPE: PRT
<213> ORGANISM: Homo sapiens

<400> SEQUENCE: 684

Cys Ala Ser Ser Leu Gly Arg Gly Asp Ser Pro Leu His Phe
1               5                   10

<210> SEQ ID NO 685
<211> LENGTH: 15
<212> TYPE: PRT
<213> ORGANISM: Homo sapiens

<400> SEQUENCE: 685

Cys Ser Ala Arg Gly Leu Ala Phe Thr Tyr Asn Glu Gln Phe Phe
1               5                   10                  15

<210> SEQ ID NO 686
<211> LENGTH: 15
<212> TYPE: PRT
<213> ORGANISM: Homo sapiens

```
<400> SEQUENCE: 686

Cys Ala Ser Ser Leu Ala Ala Lys Pro Asn Thr Glu Ala Phe Phe
1               5                   10                  15

<210> SEQ ID NO 687
<211> LENGTH: 14
<212> TYPE: PRT
<213> ORGANISM: Homo sapiens

<400> SEQUENCE: 687

Cys Ala Ser Ser Ser Thr Asn Ser Asn Gln Pro Gln His Phe
1               5                   10

<210> SEQ ID NO 688
<211> LENGTH: 14
<212> TYPE: PRT
<213> ORGANISM: Homo sapiens

<400> SEQUENCE: 688

Cys Ala Ser Ser Leu Val Ser Ser Thr His Glu Gln Tyr Phe
1               5                   10

<210> SEQ ID NO 689
<211> LENGTH: 15
<212> TYPE: PRT
<213> ORGANISM: Homo sapiens

<400> SEQUENCE: 689

Cys Ala Ser Ser Phe Gly Gln Gly Glu Val Gln Pro Gln His Phe
1               5                   10                  15

<210> SEQ ID NO 690
<211> LENGTH: 15
<212> TYPE: PRT
<213> ORGANISM: Homo sapiens

<400> SEQUENCE: 690

Cys Ala Ser Ser Phe Glu Val Asn Tyr Asn Ser Pro Leu His Phe
1               5                   10                  15

<210> SEQ ID NO 691
<211> LENGTH: 14
<212> TYPE: PRT
<213> ORGANISM: Homo sapiens

<400> SEQUENCE: 691

Cys Ala Ser Ser Leu Asp Thr Arg Ser Arg Glu Gln Tyr Phe
1               5                   10

<210> SEQ ID NO 692
<211> LENGTH: 16
<212> TYPE: PRT
<213> ORGANISM: Homo sapiens

<400> SEQUENCE: 692

Cys Ser Ala Arg Asp Arg Asp Arg Gly His Gly Asn Thr Ile Tyr Phe
1               5                   10                  15

<210> SEQ ID NO 693
<211> LENGTH: 16
<212> TYPE: PRT
<213> ORGANISM: Homo sapiens

<400> SEQUENCE: 693
```

Cys Ala Ser Ser Leu Ala Arg Leu Arg Ser Ala Gly Glu Leu Phe Phe
1               5                   10                  15

<210> SEQ ID NO 694
<211> LENGTH: 11
<212> TYPE: PRT
<213> ORGANISM: Homo sapiens

<400> SEQUENCE: 694

Cys Ala Ser Ser Tyr Ser Ser Gly Tyr Thr Phe
1               5                   10

<210> SEQ ID NO 695
<211> LENGTH: 14
<212> TYPE: PRT
<213> ORGANISM: Homo sapiens

<400> SEQUENCE: 695

Cys Ala Ile Ser Glu Ser Thr Tyr Gln Glu Thr Gln Tyr Phe
1               5                   10

<210> SEQ ID NO 696
<211> LENGTH: 14
<212> TYPE: PRT
<213> ORGANISM: Homo sapiens

<400> SEQUENCE: 696

Cys Ala Ser Ser Val Arg Arg Phe Gln Glu Thr Gln Tyr Phe
1               5                   10

<210> SEQ ID NO 697
<211> LENGTH: 13
<212> TYPE: PRT
<213> ORGANISM: Homo sapiens

<400> SEQUENCE: 697

Cys Ala Trp Gly Arg Arg Gly Arg Tyr Glu Gln Tyr Phe
1               5                   10

<210> SEQ ID NO 698
<211> LENGTH: 12
<212> TYPE: PRT
<213> ORGANISM: Homo sapiens

<400> SEQUENCE: 698

Cys Ser Ala Asp Arg Val Thr His Glu Gln Tyr Phe
1               5                   10

<210> SEQ ID NO 699
<211> LENGTH: 13
<212> TYPE: PRT
<213> ORGANISM: Homo sapiens

<400> SEQUENCE: 699

Cys Ala Trp Thr Arg Gly Thr Pro Asp Thr Gln Tyr Phe
1               5                   10

<210> SEQ ID NO 700
<211> LENGTH: 14
<212> TYPE: PRT
<213> ORGANISM: Homo sapiens

<400> SEQUENCE: 700

Cys Ala Ser Ser Tyr Leu Ala Leu Ser Tyr Glu Gln Tyr Phe
1               5                   10

<210> SEQ ID NO 701
<211> LENGTH: 16
<212> TYPE: PRT
<213> ORGANISM: Homo sapiens

<400> SEQUENCE: 701

Cys Ala Ser Ser Leu Arg Gln Gly Arg Gly Asn Gln Pro Gln His Phe
1               5                   10                  15

<210> SEQ ID NO 702
<211> LENGTH: 15
<212> TYPE: PRT
<213> ORGANISM: Homo sapiens

<400> SEQUENCE: 702

Cys Ser Ala Arg Gly Ser Gly Arg Ser Ser Asp Thr Gln Tyr Phe
1               5                   10                  15

<210> SEQ ID NO 703
<211> LENGTH: 12
<212> TYPE: PRT
<213> ORGANISM: Homo sapiens

<400> SEQUENCE: 703

Cys Ala Ile Ser Gly Gly Pro Glu Glu Gln Tyr Phe
1               5                   10

<210> SEQ ID NO 704
<211> LENGTH: 15
<212> TYPE: PRT
<213> ORGANISM: Homo sapiens

<400> SEQUENCE: 704

Cys Ala Ser Ser Gln Pro Ser Pro Ser Thr Asp Thr Gln Tyr Phe
1               5                   10                  15

<210> SEQ ID NO 705
<211> LENGTH: 13
<212> TYPE: PRT
<213> ORGANISM: Homo sapiens

<400> SEQUENCE: 705

Cys Ala Ser Ser Leu Glu Gly Asp Thr Glu Ala Phe Phe
1               5                   10

<210> SEQ ID NO 706
<211> LENGTH: 13
<212> TYPE: PRT
<213> ORGANISM: Homo sapiens

<400> SEQUENCE: 706

Cys Ala Ser Ser Gln Asp Leu Thr Arg Glu Ala Phe Phe
1               5                   10

<210> SEQ ID NO 707
<211> LENGTH: 14
<212> TYPE: PRT
<213> ORGANISM: Homo sapiens

<400> SEQUENCE: 707

Cys Ala Ser Ser Arg Thr Arg Thr Ser Tyr Glu Gln Tyr Phe
1               5                   10

```
<210> SEQ ID NO 708
<211> LENGTH: 16
<212> TYPE: PRT
<213> ORGANISM: Homo sapiens

<400> SEQUENCE: 708

Cys Ala Ser Ser Arg Gly Trp Thr Ser Gly Ser Tyr Glu Gln Tyr Phe
1               5                   10                  15

<210> SEQ ID NO 709
<211> LENGTH: 13
<212> TYPE: PRT
<213> ORGANISM: Homo sapiens

<400> SEQUENCE: 709

Cys Ala Ser Ser Pro Pro Asp Glu Asn Thr Gln Tyr Phe
1               5                   10

<210> SEQ ID NO 710
<211> LENGTH: 17
<212> TYPE: PRT
<213> ORGANISM: Homo sapiens

<400> SEQUENCE: 710

Cys Ala Ser Ser Leu Ala Pro Arg Asp Arg Gly Asn Gln Pro Gln His
1               5                   10                  15

Phe

<210> SEQ ID NO 711
<211> LENGTH: 15
<212> TYPE: PRT
<213> ORGANISM: Homo sapiens

<400> SEQUENCE: 711

Cys Ala Ser Ser Thr Gln Gly Gly Gly Thr Asp Thr Gln Tyr Phe
1               5                   10                  15

<210> SEQ ID NO 712
<211> LENGTH: 15
<212> TYPE: PRT
<213> ORGANISM: Homo sapiens

<400> SEQUENCE: 712

Cys Ser Ala Arg Leu Ala Gly Ala Gly Thr Gly Glu Leu Phe Phe
1               5                   10                  15

<210> SEQ ID NO 713
<211> LENGTH: 13
<212> TYPE: PRT
<213> ORGANISM: Homo sapiens

<400> SEQUENCE: 713

Cys Ala Ser Ser Ser Asp Arg Asp Gly Glu Ala Phe Phe
1               5                   10

<210> SEQ ID NO 714
<211> LENGTH: 15
<212> TYPE: PRT
<213> ORGANISM: Homo sapiens

<400> SEQUENCE: 714

Cys Ser Ala Arg Ser Val Pro Thr Asn Thr Gly Glu Leu Phe Phe
1               5                   10                  15
```

```
<210> SEQ ID NO 715
<211> LENGTH: 16
<212> TYPE: PRT
<213> ORGANISM: Homo sapiens

<400> SEQUENCE: 715

Cys Ala Ser Ser Pro Pro Arg Gly Pro Thr Tyr Asn Glu Gln Phe Phe
1               5                   10                  15

<210> SEQ ID NO 716
<211> LENGTH: 15
<212> TYPE: PRT
<213> ORGANISM: Homo sapiens

<400> SEQUENCE: 716

Cys Ala Ser Ser Pro Arg Asp Asn Gln Asn Thr Glu Ala Phe Phe
1               5                   10                  15

<210> SEQ ID NO 717
<211> LENGTH: 14
<212> TYPE: PRT
<213> ORGANISM: Homo sapiens

<400> SEQUENCE: 717

Cys Ala Ser Ser Thr Gly Thr Gln Tyr Tyr Glu Gln Tyr Phe
1               5                   10

<210> SEQ ID NO 718
<211> LENGTH: 12
<212> TYPE: PRT
<213> ORGANISM: Homo sapiens

<400> SEQUENCE: 718

Cys Ala Ser Ser Gln Gly Leu Asp Glu Gln Tyr Phe
1               5                   10

<210> SEQ ID NO 719
<211> LENGTH: 16
<212> TYPE: PRT
<213> ORGANISM: Homo sapiens

<400> SEQUENCE: 719

Cys Ala Thr Ser Arg Ala Ser Arg Val Ser Asn Gln Pro Gln His Phe
1               5                   10                  15

<210> SEQ ID NO 720
<211> LENGTH: 16
<212> TYPE: PRT
<213> ORGANISM: Homo sapiens

<400> SEQUENCE: 720

Cys Ala Ser Ser Gln Glu Gly Ser Gly Gly Ser Tyr Glu Gln Phe Phe
1               5                   10                  15

<210> SEQ ID NO 721
<211> LENGTH: 17
<212> TYPE: PRT
<213> ORGANISM: Homo sapiens

<400> SEQUENCE: 721

Cys Ser Ala Thr Gly Leu Ala Gly Asp Arg Ser Ser Tyr Glu Gln Tyr
1               5                   10                  15

Phe
```

```
<210> SEQ ID NO 722
<211> LENGTH: 12
<212> TYPE: PRT
<213> ORGANISM: Homo sapiens

<400> SEQUENCE: 722

Cys Ser Ala Ser Pro Glu Gly Asp Thr Gln Tyr Phe
1               5                   10

<210> SEQ ID NO 723
<211> LENGTH: 14
<212> TYPE: PRT
<213> ORGANISM: Homo sapiens

<400> SEQUENCE: 723

Cys Ala Ser Ile Pro Gly Leu Ser Tyr Asn Glu Gln Phe Phe
1               5                   10

<210> SEQ ID NO 724
<211> LENGTH: 12
<212> TYPE: PRT
<213> ORGANISM: Homo sapiens

<400> SEQUENCE: 724

Cys Ser Ala Ser Asn Gln Asn Gln Pro Gln His Phe
1               5                   10

<210> SEQ ID NO 725
<211> LENGTH: 17
<212> TYPE: PRT
<213> ORGANISM: Homo sapiens

<400> SEQUENCE: 725

Cys Ala Ser Ser Pro Gly Ala Ser Gly Gly Ala Lys Glu Thr Gln Tyr
1               5                   10                  15

Phe

<210> SEQ ID NO 726
<211> LENGTH: 15
<212> TYPE: PRT
<213> ORGANISM: Homo sapiens

<400> SEQUENCE: 726

Cys Ser Ala Arg Gly Gln Pro Thr Asn Thr Gly Glu Leu Phe Phe
1               5                   10                  15

<210> SEQ ID NO 727
<211> LENGTH: 13
<212> TYPE: PRT
<213> ORGANISM: Homo sapiens

<400> SEQUENCE: 727

Cys Ala Ser Ile Arg Pro Asn Thr Gly Glu Leu Phe Phe
1               5                   10

<210> SEQ ID NO 728
<211> LENGTH: 14
<212> TYPE: PRT
<213> ORGANISM: Homo sapiens

<400> SEQUENCE: 728

Cys Ala Ser Ser Ser Tyr Arg Glu Tyr Thr Glu Ala Phe Phe
1               5                   10
```

```
<210> SEQ ID NO 729
<211> LENGTH: 13
<212> TYPE: PRT
<213> ORGANISM: Homo sapiens

<400> SEQUENCE: 729

Cys Ser Ala Arg Asn Glu Gly Pro Glu Thr Gln Tyr Phe
1               5                   10

<210> SEQ ID NO 730
<211> LENGTH: 14
<212> TYPE: PRT
<213> ORGANISM: Homo sapiens

<400> SEQUENCE: 730

Cys Ala Ser Ser Phe Leu Thr Val Pro Tyr Glu Gln Tyr Phe
1               5                   10

<210> SEQ ID NO 731
<211> LENGTH: 11
<212> TYPE: PRT
<213> ORGANISM: Homo sapiens

<400> SEQUENCE: 731

Cys Ser Val Arg Val Ala Asn Glu Gln Phe Phe
1               5                   10

<210> SEQ ID NO 732
<211> LENGTH: 16
<212> TYPE: PRT
<213> ORGANISM: Homo sapiens

<400> SEQUENCE: 732

Cys Ala Ser Ser Gln Glu Ser Gly Thr Tyr Asn Ser Pro Leu His Phe
1               5                   10                  15

<210> SEQ ID NO 733
<211> LENGTH: 14
<212> TYPE: PRT
<213> ORGANISM: Homo sapiens

<400> SEQUENCE: 733

Cys Ala Ser Ser Pro Ile Ala Arg Asn Thr Glu Ala Phe Phe
1               5                   10

<210> SEQ ID NO 734
<211> LENGTH: 13
<212> TYPE: PRT
<213> ORGANISM: Homo sapiens

<400> SEQUENCE: 734

Cys Ala Ser Lys Arg Gln Gly Ala Tyr Glu Gln Tyr Phe
1               5                   10

<210> SEQ ID NO 735
<211> LENGTH: 15
<212> TYPE: PRT
<213> ORGANISM: Homo sapiens

<400> SEQUENCE: 735

Cys Ala Thr Ser Arg Glu Ala Gly Gly His Glu Lys Leu Phe Phe
1               5                   10                  15

<210> SEQ ID NO 736
<211> LENGTH: 13
```

<212> TYPE: PRT
<213> ORGANISM: Homo sapiens

<400> SEQUENCE: 736

Cys Ala Ser Ser Pro Val Gly Pro Tyr Gly Tyr Thr Phe
1               5                   10

<210> SEQ ID NO 737
<211> LENGTH: 14
<212> TYPE: PRT
<213> ORGANISM: Homo sapiens

<400> SEQUENCE: 737

Cys Ala Ser Ser Glu Leu Gly Leu Asn Thr Glu Ala Phe Phe
1               5                   10

<210> SEQ ID NO 738
<211> LENGTH: 13
<212> TYPE: PRT
<213> ORGANISM: Homo sapiens

<400> SEQUENCE: 738

Cys Ala Ile Ser Glu Leu Arg Gln Glu Thr Gln Tyr Phe
1               5                   10

<210> SEQ ID NO 739
<211> LENGTH: 14
<212> TYPE: PRT
<213> ORGANISM: Homo sapiens

<400> SEQUENCE: 739

Cys Ala Ser Ser Leu Val Gly Trp Asp Thr Glu Ala Phe Phe
1               5                   10

<210> SEQ ID NO 740
<211> LENGTH: 14
<212> TYPE: PRT
<213> ORGANISM: Homo sapiens

<400> SEQUENCE: 740

Cys Ala Ser Ser Leu Gln Gly Gln Asn Glu Lys Leu Phe Phe
1               5                   10

<210> SEQ ID NO 741
<211> LENGTH: 13
<212> TYPE: PRT
<213> ORGANISM: Homo sapiens

<400> SEQUENCE: 741

Cys Ser Ala Leu Arg Ala Pro Tyr Asn Glu Gln Phe Phe
1               5                   10

<210> SEQ ID NO 742
<211> LENGTH: 12
<212> TYPE: PRT
<213> ORGANISM: Homo sapiens

<400> SEQUENCE: 742

Cys Ser Ala Ser Ser Val Glu Asp Glu Gln Phe Phe
1               5                   10

<210> SEQ ID NO 743
<211> LENGTH: 14
<212> TYPE: PRT
<213> ORGANISM: Homo sapiens

```
<400> SEQUENCE: 743

Cys Ala Ser Thr Ser Leu Gly Arg Asn Tyr Gly Tyr Thr Phe
1               5                   10

<210> SEQ ID NO 744
<211> LENGTH: 15
<212> TYPE: PRT
<213> ORGANISM: Homo sapiens

<400> SEQUENCE: 744

Cys Ser Ala Lys Thr Gly Gly Asp Gly Thr Gly Glu Leu Phe Phe
1               5                   10                  15

<210> SEQ ID NO 745
<211> LENGTH: 15
<212> TYPE: PRT
<213> ORGANISM: Homo sapiens

<400> SEQUENCE: 745

Cys Ser Ala Arg Asp Lys Thr Gly Phe Arg Tyr Gly Tyr Thr Phe
1               5                   10                  15

<210> SEQ ID NO 746
<211> LENGTH: 16
<212> TYPE: PRT
<213> ORGANISM: Homo sapiens

<400> SEQUENCE: 746

Cys Ala Ser Ser Phe Gly Leu Ala Gly Asp Pro Asp Thr Gln Tyr Phe
1               5                   10                  15

<210> SEQ ID NO 747
<211> LENGTH: 16
<212> TYPE: PRT
<213> ORGANISM: Homo sapiens

<400> SEQUENCE: 747

Cys Ala Ser Ser Arg Gly Gly Gly Ser Pro Gln Glu Thr Gln Tyr Phe
1               5                   10                  15

<210> SEQ ID NO 748
<211> LENGTH: 15
<212> TYPE: PRT
<213> ORGANISM: Homo sapiens

<400> SEQUENCE: 748

Cys Ala Ser Ser Gly Ser Gly Gly Arg Ser Tyr Glu Gln Tyr Phe
1               5                   10                  15

<210> SEQ ID NO 749
<211> LENGTH: 16
<212> TYPE: PRT
<213> ORGANISM: Homo sapiens

<400> SEQUENCE: 749

Cys Ala Ser Ser Lys Gly Leu Ala Glu Ile Ser Tyr Glu Gln Tyr Phe
1               5                   10                  15

<210> SEQ ID NO 750
<211> LENGTH: 15
<212> TYPE: PRT
<213> ORGANISM: Homo sapiens

<400> SEQUENCE: 750
```

Cys Ala Ser Ser Pro Arg Asp Ser Gln Asn Thr Glu Ala Phe Phe
1               5                   10                  15

<210> SEQ ID NO 751
<211> LENGTH: 14
<212> TYPE: PRT
<213> ORGANISM: Homo sapiens

<400> SEQUENCE: 751

Cys Ala Ser Ser Tyr Leu Thr Leu Ser Tyr Glu Gln Tyr Phe
1               5                   10

<210> SEQ ID NO 752
<211> LENGTH: 13
<212> TYPE: PRT
<213> ORGANISM: Homo sapiens

<400> SEQUENCE: 752

Cys Ser Ala Gly Leu Ala Pro Tyr Asn Glu Gln Phe Phe
1               5                   10

<210> SEQ ID NO 753
<211> LENGTH: 15
<212> TYPE: PRT
<213> ORGANISM: Homo sapiens

<400> SEQUENCE: 753

Cys Ser Ala Arg Ala Ala Gly Gly Thr Gly Glu Leu Phe Phe
1               5                   10                  15

<210> SEQ ID NO 754
<211> LENGTH: 15
<212> TYPE: PRT
<213> ORGANISM: Homo sapiens

<400> SEQUENCE: 754

Cys Ser Ala Arg Phe Ser Gly Gly Gly Thr Gly Glu Leu Phe Phe
1               5                   10                  15

<210> SEQ ID NO 755
<211> LENGTH: 13
<212> TYPE: PRT
<213> ORGANISM: Homo sapiens

<400> SEQUENCE: 755

Cys Ala Ser Asn Gly Trp Glu Asn Thr Glu Ala Phe Phe
1               5                   10

<210> SEQ ID NO 756
<211> LENGTH: 16
<212> TYPE: PRT
<213> ORGANISM: Homo sapiens

<400> SEQUENCE: 756

Cys Ala Ser Ser Pro Gly Leu Ala Gly Arg Thr Asp Thr Gln Tyr Phe
1               5                   10                  15

<210> SEQ ID NO 757
<211> LENGTH: 15
<212> TYPE: PRT
<213> ORGANISM: Homo sapiens

<400> SEQUENCE: 757

Cys Ala Ser Ser Gln Glu Gly Ala Gly Ser Tyr Glu Gln Tyr Phe

-continued

```
1               5                  10                  15
```

```
<210> SEQ ID NO 758
<211> LENGTH: 14
<212> TYPE: PRT
<213> ORGANISM: Homo sapiens

<400> SEQUENCE: 758
```

Cys Ala Ser Ser Glu Asn Arg Val Glu Glu Thr Gln Tyr Phe
1               5                   10

```
<210> SEQ ID NO 759
<211> LENGTH: 14
<212> TYPE: PRT
<213> ORGANISM: Homo sapiens

<400> SEQUENCE: 759
```

Cys Ala Ser Ser Leu Leu Ala Met Gly Glu Thr Gln Tyr Phe
1               5                   10

```
<210> SEQ ID NO 760
<211> LENGTH: 16
<212> TYPE: PRT
<213> ORGANISM: Homo sapiens

<400> SEQUENCE: 760
```

Cys Ala Ser Ser Ile Ala Pro Gly Asp Ser Tyr Asn Glu Gln Phe Phe
1               5                   10                  15

```
<210> SEQ ID NO 761
<211> LENGTH: 13
<212> TYPE: PRT
<213> ORGANISM: Homo sapiens

<400> SEQUENCE: 761
```

Cys Ser Ala Pro Gly Val Pro Tyr Asn Glu Gln Phe Phe
1               5                   10

```
<210> SEQ ID NO 762
<211> LENGTH: 13
<212> TYPE: PRT
<213> ORGANISM: Homo sapiens

<400> SEQUENCE: 762
```

Cys Ala Ile Arg Gln Gly Gln Thr Tyr Glu Gln Tyr Phe
1               5                   10

```
<210> SEQ ID NO 763
<211> LENGTH: 13
<212> TYPE: PRT
<213> ORGANISM: Homo sapiens

<400> SEQUENCE: 763
```

Cys Ala Ile Arg Glu Gly Gln Glu Glu Thr Gln Tyr Phe
1               5                   10

```
<210> SEQ ID NO 764
<211> LENGTH: 14
<212> TYPE: PRT
<213> ORGANISM: Homo sapiens

<400> SEQUENCE: 764
```

Cys Ala Ser Ser Phe Arg Asp Leu Ile Tyr Gly Tyr Thr Phe
1               5                   10

<210> SEQ ID NO 765
<211> LENGTH: 14
<212> TYPE: PRT
<213> ORGANISM: Homo sapiens

<400> SEQUENCE: 765

Cys Ser Val Glu Glu Val Gln Gly Ala Gly Gly Tyr Thr Phe
1               5                   10

<210> SEQ ID NO 766
<211> LENGTH: 14
<212> TYPE: PRT
<213> ORGANISM: Homo sapiens

<400> SEQUENCE: 766

Cys Ser Ala Arg Leu Gly Thr Pro Gln Glu Thr Gln Tyr Phe
1               5                   10

<210> SEQ ID NO 767
<211> LENGTH: 15
<212> TYPE: PRT
<213> ORGANISM: Homo sapiens

<400> SEQUENCE: 767

Cys Ser Ala Arg Val Gly Gly Ser Gly Thr Gly Glu Leu Phe Phe
1               5                   10                  15

<210> SEQ ID NO 768
<211> LENGTH: 13
<212> TYPE: PRT
<213> ORGANISM: Homo sapiens

<400> SEQUENCE: 768

Cys Ala Ser Arg Gln Gly Lys Ala Gly Glu Leu Phe Phe
1               5                   10

<210> SEQ ID NO 769
<211> LENGTH: 15
<212> TYPE: PRT
<213> ORGANISM: Homo sapiens

<400> SEQUENCE: 769

Cys Ala Ser Ser Phe Gly Gln Gly Glu Ala Gly Glu Leu Phe Phe
1               5                   10                  15

<210> SEQ ID NO 770
<211> LENGTH: 13
<212> TYPE: PRT
<213> ORGANISM: Homo sapiens

<400> SEQUENCE: 770

Cys Ala Thr Arg Arg Gly Thr Thr Asp Thr Gln Tyr Phe
1               5                   10

<210> SEQ ID NO 771
<211> LENGTH: 13
<212> TYPE: PRT
<213> ORGANISM: Homo sapiens

<400> SEQUENCE: 771

Cys Ala Gly Ser Leu Ser Ser Asn Gln Pro Gln His Phe
1               5                   10

<210> SEQ ID NO 772

```
<210> SEQ ID NO 772
<211> LENGTH: 13
<212> TYPE: PRT
<213> ORGANISM: Homo sapiens

<400> SEQUENCE: 772

Cys Ala Ser Ser Gln Trp Arg Gly Asp Glu Gln Tyr Phe
1               5                   10

<210> SEQ ID NO 773
<211> LENGTH: 15
<212> TYPE: PRT
<213> ORGANISM: Homo sapiens

<400> SEQUENCE: 773

Cys Ala Ser Ser Leu Gly Gln Gly Gly Arg Tyr Gly Tyr Thr Phe
1               5                   10                  15

<210> SEQ ID NO 774
<211> LENGTH: 15
<212> TYPE: PRT
<213> ORGANISM: Homo sapiens

<400> SEQUENCE: 774

Cys Ser Ala Arg Ser Gly Gly Ala Gly Thr Gly Glu Leu Phe Phe
1               5                   10                  15

<210> SEQ ID NO 775
<211> LENGTH: 12
<212> TYPE: PRT
<213> ORGANISM: Homo sapiens

<400> SEQUENCE: 775

Cys Ala Ser Ser Pro Val Pro Ser Gly Tyr Thr Phe
1               5                   10

<210> SEQ ID NO 776
<211> LENGTH: 14
<212> TYPE: PRT
<213> ORGANISM: Homo sapiens

<400> SEQUENCE: 776

Cys Ser Ala Ser Thr Gly Ser Thr Asn Glu Lys Leu Phe Phe
1               5                   10

<210> SEQ ID NO 777
<211> LENGTH: 10
<212> TYPE: PRT
<213> ORGANISM: Homo sapiens

<400> SEQUENCE: 777

Cys Ala Ala Gly Leu Glu Thr Gln Tyr Phe
1               5                   10

<210> SEQ ID NO 778
<211> LENGTH: 15
<212> TYPE: PRT
<213> ORGANISM: Homo sapiens

<400> SEQUENCE: 778

Cys Ala Ser Ser Pro Asp Gln Gly Ala Asn Tyr Gly Tyr Thr Phe
1               5                   10                  15

<210> SEQ ID NO 779
<211> LENGTH: 15
<212> TYPE: PRT
```

```
<213> ORGANISM: Homo sapiens

<400> SEQUENCE: 779

Cys Ser Ala Arg Arg Gly Gly Ala Gly Thr Gly Glu Leu Phe Phe
1               5                   10                  15

<210> SEQ ID NO 780
<211> LENGTH: 13
<212> TYPE: PRT
<213> ORGANISM: Homo sapiens

<400> SEQUENCE: 780

Cys Ser Ala Pro Arg Pro Pro His Asn Glu Gln Phe Phe
1               5                   10

<210> SEQ ID NO 781
<211> LENGTH: 11
<212> TYPE: PRT
<213> ORGANISM: Homo sapiens

<400> SEQUENCE: 781

Cys Ser Ala Arg Ala Val Val Glu Gln Tyr Phe
1               5                   10

<210> SEQ ID NO 782
<211> LENGTH: 13
<212> TYPE: PRT
<213> ORGANISM: Homo sapiens

<400> SEQUENCE: 782

Cys Ala Ser Arg Arg Asp Arg Gly Asp Ile Gln Tyr Phe
1               5                   10

<210> SEQ ID NO 783
<211> LENGTH: 15
<212> TYPE: PRT
<213> ORGANISM: Homo sapiens

<400> SEQUENCE: 783

Cys Ser Ala Pro Phe Pro Gly Gln Gly Tyr Asn Glu Gln Phe Phe
1               5                   10                  15

<210> SEQ ID NO 784
<211> LENGTH: 15
<212> TYPE: PRT
<213> ORGANISM: Homo sapiens

<400> SEQUENCE: 784

Cys Ala Ser Ser Leu Glu Leu Ala Asn Thr Gly Glu Leu Phe Phe
1               5                   10                  15

<210> SEQ ID NO 785
<211> LENGTH: 15
<212> TYPE: PRT
<213> ORGANISM: Homo sapiens

<400> SEQUENCE: 785

Cys Ala Ser Ser Pro Leu Gly Ser Leu Thr Tyr Glu Gln Tyr Phe
1               5                   10                  15

<210> SEQ ID NO 786
<211> LENGTH: 14
<212> TYPE: PRT
<213> ORGANISM: Homo sapiens
```

```
<400> SEQUENCE: 786

Cys Ala Ser Ser Leu Asp Ser Arg Ser Glu Thr Gln Tyr Phe
1               5                   10

<210> SEQ ID NO 787
<211> LENGTH: 12
<212> TYPE: PRT
<213> ORGANISM: Homo sapiens

<400> SEQUENCE: 787

Cys Ser Ala Ala Gln Asp Glu Glu Thr Gln Tyr Phe
1               5                   10

<210> SEQ ID NO 788
<211> LENGTH: 15
<212> TYPE: PRT
<213> ORGANISM: Homo sapiens

<400> SEQUENCE: 788

Cys Ala Ser Ser Leu Asn Gln Gly Ala Leu Ser Glu Gln Tyr Phe
1               5                   10                  15

<210> SEQ ID NO 789
<211> LENGTH: 14
<212> TYPE: PRT
<213> ORGANISM: Homo sapiens

<400> SEQUENCE: 789

Cys Ala Ser Ser Ile Tyr Ser Gly Ala Tyr Glu Gln Tyr Phe
1               5                   10

<210> SEQ ID NO 790
<211> LENGTH: 17
<212> TYPE: PRT
<213> ORGANISM: Homo sapiens

<400> SEQUENCE: 790

Cys Ala Ser Ser Gln Asp Leu Ala Gly Arg Asn Tyr Asn Glu Gln Phe
1               5                   10                  15

Phe

<210> SEQ ID NO 791
<211> LENGTH: 14
<212> TYPE: PRT
<213> ORGANISM: Homo sapiens

<400> SEQUENCE: 791

Cys Ala Ser Ser Ser Gly Arg Gly Asn Glu Lys Leu Phe Phe
1               5                   10

<210> SEQ ID NO 792
<211> LENGTH: 13
<212> TYPE: PRT
<213> ORGANISM: Homo sapiens

<400> SEQUENCE: 792

Cys Ala Ser Ala Pro Gly Gln Asn Thr Glu Ala Phe Phe
1               5                   10

<210> SEQ ID NO 793
<211> LENGTH: 12
<212> TYPE: PRT
<213> ORGANISM: Homo sapiens
```

<400> SEQUENCE: 793

Cys Ala Ser Arg Tyr Arg Asp Gln Gly Tyr Thr Phe
1               5                   10

<210> SEQ ID NO 794
<211> LENGTH: 14
<212> TYPE: PRT
<213> ORGANISM: Homo sapiens

<400> SEQUENCE: 794

Cys Ala Ser Ser Asp Ser Gly Ser Ser Asp Thr Gln Tyr Phe
1               5                   10

<210> SEQ ID NO 795
<211> LENGTH: 11
<212> TYPE: PRT
<213> ORGANISM: Homo sapiens

<400> SEQUENCE: 795

Cys Ser Ala Arg Asp Glu Gly Arg Gln Phe Phe
1               5                   10

<210> SEQ ID NO 796
<211> LENGTH: 14
<212> TYPE: PRT
<213> ORGANISM: Homo sapiens

<400> SEQUENCE: 796

Cys Ala Ser Ser Ile Gly Arg Gly Asp Ser Pro Leu His Phe
1               5                   10

<210> SEQ ID NO 797
<211> LENGTH: 16
<212> TYPE: PRT
<213> ORGANISM: Homo sapiens

<400> SEQUENCE: 797

Cys Ala Ser Ser Tyr Gln Thr Gly Gly Gly Tyr Asn Glu Gln Phe Phe
1               5                   10                  15

<210> SEQ ID NO 798
<211> LENGTH: 15
<212> TYPE: PRT
<213> ORGANISM: Homo sapiens

<400> SEQUENCE: 798

Cys Ala Ser Ser Pro Thr Glu Pro Ser Gly Asn Thr Ile Tyr Phe
1               5                   10                  15

<210> SEQ ID NO 799
<211> LENGTH: 14
<212> TYPE: PRT
<213> ORGANISM: Homo sapiens

<400> SEQUENCE: 799

Cys Ala Ser Ser Ile Asn Ala Gly Asn Tyr Gly Tyr Thr Phe
1               5                   10

<210> SEQ ID NO 800
<211> LENGTH: 14
<212> TYPE: PRT
<213> ORGANISM: Homo sapiens

<400> SEQUENCE: 800

Cys Ala Ser Ser Gly Thr Gly Ala Lys Asn Ile Gln Tyr Phe
1               5                   10

<210> SEQ ID NO 801
<211> LENGTH: 14
<212> TYPE: PRT
<213> ORGANISM: Homo sapiens

<400> SEQUENCE: 801

Cys Ala Thr Ser Gly Thr Gly Ile Pro Gly Glu Leu Phe Phe
1               5                   10

<210> SEQ ID NO 802
<211> LENGTH: 14
<212> TYPE: PRT
<213> ORGANISM: Homo sapiens

<400> SEQUENCE: 802

Cys Ala Ser Met Thr Gly Thr Gly Asn Glu Lys Leu Phe Phe
1               5                   10

<210> SEQ ID NO 803
<211> LENGTH: 15
<212> TYPE: PRT
<213> ORGANISM: Homo sapiens

<400> SEQUENCE: 803

Cys Ala Ser Ser Pro Trp Arg Glu Val Asn Thr Glu Ala Phe Phe
1               5                   10                  15

<210> SEQ ID NO 804
<211> LENGTH: 11
<212> TYPE: PRT
<213> ORGANISM: Homo sapiens

<400> SEQUENCE: 804

Cys Ser Ala Arg Arg Val Thr Glu Gln Tyr Phe
1               5                   10

<210> SEQ ID NO 805
<211> LENGTH: 15
<212> TYPE: PRT
<213> ORGANISM: Homo sapiens

<400> SEQUENCE: 805

Cys Ala Ser Ser Thr Asp Gly Thr Gly Asp Thr Glu Ala Phe Phe
1               5                   10                  15

<210> SEQ ID NO 806
<211> LENGTH: 15
<212> TYPE: PRT
<213> ORGANISM: Homo sapiens

<400> SEQUENCE: 806

Cys Ala Ser Ser Ser Ile Arg Ser Gly Ala Asn Val Leu Thr Phe
1               5                   10                  15

<210> SEQ ID NO 807
<211> LENGTH: 17
<212> TYPE: PRT
<213> ORGANISM: Homo sapiens

<400> SEQUENCE: 807

Cys Ala Ser Ser Gln Gly Leu Ala Gly Pro Arg Asp Asn Glu Gln Phe
1               5                   10                  15

Phe

<210> SEQ ID NO 808
<211> LENGTH: 13
<212> TYPE: PRT
<213> ORGANISM: Homo sapiens

<400> SEQUENCE: 808

Cys Ser Ala Lys Gly Gly Gly Pro Asp Thr Gln Tyr Phe
1               5                   10

<210> SEQ ID NO 809
<211> LENGTH: 13
<212> TYPE: PRT
<213> ORGANISM: Homo sapiens

<400> SEQUENCE: 809

Cys Ser Ala Pro Leu Ser Leu Asn Thr Glu Ala Phe Phe
1               5                   10

<210> SEQ ID NO 810
<211> LENGTH: 13
<212> TYPE: PRT
<213> ORGANISM: Homo sapiens

<400> SEQUENCE: 810

Cys Ser Ala Pro Thr Pro Pro Tyr Asn Glu Gln Phe Phe
1               5                   10

<210> SEQ ID NO 811
<211> LENGTH: 15
<212> TYPE: PRT
<213> ORGANISM: Homo sapiens

<400> SEQUENCE: 811

Cys Ser Ala Arg Ala Gly Gly Ala Gly Thr Gly Glu Leu Phe Phe
1               5                   10                  15

<210> SEQ ID NO 812
<211> LENGTH: 15
<212> TYPE: PRT
<213> ORGANISM: Homo sapiens

<400> SEQUENCE: 812

Cys Ser Ala Arg Gly Ser Ala Arg Pro Thr Asp Thr Gln Tyr Phe
1               5                   10                  15

<210> SEQ ID NO 813
<211> LENGTH: 15
<212> TYPE: PRT
<213> ORGANISM: Homo sapiens

<400> SEQUENCE: 813

Cys Ser Ala Gly Thr Gly Thr Pro Asn Thr Gly Glu Leu Phe Phe
1               5                   10                  15

<210> SEQ ID NO 814
<211> LENGTH: 15
<212> TYPE: PRT
<213> ORGANISM: Homo sapiens

<400> SEQUENCE: 814

Cys Ala Ser Arg Gly Gly Gln Gly Leu Thr Asp Thr Gln Tyr Phe
1               5                   10                  15

<210> SEQ ID NO 815
<211> LENGTH: 15
<212> TYPE: PRT
<213> ORGANISM: Homo sapiens

<400> SEQUENCE: 815

Cys Ala Ser Ser Ser Gln Thr Ala Ser Tyr Glu Gln Tyr Phe
1               5                   10                  15

<210> SEQ ID NO 816
<211> LENGTH: 15
<212> TYPE: PRT
<213> ORGANISM: Homo sapiens

<400> SEQUENCE: 816

Cys Ala Ser Ser Phe Asn Ser Arg Arg Asn Gln Pro Gln His Phe
1               5                   10                  15

<210> SEQ ID NO 817
<211> LENGTH: 16
<212> TYPE: PRT
<213> ORGANISM: Homo sapiens

<400> SEQUENCE: 817

Cys Ala Ser Ser Val Gly Ser Thr Gly Gly Asn Thr Glu Ala Phe Phe
1               5                   10                  15

<210> SEQ ID NO 818
<211> LENGTH: 14
<212> TYPE: PRT
<213> ORGANISM: Homo sapiens

<400> SEQUENCE: 818

Cys Ala Ser Ser Pro Arg Leu Gly Ser Glu Thr Gln Tyr Phe
1               5                   10

<210> SEQ ID NO 819
<211> LENGTH: 14
<212> TYPE: PRT
<213> ORGANISM: Homo sapiens

<400> SEQUENCE: 819

Cys Ala Ser Ser Leu Pro Pro Glu Leu Asn Glu Gln Phe Phe
1               5                   10

<210> SEQ ID NO 820
<211> LENGTH: 14
<212> TYPE: PRT
<213> ORGANISM: Homo sapiens

<400> SEQUENCE: 820

Cys Ala Ser Asn Pro Ala Glu Asn Thr Gly Glu Leu Phe Phe
1               5                   10

<210> SEQ ID NO 821
<211> LENGTH: 13
<212> TYPE: PRT
<213> ORGANISM: Homo sapiens

<400> SEQUENCE: 821

Cys Ala Ser Ser Lys Asp Arg Ser Glu Thr Gln Tyr Phe
1               5                   10

```
<210> SEQ ID NO 822
<211> LENGTH: 17
<212> TYPE: PRT
<213> ORGANISM: Homo sapiens

<400> SEQUENCE: 822

Cys Ala Ser Ser Asp Arg Gly Pro Phe Ser Gly Ala Asn Val Leu Thr
1               5                   10                  15
Phe

<210> SEQ ID NO 823
<211> LENGTH: 14
<212> TYPE: PRT
<213> ORGANISM: Homo sapiens

<400> SEQUENCE: 823

Cys Ala Trp Arg Pro Ala Gly Arg Asn Gln Pro Gln His Phe
1               5                   10

<210> SEQ ID NO 824
<211> LENGTH: 14
<212> TYPE: PRT
<213> ORGANISM: Homo sapiens

<400> SEQUENCE: 824

Cys Ala Ser Ser Glu Asp Ile Ala Gly Asn Thr Ile Tyr Phe
1               5                   10

<210> SEQ ID NO 825
<211> LENGTH: 14
<212> TYPE: PRT
<213> ORGANISM: Homo sapiens

<400> SEQUENCE: 825

Cys Ala Ser Ser Leu Asp Gly Thr Tyr Gln Pro Gln His Phe
1               5                   10

<210> SEQ ID NO 826
<211> LENGTH: 11
<212> TYPE: PRT
<213> ORGANISM: Homo sapiens

<400> SEQUENCE: 826

Cys Ser Ala Arg Asp Lys Tyr Glu Ala Phe Phe
1               5                   10

<210> SEQ ID NO 827
<211> LENGTH: 15
<212> TYPE: PRT
<213> ORGANISM: Homo sapiens

<400> SEQUENCE: 827

Cys Ala Thr Ser Asp Leu Pro Thr Asn Thr Gly Glu Leu Phe Phe
1               5                   10                  15

<210> SEQ ID NO 828
<211> LENGTH: 12
<212> TYPE: PRT
<213> ORGANISM: Homo sapiens

<400> SEQUENCE: 828

Cys Ala Ser Arg Ser Arg Leu Tyr Gly Tyr Thr Phe
1               5                   10
```

<210> SEQ ID NO 829
<211> LENGTH: 17
<212> TYPE: PRT
<213> ORGANISM: Homo sapiens

<400> SEQUENCE: 829

Cys Ser Ala Arg Asp Ser Leu Ala Gly Arg Ser Tyr Asn Glu Gln Phe
1               5                   10                  15

Phe

<210> SEQ ID NO 830
<211> LENGTH: 13
<212> TYPE: PRT
<213> ORGANISM: Homo sapiens

<400> SEQUENCE: 830

Cys Ala Ser Ser Val Gln Trp Thr Asp Thr Gln Tyr Phe
1               5                   10

<210> SEQ ID NO 831
<211> LENGTH: 16
<212> TYPE: PRT
<213> ORGANISM: Homo sapiens

<400> SEQUENCE: 831

Cys Ala Ser Arg Arg Gly Leu Ala Gly Gly Thr Gly Glu Leu Phe Phe
1               5                   10                  15

<210> SEQ ID NO 832
<211> LENGTH: 14
<212> TYPE: PRT
<213> ORGANISM: Homo sapiens

<400> SEQUENCE: 832

Cys Ala Ser Ser Leu Gly Pro Ala Ser His Glu Gln Tyr Phe
1               5                   10

<210> SEQ ID NO 833
<211> LENGTH: 14
<212> TYPE: PRT
<213> ORGANISM: Homo sapiens

<400> SEQUENCE: 833

Cys Ala Ser Ser Gly Ser Gly Gly Lys Asp Thr Gln Tyr Phe
1               5                   10

<210> SEQ ID NO 834
<211> LENGTH: 14
<212> TYPE: PRT
<213> ORGANISM: Homo sapiens

<400> SEQUENCE: 834

Cys Ala Ser Ile Val Asp Arg Val Asn Thr Glu Ala Phe Phe
1               5                   10

<210> SEQ ID NO 835
<211> LENGTH: 13
<212> TYPE: PRT
<213> ORGANISM: Homo sapiens

<400> SEQUENCE: 835

Cys Ala Ile Arg Met Gly Gln Gln Glu Thr Gln Tyr Phe
1               5                   10

```
<210> SEQ ID NO 836
<211> LENGTH: 12
<212> TYPE: PRT
<213> ORGANISM: Homo sapiens

<400> SEQUENCE: 836

Cys Ala Ser Ser Thr Gly His Tyr Gly Tyr Thr Phe
1               5                   10

<210> SEQ ID NO 837
<211> LENGTH: 15
<212> TYPE: PRT
<213> ORGANISM: Homo sapiens

<400> SEQUENCE: 837

Cys Ser Ala Arg Glu Ala Gly Ala Gly Thr Gly Glu Leu Phe Phe
1               5                   10                  15

<210> SEQ ID NO 838
<211> LENGTH: 15
<212> TYPE: PRT
<213> ORGANISM: Homo sapiens

<400> SEQUENCE: 838

Cys Ser Ala Arg Lys Ala Gly Ala Gly Thr Gly Glu Leu Phe Phe
1               5                   10                  15

<210> SEQ ID NO 839
<211> LENGTH: 12
<212> TYPE: PRT
<213> ORGANISM: Homo sapiens

<400> SEQUENCE: 839

Cys Ser Ala Arg Asp Gly Thr Pro Glu Gln Tyr Phe
1               5                   10

<210> SEQ ID NO 840
<211> LENGTH: 13
<212> TYPE: PRT
<213> ORGANISM: Homo sapiens

<400> SEQUENCE: 840

Cys Ala Ser Thr Ser Trp Gly Gly Ser Gly Tyr Thr Phe
1               5                   10

<210> SEQ ID NO 841
<211> LENGTH: 13
<212> TYPE: PRT
<213> ORGANISM: Homo sapiens

<400> SEQUENCE: 841

Cys Ala Ser Lys Arg Gly His Leu Tyr Glu Gln Tyr Phe
1               5                   10

<210> SEQ ID NO 842
<211> LENGTH: 13
<212> TYPE: PRT
<213> ORGANISM: Homo sapiens

<400> SEQUENCE: 842

Cys Ala Ser Ser Leu Val Trp Ser Tyr Glu Gln Tyr Phe
1               5                   10

<210> SEQ ID NO 843
<211> LENGTH: 15
```

```
<212> TYPE: PRT
<213> ORGANISM: Homo sapiens

<400> SEQUENCE: 843

Cys Arg Ala Arg Arg Gly Gly Ala Gly Thr Gly Glu Leu Phe Phe
1               5                   10                  15

<210> SEQ ID NO 844
<211> LENGTH: 16
<212> TYPE: PRT
<213> ORGANISM: Homo sapiens

<400> SEQUENCE: 844

Cys Ala Thr Ser Arg Gly Gly Thr Ser Gly Arg Asn Glu Gln Phe Phe
1               5                   10                  15

<210> SEQ ID NO 845
<211> LENGTH: 15
<212> TYPE: PRT
<213> ORGANISM: Homo sapiens

<400> SEQUENCE: 845

Cys Ser Ala Arg Ala Ser Pro Thr Asn Thr Gly Glu Leu Phe Phe
1               5                   10                  15

<210> SEQ ID NO 846
<211> LENGTH: 16
<212> TYPE: PRT
<213> ORGANISM: Homo sapiens

<400> SEQUENCE: 846

Cys Ala Ser Ser Leu Ala Gly Gly Pro Gly Thr Asp Thr Gln Tyr Phe
1               5                   10                  15

<210> SEQ ID NO 847
<211> LENGTH: 15
<212> TYPE: PRT
<213> ORGANISM: Homo sapiens

<400> SEQUENCE: 847

Cys Ala Ser Ser Arg Asp Arg Glu Val Asp Gln Pro Gln His Phe
1               5                   10                  15

<210> SEQ ID NO 848
<211> LENGTH: 14
<212> TYPE: PRT
<213> ORGANISM: Homo sapiens

<400> SEQUENCE: 848

Cys Ala Ser Gly Leu Gly Gly Arg Gly Thr Glu Ala Phe Phe
1               5                   10

<210> SEQ ID NO 849
<211> LENGTH: 13
<212> TYPE: PRT
<213> ORGANISM: Homo sapiens

<400> SEQUENCE: 849

Cys Ala Trp Ser Arg Arg Gly Leu Tyr Glu Gln Tyr Phe
1               5                   10

<210> SEQ ID NO 850
<211> LENGTH: 13
<212> TYPE: PRT
<213> ORGANISM: Homo sapiens
```

```
<400> SEQUENCE: 850

Cys Ala Ser Ser Arg Ala Gly Gly Tyr Glu Gln Tyr Phe
1               5                   10

<210> SEQ ID NO 851
<211> LENGTH: 14
<212> TYPE: PRT
<213> ORGANISM: Homo sapiens

<400> SEQUENCE: 851

Cys Ala Ser Ser Gln Met Thr Gly Thr Asp Thr Gln Tyr Phe
1               5                   10

<210> SEQ ID NO 852
<211> LENGTH: 15
<212> TYPE: PRT
<213> ORGANISM: Homo sapiens

<400> SEQUENCE: 852

Cys Ala Ser Ser Lys Pro Gly Arg Val Asn Thr Glu Ala Phe Phe
1               5                   10                  15

<210> SEQ ID NO 853
<211> LENGTH: 13
<212> TYPE: PRT
<213> ORGANISM: Homo sapiens

<400> SEQUENCE: 853

Cys Ala Ser Ser Gln Gly Ala Ala Arg Glu Gln Tyr Phe
1               5                   10

<210> SEQ ID NO 854
<211> LENGTH: 18
<212> TYPE: PRT
<213> ORGANISM: Homo sapiens

<400> SEQUENCE: 854

Cys Ala Ser Ser Leu Ala Ala Gly Thr Tyr Leu Leu Asn Thr Glu Ala
1               5                   10                  15

Phe Phe

<210> SEQ ID NO 855
<211> LENGTH: 15
<212> TYPE: PRT
<213> ORGANISM: Homo sapiens

<400> SEQUENCE: 855

Cys Ser Ala Arg Gly Thr Pro Ala Asn Thr Gly Glu Leu Phe Phe
1               5                   10                  15

<210> SEQ ID NO 856
<211> LENGTH: 15
<212> TYPE: PRT
<213> ORGANISM: Homo sapiens

<400> SEQUENCE: 856

Cys Ala Ser Ser Leu Gly Thr Ser Asn Tyr Asn Glu Gln Phe Phe
1               5                   10                  15

<210> SEQ ID NO 857
<211> LENGTH: 13
<212> TYPE: PRT
<213> ORGANISM: Homo sapiens
```

<400> SEQUENCE: 857

Cys Ala Ser Ser Val Asp His Asn Tyr Gly Tyr Thr Phe
1               5                   10

<210> SEQ ID NO 858
<211> LENGTH: 15
<212> TYPE: PRT
<213> ORGANISM: Homo sapiens

<400> SEQUENCE: 858

Cys Ala Ser Ser Phe Glu Ala Asn Tyr Gly Asn Thr Ile Tyr Phe
1               5                   10                  15

<210> SEQ ID NO 859
<211> LENGTH: 15
<212> TYPE: PRT
<213> ORGANISM: Homo sapiens

<400> SEQUENCE: 859

Cys Ala Ser Ser Arg Asp Arg Val Leu Ser Tyr Glu Gln Tyr Phe
1               5                   10                  15

<210> SEQ ID NO 860
<211> LENGTH: 18
<212> TYPE: PRT
<213> ORGANISM: Homo sapiens

<400> SEQUENCE: 860

Cys Ala Ser Ser Phe Leu Ala Gly Gly Ile Thr Ser Thr Asp Thr Gln
1               5                   10                  15

Tyr Phe

<210> SEQ ID NO 861
<211> LENGTH: 16
<212> TYPE: PRT
<213> ORGANISM: Homo sapiens

<400> SEQUENCE: 861

Cys Ala Ser Ser Pro Gly His Pro Ser Gly Ala Asn Val Leu Thr Phe
1               5                   10                  15

<210> SEQ ID NO 862
<211> LENGTH: 14
<212> TYPE: PRT
<213> ORGANISM: Homo sapiens

<400> SEQUENCE: 862

Cys Ala Ser Asn Ala Ala Gly Gly Thr Asp Thr Gln Tyr Phe
1               5                   10

<210> SEQ ID NO 863
<211> LENGTH: 16
<212> TYPE: PRT
<213> ORGANISM: Homo sapiens

<400> SEQUENCE: 863

Cys Ala Ser Ser Pro Leu Gly Gly Arg Arg Pro Tyr Glu Gln Tyr Phe
1               5                   10                  15

<210> SEQ ID NO 864
<211> LENGTH: 13
<212> TYPE: PRT
<213> ORGANISM: Homo sapiens

<400> SEQUENCE: 864

Cys Ser Ala Pro Leu Ala Pro His Asn Glu Gln Phe Phe
1               5                   10

<210> SEQ ID NO 865
<211> LENGTH: 14
<212> TYPE: PRT
<213> ORGANISM: Homo sapiens

<400> SEQUENCE: 865

Cys Ala Thr Ser Gly Ile Gly Gly Asp Gln Pro Gln His Phe
1               5                   10

<210> SEQ ID NO 866
<211> LENGTH: 15
<212> TYPE: PRT
<213> ORGANISM: Homo sapiens

<400> SEQUENCE: 866

Cys Ser Ala Lys Gly Arg Gly Thr Asn Thr Gly Glu Leu Phe Phe
1               5                   10                  15

<210> SEQ ID NO 867
<211> LENGTH: 16
<212> TYPE: PRT
<213> ORGANISM: Homo sapiens

<400> SEQUENCE: 867

Cys Ala Ser Ser Pro Gln Glu Gly Leu Gly Ala Asn Val Leu Thr Phe
1               5                   10                  15

<210> SEQ ID NO 868
<211> LENGTH: 13
<212> TYPE: PRT
<213> ORGANISM: Homo sapiens

<400> SEQUENCE: 868

Cys Ser Ala Ser Arg Pro Pro Asp Asn Glu Gln Phe Phe
1               5                   10

<210> SEQ ID NO 869
<211> LENGTH: 16
<212> TYPE: PRT
<213> ORGANISM: Homo sapiens

<400> SEQUENCE: 869

Cys Ala Ser Ser Leu Glu Pro Arg Thr Asn Thr Gly Glu Leu Phe Phe
1               5                   10                  15

<210> SEQ ID NO 870
<211> LENGTH: 15
<212> TYPE: PRT
<213> ORGANISM: Homo sapiens

<400> SEQUENCE: 870

Cys Ala Ser Ser Asp Arg Gly Pro Gly Asn Gln Pro Gln His Phe
1               5                   10                  15

<210> SEQ ID NO 871
<211> LENGTH: 12
<212> TYPE: PRT
<213> ORGANISM: Homo sapiens

<400> SEQUENCE: 871

Cys Ala Ser Ser Ile Gly Glu Lys Thr Gln Tyr Phe
1               5                   10

<210> SEQ ID NO 872
<211> LENGTH: 16
<212> TYPE: PRT
<213> ORGANISM: Homo sapiens

<400> SEQUENCE: 872

Cys Ala Ser Ser Leu Gly Ala His Ser Asn Thr Gly Glu Leu Phe Phe
1               5                   10                  15

<210> SEQ ID NO 873
<211> LENGTH: 15
<212> TYPE: PRT
<213> ORGANISM: Homo sapiens

<400> SEQUENCE: 873

Cys Ala Ser Ser Phe Ala Gly Leu Tyr Asn Ser Pro Leu His Phe
1               5                   10                  15

<210> SEQ ID NO 874
<211> LENGTH: 15
<212> TYPE: PRT
<213> ORGANISM: Homo sapiens

<400> SEQUENCE: 874

Cys Ser Ala Arg Leu Ser Gly Gly Gly Thr Gly Glu Leu Phe Phe
1               5                   10                  15

<210> SEQ ID NO 875
<211> LENGTH: 15
<212> TYPE: PRT
<213> ORGANISM: Homo sapiens

<400> SEQUENCE: 875

Cys Ser Ala Arg Ile Ala Gly Gly Gly Thr Gly Glu Leu Phe Phe
1               5                   10                  15

<210> SEQ ID NO 876
<211> LENGTH: 13
<212> TYPE: PRT
<213> ORGANISM: Homo sapiens

<400> SEQUENCE: 876

Cys Ser Ala Arg Val Glu Gly Trp Glu Thr Gln Tyr Phe
1               5                   10

<210> SEQ ID NO 877
<211> LENGTH: 13
<212> TYPE: PRT
<213> ORGANISM: Homo sapiens

<400> SEQUENCE: 877

Cys Ala Trp Ser Arg Arg Gly Arg Tyr Glu Gln Tyr Phe
1               5                   10

<210> SEQ ID NO 878
<211> LENGTH: 14
<212> TYPE: PRT
<213> ORGANISM: Homo sapiens

<400> SEQUENCE: 878

Cys Ala Ser Met Thr Gly Lys Gly Asp Glu Lys Leu Phe Phe

<210> SEQ ID NO 879
<211> LENGTH: 14
<212> TYPE: PRT
<213> ORGANISM: Homo sapiens

<400> SEQUENCE: 879

Cys Ala Ser Ser Glu Gln Arg Gly His Glu Lys Leu Phe Phe
1               5                   10

<210> SEQ ID NO 880
<211> LENGTH: 16
<212> TYPE: PRT
<213> ORGANISM: Homo sapiens

<400> SEQUENCE: 880

Cys Ser Ala Arg Gly Trp Ala Ser Gly Arg Thr Tyr Glu Gln Tyr Phe
1               5                   10                  15

<210> SEQ ID NO 881
<211> LENGTH: 16
<212> TYPE: PRT
<213> ORGANISM: Homo sapiens

<400> SEQUENCE: 881

Cys Ala Ser Ser Leu Leu Gly Gln Gly Leu Asn Thr Glu Ala Phe Phe
1               5                   10                  15

<210> SEQ ID NO 882
<211> LENGTH: 13
<212> TYPE: PRT
<213> ORGANISM: Homo sapiens

<400> SEQUENCE: 882

Cys Ser Ala Pro Arg Pro Pro Tyr Asn Glu Gln Phe Phe
1               5                   10

<210> SEQ ID NO 883
<211> LENGTH: 14
<212> TYPE: PRT
<213> ORGANISM: Homo sapiens

<400> SEQUENCE: 883

Cys Ser Ala Arg Glu Trp Gly Gly Leu Tyr Glu Gln Tyr Phe
1               5                   10

<210> SEQ ID NO 884
<211> LENGTH: 15
<212> TYPE: PRT
<213> ORGANISM: Homo sapiens

<400> SEQUENCE: 884

Cys Ser Ala Arg Asp Arg Glu Gly Leu Gln Glu Thr Gln Tyr Phe
1               5                   10                  15

<210> SEQ ID NO 885
<211> LENGTH: 15
<212> TYPE: PRT
<213> ORGANISM: Homo sapiens

<400> SEQUENCE: 885

Cys Ser Ala Arg Met Gly Gly Ala Gly Thr Gly Glu Leu Phe Phe
1               5                   10                  15

<210> SEQ ID NO 886
<211> LENGTH: 15
<212> TYPE: PRT
<213> ORGANISM: Homo sapiens

<400> SEQUENCE: 886

Cys Ser Ala Arg Ala Arg Thr Ala Gly Thr Gly Glu Leu Phe Phe
1               5                   10                  15

<210> SEQ ID NO 887
<211> LENGTH: 15
<212> TYPE: PRT
<213> ORGANISM: Homo sapiens

<400> SEQUENCE: 887

Cys Ala Thr Ser Asp Ser Trp Leu Ala Asp Asn Glu Gln Phe Phe
1               5                   10                  15

<210> SEQ ID NO 888
<211> LENGTH: 18
<212> TYPE: PRT
<213> ORGANISM: Homo sapiens

<400> SEQUENCE: 888

Cys Ala Ser Ser Leu Val Gly Thr Ser Gly Gly Ala Arg Asp Thr Gln
1               5                   10                  15

Tyr Phe

<210> SEQ ID NO 889
<211> LENGTH: 16
<212> TYPE: PRT
<213> ORGANISM: Homo sapiens

<400> SEQUENCE: 889

Cys Ala Thr Ser Asp Leu Pro Gly Ala Ser Gln Glu Thr Gln Tyr Phe
1               5                   10                  15

<210> SEQ ID NO 890
<211> LENGTH: 13
<212> TYPE: PRT
<213> ORGANISM: Homo sapiens

<400> SEQUENCE: 890

Cys Ser Ala Pro Glu Pro Pro Tyr Asn Glu Gln Phe Phe
1               5                   10

<210> SEQ ID NO 891
<211> LENGTH: 14
<212> TYPE: PRT
<213> ORGANISM: Homo sapiens

<400> SEQUENCE: 891

Cys Ala Ser Ser Phe Gln Gly Gly Arg Asn Thr Ile Tyr Phe
1               5                   10

<210> SEQ ID NO 892
<211> LENGTH: 14
<212> TYPE: PRT
<213> ORGANISM: Homo sapiens

<400> SEQUENCE: 892

Cys Ala Ser Ser Leu Arg Asp Phe Gln Glu Thr Gln Tyr Phe
1               5                   10

<210> SEQ ID NO 893
<211> LENGTH: 13
<212> TYPE: PRT
<213> ORGANISM: Homo sapiens

<400> SEQUENCE: 893

Cys Ala Ser Lys Arg Gln Gly Phe Tyr Glu Gln Tyr Phe
1               5                   10

<210> SEQ ID NO 894
<211> LENGTH: 15
<212> TYPE: PRT
<213> ORGANISM: Homo sapiens

<400> SEQUENCE: 894

Cys Ala Ser Ser Pro Thr Ser Gly Ser Asn Glu Gln Phe Phe
1               5                   10                  15

<210> SEQ ID NO 895
<211> LENGTH: 15
<212> TYPE: PRT
<213> ORGANISM: Homo sapiens

<400> SEQUENCE: 895

Cys Ala Ser Ser Tyr Gly Ser Gly Gly Pro His Glu Gln Phe Phe
1               5                   10                  15

<210> SEQ ID NO 896
<211> LENGTH: 14
<212> TYPE: PRT
<213> ORGANISM: Homo sapiens

<400> SEQUENCE: 896

Cys Ala Ser Ser Asp Gly Gln Val Asp Tyr Gly Tyr Thr Phe
1               5                   10

<210> SEQ ID NO 897
<211> LENGTH: 15
<212> TYPE: PRT
<213> ORGANISM: Homo sapiens

<400> SEQUENCE: 897

Cys Ser Ala Arg Ile Ser Gly Gly Gly Thr Gly Glu Leu Phe Phe
1               5                   10                  15

<210> SEQ ID NO 898
<211> LENGTH: 15
<212> TYPE: PRT
<213> ORGANISM: Homo sapiens

<400> SEQUENCE: 898

Cys Ala Ser Ser Leu Arg Thr Gly Gly Thr Tyr Gly Tyr Thr Phe
1               5                   10                  15

<210> SEQ ID NO 899
<211> LENGTH: 14
<212> TYPE: PRT
<213> ORGANISM: Homo sapiens

<400> SEQUENCE: 899

Cys Ser Ala Ser Thr Ser Thr Ser Thr Asp Thr Gln Tyr Phe
1               5                   10

<210> SEQ ID NO 900

```
<211> LENGTH: 15
<212> TYPE: PRT
<213> ORGANISM: Homo sapiens

<400> SEQUENCE: 900

Cys Ala Ser Ser Ala Gly Thr Ser Gly Lys Asn Glu Gln Phe Phe
1               5                   10                  15

<210> SEQ ID NO 901
<211> LENGTH: 14
<212> TYPE: PRT
<213> ORGANISM: Homo sapiens

<400> SEQUENCE: 901

Cys Ser Ala Arg Ala Gly Ala Gln Gly Glu Thr Gln Tyr Phe
1               5                   10

<210> SEQ ID NO 902
<211> LENGTH: 14
<212> TYPE: PRT
<213> ORGANISM: Homo sapiens

<400> SEQUENCE: 902

Cys Ala Ser Arg Leu Gly Arg Gly Thr Gly Glu Leu Phe Phe
1               5                   10

<210> SEQ ID NO 903
<211> LENGTH: 13
<212> TYPE: PRT
<213> ORGANISM: Homo sapiens

<400> SEQUENCE: 903

Cys Ala Ser Ser Arg Gln Gly Leu Tyr Gly Tyr Thr Phe
1               5                   10

<210> SEQ ID NO 904
<211> LENGTH: 14
<212> TYPE: PRT
<213> ORGANISM: Homo sapiens

<400> SEQUENCE: 904

Cys Ala Ser Ser Ile Asp Arg Asp Arg Glu Thr Gln Tyr Phe
1               5                   10

<210> SEQ ID NO 905
<211> LENGTH: 14
<212> TYPE: PRT
<213> ORGANISM: Homo sapiens

<400> SEQUENCE: 905

Cys Ala Ser Ser Leu Pro Ala Gly Gly Glu Lys Leu Phe Phe
1               5                   10

<210> SEQ ID NO 906
<211> LENGTH: 17
<212> TYPE: PRT
<213> ORGANISM: Homo sapiens

<400> SEQUENCE: 906

Cys Ala Ser Ser Leu Ser Gly Thr Ala Ser Asn Thr Gly Glu Leu Phe
1               5                   10                  15

Phe

<210> SEQ ID NO 907
```

```
<211> LENGTH: 14
<212> TYPE: PRT
<213> ORGANISM: Homo sapiens

<400> SEQUENCE: 907

Cys Ala Thr Ser Arg Gln Gly Gly Asp Gln Pro Gln His Phe
1               5                   10

<210> SEQ ID NO 908
<211> LENGTH: 15
<212> TYPE: PRT
<213> ORGANISM: Homo sapiens

<400> SEQUENCE: 908

Cys Ala Ser Ser Leu Glu Ile Asn Tyr Asn Ser Pro Leu His Phe
1               5                   10                  15

<210> SEQ ID NO 909
<211> LENGTH: 14
<212> TYPE: PRT
<213> ORGANISM: Homo sapiens

<400> SEQUENCE: 909

Cys Ala Ser Thr Gly Pro Gly Thr Gly Thr Glu Ala Phe Phe
1               5                   10

<210> SEQ ID NO 910
<211> LENGTH: 15
<212> TYPE: PRT
<213> ORGANISM: Homo sapiens

<400> SEQUENCE: 910

Cys Ser Ala Arg Gly Gln Pro Ser Asn Thr Gly Glu Leu Phe Phe
1               5                   10                  15

<210> SEQ ID NO 911
<211> LENGTH: 15
<212> TYPE: PRT
<213> ORGANISM: Homo sapiens

<400> SEQUENCE: 911

Cys Ala Ser Ile Gly Glu Ser Ser Tyr Asn Ser Pro Leu His Phe
1               5                   10                  15

<210> SEQ ID NO 912
<211> LENGTH: 15
<212> TYPE: PRT
<213> ORGANISM: Homo sapiens

<400> SEQUENCE: 912

Cys Ser Ala Arg Gly Ser Gly Arg Thr Ser Asp Thr Gln Tyr Phe
1               5                   10                  15

<210> SEQ ID NO 913
<211> LENGTH: 15
<212> TYPE: PRT
<213> ORGANISM: Homo sapiens

<400> SEQUENCE: 913

Cys Ala Thr Ser Asp Asn Arg Glu Gly Gln Glu Thr Gln Tyr Phe
1               5                   10                  15

<210> SEQ ID NO 914
<211> LENGTH: 10
<212> TYPE: PRT
```

<213> ORGANISM: Homo sapiens

<400> SEQUENCE: 914

Cys Ser Val Glu Pro Thr Glu Ala Phe Phe
1               5                   10

<210> SEQ ID NO 915
<211> LENGTH: 13
<212> TYPE: PRT
<213> ORGANISM: Homo sapiens

<400> SEQUENCE: 915

Cys Ala Ser Ser Pro Gly Ile Asn Glu Gln Phe Phe
1               5                   10

<210> SEQ ID NO 916
<211> LENGTH: 14
<212> TYPE: PRT
<213> ORGANISM: Homo sapiens

<400> SEQUENCE: 916

Cys Ala Ser Ser Gln Asp Trp Gly Gly Asp Thr Gln Tyr Phe
1               5                   10

<210> SEQ ID NO 917
<211> LENGTH: 13
<212> TYPE: PRT
<213> ORGANISM: Homo sapiens

<400> SEQUENCE: 917

Cys Ala Ile Arg Glu Gly Gln Asn Asn Glu Gln Phe Phe
1               5                   10

<210> SEQ ID NO 918
<211> LENGTH: 15
<212> TYPE: PRT
<213> ORGANISM: Homo sapiens

<400> SEQUENCE: 918

Cys Ser Ala Arg Gly Gln Pro Ser Thr Asn Glu Lys Leu Phe Phe
1               5                   10                  15

<210> SEQ ID NO 919
<211> LENGTH: 15
<212> TYPE: PRT
<213> ORGANISM: Homo sapiens

<400> SEQUENCE: 919

Cys Ala Ile Arg Pro Thr Gly Gly Asn Thr Gly Glu Leu Phe Phe
1               5                   10                  15

<210> SEQ ID NO 920
<211> LENGTH: 15
<212> TYPE: PRT
<213> ORGANISM: Homo sapiens

<400> SEQUENCE: 920

Cys Ser Ala Arg Leu Gly Gly Ala Gly Thr Gly Glu Leu Phe Phe
1               5                   10                  15

<210> SEQ ID NO 921
<211> LENGTH: 15
<212> TYPE: PRT
<213> ORGANISM: Homo sapiens

```
<400> SEQUENCE: 921

Cys Ser Ala Arg Met Ala Gly Gly Thr Gly Glu Leu Phe Phe
1               5                   10                  15

<210> SEQ ID NO 922
<211> LENGTH: 16
<212> TYPE: PRT
<213> ORGANISM: Homo sapiens

<400> SEQUENCE: 922

Cys Ala Ser Ser Leu Pro Thr Ser Gly Ser Pro Asn Glu Gln Phe Phe
1               5                   10                  15

<210> SEQ ID NO 923
<211> LENGTH: 16
<212> TYPE: PRT
<213> ORGANISM: Homo sapiens

<400> SEQUENCE: 923

Cys Ala Ser Ser Ser Arg Pro Thr Val Ser Asn Gln Pro Gln His Phe
1               5                   10                  15

<210> SEQ ID NO 924
<211> LENGTH: 15
<212> TYPE: PRT
<213> ORGANISM: Homo sapiens

<400> SEQUENCE: 924

Cys Ala Ser Thr Pro Asp Gly Arg Val Tyr Asn Glu Gln Phe Phe
1               5                   10                  15

<210> SEQ ID NO 925
<211> LENGTH: 12
<212> TYPE: PRT
<213> ORGANISM: Homo sapiens

<400> SEQUENCE: 925

Cys Ala Ser Arg Gly Arg Leu Tyr Gly Tyr Thr Phe
1               5                   10

<210> SEQ ID NO 926
<211> LENGTH: 13
<212> TYPE: PRT
<213> ORGANISM: Homo sapiens

<400> SEQUENCE: 926

Cys Ala Ser Thr Leu Asn Ser Asn Gln Pro Gln His Phe
1               5                   10

<210> SEQ ID NO 927
<211> LENGTH: 13
<212> TYPE: PRT
<213> ORGANISM: Homo sapiens

<400> SEQUENCE: 927

Cys Ser Ala Pro Asn Pro Pro Tyr Asn Glu Gln Phe Phe
1               5                   10

<210> SEQ ID NO 928
<211> LENGTH: 13
<212> TYPE: PRT
<213> ORGANISM: Homo sapiens

<400> SEQUENCE: 928
```

Cys Ala Ser Ser Ser Asp Arg Phe Asp Glu Gln Phe Phe
1               5                   10

<210> SEQ ID NO 929
<211> LENGTH: 14
<212> TYPE: PRT
<213> ORGANISM: Homo sapiens

<400> SEQUENCE: 929

Cys Ala Ser Ser Arg Thr Asp Gly Asn Glu Lys Leu Phe Phe
1               5                   10

<210> SEQ ID NO 930
<211> LENGTH: 15
<212> TYPE: PRT
<213> ORGANISM: Homo sapiens

<400> SEQUENCE: 930

Cys Ala Ser Ser Pro Gly Gly Gly Arg Ile Asp Thr Gln Tyr Phe
1               5                   10                  15

<210> SEQ ID NO 931
<211> LENGTH: 15
<212> TYPE: PRT
<213> ORGANISM: Homo sapiens

<400> SEQUENCE: 931

Cys Ala Ser Asn Pro Ala Gly Gly Arg Ala Gly Glu Leu Phe Phe
1               5                   10                  15

<210> SEQ ID NO 932
<211> LENGTH: 12
<212> TYPE: PRT
<213> ORGANISM: Homo sapiens

<400> SEQUENCE: 932

Cys Ser Val Arg Met Ser Gly Glu Thr Gln Tyr Phe
1               5                   10

<210> SEQ ID NO 933
<211> LENGTH: 14
<212> TYPE: PRT
<213> ORGANISM: Homo sapiens

<400> SEQUENCE: 933

Cys Ala Thr Ser Asp Val Gly Arg Asn Gln Pro Gln His Phe
1               5                   10

<210> SEQ ID NO 934
<211> LENGTH: 13
<212> TYPE: PRT
<213> ORGANISM: Homo sapiens

<400> SEQUENCE: 934

Cys Ser Ala Arg Gln Gly Val Tyr Tyr Gly Tyr Thr Phe
1               5                   10

<210> SEQ ID NO 935
<211> LENGTH: 15
<212> TYPE: PRT
<213> ORGANISM: Homo sapiens

<400> SEQUENCE: 935

Cys Ser Ala Arg Tyr Ser Gly Ser Gly Thr Gly Glu Leu Phe Phe
1               5                   10                  15

<210> SEQ ID NO 936
<211> LENGTH: 15
<212> TYPE: PRT
<213> ORGANISM: Homo sapiens

<400> SEQUENCE: 936

Cys Ala Ser Ser Leu Lys Pro Ala Gly Asn Tyr Gly Tyr Thr Phe
1               5                   10                  15

<210> SEQ ID NO 937
<211> LENGTH: 15
<212> TYPE: PRT
<213> ORGANISM: Homo sapiens

<400> SEQUENCE: 937

Cys Ser Ala Arg Gly Gln Gly Ala Tyr Asn Gln Pro Gln His Phe
1               5                   10                  15

<210> SEQ ID NO 938
<211> LENGTH: 13
<212> TYPE: PRT
<213> ORGANISM: Homo sapiens

<400> SEQUENCE: 938

Cys Ala Ser Arg Val Tyr Ser Asn Gln Pro Gln His Phe
1               5                   10

<210> SEQ ID NO 939
<211> LENGTH: 16
<212> TYPE: PRT
<213> ORGANISM: Homo sapiens

<400> SEQUENCE: 939

Cys Ala Ser Ser Leu Arg Pro Asp Ser Gly Ala Asn Val Leu Thr Phe
1               5                   10                  15

<210> SEQ ID NO 940
<211> LENGTH: 9
<212> TYPE: PRT
<213> ORGANISM: Homo sapiens

<400> SEQUENCE: 940

Cys Ser Ala Arg Asp Trp Tyr Thr Phe
1               5

<210> SEQ ID NO 941
<211> LENGTH: 14
<212> TYPE: PRT
<213> ORGANISM: Homo sapiens

<400> SEQUENCE: 941

Cys Ala Ser Arg Leu Gly Gln Gly Ser Tyr Glu Gln Tyr Phe
1               5                   10

<210> SEQ ID NO 942
<211> LENGTH: 14
<212> TYPE: PRT
<213> ORGANISM: Homo sapiens

<400> SEQUENCE: 942

Cys Ala Ser Arg Pro Gln Gly Ser Asn Tyr Gly Tyr Thr Phe
1               5                   10

```
<210> SEQ ID NO 943
<211> LENGTH: 17
<212> TYPE: PRT
<213> ORGANISM: Homo sapiens

<400> SEQUENCE: 943

Cys Ala Ser Ser Ile Pro Trp Ala Ser Gly Asn Thr Gly Glu Leu Phe
1               5                   10                  15
Phe

<210> SEQ ID NO 944
<211> LENGTH: 11
<212> TYPE: PRT
<213> ORGANISM: Homo sapiens

<400> SEQUENCE: 944

Cys Ala Ser Arg Ser Gly Thr Arg Gly Phe Phe
1               5                   10

<210> SEQ ID NO 945
<211> LENGTH: 14
<212> TYPE: PRT
<213> ORGANISM: Homo sapiens

<400> SEQUENCE: 945

Cys Ala Ser Ser Ile Arg Thr Ala Asn Glu Lys Leu Phe Phe
1               5                   10

<210> SEQ ID NO 946
<211> LENGTH: 16
<212> TYPE: PRT
<213> ORGANISM: Homo sapiens

<400> SEQUENCE: 946

Cys Ala Ser Ser Pro Ser Gly Ser Arg Gly Thr Gly Glu Leu Phe Phe
1               5                   10                  15

<210> SEQ ID NO 947
<211> LENGTH: 15
<212> TYPE: PRT
<213> ORGANISM: Homo sapiens

<400> SEQUENCE: 947

Cys Ala Ser Ser Ser Pro Gly Arg Asp Thr Gly Glu Leu Phe Phe
1               5                   10                  15

<210> SEQ ID NO 948
<211> LENGTH: 15
<212> TYPE: PRT
<213> ORGANISM: Homo sapiens

<400> SEQUENCE: 948

Cys Ala Ser Ser Gln Glu Gln Gly Ile Ser Tyr Glu Gln Tyr Phe
1               5                   10                  15

<210> SEQ ID NO 949
<211> LENGTH: 16
<212> TYPE: PRT
<213> ORGANISM: Homo sapiens

<400> SEQUENCE: 949

Cys Ala Ser Ser Ser Gly Ser Gly Gly Tyr Thr Asp Thr Gln Tyr Phe
1               5                   10                  15
```

```
<210> SEQ ID NO 950
<211> LENGTH: 16
<212> TYPE: PRT
<213> ORGANISM: Homo sapiens

<400> SEQUENCE: 950

Cys Ala Ser Ser Pro Thr Ser Gly Thr Gly Ala Asn Val Leu Thr Phe
1               5                   10                  15

<210> SEQ ID NO 951
<211> LENGTH: 15
<212> TYPE: PRT
<213> ORGANISM: Homo sapiens

<400> SEQUENCE: 951

Cys Ser Ala Arg Asp Gly Ser Arg Ser Asn Tyr Gly Tyr Thr Phe
1               5                   10                  15

<210> SEQ ID NO 952
<211> LENGTH: 14
<212> TYPE: PRT
<213> ORGANISM: Homo sapiens

<400> SEQUENCE: 952

Cys Ala Ser Ser Tyr Leu His Ile Ser Tyr Glu Gln Tyr Phe
1               5                   10

<210> SEQ ID NO 953
<211> LENGTH: 14
<212> TYPE: PRT
<213> ORGANISM: Homo sapiens

<400> SEQUENCE: 953

Cys Ala Thr Thr Gly Gly Val Asn Thr Gly Glu Leu Phe Phe
1               5                   10

<210> SEQ ID NO 954
<211> LENGTH: 14
<212> TYPE: PRT
<213> ORGANISM: Homo sapiens

<400> SEQUENCE: 954

Cys Ala Ser Ser Leu Ala Pro Leu Ser Asp Thr Gln Tyr Phe
1               5                   10

<210> SEQ ID NO 955
<211> LENGTH: 17
<212> TYPE: PRT
<213> ORGANISM: Homo sapiens

<400> SEQUENCE: 955

Cys Ala Ser Ser Pro Pro Ser Gly Leu Glu Asn Thr Gly Glu Leu Phe
1               5                   10                  15

Phe

<210> SEQ ID NO 956
<211> LENGTH: 13
<212> TYPE: PRT
<213> ORGANISM: Homo sapiens

<400> SEQUENCE: 956

Cys Ser Ala Ser Leu Ser Leu Asn Thr Glu Ala Phe Phe
1               5                   10
```

```
<210> SEQ ID NO 957
<211> LENGTH: 15
<212> TYPE: PRT
<213> ORGANISM: Homo sapiens

<400> SEQUENCE: 957

Cys Ala Ser Ser Gly Gln Gly Arg Thr Tyr Glu Gln Tyr Phe
1               5                   10                  15

<210> SEQ ID NO 958
<211> LENGTH: 15
<212> TYPE: PRT
<213> ORGANISM: Homo sapiens

<400> SEQUENCE: 958

Cys Ala Ser Ser Phe Glu Ala Asp Tyr Asn Ser Pro Leu His Phe
1               5                   10                  15

<210> SEQ ID NO 959
<211> LENGTH: 15
<212> TYPE: PRT
<213> ORGANISM: Homo sapiens

<400> SEQUENCE: 959

Cys Ala Ser Ser Leu Asp Ser Gly Asn Lys Asn Ile Gln Tyr Phe
1               5                   10                  15

<210> SEQ ID NO 960
<211> LENGTH: 16
<212> TYPE: PRT
<213> ORGANISM: Homo sapiens

<400> SEQUENCE: 960

Cys Ala Ser Ser Gln Ala Arg Asp Ser Phe Asn Tyr Gly Tyr Thr Phe
1               5                   10                  15

<210> SEQ ID NO 961
<211> LENGTH: 15
<212> TYPE: PRT
<213> ORGANISM: Homo sapiens

<400> SEQUENCE: 961

Cys Ala Ser Ser Glu Leu Ser Gly Lys Thr Gly Glu Leu Phe Phe
1               5                   10                  15

<210> SEQ ID NO 962
<211> LENGTH: 17
<212> TYPE: PRT
<213> ORGANISM: Homo sapiens

<400> SEQUENCE: 962

Cys Ala Ser Ser Val Gly Thr Gly Ala Gly Gly Ala Asp Thr Gln Tyr
1               5                   10                  15

Phe

<210> SEQ ID NO 963
<211> LENGTH: 14
<212> TYPE: PRT
<213> ORGANISM: Homo sapiens

<400> SEQUENCE: 963

Cys Ser Val Glu Ala Arg Gly Trp Thr Gly Glu Leu Phe Phe
1               5                   10
```

```
<210> SEQ ID NO 964
<211> LENGTH: 15
<212> TYPE: PRT
<213> ORGANISM: Homo sapiens

<400> SEQUENCE: 964

Cys Ser Ala Arg Thr Ser Gly Ser Gly Asn Gly Glu Leu Phe Phe
1               5                   10                  15

<210> SEQ ID NO 965
<211> LENGTH: 18
<212> TYPE: PRT
<213> ORGANISM: Homo sapiens

<400> SEQUENCE: 965

Cys Ala Ser Ser Leu Ala Leu Ile Ala Gly Gly Ser Thr Asp Thr Gln
1               5                   10                  15

Tyr Phe

<210> SEQ ID NO 966
<211> LENGTH: 13
<212> TYPE: PRT
<213> ORGANISM: Homo sapiens

<400> SEQUENCE: 966

Cys Ser Ala Ser Leu Ala Pro Tyr Asn Glu Gln Phe Phe
1               5                   10

<210> SEQ ID NO 967
<211> LENGTH: 14
<212> TYPE: PRT
<213> ORGANISM: Homo sapiens

<400> SEQUENCE: 967

Cys Ala Ser Ser Leu Glu Arg Arg Glu Asn Ile Gln Tyr Phe
1               5                   10

<210> SEQ ID NO 968
<211> LENGTH: 15
<212> TYPE: PRT
<213> ORGANISM: Homo sapiens

<400> SEQUENCE: 968

Cys Ser Ala Arg Val Ser Gly Gly Gly Thr Gly Glu Leu Phe Phe
1               5                   10                  15

<210> SEQ ID NO 969
<211> LENGTH: 15
<212> TYPE: PRT
<213> ORGANISM: Homo sapiens

<400> SEQUENCE: 969

Cys Ala Ser Ser Leu Glu Thr Asn Tyr Gly Asn Thr Ile Tyr Phe
1               5                   10                  15

<210> SEQ ID NO 970
<211> LENGTH: 15
<212> TYPE: PRT
<213> ORGANISM: Homo sapiens

<400> SEQUENCE: 970

Cys Ala Ser Ser Arg Gly Gln Gly Leu Ala Gln Pro Gln His Phe
1               5                   10                  15
```

```
<210> SEQ ID NO 971
<211> LENGTH: 15
<212> TYPE: PRT
<213> ORGANISM: Homo sapiens

<400> SEQUENCE: 971

Cys Ser Ala Arg Asp Leu Ala Gly Asn Gly Glu Thr Gln Tyr Phe
1               5                   10                  15

<210> SEQ ID NO 972
<211> LENGTH: 15
<212> TYPE: PRT
<213> ORGANISM: Homo sapiens

<400> SEQUENCE: 972

Cys Ala Ser Ser Leu Leu Gly Gly Gly Gly Ser Glu Ala Phe Phe
1               5                   10                  15

<210> SEQ ID NO 973
<211> LENGTH: 13
<212> TYPE: PRT
<213> ORGANISM: Homo sapiens

<400> SEQUENCE: 973

Cys Ala Ser Lys Gly Val Tyr Asn Ser Pro Leu His Phe
1               5                   10

<210> SEQ ID NO 974
<211> LENGTH: 15
<212> TYPE: PRT
<213> ORGANISM: Homo sapiens

<400> SEQUENCE: 974

Cys Ala Ser Ser Val Gly Thr Arg Thr Ala Asp Thr Gln Tyr Phe
1               5                   10                  15

<210> SEQ ID NO 975
<211> LENGTH: 14
<212> TYPE: PRT
<213> ORGANISM: Homo sapiens

<400> SEQUENCE: 975

Cys Ser Ala Arg Phe Arg Gly Ala Thr Gly Glu Leu Phe Phe
1               5                   10

<210> SEQ ID NO 976
<211> LENGTH: 17
<212> TYPE: PRT
<213> ORGANISM: Homo sapiens

<400> SEQUENCE: 976

Cys Ala Ser Arg Pro Gly Thr Gly Gly Arg Gly Asn Glu Lys Leu Phe
1               5                   10                  15

Phe

<210> SEQ ID NO 977
<211> LENGTH: 13
<212> TYPE: PRT
<213> ORGANISM: Homo sapiens

<400> SEQUENCE: 977

Cys Ala Ser Ser Ile Asn Arg Trp Asp Gly Tyr Thr Phe
1               5                   10
```

<210> SEQ ID NO 978
<211> LENGTH: 12
<212> TYPE: PRT
<213> ORGANISM: Homo sapiens

<400> SEQUENCE: 978

Cys Ala Ser Gly Val Gly Thr Asp Thr Gln Tyr Phe
1               5                   10

<210> SEQ ID NO 979
<211> LENGTH: 13
<212> TYPE: PRT
<213> ORGANISM: Homo sapiens

<400> SEQUENCE: 979

Cys Ala Ser Ser Ile Glu Thr Asp Tyr Glu Gln Tyr Phe
1               5                   10

<210> SEQ ID NO 980
<211> LENGTH: 15
<212> TYPE: PRT
<213> ORGANISM: Homo sapiens

<400> SEQUENCE: 980

Cys Ala Ile Ser Gly Gly Arg Val Leu Asn Thr Glu Ala Phe Phe
1               5                   10                  15

<210> SEQ ID NO 981
<211> LENGTH: 16
<212> TYPE: PRT
<213> ORGANISM: Homo sapiens

<400> SEQUENCE: 981

Cys Ala Ser Ser Gln Ala Met Ala Ser Gly Tyr Asn Glu Gln Phe Phe
1               5                   10                  15

<210> SEQ ID NO 982
<211> LENGTH: 13
<212> TYPE: PRT
<213> ORGANISM: Homo sapiens

<400> SEQUENCE: 982

Cys Ala Ser Arg Arg Glu Asp Thr Asp Thr Gln Tyr Phe
1               5                   10

<210> SEQ ID NO 983
<211> LENGTH: 14
<212> TYPE: PRT
<213> ORGANISM: Homo sapiens

<400> SEQUENCE: 983

Cys Ala Ser Ser Pro Glu Thr Pro Thr Gly Glu Leu Phe Phe
1               5                   10

<210> SEQ ID NO 984
<211> LENGTH: 15
<212> TYPE: PRT
<213> ORGANISM: Homo sapiens

<400> SEQUENCE: 984

Cys Ala Ser Ser Gln Asp Arg Val Leu Ser Tyr Glu Gln Tyr Phe
1               5                   10                  15

<210> SEQ ID NO 985
<211> LENGTH: 14

```
<212> TYPE: PRT
<213> ORGANISM: Homo sapiens

<400> SEQUENCE: 985

Cys Ala Ser Ser Tyr Leu Ser Leu Ser Tyr Glu Gln Tyr Phe
1               5                   10

<210> SEQ ID NO 986
<211> LENGTH: 13
<212> TYPE: PRT
<213> ORGANISM: Homo sapiens

<400> SEQUENCE: 986

Cys Ala Ser Ser Leu Glu Ala Ala Asp Thr Gln Tyr Phe
1               5                   10

<210> SEQ ID NO 987
<211> LENGTH: 15
<212> TYPE: PRT
<213> ORGANISM: Homo sapiens

<400> SEQUENCE: 987

Cys Ala Ser Arg Pro Gln Leu Ala Thr Asn Glu Lys Leu Phe Phe
1               5                   10                  15

<210> SEQ ID NO 988
<211> LENGTH: 16
<212> TYPE: PRT
<213> ORGANISM: Homo sapiens

<400> SEQUENCE: 988

Cys Ala Ser Ser Val Gly Val Ala Arg Val Gly Glu Lys Leu Phe Phe
1               5                   10                  15

<210> SEQ ID NO 989
<211> LENGTH: 12
<212> TYPE: PRT
<213> ORGANISM: Homo sapiens

<400> SEQUENCE: 989

Cys Ser Ala Pro Pro Gly Met Asn Glu Gln Phe Phe
1               5                   10

<210> SEQ ID NO 990
<211> LENGTH: 14
<212> TYPE: PRT
<213> ORGANISM: Homo sapiens

<400> SEQUENCE: 990

Cys Ala Ser Ser Leu Thr Gly Val Ser Thr Glu Ala Phe Phe
1               5                   10

<210> SEQ ID NO 991
<211> LENGTH: 16
<212> TYPE: PRT
<213> ORGANISM: Homo sapiens

<400> SEQUENCE: 991

Cys Ala Ser Ser Gln Gly Gln Ser Ala Asn Thr Gly Glu Leu Phe Phe
1               5                   10                  15

<210> SEQ ID NO 992
<211> LENGTH: 13
<212> TYPE: PRT
<213> ORGANISM: Homo sapiens
```

```
<400> SEQUENCE: 992

Cys Ala Ser Thr Gly Gly Ile Ala Asp Thr Gln Tyr Phe
1               5                   10

<210> SEQ ID NO 993
<211> LENGTH: 16
<212> TYPE: PRT
<213> ORGANISM: Homo sapiens

<400> SEQUENCE: 993

Cys Ala Ser Ser Leu Val Gly Ser Gly Thr Tyr Asn Glu Gln Phe Phe
1               5                   10                  15

<210> SEQ ID NO 994
<211> LENGTH: 14
<212> TYPE: PRT
<213> ORGANISM: Homo sapiens

<400> SEQUENCE: 994

Cys Ala Ser Ser Ser Gly Arg Gly Ser Glu Lys Leu Phe Phe
1               5                   10

<210> SEQ ID NO 995
<211> LENGTH: 16
<212> TYPE: PRT
<213> ORGANISM: Homo sapiens

<400> SEQUENCE: 995

Cys Ala Ile Ser Val Gly Pro Ile Ser Gly Ala Asn Val Leu Thr Phe
1               5                   10                  15

<210> SEQ ID NO 996
<211> LENGTH: 17
<212> TYPE: PRT
<213> ORGANISM: Homo sapiens

<400> SEQUENCE: 996

Cys Ala Ser Ser Leu Ala Pro Arg Asp Leu Gly Asn Gln Pro Gln His
1               5                   10                  15

Phe

<210> SEQ ID NO 997
<211> LENGTH: 15
<212> TYPE: PRT
<213> ORGANISM: Homo sapiens

<400> SEQUENCE: 997

Cys Ser Ala Arg Ser Ser Gly Arg Val Ser Asp Thr Gln Tyr Phe
1               5                   10                  15

<210> SEQ ID NO 998
<211> LENGTH: 14
<212> TYPE: PRT
<213> ORGANISM: Homo sapiens

<400> SEQUENCE: 998

Cys Ala Ser Arg Asp Ser Pro Gly Asn Gln Pro Gln His Phe
1               5                   10

<210> SEQ ID NO 999
<211> LENGTH: 14
<212> TYPE: PRT
<213> ORGANISM: Homo sapiens
```

<400> SEQUENCE: 999

Cys Ser Ala Pro Ile Pro Gly Gln Asn Glu Lys Leu Phe Phe
1               5                   10

<210> SEQ ID NO 1000
<211> LENGTH: 14
<212> TYPE: PRT
<213> ORGANISM: Homo sapiens

<400> SEQUENCE: 1000

Cys Ala Ser Ser Tyr Leu Leu Leu Thr Tyr Glu Gln Tyr Phe
1               5                   10

<210> SEQ ID NO 1001
<211> LENGTH: 13
<212> TYPE: PRT
<213> ORGANISM: Homo sapiens

<400> SEQUENCE: 1001

Cys Ala Ser Ser Pro Thr Gly Arg Glu Thr Gln Tyr Phe
1               5                   10

<210> SEQ ID NO 1002
<211> LENGTH: 12
<212> TYPE: PRT
<213> ORGANISM: Homo sapiens

<400> SEQUENCE: 1002

Cys Ala Ser Arg Ser Pro Gly Gly Pro Gln His Phe
1               5                   10

<210> SEQ ID NO 1003
<211> LENGTH: 15
<212> TYPE: PRT
<213> ORGANISM: Homo sapiens

<400> SEQUENCE: 1003

Cys Ala Ser Ser Pro Tyr Gly Thr Glu Asn Thr Glu Ala Phe Phe
1               5                   10                  15

<210> SEQ ID NO 1004
<211> LENGTH: 15
<212> TYPE: PRT
<213> ORGANISM: Homo sapiens

<400> SEQUENCE: 1004

Cys Ser Ala Arg Val Ser Gly Ser Gly Thr Gly Glu Leu Phe Phe
1               5                   10                  15

<210> SEQ ID NO 1005
<211> LENGTH: 13
<212> TYPE: PRT
<213> ORGANISM: Homo sapiens

<400> SEQUENCE: 1005

Cys Ser Ala Thr Ser Gly Val Asn Ser Pro Leu His Phe
1               5                   10

<210> SEQ ID NO 1006
<211> LENGTH: 15
<212> TYPE: PRT
<213> ORGANISM: Homo sapiens

<400> SEQUENCE: 1006

```
Cys Ala Thr Ser Ser Gly Gly Arg Arg Tyr Asn Glu Gln Phe Phe
1               5                   10                  15
```

<210> SEQ ID NO 1007
<211> LENGTH: 15
<212> TYPE: PRT
<213> ORGANISM: Homo sapiens

<400> SEQUENCE: 1007

```
Cys Ala Ser Ser Leu Ala Pro Gly Ala Pro Glu Thr Gln Tyr Phe
1               5                   10                  15
```

<210> SEQ ID NO 1008
<211> LENGTH: 17
<212> TYPE: PRT
<213> ORGANISM: Homo sapiens

<400> SEQUENCE: 1008

```
Cys Ala Ser Ser Tyr Pro Glu Ser Gly Ser Ser Tyr Asn Glu Gln Phe
1               5                   10                  15

Phe
```

<210> SEQ ID NO 1009
<211> LENGTH: 15
<212> TYPE: PRT
<213> ORGANISM: Homo sapiens

<400> SEQUENCE: 1009

```
Cys Ala Ser Ser Glu Ser Ala Leu Asn Thr Gly Glu Leu Phe Phe
1               5                   10                  15
```

<210> SEQ ID NO 1010
<211> LENGTH: 15
<212> TYPE: PRT
<213> ORGANISM: Homo sapiens

<400> SEQUENCE: 1010

```
Cys Ala Ser Arg Arg Thr Gly Pro Asn Thr Gly Glu Leu Phe Phe
1               5                   10                  15
```

<210> SEQ ID NO 1011
<211> LENGTH: 15
<212> TYPE: PRT
<213> ORGANISM: Homo sapiens

<400> SEQUENCE: 1011

```
Cys Ser Ala Arg Arg Ala Gly Ala Gly Thr Gly Glu Leu Phe Phe
1               5                   10                  15
```

<210> SEQ ID NO 1012
<211> LENGTH: 14
<212> TYPE: PRT
<213> ORGANISM: Homo sapiens

<400> SEQUENCE: 1012

```
Cys Ala Ser Ser Leu Gly Ala Ala Ser Tyr Glu Gln Tyr Phe
1               5                   10
```

<210> SEQ ID NO 1013
<211> LENGTH: 15
<212> TYPE: PRT
<213> ORGANISM: Homo sapiens

<400> SEQUENCE: 1013

-continued

Cys Ser Ala Arg Gly Ser Gly Gly Thr Gly Glu Leu Phe Phe
1               5                   10                  15

<210> SEQ ID NO 1014
<211> LENGTH: 15
<212> TYPE: PRT
<213> ORGANISM: Homo sapiens

<400> SEQUENCE: 1014

Cys Ala Ser Arg Pro Ala Gly Gly Thr Asp Thr Gln Tyr Phe
1               5                   10                  15

<210> SEQ ID NO 1015
<211> LENGTH: 17
<212> TYPE: PRT
<213> ORGANISM: Homo sapiens

<400> SEQUENCE: 1015

Cys Ala Ser Ser Pro Asp Arg Gly Tyr Ser Thr Asn Glu Lys Leu Phe
1               5                   10                  15

Phe

<210> SEQ ID NO 1016
<211> LENGTH: 13
<212> TYPE: PRT
<213> ORGANISM: Homo sapiens

<400> SEQUENCE: 1016

Cys Ala Thr Ser Gly Thr Thr Tyr Gln Pro Gln His Phe
1               5                   10

<210> SEQ ID NO 1017
<211> LENGTH: 15
<212> TYPE: PRT
<213> ORGANISM: Homo sapiens

<400> SEQUENCE: 1017

Cys Ala Ser Ser Pro Ser Ser Gly His Leu Asn Glu Gln Phe Phe
1               5                   10                  15

<210> SEQ ID NO 1018
<211> LENGTH: 15
<212> TYPE: PRT
<213> ORGANISM: Homo sapiens

<400> SEQUENCE: 1018

Cys Ala Ser Ser Pro Leu Ala Gly Gly Pro Arg Glu Leu Phe Phe
1               5                   10                  15

<210> SEQ ID NO 1019
<211> LENGTH: 14
<212> TYPE: PRT
<213> ORGANISM: Homo sapiens

<400> SEQUENCE: 1019

Cys Ala Ser Ser Ala Gly Thr Gly Gly Tyr Glu Gln Phe Phe
1               5                   10

<210> SEQ ID NO 1020
<211> LENGTH: 14
<212> TYPE: PRT
<213> ORGANISM: Homo sapiens

<400> SEQUENCE: 1020

```
Cys Ala Trp Arg Gln Gly Gln Pro Asn Ser Pro Leu His Phe
1               5                   10
```

<210> SEQ ID NO 1021
<211> LENGTH: 14
<212> TYPE: PRT
<213> ORGANISM: Homo sapiens

<400> SEQUENCE: 1021

```
Cys Ala Trp Arg Gly Thr Gly Lys Asn Gln Pro Gln His Phe
1               5                   10
```

<210> SEQ ID NO 1022
<211> LENGTH: 14
<212> TYPE: PRT
<213> ORGANISM: Homo sapiens

<400> SEQUENCE: 1022

```
Cys Ala Ser Ser Leu Asp Arg Val Arg Asn Thr Gln Tyr Phe
1               5                   10
```

<210> SEQ ID NO 1023
<211> LENGTH: 15
<212> TYPE: PRT
<213> ORGANISM: Homo sapiens

<400> SEQUENCE: 1023

```
Cys Ala Ser Ser Leu Pro Thr Gly Pro Asn Tyr Glu Gln Tyr Phe
1               5                   10                  15
```

<210> SEQ ID NO 1024
<211> LENGTH: 15
<212> TYPE: PRT
<213> ORGANISM: Homo sapiens

<400> SEQUENCE: 1024

```
Cys Ala Ser Ser Gln Phe Arg Asp Thr Ser Tyr Glu Gln Tyr Phe
1               5                   10                  15
```

<210> SEQ ID NO 1025
<211> LENGTH: 13
<212> TYPE: PRT
<213> ORGANISM: Homo sapiens

<400> SEQUENCE: 1025

```
Cys Ser Ala Ile Ala Pro Pro Tyr Asn Glu Gln Phe Phe
1               5                   10
```

<210> SEQ ID NO 1026
<211> LENGTH: 15
<212> TYPE: PRT
<213> ORGANISM: Homo sapiens

<400> SEQUENCE: 1026

```
Cys Ser Ala Arg Leu Ala Gly Gly Gly Thr Gly Glu Leu Phe Phe
1               5                   10                  15
```

<210> SEQ ID NO 1027
<211> LENGTH: 13
<212> TYPE: PRT
<213> ORGANISM: Homo sapiens

<400> SEQUENCE: 1027

```
Cys Ala Ser Ser Gly Gly Gln Gly Pro Gly Tyr Thr Phe
```

```
1               5                   10
```

<210> SEQ ID NO 1028
<211> LENGTH: 15
<212> TYPE: PRT
<213> ORGANISM: Homo sapiens

<400> SEQUENCE: 1028

```
Cys Ala Ser Ser Pro Asp Arg Pro Ser Thr Asp Thr Gln Tyr Phe
1               5                   10                  15
```

<210> SEQ ID NO 1029
<211> LENGTH: 12
<212> TYPE: PRT
<213> ORGANISM: Homo sapiens

<400> SEQUENCE: 1029

```
Cys Ser Val Arg Thr Ser Ala Glu Thr Gln Tyr Phe
1               5                   10
```

<210> SEQ ID NO 1030
<211> LENGTH: 13
<212> TYPE: PRT
<213> ORGANISM: Homo sapiens

<400> SEQUENCE: 1030

```
Cys Ala Ser Arg Arg Gly Thr Asp Gln Pro Gln His Phe
1               5                   10
```

<210> SEQ ID NO 1031
<211> LENGTH: 15
<212> TYPE: PRT
<213> ORGANISM: Homo sapiens

<400> SEQUENCE: 1031

```
Cys Ala Ser Ser Phe Glu Arg Asn Tyr Asn Ser Pro Leu His Phe
1               5                   10                  15
```

<210> SEQ ID NO 1032
<211> LENGTH: 17
<212> TYPE: PRT
<213> ORGANISM: Homo sapiens

<400> SEQUENCE: 1032

```
Cys Ala Ser Ser Pro Pro Gly Gly Leu Glu Asn Thr Gly Glu Leu Phe
1               5                   10                  15

Phe
```

<210> SEQ ID NO 1033
<211> LENGTH: 17
<212> TYPE: PRT
<213> ORGANISM: Homo sapiens

<400> SEQUENCE: 1033

```
Cys Ala Ser Ser Pro Pro Glu Gly Leu Glu Asn Thr Gly Glu Leu Phe
1               5                   10                  15

Phe
```

<210> SEQ ID NO 1034
<211> LENGTH: 14
<212> TYPE: PRT
<213> ORGANISM: Homo sapiens

<400> SEQUENCE: 1034

Cys Ala Ser Ser Leu Ile Gly Gly Met Glu Thr Gln Tyr Phe
1               5                   10

<210> SEQ ID NO 1035
<211> LENGTH: 12
<212> TYPE: PRT
<213> ORGANISM: Homo sapiens

<400> SEQUENCE: 1035

Cys Ser Ala Thr Thr Thr Gly Ala Glu Ala Phe Phe
1               5                   10

<210> SEQ ID NO 1036
<211> LENGTH: 14
<212> TYPE: PRT
<213> ORGANISM: Homo sapiens

<400> SEQUENCE: 1036

Cys Ala Ser Ser Asp Lys Gly Arg Thr Gly Glu Leu Phe Phe
1               5                   10

<210> SEQ ID NO 1037
<211> LENGTH: 16
<212> TYPE: PRT
<213> ORGANISM: Homo sapiens

<400> SEQUENCE: 1037

Cys Ala Ser Ser Leu Ala Leu Val Gly Ser Thr Asp Thr Gln Tyr Phe
1               5                   10                  15

<210> SEQ ID NO 1038
<211> LENGTH: 16
<212> TYPE: PRT
<213> ORGANISM: Homo sapiens

<400> SEQUENCE: 1038

Cys Ala Ser Ser Val Glu Gly Glu Gly Leu Gln Glu Thr Gln Tyr Phe
1               5                   10                  15

<210> SEQ ID NO 1039
<211> LENGTH: 15
<212> TYPE: PRT
<213> ORGANISM: Homo sapiens

<400> SEQUENCE: 1039

Cys Ala Ser Ser Asn Arg Val Ser Gly Ala Asn Val Leu Thr Phe
1               5                   10                  15

<210> SEQ ID NO 1040
<211> LENGTH: 14
<212> TYPE: PRT
<213> ORGANISM: Homo sapiens

<400> SEQUENCE: 1040

Cys Ser Ala Ala Gly Gln Gly Ser Thr Asp Thr Gln Tyr Phe
1               5                   10

<210> SEQ ID NO 1041
<211> LENGTH: 13
<212> TYPE: PRT
<213> ORGANISM: Homo sapiens

<400> SEQUENCE: 1041

Cys Ala Ser Ser Thr Asp Arg Asp Arg Glu Gln Phe Phe

```
1               5                   10
```

<210> SEQ ID NO 1042
<211> LENGTH: 13
<212> TYPE: PRT
<213> ORGANISM: Homo sapiens

<400> SEQUENCE: 1042

```
Cys Ala Trp Ser Arg Arg Gly Ala Tyr Glu Gln Tyr Phe
1               5                   10
```

<210> SEQ ID NO 1043
<211> LENGTH: 15
<212> TYPE: PRT
<213> ORGANISM: Homo sapiens

<400> SEQUENCE: 1043

```
Cys Ser Ala Arg Arg Ala Gly Ala Gly Thr Asp Thr Gln Tyr Phe
1               5                   10                  15
```

<210> SEQ ID NO 1044
<211> LENGTH: 13
<212> TYPE: PRT
<213> ORGANISM: Homo sapiens

<400> SEQUENCE: 1044

```
Cys Ala Ser Ser Ser Gly Ser Ile Ala Glu Ala Phe Phe
1               5                   10
```

<210> SEQ ID NO 1045
<211> LENGTH: 13
<212> TYPE: PRT
<213> ORGANISM: Homo sapiens

<400> SEQUENCE: 1045

```
Cys Ala Ser Ser Thr His Asp Arg Gly Glu Gln Tyr Phe
1               5                   10
```

<210> SEQ ID NO 1046
<211> LENGTH: 13
<212> TYPE: PRT
<213> ORGANISM: Homo sapiens

<400> SEQUENCE: 1046

```
Cys Ala Ser Ser Leu Ala Gly Leu Asn Glu Gln Tyr Phe
1               5                   10
```

<210> SEQ ID NO 1047
<211> LENGTH: 17
<212> TYPE: PRT
<213> ORGANISM: Homo sapiens

<400> SEQUENCE: 1047

```
Cys Ala Ser Ser Leu Ala Pro Arg Asp Arg Gly Asn Ser Pro Leu His
1               5                   10                  15

Phe
```

<210> SEQ ID NO 1048
<211> LENGTH: 14
<212> TYPE: PRT
<213> ORGANISM: Homo sapiens

<400> SEQUENCE: 1048

```
Cys Ala Ser Asn Arg Arg Gln Gly Tyr Asn Glu Gln Phe Phe
```

```
1               5                   10
```

<210> SEQ ID NO 1049
<211> LENGTH: 14
<212> TYPE: PRT
<213> ORGANISM: Homo sapiens

<400> SEQUENCE: 1049

```
Cys Ala Ser Ser Arg Gly Gly Arg Gly Asn Glu Gln Phe Phe
1               5                   10
```

<210> SEQ ID NO 1050
<211> LENGTH: 13
<212> TYPE: PRT
<213> ORGANISM: Homo sapiens

<400> SEQUENCE: 1050

```
Cys Ala Ser Arg Glu Thr Gly Glu Gly Pro Gln His Phe
1               5                   10
```

<210> SEQ ID NO 1051
<211> LENGTH: 16
<212> TYPE: PRT
<213> ORGANISM: Homo sapiens

<400> SEQUENCE: 1051

```
Cys Ala Ser Ser Val Leu Gln Gly Leu Ser Thr Asp Thr Gln Tyr Phe
1               5                   10                  15
```

<210> SEQ ID NO 1052
<211> LENGTH: 13
<212> TYPE: PRT
<213> ORGANISM: Homo sapiens

<400> SEQUENCE: 1052

```
Cys Ala Ser Ser Val Ser Gly Gly Asn Thr Ile Tyr Phe
1               5                   10
```

<210> SEQ ID NO 1053
<211> LENGTH: 15
<212> TYPE: PRT
<213> ORGANISM: Homo sapiens

<400> SEQUENCE: 1053

```
Cys Ala Ser Ser Leu Met Ser Gly Ser Gly Asn Glu Gln Phe Phe
1               5                   10                  15
```

<210> SEQ ID NO 1054
<211> LENGTH: 14
<212> TYPE: PRT
<213> ORGANISM: Homo sapiens

<400> SEQUENCE: 1054

```
Cys Ala Ser Ser Phe Arg Arg Thr Asp Tyr Glu Gln Tyr Phe
1               5                   10
```

<210> SEQ ID NO 1055
<211> LENGTH: 14
<212> TYPE: PRT
<213> ORGANISM: Homo sapiens

<400> SEQUENCE: 1055

```
Cys Ala Ser Ser Arg Gly Leu Val Val Tyr Glu Gln Tyr Phe
1               5                   10
```

```
<210> SEQ ID NO 1056
<211> LENGTH: 11
<212> TYPE: PRT
<213> ORGANISM: Homo sapiens

<400> SEQUENCE: 1056

Cys Ala Ser Leu Ala Pro Gly Glu Leu Phe Phe
1               5                   10

<210> SEQ ID NO 1057
<211> LENGTH: 11
<212> TYPE: PRT
<213> ORGANISM: Homo sapiens

<400> SEQUENCE: 1057

Cys Ser Ala Arg Gln Val Val Glu Gln Tyr Phe
1               5                   10

<210> SEQ ID NO 1058
<211> LENGTH: 15
<212> TYPE: PRT
<213> ORGANISM: Homo sapiens

<400> SEQUENCE: 1058

Cys Ala Ser Ser Leu Asp Leu Gly Pro Gly Asn Glu Gln Phe Phe
1               5                   10                  15

<210> SEQ ID NO 1059
<211> LENGTH: 14
<212> TYPE: PRT
<213> ORGANISM: Homo sapiens

<400> SEQUENCE: 1059

Cys Ala Ser Ser Arg Gln Gly Ser Leu Asn Glu Gln Phe Phe
1               5                   10

<210> SEQ ID NO 1060
<211> LENGTH: 14
<212> TYPE: PRT
<213> ORGANISM: Homo sapiens

<400> SEQUENCE: 1060

Cys Ala Ser Ser Arg Glu Thr Ala Asn Tyr Gly Tyr Thr Phe
1               5                   10

<210> SEQ ID NO 1061
<211> LENGTH: 14
<212> TYPE: PRT
<213> ORGANISM: Homo sapiens

<400> SEQUENCE: 1061

Cys Ala Ser Ser Arg Gly Gln Lys Gly Glu Lys Leu Phe Phe
1               5                   10

<210> SEQ ID NO 1062
<211> LENGTH: 14
<212> TYPE: PRT
<213> ORGANISM: Homo sapiens

<400> SEQUENCE: 1062

Cys Ala Ser Arg Gly Gly Val Arg Ser Tyr Glu Gln Tyr Phe
1               5                   10

<210> SEQ ID NO 1063
```

```
<211> LENGTH: 14
<212> TYPE: PRT
<213> ORGANISM: Homo sapiens

<400> SEQUENCE: 1063

Cys Ala Ser Ser Leu Ser Pro Leu Ser Glu Thr Gln Tyr Phe
1               5                   10

<210> SEQ ID NO 1064
<211> LENGTH: 15
<212> TYPE: PRT
<213> ORGANISM: Homo sapiens

<400> SEQUENCE: 1064

Cys Ala Ser Ser Pro Met Gly Gly Arg Gly Asn Glu Gln Phe Phe
1               5                   10                  15

<210> SEQ ID NO 1065
<211> LENGTH: 11
<212> TYPE: PRT
<213> ORGANISM: Homo sapiens

<400> SEQUENCE: 1065

Cys Ala Ser Gln Leu Gly Tyr Glu Gln Tyr Phe
1               5                   10

<210> SEQ ID NO 1066
<211> LENGTH: 16
<212> TYPE: PRT
<213> ORGANISM: Homo sapiens

<400> SEQUENCE: 1066

Cys Ala Thr Ser Arg Glu Asp Arg Gly Leu Ser Tyr Glu Gln Tyr Phe
1               5                   10                  15

<210> SEQ ID NO 1067
<211> LENGTH: 15
<212> TYPE: PRT
<213> ORGANISM: Homo sapiens

<400> SEQUENCE: 1067

Cys Ser Ala Arg Gln Gln Pro Ser Asn Thr Gly Glu Leu Phe Phe
1               5                   10                  15

<210> SEQ ID NO 1068
<211> LENGTH: 15
<212> TYPE: PRT
<213> ORGANISM: Homo sapiens

<400> SEQUENCE: 1068

Cys Ala Ser Ser Gln Asp Gly Gly Ser Trp Tyr Glu Gln Tyr Phe
1               5                   10                  15

<210> SEQ ID NO 1069
<211> LENGTH: 13
<212> TYPE: PRT
<213> ORGANISM: Homo sapiens

<400> SEQUENCE: 1069

Cys Ser Ala Pro Gln Gly Val Ala Tyr Glu Gln Tyr Phe
1               5                   10

<210> SEQ ID NO 1070
<211> LENGTH: 15
<212> TYPE: PRT
```

<213> ORGANISM: Homo sapiens

<400> SEQUENCE: 1070

Cys Ala Ser Ser Gln Glu Gln Gly Val Asn Gln Pro Gln His Phe
1               5                   10                  15

<210> SEQ ID NO 1071
<211> LENGTH: 15
<212> TYPE: PRT
<213> ORGANISM: Homo sapiens

<400> SEQUENCE: 1071

Cys Ala Ser Ser Pro Arg Glu Thr Gly Gly Gly Gly Tyr Thr Phe
1               5                   10                  15

<210> SEQ ID NO 1072
<211> LENGTH: 12
<212> TYPE: PRT
<213> ORGANISM: Homo sapiens

<400> SEQUENCE: 1072

Cys Ala Arg Gly Thr Gly Phe Ser Glu Gln Tyr Phe
1               5                   10

<210> SEQ ID NO 1073
<211> LENGTH: 13
<212> TYPE: PRT
<213> ORGANISM: Homo sapiens

<400> SEQUENCE: 1073

Cys Ala Ser Asn Gly Gly Val Arg Glu Thr Gln Tyr Phe
1               5                   10

<210> SEQ ID NO 1074
<211> LENGTH: 13
<212> TYPE: PRT
<213> ORGANISM: Homo sapiens

<400> SEQUENCE: 1074

Cys Ser Ala Arg His Asp Gly Asp Thr Glu Ala Phe Phe
1               5                   10

<210> SEQ ID NO 1075
<211> LENGTH: 13
<212> TYPE: PRT
<213> ORGANISM: Homo sapiens

<400> SEQUENCE: 1075

Cys Ala Ser Ser Leu Val Leu Gly Asn Thr Gln Tyr Phe
1               5                   10

<210> SEQ ID NO 1076
<211> LENGTH: 13
<212> TYPE: PRT
<213> ORGANISM: Homo sapiens

<400> SEQUENCE: 1076

Cys Ala Ser Ser Thr Arg Arg Gly Asp Glu Gln Tyr Phe
1               5                   10

<210> SEQ ID NO 1077
<211> LENGTH: 16
<212> TYPE: PRT
<213> ORGANISM: Homo sapiens

```
<400> SEQUENCE: 1077

Cys Ala Ser Ser Leu Gly Gln Gly Arg Arg Thr Tyr Glu Gln Tyr Phe
1               5                   10                  15

<210> SEQ ID NO 1078
<211> LENGTH: 14
<212> TYPE: PRT
<213> ORGANISM: Homo sapiens

<400> SEQUENCE: 1078

Cys Ser Ala Gly Pro Leu Ala Gly Gly Tyr Glu Gln Tyr Phe
1               5                   10

<210> SEQ ID NO 1079
<211> LENGTH: 13
<212> TYPE: PRT
<213> ORGANISM: Homo sapiens

<400> SEQUENCE: 1079

Cys Ala Ser Thr Gly Gly Gly Ala Asn Val Leu Thr Phe
1               5                   10

<210> SEQ ID NO 1080
<211> LENGTH: 13
<212> TYPE: PRT
<213> ORGANISM: Homo sapiens

<400> SEQUENCE: 1080

Cys Ala Ser Asn Pro Ser Gly Gly Ser Pro Leu His Phe
1               5                   10

<210> SEQ ID NO 1081
<211> LENGTH: 17
<212> TYPE: PRT
<213> ORGANISM: Homo sapiens

<400> SEQUENCE: 1081

Cys Ala Ser Ser Leu Gly Asn Ser Gly Asp Pro Pro Asp Thr Gln Tyr
1               5                   10                  15

Phe

<210> SEQ ID NO 1082
<211> LENGTH: 16
<212> TYPE: PRT
<213> ORGANISM: Homo sapiens

<400> SEQUENCE: 1082

Cys Ala Ser Ser Thr Ser Ser Gly Ser Pro Tyr Asn Glu Gln Phe Phe
1               5                   10                  15

<210> SEQ ID NO 1083
<211> LENGTH: 15
<212> TYPE: PRT
<213> ORGANISM: Homo sapiens

<400> SEQUENCE: 1083

Cys Ser Ala Arg Ile Ser Gly Ser Gly Thr Gly Glu Leu Phe Phe
1               5                   10                  15

<210> SEQ ID NO 1084
<211> LENGTH: 15
<212> TYPE: PRT
<213> ORGANISM: Homo sapiens
```

```
<400> SEQUENCE: 1084

Cys Ser Ala Arg Val Gly Gly Ala Gly Thr Gly Glu Leu Phe Phe
1               5                   10                  15

<210> SEQ ID NO 1085
<211> LENGTH: 17
<212> TYPE: PRT
<213> ORGANISM: Homo sapiens

<400> SEQUENCE: 1085

Cys Ala Ser Ser Leu Gly Leu Ala Gly Gly Arg Ala Asp Thr Gln Tyr
1               5                   10                  15

Phe

<210> SEQ ID NO 1086
<211> LENGTH: 14
<212> TYPE: PRT
<213> ORGANISM: Homo sapiens

<400> SEQUENCE: 1086

Cys Ala Ser Lys Arg Gly Thr His Thr Asp Thr Gln Tyr Phe
1               5                   10

<210> SEQ ID NO 1087
<211> LENGTH: 15
<212> TYPE: PRT
<213> ORGANISM: Homo sapiens

<400> SEQUENCE: 1087

Cys Ser Ala Arg Ser Ser Gly Arg Ala Ser Asp Thr Gln Tyr Phe
1               5                   10                  15

<210> SEQ ID NO 1088
<211> LENGTH: 12
<212> TYPE: PRT
<213> ORGANISM: Homo sapiens

<400> SEQUENCE: 1088

Cys Ser Ala Phe Arg Gly Gly Tyr Glu Gln Tyr Phe
1               5                   10

<210> SEQ ID NO 1089
<211> LENGTH: 17
<212> TYPE: PRT
<213> ORGANISM: Homo sapiens

<400> SEQUENCE: 1089

Cys Ala Thr Ser Asp Ser Asn Leu Ala Gly Gly Tyr Asn Glu Gln Phe
1               5                   10                  15

Phe

<210> SEQ ID NO 1090
<211> LENGTH: 14
<212> TYPE: PRT
<213> ORGANISM: Homo sapiens

<400> SEQUENCE: 1090

Cys Ala Ser Ser Leu Ser Ser Gly Val Ser Gly Tyr Thr Phe
1               5                   10

<210> SEQ ID NO 1091
<211> LENGTH: 16
<212> TYPE: PRT
```

<213> ORGANISM: Homo sapiens

<400> SEQUENCE: 1091

Cys Ala Ser Ser Asn Arg Arg Arg Ala Thr Asn Glu Lys Leu Phe Phe
1               5                   10                  15

<210> SEQ ID NO 1092
<211> LENGTH: 10
<212> TYPE: PRT
<213> ORGANISM: Homo sapiens

<400> SEQUENCE: 1092

Cys Ala Ser Gly Leu Glu Thr Gln Tyr Phe
1               5                   10

<210> SEQ ID NO 1093
<211> LENGTH: 15
<212> TYPE: PRT
<213> ORGANISM: Homo sapiens

<400> SEQUENCE: 1093

Cys Ala Ser Ser Val Asp Arg Val Leu Ser Tyr Glu Gln Tyr Phe
1               5                   10                  15

<210> SEQ ID NO 1094
<211> LENGTH: 14
<212> TYPE: PRT
<213> ORGANISM: Homo sapiens

<400> SEQUENCE: 1094

Cys Ala Ser Ser Leu Ala Glu Arg Pro Glu Thr Gln Tyr Phe
1               5                   10

<210> SEQ ID NO 1095
<211> LENGTH: 13
<212> TYPE: PRT
<213> ORGANISM: Homo sapiens

<400> SEQUENCE: 1095

Cys Ala Trp Asn Arg Arg Gly Leu Tyr Glu Gln Tyr Phe
1               5                   10

<210> SEQ ID NO 1096
<211> LENGTH: 11
<212> TYPE: PRT
<213> ORGANISM: Homo sapiens

<400> SEQUENCE: 1096

Cys Ser Val Asp Leu Gly Gly Glu Gln Tyr Phe
1               5                   10

<210> SEQ ID NO 1097
<211> LENGTH: 14
<212> TYPE: PRT
<213> ORGANISM: Homo sapiens

<400> SEQUENCE: 1097

Cys Ala Ser Ile Ser Gly Gln Gly Gly Gln Pro Gln His Phe
1               5                   10

<210> SEQ ID NO 1098
<211> LENGTH: 14
<212> TYPE: PRT
<213> ORGANISM: Homo sapiens

```
<400> SEQUENCE: 1098

Cys Ala Ser Lys Thr Gly Ala Tyr Asn Ser Pro Leu His Phe
1               5                   10

<210> SEQ ID NO 1099
<211> LENGTH: 17
<212> TYPE: PRT
<213> ORGANISM: Homo sapiens

<400> SEQUENCE: 1099

Cys Ser Ala Arg Asp Arg Pro Thr Thr Ser Gly Ala Asn Val Leu Thr
1               5                   10                  15

Phe

<210> SEQ ID NO 1100
<211> LENGTH: 15
<212> TYPE: PRT
<213> ORGANISM: Homo sapiens

<400> SEQUENCE: 1100

Cys Ala Ser Ser Phe Glu Gly Asn Tyr Gly Asn Thr Ile Tyr Phe
1               5                   10                  15

<210> SEQ ID NO 1101
<211> LENGTH: 14
<212> TYPE: PRT
<213> ORGANISM: Homo sapiens

<400> SEQUENCE: 1101

Cys Ala Ser Ser Phe Ser Ser Ala Asn Asn Glu Gln Phe Phe
1               5                   10

<210> SEQ ID NO 1102
<211> LENGTH: 16
<212> TYPE: PRT
<213> ORGANISM: Homo sapiens

<400> SEQUENCE: 1102

Cys Ala Thr Ser Arg Glu Leu Ala Gly Gly Ser Asp Thr Gln Tyr Phe
1               5                   10                  15

<210> SEQ ID NO 1103
<211> LENGTH: 15
<212> TYPE: PRT
<213> ORGANISM: Homo sapiens

<400> SEQUENCE: 1103

Cys Ala Ser Ser Glu Asp Arg Val Pro Ser Tyr Glu Gln Tyr Phe
1               5                   10                  15

<210> SEQ ID NO 1104
<211> LENGTH: 15
<212> TYPE: PRT
<213> ORGANISM: Homo sapiens

<400> SEQUENCE: 1104

Cys Ala Ser Ser Pro Ser Arg Gly Ser Tyr Asn Glu Gln Phe Phe
1               5                   10                  15

<210> SEQ ID NO 1105
<211> LENGTH: 15
<212> TYPE: PRT
<213> ORGANISM: Homo sapiens
```

```
<400> SEQUENCE: 1105

Cys Ala Ser Ser Gly Gly Gln Gly His Tyr Gly Tyr Thr Phe
1               5                   10                  15

<210> SEQ ID NO 1106
<211> LENGTH: 15
<212> TYPE: PRT
<213> ORGANISM: Homo sapiens

<400> SEQUENCE: 1106

Cys Ala Ser Ser Ile Arg Pro Ser Gly Ala Asn Val Leu Thr Phe
1               5                   10                  15

<210> SEQ ID NO 1107
<211> LENGTH: 17
<212> TYPE: PRT
<213> ORGANISM: Homo sapiens

<400> SEQUENCE: 1107

Cys Ala Ser Ser Asp Pro Leu Ala Gly Gly Arg Thr Asp Thr Gln Tyr
1               5                   10                  15

Phe

<210> SEQ ID NO 1108
<211> LENGTH: 17
<212> TYPE: PRT
<213> ORGANISM: Homo sapiens

<400> SEQUENCE: 1108

Cys Ser Ala Arg Asp Pro Gly Gln Pro Ser Gly Ala Asn Val Leu Thr
1               5                   10                  15

Phe

<210> SEQ ID NO 1109
<211> LENGTH: 13
<212> TYPE: PRT
<213> ORGANISM: Homo sapiens

<400> SEQUENCE: 1109

Cys Ala Ser Ser Arg Pro Arg Asp Tyr Glu Gln Tyr Phe
1               5                   10

<210> SEQ ID NO 1110
<211> LENGTH: 14
<212> TYPE: PRT
<213> ORGANISM: Homo sapiens

<400> SEQUENCE: 1110

Cys Ala Ser Ser Ser Asp Arg Lys Gly Tyr Glu Gln Tyr Phe
1               5                   10

<210> SEQ ID NO 1111
<211> LENGTH: 16
<212> TYPE: PRT
<213> ORGANISM: Homo sapiens

<400> SEQUENCE: 1111

Cys Ala Ser Ser Leu Leu Arg Gly Tyr Ser Ser Tyr Glu Gln Tyr Phe
1               5                   10                  15

<210> SEQ ID NO 1112
<211> LENGTH: 14
<212> TYPE: PRT
```

<213> ORGANISM: Homo sapiens

<400> SEQUENCE: 1112

Cys Ala Ile Lys Glu Trp Ser Ser Gly Asn Thr Ile Tyr Phe
1               5                   10

<210> SEQ ID NO 1113
<211> LENGTH: 16
<212> TYPE: PRT
<213> ORGANISM: Homo sapiens

<400> SEQUENCE: 1113

Cys Ala Ser Ser Gln Ala Arg Gly Gln Gly Val Thr Glu Ala Phe Phe
1               5                   10                  15

<210> SEQ ID NO 1114
<211> LENGTH: 14
<212> TYPE: PRT
<213> ORGANISM: Homo sapiens

<400> SEQUENCE: 1114

Cys Ala Ser Thr Gln Arg Gly Gly Ala Asn Glu Gln Phe Phe
1               5                   10

<210> SEQ ID NO 1115
<211> LENGTH: 17
<212> TYPE: PRT
<213> ORGANISM: Homo sapiens

<400> SEQUENCE: 1115

Cys Ala Ser Ser Leu Gly Ser Arg Trp Gly Ser Thr Asp Thr Gln Tyr
1               5                   10                  15

Phe

<210> SEQ ID NO 1116
<211> LENGTH: 15
<212> TYPE: PRT
<213> ORGANISM: Homo sapiens

<400> SEQUENCE: 1116

Cys Ala Ser Ser Leu Phe Ser Gly Glu Gly Glu Thr Gln Tyr Phe
1               5                   10                  15

<210> SEQ ID NO 1117
<211> LENGTH: 15
<212> TYPE: PRT
<213> ORGANISM: Homo sapiens

<400> SEQUENCE: 1117

Cys Ser Ala Arg Arg Gly Gly Gln Gly Thr Gly Glu Leu Phe Phe
1               5                   10                  15

<210> SEQ ID NO 1118
<211> LENGTH: 14
<212> TYPE: PRT
<213> ORGANISM: Homo sapiens

<400> SEQUENCE: 1118

Cys Ala Ser Ser Tyr Leu Asp Leu Ser Tyr Glu Gln Tyr Phe
1               5                   10

<210> SEQ ID NO 1119
<211> LENGTH: 15
<212> TYPE: PRT

<213> ORGANISM: Homo sapiens

<400> SEQUENCE: 1119

Cys Ala Ser Ser Pro Val Ser Ile Ser Tyr Glu Gln Tyr Phe
1               5                   10                  15

<210> SEQ ID NO 1120
<211> LENGTH: 14
<212> TYPE: PRT
<213> ORGANISM: Homo sapiens

<400> SEQUENCE: 1120

Cys Ala Ser Ser Ser Val Asp Ser Ser Tyr Glu Gln Tyr Phe
1               5                   10

<210> SEQ ID NO 1121
<211> LENGTH: 13
<212> TYPE: PRT
<213> ORGANISM: Homo sapiens

<400> SEQUENCE: 1121

Cys Ser Val Val Pro Gly Gly Val Asp Thr Gln Tyr Phe
1               5                   10

<210> SEQ ID NO 1122
<211> LENGTH: 14
<212> TYPE: PRT
<213> ORGANISM: Homo sapiens

<400> SEQUENCE: 1122

Cys Ser Ala Lys Ser Pro Gly Phe Thr Asp Thr Gln Tyr Phe
1               5                   10

<210> SEQ ID NO 1123
<211> LENGTH: 15
<212> TYPE: PRT
<213> ORGANISM: Homo sapiens

<400> SEQUENCE: 1123

Cys Ala Ser Ser Leu Ala Gly Gly Thr Phe Tyr Glu Gln Tyr Phe
1               5                   10                  15

<210> SEQ ID NO 1124
<211> LENGTH: 16
<212> TYPE: PRT
<213> ORGANISM: Homo sapiens

<400> SEQUENCE: 1124

Cys Ala Ser Ser Leu Gly Ala Ser Phe Ser Gly Asn Thr Ile Tyr Phe
1               5                   10                  15

<210> SEQ ID NO 1125
<211> LENGTH: 18
<212> TYPE: PRT
<213> ORGANISM: Homo sapiens

<400> SEQUENCE: 1125

Cys Ala Ser Ser Arg Arg Leu Ala Gly Gly Pro Gly Thr Asp Thr Gln
1               5                   10                  15

Tyr Phe

<210> SEQ ID NO 1126
<211> LENGTH: 14
<212> TYPE: PRT

<213> ORGANISM: Homo sapiens

<400> SEQUENCE: 1126

Cys Ala Ser Ser Glu Ala Ser Lys Gly Tyr Glu Gln Tyr Phe
1               5                   10

<210> SEQ ID NO 1127
<211> LENGTH: 14
<212> TYPE: PRT
<213> ORGANISM: Homo sapiens

<400> SEQUENCE: 1127

Cys Ala Ser Ala Gly Gln Ile Ser Asn Gln Pro Gln His Phe
1               5                   10

<210> SEQ ID NO 1128
<211> LENGTH: 15
<212> TYPE: PRT
<213> ORGANISM: Homo sapiens

<400> SEQUENCE: 1128

Cys Ala Ser Ser Ala Pro Gly Thr Ser Phe Tyr Glu Gln Tyr Phe
1               5                   10                  15

<210> SEQ ID NO 1129
<211> LENGTH: 15
<212> TYPE: PRT
<213> ORGANISM: Homo sapiens

<400> SEQUENCE: 1129

Cys Ala Ser Ser Gln Asp Ile Gly Gly Thr Tyr Gly Tyr Thr Phe
1               5                   10                  15

<210> SEQ ID NO 1130
<211> LENGTH: 16
<212> TYPE: PRT
<213> ORGANISM: Homo sapiens

<400> SEQUENCE: 1130

Cys Ser Ala Arg Leu Thr Ser Gly Gly Gly Thr Gly Glu Leu Phe Phe
1               5                   10                  15

<210> SEQ ID NO 1131
<211> LENGTH: 14
<212> TYPE: PRT
<213> ORGANISM: Homo sapiens

<400> SEQUENCE: 1131

Cys Ala Trp Glu Ser Gly Arg Ser Thr Asp Thr Gln Tyr Phe
1               5                   10

<210> SEQ ID NO 1132
<211> LENGTH: 15
<212> TYPE: PRT
<213> ORGANISM: Homo sapiens

<400> SEQUENCE: 1132

Cys Ala Ser Ser Val Gly Leu Glu Leu Thr Asp Thr Gln Tyr Phe
1               5                   10                  15

<210> SEQ ID NO 1133
<211> LENGTH: 15
<212> TYPE: PRT
<213> ORGANISM: Homo sapiens

<400> SEQUENCE: 1133

Cys Ala Ser Ser Pro Gly Gly Arg Gly Asp Gln Pro Gln His Phe
1               5                   10                  15

<210> SEQ ID NO 1134
<211> LENGTH: 15
<212> TYPE: PRT
<213> ORGANISM: Homo sapiens

<400> SEQUENCE: 1134

Cys Ala Ser Ser Ser Ala Gly Gln Asp Asn Gln Pro Gln His Phe
1               5                   10                  15

<210> SEQ ID NO 1135
<211> LENGTH: 14
<212> TYPE: PRT
<213> ORGANISM: Homo sapiens

<400> SEQUENCE: 1135

Cys Ala Ser Ser Pro Gly Ser Leu Pro Asp Thr Gln Tyr Phe
1               5                   10

<210> SEQ ID NO 1136
<211> LENGTH: 13
<212> TYPE: PRT
<213> ORGANISM: Homo sapiens

<400> SEQUENCE: 1136

Cys Ala Ser Ser Leu Glu Leu Val Asp Thr Gln Tyr Phe
1               5                   10

<210> SEQ ID NO 1137
<211> LENGTH: 13
<212> TYPE: PRT
<213> ORGANISM: Homo sapiens

<400> SEQUENCE: 1137

Cys Ala Ser Ser Gln Trp Gly Gly Ser Gly Tyr Thr Phe
1               5                   10

<210> SEQ ID NO 1138
<211> LENGTH: 15
<212> TYPE: PRT
<213> ORGANISM: Homo sapiens

<400> SEQUENCE: 1138

Cys Ala Ser Ser Val Trp Ala Gly Arg Gly Glu Thr Gln Tyr Phe
1               5                   10                  15

<210> SEQ ID NO 1139
<211> LENGTH: 12
<212> TYPE: PRT
<213> ORGANISM: Homo sapiens

<400> SEQUENCE: 1139

Cys Ser Ala Arg Asp Gly Ser Ala Thr Gln Tyr Phe
1               5                   10

<210> SEQ ID NO 1140
<211> LENGTH: 15
<212> TYPE: PRT
<213> ORGANISM: Homo sapiens

<400> SEQUENCE: 1140

Cys Ala Ser Ser Tyr Ser Gly Asp Ala Asp Thr Gln Tyr Phe
1               5                   10                  15

<210> SEQ ID NO 1141
<211> LENGTH: 15
<212> TYPE: PRT
<213> ORGANISM: Homo sapiens

<400> SEQUENCE: 1141

Cys Ala Ser Ser Val Gly Thr Thr Tyr Asn Glu Gln Phe Phe
1               5                   10                  15

<210> SEQ ID NO 1142
<211> LENGTH: 14
<212> TYPE: PRT
<213> ORGANISM: Homo sapiens

<400> SEQUENCE: 1142

Cys Ser Ala Tyr Pro Arg Leu Val Ser Tyr Glu Gln Tyr Phe
1               5                   10

<210> SEQ ID NO 1143
<211> LENGTH: 15
<212> TYPE: PRT
<213> ORGANISM: Homo sapiens

<400> SEQUENCE: 1143

Cys Ala Ser Ser Ser Asp Arg Phe Thr Tyr Asn Glu Gln Phe Phe
1               5                   10                  15

<210> SEQ ID NO 1144
<211> LENGTH: 15
<212> TYPE: PRT
<213> ORGANISM: Homo sapiens

<400> SEQUENCE: 1144

Cys Ala Ser Ser Gln Thr Gly Gly Arg Ser Gly Glu Leu Phe Phe
1               5                   10                  15

<210> SEQ ID NO 1145
<211> LENGTH: 14
<212> TYPE: PRT
<213> ORGANISM: Homo sapiens

<400> SEQUENCE: 1145

Cys Ala Ser Ser Gln Ala Pro Leu Thr Asp Thr Gln Tyr Phe
1               5                   10

<210> SEQ ID NO 1146
<211> LENGTH: 16
<212> TYPE: PRT
<213> ORGANISM: Homo sapiens

<400> SEQUENCE: 1146

Cys Ser Ala Arg Val Leu Ala Gly Gly Gln Tyr Asn Glu Gln Phe Phe
1               5                   10                  15

<210> SEQ ID NO 1147
<211> LENGTH: 15
<212> TYPE: PRT
<213> ORGANISM: Homo sapiens

<400> SEQUENCE: 1147

Cys Ala Ser Ser Phe Arg Pro Arg Gly Ala Asn Val Leu Thr Phe
1               5                   10                  15

<210> SEQ ID NO 1148
<211> LENGTH: 15
<212> TYPE: PRT
<213> ORGANISM: Homo sapiens

<400> SEQUENCE: 1148

Cys Ser Ala Arg Arg Gln Pro Ser Asn Thr Gly Glu Leu Phe Phe
1               5                   10                  15

<210> SEQ ID NO 1149
<211> LENGTH: 14
<212> TYPE: PRT
<213> ORGANISM: Homo sapiens

<400> SEQUENCE: 1149

Cys Ala Ser Ser Pro Gly Ala Ala His Gln Pro Gln His Phe
1               5                   10

<210> SEQ ID NO 1150
<211> LENGTH: 15
<212> TYPE: PRT
<213> ORGANISM: Homo sapiens

<400> SEQUENCE: 1150

Cys Ala Ser Ser Leu Gln Ala Gly Ala Tyr Asn Glu Gln Phe Phe
1               5                   10                  15

<210> SEQ ID NO 1151
<211> LENGTH: 13
<212> TYPE: PRT
<213> ORGANISM: Homo sapiens

<400> SEQUENCE: 1151

Cys Ala Ser Ser Leu Gly Arg Asn Asn Glu Gln Phe Phe
1               5                   10

<210> SEQ ID NO 1152
<211> LENGTH: 15
<212> TYPE: PRT
<213> ORGANISM: Homo sapiens

<400> SEQUENCE: 1152

Cys Ser Ala Pro Tyr Ser Gly Gln Gly Tyr Asn Glu Gln Phe Phe
1               5                   10                  15

<210> SEQ ID NO 1153
<211> LENGTH: 16
<212> TYPE: PRT
<213> ORGANISM: Homo sapiens

<400> SEQUENCE: 1153

Cys Ala Ser Thr Leu Pro Gly Leu Ala Gly Val Asn Glu Gln Phe Phe
1               5                   10                  15

<210> SEQ ID NO 1154
<211> LENGTH: 15
<212> TYPE: PRT
<213> ORGANISM: Homo sapiens

<400> SEQUENCE: 1154

Cys Ala Ser Ser Thr Gly Arg Gly Ala Asn Glu Lys Leu Phe Phe
1               5                   10                  15

```
<210> SEQ ID NO 1155
<211> LENGTH: 13
<212> TYPE: PRT
<213> ORGANISM: Homo sapiens

<400> SEQUENCE: 1155

Cys Ser Ala Gly Arg Leu Ala Gly Ser Glu Gln Phe Phe
1               5                   10

<210> SEQ ID NO 1156
<211> LENGTH: 13
<212> TYPE: PRT
<213> ORGANISM: Homo sapiens

<400> SEQUENCE: 1156

Cys Ser Ala Arg Trp Thr Ser Leu Asp Thr Gln Tyr Phe
1               5                   10

<210> SEQ ID NO 1157
<211> LENGTH: 13
<212> TYPE: PRT
<213> ORGANISM: Homo sapiens

<400> SEQUENCE: 1157

Cys Ala Ser Ser Pro Pro Ala Thr Asp Thr Gln Tyr Phe
1               5                   10

<210> SEQ ID NO 1158
<211> LENGTH: 16
<212> TYPE: PRT
<213> ORGANISM: Homo sapiens

<400> SEQUENCE: 1158

Cys Ala Ser Ser Gln Thr Thr Ser Gly Arg Gly Asn Glu Gln Phe Phe
1               5                   10                  15

<210> SEQ ID NO 1159
<211> LENGTH: 13
<212> TYPE: PRT
<213> ORGANISM: Homo sapiens

<400> SEQUENCE: 1159

Cys Ala Ser Ser Leu Ala Gly Val Gly Lys Leu Phe Phe
1               5                   10

<210> SEQ ID NO 1160
<211> LENGTH: 14
<212> TYPE: PRT
<213> ORGANISM: Homo sapiens

<400> SEQUENCE: 1160

Cys Ala Ser Ser Tyr Gly Gln Gly Asp Thr Glu Ala Phe Phe
1               5                   10

<210> SEQ ID NO 1161
<211> LENGTH: 16
<212> TYPE: PRT
<213> ORGANISM: Homo sapiens

<400> SEQUENCE: 1161

Cys Ser Ala Arg Arg Thr Ser Gly Gly Gly Thr Gly Glu Leu Phe Phe
1               5                   10                  15

<210> SEQ ID NO 1162
<211> LENGTH: 18
```

```
<212> TYPE: PRT
<213> ORGANISM: Homo sapiens

<400> SEQUENCE: 1162

Cys Ala Ser Ser Leu Val Gly Thr Ser Gly Gly Ala Arg Asp Glu Gln
1               5                   10                  15

Phe Phe

<210> SEQ ID NO 1163
<211> LENGTH: 16
<212> TYPE: PRT
<213> ORGANISM: Homo sapiens

<400> SEQUENCE: 1163

Cys Ala Ser Ser Pro Gly Thr Val Ile Met Asn Thr Glu Ala Phe Phe
1               5                   10                  15

<210> SEQ ID NO 1164
<211> LENGTH: 15
<212> TYPE: PRT
<213> ORGANISM: Homo sapiens

<400> SEQUENCE: 1164

Cys Ala Ser Ser Pro Gly Thr Gly Gly Ser Asp Gly Tyr Thr Phe
1               5                   10                  15

<210> SEQ ID NO 1165
<211> LENGTH: 13
<212> TYPE: PRT
<213> ORGANISM: Homo sapiens

<400> SEQUENCE: 1165

Cys Ala Ser Arg Gln Gly Pro Asn Thr Glu Ala Phe Phe
1               5                   10

<210> SEQ ID NO 1166
<211> LENGTH: 13
<212> TYPE: PRT
<213> ORGANISM: Homo sapiens

<400> SEQUENCE: 1166

Cys Ala Ile Arg Gly Arg Glu Gln Glu Thr Gln Tyr Phe
1               5                   10

<210> SEQ ID NO 1167
<211> LENGTH: 12
<212> TYPE: PRT
<213> ORGANISM: Homo sapiens

<400> SEQUENCE: 1167

Cys Ala Ser Arg Tyr Arg Asp Lys Gly Tyr Thr Phe
1               5                   10

<210> SEQ ID NO 1168
<211> LENGTH: 16
<212> TYPE: PRT
<213> ORGANISM: Homo sapiens

<400> SEQUENCE: 1168

Cys Ala Ser Ser Pro Gly Thr Ser Ser Thr Asp Thr Gln Tyr Phe
1               5                   10                  15

<210> SEQ ID NO 1169
<211> LENGTH: 14
```

```
<212> TYPE: PRT
<213> ORGANISM: Homo sapiens

<400> SEQUENCE: 1169

Cys Ala Ser Ser Ala Arg Asp Thr His Tyr Glu Gln Tyr Phe
1               5                   10

<210> SEQ ID NO 1170
<211> LENGTH: 16
<212> TYPE: PRT
<213> ORGANISM: Homo sapiens

<400> SEQUENCE: 1170

Cys Ala Ser Ser Leu Ala Arg Gly Arg Asp Thr Gly Glu Leu Phe Phe
1               5                   10                  15

<210> SEQ ID NO 1171
<211> LENGTH: 15
<212> TYPE: PRT
<213> ORGANISM: Homo sapiens

<400> SEQUENCE: 1171

Cys Ala Ser Ser Ser Gly Gln Val Phe Gly Glu Lys Leu Phe Phe
1               5                   10                  15

<210> SEQ ID NO 1172
<211> LENGTH: 12
<212> TYPE: PRT
<213> ORGANISM: Homo sapiens

<400> SEQUENCE: 1172

Cys Ser Ala Pro Val Pro Ala Asp Thr Gln Tyr Phe
1               5                   10

<210> SEQ ID NO 1173
<211> LENGTH: 14
<212> TYPE: PRT
<213> ORGANISM: Homo sapiens

<400> SEQUENCE: 1173

Cys Ala Ser Ser Leu Ala Pro Leu Gly Asp Glu Gln Phe Phe
1               5                   10

<210> SEQ ID NO 1174
<211> LENGTH: 15
<212> TYPE: PRT
<213> ORGANISM: Homo sapiens

<400> SEQUENCE: 1174

Cys Ser Ala Arg Ser Ser Gly Ala Gly Thr Gly Glu Leu Phe Phe
1               5                   10                  15

<210> SEQ ID NO 1175
<211> LENGTH: 14
<212> TYPE: PRT
<213> ORGANISM: Homo sapiens

<400> SEQUENCE: 1175

Cys Ala Ser Ser Gly Gly Thr Lys Asn Thr Glu Ala Phe Phe
1               5                   10

<210> SEQ ID NO 1176
<211> LENGTH: 14
<212> TYPE: PRT
<213> ORGANISM: Homo sapiens
```

<400> SEQUENCE: 1176

Cys Ala Ser Leu Gly Val Ser Ser Tyr Asn Glu Gln Phe Phe
1               5                   10

<210> SEQ ID NO 1177
<211> LENGTH: 12
<212> TYPE: PRT
<213> ORGANISM: Homo sapiens

<400> SEQUENCE: 1177

Cys Ala Ser Ser Leu Leu Val Asp Glu Gln Phe Phe
1               5                   10

<210> SEQ ID NO 1178
<211> LENGTH: 17
<212> TYPE: PRT
<213> ORGANISM: Homo sapiens

<400> SEQUENCE: 1178

Cys Ala Ser Ser Val Ala Thr Gly Gly Lys Gly Thr Asp Thr Gln Tyr
1               5                   10                  15
Phe

<210> SEQ ID NO 1179
<211> LENGTH: 15
<212> TYPE: PRT
<213> ORGANISM: Homo sapiens

<400> SEQUENCE: 1179

Cys Ala Ser Arg Ile Ala Gly Gly Pro Thr Asp Thr Gln Tyr Phe
1               5                   10                  15

<210> SEQ ID NO 1180
<211> LENGTH: 12
<212> TYPE: PRT
<213> ORGANISM: Homo sapiens

<400> SEQUENCE: 1180

Cys Ala Ser Ser Phe Arg Gly Pro Gly Tyr Thr Phe
1               5                   10

<210> SEQ ID NO 1181
<211> LENGTH: 15
<212> TYPE: PRT
<213> ORGANISM: Homo sapiens

<400> SEQUENCE: 1181

Cys Ala Ser Ser Ser Val Thr Gly Arg Gly Asn Thr Ile Tyr Phe
1               5                   10                  15

<210> SEQ ID NO 1182
<211> LENGTH: 14
<212> TYPE: PRT
<213> ORGANISM: Homo sapiens

<400> SEQUENCE: 1182

Cys Ala Ser Ser Pro Thr Thr Trp Gly Glu Lys Leu Phe Phe
1               5                   10

<210> SEQ ID NO 1183
<211> LENGTH: 13
<212> TYPE: PRT
<213> ORGANISM: Homo sapiens

<400> SEQUENCE: 1183

Cys Ala Ser Ser Trp Gln Thr Asn Glu Lys Leu Phe Phe
1               5                   10

<210> SEQ ID NO 1184
<211> LENGTH: 15
<212> TYPE: PRT
<213> ORGANISM: Homo sapiens

<400> SEQUENCE: 1184

Cys Ala Ser Ser Gln Leu Gly Phe Leu Asn Thr Glu Ala Phe Phe
1               5                   10                  15

<210> SEQ ID NO 1185
<211> LENGTH: 15
<212> TYPE: PRT
<213> ORGANISM: Homo sapiens

<400> SEQUENCE: 1185

Cys Ser Ala Arg Gly Ala Gly Ser Gly Thr Gly Glu Leu Phe Phe
1               5                   10                  15

<210> SEQ ID NO 1186
<211> LENGTH: 15
<212> TYPE: PRT
<213> ORGANISM: Homo sapiens

<400> SEQUENCE: 1186

Cys Ser Ala Arg Gly Ser Gly Arg Ala Gly Asp Thr Gln Tyr Phe
1               5                   10                  15

<210> SEQ ID NO 1187
<211> LENGTH: 15
<212> TYPE: PRT
<213> ORGANISM: Homo sapiens

<400> SEQUENCE: 1187

Cys Ala Ser Ser Arg Arg Gly Gln Ala Asp Ser Pro Leu His Phe
1               5                   10                  15

<210> SEQ ID NO 1188
<211> LENGTH: 13
<212> TYPE: PRT
<213> ORGANISM: Homo sapiens

<400> SEQUENCE: 1188

Cys Ala Ser Ser Pro Thr Phe Asp Gly Glu Ala Phe Phe
1               5                   10

<210> SEQ ID NO 1189
<211> LENGTH: 17
<212> TYPE: PRT
<213> ORGANISM: Homo sapiens

<400> SEQUENCE: 1189

Cys Ala Ser Ser Gln Asp Thr Ser Gly Gly Trp Gly Glu Thr Gln Tyr
1               5                   10                  15

Phe

<210> SEQ ID NO 1190
<211> LENGTH: 15
<212> TYPE: PRT
<213> ORGANISM: Homo sapiens

```
<400> SEQUENCE: 1190

Cys Ala Ser Ser Ala Ser His Gly Ser Asn Gln Pro Gln His Phe
1               5                   10                  15

<210> SEQ ID NO 1191
<211> LENGTH: 13
<212> TYPE: PRT
<213> ORGANISM: Homo sapiens

<400> SEQUENCE: 1191

Cys Ala Ser Ser Glu Gln Gly Ala Ile Glu Gln Tyr Phe
1               5                   10

<210> SEQ ID NO 1192
<211> LENGTH: 10
<212> TYPE: PRT
<213> ORGANISM: Homo sapiens

<400> SEQUENCE: 1192

Cys Ala Ser Thr Ser Asp Thr Gln Tyr Phe
1               5                   10

<210> SEQ ID NO 1193
<211> LENGTH: 17
<212> TYPE: PRT
<213> ORGANISM: Homo sapiens

<400> SEQUENCE: 1193

Cys Ala Ser Ser Leu Gly Leu Ala Asp Pro Ser Thr Asp Thr Gln Tyr
1               5                   10                  15

Phe

<210> SEQ ID NO 1194
<211> LENGTH: 15
<212> TYPE: PRT
<213> ORGANISM: Homo sapiens

<400> SEQUENCE: 1194

Cys Ala Ser Ser Pro Arg Gln Gly Thr Ala Tyr Glu Gln Tyr Phe
1               5                   10                  15

<210> SEQ ID NO 1195
<211> LENGTH: 14
<212> TYPE: PRT
<213> ORGANISM: Homo sapiens

<400> SEQUENCE: 1195

Cys Ala Ser Ser Pro Arg Leu Val Gly Asp Glu Gln Phe Phe
1               5                   10

<210> SEQ ID NO 1196
<211> LENGTH: 12
<212> TYPE: PRT
<213> ORGANISM: Homo sapiens

<400> SEQUENCE: 1196

Cys Val Gly Gly Arg Asp Tyr Asn Glu Gln Phe Phe
1               5                   10

<210> SEQ ID NO 1197
<211> LENGTH: 16
<212> TYPE: PRT
<213> ORGANISM: Homo sapiens
```

<400> SEQUENCE: 1197

Cys Ala Ser Ser Leu Ala Pro Gly Gly Thr Tyr Asn Glu Gln Phe Phe
1               5                   10                  15

<210> SEQ ID NO 1198
<211> LENGTH: 12
<212> TYPE: PRT
<213> ORGANISM: Homo sapiens

<400> SEQUENCE: 1198

Cys Ser Ala Arg Asp Gly Thr Pro Glu Gln Phe Phe
1               5                   10

<210> SEQ ID NO 1199
<211> LENGTH: 16
<212> TYPE: PRT
<213> ORGANISM: Homo sapiens

<400> SEQUENCE: 1199

Cys Ala Ser Ser Pro Ser Asp Leu Ser Ser Tyr Asn Glu Gln Phe Phe
1               5                   10                  15

<210> SEQ ID NO 1200
<211> LENGTH: 13
<212> TYPE: PRT
<213> ORGANISM: Homo sapiens

<400> SEQUENCE: 1200

Cys Ser Ala Leu Arg Pro Pro Tyr Asn Glu Gln Phe Phe
1               5                   10

<210> SEQ ID NO 1201
<211> LENGTH: 17
<212> TYPE: PRT
<213> ORGANISM: Homo sapiens

<400> SEQUENCE: 1201

Cys Ala Ser Ser Ser Asn Pro Gly Gln Gly Ser Tyr Asn Glu Gln Phe
1               5                   10                  15

Phe

<210> SEQ ID NO 1202
<211> LENGTH: 12
<212> TYPE: PRT
<213> ORGANISM: Homo sapiens

<400> SEQUENCE: 1202

Cys Ala Ser Ser Ser Pro Gly Arg Glu Lys Tyr Phe
1               5                   10

<210> SEQ ID NO 1203
<211> LENGTH: 15
<212> TYPE: PRT
<213> ORGANISM: Homo sapiens

<400> SEQUENCE: 1203

Cys Ala Ser Ser Pro Arg Thr Glu Asn Thr Asp Thr Gln Tyr Phe
1               5                   10                  15

<210> SEQ ID NO 1204
<211> LENGTH: 15
<212> TYPE: PRT
<213> ORGANISM: Homo sapiens

<400> SEQUENCE: 1204

Cys Ala Ser Arg Ser Gly Ala Gly Gly Ala Asn Val Leu Thr Phe
1               5                   10                  15

<210> SEQ ID NO 1205
<211> LENGTH: 13
<212> TYPE: PRT
<213> ORGANISM: Homo sapiens

<400> SEQUENCE: 1205

Cys Ser Ala Ser Asp Pro Pro Tyr Asn Glu Gln Phe Phe
1               5                   10

<210> SEQ ID NO 1206
<211> LENGTH: 13
<212> TYPE: PRT
<213> ORGANISM: Homo sapiens

<400> SEQUENCE: 1206

Cys Ala Ser Lys Asn Ser Gly Thr Tyr Glu Gln Tyr Phe
1               5                   10

<210> SEQ ID NO 1207
<211> LENGTH: 13
<212> TYPE: PRT
<213> ORGANISM: Homo sapiens

<400> SEQUENCE: 1207

Cys Ala Ser Ser Trp Tyr Arg Gly Asn Gly Tyr Thr Phe
1               5                   10

<210> SEQ ID NO 1208
<211> LENGTH: 16
<212> TYPE: PRT
<213> ORGANISM: Homo sapiens

<400> SEQUENCE: 1208

Cys Ser Ala Arg Gly Gln Gly Gln Ser Tyr Asn Ser Pro Leu His Phe
1               5                   10                  15

<210> SEQ ID NO 1209
<211> LENGTH: 15
<212> TYPE: PRT
<213> ORGANISM: Homo sapiens

<400> SEQUENCE: 1209

Cys Ala Ser Ser Pro Ser Thr Gly Ser Arg Gln Pro Gln His Phe
1               5                   10                  15

<210> SEQ ID NO 1210
<211> LENGTH: 15
<212> TYPE: PRT
<213> ORGANISM: Homo sapiens

<400> SEQUENCE: 1210

Cys Ala Ser Ser Ile Trp Ala Glu Pro Asn Ser Pro Leu His Phe
1               5                   10                  15

<210> SEQ ID NO 1211
<211> LENGTH: 12
<212> TYPE: PRT
<213> ORGANISM: Homo sapiens

<400> SEQUENCE: 1211

```
Cys Ala Ser Ser Leu Gly Asp Thr Gly Tyr Thr Phe
1               5                   10
```

<210> SEQ ID NO 1212
<211> LENGTH: 15
<212> TYPE: PRT
<213> ORGANISM: Homo sapiens

<400> SEQUENCE: 1212

```
Cys Ser Ala Arg Arg Ala Gly Ser Gly Thr Gly Glu Leu Phe Phe
1               5                   10                  15
```

<210> SEQ ID NO 1213
<211> LENGTH: 17
<212> TYPE: PRT
<213> ORGANISM: Homo sapiens

<400> SEQUENCE: 1213

```
Cys Ala Ser Ser Gln Gly Gly Leu Ala Gly Val Tyr Asn Glu Gln Phe
1               5                   10                  15

Phe
```

<210> SEQ ID NO 1214
<211> LENGTH: 12
<212> TYPE: PRT
<213> ORGANISM: Homo sapiens

<400> SEQUENCE: 1214

```
Cys Ser Ala Ser Ser Thr Glu Glu Thr Gln Tyr Phe
1               5                   10
```

<210> SEQ ID NO 1215
<211> LENGTH: 15
<212> TYPE: PRT
<213> ORGANISM: Homo sapiens

<400> SEQUENCE: 1215

```
Cys Ala Ser Ser Pro Glu Gly Val Glu Asn Thr Glu Ala Phe Phe
1               5                   10                  15
```

<210> SEQ ID NO 1216
<211> LENGTH: 15
<212> TYPE: PRT
<213> ORGANISM: Homo sapiens

<400> SEQUENCE: 1216

```
Cys Ala Ser Arg Asn Asp Arg Ala Thr Asn Thr Glu Ala Phe Phe
1               5                   10                  15
```

<210> SEQ ID NO 1217
<211> LENGTH: 13
<212> TYPE: PRT
<213> ORGANISM: Homo sapiens

<400> SEQUENCE: 1217

```
Cys Ala Ser Arg Leu Gln Gly Ala Asn Glu Gln Phe Phe
1               5                   10
```

<210> SEQ ID NO 1218
<211> LENGTH: 14
<212> TYPE: PRT
<213> ORGANISM: Homo sapiens

<400> SEQUENCE: 1218

Cys Ala Ser Ser Gln Gly Ile Val Gln Glu Thr Gln Tyr Phe
1               5                   10

<210> SEQ ID NO 1219
<211> LENGTH: 14
<212> TYPE: PRT
<213> ORGANISM: Homo sapiens

<400> SEQUENCE: 1219

Cys Ala Ser Ser Tyr Leu Gln Leu Ser Tyr Glu Gln Tyr Phe
1               5                   10

<210> SEQ ID NO 1220
<211> LENGTH: 16
<212> TYPE: PRT
<213> ORGANISM: Homo sapiens

<400> SEQUENCE: 1220

Cys Ser Ala Arg Asp Pro Leu Ala Gly Lys Ala Asp Thr Gln Tyr Phe
1               5                   10                  15

<210> SEQ ID NO 1221
<211> LENGTH: 15
<212> TYPE: PRT
<213> ORGANISM: Homo sapiens

<400> SEQUENCE: 1221

Cys Ser Ala Arg Arg Gly Gly Ser Gly Thr Gly Glu Leu Phe Phe
1               5                   10                  15

<210> SEQ ID NO 1222
<211> LENGTH: 13
<212> TYPE: PRT
<213> ORGANISM: Homo sapiens

<400> SEQUENCE: 1222

Cys Ser Ala Thr Leu Ala Pro Tyr Asn Glu Gln Phe Phe
1               5                   10

<210> SEQ ID NO 1223
<211> LENGTH: 14
<212> TYPE: PRT
<213> ORGANISM: Homo sapiens

<400> SEQUENCE: 1223

Cys Ser Ala Pro Gly Arg Lys Gly Asn Gln Pro Gln His Phe
1               5                   10

<210> SEQ ID NO 1224
<211> LENGTH: 13
<212> TYPE: PRT
<213> ORGANISM: Homo sapiens

<400> SEQUENCE: 1224

Cys Ala Ser Ser Pro Ser Leu Ala Asn Ile Gln Tyr Phe
1               5                   10

<210> SEQ ID NO 1225
<211> LENGTH: 14
<212> TYPE: PRT
<213> ORGANISM: Homo sapiens

<400> SEQUENCE: 1225

Cys Ala Ser Ser Tyr Leu Asp Asn Ser Tyr Glu Gln Tyr Phe

-continued

```
1               5                   10
```

<210> SEQ ID NO 1226
<211> LENGTH: 13
<212> TYPE: PRT
<213> ORGANISM: Homo sapiens

<400> SEQUENCE: 1226

```
Cys Ser Ala Arg Phe Thr Arg Ser Tyr Glu Gln Tyr Phe
1               5                   10
```

<210> SEQ ID NO 1227
<211> LENGTH: 13
<212> TYPE: PRT
<213> ORGANISM: Homo sapiens

<400> SEQUENCE: 1227

```
Cys Ala Ser Ser Val Arg Asp Thr Gly Glu Leu Phe Phe
1               5                   10
```

<210> SEQ ID NO 1228
<211> LENGTH: 14
<212> TYPE: PRT
<213> ORGANISM: Homo sapiens

<400> SEQUENCE: 1228

```
Cys Ser Val Val Gly Gly Pro Ser Tyr Asn Glu Gln Phe Phe
1               5                   10
```

<210> SEQ ID NO 1229
<211> LENGTH: 16
<212> TYPE: PRT
<213> ORGANISM: Homo sapiens

<400> SEQUENCE: 1229

```
Cys Ala Ser Ser Ser Pro Gly Gly Thr Gly Val Asp Glu Gln Tyr Phe
1               5                   10                  15
```

<210> SEQ ID NO 1230
<211> LENGTH: 12
<212> TYPE: PRT
<213> ORGANISM: Homo sapiens

<400> SEQUENCE: 1230

```
Cys Ala Ser Ser Leu Trp Ser Gly Glu Gln Phe Phe
1               5                   10
```

<210> SEQ ID NO 1231
<211> LENGTH: 14
<212> TYPE: PRT
<213> ORGANISM: Homo sapiens

<400> SEQUENCE: 1231

```
Cys Ala Ser Ser Gly Asp Arg Tyr Asn Glu Lys Leu Phe Phe
1               5                   10
```

<210> SEQ ID NO 1232
<211> LENGTH: 15
<212> TYPE: PRT
<213> ORGANISM: Homo sapiens

<400> SEQUENCE: 1232

```
Cys Ala Ser Ser Leu Gly Ala Gln Thr Asn Glu Lys Leu Phe Phe
1               5                   10                  15
```

<210> SEQ ID NO 1233
<211> LENGTH: 14
<212> TYPE: PRT
<213> ORGANISM: Homo sapiens

<400> SEQUENCE: 1233

Cys Ala Ser Ser Ile Arg Gly Phe Glu Glu Lys Leu Phe Phe
1               5                   10

<210> SEQ ID NO 1234
<211> LENGTH: 15
<212> TYPE: PRT
<213> ORGANISM: Homo sapiens

<400> SEQUENCE: 1234

Cys Ala Ser Ser Phe Glu Ala Asn Tyr Asn Ser Pro Leu His Phe
1               5                   10                  15

<210> SEQ ID NO 1235
<211> LENGTH: 12
<212> TYPE: PRT
<213> ORGANISM: Homo sapiens

<400> SEQUENCE: 1235

Cys Ser Val Arg Arg Gly Met His Glu Gln Phe Phe
1               5                   10

<210> SEQ ID NO 1236
<211> LENGTH: 14
<212> TYPE: PRT
<213> ORGANISM: Homo sapiens

<400> SEQUENCE: 1236

Cys Ala Ser Ser Arg Thr Gly Ser Phe Ser Pro Leu His Phe
1               5                   10

<210> SEQ ID NO 1237
<211> LENGTH: 15
<212> TYPE: PRT
<213> ORGANISM: Homo sapiens

<400> SEQUENCE: 1237

Cys Ala Ser Arg Glu Gly Gly Gly Thr Gly Asn Thr Ile Tyr Phe
1               5                   10                  15

<210> SEQ ID NO 1238
<211> LENGTH: 13
<212> TYPE: PRT
<213> ORGANISM: Homo sapiens

<400> SEQUENCE: 1238

Cys Ala Ser Ser Leu Met Thr Asn Tyr Glu Gln Tyr Phe
1               5                   10

<210> SEQ ID NO 1239
<211> LENGTH: 13
<212> TYPE: PRT
<213> ORGANISM: Homo sapiens

<400> SEQUENCE: 1239

Cys Ser Ala Gly Gly Ser Val Gly Glu Lys Leu Phe Phe
1               5                   10

<210> SEQ ID NO 1240

```
<211> LENGTH: 16
<212> TYPE: PRT
<213> ORGANISM: Homo sapiens

<400> SEQUENCE: 1240

Cys Ala Ser Gly Phe Gly Gln Gly Thr Asn Thr Gly Glu Leu Phe Phe
1               5                   10                  15

<210> SEQ ID NO 1241
<211> LENGTH: 15
<212> TYPE: PRT
<213> ORGANISM: Homo sapiens

<400> SEQUENCE: 1241

Cys Ala Ser Ser Phe Glu Gln Asn Tyr Asn Ser Pro Leu His Phe
1               5                   10                  15

<210> SEQ ID NO 1242
<211> LENGTH: 12
<212> TYPE: PRT
<213> ORGANISM: Homo sapiens

<400> SEQUENCE: 1242

Cys Ser Val Glu Thr Gly Val Asp Thr Gln Tyr Phe
1               5                   10

<210> SEQ ID NO 1243
<211> LENGTH: 15
<212> TYPE: PRT
<213> ORGANISM: Homo sapiens

<400> SEQUENCE: 1243

Cys Ala Ser Ser Thr Gly Gln Gly Val Asp Asn Glu Gln Phe Phe
1               5                   10                  15

<210> SEQ ID NO 1244
<211> LENGTH: 12
<212> TYPE: PRT
<213> ORGANISM: Homo sapiens

<400> SEQUENCE: 1244

Cys Ser Ala Arg Asp Gly Thr Pro Glu Ala Phe Phe
1               5                   10

<210> SEQ ID NO 1245
<211> LENGTH: 16
<212> TYPE: PRT
<213> ORGANISM: Homo sapiens

<400> SEQUENCE: 1245

Cys Ala Ser Ser Pro Ala Gly Thr Gly Tyr Gln Glu Thr Gln Tyr Phe
1               5                   10                  15

<210> SEQ ID NO 1246
<211> LENGTH: 14
<212> TYPE: PRT
<213> ORGANISM: Homo sapiens

<400> SEQUENCE: 1246

Cys Ala Ser Ser Thr Gly Leu Arg Asp Thr Glu Ala Phe Phe
1               5                   10

<210> SEQ ID NO 1247
<211> LENGTH: 15
<212> TYPE: PRT
```

```
<213> ORGANISM: Homo sapiens

<400> SEQUENCE: 1247

Cys Ser Ala Arg Gly Ser Ala Arg Ser Thr Asp Thr Gln Tyr Phe
1               5                   10                  15

<210> SEQ ID NO 1248
<211> LENGTH: 15
<212> TYPE: PRT
<213> ORGANISM: Homo sapiens

<400> SEQUENCE: 1248

Cys Ala Trp Ser Val His Leu Thr Gly Gly Asn Thr Ile Tyr Phe
1               5                   10                  15

<210> SEQ ID NO 1249
<211> LENGTH: 15
<212> TYPE: PRT
<213> ORGANISM: Homo sapiens

<400> SEQUENCE: 1249

Cys Ala Ser Ser Leu Glu Gly Thr Gly Gly Glu Gln Phe Phe
1               5                   10                  15

<210> SEQ ID NO 1250
<211> LENGTH: 17
<212> TYPE: PRT
<213> ORGANISM: Homo sapiens

<400> SEQUENCE: 1250

Cys Ala Ser Ser Pro Arg Ala Ser Gly Thr Asn Thr Gly Glu Leu Phe
1               5                   10                  15

Phe

<210> SEQ ID NO 1251
<211> LENGTH: 13
<212> TYPE: PRT
<213> ORGANISM: Homo sapiens

<400> SEQUENCE: 1251

Cys Ala Ser Ser Leu Pro Pro Gly Glu Thr Gln Tyr Phe
1               5                   10

<210> SEQ ID NO 1252
<211> LENGTH: 17
<212> TYPE: PRT
<213> ORGANISM: Homo sapiens

<400> SEQUENCE: 1252

Cys Ala Ser Ser Leu Thr Ser Gly Gly Ile Ala Lys Asn Ile Gln Tyr
1               5                   10                  15

Phe

<210> SEQ ID NO 1253
<211> LENGTH: 13
<212> TYPE: PRT
<213> ORGANISM: Homo sapiens

<400> SEQUENCE: 1253

Cys Ala Ser Ser Asn Gln Glu Asn Thr Glu Ala Phe Phe
1               5                   10

<210> SEQ ID NO 1254
```

```
<211> LENGTH: 13
<212> TYPE: PRT
<213> ORGANISM: Homo sapiens

<400> SEQUENCE: 1254

Cys Ala Trp Asn Pro Gly Gly Thr Gly Glu Leu Phe Phe
1               5                   10

<210> SEQ ID NO 1255
<211> LENGTH: 13
<212> TYPE: PRT
<213> ORGANISM: Homo sapiens

<400> SEQUENCE: 1255

Cys Ala Ser Ser Gln Gly Arg Asn Asn Glu Gln Phe Phe
1               5                   10

<210> SEQ ID NO 1256
<211> LENGTH: 16
<212> TYPE: PRT
<213> ORGANISM: Homo sapiens

<400> SEQUENCE: 1256

Cys Ser Ala Thr Leu Arg Gln Gly Gly Ser Asn Gln Pro Gln His Phe
1               5                   10                  15

<210> SEQ ID NO 1257
<211> LENGTH: 13
<212> TYPE: PRT
<213> ORGANISM: Homo sapiens

<400> SEQUENCE: 1257

Cys Ser Ala Pro Ala Arg Ser Gly Asn Thr Ile Tyr Phe
1               5                   10

<210> SEQ ID NO 1258
<211> LENGTH: 15
<212> TYPE: PRT
<213> ORGANISM: Homo sapiens

<400> SEQUENCE: 1258

Cys Ser Ala Arg Pro Ser Gly Ser Gly Thr Gly Glu Leu Phe Phe
1               5                   10                  15

<210> SEQ ID NO 1259
<211> LENGTH: 15
<212> TYPE: PRT
<213> ORGANISM: Homo sapiens

<400> SEQUENCE: 1259

Cys Ala Ser Ser Pro Ala Gly Gln Gly Ala Asp Gly Tyr Thr Phe
1               5                   10                  15

<210> SEQ ID NO 1260
<211> LENGTH: 15
<212> TYPE: PRT
<213> ORGANISM: Homo sapiens

<400> SEQUENCE: 1260

Cys Ala Ser Ser Ser Pro Arg Gln Pro Asn Thr Glu Ala Phe Phe
1               5                   10                  15

<210> SEQ ID NO 1261
<211> LENGTH: 15
<212> TYPE: PRT
```

-continued

```
<213> ORGANISM: Homo sapiens

<400> SEQUENCE: 1261

Cys Ala Ser Ser Val Ser Ser Gly Ser Val Tyr Glu Gln Phe Phe
1               5                   10                  15

<210> SEQ ID NO 1262
<211> LENGTH: 16
<212> TYPE: PRT
<213> ORGANISM: Homo sapiens

<400> SEQUENCE: 1262

Cys Ala Ser Ser Leu Glu Ala Ser Gly Gly Trp Asn Glu Gln Phe Phe
1               5                   10                  15

<210> SEQ ID NO 1263
<211> LENGTH: 14
<212> TYPE: PRT
<213> ORGANISM: Homo sapiens

<400> SEQUENCE: 1263

Cys Ala Ser Ser His Ser Gly Ala Lys Asn Ile Gln Tyr Phe
1               5                   10

<210> SEQ ID NO 1264
<211> LENGTH: 15
<212> TYPE: PRT
<213> ORGANISM: Homo sapiens

<400> SEQUENCE: 1264

Cys Ala Ser Ser Val Leu Ser Thr Ser Thr Gly Glu Leu Phe Phe
1               5                   10                  15

<210> SEQ ID NO 1265
<211> LENGTH: 15
<212> TYPE: PRT
<213> ORGANISM: Homo sapiens

<400> SEQUENCE: 1265

Cys Ser Ala Arg Lys Ser Pro Thr Asn Thr Gly Glu Leu Phe Phe
1               5                   10                  15

<210> SEQ ID NO 1266
<211> LENGTH: 15
<212> TYPE: PRT
<213> ORGANISM: Homo sapiens

<400> SEQUENCE: 1266

Cys Ala Ser Ser Ser Val Gln Ser Ser Tyr Asn Glu Gln Phe Phe
1               5                   10                  15

<210> SEQ ID NO 1267
<211> LENGTH: 14
<212> TYPE: PRT
<213> ORGANISM: Homo sapiens

<400> SEQUENCE: 1267

Cys Ala Ser Ser Pro Arg Thr Gly Ser Gly Glu Leu Phe Phe
1               5                   10

<210> SEQ ID NO 1268
<211> LENGTH: 16
<212> TYPE: PRT
<213> ORGANISM: Homo sapiens
```

```
<400> SEQUENCE: 1268

Cys Ala Ser Ser Pro His Arg Val Pro Met Asn Thr Glu Ala Phe Phe
1               5                   10                  15

<210> SEQ ID NO 1269
<211> LENGTH: 17
<212> TYPE: PRT
<213> ORGANISM: Homo sapiens

<400> SEQUENCE: 1269

Cys Ala Ser Ser Ser Pro Leu Ala Gly Gly Arg Ser Asp Thr Gln Tyr
1               5                   10                  15

Phe

<210> SEQ ID NO 1270
<211> LENGTH: 15
<212> TYPE: PRT
<213> ORGANISM: Homo sapiens

<400> SEQUENCE: 1270

Cys Ala Ser Ser Ser Thr Glu Pro Ser Gly Asn Thr Ile Tyr Phe
1               5                   10                  15

<210> SEQ ID NO 1271
<211> LENGTH: 15
<212> TYPE: PRT
<213> ORGANISM: Homo sapiens

<400> SEQUENCE: 1271

Cys Ala Ser Ser Gln Asp Arg Glu Leu Gly Thr Gln Tyr Phe
1               5                   10                  15

<210> SEQ ID NO 1272
<211> LENGTH: 15
<212> TYPE: PRT
<213> ORGANISM: Homo sapiens

<400> SEQUENCE: 1272

Cys Ser Ala Arg Pro Ala Gly Gly Thr Gly Glu Leu Phe Phe
1               5                   10                  15

<210> SEQ ID NO 1273
<211> LENGTH: 16
<212> TYPE: PRT
<213> ORGANISM: Homo sapiens

<400> SEQUENCE: 1273

Cys Ala Ser Ser Leu Ser Arg Arg Gly His Thr Gly Glu Leu Phe Phe
1               5                   10                  15

<210> SEQ ID NO 1274
<211> LENGTH: 14
<212> TYPE: PRT
<213> ORGANISM: Homo sapiens

<400> SEQUENCE: 1274

Cys Ala Ser Ser Pro Gln Gly Gly Ile Asp Thr Gln Tyr Phe
1               5                   10

<210> SEQ ID NO 1275
<211> LENGTH: 13
<212> TYPE: PRT
<213> ORGANISM: Homo sapiens
```

<400> SEQUENCE: 1275

Cys Ala Ser Ser Thr Gln Gly Leu Gly Pro Gln His Phe
1               5                   10

<210> SEQ ID NO 1276
<211> LENGTH: 15
<212> TYPE: PRT
<213> ORGANISM: Homo sapiens

<400> SEQUENCE: 1276

Cys Ala Ser Ser Arg Gly Gln Leu Ser Thr Asp Thr Gln Tyr Phe
1               5                   10                  15

<210> SEQ ID NO 1277
<211> LENGTH: 13
<212> TYPE: PRT
<213> ORGANISM: Homo sapiens

<400> SEQUENCE: 1277

Cys Ala Ser Gly Ala Gly Gly Asp Tyr Gly Tyr Thr Phe
1               5                   10

<210> SEQ ID NO 1278
<211> LENGTH: 15
<212> TYPE: PRT
<213> ORGANISM: Homo sapiens

<400> SEQUENCE: 1278

Cys Ala Ser Ser Ser Pro Thr Gly Leu Asn Thr Glu Ala Phe Phe
1               5                   10                  15

<210> SEQ ID NO 1279
<211> LENGTH: 15
<212> TYPE: PRT
<213> ORGANISM: Homo sapiens

<400> SEQUENCE: 1279

Cys Ala Thr Ser Pro Gly Gly Gly Pro Gln Glu Thr Gln Tyr Phe
1               5                   10                  15

<210> SEQ ID NO 1280
<211> LENGTH: 17
<212> TYPE: PRT
<213> ORGANISM: Homo sapiens

<400> SEQUENCE: 1280

Cys Ala Ser Ser Tyr Gly Gln Gly Ala Thr Asn Thr Gly Glu Leu Phe
1               5                   10                  15
Phe

<210> SEQ ID NO 1281
<211> LENGTH: 13
<212> TYPE: PRT
<213> ORGANISM: Homo sapiens

<400> SEQUENCE: 1281

Cys Ser Ala Thr Gln Gln Gly Asn Thr Glu Ala Phe Phe
1               5                   10

<210> SEQ ID NO 1282
<211> LENGTH: 16
<212> TYPE: PRT
<213> ORGANISM: Homo sapiens

```
<400> SEQUENCE: 1282

Cys Ala Ser Ser Gln Ala Ser Leu Ala Gly Leu Tyr Glu Gln Tyr Phe
1               5                   10                  15

<210> SEQ ID NO 1283
<211> LENGTH: 13
<212> TYPE: PRT
<213> ORGANISM: Homo sapiens

<400> SEQUENCE: 1283

Cys Ala Ser Ser Gly Ser Ser Thr Asp Thr Gln Tyr Phe
1               5                   10

<210> SEQ ID NO 1284
<211> LENGTH: 17
<212> TYPE: PRT
<213> ORGANISM: Homo sapiens

<400> SEQUENCE: 1284

Cys Ala Ser Ser Gly Arg Asp Arg Gly Pro Thr Asn Glu Lys Leu Phe
1               5                   10                  15

Phe

<210> SEQ ID NO 1285
<211> LENGTH: 15
<212> TYPE: PRT
<213> ORGANISM: Homo sapiens

<400> SEQUENCE: 1285

Cys Ala Ser Ser Arg Asp Gly Gly Arg Asn Gln Pro Gln His Phe
1               5                   10                  15

<210> SEQ ID NO 1286
<211> LENGTH: 14
<212> TYPE: PRT
<213> ORGANISM: Homo sapiens

<400> SEQUENCE: 1286

Cys Ala Ser Ser Ser Asn Arg Gly His Glu Lys Leu Phe Phe
1               5                   10

<210> SEQ ID NO 1287
<211> LENGTH: 14
<212> TYPE: PRT
<213> ORGANISM: Homo sapiens

<400> SEQUENCE: 1287

Cys Ala Ser Ser Pro Gly Thr Gly Lys Asp Glu Gln Phe Phe
1               5                   10

<210> SEQ ID NO 1288
<211> LENGTH: 15
<212> TYPE: PRT
<213> ORGANISM: Homo sapiens

<400> SEQUENCE: 1288

Cys Ala Ser Ser Pro Ser Arg Gly Arg Asn Tyr Gly Tyr Thr Phe
1               5                   10                  15

<210> SEQ ID NO 1289
<211> LENGTH: 15
<212> TYPE: PRT
<213> ORGANISM: Homo sapiens
```

```
<400> SEQUENCE: 1289

Cys Ala Ser Ser Glu Tyr Gly Val Gly Asp Thr Glu Ala Phe Phe
1               5                   10                  15

<210> SEQ ID NO 1290
<211> LENGTH: 17
<212> TYPE: PRT
<213> ORGANISM: Homo sapiens

<400> SEQUENCE: 1290

Cys Ala Ser Ser Leu Thr Gly Gly Leu Ser Gly Thr Gly Glu Leu Phe
1               5                   10                  15

Phe

<210> SEQ ID NO 1291
<211> LENGTH: 15
<212> TYPE: PRT
<213> ORGANISM: Homo sapiens

<400> SEQUENCE: 1291

Cys Ala Ser Arg Pro Thr Val Ala Thr Asn Glu Lys Leu Phe Phe
1               5                   10                  15

<210> SEQ ID NO 1292
<211> LENGTH: 15
<212> TYPE: PRT
<213> ORGANISM: Homo sapiens

<400> SEQUENCE: 1292

Cys Ala Ser Arg Pro Thr Gly Phe Leu Asn Thr Glu Ala Phe Phe
1               5                   10                  15

<210> SEQ ID NO 1293
<211> LENGTH: 15
<212> TYPE: PRT
<213> ORGANISM: Homo sapiens

<400> SEQUENCE: 1293

Cys Ala Ser Ser Leu Gly Gly Asp Ser Ser Asn Glu Gln Phe Phe
1               5                   10                  15

<210> SEQ ID NO 1294
<211> LENGTH: 15
<212> TYPE: PRT
<213> ORGANISM: Homo sapiens

<400> SEQUENCE: 1294

Cys Ala Thr Ser Glu Thr Gly Ala Val Thr Asp Thr Gln Tyr Phe
1               5                   10                  15

<210> SEQ ID NO 1295
<211> LENGTH: 14
<212> TYPE: PRT
<213> ORGANISM: Homo sapiens

<400> SEQUENCE: 1295

Cys Ser Ala Val Arg Gly Gly Pro Thr Gly Glu Leu Phe Phe
1               5                   10

<210> SEQ ID NO 1296
<211> LENGTH: 12
<212> TYPE: PRT
<213> ORGANISM: Homo sapiens
```

-continued

```
<400> SEQUENCE: 1296

Cys Ala Ser Ser Trp Asp Gln Glu Thr Gln Tyr Phe
1               5                   10

<210> SEQ ID NO 1297
<211> LENGTH: 16
<212> TYPE: PRT
<213> ORGANISM: Homo sapiens

<400> SEQUENCE: 1297

Cys Ala Ser Ser Pro Arg Arg Gly Phe Asn Glu Lys Leu Phe Phe
1               5                   10                  15

<210> SEQ ID NO 1298
<211> LENGTH: 15
<212> TYPE: PRT
<213> ORGANISM: Homo sapiens

<400> SEQUENCE: 1298

Cys Ala Ser Ser Pro His Gly Thr Glu Asn Thr Glu Ala Phe Phe
1               5                   10                  15

<210> SEQ ID NO 1299
<211> LENGTH: 15
<212> TYPE: PRT
<213> ORGANISM: Homo sapiens

<400> SEQUENCE: 1299

Cys Ala Ser Ser Leu Glu Val Asn Tyr Asn Ser Pro Leu His Phe
1               5                   10                  15

<210> SEQ ID NO 1300
<211> LENGTH: 15
<212> TYPE: PRT
<213> ORGANISM: Homo sapiens

<400> SEQUENCE: 1300

Cys Ser Ala Arg Ala Ala Gly Ser Gly Thr Gly Glu Leu Phe Phe
1               5                   10                  15

<210> SEQ ID NO 1301
<211> LENGTH: 15
<212> TYPE: PRT
<213> ORGANISM: Homo sapiens

<400> SEQUENCE: 1301

Cys Ala Ser Ser Pro Pro Gly Arg Thr Thr Asp Thr Gln Tyr Phe
1               5                   10                  15

<210> SEQ ID NO 1302
<211> LENGTH: 16
<212> TYPE: PRT
<213> ORGANISM: Homo sapiens

<400> SEQUENCE: 1302

Cys Ala Ser Ser Ala Pro Ala Ser Gly Gly Ala Gly Glu Gln Phe Phe
1               5                   10                  15

<210> SEQ ID NO 1303
<211> LENGTH: 14
<212> TYPE: PRT
<213> ORGANISM: Homo sapiens

<400> SEQUENCE: 1303
```

Cys Ala Ser Ser Phe Leu Ala Gly Arg Asp Glu Gln Phe Phe
1               5                   10

<210> SEQ ID NO 1304
<211> LENGTH: 14
<212> TYPE: PRT
<213> ORGANISM: Homo sapiens

<400> SEQUENCE: 1304

Cys Ala Ser Ser Thr Gly Leu Ala Thr Glu Thr Gln Tyr Phe
1               5                   10

<210> SEQ ID NO 1305
<211> LENGTH: 13
<212> TYPE: PRT
<213> ORGANISM: Homo sapiens

<400> SEQUENCE: 1305

Cys Ala Ser Lys Arg Asp Thr His Tyr Glu Gln Tyr Phe
1               5                   10

<210> SEQ ID NO 1306
<211> LENGTH: 14
<212> TYPE: PRT
<213> ORGANISM: Homo sapiens

<400> SEQUENCE: 1306

Cys Ser Ala Arg Arg Gln Gly Asn Asp Gln Pro Gln His Phe
1               5                   10

<210> SEQ ID NO 1307
<211> LENGTH: 15
<212> TYPE: PRT
<213> ORGANISM: Homo sapiens

<400> SEQUENCE: 1307

Cys Ala Ser Ser Ser Trp Asp Arg Val Thr Tyr Glu Gln Tyr Phe
1               5                   10                  15

<210> SEQ ID NO 1308
<211> LENGTH: 15
<212> TYPE: PRT
<213> ORGANISM: Homo sapiens

<400> SEQUENCE: 1308

Cys Ala Ser Ser Pro Asn Val Gly Gly Asn Thr Glu Ala Phe Phe
1               5                   10                  15

<210> SEQ ID NO 1309
<211> LENGTH: 15
<212> TYPE: PRT
<213> ORGANISM: Homo sapiens

<400> SEQUENCE: 1309

Cys Ala Ser Ser Pro Ala Thr Gly Val Tyr Asn Glu Gln Phe Phe
1               5                   10                  15

<210> SEQ ID NO 1310
<211> LENGTH: 11
<212> TYPE: PRT
<213> ORGANISM: Homo sapiens

<400> SEQUENCE: 1310

Cys Ala Ser Ser Thr Ser Tyr Glu Gln Tyr Val
1               5                   10

<210> SEQ ID NO 1311
<211> LENGTH: 11
<212> TYPE: PRT
<213> ORGANISM: Homo sapiens

<400> SEQUENCE: 1311

Cys Ser Val Gly Arg Leu Tyr Glu Gln Tyr Phe
1               5                   10

<210> SEQ ID NO 1312
<211> LENGTH: 14
<212> TYPE: PRT
<213> ORGANISM: Homo sapiens

<400> SEQUENCE: 1312

Cys Ala Ser Ser Leu Gly Gln Arg Asn Tyr Gly Tyr Thr Phe
1               5                   10

<210> SEQ ID NO 1313
<211> LENGTH: 15
<212> TYPE: PRT
<213> ORGANISM: Homo sapiens

<400> SEQUENCE: 1313

Cys Ser Ala Arg Ala Ser Gly Gly Gly Thr Gly Glu Leu Phe Phe
1               5                   10                  15

<210> SEQ ID NO 1314
<211> LENGTH: 15
<212> TYPE: PRT
<213> ORGANISM: Homo sapiens

<400> SEQUENCE: 1314

Cys Ser Ala Arg Gly Ser Gly Ala Gly Thr Gly Glu Leu Phe Phe
1               5                   10                  15

<210> SEQ ID NO 1315
<211> LENGTH: 12
<212> TYPE: PRT
<213> ORGANISM: Homo sapiens

<400> SEQUENCE: 1315

Cys Ser Ala Ser Ala Leu Glu Asp Glu Gln Phe Phe
1               5                   10

<210> SEQ ID NO 1316
<211> LENGTH: 16
<212> TYPE: PRT
<213> ORGANISM: Homo sapiens

<400> SEQUENCE: 1316

Cys Ala Ser Ser Gln Glu Ser Gly Arg Phe Ala Asp Thr Gln Tyr Phe
1               5                   10                  15

<210> SEQ ID NO 1317
<211> LENGTH: 16
<212> TYPE: PRT
<213> ORGANISM: Homo sapiens

<400> SEQUENCE: 1317

Cys Ala Ser Ser Gln Gly Gln Gly Gln Tyr Gln Glu Thr Gln Tyr Phe
1               5                   10                  15

```
<210> SEQ ID NO 1318
<211> LENGTH: 15
<212> TYPE: PRT
<213> ORGANISM: Homo sapiens

<400> SEQUENCE: 1318

Cys Ala Ser Arg Lys Ile Ser Thr Gly Asn Thr Glu Ala Phe Phe
1               5                   10                  15

<210> SEQ ID NO 1319
<211> LENGTH: 15
<212> TYPE: PRT
<213> ORGANISM: Homo sapiens

<400> SEQUENCE: 1319

Cys Ala Ser Ser Pro Arg Gly Gln Gly Ile Gly Gly Tyr Thr Phe
1               5                   10                  15

<210> SEQ ID NO 1320
<211> LENGTH: 13
<212> TYPE: PRT
<213> ORGANISM: Homo sapiens

<400> SEQUENCE: 1320

Cys Ala Ser Lys Arg Gln Gly Gly Tyr Glu Gln Tyr Phe
1               5                   10

<210> SEQ ID NO 1321
<211> LENGTH: 15
<212> TYPE: PRT
<213> ORGANISM: Homo sapiens

<400> SEQUENCE: 1321

Cys Ser Ala Arg Lys Ala Gly Ser Gly Thr Gly Glu Leu Phe Phe
1               5                   10                  15

<210> SEQ ID NO 1322
<211> LENGTH: 14
<212> TYPE: PRT
<213> ORGANISM: Homo sapiens

<400> SEQUENCE: 1322

Cys Ala Ser Ser Leu Gly Gly Gly Leu Asn Glu Gln Tyr Phe
1               5                   10

<210> SEQ ID NO 1323
<211> LENGTH: 12
<212> TYPE: PRT
<213> ORGANISM: Homo sapiens

<400> SEQUENCE: 1323

Cys Ala Ser Met Gly Trp Gly Gln Pro Gln His Phe
1               5                   10

<210> SEQ ID NO 1324
<211> LENGTH: 15
<212> TYPE: PRT
<213> ORGANISM: Homo sapiens

<400> SEQUENCE: 1324

Cys Ala Ser Ser Leu Met Thr Ser Leu Ser Tyr Glu Gln Tyr Phe
1               5                   10                  15

<210> SEQ ID NO 1325
<211> LENGTH: 15
```

```
<212> TYPE: PRT
<213> ORGANISM: Homo sapiens

<400> SEQUENCE: 1325

Cys Ala Ser Ser Pro Leu Ala Gly Asp Arg Lys Thr Gln Tyr Phe
1               5                   10                  15

<210> SEQ ID NO 1326
<211> LENGTH: 15
<212> TYPE: PRT
<213> ORGANISM: Homo sapiens

<400> SEQUENCE: 1326

Cys Ala Ser Ser Arg Pro Thr Gly Gly Arg Glu Thr Gln Tyr Phe
1               5                   10                  15

<210> SEQ ID NO 1327
<211> LENGTH: 14
<212> TYPE: PRT
<213> ORGANISM: Homo sapiens

<400> SEQUENCE: 1327

Cys Ala Ser Ser Leu Ala Pro Ala Ser Tyr Glu Gln Tyr Phe
1               5                   10

<210> SEQ ID NO 1328
<211> LENGTH: 13
<212> TYPE: PRT
<213> ORGANISM: Homo sapiens

<400> SEQUENCE: 1328

Cys Ser Ala Pro Gln Ser Leu Asn Thr Glu Ala Phe Phe
1               5                   10

<210> SEQ ID NO 1329
<211> LENGTH: 11
<212> TYPE: PRT
<213> ORGANISM: Homo sapiens

<400> SEQUENCE: 1329

Cys Ser Ala Arg Ala Val Val Glu Gln Phe Phe
1               5                   10

<210> SEQ ID NO 1330
<211> LENGTH: 14
<212> TYPE: PRT
<213> ORGANISM: Homo sapiens

<400> SEQUENCE: 1330

Cys Ala Ser Ser Leu Leu Pro Val Gly Thr Glu Ala Phe Phe
1               5                   10

<210> SEQ ID NO 1331
<211> LENGTH: 13
<212> TYPE: PRT
<213> ORGANISM: Homo sapiens

<400> SEQUENCE: 1331

Cys Ala Asn Arg Arg Gly Leu Asn Thr Glu Ala Phe Phe
1               5                   10

<210> SEQ ID NO 1332
<211> LENGTH: 16
<212> TYPE: PRT
<213> ORGANISM: Homo sapiens
```

<400> SEQUENCE: 1332

Cys Ala Ser Ser Gly Gly Thr Ser Ala Ser Thr Asp Thr Gln Tyr Phe
1               5                   10                  15

<210> SEQ ID NO 1333
<211> LENGTH: 13
<212> TYPE: PRT
<213> ORGANISM: Homo sapiens

<400> SEQUENCE: 1333

Cys Ala Thr Ser Ala Gly Trp Tyr Asn Glu Gln Phe Phe
1               5                   10

<210> SEQ ID NO 1334
<211> LENGTH: 13
<212> TYPE: PRT
<213> ORGANISM: Homo sapiens

<400> SEQUENCE: 1334

Cys Ala Ser Ser Pro Gln Gly Asn Asn Glu Gln Phe Phe
1               5                   10

<210> SEQ ID NO 1335
<211> LENGTH: 15
<212> TYPE: PRT
<213> ORGANISM: Homo sapiens

<400> SEQUENCE: 1335

Cys Ala Ser Ser Pro Leu Gly Arg Thr Asn Tyr Glu Gln Tyr Phe
1               5                   10                  15

<210> SEQ ID NO 1336
<211> LENGTH: 14
<212> TYPE: PRT
<213> ORGANISM: Homo sapiens

<400> SEQUENCE: 1336

Cys Ala Ser Arg Ala Asp Arg Lys Asn Thr Glu Ala Phe Phe
1               5                   10

<210> SEQ ID NO 1337
<211> LENGTH: 15
<212> TYPE: PRT
<213> ORGANISM: Homo sapiens

<400> SEQUENCE: 1337

Cys Ala Thr Ser Arg Gly Ala Arg Arg Thr Asp Thr Gln Tyr Phe
1               5                   10                  15

<210> SEQ ID NO 1338
<211> LENGTH: 15
<212> TYPE: PRT
<213> ORGANISM: Homo sapiens

<400> SEQUENCE: 1338

Cys Ser Ala Arg Arg Ser Gly Ser Gly Thr Gly Glu Leu Phe Phe
1               5                   10                  15

<210> SEQ ID NO 1339
<211> LENGTH: 14
<212> TYPE: PRT
<213> ORGANISM: Homo sapiens

<400> SEQUENCE: 1339

```
Cys Ala Ser Ser Arg Thr Gly Gly Leu Asp Thr Gln Tyr Phe
1               5                   10
```

<210> SEQ ID NO 1340
<211> LENGTH: 14
<212> TYPE: PRT
<213> ORGANISM: Homo sapiens

<400> SEQUENCE: 1340

```
Cys Ser Ala Arg Glu Trp Gly Glu His Thr Glu Ala Phe Phe
1               5                   10
```

<210> SEQ ID NO 1341
<211> LENGTH: 15
<212> TYPE: PRT
<213> ORGANISM: Homo sapiens

<400> SEQUENCE: 1341

```
Cys Ala Ser Ser Ile Thr Gly Phe Gly Ala Asn Val Leu Thr Phe
1               5                   10                  15
```

<210> SEQ ID NO 1342
<211> LENGTH: 14
<212> TYPE: PRT
<213> ORGANISM: Homo sapiens

<400> SEQUENCE: 1342

```
Cys Ala Ser Ser Met Gly Ala Leu Asn Asn Glu Gln Phe Phe
1               5                   10
```

<210> SEQ ID NO 1343
<211> LENGTH: 13
<212> TYPE: PRT
<213> ORGANISM: Homo sapiens

<400> SEQUENCE: 1343

```
Cys Ala Ser Ser Val Gly Trp Asp Tyr Gly Tyr Thr Phe
1               5                   10
```

<210> SEQ ID NO 1344
<211> LENGTH: 15
<212> TYPE: PRT
<213> ORGANISM: Homo sapiens

<400> SEQUENCE: 1344

```
Cys Ser Ala Arg Ala Ser Gln Gly Val Asn Gln Pro Gln His Phe
1               5                   10                  15
```

<210> SEQ ID NO 1345
<211> LENGTH: 13
<212> TYPE: PRT
<213> ORGANISM: Homo sapiens

<400> SEQUENCE: 1345

```
Cys Ser Ala Pro Pro Ser Val Asn Ser Pro Leu His Phe
1               5                   10
```

<210> SEQ ID NO 1346
<211> LENGTH: 14
<212> TYPE: PRT
<213> ORGANISM: Homo sapiens

<400> SEQUENCE: 1346

```
Cys Ala Ser Ser Pro Ser Gly Arg Arg Asn Thr Gln Tyr Phe
```

<210> SEQ ID NO 1347
<211> LENGTH: 15
<212> TYPE: PRT
<213> ORGANISM: Homo sapiens

<400> SEQUENCE: 1347

Cys Ala Ser Ser Thr Gly Thr Ala Gly Asn Thr Ile Tyr Phe
1               5                   10                  15

<210> SEQ ID NO 1348
<211> LENGTH: 12
<212> TYPE: PRT
<213> ORGANISM: Homo sapiens

<400> SEQUENCE: 1348

Cys Ser Ala Thr Pro Gly Thr Thr Glu Ala Phe Phe
1               5                   10

<210> SEQ ID NO 1349
<211> LENGTH: 15
<212> TYPE: PRT
<213> ORGANISM: Homo sapiens

<400> SEQUENCE: 1349

Cys Ser Ala Pro Pro Gly Leu Gly Arg Ala Asp Thr Gln Tyr Phe
1               5                   10                  15

<210> SEQ ID NO 1350
<211> LENGTH: 12
<212> TYPE: PRT
<213> ORGANISM: Homo sapiens

<400> SEQUENCE: 1350

Cys Ser Ala Gly Arg Gly Arg Lys Thr Gln Tyr Phe
1               5                   10

<210> SEQ ID NO 1351
<211> LENGTH: 16
<212> TYPE: PRT
<213> ORGANISM: Homo sapiens

<400> SEQUENCE: 1351

Cys Ala Ser Ser Leu Asp Leu Gly Gly Val Thr Asp Thr Gln Tyr Phe
1               5                   10                  15

<210> SEQ ID NO 1352
<211> LENGTH: 15
<212> TYPE: PRT
<213> ORGANISM: Homo sapiens

<400> SEQUENCE: 1352

Cys Ala Ser Ser Arg Thr Gly Gly Gly Ser Asp Thr Gln Tyr Phe
1               5                   10                  15

<210> SEQ ID NO 1353
<211> LENGTH: 14
<212> TYPE: PRT
<213> ORGANISM: Homo sapiens

<400> SEQUENCE: 1353

Cys Ala Ser Ser Ser Gly Thr Gly Ser Glu Lys Leu Phe Phe
1               5                   10

<210> SEQ ID NO 1354
<211> LENGTH: 13
<212> TYPE: PRT
<213> ORGANISM: Homo sapiens

<400> SEQUENCE: 1354

Cys Ser Ala Arg Glu Pro Pro Tyr Asn Glu Gln Phe Phe
1               5                   10

<210> SEQ ID NO 1355
<211> LENGTH: 14
<212> TYPE: PRT
<213> ORGANISM: Homo sapiens

<400> SEQUENCE: 1355

Cys Ala Ser Ser Pro Thr Arg Asp Asp Tyr Gly Tyr Thr Phe
1               5                   10

<210> SEQ ID NO 1356
<211> LENGTH: 14
<212> TYPE: PRT
<213> ORGANISM: Homo sapiens

<400> SEQUENCE: 1356

Cys Ala Ile Lys Gly Thr Ser Gly Gly Asn Glu Gln Phe Phe
1               5                   10

<210> SEQ ID NO 1357
<211> LENGTH: 13
<212> TYPE: PRT
<213> ORGANISM: Homo sapiens

<400> SEQUENCE: 1357

Cys Ala Ser Arg Thr Gly Gly Gly Glu Thr Gln Tyr Phe
1               5                   10

<210> SEQ ID NO 1358
<211> LENGTH: 15
<212> TYPE: PRT
<213> ORGANISM: Homo sapiens

<400> SEQUENCE: 1358

Cys Ala Ser Ser Ala Pro Gln Gly Thr Gly Asn Thr Ile Tyr Phe
1               5                   10                  15

<210> SEQ ID NO 1359
<211> LENGTH: 15
<212> TYPE: PRT
<213> ORGANISM: Homo sapiens

<400> SEQUENCE: 1359

Cys Ala Ser Ser Gly Arg Gly Arg Ala Asn Thr Glu Ala Phe Phe
1               5                   10                  15

<210> SEQ ID NO 1360
<211> LENGTH: 15
<212> TYPE: PRT
<213> ORGANISM: Homo sapiens

<400> SEQUENCE: 1360

Cys Ser Ala Arg Gly Ser Ala Arg Thr Thr Asp Thr Gln Tyr Phe
1               5                   10                  15

<210> SEQ ID NO 1361

```
<211> LENGTH: 13
<212> TYPE: PRT
<213> ORGANISM: Homo sapiens

<400> SEQUENCE: 1361

Cys Ser Ala Arg Gln Gly Val Gly Asn Ile Gln Tyr Phe
1               5                   10

<210> SEQ ID NO 1362
<211> LENGTH: 13
<212> TYPE: PRT
<213> ORGANISM: Homo sapiens

<400> SEQUENCE: 1362

Cys Ala Trp Gly Arg Arg Gly Leu Tyr Glu Gln Tyr Phe
1               5                   10

<210> SEQ ID NO 1363
<211> LENGTH: 16
<212> TYPE: PRT
<213> ORGANISM: Homo sapiens

<400> SEQUENCE: 1363

Cys Ala Ser Ser Glu Arg Ala Ser Gly Ile Tyr Asn Glu Gln Phe Phe
1               5                   10                  15

<210> SEQ ID NO 1364
<211> LENGTH: 15
<212> TYPE: PRT
<213> ORGANISM: Homo sapiens

<400> SEQUENCE: 1364

Cys Ser Ala Arg Ile Gly Gly Ala Gly Thr Gly Glu Leu Phe Phe
1               5                   10                  15

<210> SEQ ID NO 1365
<211> LENGTH: 12
<212> TYPE: PRT
<213> ORGANISM: Homo sapiens

<400> SEQUENCE: 1365

Cys Ala Ser Lys Gln Gly Ser Gly Glu Leu Phe Phe
1               5                   10

<210> SEQ ID NO 1366
<211> LENGTH: 15
<212> TYPE: PRT
<213> ORGANISM: Homo sapiens

<400> SEQUENCE: 1366

Cys Ala Ser Ser Ser Arg Thr Gly Gly Thr Tyr Gly Tyr Thr Phe
1               5                   10                  15

<210> SEQ ID NO 1367
<211> LENGTH: 16
<212> TYPE: PRT
<213> ORGANISM: Homo sapiens

<400> SEQUENCE: 1367

Cys Ser Ala Arg Gly Gly Leu Gly Gly Thr Tyr Asn Glu Gln Phe Phe
1               5                   10                  15

<210> SEQ ID NO 1368
<211> LENGTH: 15
<212> TYPE: PRT
```

<213> ORGANISM: Homo sapiens

<400> SEQUENCE: 1368

Cys Ala Ser Ser Phe Glu Ile Asn Tyr Asn Ser Pro Leu His Phe
1               5                   10                  15

<210> SEQ ID NO 1369
<211> LENGTH: 15
<212> TYPE: PRT
<213> ORGANISM: Homo sapiens

<400> SEQUENCE: 1369

Cys Ala Ser Ser Gln Glu Asp Arg Arg Asn Tyr Gly Tyr Thr Phe
1               5                   10                  15

<210> SEQ ID NO 1370
<211> LENGTH: 14
<212> TYPE: PRT
<213> ORGANISM: Homo sapiens

<400> SEQUENCE: 1370

Cys Ala Ser Arg Gly Gly Val His Thr Gly Glu Leu Phe Phe
1               5                   10

<210> SEQ ID NO 1371
<211> LENGTH: 15
<212> TYPE: PRT
<213> ORGANISM: Homo sapiens

<400> SEQUENCE: 1371

Cys Ala Ser Ser Leu Glu Gln Asn Tyr Asn Ser Pro Leu His Phe
1               5                   10                  15

<210> SEQ ID NO 1372
<211> LENGTH: 12
<212> TYPE: PRT
<213> ORGANISM: Homo sapiens

<400> SEQUENCE: 1372

Cys Ser Val Gly Ala Lys Asn Thr Glu Ala Phe Phe
1               5                   10

<210> SEQ ID NO 1373
<211> LENGTH: 16
<212> TYPE: PRT
<213> ORGANISM: Homo sapiens

<400> SEQUENCE: 1373

Cys Ala Ser Ser Leu Ala Val Gly Thr Thr Tyr Asn Glu Gln Phe Phe
1               5                   10                  15

<210> SEQ ID NO 1374
<211> LENGTH: 19
<212> TYPE: PRT
<213> ORGANISM: Homo sapiens

<400> SEQUENCE: 1374

Cys Ala Ser Ser Pro Phe Arg Thr Ser Gly Gly Pro Ser Thr Asp Thr
1               5                   10                  15

Gln Tyr Phe

<210> SEQ ID NO 1375
<211> LENGTH: 14
<212> TYPE: PRT

```
<213> ORGANISM: Homo sapiens

<400> SEQUENCE: 1375

Cys Ala Ser Ser Thr Gly Thr Gly Leu Glu Lys Leu Phe Phe
1               5                   10

<210> SEQ ID NO 1376
<211> LENGTH: 16
<212> TYPE: PRT
<213> ORGANISM: Homo sapiens

<400> SEQUENCE: 1376

Cys Ala Ser Ser Tyr Leu Gly Gly Gly Val Tyr Asn Glu Gln Phe Phe
1               5                   10                  15

<210> SEQ ID NO 1377
<211> LENGTH: 16
<212> TYPE: PRT
<213> ORGANISM: Homo sapiens

<400> SEQUENCE: 1377

Cys Ala Ser Ser Ile Leu Gly Gly Thr Ser Val Tyr Glu Gln Tyr Phe
1               5                   10                  15

<210> SEQ ID NO 1378
<211> LENGTH: 16
<212> TYPE: PRT
<213> ORGANISM: Homo sapiens

<400> SEQUENCE: 1378

Cys Ala Ser Ser Tyr Ser Gly Arg Leu Ser Tyr Asn Glu Gln Phe Phe
1               5                   10                  15

<210> SEQ ID NO 1379
<211> LENGTH: 16
<212> TYPE: PRT
<213> ORGANISM: Homo sapiens

<400> SEQUENCE: 1379

Cys Ala Ser Ser Arg Thr Ser Gly Gln Ser Thr Asp Thr Gln Tyr Phe
1               5                   10                  15

<210> SEQ ID NO 1380
<211> LENGTH: 15
<212> TYPE: PRT
<213> ORGANISM: Homo sapiens

<400> SEQUENCE: 1380

Cys Ala Ser Ser Phe Glu Ser Asn Tyr Asn Ser Pro Leu His Phe
1               5                   10                  15

<210> SEQ ID NO 1381
<211> LENGTH: 12
<212> TYPE: PRT
<213> ORGANISM: Homo sapiens

<400> SEQUENCE: 1381

Cys Ala Ser Ser Leu Gly Asp Arg Gly Tyr Thr Phe
1               5                   10

<210> SEQ ID NO 1382
<211> LENGTH: 15
<212> TYPE: PRT
<213> ORGANISM: Homo sapiens
```

```
<400> SEQUENCE: 1382

Cys Ser Ala Lys Gly Gln Pro Ser Asn Thr Gly Glu Leu Phe Phe
1               5                   10                  15

<210> SEQ ID NO 1383
<211> LENGTH: 15
<212> TYPE: PRT
<213> ORGANISM: Homo sapiens

<400> SEQUENCE: 1383

Cys Ser Ala Arg Leu Ser Gly Ala Gly Thr Gly Glu Leu Phe Phe
1               5                   10                  15

<210> SEQ ID NO 1384
<211> LENGTH: 15
<212> TYPE: PRT
<213> ORGANISM: Homo sapiens

<400> SEQUENCE: 1384

Cys Ser Ala Arg Ser Gln Pro Ser Asn Thr Gly Glu Leu Phe Phe
1               5                   10                  15

<210> SEQ ID NO 1385
<211> LENGTH: 14
<212> TYPE: PRT
<213> ORGANISM: Homo sapiens

<400> SEQUENCE: 1385

Cys Ala Ser Ser Gln Asp Leu Ile Gln Glu Thr Gln Tyr Phe
1               5                   10

<210> SEQ ID NO 1386
<211> LENGTH: 14
<212> TYPE: PRT
<213> ORGANISM: Homo sapiens

<400> SEQUENCE: 1386

Cys Ala Ser Ser Pro Ala Leu Ile Gln Glu Thr Gln Tyr Phe
1               5                   10

<210> SEQ ID NO 1387
<211> LENGTH: 13
<212> TYPE: PRT
<213> ORGANISM: Homo sapiens

<400> SEQUENCE: 1387

Cys Ser Ala Gly Pro Gln Val Gln Glu Thr Gln Tyr Phe
1               5                   10

<210> SEQ ID NO 1388
<211> LENGTH: 12
<212> TYPE: PRT
<213> ORGANISM: Homo sapiens

<400> SEQUENCE: 1388

Cys Ala Ala Val Gly Ser Gly Asn Thr Ile Tyr Phe
1               5                   10

<210> SEQ ID NO 1389
<211> LENGTH: 16
<212> TYPE: PRT
<213> ORGANISM: Homo sapiens

<400> SEQUENCE: 1389
```

Cys Ala Ser Ser Ile Leu Gly Thr Ala Asn Asn Gln Pro Gln His Phe
1               5                   10                  15

<210> SEQ ID NO 1390
<211> LENGTH: 14
<212> TYPE: PRT
<213> ORGANISM: Homo sapiens

<400> SEQUENCE: 1390

Cys Ala Thr Ser Ser Gly Arg Glu Ile Glu Thr Gln Tyr Phe
1               5                   10

<210> SEQ ID NO 1391
<211> LENGTH: 13
<212> TYPE: PRT
<213> ORGANISM: Homo sapiens

<400> SEQUENCE: 1391

Cys Ser Ala Met Arg Glu Gly Pro Glu Thr Gln Tyr Phe
1               5                   10

<210> SEQ ID NO 1392
<211> LENGTH: 14
<212> TYPE: PRT
<213> ORGANISM: Homo sapiens

<400> SEQUENCE: 1392

Cys Ser Ala Gly Leu Ala Gly Arg Gln Glu Thr Gln Tyr Phe
1               5                   10

<210> SEQ ID NO 1393
<211> LENGTH: 15
<212> TYPE: PRT
<213> ORGANISM: Homo sapiens

<400> SEQUENCE: 1393

Cys Ala Ser Ser Phe Glu Tyr Asn Tyr Asn Ser Pro Leu His Phe
1               5                   10                  15

<210> SEQ ID NO 1394
<211> LENGTH: 13
<212> TYPE: PRT
<213> ORGANISM: Homo sapiens

<400> SEQUENCE: 1394

Cys Ser Ala Pro Arg Ala Pro Tyr Asn Glu Gln Phe Phe
1               5                   10

<210> SEQ ID NO 1395
<211> LENGTH: 16
<212> TYPE: PRT
<213> ORGANISM: Homo sapiens

<400> SEQUENCE: 1395

Cys Ala Ser Ser Leu Val Gly Val Ser Gly Thr Gly Glu Leu Phe Phe
1               5                   10                  15

<210> SEQ ID NO 1396
<211> LENGTH: 15
<212> TYPE: PRT
<213> ORGANISM: Homo sapiens

<400> SEQUENCE: 1396

Cys Ala Ser Thr Leu Ala Gly Lys Ser Tyr Asn Glu Gln Phe Phe
1               5                   10                  15

<210> SEQ ID NO 1397
<211> LENGTH: 13
<212> TYPE: PRT
<213> ORGANISM: Homo sapiens

<400> SEQUENCE: 1397

Cys Ala Ser Arg Ser Gly Thr Asp Tyr Glu Gln Tyr Phe
1               5                   10

<210> SEQ ID NO 1398
<211> LENGTH: 14
<212> TYPE: PRT
<213> ORGANISM: Homo sapiens

<400> SEQUENCE: 1398

Cys Ala Ser Ser Ile Arg Arg Asp Lys Asn Ile Gln Tyr Phe
1               5                   10

<210> SEQ ID NO 1399
<211> LENGTH: 13
<212> TYPE: PRT
<213> ORGANISM: Homo sapiens

<400> SEQUENCE: 1399

Cys Ala Ser Ser Leu Ser Lys Glu Tyr Glu Gln Tyr Phe
1               5                   10

<210> SEQ ID NO 1400
<211> LENGTH: 14
<212> TYPE: PRT
<213> ORGANISM: Homo sapiens

<400> SEQUENCE: 1400

Cys Ala Ser Ser Lys Ala Gly Leu Tyr Thr Glu Ala Phe Phe
1               5                   10

<210> SEQ ID NO 1401
<211> LENGTH: 14
<212> TYPE: PRT
<213> ORGANISM: Homo sapiens

<400> SEQUENCE: 1401

Cys Ala Ser Ser Asp Gln Gly Val Arg Glu Thr Gln Tyr Phe
1               5                   10

<210> SEQ ID NO 1402
<211> LENGTH: 15
<212> TYPE: PRT
<213> ORGANISM: Homo sapiens

<400> SEQUENCE: 1402

Cys Ala Ser Ser Pro Leu Ala Ser Thr Ser Tyr Glu Gln Tyr Phe
1               5                   10                  15

<210> SEQ ID NO 1403
<211> LENGTH: 15
<212> TYPE: PRT
<213> ORGANISM: Homo sapiens

<400> SEQUENCE: 1403

Cys Ser Ala Arg Arg Gln Pro Thr Asn Thr Gly Glu Leu Phe Phe
1               5                   10                  15

```
<210> SEQ ID NO 1404
<211> LENGTH: 15
<212> TYPE: PRT
<213> ORGANISM: Homo sapiens

<400> SEQUENCE: 1404

Cys Ser Ala Arg Gly Gly Gly Ala Gly Thr Gly Glu Leu Phe Phe
1               5                   10                  15

<210> SEQ ID NO 1405
<211> LENGTH: 13
<212> TYPE: PRT
<213> ORGANISM: Homo sapiens

<400> SEQUENCE: 1405

Cys Ala Ser Ser Met Gly Pro Thr Asn Thr Gln Tyr Phe
1               5                   10

<210> SEQ ID NO 1406
<211> LENGTH: 16
<212> TYPE: PRT
<213> ORGANISM: Homo sapiens

<400> SEQUENCE: 1406

Cys Ala Ser Ser Ile Gly Gly Ser Gly Gly Ile Tyr Glu Gln Tyr Phe
1               5                   10                  15

<210> SEQ ID NO 1407
<211> LENGTH: 12
<212> TYPE: PRT
<213> ORGANISM: Homo sapiens

<400> SEQUENCE: 1407

Cys Ala Ser Arg Thr Pro Gly Asp Thr Gln Tyr Phe
1               5                   10

<210> SEQ ID NO 1408
<211> LENGTH: 14
<212> TYPE: PRT
<213> ORGANISM: Homo sapiens

<400> SEQUENCE: 1408

Cys Ala Thr Ser Ser Asn Ser Gly Asn Gln Pro Gln His Phe
1               5                   10

<210> SEQ ID NO 1409
<211> LENGTH: 14
<212> TYPE: PRT
<213> ORGANISM: Homo sapiens

<400> SEQUENCE: 1409

Cys Ala Ser Thr Ala Ser Asp Arg Ala Tyr Glu Gln Tyr Phe
1               5                   10

<210> SEQ ID NO 1410
<211> LENGTH: 16
<212> TYPE: PRT
<213> ORGANISM: Homo sapiens

<400> SEQUENCE: 1410

Cys Ala Thr Ser Asp Gln Thr Ser Gly Asn Arg Asn Glu Gln Phe Phe
1               5                   10                  15

<210> SEQ ID NO 1411
<211> LENGTH: 12
```

```
<212> TYPE: PRT
<213> ORGANISM: Homo sapiens

<400> SEQUENCE: 1411

Cys Ala Ser Arg Tyr Lys Asp Thr Glu Ala Phe Phe
1               5                   10

<210> SEQ ID NO 1412
<211> LENGTH: 14
<212> TYPE: PRT
<213> ORGANISM: Homo sapiens

<400> SEQUENCE: 1412

Cys Ala Ser Ser Leu Gly Gln Gly Asp Thr Glu Ala Phe Phe
1               5                   10

<210> SEQ ID NO 1413
<211> LENGTH: 15
<212> TYPE: PRT
<213> ORGANISM: Homo sapiens

<400> SEQUENCE: 1413

Cys Ala Ser Ser Phe Asn Arg Gly Asn Thr Gly Glu Leu Phe Phe
1               5                   10                  15

<210> SEQ ID NO 1414
<211> LENGTH: 15
<212> TYPE: PRT
<213> ORGANISM: Homo sapiens

<400> SEQUENCE: 1414

Cys Ala Ser Ser Pro Arg Gly Arg Gly Val Ser Gly Tyr Thr Phe
1               5                   10                  15

<210> SEQ ID NO 1415
<211> LENGTH: 14
<212> TYPE: PRT
<213> ORGANISM: Homo sapiens

<400> SEQUENCE: 1415

Cys Ala Ser Ser Arg Thr Arg Ser Ser Tyr Glu Gln Tyr Phe
1               5                   10

<210> SEQ ID NO 1416
<211> LENGTH: 15
<212> TYPE: PRT
<213> ORGANISM: Homo sapiens

<400> SEQUENCE: 1416

Cys Ala Ser Ser Leu Leu Leu Gly Gln Gly Tyr Glu Gln Tyr Phe
1               5                   10                  15

<210> SEQ ID NO 1417
<211> LENGTH: 14
<212> TYPE: PRT
<213> ORGANISM: Homo sapiens

<400> SEQUENCE: 1417

Cys Ala Ser Arg Pro Gly Leu Ala Tyr Asp Thr Gln Tyr Phe
1               5                   10

<210> SEQ ID NO 1418
<211> LENGTH: 12
<212> TYPE: PRT
<213> ORGANISM: Homo sapiens
```

<400> SEQUENCE: 1418

Cys Ala Ser Arg Tyr Arg Asp Ser Gly Tyr Thr Phe
1               5                   10

<210> SEQ ID NO 1419
<211> LENGTH: 14
<212> TYPE: PRT
<213> ORGANISM: Homo sapiens

<400> SEQUENCE: 1419

Cys Ser Ala Arg Leu Asp Arg Gly Gly Tyr Glu Gln Tyr Phe
1               5                   10

<210> SEQ ID NO 1420
<211> LENGTH: 16
<212> TYPE: PRT
<213> ORGANISM: Homo sapiens

<400> SEQUENCE: 1420

Cys Ala Ser Ser Gly Pro Gly Thr Ser Gly Asn Asn Glu Gln Phe Phe
1               5                   10                  15

<210> SEQ ID NO 1421
<211> LENGTH: 15
<212> TYPE: PRT
<213> ORGANISM: Homo sapiens

<400> SEQUENCE: 1421

Cys Ser Ala Arg Val Ala Gly Ala Gly Thr Gly Glu Leu Phe Phe
1               5                   10                  15

<210> SEQ ID NO 1422
<211> LENGTH: 14
<212> TYPE: PRT
<213> ORGANISM: Homo sapiens

<400> SEQUENCE: 1422

Cys Ala Ser Ser Leu Ala Pro Leu Gly Asp Thr Gln Tyr Phe
1               5                   10

<210> SEQ ID NO 1423
<211> LENGTH: 14
<212> TYPE: PRT
<213> ORGANISM: Homo sapiens

<400> SEQUENCE: 1423

Cys Ala Ser Ser Ser Gly Arg Gly His Glu Lys Leu Phe Phe
1               5                   10

<210> SEQ ID NO 1424
<211> LENGTH: 15
<212> TYPE: PRT
<213> ORGANISM: Homo sapiens

<400> SEQUENCE: 1424

Cys Ala Ser Ser Leu Ser Gly Thr Pro Tyr Asn Glu Gln Phe Phe
1               5                   10                  15

<210> SEQ ID NO 1425
<211> LENGTH: 14
<212> TYPE: PRT
<213> ORGANISM: Homo sapiens

<400> SEQUENCE: 1425

Cys Ala Ser Thr Pro Gly Gln Glu Ala Tyr Glu Gln Tyr Phe
1               5                   10

<210> SEQ ID NO 1426
<211> LENGTH: 13
<212> TYPE: PRT
<213> ORGANISM: Homo sapiens

<400> SEQUENCE: 1426

Cys Ala Ser Ser Ser Val Gln Tyr Asn Glu Gln Phe Phe
1               5                   10

<210> SEQ ID NO 1427
<211> LENGTH: 12
<212> TYPE: PRT
<213> ORGANISM: Homo sapiens

<400> SEQUENCE: 1427

Cys Ala Ser Ser Gln Trp Gln Asp Thr Gln Tyr Phe
1               5                   10

<210> SEQ ID NO 1428
<211> LENGTH: 12
<212> TYPE: PRT
<213> ORGANISM: Homo sapiens

<400> SEQUENCE: 1428

Cys Ser Ala Glu Glu Gly Ala Glu Thr Gln Tyr Phe
1               5                   10

<210> SEQ ID NO 1429
<211> LENGTH: 14
<212> TYPE: PRT
<213> ORGANISM: Homo sapiens

<400> SEQUENCE: 1429

Cys Ala Ser Ser Leu Asp Arg Gly Gln Asn Ile Gln Tyr Phe
1               5                   10

<210> SEQ ID NO 1430
<211> LENGTH: 15
<212> TYPE: PRT
<213> ORGANISM: Homo sapiens

<400> SEQUENCE: 1430

Cys Ala Ser Ser Ile Thr Gly Gly Pro Arg Asp Thr Gln Tyr Phe
1               5                   10                  15

<210> SEQ ID NO 1431
<211> LENGTH: 16
<212> TYPE: PRT
<213> ORGANISM: Homo sapiens

<400> SEQUENCE: 1431

Cys Ala Ser Ser Ser Gly Arg Ala Ser Gly Ala Asn Val Leu Thr Phe
1               5                   10                  15

<210> SEQ ID NO 1432
<211> LENGTH: 16
<212> TYPE: PRT
<213> ORGANISM: Homo sapiens

<400> SEQUENCE: 1432

Cys Ala Ser Ser Arg Gly Gln Pro Phe Ser Gly Asn Thr Ile Tyr Phe

```
1               5                   10                  15

<210> SEQ ID NO 1433
<211> LENGTH: 12
<212> TYPE: PRT
<213> ORGANISM: Homo sapiens

<400> SEQUENCE: 1433

Cys Ala Ser Arg Tyr Arg Asp Thr Glu Ala Phe Phe
1               5                   10

<210> SEQ ID NO 1434
<211> LENGTH: 14
<212> TYPE: PRT
<213> ORGANISM: Homo sapiens

<400> SEQUENCE: 1434

Cys Ala Ser Ser Leu Glu Phe Gly Pro Asn Glu Gln Phe Phe
1               5                   10

<210> SEQ ID NO 1435
<211> LENGTH: 14
<212> TYPE: PRT
<213> ORGANISM: Homo sapiens

<400> SEQUENCE: 1435

Cys Ala Ser Arg Glu Gly Gly Lys Thr Gly Glu Leu Phe Phe
1               5                   10

<210> SEQ ID NO 1436
<211> LENGTH: 16
<212> TYPE: PRT
<213> ORGANISM: Homo sapiens

<400> SEQUENCE: 1436

Cys Ala Ser Ser Ile Asp Phe Gly Gln Gly Asp Ser Pro Leu His Phe
1               5                   10                  15

<210> SEQ ID NO 1437
<211> LENGTH: 12
<212> TYPE: PRT
<213> ORGANISM: Homo sapiens

<400> SEQUENCE: 1437

Cys Ala Ser Arg Tyr Lys Asp Glu Lys Leu Phe Phe
1               5                   10

<210> SEQ ID NO 1438
<211> LENGTH: 17
<212> TYPE: PRT
<213> ORGANISM: Homo sapiens

<400> SEQUENCE: 1438

Cys Ala Ser Ser Leu Ala Gly Ala Gly Pro Ser Thr Asp Thr Gln Tyr
1               5                   10                  15

Phe

<210> SEQ ID NO 1439
<211> LENGTH: 13
<212> TYPE: PRT
<213> ORGANISM: Homo sapiens

<400> SEQUENCE: 1439

Cys Ala Ser Arg Thr Gly His Arg Tyr Gly Tyr Thr Phe
```

```
1               5                   10
```

<210> SEQ ID NO 1440
<211> LENGTH: 16
<212> TYPE: PRT
<213> ORGANISM: Homo sapiens

<400> SEQUENCE: 1440

```
Cys Ala Thr Ser Arg Ala Ser Arg Val Ser Gly Asn Thr Ile Tyr Phe
1               5                   10                  15
```

<210> SEQ ID NO 1441
<211> LENGTH: 13
<212> TYPE: PRT
<213> ORGANISM: Homo sapiens

<400> SEQUENCE: 1441

```
Cys Ser Ala Pro Val Pro Pro Asn Thr Glu Ala Phe Phe
1               5                   10
```

<210> SEQ ID NO 1442
<211> LENGTH: 13
<212> TYPE: PRT
<213> ORGANISM: Homo sapiens

<400> SEQUENCE: 1442

```
Cys Ala Ser Ser Ser Pro Gly His Asp Glu Gln Tyr Phe
1               5                   10
```

<210> SEQ ID NO 1443
<211> LENGTH: 13
<212> TYPE: PRT
<213> ORGANISM: Homo sapiens

<400> SEQUENCE: 1443

```
Cys Ala Ile Arg Glu Gly Gln Thr Tyr Glu Gln Tyr Phe
1               5                   10
```

<210> SEQ ID NO 1444
<211> LENGTH: 14
<212> TYPE: PRT
<213> ORGANISM: Homo sapiens

<400> SEQUENCE: 1444

```
Cys Ala Ser Ser Phe Gly Gly Glu Gly Ser Pro Leu His Phe
1               5                   10
```

<210> SEQ ID NO 1445
<211> LENGTH: 14
<212> TYPE: PRT
<213> ORGANISM: Homo sapiens

<400> SEQUENCE: 1445

```
Cys Ala Ser Ser Arg Ala Pro Ala Asn Thr Glu Ala Phe Phe
1               5                   10
```

<210> SEQ ID NO 1446
<211> LENGTH: 14
<212> TYPE: PRT
<213> ORGANISM: Homo sapiens

<400> SEQUENCE: 1446

```
Cys Ala Trp Ser Val Asn Arg Gly Arg Thr Glu Ala Phe Phe
1               5                   10
```

<210> SEQ ID NO 1447
<211> LENGTH: 15
<212> TYPE: PRT
<213> ORGANISM: Homo sapiens

<400> SEQUENCE: 1447

Cys Ala Ser Ser Pro Ser Arg Leu Met Asn Thr Glu Ala Phe Phe
1               5                   10                  15

<210> SEQ ID NO 1448
<211> LENGTH: 18
<212> TYPE: PRT
<213> ORGANISM: Homo sapiens

<400> SEQUENCE: 1448

Cys Ala Ser Ser Pro Pro Gly Leu Ala Gly Gly Ser Thr Gly Glu Leu
1               5                   10                  15

Phe Phe

<210> SEQ ID NO 1449
<211> LENGTH: 16
<212> TYPE: PRT
<213> ORGANISM: Homo sapiens

<400> SEQUENCE: 1449

Cys Ala Ser Ser Gln Gly Leu Ala Ser Ser Tyr Asn Glu Gln Phe Phe
1               5                   10                  15

<210> SEQ ID NO 1450
<211> LENGTH: 12
<212> TYPE: PRT
<213> ORGANISM: Homo sapiens

<400> SEQUENCE: 1450

Cys Ala Ser Ser Gln Ser Arg Gly Lys Leu Phe Phe
1               5                   10

<210> SEQ ID NO 1451
<211> LENGTH: 15
<212> TYPE: PRT
<213> ORGANISM: Homo sapiens

<400> SEQUENCE: 1451

Cys Ser Ala Arg Phe Ser Gly Arg Ala Ser Asp Thr Gln Tyr Phe
1               5                   10                  15

<210> SEQ ID NO 1452
<211> LENGTH: 17
<212> TYPE: PRT
<213> ORGANISM: Homo sapiens

<400> SEQUENCE: 1452

Cys Ala Ser Ser Leu Phe Gln Arg Gly Gly Ser Tyr Asn Glu Gln Phe
1               5                   10                  15

Phe

<210> SEQ ID NO 1453
<211> LENGTH: 14
<212> TYPE: PRT
<213> ORGANISM: Homo sapiens

<400> SEQUENCE: 1453

Cys Ala Ser Ser Pro Gly Thr Trp Gly Asp Thr Gln Tyr Phe

```
<210> SEQ ID NO 1454
<211> LENGTH: 11
<212> TYPE: PRT
<213> ORGANISM: Homo sapiens

<400> SEQUENCE: 1454

Cys Ala Ser Ala Gly Pro Trp Thr Gln Tyr Phe
1               5                   10

<210> SEQ ID NO 1455
<211> LENGTH: 14
<212> TYPE: PRT
<213> ORGANISM: Homo sapiens

<400> SEQUENCE: 1455

Cys Ala Trp Lys Val Arg Ala Asn Thr Gly Glu Leu Phe Phe
1               5                   10

<210> SEQ ID NO 1456
<211> LENGTH: 16
<212> TYPE: PRT
<213> ORGANISM: Homo sapiens

<400> SEQUENCE: 1456

Cys Ala Ser Ser Leu Leu Ala Gly Gln Gly Val Glu Thr Gln Tyr Phe
1               5                   10                  15

<210> SEQ ID NO 1457
<211> LENGTH: 12
<212> TYPE: PRT
<213> ORGANISM: Homo sapiens

<400> SEQUENCE: 1457

Cys Ala Thr Ser Phe Ser Gly Asn Thr Ile Tyr Phe
1               5                   10

<210> SEQ ID NO 1458
<211> LENGTH: 17
<212> TYPE: PRT
<213> ORGANISM: Homo sapiens

<400> SEQUENCE: 1458

Cys Ala Ser Ser Ser Arg Thr Gly Pro Thr Ser Thr Asp Thr Gln Tyr
1               5                   10                  15

Phe

<210> SEQ ID NO 1459
<211> LENGTH: 13
<212> TYPE: PRT
<213> ORGANISM: Homo sapiens

<400> SEQUENCE: 1459

Cys Ala Ser Ile Gln Gly Phe Asn Gln Pro Gln His Phe
1               5                   10

<210> SEQ ID NO 1460
<211> LENGTH: 17
<212> TYPE: PRT
<213> ORGANISM: Homo sapiens

<400> SEQUENCE: 1460

Cys Ala Ser Ser Leu Gly Ser Ile Trp Gly Ser Thr Asp Thr Gln Tyr
```

```
                1               5                  10                 15

Phe

<210> SEQ ID NO 1461
<211> LENGTH: 15
<212> TYPE: PRT
<213> ORGANISM: Homo sapiens

<400> SEQUENCE: 1461

Cys Ala Ser Ser Gln Gly Ser Asp Phe Gly Tyr Gly Tyr Thr Phe
1               5                   10                  15

<210> SEQ ID NO 1462
<211> LENGTH: 14
<212> TYPE: PRT
<213> ORGANISM: Homo sapiens

<400> SEQUENCE: 1462

Cys Ser Ala Arg Asp Ala Ser Val Ser Asp Thr Gln Tyr Phe
1               5                   10

<210> SEQ ID NO 1463
<211> LENGTH: 15
<212> TYPE: PRT
<213> ORGANISM: Homo sapiens

<400> SEQUENCE: 1463

Cys Ser Ala Arg Val Gly Gly Gly Thr Gly Glu Leu Phe Phe
1               5                   10                  15

<210> SEQ ID NO 1464
<211> LENGTH: 12
<212> TYPE: PRT
<213> ORGANISM: Homo sapiens

<400> SEQUENCE: 1464

Cys Ala Ser Ser Glu Gly Arg Gly Ile Gln Tyr Phe
1               5                   10

<210> SEQ ID NO 1465
<211> LENGTH: 15
<212> TYPE: PRT
<213> ORGANISM: Homo sapiens

<400> SEQUENCE: 1465

Cys Ala Ser Ser Thr Gln Gly Gly Arg Asn Gln Pro Gln His Phe
1               5                   10                  15

<210> SEQ ID NO 1466
<211> LENGTH: 14
<212> TYPE: PRT
<213> ORGANISM: Homo sapiens

<400> SEQUENCE: 1466

Cys Ala Ser Ser Pro Asp Arg Gly Asp Glu Lys Leu Phe Phe
1               5                   10

<210> SEQ ID NO 1467
<211> LENGTH: 13
<212> TYPE: PRT
<213> ORGANISM: Homo sapiens

<400> SEQUENCE: 1467

Cys Ser Ala Pro Ala Ile Ser Gly Asn Thr Ile Tyr Phe
```

```
1               5                    10
```

<210> SEQ ID NO 1468
<211> LENGTH: 14
<212> TYPE: PRT
<213> ORGANISM: Homo sapiens

<400> SEQUENCE: 1468

```
Cys Ala Ser Arg Ile Gly Leu Val Tyr Asn Glu Gln Phe Phe
1               5                   10
```

<210> SEQ ID NO 1469
<211> LENGTH: 15
<212> TYPE: PRT
<213> ORGANISM: Homo sapiens

<400> SEQUENCE: 1469

```
Cys Ser Ala Arg Asp Gln Gly Gln Arg Asn Ser Pro Leu His Phe
1               5                   10                  15
```

<210> SEQ ID NO 1470
<211> LENGTH: 12
<212> TYPE: PRT
<213> ORGANISM: Homo sapiens

<400> SEQUENCE: 1470

```
Cys Ala Ser Arg Tyr Arg Asp Tyr Gly Tyr Thr Phe
1               5                   10
```

<210> SEQ ID NO 1471
<211> LENGTH: 15
<212> TYPE: PRT
<213> ORGANISM: Homo sapiens

<400> SEQUENCE: 1471

```
Cys Ala Ser Ser Glu Gly Gly Gly Gly Gln Pro Gln His Phe
1               5                   10                  15
```

<210> SEQ ID NO 1472
<211> LENGTH: 16
<212> TYPE: PRT
<213> ORGANISM: Homo sapiens

<400> SEQUENCE: 1472

```
Cys Ala Ser Ser Gln Asp Pro Thr Gly Glu Gly Tyr Gly Tyr Thr Phe
1               5                   10                  15
```

<210> SEQ ID NO 1473
<211> LENGTH: 12
<212> TYPE: PRT
<213> ORGANISM: Homo sapiens

<400> SEQUENCE: 1473

```
Cys Ser Val Val Gly Gln Phe Glu Thr Gln Tyr Phe
1               5                   10
```

<210> SEQ ID NO 1474
<211> LENGTH: 14
<212> TYPE: PRT
<213> ORGANISM: Homo sapiens

<400> SEQUENCE: 1474

```
Cys Ser Ala Arg Phe Gly Thr Gly Ala Glu Lys Leu Phe Phe
1               5                   10
```

<210> SEQ ID NO 1475
<211> LENGTH: 13
<212> TYPE: PRT
<213> ORGANISM: Homo sapiens

<400> SEQUENCE: 1475

Cys Ala Thr Ser Glu Asn Arg Asn Thr Glu Ala Phe Phe
1               5                   10

<210> SEQ ID NO 1476
<211> LENGTH: 12
<212> TYPE: PRT
<213> ORGANISM: Homo sapiens

<400> SEQUENCE: 1476

Cys Ala Ser Ser Asn Asn Gly Asn Thr Ile Tyr Phe
1               5                   10

<210> SEQ ID NO 1477
<211> LENGTH: 14
<212> TYPE: PRT
<213> ORGANISM: Homo sapiens

<400> SEQUENCE: 1477

Cys Ala Ser Ser Ser Ser Pro Leu Thr Asp Thr Gln Tyr Phe
1               5                   10

<210> SEQ ID NO 1478
<211> LENGTH: 14
<212> TYPE: PRT
<213> ORGANISM: Homo sapiens

<400> SEQUENCE: 1478

Cys Ala Ser Ser Leu Pro Arg Ala Arg Tyr Glu Gln Tyr Phe
1               5                   10

<210> SEQ ID NO 1479
<211> LENGTH: 12
<212> TYPE: PRT
<213> ORGANISM: Homo sapiens

<400> SEQUENCE: 1479

Cys Ala Ser Arg Leu Gly Leu Gly Gly Tyr Thr Phe
1               5                   10

<210> SEQ ID NO 1480
<211> LENGTH: 14
<212> TYPE: PRT
<213> ORGANISM: Homo sapiens

<400> SEQUENCE: 1480

Cys Ala Ser Ser Pro Gln Trp Tyr Gln Glu Thr Gln Tyr Phe
1               5                   10

<210> SEQ ID NO 1481
<211> LENGTH: 17
<212> TYPE: PRT
<213> ORGANISM: Homo sapiens

<400> SEQUENCE: 1481

Cys Ala Ser Ser Ser Pro Thr Ser Gly Gly Arg Thr Asp Thr Gln Tyr
1               5                   10                  15

Phe

<210> SEQ ID NO 1482
<211> LENGTH: 16
<212> TYPE: PRT
<213> ORGANISM: Homo sapiens

<400> SEQUENCE: 1482

Cys Ala Ser Ser Met Gly Arg Gly Ala Gly Ala Asn Val Leu Thr Phe
1               5                   10                  15

<210> SEQ ID NO 1483
<211> LENGTH: 13
<212> TYPE: PRT
<213> ORGANISM: Homo sapiens

<400> SEQUENCE: 1483

Cys Ala Ser Ser Leu Gly Ile Gly Asp Thr Gln Tyr Phe
1               5                   10

<210> SEQ ID NO 1484
<211> LENGTH: 11
<212> TYPE: PRT
<213> ORGANISM: Homo sapiens

<400> SEQUENCE: 1484

Cys Ala Trp Asn Arg Arg Asp Glu Ala Phe Phe
1               5                   10

<210> SEQ ID NO 1485
<211> LENGTH: 13
<212> TYPE: PRT
<213> ORGANISM: Homo sapiens

<400> SEQUENCE: 1485

Cys Ser Ala Pro Leu Pro Gly Leu Asp Thr Gln Tyr Phe
1               5                   10

<210> SEQ ID NO 1486
<211> LENGTH: 15
<212> TYPE: PRT
<213> ORGANISM: Homo sapiens

<400> SEQUENCE: 1486

Cys Ser Ala Gln Gly Gln Pro Thr Asn Thr Gly Glu Leu Phe Phe
1               5                   10                  15

<210> SEQ ID NO 1487
<211> LENGTH: 16
<212> TYPE: PRT
<213> ORGANISM: Homo sapiens

<400> SEQUENCE: 1487

Cys Ala Ser Ser Ser Pro Leu Gly Gly Gly Ala Asp Thr Gln Tyr Phe
1               5                   10                  15

<210> SEQ ID NO 1488
<211> LENGTH: 15
<212> TYPE: PRT
<213> ORGANISM: Homo sapiens

<400> SEQUENCE: 1488

Cys Ala Ser Ser Gly Ala Leu Ala Val Thr Gly Glu Leu Phe Phe
1               5                   10                  15

<210> SEQ ID NO 1489

```
<211> LENGTH: 14
<212> TYPE: PRT
<213> ORGANISM: Homo sapiens

<400> SEQUENCE: 1489

Cys Ala Ser Arg Ala Gly Arg Glu Asp Thr Glu Ala Phe Phe
1               5                   10

<210> SEQ ID NO 1490
<211> LENGTH: 13
<212> TYPE: PRT
<213> ORGANISM: Homo sapiens

<400> SEQUENCE: 1490

Cys Ala Ile Arg Glu Gly Gln Lys Glu Thr Gln Tyr Phe
1               5                   10

<210> SEQ ID NO 1491
<211> LENGTH: 14
<212> TYPE: PRT
<213> ORGANISM: Homo sapiens

<400> SEQUENCE: 1491

Cys Ala Ser Ser Leu Gly Pro His Pro Tyr Glu Gln Tyr Phe
1               5                   10

<210> SEQ ID NO 1492
<211> LENGTH: 13
<212> TYPE: PRT
<213> ORGANISM: Homo sapiens

<400> SEQUENCE: 1492

Cys Ala Ser Gly Arg Gln Gly Gly Tyr Glu Gln Tyr Phe
1               5                   10

<210> SEQ ID NO 1493
<211> LENGTH: 16
<212> TYPE: PRT
<213> ORGANISM: Homo sapiens

<400> SEQUENCE: 1493

Cys Ala Ser Ser Leu Ala Asp Ser Val Ser Gly Asn Thr Ile Tyr Phe
1               5                   10                  15

<210> SEQ ID NO 1494
<211> LENGTH: 16
<212> TYPE: PRT
<213> ORGANISM: Homo sapiens

<400> SEQUENCE: 1494

Cys Ala Ser Ser Glu Lys Ala Gly Gly Ser Ser Tyr Glu Gln Tyr Phe
1               5                   10                  15

<210> SEQ ID NO 1495
<211> LENGTH: 13
<212> TYPE: PRT
<213> ORGANISM: Homo sapiens

<400> SEQUENCE: 1495

Cys Ser Ala Ser Ile Ala Pro Tyr Asn Glu Gln Phe Phe
1               5                   10

<210> SEQ ID NO 1496
<211> LENGTH: 14
<212> TYPE: PRT
```

<213> ORGANISM: Homo sapiens

<400> SEQUENCE: 1496

Cys Ala Ser Ser Gln Asp Arg Asp Leu Tyr Gly Tyr Thr Phe
1               5                   10

<210> SEQ ID NO 1497
<211> LENGTH: 12
<212> TYPE: PRT
<213> ORGANISM: Homo sapiens

<400> SEQUENCE: 1497

Cys Ala Ser Gly Leu Gln Asp Asn Glu Gln Phe Phe
1               5                   10

<210> SEQ ID NO 1498
<211> LENGTH: 17
<212> TYPE: PRT
<213> ORGANISM: Homo sapiens

<400> SEQUENCE: 1498

Cys Ala Ser Ser Leu Ala Gly Ser Gly Gly Gly Gln Glu Thr Gln Tyr
1               5                   10                  15

Phe

<210> SEQ ID NO 1499
<211> LENGTH: 15
<212> TYPE: PRT
<213> ORGANISM: Homo sapiens

<400> SEQUENCE: 1499

Cys Ser Ala Arg Val Ala Ser Gly Ser Ser Asp Thr Gln Tyr Phe
1               5                   10                  15

<210> SEQ ID NO 1500
<211> LENGTH: 12
<212> TYPE: PRT
<213> ORGANISM: Homo sapiens

<400> SEQUENCE: 1500

Cys Ala Ser Ser Gln Asp Val Gly Arg Gln Phe Phe
1               5                   10

<210> SEQ ID NO 1501
<211> LENGTH: 15
<212> TYPE: PRT
<213> ORGANISM: Homo sapiens

<400> SEQUENCE: 1501

Cys Ala Ser Ser Trp Pro Gly Thr Gly Ala Asn Val Leu Thr Phe
1               5                   10                  15

<210> SEQ ID NO 1502
<211> LENGTH: 14
<212> TYPE: PRT
<213> ORGANISM: Homo sapiens

<400> SEQUENCE: 1502

Cys Ala Ser Thr Gln Gly Thr Ile Gly Asn Thr Ile Tyr Phe
1               5                   10

<210> SEQ ID NO 1503
<211> LENGTH: 12
<212> TYPE: PRT

<213> ORGANISM: Homo sapiens

<400> SEQUENCE: 1503

Cys Ser Ala Arg Asp Gly Gln Ala Glu Gln Tyr Phe
1               5                   10

<210> SEQ ID NO 1504
<211> LENGTH: 15
<212> TYPE: PRT
<213> ORGANISM: Homo sapiens

<400> SEQUENCE: 1504

Cys Ala Ser Ser Thr Arg Arg Ala Pro Tyr Asn Glu Gln Phe Phe
1               5                   10                  15

<210> SEQ ID NO 1505
<211> LENGTH: 14
<212> TYPE: PRT
<213> ORGANISM: Homo sapiens

<400> SEQUENCE: 1505

Cys Ala Ser Ser Leu Ala Pro Ala Ser Gly Glu Gln Tyr Phe
1               5                   10

<210> SEQ ID NO 1506
<211> LENGTH: 15
<212> TYPE: PRT
<213> ORGANISM: Homo sapiens

<400> SEQUENCE: 1506

Cys Ser Ala Arg Asp Arg Gln Gly Leu Gln Glu Thr Gln Tyr Phe
1               5                   10                  15

<210> SEQ ID NO 1507
<211> LENGTH: 14
<212> TYPE: PRT
<213> ORGANISM: Homo sapiens

<400> SEQUENCE: 1507

Cys Ala Ser Ile Trp Thr Ala Tyr Asn Ser Pro Leu His Phe
1               5                   10

<210> SEQ ID NO 1508
<211> LENGTH: 13
<212> TYPE: PRT
<213> ORGANISM: Homo sapiens

<400> SEQUENCE: 1508

Cys Ala Ile Arg Leu Arg Glu Gln Glu Thr Gln Tyr Phe
1               5                   10

<210> SEQ ID NO 1509
<211> LENGTH: 16
<212> TYPE: PRT
<213> ORGANISM: Homo sapiens

<400> SEQUENCE: 1509

Cys Ala Ser Ser Leu Thr Arg Thr Ser Gly Ser Gly Glu Gln Tyr Phe
1               5                   10                  15

<210> SEQ ID NO 1510
<211> LENGTH: 15
<212> TYPE: PRT
<213> ORGANISM: Homo sapiens

<400> SEQUENCE: 1510

Cys Ala Ser Ser Pro Leu Ala Gly Glu Lys Asp Thr Gln Tyr Phe
1               5                   10                  15

<210> SEQ ID NO 1511
<211> LENGTH: 16
<212> TYPE: PRT
<213> ORGANISM: Homo sapiens

<400> SEQUENCE: 1511

Cys Ala Ser Ser Leu Val Glu Ser Gly Ser Gly Asn Thr Ile Tyr Phe
1               5                   10                  15

<210> SEQ ID NO 1512
<211> LENGTH: 15
<212> TYPE: PRT
<213> ORGANISM: Homo sapiens

<400> SEQUENCE: 1512

Cys Ala Thr Ser Val Gly Ser Gly Gly Arg Asp Thr Gln Tyr Phe
1               5                   10                  15

<210> SEQ ID NO 1513
<211> LENGTH: 14
<212> TYPE: PRT
<213> ORGANISM: Homo sapiens

<400> SEQUENCE: 1513

Cys Ala Ser Ser Pro Trp Pro Gly Thr Asp Thr Gln Tyr Phe
1               5                   10

<210> SEQ ID NO 1514
<211> LENGTH: 14
<212> TYPE: PRT
<213> ORGANISM: Homo sapiens

<400> SEQUENCE: 1514

Cys Ala Ser Ser Gln Gly Thr Glu Phe Tyr Gly Tyr Thr Phe
1               5                   10

<210> SEQ ID NO 1515
<211> LENGTH: 15
<212> TYPE: PRT
<213> ORGANISM: Homo sapiens

<400> SEQUENCE: 1515

Cys Ala Ser Ser Leu Val Gly Leu Val Arg Asp Thr Gln Tyr Phe
1               5                   10                  15

<210> SEQ ID NO 1516
<211> LENGTH: 15
<212> TYPE: PRT
<213> ORGANISM: Homo sapiens

<400> SEQUENCE: 1516

Cys Ala Ser Ser Pro Thr Gly Gly Lys Ser Asp Thr Gln Tyr Phe
1               5                   10                  15

<210> SEQ ID NO 1517
<211> LENGTH: 13
<212> TYPE: PRT
<213> ORGANISM: Homo sapiens

<400> SEQUENCE: 1517

Cys Ala Ser Ser Asp Arg Ser Gln Glu Thr Gln Tyr Phe
1               5                   10

<210> SEQ ID NO 1518
<211> LENGTH: 15
<212> TYPE: PRT
<213> ORGANISM: Homo sapiens

<400> SEQUENCE: 1518

Cys Ala Ile Ser Pro Arg Asp Ser Leu Gln Glu Thr Gln Tyr Phe
1               5                   10                  15

<210> SEQ ID NO 1519
<211> LENGTH: 16
<212> TYPE: PRT
<213> ORGANISM: Homo sapiens

<400> SEQUENCE: 1519

Cys Ala Ser Gly Asp Arg Gly Gln Thr Gly Ala Asn Val Leu Thr Phe
1               5                   10                  15

<210> SEQ ID NO 1520
<211> LENGTH: 14
<212> TYPE: PRT
<213> ORGANISM: Homo sapiens

<400> SEQUENCE: 1520

Cys Ala Ser Ser Val Gly Leu Thr Gly Ser Glu Gln Tyr Phe
1               5                   10

<210> SEQ ID NO 1521
<211> LENGTH: 13
<212> TYPE: PRT
<213> ORGANISM: Homo sapiens

<400> SEQUENCE: 1521

Cys Ala Ser Gln Arg Gln Gly Ala Tyr Glu Gln Tyr Phe
1               5                   10

<210> SEQ ID NO 1522
<211> LENGTH: 15
<212> TYPE: PRT
<213> ORGANISM: Homo sapiens

<400> SEQUENCE: 1522

Cys Ala Ser Thr Leu Arg Ser Gly Ala Asn Tyr Gly Tyr Thr Phe
1               5                   10                  15

<210> SEQ ID NO 1523
<211> LENGTH: 15
<212> TYPE: PRT
<213> ORGANISM: Homo sapiens

<400> SEQUENCE: 1523

Cys Ser Ala Arg Glu Gly Gly Ala Gly Thr Gly Glu Leu Phe Phe
1               5                   10                  15

<210> SEQ ID NO 1524
<211> LENGTH: 16
<212> TYPE: PRT
<213> ORGANISM: Homo sapiens

<400> SEQUENCE: 1524

Cys Ala Ser Ser Ile Glu Val Gly Phe Gly Ala Asn Val Leu Thr Phe
1               5                   10                  15

```
<210> SEQ ID NO 1525
<211> LENGTH: 15
<212> TYPE: PRT
<213> ORGANISM: Homo sapiens

<400> SEQUENCE: 1525

Cys Ala Ser Ser Gly Leu Thr Gly Tyr Thr Asp Thr Gln Tyr Phe
1               5                   10                  15

<210> SEQ ID NO 1526
<211> LENGTH: 15
<212> TYPE: PRT
<213> ORGANISM: Homo sapiens

<400> SEQUENCE: 1526

Cys Ala Ser Thr Lys Gly Gly Ala Ala Gly Asn Thr Ile Tyr Phe
1               5                   10                  15

<210> SEQ ID NO 1527
<211> LENGTH: 14
<212> TYPE: PRT
<213> ORGANISM: Homo sapiens

<400> SEQUENCE: 1527

Cys Ala Ser Thr Arg Gly Pro Glu Gly Ser Pro Leu His Phe
1               5                   10

<210> SEQ ID NO 1528
<211> LENGTH: 12
<212> TYPE: PRT
<213> ORGANISM: Homo sapiens

<400> SEQUENCE: 1528

Cys Ala Ser Ser Pro Gly Ser His Thr Ile Tyr Phe
1               5                   10

<210> SEQ ID NO 1529
<211> LENGTH: 17
<212> TYPE: PRT
<213> ORGANISM: Homo sapiens

<400> SEQUENCE: 1529

Cys Ala Ser Ser Pro Arg Pro Gly Thr Gly Thr Asn Thr Glu Ala Phe
1               5                   10                  15

Phe

<210> SEQ ID NO 1530
<211> LENGTH: 14
<212> TYPE: PRT
<213> ORGANISM: Homo sapiens

<400> SEQUENCE: 1530

Cys Ala Ser Ser Pro Gln Gly Val Gly Asn Glu Gln Phe Phe
1               5                   10

<210> SEQ ID NO 1531
<211> LENGTH: 14
<212> TYPE: PRT
<213> ORGANISM: Homo sapiens

<400> SEQUENCE: 1531

Cys Ala Ser Ser Gln Arg Ala Val Asn Tyr Gly Tyr Thr Phe
1               5                   10
```

<210> SEQ ID NO 1532
<211> LENGTH: 16
<212> TYPE: PRT
<213> ORGANISM: Homo sapiens

<400> SEQUENCE: 1532

Cys Ser Ala Arg Thr Val Ala Gly Ala Ser Thr Asp Thr Gln Tyr Phe
1               5                   10                  15

<210> SEQ ID NO 1533
<211> LENGTH: 15
<212> TYPE: PRT
<213> ORGANISM: Homo sapiens

<400> SEQUENCE: 1533

Cys Ala Ser Ser Leu Asp Gly Arg Thr His Ser Pro Leu His Phe
1               5                   10                  15

<210> SEQ ID NO 1534
<211> LENGTH: 13
<212> TYPE: PRT
<213> ORGANISM: Homo sapiens

<400> SEQUENCE: 1534

Cys Ala Ser Thr Lys Asp Gly Ser Tyr Gly Tyr Thr Phe
1               5                   10

<210> SEQ ID NO 1535
<211> LENGTH: 15
<212> TYPE: PRT
<213> ORGANISM: Homo sapiens

<400> SEQUENCE: 1535

Cys Ala Ser Ser Pro Thr Gly Leu Gly Ala Tyr Glu Gln Tyr Phe
1               5                   10                  15

<210> SEQ ID NO 1536
<211> LENGTH: 13
<212> TYPE: PRT
<213> ORGANISM: Homo sapiens

<400> SEQUENCE: 1536

Cys Ser Ala Ser Ser Val Pro Tyr Asn Glu Gln Phe Phe
1               5                   10

<210> SEQ ID NO 1537
<211> LENGTH: 13
<212> TYPE: PRT
<213> ORGANISM: Homo sapiens

<400> SEQUENCE: 1537

Cys Ala Ser Ser Arg Gly Gln Ile Tyr Glu Gln Tyr Phe
1               5                   10

<210> SEQ ID NO 1538
<211> LENGTH: 14
<212> TYPE: PRT
<213> ORGANISM: Homo sapiens

<400> SEQUENCE: 1538

Cys Ala Ser Ser Ala Arg Leu Val Pro Gly Glu Leu Phe Phe
1               5                   10

```
<210> SEQ ID NO 1539
<211> LENGTH: 14
<212> TYPE: PRT
<213> ORGANISM: Homo sapiens

<400> SEQUENCE: 1539

Cys Ala Ser Ser Gln Asp Leu Val Arg Thr Glu Ala Phe Phe
1               5                   10

<210> SEQ ID NO 1540
<211> LENGTH: 17
<212> TYPE: PRT
<213> ORGANISM: Homo sapiens

<400> SEQUENCE: 1540

Cys Ala Ser Ser Gln Gly Val Leu Ala Gly His Tyr Asn Glu Gln Phe
1               5                   10                  15

Phe

<210> SEQ ID NO 1541
<211> LENGTH: 15
<212> TYPE: PRT
<213> ORGANISM: Homo sapiens

<400> SEQUENCE: 1541

Cys Ala Ser Ser Ser Thr Gly Ala Pro Glu Glu Lys Leu Phe Phe
1               5                   10                  15

<210> SEQ ID NO 1542
<211> LENGTH: 14
<212> TYPE: PRT
<213> ORGANISM: Homo sapiens

<400> SEQUENCE: 1542

Cys Ser Ala Ser Asn Leu Ala Gly His Asn Glu Gln Phe Phe
1               5                   10

<210> SEQ ID NO 1543
<211> LENGTH: 15
<212> TYPE: PRT
<213> ORGANISM: Homo sapiens

<400> SEQUENCE: 1543

Cys Ser Ala Arg Tyr Gly Gly Ala Gly Thr Gly Glu Leu Phe Phe
1               5                   10                  15

<210> SEQ ID NO 1544
<211> LENGTH: 14
<212> TYPE: PRT
<213> ORGANISM: Homo sapiens

<400> SEQUENCE: 1544

Cys Ala Thr Ser Arg Val Gly Gln Gly Asn Glu Gln Phe Phe
1               5                   10

<210> SEQ ID NO 1545
<211> LENGTH: 14
<212> TYPE: PRT
<213> ORGANISM: Homo sapiens

<400> SEQUENCE: 1545

Cys Ser Ala Arg Val Arg Asn Arg Asn Ser Pro Leu His Phe
1               5                   10
```

<210> SEQ ID NO 1546
<211> LENGTH: 16
<212> TYPE: PRT
<213> ORGANISM: Homo sapiens

<400> SEQUENCE: 1546

Cys Ala Ser Ser Glu Arg Gln Gly Ala Gly Thr Gly Glu Leu Phe Phe
1               5                   10                  15

<210> SEQ ID NO 1547
<211> LENGTH: 15
<212> TYPE: PRT
<213> ORGANISM: Homo sapiens

<400> SEQUENCE: 1547

Cys Ala Ser Ser Pro Arg Thr Ser Ser Thr Gly Glu Leu Phe Phe
1               5                   10                  15

<210> SEQ ID NO 1548
<211> LENGTH: 15
<212> TYPE: PRT
<213> ORGANISM: Homo sapiens

<400> SEQUENCE: 1548

Cys Ala Ser Ser Leu Gly Gly Ser Gly Glu Glu Thr Gln Tyr Phe
1               5                   10                  15

<210> SEQ ID NO 1549
<211> LENGTH: 14
<212> TYPE: PRT
<213> ORGANISM: Homo sapiens

<400> SEQUENCE: 1549

Cys Ser Ala Arg Val Gly Arg Ser Val Glu Thr Gln Tyr Phe
1               5                   10

<210> SEQ ID NO 1550
<211> LENGTH: 14
<212> TYPE: PRT
<213> ORGANISM: Homo sapiens

<400> SEQUENCE: 1550

Cys Ala Ser Ser Arg Ser Gly Tyr Ser Tyr Glu Gln Tyr Phe
1               5                   10

<210> SEQ ID NO 1551
<211> LENGTH: 13
<212> TYPE: PRT
<213> ORGANISM: Homo sapiens

<400> SEQUENCE: 1551

Cys Ala Ile Ser Arg Gly Gly Tyr Thr Glu Ala Phe Phe
1               5                   10

<210> SEQ ID NO 1552
<211> LENGTH: 13
<212> TYPE: PRT
<213> ORGANISM: Homo sapiens

<400> SEQUENCE: 1552

Cys Ser Ala Thr Gln Gly Val Asn Thr Glu Ala Phe Phe
1               5                   10

<210> SEQ ID NO 1553
<211> LENGTH: 15

```
<212> TYPE: PRT
<213> ORGANISM: Homo sapiens

<400> SEQUENCE: 1553

Cys Ala Ser Ser Gly Pro Gln Gly Tyr Asn Ser Pro Leu His Phe
1               5                   10                  15

<210> SEQ ID NO 1554
<211> LENGTH: 14
<212> TYPE: PRT
<213> ORGANISM: Homo sapiens

<400> SEQUENCE: 1554

Cys Ala Ser Ser Gln Asp Leu Thr Gly Thr Glu Ala Phe Phe
1               5                   10

<210> SEQ ID NO 1555
<211> LENGTH: 15
<212> TYPE: PRT
<213> ORGANISM: Homo sapiens

<400> SEQUENCE: 1555

Cys Ala Ser Ser Phe Glu His Asn Tyr Asn Ser Pro Leu His Phe
1               5                   10                  15

<210> SEQ ID NO 1556
<211> LENGTH: 15
<212> TYPE: PRT
<213> ORGANISM: Homo sapiens

<400> SEQUENCE: 1556

Cys Ser Ala Arg Asp Pro Trp Arg Asp Thr Asp Thr Gln Tyr Phe
1               5                   10                  15

<210> SEQ ID NO 1557
<211> LENGTH: 15
<212> TYPE: PRT
<213> ORGANISM: Homo sapiens

<400> SEQUENCE: 1557

Cys Ala Ser Ser Tyr Ser Phe Ala Ser Gly Glu Thr Gln Tyr Phe
1               5                   10                  15

<210> SEQ ID NO 1558
<211> LENGTH: 15
<212> TYPE: PRT
<213> ORGANISM: Homo sapiens

<400> SEQUENCE: 1558

Cys Ser Ala Arg Thr Ser Gly Gly Gly Thr Gly Glu Leu Phe Phe
1               5                   10                  15

<210> SEQ ID NO 1559
<211> LENGTH: 15
<212> TYPE: PRT
<213> ORGANISM: Homo sapiens

<400> SEQUENCE: 1559

Cys Ala Ser Ser Gln Leu Val Gly Ser Tyr Asn Glu Gln Phe Phe
1               5                   10                  15

<210> SEQ ID NO 1560
<211> LENGTH: 17
<212> TYPE: PRT
<213> ORGANISM: Homo sapiens
```

-continued

<400> SEQUENCE: 1560

Cys Ala Ser Ser Pro Phe Thr Ser Gly Gly Ser Tyr Asn Glu Gln Phe
1               5                   10                  15

Phe

<210> SEQ ID NO 1561
<211> LENGTH: 13
<212> TYPE: PRT
<213> ORGANISM: Homo sapiens

<400> SEQUENCE: 1561

Cys Ala Ser Ser Phe Pro Ser Ser Glu Thr Gln Tyr Phe
1               5                   10

<210> SEQ ID NO 1562
<211> LENGTH: 16
<212> TYPE: PRT
<213> ORGANISM: Homo sapiens

<400> SEQUENCE: 1562

Cys Ala Ser Ser Leu Gly Arg Thr Gly Arg Asp Tyr Gly Tyr Thr Phe
1               5                   10                  15

<210> SEQ ID NO 1563
<211> LENGTH: 12
<212> TYPE: PRT
<213> ORGANISM: Homo sapiens

<400> SEQUENCE: 1563

Cys Ala Ser Gly Gly Val Gln Glu Thr Gln Tyr Phe
1               5                   10

<210> SEQ ID NO 1564
<211> LENGTH: 14
<212> TYPE: PRT
<213> ORGANISM: Homo sapiens

<400> SEQUENCE: 1564

Cys Ala Ser Ser Gln Arg Asp Ser Tyr Thr Glu Ala Phe Phe
1               5                   10

<210> SEQ ID NO 1565
<211> LENGTH: 16
<212> TYPE: PRT
<213> ORGANISM: Homo sapiens

<400> SEQUENCE: 1565

Cys Ala Ser Ser Gln Leu Pro Gly Arg Thr Asn Ser Pro Leu His Phe
1               5                   10                  15

<210> SEQ ID NO 1566
<211> LENGTH: 17
<212> TYPE: PRT
<213> ORGANISM: Homo sapiens

<400> SEQUENCE: 1566

Cys Ala Ser Ser Ser Pro Leu Ala Gly Gly Arg Thr Asp Thr Gln Tyr
1               5                   10                  15

Phe

<210> SEQ ID NO 1567
<211> LENGTH: 11

```
<212> TYPE: PRT
<213> ORGANISM: Homo sapiens

<400> SEQUENCE: 1567

Cys Ala Ser Ser Pro Gly Asp Tyr Thr Phe
1               5                   10

<210> SEQ ID NO 1568
<211> LENGTH: 15
<212> TYPE: PRT
<213> ORGANISM: Homo sapiens

<400> SEQUENCE: 1568

Cys Ser Ala Arg His Gly Gly Ala Gly Thr Gly Glu Leu Phe Phe
1               5                   10                  15

<210> SEQ ID NO 1569
<211> LENGTH: 14
<212> TYPE: PRT
<213> ORGANISM: Homo sapiens

<400> SEQUENCE: 1569

Cys Ala Thr Ser Asp Val Gly Thr Asn Glu Lys Leu Phe Phe
1               5                   10

<210> SEQ ID NO 1570
<211> LENGTH: 15
<212> TYPE: PRT
<213> ORGANISM: Homo sapiens

<400> SEQUENCE: 1570

Cys Ala Ser Ser Leu Gly Pro Ser Gly Asn Asn Glu Gln Phe Phe
1               5                   10                  15

<210> SEQ ID NO 1571
<211> LENGTH: 15
<212> TYPE: PRT
<213> ORGANISM: Homo sapiens

<400> SEQUENCE: 1571

Cys Ser Ala Arg Arg Gly Gly Gly Gly Thr Gly Glu Leu Phe Phe
1               5                   10                  15

<210> SEQ ID NO 1572
<211> LENGTH: 16
<212> TYPE: PRT
<213> ORGANISM: Homo sapiens

<400> SEQUENCE: 1572

Cys Ser Ala Arg Arg Asp Arg Gly Pro Gly Asn Tyr Gly Tyr Thr Phe
1               5                   10                  15

<210> SEQ ID NO 1573
<211> LENGTH: 15
<212> TYPE: PRT
<213> ORGANISM: Homo sapiens

<400> SEQUENCE: 1573

Cys Ala Ser Ser Arg Val Pro Gln Ser Ser Tyr Glu Gln Tyr Phe
1               5                   10                  15

<210> SEQ ID NO 1574
<211> LENGTH: 14
<212> TYPE: PRT
<213> ORGANISM: Homo sapiens
```

<400> SEQUENCE: 1574

Cys Ala Ser Ser Phe Thr Gly Trp Gln Glu Thr Gln Tyr Phe
1               5                   10

<210> SEQ ID NO 1575
<211> LENGTH: 13
<212> TYPE: PRT
<213> ORGANISM: Homo sapiens

<400> SEQUENCE: 1575

Cys Ala Ser Ser Phe Gln Ala Ser Asp Thr Gln Tyr Phe
1               5                   10

<210> SEQ ID NO 1576
<211> LENGTH: 13
<212> TYPE: PRT
<213> ORGANISM: Homo sapiens

<400> SEQUENCE: 1576

Cys Ser Ala Leu Ser Pro Pro Tyr Asn Glu Gln Phe Phe
1               5                   10

<210> SEQ ID NO 1577
<211> LENGTH: 12
<212> TYPE: PRT
<213> ORGANISM: Homo sapiens

<400> SEQUENCE: 1577

Cys Ala Ser Gly Ala Ser Gly Asn Thr Ile Tyr Phe
1               5                   10

<210> SEQ ID NO 1578
<211> LENGTH: 15
<212> TYPE: PRT
<213> ORGANISM: Homo sapiens

<400> SEQUENCE: 1578

Cys Ala Ser Ser Leu Asp Pro Arg Ala Tyr Asn Glu Gln Phe Phe
1               5                   10                  15

<210> SEQ ID NO 1579
<211> LENGTH: 14
<212> TYPE: PRT
<213> ORGANISM: Homo sapiens

<400> SEQUENCE: 1579

Cys Ala Ser Ser Ser Asn Gly Gln His Tyr Glu Gln Tyr Phe
1               5                   10

<210> SEQ ID NO 1580
<211> LENGTH: 13
<212> TYPE: PRT
<213> ORGANISM: Homo sapiens

<400> SEQUENCE: 1580

Cys Ser Val Glu Arg Ser Gly Ala Tyr Glu Gln Tyr Phe
1               5                   10

<210> SEQ ID NO 1581
<211> LENGTH: 12
<212> TYPE: PRT
<213> ORGANISM: Homo sapiens

<400> SEQUENCE: 1581

Cys Ala Ile Leu Ser Ser Asn Gln Pro Gln His Phe
1               5                   10

<210> SEQ ID NO 1582
<211> LENGTH: 14
<212> TYPE: PRT
<213> ORGANISM: Homo sapiens

<400> SEQUENCE: 1582

Cys Ala Ser Ser Leu Ala Pro Ala Gly Tyr Glu Gln Tyr Phe
1               5                   10

<210> SEQ ID NO 1583
<211> LENGTH: 15
<212> TYPE: PRT
<213> ORGANISM: Homo sapiens

<400> SEQUENCE: 1583

Cys Ala Ser Ser Leu Glu Ser Asn Tyr Asn Ser Pro Leu His Phe
1               5                   10                  15

<210> SEQ ID NO 1584
<211> LENGTH: 13
<212> TYPE: PRT
<213> ORGANISM: Homo sapiens

<400> SEQUENCE: 1584

Cys Ala Ser Ser Pro Arg Asp Ile Asn Glu Gln Phe Phe
1               5                   10

<210> SEQ ID NO 1585
<211> LENGTH: 15
<212> TYPE: PRT
<213> ORGANISM: Homo sapiens

<400> SEQUENCE: 1585

Cys Ala Ser Ser Ser Ala Gly Gly Arg Gly Glu Thr Gln Tyr Phe
1               5                   10                  15

<210> SEQ ID NO 1586
<211> LENGTH: 13
<212> TYPE: PRT
<213> ORGANISM: Homo sapiens

<400> SEQUENCE: 1586

Cys Ser Ala Pro Leu Ala Pro Tyr Asn Glu Gln Phe Phe
1               5                   10

<210> SEQ ID NO 1587
<211> LENGTH: 16
<212> TYPE: PRT
<213> ORGANISM: Homo sapiens

<400> SEQUENCE: 1587

Cys Ser Ala Arg Leu Thr Gly Asp Tyr Ser Asn Gln Pro Gln His Phe
1               5                   10                  15

<210> SEQ ID NO 1588
<211> LENGTH: 16
<212> TYPE: PRT
<213> ORGANISM: Homo sapiens

<400> SEQUENCE: 1588

Cys Ala Ser Arg Gly Thr Gly Thr Pro Ser Asn Gln Pro Gln His Phe

<210> SEQ ID NO 1589
<211> LENGTH: 13
<212> TYPE: PRT
<213> ORGANISM: Homo sapiens

<400> SEQUENCE: 1589

Cys Ser Ala Arg Asp Glu Gly Pro Asp Thr Gln Tyr Phe
1               5                   10

<210> SEQ ID NO 1590
<211> LENGTH: 15
<212> TYPE: PRT
<213> ORGANISM: Homo sapiens

<400> SEQUENCE: 1590

Cys Ala Ser Ser Leu Glu Pro Asn Tyr Asn Ser Pro Leu His Phe
1               5                   10                  15

<210> SEQ ID NO 1591
<211> LENGTH: 12
<212> TYPE: PRT
<213> ORGANISM: Homo sapiens

<400> SEQUENCE: 1591

Cys Ala Ser Ser Lys Gly Phe Asn Glu Gln Tyr Phe
1               5                   10

<210> SEQ ID NO 1592
<211> LENGTH: 14
<212> TYPE: PRT
<213> ORGANISM: Homo sapiens

<400> SEQUENCE: 1592

Cys Ala Ser Ser Leu Gly His Trp Asn Glu Lys Leu Phe Phe
1               5                   10

<210> SEQ ID NO 1593
<211> LENGTH: 15
<212> TYPE: PRT
<213> ORGANISM: Homo sapiens

<400> SEQUENCE: 1593

Cys Ala Ser Ser Gln Gly Arg Gly Gly Lys Glu Thr Gln Tyr Phe
1               5                   10                  15

<210> SEQ ID NO 1594
<211> LENGTH: 12
<212> TYPE: PRT
<213> ORGANISM: Homo sapiens

<400> SEQUENCE: 1594

Cys Ser Val Arg Thr Ser Ser Glu Thr Gln Tyr Phe
1               5                   10

<210> SEQ ID NO 1595
<211> LENGTH: 16
<212> TYPE: PRT
<213> ORGANISM: Homo sapiens

<400> SEQUENCE: 1595

Cys Ala Ser Ser Phe Gly Leu Ala Gly Val Gly Asn Glu Gln Phe Phe
1               5                   10                  15

<210> SEQ ID NO 1596
<211> LENGTH: 16
<212> TYPE: PRT
<213> ORGANISM: Homo sapiens

<400> SEQUENCE: 1596

Cys Ala Ser Ser Gly Arg Gly Gln Gly Ser Thr Asp Thr Gln Tyr Phe
1               5                   10                  15

<210> SEQ ID NO 1597
<211> LENGTH: 15
<212> TYPE: PRT
<213> ORGANISM: Homo sapiens

<400> SEQUENCE: 1597

Cys Ala Thr Ser Arg Gly Asp Arg Thr Gln Glu Thr Gln Tyr Phe
1               5                   10                  15

<210> SEQ ID NO 1598
<211> LENGTH: 15
<212> TYPE: PRT
<213> ORGANISM: Homo sapiens

<400> SEQUENCE: 1598

Cys Ala Ser Ser Pro Ser Pro Gly Gly His Thr Glu Ala Phe Phe
1               5                   10                  15

<210> SEQ ID NO 1599
<211> LENGTH: 15
<212> TYPE: PRT
<213> ORGANISM: Homo sapiens

<400> SEQUENCE: 1599

Cys Ala Ser Ser Gln Thr Arg Ser Gly Ala Asn Val Leu Thr Phe
1               5                   10                  15

<210> SEQ ID NO 1600
<211> LENGTH: 14
<212> TYPE: PRT
<213> ORGANISM: Homo sapiens

<400> SEQUENCE: 1600

Cys Ala Ser Arg Pro Gly Thr Gly Thr Tyr Gly Tyr Thr Phe
1               5                   10

<210> SEQ ID NO 1601
<211> LENGTH: 15
<212> TYPE: PRT
<213> ORGANISM: Homo sapiens

<400> SEQUENCE: 1601

Cys Ala Ser Ser Leu Gly Gly Gln Gly His Tyr Gly Tyr Thr Phe
1               5                   10                  15

<210> SEQ ID NO 1602
<211> LENGTH: 11
<212> TYPE: PRT
<213> ORGANISM: Homo sapiens

<400> SEQUENCE: 1602

Cys Ala Ser Ser Ser Pro Gly Gly Tyr Thr Phe
1               5                   10

<210> SEQ ID NO 1603

```
<211> LENGTH: 13
<212> TYPE: PRT
<213> ORGANISM: Homo sapiens

<400> SEQUENCE: 1603

Cys Ser Ala Pro Arg Ser Leu Asn Thr Glu Ala Phe Phe
1               5                   10

<210> SEQ ID NO 1604
<211> LENGTH: 14
<212> TYPE: PRT
<213> ORGANISM: Homo sapiens

<400> SEQUENCE: 1604

Cys Ala Ile Ser Gly Arg Asp Lys Asn Ser Pro Leu His Phe
1               5                   10

<210> SEQ ID NO 1605
<211> LENGTH: 13
<212> TYPE: PRT
<213> ORGANISM: Homo sapiens

<400> SEQUENCE: 1605

Cys Ala Ser Arg Arg Gly Thr Asp Thr Glu Ala Phe Phe
1               5                   10

<210> SEQ ID NO 1606
<211> LENGTH: 14
<212> TYPE: PRT
<213> ORGANISM: Homo sapiens

<400> SEQUENCE: 1606

Cys Ala Ser Ser Pro Gly Gly Ala Arg Tyr Glu Gln Tyr Phe
1               5                   10

<210> SEQ ID NO 1607
<211> LENGTH: 17
<212> TYPE: PRT
<213> ORGANISM: Homo sapiens

<400> SEQUENCE: 1607

Cys Ala Ser Ser Gly Gly Gly Arg Thr Ser Ser Tyr Asn Glu Gln Phe
1               5                   10                  15

Phe

<210> SEQ ID NO 1608
<211> LENGTH: 15
<212> TYPE: PRT
<213> ORGANISM: Homo sapiens

<400> SEQUENCE: 1608

Cys Ala Ser Ser Leu Thr Leu Ser Leu Ser Tyr Glu Gln Tyr Phe
1               5                   10                  15

<210> SEQ ID NO 1609
<211> LENGTH: 13
<212> TYPE: PRT
<213> ORGANISM: Homo sapiens

<400> SEQUENCE: 1609

Cys Ala Ser Ser Tyr Pro Gly Leu Glu Thr Gln Tyr Phe
1               5                   10

<210> SEQ ID NO 1610
```

```
<211> LENGTH: 14
<212> TYPE: PRT
<213> ORGANISM: Homo sapiens

<400> SEQUENCE: 1610

Cys Ala Ser Ser Gly Phe Arg Asp Tyr Thr Glu Ala Phe Phe
1               5                   10

<210> SEQ ID NO 1611
<211> LENGTH: 14
<212> TYPE: PRT
<213> ORGANISM: Homo sapiens

<400> SEQUENCE: 1611

Cys Ser Ala Ser Gly Ala Val Ser Ser Tyr Glu Gln Tyr Phe
1               5                   10

<210> SEQ ID NO 1612
<211> LENGTH: 15
<212> TYPE: PRT
<213> ORGANISM: Homo sapiens

<400> SEQUENCE: 1612

Cys Ser Ala Arg Thr Ser Gly Ser Gly Ala Gly Glu Leu Phe Phe
1               5                   10                  15

<210> SEQ ID NO 1613
<211> LENGTH: 16
<212> TYPE: PRT
<213> ORGANISM: Homo sapiens

<400> SEQUENCE: 1613

Cys Ala Ser Ser Leu Leu Asp Ser Ala Asn Thr Gly Glu Leu Phe Phe
1               5                   10                  15

<210> SEQ ID NO 1614
<211> LENGTH: 15
<212> TYPE: PRT
<213> ORGANISM: Homo sapiens

<400> SEQUENCE: 1614

Cys Ala Ser Ser Tyr Ser Ser Arg Ala His Tyr Glu Gln Tyr Phe
1               5                   10                  15

<210> SEQ ID NO 1615
<211> LENGTH: 16
<212> TYPE: PRT
<213> ORGANISM: Homo sapiens

<400> SEQUENCE: 1615

Cys Ala Ser Ser Arg Gly Gln Gly Thr Ser Asn Gln Pro Gln His Phe
1               5                   10                  15

<210> SEQ ID NO 1616
<211> LENGTH: 17
<212> TYPE: PRT
<213> ORGANISM: Homo sapiens

<400> SEQUENCE: 1616

Cys Ala Ser Ser Leu Val Gly Gln Gly Pro Ala Asn Tyr Gly Tyr Thr
1               5                   10                  15

Phe

<210> SEQ ID NO 1617
```

-continued

```
<211> LENGTH: 14
<212> TYPE: PRT
<213> ORGANISM: Homo sapiens

<400> SEQUENCE: 1617

Cys Ala Ser Thr Phe Ser Gly Arg Thr Asp Thr Gln Tyr Phe
1               5                   10

<210> SEQ ID NO 1618
<211> LENGTH: 14
<212> TYPE: PRT
<213> ORGANISM: Homo sapiens

<400> SEQUENCE: 1618

Cys Ala Ser Ser Ser Val Gly Ala Asp Thr Glu Ala Phe Phe
1               5                   10

<210> SEQ ID NO 1619
<211> LENGTH: 12
<212> TYPE: PRT
<213> ORGANISM: Homo sapiens

<400> SEQUENCE: 1619

Cys Ala Trp Asn Pro Ser Thr Asp Thr Gln Tyr Phe
1               5                   10

<210> SEQ ID NO 1620
<211> LENGTH: 16
<212> TYPE: PRT
<213> ORGANISM: Homo sapiens

<400> SEQUENCE: 1620

Cys Ala Ser Ser Phe Arg Arg Ser Ser Ser Tyr Asn Glu Gln Phe Phe
1               5                   10                  15

<210> SEQ ID NO 1621
<211> LENGTH: 14
<212> TYPE: PRT
<213> ORGANISM: Homo sapiens

<400> SEQUENCE: 1621

Cys Ala Ser Ser Pro Arg Gly Gly Leu Asn Ile Gln Tyr Phe
1               5                   10

<210> SEQ ID NO 1622
<211> LENGTH: 15
<212> TYPE: PRT
<213> ORGANISM: Homo sapiens

<400> SEQUENCE: 1622

Cys Ala Ser Arg Asp Leu Thr Ser Ser Tyr Asn Glu Gln Phe Phe
1               5                   10                  15

<210> SEQ ID NO 1623
<211> LENGTH: 16
<212> TYPE: PRT
<213> ORGANISM: Homo sapiens

<400> SEQUENCE: 1623

Cys Ala Ser Ser Phe Phe Gly Gly Arg Arg Asn Thr Glu Ala Phe Phe
1               5                   10                  15

<210> SEQ ID NO 1624
<211> LENGTH: 12
<212> TYPE: PRT
```

-continued

<213> ORGANISM: Homo sapiens

<400> SEQUENCE: 1624

Cys Ala Trp Gly Leu Gly Thr Asp Thr Gln Tyr Phe
1               5                   10

<210> SEQ ID NO 1625
<211> LENGTH: 14
<212> TYPE: PRT
<213> ORGANISM: Homo sapiens

<400> SEQUENCE: 1625

Cys Ala Ser Arg Pro Pro Glu Ser Gly Asn Thr Ile Tyr Phe
1               5                   10

<210> SEQ ID NO 1626
<211> LENGTH: 15
<212> TYPE: PRT
<213> ORGANISM: Homo sapiens

<400> SEQUENCE: 1626

Cys Ala Ser Ser Pro Gly Gln Gly Arg Phe Glu Thr Gln Tyr Phe
1               5                   10                  15

<210> SEQ ID NO 1627
<211> LENGTH: 13
<212> TYPE: PRT
<213> ORGANISM: Homo sapiens

<400> SEQUENCE: 1627

Cys Ser Ala Ser Pro Pro His Asn Glu Gln Phe Phe
1               5                   10

<210> SEQ ID NO 1628
<211> LENGTH: 16
<212> TYPE: PRT
<213> ORGANISM: Homo sapiens

<400> SEQUENCE: 1628

Cys Ala Ser Ser Arg Ala Ser Gly Thr Ser Ser Tyr Glu Gln Tyr Phe
1               5                   10                  15

<210> SEQ ID NO 1629
<211> LENGTH: 15
<212> TYPE: PRT
<213> ORGANISM: Homo sapiens

<400> SEQUENCE: 1629

Cys Ala Trp Ser His Gly Arg Ala Ser Tyr Asn Glu Gln Phe Phe
1               5                   10                  15

<210> SEQ ID NO 1630
<211> LENGTH: 16
<212> TYPE: PRT
<213> ORGANISM: Homo sapiens

<400> SEQUENCE: 1630

Cys Ala Ser Ser Leu Ala Pro Arg Asp Arg Gly Asn Glu Gln Phe Phe
1               5                   10                  15

<210> SEQ ID NO 1631
<211> LENGTH: 16
<212> TYPE: PRT
<213> ORGANISM: Homo sapiens

<400> SEQUENCE: 1631

Cys Ala Ser Ser Leu Gly Gln Gly Gly Thr Tyr Asn Glu Gln Phe Phe
1               5                   10                  15

<210> SEQ ID NO 1632
<211> LENGTH: 14
<212> TYPE: PRT
<213> ORGANISM: Homo sapiens

<400> SEQUENCE: 1632

Cys Ser Ala Arg Asp Pro Leu Gly Gln Glu Thr Gln Tyr Phe
1               5                   10

<210> SEQ ID NO 1633
<211> LENGTH: 13
<212> TYPE: PRT
<213> ORGANISM: Homo sapiens

<400> SEQUENCE: 1633

Cys Ala Ser Arg Arg Asp Arg Gly Asp Glu Gln Phe Phe
1               5                   10

<210> SEQ ID NO 1634
<211> LENGTH: 15
<212> TYPE: PRT
<213> ORGANISM: Homo sapiens

<400> SEQUENCE: 1634

Cys Ala Ser Ser Arg Asp Arg Gly Arg Gly Glu Thr Gln Tyr Phe
1               5                   10                  15

<210> SEQ ID NO 1635
<211> LENGTH: 14
<212> TYPE: PRT
<213> ORGANISM: Homo sapiens

<400> SEQUENCE: 1635

Cys Ala Ser Ser Gly Arg Gly Ile Tyr Asn Glu Gln Phe Phe
1               5                   10

<210> SEQ ID NO 1636
<211> LENGTH: 15
<212> TYPE: PRT
<213> ORGANISM: Homo sapiens

<400> SEQUENCE: 1636

Cys Ala Ser Ser Leu Ala Gly Thr Gly Thr His Gly Tyr Thr Phe
1               5                   10                  15

<210> SEQ ID NO 1637
<211> LENGTH: 14
<212> TYPE: PRT
<213> ORGANISM: Homo sapiens

<400> SEQUENCE: 1637

Cys Ala Ser Ser Arg Thr Tyr Ser Asn Gln Pro Gln His Phe
1               5                   10

<210> SEQ ID NO 1638
<211> LENGTH: 13
<212> TYPE: PRT
<213> ORGANISM: Homo sapiens

<400> SEQUENCE: 1638

Cys Ala Ser Ser Glu Gly Ser Ala Glu Thr Gln Tyr Phe
1               5                   10

<210> SEQ ID NO 1639
<211> LENGTH: 12
<212> TYPE: PRT
<213> ORGANISM: Homo sapiens

<400> SEQUENCE: 1639

Cys Ala Ser Ser Ile His Pro Asn Glu Gln Phe Phe
1               5                   10

<210> SEQ ID NO 1640
<211> LENGTH: 13
<212> TYPE: PRT
<213> ORGANISM: Homo sapiens

<400> SEQUENCE: 1640

Cys Ala Ser Ser Ser Gly Gly Ser Gly Gly Tyr Thr Phe
1               5                   10

<210> SEQ ID NO 1641
<211> LENGTH: 15
<212> TYPE: PRT
<213> ORGANISM: Homo sapiens

<400> SEQUENCE: 1641

Cys Ala Ser Ser Val Glu Gly Gly Gly Thr Asp Thr Gln Tyr Phe
1               5                   10                  15

<210> SEQ ID NO 1642
<211> LENGTH: 13
<212> TYPE: PRT
<213> ORGANISM: Homo sapiens

<400> SEQUENCE: 1642

Cys Ala Ser Ser Gln Asp Thr Gly Arg Glu Gln Tyr Phe
1               5                   10

<210> SEQ ID NO 1643
<211> LENGTH: 15
<212> TYPE: PRT
<213> ORGANISM: Homo sapiens

<400> SEQUENCE: 1643

Cys Ala Ser Thr Pro Arg Val Ser Ser Tyr Asn Glu Gln Phe Phe
1               5                   10                  15

<210> SEQ ID NO 1644
<211> LENGTH: 14
<212> TYPE: PRT
<213> ORGANISM: Homo sapiens

<400> SEQUENCE: 1644

Cys Ala Ser Ser Ala Thr Gly Gly Asp Gln Pro Gln His Phe
1               5                   10

<210> SEQ ID NO 1645
<211> LENGTH: 16
<212> TYPE: PRT
<213> ORGANISM: Homo sapiens

<400> SEQUENCE: 1645

Cys Ala Ser Ser Glu Ala Leu Arg Arg Gly Gly Gln Pro Gln His Phe
1               5                   10                  15

<210> SEQ ID NO 1646
<211> LENGTH: 15
<212> TYPE: PRT
<213> ORGANISM: Homo sapiens

<400> SEQUENCE: 1646

Cys Ala Ser Ser Pro Asp Arg Pro Thr Lys Asn Ile Gln Tyr Phe
1               5                   10                  15

<210> SEQ ID NO 1647
<211> LENGTH: 14
<212> TYPE: PRT
<213> ORGANISM: Homo sapiens

<400> SEQUENCE: 1647

Cys Ala Ser Ser Tyr Leu Gly Leu Ser Tyr Glu Gln Tyr Val
1               5                   10

<210> SEQ ID NO 1648
<211> LENGTH: 12
<212> TYPE: PRT
<213> ORGANISM: Homo sapiens

<400> SEQUENCE: 1648

Cys Ala Ser Ser Gln Gly Gly Tyr Glu Gln Phe Phe
1               5                   10

<210> SEQ ID NO 1649
<211> LENGTH: 15
<212> TYPE: PRT
<213> ORGANISM: Homo sapiens

<400> SEQUENCE: 1649

Cys Ser Ala Arg Gly Ser Gly Arg Pro Ser Asp Thr Gln Tyr Phe
1               5                   10                  15

<210> SEQ ID NO 1650
<211> LENGTH: 15
<212> TYPE: PRT
<213> ORGANISM: Homo sapiens

<400> SEQUENCE: 1650

Cys Ala Ser Ser Val Leu Gln Gly Asn Ala Gly Glu Leu Phe Phe
1               5                   10                  15

<210> SEQ ID NO 1651
<211> LENGTH: 14
<212> TYPE: PRT
<213> ORGANISM: Homo sapiens

<400> SEQUENCE: 1651

Cys Ala Ser Ser Phe Arg Ala Gly Thr Glu Thr Gln Tyr Phe
1               5                   10

<210> SEQ ID NO 1652
<211> LENGTH: 12
<212> TYPE: PRT
<213> ORGANISM: Homo sapiens

<400> SEQUENCE: 1652

Cys Ala Ser Arg Arg Arg Leu Tyr Glu Gln Tyr Phe
1               5                   10

```
<210> SEQ ID NO 1653
<211> LENGTH: 14
<212> TYPE: PRT
<213> ORGANISM: Homo sapiens

<400> SEQUENCE: 1653

Cys Ser Ala Asp Gly Thr Ser Gly Tyr Asn Glu Gln Phe Phe
1               5                   10

<210> SEQ ID NO 1654
<211> LENGTH: 15
<212> TYPE: PRT
<213> ORGANISM: Homo sapiens

<400> SEQUENCE: 1654

Cys Ala Ser Ser Val Val Ser Gly Ala Ser Tyr Glu Gln Tyr Phe
1               5                   10                  15

<210> SEQ ID NO 1655
<211> LENGTH: 14
<212> TYPE: PRT
<213> ORGANISM: Homo sapiens

<400> SEQUENCE: 1655

Cys Ala Ser Ser Glu Ser Gly Asp Trp Glu Thr Gln Tyr Phe
1               5                   10

<210> SEQ ID NO 1656
<211> LENGTH: 13
<212> TYPE: PRT
<213> ORGANISM: Homo sapiens

<400> SEQUENCE: 1656

Cys Ser Ala Arg Gly Arg Thr Tyr Asn Glu Gln Phe Phe
1               5                   10

<210> SEQ ID NO 1657
<211> LENGTH: 14
<212> TYPE: PRT
<213> ORGANISM: Homo sapiens

<400> SEQUENCE: 1657

Cys Ala Ser Thr Ser Pro Gly Ala Pro Tyr Gly Tyr Thr Phe
1               5                   10

<210> SEQ ID NO 1658
<211> LENGTH: 17
<212> TYPE: PRT
<213> ORGANISM: Homo sapiens

<400> SEQUENCE: 1658

Cys Ala Ser Ser Gln Gly Val Leu Ala Gly Gly Thr Tyr Glu Gln Tyr
1               5                   10                  15

Phe

<210> SEQ ID NO 1659
<211> LENGTH: 15
<212> TYPE: PRT
<213> ORGANISM: Homo sapiens

<400> SEQUENCE: 1659

Cys Ala Ser Ser His Gln Leu Ala Gly Ala Asp Thr Gln Tyr Phe
1               5                   10                  15
```

```
<210> SEQ ID NO 1660
<211> LENGTH: 14
<212> TYPE: PRT
<213> ORGANISM: Homo sapiens

<400> SEQUENCE: 1660

Cys Ala Ser Ser Glu Gly Ala Val Ser Tyr Gly Tyr Thr Phe
1               5                   10

<210> SEQ ID NO 1661
<211> LENGTH: 15
<212> TYPE: PRT
<213> ORGANISM: Homo sapiens

<400> SEQUENCE: 1661

Cys Ala Ser Ser Leu Ala Gly Arg Thr Arg Glu Thr Gln Tyr Phe
1               5                   10                  15

<210> SEQ ID NO 1662
<211> LENGTH: 13
<212> TYPE: PRT
<213> ORGANISM: Homo sapiens

<400> SEQUENCE: 1662

Cys Ser Ala Arg Asp Glu Gly Pro Asp Gly Tyr Thr Phe
1               5                   10

<210> SEQ ID NO 1663
<211> LENGTH: 14
<212> TYPE: PRT
<213> ORGANISM: Homo sapiens

<400> SEQUENCE: 1663

Cys Ala Ser Ser Arg Thr Ser Gly Asn Pro Glu Gln Tyr Phe
1               5                   10

<210> SEQ ID NO 1664
<211> LENGTH: 14
<212> TYPE: PRT
<213> ORGANISM: Homo sapiens

<400> SEQUENCE: 1664

Cys Ala Ser Ser Thr Gly Leu Ala Gly Glu Glu Gln Phe Phe
1               5                   10

<210> SEQ ID NO 1665
<211> LENGTH: 12
<212> TYPE: PRT
<213> ORGANISM: Homo sapiens

<400> SEQUENCE: 1665

Cys Ser Ile Pro Gly Ser Gly Asn Thr Ile Tyr Phe
1               5                   10

<210> SEQ ID NO 1666
<211> LENGTH: 14
<212> TYPE: PRT
<213> ORGANISM: Homo sapiens

<400> SEQUENCE: 1666

Cys Ala Ser Ser Ile Thr Pro Val Asn Glu Lys Leu Phe Phe
1               5                   10

<210> SEQ ID NO 1667
<211> LENGTH: 13
```

```
<212> TYPE: PRT
<213> ORGANISM: Homo sapiens

<400> SEQUENCE: 1667

Cys Ala Ser Ser Pro Met Gly Gly Tyr Glu Gln Tyr Phe
1               5                   10

<210> SEQ ID NO 1668
<211> LENGTH: 17
<212> TYPE: PRT
<213> ORGANISM: Homo sapiens

<400> SEQUENCE: 1668

Cys Ala Ser Ser Leu Thr Gly Gly Arg Gly Ala Lys Asn Ile Gln Tyr
1               5                   10                  15

Phe

<210> SEQ ID NO 1669
<211> LENGTH: 15
<212> TYPE: PRT
<213> ORGANISM: Homo sapiens

<400> SEQUENCE: 1669

Cys Ala Ser Ser Leu Ala Leu Ala Gly Arg Gly Thr Gln Tyr Phe
1               5                   10                  15

<210> SEQ ID NO 1670
<211> LENGTH: 13
<212> TYPE: PRT
<213> ORGANISM: Homo sapiens

<400> SEQUENCE: 1670

Cys Ala Ser Ser Arg Gln Gly Ala Tyr Glu Gln Tyr Phe
1               5                   10

<210> SEQ ID NO 1671
<211> LENGTH: 15
<212> TYPE: PRT
<213> ORGANISM: Homo sapiens

<400> SEQUENCE: 1671

Cys Ala Ser Ser Leu Leu Thr Val Ser Thr Asp Thr Gln Tyr Phe
1               5                   10                  15

<210> SEQ ID NO 1672
<211> LENGTH: 13
<212> TYPE: PRT
<213> ORGANISM: Homo sapiens

<400> SEQUENCE: 1672

Cys Ala Ser Ser Ile Gly Leu Arg Asp Ile Gln Tyr Phe
1               5                   10

<210> SEQ ID NO 1673
<211> LENGTH: 14
<212> TYPE: PRT
<213> ORGANISM: Homo sapiens

<400> SEQUENCE: 1673

Cys Ala Ser Ser Glu Arg Pro Val Thr Asp Thr Gln Tyr Phe
1               5                   10

<210> SEQ ID NO 1674
<211> LENGTH: 13
```

```
<212> TYPE: PRT
<213> ORGANISM: Homo sapiens

<400> SEQUENCE: 1674

Cys Ala Ser Ser Asp Ile Gly Gly Val Gly Tyr Thr Phe
1               5                   10

<210> SEQ ID NO 1675
<211> LENGTH: 14
<212> TYPE: PRT
<213> ORGANISM: Homo sapiens

<400> SEQUENCE: 1675

Cys Ala Ser Ser Leu Gln Arg Gly Ala Gly Glu Gln Tyr Phe
1               5                   10

<210> SEQ ID NO 1676
<211> LENGTH: 13
<212> TYPE: PRT
<213> ORGANISM: Homo sapiens

<400> SEQUENCE: 1676

Cys Ala Ser Ser Leu Thr Gly Ser Gly Thr Gln Tyr Phe
1               5                   10

<210> SEQ ID NO 1677
<211> LENGTH: 13
<212> TYPE: PRT
<213> ORGANISM: Homo sapiens

<400> SEQUENCE: 1677

Cys Ala Ser Ser Phe Thr Asn Gln Glu Thr Gln Tyr Phe
1               5                   10

<210> SEQ ID NO 1678
<211> LENGTH: 16
<212> TYPE: PRT
<213> ORGANISM: Homo sapiens

<400> SEQUENCE: 1678

Cys Ser Val Pro Pro Gly Leu Ala Gly Gly Tyr Asn Glu Gln Phe Phe
1               5                   10                  15

<210> SEQ ID NO 1679
<211> LENGTH: 14
<212> TYPE: PRT
<213> ORGANISM: Homo sapiens

<400> SEQUENCE: 1679

Cys Ser Ala Arg Glu Leu Gln Gly Ala Ser Glu Gln Tyr Phe
1               5                   10

<210> SEQ ID NO 1680
<211> LENGTH: 14
<212> TYPE: PRT
<213> ORGANISM: Homo sapiens

<400> SEQUENCE: 1680

Cys Ala Ser Ser Leu Ala Gly Val Ser Thr Glu Ala Phe Phe
1               5                   10

<210> SEQ ID NO 1681
<211> LENGTH: 15
<212> TYPE: PRT
<213> ORGANISM: Homo sapiens
```

<400> SEQUENCE: 1681

Cys Ser Ala Arg Ser Ser Gly Arg Ser Ser Asp Thr Gln Tyr Phe
1               5                   10                  15

<210> SEQ ID NO 1682
<211> LENGTH: 15
<212> TYPE: PRT
<213> ORGANISM: Homo sapiens

<400> SEQUENCE: 1682

Cys Ala Thr Ser Arg Gly Ala Gly Gly Ser Tyr Glu Gln Tyr Phe
1               5                   10                  15

<210> SEQ ID NO 1683
<211> LENGTH: 14
<212> TYPE: PRT
<213> ORGANISM: Homo sapiens

<400> SEQUENCE: 1683

Cys Ser Ala Arg Ser Thr Leu Ala Ser Tyr Glu Gln Tyr Phe
1               5                   10

<210> SEQ ID NO 1684
<211> LENGTH: 18
<212> TYPE: PRT
<213> ORGANISM: Homo sapiens

<400> SEQUENCE: 1684

Cys Ala Ser Ser Leu Ala Gly Gly Thr Tyr Ile Ser Tyr Asn Glu Gln
1               5                   10                  15

Phe Phe

<210> SEQ ID NO 1685
<211> LENGTH: 13
<212> TYPE: PRT
<213> ORGANISM: Homo sapiens

<400> SEQUENCE: 1685

Cys Ala Ser Ser Gln Asp Arg Gln Asp Glu Gln Tyr Phe
1               5                   10

<210> SEQ ID NO 1686
<211> LENGTH: 16
<212> TYPE: PRT
<213> ORGANISM: Homo sapiens

<400> SEQUENCE: 1686

Cys Ala Ser Ser Glu Pro Gly Thr Gly Val Tyr Asn Glu Gln Phe Phe
1               5                   10                  15

<210> SEQ ID NO 1687
<211> LENGTH: 15
<212> TYPE: PRT
<213> ORGANISM: Homo sapiens

<400> SEQUENCE: 1687

Cys Ser Ala Arg Ser Ser Gly Ser Gly Thr Gly Glu Leu Phe Phe
1               5                   10                  15

<210> SEQ ID NO 1688
<211> LENGTH: 15
<212> TYPE: PRT
<213> ORGANISM: Homo sapiens

<400> SEQUENCE: 1688

Cys Ser Ala Arg Val Ala Gly Gly Gly Thr Gly Glu Leu Phe Phe
1               5                   10                  15

<210> SEQ ID NO 1689
<211> LENGTH: 14
<212> TYPE: PRT
<213> ORGANISM: Homo sapiens

<400> SEQUENCE: 1689

Cys Ala Ser Ser Tyr Ser Thr Phe Arg Asn Glu Gln Phe Phe
1               5                   10

<210> SEQ ID NO 1690
<211> LENGTH: 13
<212> TYPE: PRT
<213> ORGANISM: Homo sapiens

<400> SEQUENCE: 1690

Cys Ser Asp Ala Gly Thr Gly Gly Glu Thr Gln Tyr Phe
1               5                   10

<210> SEQ ID NO 1691
<211> LENGTH: 15
<212> TYPE: PRT
<213> ORGANISM: Homo sapiens

<400> SEQUENCE: 1691

Cys Ala Ser Arg Ile Gly Arg His Ser Gly Asn Thr Ile Tyr Phe
1               5                   10                  15

<210> SEQ ID NO 1692
<211> LENGTH: 14
<212> TYPE: PRT
<213> ORGANISM: Homo sapiens

<400> SEQUENCE: 1692

Cys Ala Ser Ser Pro Gln Asp Gly Asn Glu Lys Leu Phe Phe
1               5                   10

<210> SEQ ID NO 1693
<211> LENGTH: 15
<212> TYPE: PRT
<213> ORGANISM: Homo sapiens

<400> SEQUENCE: 1693

Cys Ala Ser Ser Pro Gly Thr Gly Thr Tyr Asn Glu Gln Phe Phe
1               5                   10                  15

<210> SEQ ID NO 1694
<211> LENGTH: 13
<212> TYPE: PRT
<213> ORGANISM: Homo sapiens

<400> SEQUENCE: 1694

Cys Ser Ala Ser Gly Gln Gly His Ser Gly Tyr Thr Phe
1               5                   10

<210> SEQ ID NO 1695
<211> LENGTH: 12
<212> TYPE: PRT
<213> ORGANISM: Homo sapiens

<400> SEQUENCE: 1695

Cys Ser Ala Gln His Ile Thr Gly Glu Leu Phe Phe
1               5                   10

<210> SEQ ID NO 1696
<211> LENGTH: 13
<212> TYPE: PRT
<213> ORGANISM: Homo sapiens

<400> SEQUENCE: 1696

Cys Ala Ser Ser Glu Asn Arg Asn Thr Glu Ala Phe Phe
1               5                   10

<210> SEQ ID NO 1697
<211> LENGTH: 14
<212> TYPE: PRT
<213> ORGANISM: Homo sapiens

<400> SEQUENCE: 1697

Cys Ser Ala Asn Gly Gln Gly Phe Thr Asp Thr Gln Tyr Phe
1               5                   10

<210> SEQ ID NO 1698
<211> LENGTH: 14
<212> TYPE: PRT
<213> ORGANISM: Homo sapiens

<400> SEQUENCE: 1698

Cys Ser Ala Gly Leu Ala Gly Gly Phe Tyr Glu Gln Tyr Phe
1               5                   10

<210> SEQ ID NO 1699
<211> LENGTH: 15
<212> TYPE: PRT
<213> ORGANISM: Homo sapiens

<400> SEQUENCE: 1699

Cys Ala Ser Ser Pro Thr Ser Gly Arg Ala Tyr Glu Gln Tyr Phe
1               5                   10                  15

<210> SEQ ID NO 1700
<211> LENGTH: 14
<212> TYPE: PRT
<213> ORGANISM: Homo sapiens

<400> SEQUENCE: 1700

Cys Ala Trp Ala Gly Leu Ser Gly Ala Asn Val Leu Thr Phe
1               5                   10

<210> SEQ ID NO 1701
<211> LENGTH: 15
<212> TYPE: PRT
<213> ORGANISM: Homo sapiens

<400> SEQUENCE: 1701

Cys Ala Thr Ser Arg Gly Val Arg Arg Thr Asp Thr Gln Tyr Phe
1               5                   10                  15

<210> SEQ ID NO 1702
<211> LENGTH: 18
<212> TYPE: PRT
<213> ORGANISM: Homo sapiens

<400> SEQUENCE: 1702

Cys Ala Ser Ser Leu Leu Ala Gly Ala Gly Leu Ser Thr Asp Thr Gln

-continued

```
1               5                   10                  15

Tyr Phe

<210> SEQ ID NO 1703
<211> LENGTH: 16
<212> TYPE: PRT
<213> ORGANISM: Homo sapiens

<400> SEQUENCE: 1703

Cys Ala Ser Ser Lys Asp Asp Arg Gly Ser Gly Asn Thr Ile Tyr Phe
1               5                   10                  15

<210> SEQ ID NO 1704
<211> LENGTH: 13
<212> TYPE: PRT
<213> ORGANISM: Homo sapiens

<400> SEQUENCE: 1704

Cys Ser Ala Pro Arg Val Pro Tyr Asn Glu Gln Phe Phe
1               5                   10

<210> SEQ ID NO 1705
<211> LENGTH: 15
<212> TYPE: PRT
<213> ORGANISM: Homo sapiens

<400> SEQUENCE: 1705

Cys Ser Ala Arg Pro Gly Gly Ala Gly Thr Gly Glu Leu Phe Phe
1               5                   10                  15

<210> SEQ ID NO 1706
<211> LENGTH: 14
<212> TYPE: PRT
<213> ORGANISM: Homo sapiens

<400> SEQUENCE: 1706

Cys Ala Ser Ser Gln Ala Gly Arg Ala Asp Thr Gln Tyr Phe
1               5                   10

<210> SEQ ID NO 1707
<211> LENGTH: 17
<212> TYPE: PRT
<213> ORGANISM: Homo sapiens

<400> SEQUENCE: 1707

Cys Ala Ser Ser Ser Ser Arg Gln Gly Arg Asn Asn Ser Pro Leu His
1               5                   10                  15

Phe

<210> SEQ ID NO 1708
<211> LENGTH: 18
<212> TYPE: PRT
<213> ORGANISM: Homo sapiens

<400> SEQUENCE: 1708

Cys Ala Ser Ser Ser Gly Leu Ala Gly Gly Thr Ser Ser Tyr Glu Gln
1               5                   10                  15

Tyr Phe

<210> SEQ ID NO 1709
<211> LENGTH: 16
<212> TYPE: PRT
<213> ORGANISM: Homo sapiens
```

<400> SEQUENCE: 1709

Cys Ala Ser Ser Gln Gly Thr Ser Gly Ser Tyr Asn Glu Gln Phe Phe
1               5                   10                  15

<210> SEQ ID NO 1710
<211> LENGTH: 13
<212> TYPE: PRT
<213> ORGANISM: Homo sapiens

<400> SEQUENCE: 1710

Cys Ala Ser Ser Leu Pro Gly Leu Gly Val Ala Phe Phe
1               5                   10

<210> SEQ ID NO 1711
<211> LENGTH: 16
<212> TYPE: PRT
<213> ORGANISM: Homo sapiens

<400> SEQUENCE: 1711

Cys Ala Ser Ser Val Gly Phe Ala Gly Gly Ser Asp Thr Gln Tyr Phe
1               5                   10                  15

<210> SEQ ID NO 1712
<211> LENGTH: 15
<212> TYPE: PRT
<213> ORGANISM: Homo sapiens

<400> SEQUENCE: 1712

Cys Ala Ser Ser Ser Arg Gly Gln Gly Val His Glu Gln Tyr Phe
1               5                   10                  15

<210> SEQ ID NO 1713
<211> LENGTH: 14
<212> TYPE: PRT
<213> ORGANISM: Homo sapiens

<400> SEQUENCE: 1713

Cys Ala Ser Ser Tyr Arg Gly Glu Thr Asp Thr Gln Tyr Phe
1               5                   10

<210> SEQ ID NO 1714
<211> LENGTH: 13
<212> TYPE: PRT
<213> ORGANISM: Homo sapiens

<400> SEQUENCE: 1714

Cys Ala Ser Ser Leu Leu Thr Thr Tyr Glu Gln Tyr Phe
1               5                   10

<210> SEQ ID NO 1715
<211> LENGTH: 14
<212> TYPE: PRT
<213> ORGANISM: Homo sapiens

<400> SEQUENCE: 1715

Cys Ser Ala Arg Met Asp Arg Gly Arg Asn Glu Gln Phe Phe
1               5                   10

<210> SEQ ID NO 1716
<211> LENGTH: 15
<212> TYPE: PRT
<213> ORGANISM: Homo sapiens

<400> SEQUENCE: 1716

Cys Ala Thr Arg Gly Gly Ala Thr Asn Glu Lys Leu Phe Phe
1               5                   10                  15

<210> SEQ ID NO 1717
<211> LENGTH: 17
<212> TYPE: PRT
<213> ORGANISM: Homo sapiens

<400> SEQUENCE: 1717

Cys Ala Ser Ser Phe Arg Thr Gly Gly Pro Gly Ala Asn Val Leu Thr
1               5                   10                  15

Phe

<210> SEQ ID NO 1718
<211> LENGTH: 15
<212> TYPE: PRT
<213> ORGANISM: Homo sapiens

<400> SEQUENCE: 1718

Cys Ser Ala Arg Ser Ser Gly Gly Gly Thr Gly Glu Leu Phe Phe
1               5                   10                  15

<210> SEQ ID NO 1719
<211> LENGTH: 15
<212> TYPE: PRT
<213> ORGANISM: Homo sapiens

<400> SEQUENCE: 1719

Cys Ala Ser Ser Leu Glu Gln Gly Thr Tyr Asn Glu Gln Phe Phe
1               5                   10                  15

<210> SEQ ID NO 1720
<211> LENGTH: 15
<212> TYPE: PRT
<213> ORGANISM: Homo sapiens

<400> SEQUENCE: 1720

Cys Ser Ala Arg Asp Arg Arg Gly Leu Gln Glu Thr Gln Tyr Phe
1               5                   10                  15

<210> SEQ ID NO 1721
<211> LENGTH: 17
<212> TYPE: PRT
<213> ORGANISM: Homo sapiens

<400> SEQUENCE: 1721

Cys Ala Ser Ser Gln Ala Gly Arg Gln Gly Gly Tyr Asn Glu Gln Phe
1               5                   10                  15

Phe

<210> SEQ ID NO 1722
<211> LENGTH: 15
<212> TYPE: PRT
<213> ORGANISM: Homo sapiens

<400> SEQUENCE: 1722

Cys Ala Ile Ser Gly Asp Gly Gly Gly Tyr Thr Glu Ala Phe Phe
1               5                   10                  15

<210> SEQ ID NO 1723
<211> LENGTH: 16
<212> TYPE: PRT
<213> ORGANISM: Homo sapiens

<400> SEQUENCE: 1723

Cys Ala Ser Ser Pro Ile Gly Gly Gln Gly Asn Gln Pro Gln His Phe
1               5                   10                  15

<210> SEQ ID NO 1724
<211> LENGTH: 14
<212> TYPE: PRT
<213> ORGANISM: Homo sapiens

<400> SEQUENCE: 1724

Cys Ala Ser Ser Pro Gly Arg Gly Trp Glu Lys Leu Phe Phe
1               5                   10

<210> SEQ ID NO 1725
<211> LENGTH: 16
<212> TYPE: PRT
<213> ORGANISM: Homo sapiens

<400> SEQUENCE: 1725

Cys Ala Thr Ser Ser Pro Gly Thr Gly Gly Arg Asn Glu Gln Phe Phe
1               5                   10                  15

<210> SEQ ID NO 1726
<211> LENGTH: 11
<212> TYPE: PRT
<213> ORGANISM: Homo sapiens

<400> SEQUENCE: 1726

Cys Ala Ser Ser Arg Gly Asn Glu Gln Tyr Phe
1               5                   10

<210> SEQ ID NO 1727
<211> LENGTH: 14
<212> TYPE: PRT
<213> ORGANISM: Homo sapiens

<400> SEQUENCE: 1727

Cys Ala Ser Thr Pro Leu Gly Asp Tyr Asn Glu Gln Phe Phe
1               5                   10

<210> SEQ ID NO 1728
<211> LENGTH: 16
<212> TYPE: PRT
<213> ORGANISM: Homo sapiens

<400> SEQUENCE: 1728

Cys Ala Ser Ser Arg Asp Arg Val Gly Asn Thr Gly Glu Leu Phe Phe
1               5                   10                  15

<210> SEQ ID NO 1729
<211> LENGTH: 15
<212> TYPE: PRT
<213> ORGANISM: Homo sapiens

<400> SEQUENCE: 1729

Cys Ala Ser Ser Ala Asp Gly Thr Gly Gly Glu Lys Leu Phe Phe
1               5                   10                  15

<210> SEQ ID NO 1730
<211> LENGTH: 14
<212> TYPE: PRT
<213> ORGANISM: Homo sapiens

<400> SEQUENCE: 1730

Cys Ala Ser Ser Leu Lys Arg Val Gln Glu Thr Gln Tyr Phe
1               5                   10

<210> SEQ ID NO 1731
<211> LENGTH: 11
<212> TYPE: PRT
<213> ORGANISM: Homo sapiens

<400> SEQUENCE: 1731

Cys Ala Ser Thr Arg Gln Asp Thr Gln Tyr Phe
1               5                   10

<210> SEQ ID NO 1732
<211> LENGTH: 13
<212> TYPE: PRT
<213> ORGANISM: Homo sapiens

<400> SEQUENCE: 1732

Cys Ala Ser Ser Ala Gly Gln Trp Asp Glu Gln Tyr Phe
1               5                   10

<210> SEQ ID NO 1733
<211> LENGTH: 14
<212> TYPE: PRT
<213> ORGANISM: Homo sapiens

<400> SEQUENCE: 1733

Cys Ala Ser Ser His Pro Leu Arg Glu Glu Thr Gln Tyr Phe
1               5                   10

<210> SEQ ID NO 1734
<211> LENGTH: 14
<212> TYPE: PRT
<213> ORGANISM: Homo sapiens

<400> SEQUENCE: 1734

Cys Ala Ser Ser Gln Glu Ala Arg Ser Asp Thr Gln Tyr Phe
1               5                   10

<210> SEQ ID NO 1735
<211> LENGTH: 15
<212> TYPE: PRT
<213> ORGANISM: Homo sapiens

<400> SEQUENCE: 1735

Cys Ser Ala Arg Phe Gly Gly Ala Gly Thr Gly Glu Leu Phe Phe
1               5                   10                  15

<210> SEQ ID NO 1736
<211> LENGTH: 15
<212> TYPE: PRT
<213> ORGANISM: Homo sapiens

<400> SEQUENCE: 1736

Cys Ser Ala Arg Gly Gln Pro Val Asn Thr Gly Glu Leu Phe Phe
1               5                   10                  15

<210> SEQ ID NO 1737
<211> LENGTH: 15
<212> TYPE: PRT
<213> ORGANISM: Homo sapiens

<400> SEQUENCE: 1737

Cys Ala Ser Ser Leu Asp Ala Thr Phe Thr Asp Thr Gln Tyr Phe

```
1               5                  10                 15
```

<210> SEQ ID NO 1738
<211> LENGTH: 14
<212> TYPE: PRT
<213> ORGANISM: Homo sapiens

<400> SEQUENCE: 1738

```
Cys Ala Ser Ser Glu Gly Thr Gly Ser Ser Pro Leu His Phe
1               5                  10
```

<210> SEQ ID NO 1739
<211> LENGTH: 16
<212> TYPE: PRT
<213> ORGANISM: Homo sapiens

<400> SEQUENCE: 1739

```
Cys Ala Ser Ser Arg Gly Gln Pro Leu Ser Gly Asn Thr Ile Tyr Phe
1               5                  10                 15
```

<210> SEQ ID NO 1740
<211> LENGTH: 15
<212> TYPE: PRT
<213> ORGANISM: Homo sapiens

<400> SEQUENCE: 1740

```
Cys Ala Ser Ser Ile Gly Gly Thr Ser Thr Asp Thr Gln Tyr Phe
1               5                  10                 15
```

<210> SEQ ID NO 1741
<211> LENGTH: 15
<212> TYPE: PRT
<213> ORGANISM: Homo sapiens

<400> SEQUENCE: 1741

```
Cys Ala Ser Ser Asn Arg Arg Gly Arg Ser Tyr Gly Tyr Thr Phe
1               5                  10                 15
```

<210> SEQ ID NO 1742
<211> LENGTH: 14
<212> TYPE: PRT
<213> ORGANISM: Homo sapiens

<400> SEQUENCE: 1742

```
Cys Ala Ser Thr Leu Ala Gly Val Thr Tyr Glu Gln Tyr Phe
1               5                  10
```

<210> SEQ ID NO 1743
<211> LENGTH: 16
<212> TYPE: PRT
<213> ORGANISM: Homo sapiens

<400> SEQUENCE: 1743

```
Cys Ala Ser Ser Leu Gly Thr Gly Ala Gly Ala Asn Val Leu Thr Phe
1               5                  10                 15
```

<210> SEQ ID NO 1744
<211> LENGTH: 13
<212> TYPE: PRT
<213> ORGANISM: Homo sapiens

<400> SEQUENCE: 1744

```
Cys Ala Ser Arg Leu Arg Asp Ser Tyr Glu Gln Tyr Phe
1               5                  10
```

<210> SEQ ID NO 1745
<211> LENGTH: 14
<212> TYPE: PRT
<213> ORGANISM: Homo sapiens

<400> SEQUENCE: 1745

Cys Ala Trp Thr Pro Gly Gly Thr Tyr Gln Pro Gln His Phe
1               5                   10

<210> SEQ ID NO 1746
<211> LENGTH: 14
<212> TYPE: PRT
<213> ORGANISM: Homo sapiens

<400> SEQUENCE: 1746

Cys Ser Ala Ser Leu Gly Ala Gln Gly Tyr Gly Tyr Thr Phe
1               5                   10

<210> SEQ ID NO 1747
<211> LENGTH: 15
<212> TYPE: PRT
<213> ORGANISM: Homo sapiens

<400> SEQUENCE: 1747

Cys Ala Ser Lys Glu Asp Gly Ala Asn Thr Gly Glu Leu Phe Phe
1               5                   10                  15

<210> SEQ ID NO 1748
<211> LENGTH: 17
<212> TYPE: PRT
<213> ORGANISM: Homo sapiens

<400> SEQUENCE: 1748

Cys Ser Ala Arg Glu Gly Val Gly Ala Leu Ala Lys Asn Ile Gln Tyr
1               5                   10                  15

Phe

<210> SEQ ID NO 1749
<211> LENGTH: 13
<212> TYPE: PRT
<213> ORGANISM: Homo sapiens

<400> SEQUENCE: 1749

Cys Ala Ser Lys Glu Ala Gly Asp Asn Glu Gln Phe Phe
1               5                   10

<210> SEQ ID NO 1750
<211> LENGTH: 14
<212> TYPE: PRT
<213> ORGANISM: Homo sapiens

<400> SEQUENCE: 1750

Cys Ser Ala Arg Gly Thr Asp Tyr Gln Glu Thr Gln Tyr Phe
1               5                   10

<210> SEQ ID NO 1751
<211> LENGTH: 17
<212> TYPE: PRT
<213> ORGANISM: Homo sapiens

<400> SEQUENCE: 1751

Cys Ala Ser Ser Pro Leu Ala Gly Leu Glu Asn Thr Gly Glu Leu Phe
1               5                   10                  15

Phe

<210> SEQ ID NO 1752
<211> LENGTH: 15
<212> TYPE: PRT
<213> ORGANISM: Homo sapiens

<400> SEQUENCE: 1752

Cys Ala Ser Ser Glu Arg Glu Gly Val Asn Thr Glu Ala Phe Phe
1               5                   10                  15

<210> SEQ ID NO 1753
<211> LENGTH: 13
<212> TYPE: PRT
<213> ORGANISM: Homo sapiens

<400> SEQUENCE: 1753

Cys Ala Ser Ser Pro Ser Phe Ser Gly Glu Gln Tyr Phe
1               5                   10

<210> SEQ ID NO 1754
<211> LENGTH: 16
<212> TYPE: PRT
<213> ORGANISM: Homo sapiens

<400> SEQUENCE: 1754

Cys Ala Ser Ser Ser Glu Gly Arg Gly Leu Gly Asn Thr Ile Tyr Phe
1               5                   10                  15

<210> SEQ ID NO 1755
<211> LENGTH: 13
<212> TYPE: PRT
<213> ORGANISM: Homo sapiens

<400> SEQUENCE: 1755

Cys Ser Ala Pro Leu Val Pro Tyr Asn Glu Gln Phe Phe
1               5                   10

<210> SEQ ID NO 1756
<211> LENGTH: 13
<212> TYPE: PRT
<213> ORGANISM: Homo sapiens

<400> SEQUENCE: 1756

Cys Ala Ser Thr Ser Pro Gly Ala Asn Val Leu Thr Phe
1               5                   10

<210> SEQ ID NO 1757
<211> LENGTH: 12
<212> TYPE: PRT
<213> ORGANISM: Homo sapiens

<400> SEQUENCE: 1757

Cys Ala Ser Ser Ala Arg Ser Asp Thr Gln Tyr Phe
1               5                   10

<210> SEQ ID NO 1758
<211> LENGTH: 15
<212> TYPE: PRT
<213> ORGANISM: Homo sapiens

<400> SEQUENCE: 1758

Cys Ala Ser Ser Ser Gly Gly Gly Ala Pro Gly Glu Leu Phe Phe
1               5                   10                  15

<210> SEQ ID NO 1759
<211> LENGTH: 17
<212> TYPE: PRT
<213> ORGANISM: Homo sapiens

<400> SEQUENCE: 1759

Cys Ala Ser Ser Ser Pro Gly Ala Gly Ser Ser Tyr Asn Glu Gln Phe
1               5                   10                  15

Phe

<210> SEQ ID NO 1760
<211> LENGTH: 14
<212> TYPE: PRT
<213> ORGANISM: Homo sapiens

<400> SEQUENCE: 1760

Cys Ala Ser Thr Pro Gly Gln Asp Asn Ser Pro Leu His Phe
1               5                   10

<210> SEQ ID NO 1761
<211> LENGTH: 15
<212> TYPE: PRT
<213> ORGANISM: Homo sapiens

<400> SEQUENCE: 1761

Cys Ser Ala Gly Pro Gly Thr Gly Asn Thr Gly Glu Leu Phe Phe
1               5                   10                  15

<210> SEQ ID NO 1762
<211> LENGTH: 13
<212> TYPE: PRT
<213> ORGANISM: Homo sapiens

<400> SEQUENCE: 1762

Cys Ser Ala Arg Arg Val Pro Tyr Asn Glu Gln Phe Phe
1               5                   10

<210> SEQ ID NO 1763
<211> LENGTH: 15
<212> TYPE: PRT
<213> ORGANISM: Homo sapiens

<400> SEQUENCE: 1763

Cys Ala Ser Ser Ser Ala Arg Gly Val Trp Glu Thr Gln Tyr Phe
1               5                   10                  15

<210> SEQ ID NO 1764
<211> LENGTH: 12
<212> TYPE: PRT
<213> ORGANISM: Homo sapiens

<400> SEQUENCE: 1764

Cys Ala Ser Thr Pro Lys Ser Tyr Gly Tyr Thr Phe
1               5                   10

<210> SEQ ID NO 1765
<211> LENGTH: 15
<212> TYPE: PRT
<213> ORGANISM: Homo sapiens

<400> SEQUENCE: 1765

Cys Ala Ile Ser Gly Asp Gly Gly Ser Tyr Asn Glu Gln Phe Phe
1               5                   10                  15

<210> SEQ ID NO 1766
<211> LENGTH: 14
<212> TYPE: PRT
<213> ORGANISM: Homo sapiens

<400> SEQUENCE: 1766

Cys Ala Ser Ser Leu Lys Gly Asp Glu Asp Gly Tyr Thr Phe
1               5                   10

<210> SEQ ID NO 1767
<211> LENGTH: 16
<212> TYPE: PRT
<213> ORGANISM: Homo sapiens

<400> SEQUENCE: 1767

Cys Ala Ser Gly Gly Leu Ala Gly Gly Pro Lys Glu Thr Gln Tyr Phe
1               5                   10                  15

<210> SEQ ID NO 1768
<211> LENGTH: 15
<212> TYPE: PRT
<213> ORGANISM: Homo sapiens

<400> SEQUENCE: 1768

Cys Ala Ser Ser Pro Arg Thr Gly Gly Ser Gln Pro Gln His Phe
1               5                   10                  15

<210> SEQ ID NO 1769
<211> LENGTH: 16
<212> TYPE: PRT
<213> ORGANISM: Homo sapiens

<400> SEQUENCE: 1769

Cys Ala Ser Ser Phe Ser Gly Thr Gly Phe Asn Ser Pro Leu His Phe
1               5                   10                  15

<210> SEQ ID NO 1770
<211> LENGTH: 14
<212> TYPE: PRT
<213> ORGANISM: Homo sapiens

<400> SEQUENCE: 1770

Cys Ala Ser Arg Tyr Gly Thr Gly Asp Gln Pro Gln His Phe
1               5                   10

<210> SEQ ID NO 1771
<211> LENGTH: 15
<212> TYPE: PRT
<213> ORGANISM: Homo sapiens

<400> SEQUENCE: 1771

Cys Ala Ser Ser Ser Thr Leu Ser Leu Ser Tyr Glu Gln Tyr Phe
1               5                   10                  15

<210> SEQ ID NO 1772
<211> LENGTH: 15
<212> TYPE: PRT
<213> ORGANISM: Homo sapiens

<400> SEQUENCE: 1772

Cys Ala Ser Ser Val Val Met Gly Arg Thr Asp Thr Gln Tyr Phe
1               5                   10                  15

<210> SEQ ID NO 1773

<211> LENGTH: 15
<212> TYPE: PRT
<213> ORGANISM: Homo sapiens

<400> SEQUENCE: 1773

Cys Ser Ala Arg Pro Ala Gly Ala Gly Thr Gly Glu Leu Phe Phe
1               5                   10                  15

<210> SEQ ID NO 1774
<211> LENGTH: 11
<212> TYPE: PRT
<213> ORGANISM: Homo sapiens

<400> SEQUENCE: 1774

Cys Ser Val Gly Gly Leu Arg Glu Gln Tyr Phe
1               5                   10

<210> SEQ ID NO 1775
<211> LENGTH: 14
<212> TYPE: PRT
<213> ORGANISM: Homo sapiens

<400> SEQUENCE: 1775

Cys Ala Ser Ser Leu Pro Glu Ser Ser Tyr Glu Gln Tyr Phe
1               5                   10

<210> SEQ ID NO 1776
<211> LENGTH: 13
<212> TYPE: PRT
<213> ORGANISM: Homo sapiens

<400> SEQUENCE: 1776

Cys Ser Ala Lys Trp Glu Gly Thr Asp Thr Gln Tyr Phe
1               5                   10

<210> SEQ ID NO 1777
<211> LENGTH: 13
<212> TYPE: PRT
<213> ORGANISM: Homo sapiens

<400> SEQUENCE: 1777

Cys Ala Ser Ser Gly Ala Phe Asn Ser Pro Leu His Phe
1               5                   10

<210> SEQ ID NO 1778
<211> LENGTH: 14
<212> TYPE: PRT
<213> ORGANISM: Homo sapiens

<400> SEQUENCE: 1778

Cys Ala Ser Ile Glu Ala Gly Phe Thr Asp Thr Gln Tyr Phe
1               5                   10

<210> SEQ ID NO 1779
<211> LENGTH: 16
<212> TYPE: PRT
<213> ORGANISM: Homo sapiens

<400> SEQUENCE: 1779

Cys Ala Ser Ser Lys Gly Gln Ala Tyr Ser Gly Asn Thr Ile Tyr Phe
1               5                   10                  15

<210> SEQ ID NO 1780
<211> LENGTH: 14
<212> TYPE: PRT

<213> ORGANISM: Homo sapiens

<400> SEQUENCE: 1780

Cys Ala Ser Ser Val Glu Gly Ser Ser Tyr Glu Gln Tyr Phe
1               5                   10

<210> SEQ ID NO 1781
<211> LENGTH: 13
<212> TYPE: PRT
<213> ORGANISM: Homo sapiens

<400> SEQUENCE: 1781

Cys Ser Ala Pro Ser Pro Pro Tyr Asn Glu Gln Phe Phe
1               5                   10

<210> SEQ ID NO 1782
<211> LENGTH: 15
<212> TYPE: PRT
<213> ORGANISM: Homo sapiens

<400> SEQUENCE: 1782

Cys Ser Ala Arg Leu Ala Gly Ser Gly Thr Gly Glu Leu Phe Phe
1               5                   10                  15

<210> SEQ ID NO 1783
<211> LENGTH: 13
<212> TYPE: PRT
<213> ORGANISM: Homo sapiens

<400> SEQUENCE: 1783

Cys Ser Ala Arg Ser Glu Gly Pro Asp Thr Gln Tyr Phe
1               5                   10

<210> SEQ ID NO 1784
<211> LENGTH: 12
<212> TYPE: PRT
<213> ORGANISM: Homo sapiens

<400> SEQUENCE: 1784

Cys Ser Gly Val Arg Gly Gly Asn Glu Gln Phe Phe
1               5                   10

<210> SEQ ID NO 1785
<211> LENGTH: 12
<212> TYPE: PRT
<213> ORGANISM: Homo sapiens

<400> SEQUENCE: 1785

Cys Ser Ala Ser Gln Val Glu Asp Thr Gln Tyr Phe
1               5                   10

<210> SEQ ID NO 1786
<211> LENGTH: 13
<212> TYPE: PRT
<213> ORGANISM: Homo sapiens

<400> SEQUENCE: 1786

Cys Ala Ser Ser Ser Glu Ser Ala Asp Thr Gln Tyr Phe
1               5                   10

<210> SEQ ID NO 1787
<211> LENGTH: 16
<212> TYPE: PRT
<213> ORGANISM: Homo sapiens

<400> SEQUENCE: 1787

Cys Ala Ser Ser Phe Gly Leu Ala Gly Asp Pro Gly Glu Leu Phe Phe
1               5                   10                  15

<210> SEQ ID NO 1788
<211> LENGTH: 12
<212> TYPE: PRT
<213> ORGANISM: Homo sapiens

<400> SEQUENCE: 1788

Cys Ala Ser Ser Leu Gly Asp Val Gly Tyr Thr Phe
1               5                   10

<210> SEQ ID NO 1789
<211> LENGTH: 15
<212> TYPE: PRT
<213> ORGANISM: Homo sapiens

<400> SEQUENCE: 1789

Cys Ala Ser Ser Pro Thr Gly Thr Glu Asn Thr Glu Ala Phe Phe
1               5                   10                  15

<210> SEQ ID NO 1790
<211> LENGTH: 12
<212> TYPE: PRT
<213> ORGANISM: Homo sapiens

<400> SEQUENCE: 1790

Cys Ala Ser Thr Leu Pro Ser Tyr Glu Gln Tyr Phe
1               5                   10

<210> SEQ ID NO 1791
<211> LENGTH: 16
<212> TYPE: PRT
<213> ORGANISM: Homo sapiens

<400> SEQUENCE: 1791

Cys Ala Ser Ser Pro Arg Gly Arg Ser Tyr Asn Glu Gln Phe Phe
1               5                   10                  15

<210> SEQ ID NO 1792
<211> LENGTH: 15
<212> TYPE: PRT
<213> ORGANISM: Homo sapiens

<400> SEQUENCE: 1792

Cys Ala Thr Ser Arg Ser Thr Gly Asp Asn Gln Pro Gln His Phe
1               5                   10                  15

<210> SEQ ID NO 1793
<211> LENGTH: 16
<212> TYPE: PRT
<213> ORGANISM: Homo sapiens

<400> SEQUENCE: 1793

Cys Ala Ser Ser Leu Leu Trp Thr Gly Ser Thr Asp Thr Gln Tyr Phe
1               5                   10                  15

<210> SEQ ID NO 1794
<211> LENGTH: 16
<212> TYPE: PRT
<213> ORGANISM: Homo sapiens

<400> SEQUENCE: 1794

Cys Ala Ser Ser Leu Val Pro Thr Gly Phe Asn Ser Pro Leu His Phe
1               5                   10                  15

<210> SEQ ID NO 1795
<211> LENGTH: 13
<212> TYPE: PRT
<213> ORGANISM: Homo sapiens

<400> SEQUENCE: 1795

Cys Ala Thr Val Gly Gln Gly Asn Ser Pro Leu His Phe
1               5                   10

<210> SEQ ID NO 1796
<211> LENGTH: 15
<212> TYPE: PRT
<213> ORGANISM: Homo sapiens

<400> SEQUENCE: 1796

Cys Ser Ala Ser Pro Gly Thr Gly Ser Thr Asp Thr Gln Tyr Phe
1               5                   10                  15

<210> SEQ ID NO 1797
<211> LENGTH: 15
<212> TYPE: PRT
<213> ORGANISM: Homo sapiens

<400> SEQUENCE: 1797

Cys Ala Ser Ser Leu Ala Pro Ser Ile Thr Asp Thr Gln Tyr Phe
1               5                   10                  15

<210> SEQ ID NO 1798
<211> LENGTH: 12
<212> TYPE: PRT
<213> ORGANISM: Homo sapiens

<400> SEQUENCE: 1798

Cys Ser Ala Lys Pro Gly Pro Arg Glu Gln Tyr Phe
1               5                   10

<210> SEQ ID NO 1799
<211> LENGTH: 13
<212> TYPE: PRT
<213> ORGANISM: Homo sapiens

<400> SEQUENCE: 1799

Cys Ser Ala Arg Val Pro Pro Tyr Asn Glu Gln Phe Phe
1               5                   10

<210> SEQ ID NO 1800
<211> LENGTH: 15
<212> TYPE: PRT
<213> ORGANISM: Homo sapiens

<400> SEQUENCE: 1800

Cys Ala Ser Ser His Leu Leu Gly Gly Ala Asp Thr Gln Tyr Phe
1               5                   10                  15

<210> SEQ ID NO 1801
<211> LENGTH: 15
<212> TYPE: PRT
<213> ORGANISM: Homo sapiens

<400> SEQUENCE: 1801

Cys Ala Ser Ser Leu Glu Ala Asn Tyr Asn Gln Pro Gln His Phe
1               5                   10                  15

```
<210> SEQ ID NO 1802
<211> LENGTH: 14
<212> TYPE: PRT
<213> ORGANISM: Homo sapiens

<400> SEQUENCE: 1802

Cys Ala Ser Ser Tyr Leu His Met Ser Tyr Glu Gln Tyr Phe
1               5                   10

<210> SEQ ID NO 1803
<211> LENGTH: 14
<212> TYPE: PRT
<213> ORGANISM: Homo sapiens

<400> SEQUENCE: 1803

Cys Ala Ser Ser Gln Val His Phe His Asn Glu Gln Phe Phe
1               5                   10

<210> SEQ ID NO 1804
<211> LENGTH: 14
<212> TYPE: PRT
<213> ORGANISM: Homo sapiens

<400> SEQUENCE: 1804

Cys Ala Ser Ser Ser Pro Gly Gln Gly Ser Glu Gln Phe Phe
1               5                   10

<210> SEQ ID NO 1805
<211> LENGTH: 16
<212> TYPE: PRT
<213> ORGANISM: Homo sapiens

<400> SEQUENCE: 1805

Cys Ala Ser Ser Pro Gln Gln Ser Leu Ser Gly Asn Thr Ile Tyr Phe
1               5                   10                  15

<210> SEQ ID NO 1806
<211> LENGTH: 15
<212> TYPE: PRT
<213> ORGANISM: Homo sapiens

<400> SEQUENCE: 1806

Cys Ala Ser Arg Ser Ser Gly Gly Ala Val Asn Glu Gln Phe Phe
1               5                   10                  15

<210> SEQ ID NO 1807
<211> LENGTH: 15
<212> TYPE: PRT
<213> ORGANISM: Homo sapiens

<400> SEQUENCE: 1807

Cys Ala Ser Ser Gly Gln Gly Gly Arg Asn Gln Pro Gln His Phe
1               5                   10                  15

<210> SEQ ID NO 1808
<211> LENGTH: 13
<212> TYPE: PRT
<213> ORGANISM: Homo sapiens

<400> SEQUENCE: 1808

Cys Ala Ser Ser Leu Asp Gly Leu Tyr Glu Gln Tyr Phe
1               5                   10
```

```
<210> SEQ ID NO 1809
<211> LENGTH: 14
<212> TYPE: PRT
<213> ORGANISM: Homo sapiens

<400> SEQUENCE: 1809

Cys Ala Ser Ser Tyr Leu Gly Leu Ser Tyr Glu Gln Tyr Phe
1               5                   10

<210> SEQ ID NO 1810
<211> LENGTH: 15
<212> TYPE: PRT
<213> ORGANISM: Homo sapiens

<400> SEQUENCE: 1810

Cys Ala Ser Ser Leu Gly Arg Ala Gly Arg Asp Glu Gln Tyr Phe
1               5                   10                  15

<210> SEQ ID NO 1811
<211> LENGTH: 13
<212> TYPE: PRT
<213> ORGANISM: Homo sapiens

<400> SEQUENCE: 1811

Cys Ser Ala Pro Leu Ala Leu Asn Thr Glu Ala Phe Phe
1               5                   10

<210> SEQ ID NO 1812
<211> LENGTH: 13
<212> TYPE: PRT
<213> ORGANISM: Homo sapiens

<400> SEQUENCE: 1812

Cys Ala Trp Thr Leu Gln Gly Ala Asn Gly Tyr Thr Phe
1               5                   10

<210> SEQ ID NO 1813
<211> LENGTH: 15
<212> TYPE: PRT
<213> ORGANISM: Homo sapiens

<400> SEQUENCE: 1813

Cys Ser Ala Arg Ala Gly Gly Leu Ser Asn Glu Lys Leu Phe Phe
1               5                   10                  15

<210> SEQ ID NO 1814
<211> LENGTH: 14
<212> TYPE: PRT
<213> ORGANISM: Homo sapiens

<400> SEQUENCE: 1814

Cys Ala Ser Lys Gly Gly Thr Phe Thr Asp Thr Gln Tyr Phe
1               5                   10

<210> SEQ ID NO 1815
<211> LENGTH: 11
<212> TYPE: PRT
<213> ORGANISM: Homo sapiens

<400> SEQUENCE: 1815

Cys Ser Met Gly Leu Gln Glu Thr Gln Tyr Phe
1               5                   10

<210> SEQ ID NO 1816
<211> LENGTH: 14
```

<212> TYPE: PRT
<213> ORGANISM: Homo sapiens

<400> SEQUENCE: 1816

Cys Ala Ser Ser Arg Thr Gly Asn Pro Glu Gln Tyr Phe
1               5                   10

<210> SEQ ID NO 1817
<211> LENGTH: 15
<212> TYPE: PRT
<213> ORGANISM: Homo sapiens

<400> SEQUENCE: 1817

Cys Ser Ala Arg Glu Gly Gly Ser Gly Thr Gly Glu Leu Phe Phe
1               5                   10                  15

<210> SEQ ID NO 1818
<211> LENGTH: 16
<212> TYPE: PRT
<213> ORGANISM: Homo sapiens

<400> SEQUENCE: 1818

Cys Ala Ser Ser Leu Val Gly Asp Arg Val Arg Glu Thr Gln Tyr Phe
1               5                   10                  15

<210> SEQ ID NO 1819
<211> LENGTH: 13
<212> TYPE: PRT
<213> ORGANISM: Homo sapiens

<400> SEQUENCE: 1819

Cys Ala Ser Ser Tyr Arg Val Gln Ser Pro Leu His Phe
1               5                   10

<210> SEQ ID NO 1820
<211> LENGTH: 14
<212> TYPE: PRT
<213> ORGANISM: Homo sapiens

<400> SEQUENCE: 1820

Cys Ala Thr Ser Asp Val Gly Ser Asn Glu Lys Leu Phe Phe
1               5                   10

<210> SEQ ID NO 1821
<211> LENGTH: 15
<212> TYPE: PRT
<213> ORGANISM: Homo sapiens

<400> SEQUENCE: 1821

Cys Ser Ala Arg Ser Ala Gly Ala Gly Thr Gly Glu Leu Phe Phe
1               5                   10                  15

<210> SEQ ID NO 1822
<211> LENGTH: 15
<212> TYPE: PRT
<213> ORGANISM: Homo sapiens

<400> SEQUENCE: 1822

Cys Ala Ser Ser Gln Gly Val Ser Val Thr Gly Glu Leu Phe Phe
1               5                   10                  15

<210> SEQ ID NO 1823
<211> LENGTH: 15
<212> TYPE: PRT
<213> ORGANISM: Homo sapiens

<400> SEQUENCE: 1823

Cys Ser Val Glu Glu Pro Pro Gly Val Gly Thr Glu Ala Phe Phe
1               5                   10                  15

<210> SEQ ID NO 1824
<211> LENGTH: 13
<212> TYPE: PRT
<213> ORGANISM: Homo sapiens

<400> SEQUENCE: 1824

Cys Ala Ser Ser Pro Ser Arg Ala Tyr Gly Tyr Thr Phe
1               5                   10

<210> SEQ ID NO 1825
<211> LENGTH: 15
<212> TYPE: PRT
<213> ORGANISM: Homo sapiens

<400> SEQUENCE: 1825

Cys Ala Ser Ser Val Arg Leu Ala Glu Tyr Asn Glu Gln Phe Phe
1               5                   10                  15

<210> SEQ ID NO 1826
<211> LENGTH: 15
<212> TYPE: PRT
<213> ORGANISM: Homo sapiens

<400> SEQUENCE: 1826

Cys Ser Ala Arg Lys Gly Gly Gly Thr Gly Glu Leu Phe Phe
1               5                   10                  15

<210> SEQ ID NO 1827
<211> LENGTH: 15
<212> TYPE: PRT
<213> ORGANISM: Homo sapiens

<400> SEQUENCE: 1827

Cys Ala Ser Ser Pro Arg Glu Gly Arg Glu Asp Thr Gln Tyr Phe
1               5                   10                  15

<210> SEQ ID NO 1828
<211> LENGTH: 15
<212> TYPE: PRT
<213> ORGANISM: Homo sapiens

<400> SEQUENCE: 1828

Cys Ala Ser Ser Thr Pro Arg Arg Gly Gln Glu Thr Gln Tyr Phe
1               5                   10                  15

<210> SEQ ID NO 1829
<211> LENGTH: 14
<212> TYPE: PRT
<213> ORGANISM: Homo sapiens

<400> SEQUENCE: 1829

Cys Ala Ser Ser Leu Ala Pro Ala Asn Thr Glu Ala Phe Phe
1               5                   10

<210> SEQ ID NO 1830
<211> LENGTH: 14
<212> TYPE: PRT
<213> ORGANISM: Homo sapiens

<400> SEQUENCE: 1830

```
Cys Ser Ala Arg Val Ala Arg Gly Arg Asp Thr Gln Tyr Phe
1               5                   10

<210> SEQ ID NO 1831
<211> LENGTH: 13
<212> TYPE: PRT
<213> ORGANISM: Homo sapiens

<400> SEQUENCE: 1831

Cys Ala Ser Ser Leu Thr Ser Ala Gly Glu Leu Phe Phe
1               5                   10

<210> SEQ ID NO 1832
<211> LENGTH: 16
<212> TYPE: PRT
<213> ORGANISM: Homo sapiens

<400> SEQUENCE: 1832

Cys Ala Ser Ser Leu Trp Gln Gly Ala Gly Ala Asn Val Leu Thr Phe
1               5                   10                  15

<210> SEQ ID NO 1833
<211> LENGTH: 15
<212> TYPE: PRT
<213> ORGANISM: Homo sapiens

<400> SEQUENCE: 1833

Cys Ala Ser Ser Tyr Gln His Ser Ser Thr Asp Thr Gln Tyr Phe
1               5                   10                  15

<210> SEQ ID NO 1834
<211> LENGTH: 15
<212> TYPE: PRT
<213> ORGANISM: Homo sapiens

<400> SEQUENCE: 1834

Cys Ala Ser Ser Trp Glu Ala Asn Tyr Asn Ser Pro Leu His Phe
1               5                   10                  15

<210> SEQ ID NO 1835
<211> LENGTH: 15
<212> TYPE: PRT
<213> ORGANISM: Homo sapiens

<400> SEQUENCE: 1835

Cys Ala Ser Ser Tyr Thr Pro Gly Gly Arg Asn Glu Gln Phe Phe
1               5                   10                  15

<210> SEQ ID NO 1836
<211> LENGTH: 16
<212> TYPE: PRT
<213> ORGANISM: Homo sapiens

<400> SEQUENCE: 1836

Cys Ala Ser Ser Pro Pro Asn Arg Gln Gly Gly Tyr Glu Gln Tyr Phe
1               5                   10                  15

<210> SEQ ID NO 1837
<211> LENGTH: 15
<212> TYPE: PRT
<213> ORGANISM: Homo sapiens

<400> SEQUENCE: 1837

Cys Ala Ser Ser Leu Gly Val Gly Thr Tyr Asn Glu Gln Phe Phe
```

-continued

```
1               5                   10                  15

<210> SEQ ID NO 1838
<211> LENGTH: 14
<212> TYPE: PRT
<213> ORGANISM: Homo sapiens

<400> SEQUENCE: 1838

Cys Ala Ser Ser Leu Ala Pro Gly Ala Asn Val Leu Thr Phe
1               5                   10

<210> SEQ ID NO 1839
<211> LENGTH: 14
<212> TYPE: PRT
<213> ORGANISM: Homo sapiens

<400> SEQUENCE: 1839

Cys Ala Ser Ser Leu Gly Ala Thr Asn Glu Lys Leu Phe Phe
1               5                   10

<210> SEQ ID NO 1840
<211> LENGTH: 14
<212> TYPE: PRT
<213> ORGANISM: Homo sapiens

<400> SEQUENCE: 1840

Cys Ala Ser Ser Leu Gly Ala Val Asn Thr Glu Ala Phe Phe
1               5                   10

<210> SEQ ID NO 1841
<211> LENGTH: 15
<212> TYPE: PRT
<213> ORGANISM: Homo sapiens

<400> SEQUENCE: 1841

Cys Ala Ser Ser Val Val Thr Gly Arg Thr Asp Thr Gln Tyr Phe
1               5                   10                  15

<210> SEQ ID NO 1842
<211> LENGTH: 14
<212> TYPE: PRT
<213> ORGANISM: Homo sapiens

<400> SEQUENCE: 1842

Cys Ala Ser Arg Met Asp Arg Gly Thr Asp Thr Gln Tyr Phe
1               5                   10

<210> SEQ ID NO 1843
<211> LENGTH: 12
<212> TYPE: PRT
<213> ORGANISM: Homo sapiens

<400> SEQUENCE: 1843

Cys Ser Ala Lys Gly Ala Arg Glu Thr Gln Tyr Phe
1               5                   10

<210> SEQ ID NO 1844
<211> LENGTH: 14
<212> TYPE: PRT
<213> ORGANISM: Homo sapiens

<400> SEQUENCE: 1844

Cys Ala Ser Ser Phe Arg Arg Gly Thr Asp Thr Gln Tyr Phe
1               5                   10
```

<210> SEQ ID NO 1845
<211> LENGTH: 14
<212> TYPE: PRT
<213> ORGANISM: Homo sapiens

<400> SEQUENCE: 1845

Cys Ala Ser Ser Phe Gly Gly Phe Gly Asn Thr Ile Tyr Phe
1               5                   10

<210> SEQ ID NO 1846
<211> LENGTH: 10
<212> TYPE: PRT
<213> ORGANISM: Homo sapiens

<400> SEQUENCE: 1846

Cys Ala Ser Ser Thr Asp Thr Gln Tyr Phe
1               5                   10

<210> SEQ ID NO 1847
<211> LENGTH: 12
<212> TYPE: PRT
<213> ORGANISM: Homo sapiens

<400> SEQUENCE: 1847

Cys Ala Ser Ser Leu Glu Gly Asn Ile Gln Tyr Phe
1               5                   10

<210> SEQ ID NO 1848
<211> LENGTH: 13
<212> TYPE: PRT
<213> ORGANISM: Homo sapiens

<400> SEQUENCE: 1848

Cys Ser Ala Thr Val Asp Pro Asn Gln Pro Gln His Phe
1               5                   10

<210> SEQ ID NO 1849
<211> LENGTH: 13
<212> TYPE: PRT
<213> ORGANISM: Homo sapiens

<400> SEQUENCE: 1849

Cys Ala Thr Gly Arg Gly Leu Gly Glu Thr Gln Tyr Phe
1               5                   10

<210> SEQ ID NO 1850
<211> LENGTH: 14
<212> TYPE: PRT
<213> ORGANISM: Homo sapiens

<400> SEQUENCE: 1850

Cys Ala Ser Ser Leu Gly Ala Ser Tyr Thr Glu Ala Phe Phe
1               5                   10

<210> SEQ ID NO 1851
<211> LENGTH: 16
<212> TYPE: PRT
<213> ORGANISM: Homo sapiens

<400> SEQUENCE: 1851

Cys Ala Ser Ser Arg Pro Pro Gly Ala Thr Asn Glu Lys Leu Phe Phe
1               5                   10                  15

<210> SEQ ID NO 1852

```
<211> LENGTH: 13
<212> TYPE: PRT
<213> ORGANISM: Homo sapiens

<400> SEQUENCE: 1852

Cys Ser Val Asp Ser Gly Gly Ala Arg Glu Gln Phe Phe
1               5                   10

<210> SEQ ID NO 1853
<211> LENGTH: 13
<212> TYPE: PRT
<213> ORGANISM: Homo sapiens

<400> SEQUENCE: 1853

Cys Ala Ser Ser Pro Asn Glu Leu Asp Thr Gln Tyr Phe
1               5                   10

<210> SEQ ID NO 1854
<211> LENGTH: 13
<212> TYPE: PRT
<213> ORGANISM: Homo sapiens

<400> SEQUENCE: 1854

Cys Ala Ser Ser Glu Ser Ala Gly Ala Glu Gln Phe Phe
1               5                   10

<210> SEQ ID NO 1855
<211> LENGTH: 16
<212> TYPE: PRT
<213> ORGANISM: Homo sapiens

<400> SEQUENCE: 1855

Cys Ala Ser Ser Leu Ser Pro Gly Ser Gly Thr Gly Glu Leu Phe Phe
1               5                   10                  15

<210> SEQ ID NO 1856
<211> LENGTH: 14
<212> TYPE: PRT
<213> ORGANISM: Homo sapiens

<400> SEQUENCE: 1856

Cys Ala Ser Ser Tyr Ser Ser Gln Gly Ala Gly Tyr Thr Phe
1               5                   10

<210> SEQ ID NO 1857
<211> LENGTH: 15
<212> TYPE: PRT
<213> ORGANISM: Homo sapiens

<400> SEQUENCE: 1857

Cys Ala Ser Ser Leu Ala Gly Gln Leu Asn Glu Lys Leu Phe Phe
1               5                   10                  15

<210> SEQ ID NO 1858
<211> LENGTH: 13
<212> TYPE: PRT
<213> ORGANISM: Homo sapiens

<400> SEQUENCE: 1858

Cys Ala Ser Ser Leu Arg Gly Ile Tyr Gly Tyr Thr Phe
1               5                   10

<210> SEQ ID NO 1859
<211> LENGTH: 14
<212> TYPE: PRT
```

-continued

```
<213> ORGANISM: Homo sapiens

<400> SEQUENCE: 1859

Cys Ser Ala Arg Pro Leu Glu Thr Thr Asp Thr Gln Tyr Phe
1               5                   10

<210> SEQ ID NO 1860
<211> LENGTH: 14
<212> TYPE: PRT
<213> ORGANISM: Homo sapiens

<400> SEQUENCE: 1860

Cys Ala Ser Ser Glu Val Trp Gly Gly Tyr Gly Tyr Thr Phe
1               5                   10

<210> SEQ ID NO 1861
<211> LENGTH: 14
<212> TYPE: PRT
<213> ORGANISM: Homo sapiens

<400> SEQUENCE: 1861

Cys Ala Ser Thr Thr Gly Val Gly Ala Asn Val Leu Thr Phe
1               5                   10

<210> SEQ ID NO 1862
<211> LENGTH: 13
<212> TYPE: PRT
<213> ORGANISM: Homo sapiens

<400> SEQUENCE: 1862

Cys Ser Val Gly Gly Thr Arg Ala Tyr Glu Gln Tyr Phe
1               5                   10

<210> SEQ ID NO 1863
<211> LENGTH: 13
<212> TYPE: PRT
<213> ORGANISM: Homo sapiens

<400> SEQUENCE: 1863

Cys Ser Ala Arg Gln Thr Gly Ile Thr Glu Ala Phe Phe
1               5                   10

<210> SEQ ID NO 1864
<211> LENGTH: 14
<212> TYPE: PRT
<213> ORGANISM: Homo sapiens

<400> SEQUENCE: 1864

Cys Ala Ser Ser Leu Ala Asp Pro Thr Asp Thr Gln Tyr Phe
1               5                   10

<210> SEQ ID NO 1865
<211> LENGTH: 15
<212> TYPE: PRT
<213> ORGANISM: Homo sapiens

<400> SEQUENCE: 1865

Cys Ala Ser Ser Leu Val Gly Arg Pro Gly Glu Thr Gln Tyr Phe
1               5                   10                  15

<210> SEQ ID NO 1866
<211> LENGTH: 16
<212> TYPE: PRT
<213> ORGANISM: Homo sapiens
```

```
<400> SEQUENCE: 1866

Cys Ala Ser Ser Phe Leu Ala Gly Gly Tyr Gln Glu Thr Gln Tyr Phe
1               5                   10                  15

<210> SEQ ID NO 1867
<211> LENGTH: 13
<212> TYPE: PRT
<213> ORGANISM: Homo sapiens

<400> SEQUENCE: 1867

Cys Ala Ser Ser Arg Ile Arg Asp Glu Lys Leu Phe Phe
1               5                   10

<210> SEQ ID NO 1868
<211> LENGTH: 17
<212> TYPE: PRT
<213> ORGANISM: Homo sapiens

<400> SEQUENCE: 1868

Cys Ala Ile Ser Glu Pro Gly Leu Ala Gly Gly Arg Asp Thr Gln Tyr
1               5                   10                  15

Phe

<210> SEQ ID NO 1869
<211> LENGTH: 14
<212> TYPE: PRT
<213> ORGANISM: Homo sapiens

<400> SEQUENCE: 1869

Cys Ala Ser Ser Val Thr Gly Ala Glu Thr Glu Ala Phe Phe
1               5                   10

<210> SEQ ID NO 1870
<211> LENGTH: 13
<212> TYPE: PRT
<213> ORGANISM: Homo sapiens

<400> SEQUENCE: 1870

Cys Ala Ser Ser Leu Gly His Pro Thr Glu Ala Phe Phe
1               5                   10

<210> SEQ ID NO 1871
<211> LENGTH: 14
<212> TYPE: PRT
<213> ORGANISM: Homo sapiens

<400> SEQUENCE: 1871

Cys Ala Ser Ser Leu Val Pro Gly Ser Asn Glu Gln Tyr Phe
1               5                   10

<210> SEQ ID NO 1872
<211> LENGTH: 14
<212> TYPE: PRT
<213> ORGANISM: Homo sapiens

<400> SEQUENCE: 1872

Cys Ala Ser Ser Leu Ser Gly Ser Arg Gly Glu Ala Phe Phe
1               5                   10

<210> SEQ ID NO 1873
<211> LENGTH: 14
<212> TYPE: PRT
<213> ORGANISM: Homo sapiens
```

```
<400> SEQUENCE: 1873

Cys Ala Ser Ser Pro Gly Ser Arg Asn Glu Gln Tyr Phe
1               5                   10

<210> SEQ ID NO 1874
<211> LENGTH: 12
<212> TYPE: PRT
<213> ORGANISM: Homo sapiens

<400> SEQUENCE: 1874

Cys Ala Ser Arg Gln Gly Leu Arg Pro Gln His Phe
1               5                   10

<210> SEQ ID NO 1875
<211> LENGTH: 16
<212> TYPE: PRT
<213> ORGANISM: Homo sapiens

<400> SEQUENCE: 1875

Cys Ala Ser Ser Pro Arg Gln Gly Leu Thr Tyr Asn Glu Gln Phe Phe
1               5                   10                  15

<210> SEQ ID NO 1876
<211> LENGTH: 15
<212> TYPE: PRT
<213> ORGANISM: Homo sapiens

<400> SEQUENCE: 1876

Cys Ala Ser Ser Leu Gly Gln Ala Leu Asn Glu Lys Leu Phe Phe
1               5                   10                  15

<210> SEQ ID NO 1877
<211> LENGTH: 15
<212> TYPE: PRT
<213> ORGANISM: Homo sapiens

<400> SEQUENCE: 1877

Cys Ala Ser Ser Leu Arg Thr Trp Asp Thr Gly Glu Leu Phe Phe
1               5                   10                  15

<210> SEQ ID NO 1878
<211> LENGTH: 13
<212> TYPE: PRT
<213> ORGANISM: Homo sapiens

<400> SEQUENCE: 1878

Cys Ala Ser Ser Phe Val Glu Asp Gln Pro Gln His Phe
1               5                   10

<210> SEQ ID NO 1879
<211> LENGTH: 14
<212> TYPE: PRT
<213> ORGANISM: Homo sapiens

<400> SEQUENCE: 1879

Cys Ser Val Glu Thr Gly Gln Gly Ala Asp Thr Gln Tyr Phe
1               5                   10

<210> SEQ ID NO 1880
<211> LENGTH: 15
<212> TYPE: PRT
<213> ORGANISM: Homo sapiens

<400> SEQUENCE: 1880
```

Cys Ala Thr Ser Arg Gly Thr Arg Asp Thr Gly Glu Leu Phe Phe
1               5                   10                  15

<210> SEQ ID NO 1881
<211> LENGTH: 12
<212> TYPE: PRT
<213> ORGANISM: Homo sapiens

<400> SEQUENCE: 1881

Cys Ala Ser Ser Leu Asp Val Ser Pro Leu His Phe
1               5                   10

<210> SEQ ID NO 1882
<211> LENGTH: 15
<212> TYPE: PRT
<213> ORGANISM: Homo sapiens

<400> SEQUENCE: 1882

Cys Ala Ser Ser Leu Ala Gly Gln Gly Val Ser Glu Ala Phe Phe
1               5                   10                  15

<210> SEQ ID NO 1883
<211> LENGTH: 12
<212> TYPE: PRT
<213> ORGANISM: Homo sapiens

<400> SEQUENCE: 1883

Cys Ala Ser Arg Gly Pro Glu Ser Pro Leu His Phe
1               5                   10

<210> SEQ ID NO 1884
<211> LENGTH: 12
<212> TYPE: PRT
<213> ORGANISM: Homo sapiens

<400> SEQUENCE: 1884

Cys Ala Trp Ala Phe Tyr Asn Ser Pro Leu His Phe
1               5                   10

<210> SEQ ID NO 1885
<211> LENGTH: 14
<212> TYPE: PRT
<213> ORGANISM: Homo sapiens

<400> SEQUENCE: 1885

Cys Ala Ser Arg Asp Thr Gly Gly Asp Tyr Gly Tyr Thr Phe
1               5                   10

<210> SEQ ID NO 1886
<211> LENGTH: 14
<212> TYPE: PRT
<213> ORGANISM: Homo sapiens

<400> SEQUENCE: 1886

Cys Ala Ser Ser Leu Val Gly Gly Thr Gly Glu Gln Phe Phe
1               5                   10

<210> SEQ ID NO 1887
<211> LENGTH: 13
<212> TYPE: PRT
<213> ORGANISM: Homo sapiens

<400> SEQUENCE: 1887

Cys Ala Thr Lys Arg Glu Gly Ser Tyr Glu Gln Tyr Phe
1               5                   10

<210> SEQ ID NO 1888
<211> LENGTH: 12
<212> TYPE: PRT
<213> ORGANISM: Homo sapiens

<400> SEQUENCE: 1888

Cys Ala Ser Trp Asp Gly Phe Tyr Glu Gln Tyr Phe
1               5                   10

<210> SEQ ID NO 1889
<211> LENGTH: 14
<212> TYPE: PRT
<213> ORGANISM: Homo sapiens

<400> SEQUENCE: 1889

Cys Ala Ser Gly Phe Pro Gly Pro Thr Asp Thr Gln Tyr Phe
1               5                   10

<210> SEQ ID NO 1890
<211> LENGTH: 12
<212> TYPE: PRT
<213> ORGANISM: Homo sapiens

<400> SEQUENCE: 1890

Cys Arg Val Gly Gly Ser Asn Gln Pro Gln His Phe
1               5                   10

<210> SEQ ID NO 1891
<211> LENGTH: 13
<212> TYPE: PRT
<213> ORGANISM: Homo sapiens

<400> SEQUENCE: 1891

Cys Ala Ser Ser Leu Val Pro Asp Glu Lys Leu Phe Phe
1               5                   10

<210> SEQ ID NO 1892
<211> LENGTH: 17
<212> TYPE: PRT
<213> ORGANISM: Homo sapiens

<400> SEQUENCE: 1892

Cys Ala Ser Ser Val Gly Arg Ala Gly Gly Arg Thr Asp Thr Gln Tyr
1               5                   10                  15

Phe

<210> SEQ ID NO 1893
<211> LENGTH: 13
<212> TYPE: PRT
<213> ORGANISM: Homo sapiens

<400> SEQUENCE: 1893

Cys Ala Ser Ser Gln Asp Arg Val Tyr Gly Tyr Thr Phe
1               5                   10

<210> SEQ ID NO 1894
<211> LENGTH: 11
<212> TYPE: PRT
<213> ORGANISM: Homo sapiens

<400> SEQUENCE: 1894

Cys Ala Ser Gly Glu Tyr Gln Pro Gln His Phe
1               5                   10

<210> SEQ ID NO 1895
<211> LENGTH: 14
<212> TYPE: PRT
<213> ORGANISM: Homo sapiens

<400> SEQUENCE: 1895

Cys Ala Ser Ser Leu Gly Gly Gly Phe Ser Pro Leu His Phe
1               5                   10

<210> SEQ ID NO 1896
<211> LENGTH: 18
<212> TYPE: PRT
<213> ORGANISM: Homo sapiens

<400> SEQUENCE: 1896

Cys Ala Ser Ser Leu Gly Leu Ala Gly Thr Ser Gly Ala Asn Val Leu
1               5                   10                  15

Thr Phe

<210> SEQ ID NO 1897
<211> LENGTH: 15
<212> TYPE: PRT
<213> ORGANISM: Homo sapiens

<400> SEQUENCE: 1897

Cys Ala Ser Ser Pro Gln Gly Ser Leu Asn Thr Glu Ala Phe Phe
1               5                   10                  15

<210> SEQ ID NO 1898
<211> LENGTH: 14
<212> TYPE: PRT
<213> ORGANISM: Homo sapiens

<400> SEQUENCE: 1898

Cys Ala Ser Ser Leu Asn Arg Glu Thr Gly Glu Leu Phe Phe
1               5                   10

<210> SEQ ID NO 1899
<211> LENGTH: 14
<212> TYPE: PRT
<213> ORGANISM: Homo sapiens

<400> SEQUENCE: 1899

Cys Ala Ser Ser Tyr Gly Thr Glu Asn Gln Pro Gln His Phe
1               5                   10

<210> SEQ ID NO 1900
<211> LENGTH: 13
<212> TYPE: PRT
<213> ORGANISM: Homo sapiens

<400> SEQUENCE: 1900

Cys Ala Ser Ser Tyr Pro Thr Asn Asn Glu Gln Phe Phe
1               5                   10

<210> SEQ ID NO 1901
<211> LENGTH: 13
<212> TYPE: PRT
<213> ORGANISM: Homo sapiens

<400> SEQUENCE: 1901

Cys Ala Ser Ser Ile Phe Gln Gly Tyr Glu Gln Tyr Phe
1               5                   10

-continued

<210> SEQ ID NO 1902
<211> LENGTH: 16
<212> TYPE: PRT
<213> ORGANISM: Homo sapiens

<400> SEQUENCE: 1902

Cys Ala Ser Ser Pro Gly Leu Ala Gly Ala Gly Asn Glu Gln Phe Phe
1               5                   10                  15

<210> SEQ ID NO 1903
<211> LENGTH: 17
<212> TYPE: PRT
<213> ORGANISM: Homo sapiens

<400> SEQUENCE: 1903

Cys Ala Ser Ser Pro Gly Thr Ser Gly Ala Asn Thr Gly Glu Leu Phe
1               5                   10                  15

Phe

<210> SEQ ID NO 1904
<211> LENGTH: 14
<212> TYPE: PRT
<213> ORGANISM: Homo sapiens

<400> SEQUENCE: 1904

Cys Ala Ser Ser Leu Ser Thr Ala Gly Glu Thr Gln Tyr Phe
1               5                   10

<210> SEQ ID NO 1905
<211> LENGTH: 15
<212> TYPE: PRT
<213> ORGANISM: Homo sapiens

<400> SEQUENCE: 1905

Cys Ala Ser Ser Val Asp Gln Gly Ala Gly Tyr Glu Gln Tyr Phe
1               5                   10                  15

<210> SEQ ID NO 1906
<211> LENGTH: 13
<212> TYPE: PRT
<213> ORGANISM: Homo sapiens

<400> SEQUENCE: 1906

Cys Ala Ser Ser Ser Thr Asn Gln Glu Thr Gln Tyr Phe
1               5                   10

<210> SEQ ID NO 1907
<211> LENGTH: 11
<212> TYPE: PRT
<213> ORGANISM: Homo sapiens

<400> SEQUENCE: 1907

Cys Ala Ser Ser Tyr Ser Tyr Thr Gln Tyr Phe
1               5                   10

<210> SEQ ID NO 1908
<211> LENGTH: 13
<212> TYPE: PRT
<213> ORGANISM: Homo sapiens

<400> SEQUENCE: 1908

Cys Ala Thr Ser Arg Val Asp Ala Tyr Glu Gln Tyr Phe
1               5                   10

<210> SEQ ID NO 1909
<211> LENGTH: 15
<212> TYPE: PRT
<213> ORGANISM: Homo sapiens

<400> SEQUENCE: 1909

Cys Ala Ser Ser Gln Asp Gly Ala Asn Thr Gly Glu Leu Phe Phe
1               5                   10                  15

<210> SEQ ID NO 1910
<211> LENGTH: 13
<212> TYPE: PRT
<213> ORGANISM: Homo sapiens

<400> SEQUENCE: 1910

Cys Ala Ser Ser Leu Asn Ala Arg Gly Glu Leu Phe Phe
1               5                   10

<210> SEQ ID NO 1911
<211> LENGTH: 15
<212> TYPE: PRT
<213> ORGANISM: Homo sapiens

<400> SEQUENCE: 1911

Cys Ala Ser Ser Thr Arg Thr Gly Gly Asn Asn Glu Gln Phe Phe
1               5                   10                  15

<210> SEQ ID NO 1912
<211> LENGTH: 14
<212> TYPE: PRT
<213> ORGANISM: Homo sapiens

<400> SEQUENCE: 1912

Cys Ala Ser Ser Pro Gly Leu Ala Gly Val Arg Gln Phe Phe
1               5                   10

<210> SEQ ID NO 1913
<211> LENGTH: 12
<212> TYPE: PRT
<213> ORGANISM: Homo sapiens

<400> SEQUENCE: 1913

Cys Ala Thr Ser Gly Ser Thr Asp Thr Gln Tyr Phe
1               5                   10

<210> SEQ ID NO 1914
<211> LENGTH: 15
<212> TYPE: PRT
<213> ORGANISM: Homo sapiens

<400> SEQUENCE: 1914

Cys Ala Ser Ser Thr Ser Gly Gly Gly Arg Gln Pro Gln His Phe
1               5                   10                  15

<210> SEQ ID NO 1915
<211> LENGTH: 14
<212> TYPE: PRT
<213> ORGANISM: Homo sapiens

<400> SEQUENCE: 1915

Cys Ala Ser Ser Thr Gly Gly Leu Gly Thr Glu Ala Phe Phe
1               5                   10

```
<210> SEQ ID NO 1916
<211> LENGTH: 14
<212> TYPE: PRT
<213> ORGANISM: Homo sapiens

<400> SEQUENCE: 1916

Cys Ala Ser Ser Leu Val Asp Ser Gly Tyr Glu Gln Tyr Phe
1               5                   10

<210> SEQ ID NO 1917
<211> LENGTH: 13
<212> TYPE: PRT
<213> ORGANISM: Homo sapiens

<400> SEQUENCE: 1917

Cys Ala Ser Arg Gly Gly Gln Ser Tyr Glu Gln Tyr Phe
1               5                   10

<210> SEQ ID NO 1918
<211> LENGTH: 16
<212> TYPE: PRT
<213> ORGANISM: Homo sapiens

<400> SEQUENCE: 1918

Cys Ala Ser Ser Ala Arg Leu Ala Gly Gly Gly Asn Glu Gln Phe Phe
1               5                   10                  15

<210> SEQ ID NO 1919
<211> LENGTH: 10
<212> TYPE: PRT
<213> ORGANISM: Homo sapiens

<400> SEQUENCE: 1919

Cys Ala Trp Ala Gly Asn Glu Gln Tyr Phe
1               5                   10

<210> SEQ ID NO 1920
<211> LENGTH: 13
<212> TYPE: PRT
<213> ORGANISM: Homo sapiens

<400> SEQUENCE: 1920

Cys Ala Ser Ser Ser Leu Gly His Gln Pro Gln His Phe
1               5                   10

<210> SEQ ID NO 1921
<211> LENGTH: 13
<212> TYPE: PRT
<213> ORGANISM: Homo sapiens

<400> SEQUENCE: 1921

Cys Ala Ser Ser Pro Gly Thr Arg Arg Glu Gln Tyr Phe
1               5                   10

<210> SEQ ID NO 1922
<211> LENGTH: 13
<212> TYPE: PRT
<213> ORGANISM: Homo sapiens

<400> SEQUENCE: 1922

Cys Ala Trp Ser Gly Gln Val Ser Thr Glu Ala Phe Phe
1               5                   10

<210> SEQ ID NO 1923
<211> LENGTH: 14
```

<212> TYPE: PRT
<213> ORGANISM: Homo sapiens

<400> SEQUENCE: 1923

Cys Ala Ser Ser Gln Asp Asn Ser Pro Tyr Glu Gln Tyr Phe
1               5                   10

<210> SEQ ID NO 1924
<211> LENGTH: 11
<212> TYPE: PRT
<213> ORGANISM: Homo sapiens

<400> SEQUENCE: 1924

Cys Ala Ser Arg Arg Thr Val Gly Tyr Thr Phe
1               5                   10

<210> SEQ ID NO 1925
<211> LENGTH: 13
<212> TYPE: PRT
<213> ORGANISM: Homo sapiens

<400> SEQUENCE: 1925

Cys Ala Ser Met Arg Gly Asp Thr Gly Glu Leu Phe Phe
1               5                   10

<210> SEQ ID NO 1926
<211> LENGTH: 14
<212> TYPE: PRT
<213> ORGANISM: Homo sapiens

<400> SEQUENCE: 1926

Cys Ala Ser Ser Thr Gly Gln Gly Glu Asp Glu Gln Tyr Phe
1               5                   10

<210> SEQ ID NO 1927
<211> LENGTH: 15
<212> TYPE: PRT
<213> ORGANISM: Homo sapiens

<400> SEQUENCE: 1927

Cys Ser Ala Arg Asp Gln Gly Gln Val Ala Tyr Gly Tyr Thr Phe
1               5                   10                  15

<210> SEQ ID NO 1928
<211> LENGTH: 15
<212> TYPE: PRT
<213> ORGANISM: Homo sapiens

<400> SEQUENCE: 1928

Cys Ala Ser Ser Ile Leu Thr Gly Phe Asn Gln Pro Gln His Phe
1               5                   10                  15

<210> SEQ ID NO 1929
<211> LENGTH: 12
<212> TYPE: PRT
<213> ORGANISM: Homo sapiens

<400> SEQUENCE: 1929

Cys Ser Val Gln Gly Asn Asp Tyr Gly Tyr Thr Phe
1               5                   10

<210> SEQ ID NO 1930
<211> LENGTH: 14
<212> TYPE: PRT
<213> ORGANISM: Homo sapiens

<400> SEQUENCE: 1930

Cys Ala Ser Ser Pro Asp Arg Gly Gln Ser Glu Ala Phe Phe
1               5                   10

<210> SEQ ID NO 1931
<211> LENGTH: 15
<212> TYPE: PRT
<213> ORGANISM: Homo sapiens

<400> SEQUENCE: 1931

Cys Ala Ser Ser Gln Asp Arg Gly Thr Ala Asp Thr Gln Tyr Phe
1               5                   10                  15

<210> SEQ ID NO 1932
<211> LENGTH: 16
<212> TYPE: PRT
<213> ORGANISM: Homo sapiens

<400> SEQUENCE: 1932

Cys Ala Ser Ser Arg Asp Ser Ser Ser Gly Asn Thr Ile Tyr Phe
1               5                   10                  15

<210> SEQ ID NO 1933
<211> LENGTH: 12
<212> TYPE: PRT
<213> ORGANISM: Homo sapiens

<400> SEQUENCE: 1933

Cys Ala Ser Ser Arg Thr Pro Asp Gly Tyr Thr Phe
1               5                   10

<210> SEQ ID NO 1934
<211> LENGTH: 16
<212> TYPE: PRT
<213> ORGANISM: Homo sapiens

<400> SEQUENCE: 1934

Cys Ala Ser Ser Gln Gly Thr Gly Gly Arg Gly Glu Thr Gln Tyr Phe
1               5                   10                  15

<210> SEQ ID NO 1935
<211> LENGTH: 13
<212> TYPE: PRT
<213> ORGANISM: Homo sapiens

<400> SEQUENCE: 1935

Cys Ala Ser Ser Leu Leu Glu Gly Arg Gly Tyr Thr Phe
1               5                   10

<210> SEQ ID NO 1936
<211> LENGTH: 13
<212> TYPE: PRT
<213> ORGANISM: Homo sapiens

<400> SEQUENCE: 1936

Cys Ser Ala Pro Gly Arg Asp Asn Gln Pro Gln His Phe
1               5                   10

<210> SEQ ID NO 1937
<211> LENGTH: 16
<212> TYPE: PRT
<213> ORGANISM: Homo sapiens

<400> SEQUENCE: 1937

```
Cys Ala Ser Ser Leu Gly Gln Gly Gly Gln Glu Thr Gln Tyr Phe
1               5                   10                  15

<210> SEQ ID NO 1938
<211> LENGTH: 15
<212> TYPE: PRT
<213> ORGANISM: Homo sapiens

<400> SEQUENCE: 1938

Cys Ala Ser Ser Glu Val Arg Gly Pro Asn Tyr Gly Tyr Thr Phe
1               5                   10                  15

<210> SEQ ID NO 1939
<211> LENGTH: 11
<212> TYPE: PRT
<213> ORGANISM: Homo sapiens

<400> SEQUENCE: 1939

Cys Ser Ala Pro Ser Gly Asp Gly Tyr Thr Phe
1               5                   10

<210> SEQ ID NO 1940
<211> LENGTH: 15
<212> TYPE: PRT
<213> ORGANISM: Homo sapiens

<400> SEQUENCE: 1940

Cys Ala Ile Ser Pro Gly Gln Gly Val Gln Glu Thr Gln Tyr Phe
1               5                   10                  15

<210> SEQ ID NO 1941
<211> LENGTH: 11
<212> TYPE: PRT
<213> ORGANISM: Homo sapiens

<400> SEQUENCE: 1941

Cys Ala Ser Ser Gly Arg Gly Glu Leu Phe Phe
1               5                   10

<210> SEQ ID NO 1942
<211> LENGTH: 15
<212> TYPE: PRT
<213> ORGANISM: Homo sapiens

<400> SEQUENCE: 1942

Cys Ala Ser Ser Leu Gly Ala Gln Gly Tyr Asn Glu Gln Phe Phe
1               5                   10                  15

<210> SEQ ID NO 1943
<211> LENGTH: 14
<212> TYPE: PRT
<213> ORGANISM: Homo sapiens

<400> SEQUENCE: 1943

Cys Ala Trp Ser Arg Ser Arg Gly Gln Thr Glu Ala Phe Phe
1               5                   10

<210> SEQ ID NO 1944
<211> LENGTH: 15
<212> TYPE: PRT
<213> ORGANISM: Homo sapiens

<400> SEQUENCE: 1944

Cys Ala Ser Leu Ser Gly Gly Ser Gly Ala Asn Val Leu Thr Phe
```

```
1               5                   10                  15
```

<210> SEQ ID NO 1945
<211> LENGTH: 13
<212> TYPE: PRT
<213> ORGANISM: Homo sapiens

<400> SEQUENCE: 1945

```
Cys Ala Ser Trp Thr Gly Gly Arg Tyr Glu Gln Tyr Phe
1               5                   10
```

<210> SEQ ID NO 1946
<211> LENGTH: 12
<212> TYPE: PRT
<213> ORGANISM: Homo sapiens

<400> SEQUENCE: 1946

```
Cys Ala Ser Ser Gly Gln Ser Pro Glu Ala Phe Phe
1               5                   10
```

<210> SEQ ID NO 1947
<211> LENGTH: 17
<212> TYPE: PRT
<213> ORGANISM: Homo sapiens

<400> SEQUENCE: 1947

```
Cys Ala Ser Ser Leu Val Gly Ile Ser Ser Tyr Asn Ser Pro Leu His
1               5                   10                  15

Phe
```

<210> SEQ ID NO 1948
<211> LENGTH: 15
<212> TYPE: PRT
<213> ORGANISM: Homo sapiens

<400> SEQUENCE: 1948

```
Cys Ala Ser Ser Arg Pro Arg Gly Gly Gly Glu Thr Gln Tyr Phe
1               5                   10                  15
```

<210> SEQ ID NO 1949
<211> LENGTH: 15
<212> TYPE: PRT
<213> ORGANISM: Homo sapiens

<400> SEQUENCE: 1949

```
Cys Ala Ser Ser Gln Ala Asn Arg Asn Thr Gly Glu Leu Phe Phe
1               5                   10                  15
```

<210> SEQ ID NO 1950
<211> LENGTH: 17
<212> TYPE: PRT
<213> ORGANISM: Homo sapiens

<400> SEQUENCE: 1950

```
Cys Ala Ile Ser Glu Ser Gln Gly Gln Gly Ser Thr Asp Thr Gln Tyr
1               5                   10                  15

Phe
```

<210> SEQ ID NO 1951
<211> LENGTH: 12
<212> TYPE: PRT
<213> ORGANISM: Homo sapiens

<400> SEQUENCE: 1951

```
Cys Ala Thr Ser Asp Ala Ser Gly Pro Gln His Phe
1               5                   10

<210> SEQ ID NO 1952
<211> LENGTH: 15
<212> TYPE: PRT
<213> ORGANISM: Homo sapiens

<400> SEQUENCE: 1952

Cys Ala Ser Ser Gln Glu Ser Gly Arg Arg Tyr Glu Gln Tyr Phe
1               5                   10                  15

<210> SEQ ID NO 1953
<211> LENGTH: 15
<212> TYPE: PRT
<213> ORGANISM: Homo sapiens

<400> SEQUENCE: 1953

Cys Ala Ser Ser Pro Gly Ser Gly Val Tyr Asn Glu Gln Phe Phe
1               5                   10                  15

<210> SEQ ID NO 1954
<211> LENGTH: 13
<212> TYPE: PRT
<213> ORGANISM: Homo sapiens

<400> SEQUENCE: 1954

Cys Ala Ser Ser Pro Ser Ser Gly Leu Glu Ala Phe Phe
1               5                   10

<210> SEQ ID NO 1955
<211> LENGTH: 15
<212> TYPE: PRT
<213> ORGANISM: Homo sapiens

<400> SEQUENCE: 1955

Cys Ala Ser Ser Arg Arg Gly Asp Tyr Asn Ser Pro Leu His Phe
1               5                   10                  15

<210> SEQ ID NO 1956
<211> LENGTH: 14
<212> TYPE: PRT
<213> ORGANISM: Homo sapiens

<400> SEQUENCE: 1956

Cys Ala Ser Ser Tyr Val Gly Gln Gly Ser Pro Leu His Phe
1               5                   10

<210> SEQ ID NO 1957
<211> LENGTH: 15
<212> TYPE: PRT
<213> ORGANISM: Homo sapiens

<400> SEQUENCE: 1957

Cys Ala Ser Ser Ser Ser Gly Arg Val Gln Glu Thr Gln Tyr Phe
1               5                   10                  15

<210> SEQ ID NO 1958
<211> LENGTH: 15
<212> TYPE: PRT
<213> ORGANISM: Homo sapiens

<400> SEQUENCE: 1958

Cys Ala Ser Ser Ser Asn Arg Gly Pro Gly Glu Lys Leu Phe Phe
```

<210> SEQ ID NO 1959
<211> LENGTH: 14
<212> TYPE: PRT
<213> ORGANISM: Homo sapiens

<400> SEQUENCE: 1959

Cys Ser Ala Ser Gly Ala Thr Gly Asn Gln Pro Gln His Phe
1               5                   10

<210> SEQ ID NO 1960
<211> LENGTH: 13
<212> TYPE: PRT
<213> ORGANISM: Homo sapiens

<400> SEQUENCE: 1960

Cys Ala Trp Ser Ala Gln Gly Ala Thr Gly Tyr Thr Phe
1               5                   10

<210> SEQ ID NO 1961
<211> LENGTH: 14
<212> TYPE: PRT
<213> ORGANISM: Homo sapiens

<400> SEQUENCE: 1961

Cys Ala Ser Ser Asp Gly Gln Gly Tyr Ser Pro Leu His Phe
1               5                   10

<210> SEQ ID NO 1962
<211> LENGTH: 13
<212> TYPE: PRT
<213> ORGANISM: Homo sapiens

<400> SEQUENCE: 1962

Cys Ala Ser Ser Pro Thr Ser Gly Ser Glu Gln Phe Phe
1               5                   10

<210> SEQ ID NO 1963
<211> LENGTH: 14
<212> TYPE: PRT
<213> ORGANISM: Homo sapiens

<400> SEQUENCE: 1963

Cys Ala Ser Ser Val Gly His Arg Asn Thr Glu Ala Phe Phe
1               5                   10

<210> SEQ ID NO 1964
<211> LENGTH: 15
<212> TYPE: PRT
<213> ORGANISM: Homo sapiens

<400> SEQUENCE: 1964

Cys Ala Ser Ser Gln Asp Arg Val Tyr Gln Glu Thr Gln Tyr Phe
1               5                   10                  15

<210> SEQ ID NO 1965
<211> LENGTH: 14
<212> TYPE: PRT
<213> ORGANISM: Homo sapiens

<400> SEQUENCE: 1965

Cys Ala Ile Ser Pro Asp Thr Thr Asn Glu Lys Leu Phe Phe
1               5                   10

<210> SEQ ID NO 1966
<211> LENGTH: 14
<212> TYPE: PRT
<213> ORGANISM: Homo sapiens

<400> SEQUENCE: 1966

Cys Ala Ser Ser Ser Gly Gly Asn Gln Glu Thr Gln Tyr Phe
1               5                   10

<210> SEQ ID NO 1967
<211> LENGTH: 15
<212> TYPE: PRT
<213> ORGANISM: Homo sapiens

<400> SEQUENCE: 1967

Cys Ala Ser Arg Leu Ala Gly Val Ala Tyr Asn Glu Gln Phe Phe
1               5                   10                  15

<210> SEQ ID NO 1968
<211> LENGTH: 14
<212> TYPE: PRT
<213> ORGANISM: Homo sapiens

<400> SEQUENCE: 1968

Cys Ala Ser Arg Glu Asp Arg Gly Asn Tyr Gly Tyr Thr Phe
1               5                   10

<210> SEQ ID NO 1969
<211> LENGTH: 13
<212> TYPE: PRT
<213> ORGANISM: Homo sapiens

<400> SEQUENCE: 1969

Cys Ala Ser Ser Arg Thr Arg Ala Tyr Glu Gln Tyr Phe
1               5                   10

<210> SEQ ID NO 1970
<211> LENGTH: 13
<212> TYPE: PRT
<213> ORGANISM: Homo sapiens

<400> SEQUENCE: 1970

Cys Ala Ser Gly Leu Asp Arg Pro Gly Glu Leu Phe Phe
1               5                   10

<210> SEQ ID NO 1971
<211> LENGTH: 13
<212> TYPE: PRT
<213> ORGANISM: Homo sapiens

<400> SEQUENCE: 1971

Cys Ala Ser Ser Thr Trp Gly Asn Tyr Gly Tyr Thr Phe
1               5                   10

<210> SEQ ID NO 1972
<211> LENGTH: 14
<212> TYPE: PRT
<213> ORGANISM: Homo sapiens

<400> SEQUENCE: 1972

Cys Ala Ser Ser Glu Leu Ala Ala Asp Asn Glu Gln Phe Phe
1               5                   10

<210> SEQ ID NO 1973

```
<211> LENGTH: 15
<212> TYPE: PRT
<213> ORGANISM: Homo sapiens

<400> SEQUENCE: 1973

Cys Ala Ser Ser Leu Val Gly Gly Gly Thr Asp Thr Gln Tyr Phe
1               5                   10                  15

<210> SEQ ID NO 1974
<211> LENGTH: 18
<212> TYPE: PRT
<213> ORGANISM: Homo sapiens

<400> SEQUENCE: 1974

Cys Ala Ser Ser Pro Arg Thr Ser Gly Arg Glu Tyr Gln Glu Thr Gln
1               5                   10                  15

Tyr Phe

<210> SEQ ID NO 1975
<211> LENGTH: 15
<212> TYPE: PRT
<213> ORGANISM: Homo sapiens

<400> SEQUENCE: 1975

Cys Ala Ser Ser Gln Gln Gly Ala Gly Tyr Asn Glu Gln Phe Phe
1               5                   10                  15

<210> SEQ ID NO 1976
<211> LENGTH: 13
<212> TYPE: PRT
<213> ORGANISM: Homo sapiens

<400> SEQUENCE: 1976

Cys Ala Ser Ser Ser Arg Arg Gly Asp Glu Gln Phe Phe
1               5                   10

<210> SEQ ID NO 1977
<211> LENGTH: 14
<212> TYPE: PRT
<213> ORGANISM: Homo sapiens

<400> SEQUENCE: 1977

Cys Ala Ser Ser Ser Arg Ala Gly Ser Tyr Glu Gln Tyr Phe
1               5                   10
```